(12) United States Patent
Toure et al.

(10) Patent No.: US 11,667,624 B2
(45) Date of Patent: Jun. 6, 2023

(54) INDOLE COMPOUNDS AS ANDROGEN RECEPTOR MODULATORS

(71) Applicant: NIDO BIOSCIENCES, INC., Cambridge, MA (US)

(72) Inventors: Bakary-Barry Toure, Weston, MA (US); Mark Andrew Gallop, San Francisco, CA (US); Paul Andrew Barsanti, Walnut Creek, CA (US)

(73) Assignee: NIDO BIOSCIENCES, INC., Cambridge, MA (US)

( * ) Notice: Subject to any disclaimer, the term of this patent is extended or adjusted under 35 U.S.C. 154(b) by 0 days.

(21) Appl. No.: 17/380,736

(22) Filed: Jul. 20, 2021

(65) Prior Publication Data

US 2023/0049406 A1    Feb. 16, 2023

Related U.S. Application Data

(60) Provisional application No. 63/164,820, filed on Mar. 23, 2021, provisional application No. 63/113,014, filed on Nov. 12, 2020, provisional application No. 63/054,191, filed on Jul. 20, 2020.

(51) Int. Cl.

| | | |
|---|---|---|
| *C07D 403/14* | (2006.01) |
| *C07D 471/04* | (2006.01) |
| *C07D 401/14* | (2006.01) |
| *C07D 405/14* | (2006.01) |
| *C07D 401/04* | (2006.01) |
| *C07D 403/04* | (2006.01) |

(52) U.S. Cl.
CPC ......... *C07D 403/14* (2013.01); *C07D 401/04* (2013.01); *C07D 401/14* (2013.01); *C07D 403/04* (2013.01); *C07D 405/14* (2013.01); *C07D 471/04* (2013.01)

(58) Field of Classification Search
None
See application file for complete search history.

(56) References Cited

U.S. PATENT DOCUMENTS

| | | |
|---|---|---|
| 2012/0214994 A1 | 8/2012 | Chi et al. |
| 2016/0168140 A1 | 6/2016 | Jones et al. |
| 2019/0016707 A1 | 1/2019 | Kane, Jr. et al. |

FOREIGN PATENT DOCUMENTS

| | | |
|---|---|---|
| WO | WO 2015/154169 A1 | 10/2015 |
| WO | WO 2016/020526 A1 | 2/2016 |
| WO | WO 2019/084365 A1 | 5/2019 |

OTHER PUBLICATIONS

Fujii et al., "Androgen receptor modulators: a review of recent patents and reports", *Expert Opinion on Therapeutic Patents* 29(6):439-453, XP055853428, doi:10.1080/13543776.2019.1618831, May 2019.
International Search Report and Written Opinion for International Application No. PCT/US2021/042355, dated Nov. 2, 2021, 12 pages.

*Primary Examiner* — Samantha L Shterengarts
(74) *Attorney, Agent, or Firm* — Brian C. Trinque; Nicole Sassu; Lathrop GPM LLP

(57) ABSTRACT

Provided herein are indole compounds that bind to BF3 of an androgen receptor (AR), which can modulate the AR for the treatment of Kennedy's disease.

19 Claims, No Drawings

INDOLE COMPOUNDS AS ANDROGEN RECEPTOR MODULATORS

RELATED APPLICATIONS

This claims priority to U.S. Provisional Application No. 63/054,191, filed on Jul. 20, 2020; U.S. Provisional Application 63/113,014; filed on Nov. 12, 2020; and U.S. Provisional Application 63/164,820, filed on Mar. 23, 2021; the entire contents of which are hereby incorporated in their entirety.

BACKGROUND

Prostate cancer is the second leading cause of male cancer-related death in Western countries (Damber, J. E. and Aus, G. *Lancet* (2008) 371:1710-1721). Numerous studies have shown that the androgen receptor (AR) is central not only to the development of prostate cancer, but also the progression of the disease to the castration resistance state (Taplin, M. E. et al. J. Clin. Oncol. (2003) 21:2673-8; and Tilley, W. D. et al. Cancer Res. (1994) 54:4096-4102). Thus, effective inhibition of human AR remains one of the most effective therapeutic approaches to the treatment of advanced, metastatic prostate cancer.

Kennedys disease or Spinal Bulbar Muscular Atrophy (SBMA) is an x-linked recessive motor neuron disease resulting from disruptions in the transmission of nerve cell signals in the brain stem and spinal cord. The motor neuron disruptions are more noticeable relative to other cells because of the higher number of the androgen receptors residing in nerve cells. The nerve cells in a Kennedy's patient gradually become increasingly dysfunctional and eventually die, leaving the muscles unable to contract, resulting in atrophy of the muscles throughout the body, but most noticeably in the extremities, face and throat. The binding of testosterone to the AR is thought to cause the disease. At present there is no treatment for Kennedy's disease.

SUMMARY

Provided herein are compound that modulate androgen receptor (AR) activity. In particular, the compounds disclosed herein show inhibition of Androgen Receptor Binding Function-3 (BF3).

In an aspect, provided herein is a compound of Formula I:

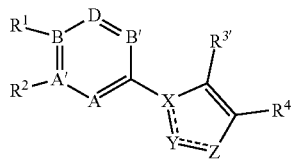

I or a pharmaceutically acceptable salt thereof; wherein the variables are defined herein.

In an embodiment, the compound of Formula I is a compound of Formula II

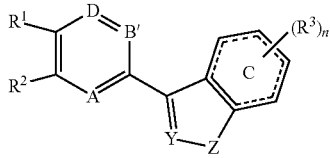

(II)

or a pharmaceutically acceptable salt thereof.

In another embodiment, the compound of Formula I is a compound of Formula III:

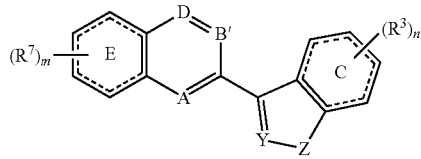

(III)

or a pharmaceutically acceptable salt thereof.

In still another embodiment, the compound of Formula I is a compound of Formula IV:

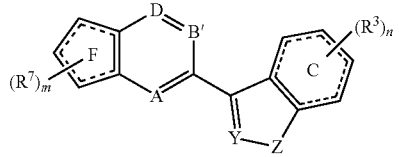

(IV)

or a pharmaceutically acceptable salt thereof.

In yet another embodiment, the compound of Formula I is a compound of Formula V:

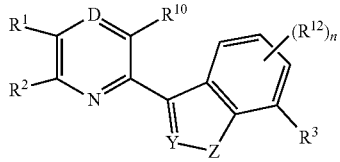

(V)

or a pharmaceutically acceptable salt thereof.

In an aspect, provided herein is a compound of Formula X:

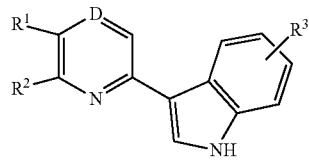

(X)

or a pharmaceutically acceptable salt thereof.

In an embodiment, the compound of Formula X is a compound of Formula VII:

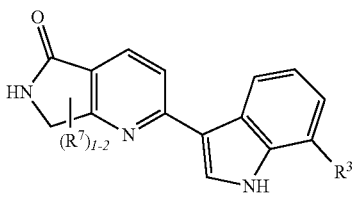

or a pharmaceutically acceptable salt thereof.

In an embodiment, the compound of Formula X is a compound of Formula VII':

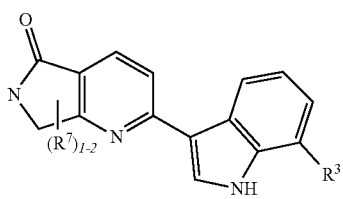

or a pharmaceutically acceptable salt thereof.

In another embodiment, the compound of Formula X is a compound of Formula VIII:

or a pharmaceutically acceptable salt thereof.

In another aspect, provided herein is a pharmaceutical composition comprising a compound of Formula I and a pharmaceutically acceptable carrier.

In yet another aspect, provided herein is a method of treating a neurodegenerative disorder in a subject in need thereof comprising administering to the subject a therapeutically effective amount of a compound of Formula I.

In an embodiment of the methods, the neurodegenerative disorder is spinal bulbar muscular atrophy (SBMA).

In still another aspect, provided herein is a method of modulating androgen receptor (AR) activity in a subject in need thereof comprising administering to the subject a therapeutically effective amount of a compound of Formula I.

DETAILED DESCRIPTION

Androgens play a role in a wide range of developmental and physiological responses, for example, male sexual differentiation, maintenance of spermatogenesis, and male gonadotropin regulation (Ross, R. K., et al., Eur. Urol. 35, 355-361 (1999); Thomson, A. A., Reproduction 121, 187-195 (2001); Tanji, N., et al., Arch. Androl. 47, 1-7 (2001)). Androgens are also associated with the development of prostate carcinogenesis. Induction of prostatic carcinogenesis in rodent models has been associated with androgens (R. L. Noble, Cancer Res. 37, 1929-1933 (1977); R. L. Noble, Oncology 34, 138-141 (1977)), and men receiving androgens in the form of anabolic steroids are reported to have a higher incidence of prostate cancer (Roberts, J. T., and Essenhigh, D. M., Lancet 2, 742 (1986); Jackson, J. A., et al., Arch. Intern. Med. 149, 2365-2366 (1989); Guinan, P. D., et al., Am. J. Surg. 131, 599-600 (1976)). Furthermore, prostate cancer does not develop if humans or dogs are castrated before puberty (Wilson, J. D., and Roehrborn, C., J. Clin. Endocrinol. Metab. 84, 4324-4331 (1999); G. Wilding, Cancer Surv. 14, 113-130 (1992)). Castration of adult males causes involution of the prostate and apoptosis of prostatic epithelium (Bruckheimer, E. M., and Kyprianou, N., Cell Tissue Res. 301, 153-162 (2000); J. T. Isaacs, Prostate 5, 545-557 (1984)). This dependency on androgens provides the underlying rationale for treating prostate cancer with chemical or surgical castration (i.e., androgen ablation).

The AR possesses a modular organization characteristic of all nuclear receptors. It is comprised of an N-terminal domain, a central DNA binding domain, a short hinge region, and C-terminal domain that contains a hormone ligand binding pocket and the Activation Function-2 (AF2) site (Gao, W. Q. et al. Chem. Rev. (2005) 105:3352-3370). The latter represents a hydrophobic groove on the AR surface which is flanked with regions of positive and negative charges, "charge clamps," that are significant for binding AR activation factors (Zhou, X. E. et al. J. Biol. Chem. (2010) 285:9161-9171). Recent studies have identified a novel site on the AR called Binding Function 3 (BF3) that is involved into AR transcriptional activity.

It has been proposed that a small molecule bound to the BF3 site could cause the AR protein to undergo an allosteric modification that prevents AR interactions with co-activators. Importantly, the BF3 site is located near, but distinct from, the ligand-binding site that is normally targeted by conventional anti-androgen drugs. Compounds such as flufenamic acid (FLUF), thriiodothyronine (T3) and 3,3',5-triiodo thyroacetic acid (TRIAC) can bind to the BF3 cleft, inhibit AF2 interactions, and interfere with AR activity (Estebanez-Perpina, E. et al. Proc. Natl. Acad. Sci. USA (2007) 104:16074-16079). While these compounds revealed the importance of the BF3 site, they have shown a low potency ($IC_{50}$>50 µM) and were found to bind non-specifically to the AR.

The activation of AR follows a well characterized pathway: in the cytoplasm, the receptor is associated with chaperone proteins that maintain agonist binding conformation of the AR (Georget, V. et al. Biochemistry (2002) 41:11824-11831). Upon binding of an androgen, the AR undergoes a series of conformational changes, disassociation from chaperones, dimerization and translocation into the nucleus (Fang, Y. F. et al. J. Biol. Chem. (1996) 271: 28697-28702; and Wong, C. I. et al. J. Biol. Chem. (1993) 268:19004-19012) where it further interacts with co-activator proteins at the AF2 site (Zhou, X. E. et al. J. Biol. Chem. (2010) 285:9161-9171). This event triggers the recruitment of RNA polymerase II and other factors to form a functional transcriptional complex with the AR.

Notably, the current anti-androgens such as bicalutamide, flutamide, nilutamide and MDV3100, all target this particular process. However, instead of affecting the AR-cofactor interaction directly, these anti-androgens act indirectly, by binding to the AR ligand binding site. Thus, by preventing androgens from binding they also prevent conformational changes of the receptor that are necessary for co-activator interactions. While treatment with these AR inhibitors can initially suppress the prostate cancer growth, long term hormone therapy becomes progressively less effective (Taplin, M. E. et al. J. Clin. Oncol. (2003) 21:2673-8; and Tilley, W. D. et al. Cancer Res. (1994) 54:4096-4102). Factors that make the AR less sensitive to conventional anti-androgens include resistance mutations at the ligand binding site that can even lead AR antagonists to act as agonists further contributing to cancer progression (Chen, Y. et al. Lancet Oncol. (2009) 10:981-991).

Androgens also play a role in female cancers. One example is ovarian cancer where elevated levels of androgens are associated with an increased risk of developing ovarian cancer (K. J. Helzlsouer, et al., *JAMA* 274, 1926-1930 (1995); R. J. Edmondson, et al, *Br J Cancer* 86, 879-885 (2002)). The AR has been detected in a majority of ovarian cancers (H. A. Risch, *J. Natl. Cancer Inst.* 90, 1774-1786 (1998); B. R. Rao & B. J. Slotman, *Endocr. Rev.* 12, 14-26 (1991); G. M. Clinton & W. Hua, *Crit. Rev. Oncol. Hematol.* 25, 1-9 (1997)), whereas estrogen receptor-alpha (ERα) and the progesterone receptor are detected in less than 50% of ovarian tumors.

Spinal and bulbar muscular atrophy (SBMA), popularly known as Kennedys disease, is a progressive debilitating neurodegenerative disorder resulting in muscle cramps and progressive weakness due to degeneration of motor neurons in the brainstem and spinal cord. The condition is associated with mutation of the androgen receptor (AR) gene and is inherited in an X-linked recessive manner. As with many genetic disorders, no cure is known, although research continues. Because of its endocrine manifestations related to the impairment of the AR gene, SBMA can be viewed as a variation of the disorders of the androgen insensitivity syndrome (AIS). It is also related to other neurodegenerative diseases caused by similar mutations, such as Huntington's disease.

The BF3 site is an attractive target for direct inhibition of the AR co-activation. In silico computational drug discovery methods were used to predict potential BF3 binders. The in silico methods included large-scale docking, in-site rescoring and consensus voting procedures.

Definitions

It is appreciated that certain features of the present disclosure, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —$OCH_2CH_2O$— and $OCH_2CH_2CH_2O$—. In some embodiments, the two O atoms of a $C_{n-m}$ dialkoxy group may be attached to the same B atom to form a 5- or 6-membered heterocycloalkyl group. The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2 (n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments, aryl groups have 6 carbon atoms. In some embodiments, aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thio-phenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazabicyclo[2.2.1]-heptanyl; pyrrolidinyl; hexahydropyrrolo[3,4-b]pyrrol-1(2H)-yl; 1,6-dihydropyridinyl; morpholinyl; azetidinyl; piperazinyl; and 4,7-diazaspiro[2.5]octan-7-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound," as used herein, is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds provided herein, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences, 17$^{th}$ Ed.*, (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

Compounds as described herein may be administered to a subject. As used herein, a "subject" may be a human, non-human primate, rat, mouse, cow, horse, pig, sheep, goat, dog, cat, etc. In an embodiment, the subject is human.

Definitions used include ligand-dependent activation of the androgen receptor (AR) by androgens such as dihydrotestosterone (DHT) or the synthetic androgen (R1881) used for research purposes. Ligand-independent activation of the AR refers to transactivation of the AR in the absence of androgen (ligand) by, for example, stimulation of the cAMP-dependent protein kinase (PKA) pathway with forskolin (FSK).

Some compounds and compositions as described herein may interfere with a mechanism specific to ligand-dependent activation (e.g., accessibility of the ligand binding domain (LBD) to androgen) or to ligand-independent activation of the AR.

Various alternative embodiments and examples of the invention are described herein. These embodiments and examples are illustrative and should not be construed as limiting the scope of the invention.

Compounds

In an aspect, provided herein is a compound of Formula I:

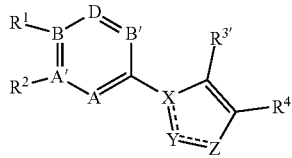

(I)

or a pharmaceutically acceptable salt thereof;
wherein
 ==== is an optional double bond;
A is N or CH;
A' is N or C, wherein when A' is N, $R^2$ is absent;
B is N or C, wherein when B is N, $R^1$ is absent;
B' is N, CH, or $CR^{10}$;
D is N, CH, or $CR^{10}$;
X is N or C;
Y is CH, C—$CH_3$, or N;
Z is O, NH, or $NR^{10}$;
$R^1$ is selected from the group consisting of H, halo, $N(R^5)_2$, $OR^5$, $SR^5$, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, 3-10 membered heterocycloalkyl, $C_{6-10}$ aryl, 5-10 membered heteroaryl, CN, $NO_2$, $N(R^5)C(O)R^5$, $COR^5$, and $SO_2R^5$, wherein alkyl, alkenyl, alkynyl, cycloalkyl, heterocycloalkyl, aryl, and heteroaryl are optionally substituted one, two, or three times with $R^6$;
$R^2$ is selected from the group consisting of H, halo, $N(R^5)_2$, $OR^5$, $SR^5$, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, 3-10 membered heterocycloalkyl, $C_{6-10}$ aryl, 5-10 membered heteroaryl, CN, $NO_2$, and $SO_2R^5$, wherein alkyl, alkenyl, alkynyl, cycloalkyl, heterocycloalkyl, aryl, and heteroaryl are optionally substituted one, two, or three times with $R^6$;

alternatively, $R^1$ and $R^2$, together with the atoms to which they are attached, are optionally combined to form a 4-10 membered ring that is fused to the adjacent ring, wherein the 4-10 membered ring optionally contains one, two, or three heteroatoms, and the 4-10 membered ring is optionally substituted one, two, three, or four times with $R^7$;
$R^{3'}$ and $R^4$ are each independently selected from the group consisting of H, $C_{1-3}$ alkyl, $C_{6-10}$ aryl, and 5-10 membered heteroaryl;
wherein when $R^{3'}$ is H, $R^4$ is not H, and when $R^4$ is H, $R^{3'}$ is not H;
alternatively, $R^{3'}$ and $R^4$, together with the atoms to which they are attached, are optionally combined to form a 5-10 membered ring that is fused to the adjacent ring, wherein the 5-10 membered ring optionally contains one, two, or three heteroatoms, and the 5-10 membered ring is optionally substituted one, two, or three times with $R^3$;
each $R^3$ is independently, at each occurrence, selected from the group consisting of CN, OH, $SO_2C_{1-3}$ alkyl, $NH_2$, $NH(C_{1-3}$ alkyl), $N(C_{1-3}$ alkyl$)_2$, $NO_2$, $COR^9$, $CO_2R^9$, $OSO_3H$, halo, $C_{1-3}$ alkyl, $C_{1-3}$ alkoxy, $C_{1-3}$ haloalkyl, $C_{1-3}$ alkyl-$NH_2$, $C_{1-3}$ alkyl-NH—$C_{1-3}$ alkyl, $C_{3-10}$ cycloalkyl, 3-10 membered heterocycloalkyl, $C_{6-10}$ aryl, 5-10 membered heteroaryl, and $C_{1-3}$ haloalkyl; each $R^5$ is independently, at each occurrence, selected from the group consisting of H, $C_{1-6}$ alkyl, $C_{1-3}$ haloalkyl, $C_{1-3}$ alkyl-O—$C_{1-3}$ alkyl, $C_{1-6}$ alkyl-OH, $C_{1-3}$ alkyl-$NH_2$, $C_{1-3}$ alkyl-$N(C_{1-3}$ alkyl$)_2$, $C_{3-10}$ cycloalkyl, 3-10 membered heterocycloalkyl, $NH_2$, $NH(C_{1-3}$ alkyl), $N(C_{1-3}$ alkyl$)_2$, $C_{6-10}$ aryl, and 5-10 membered heteroaryl, wherein alkyl, cycloalkyl, heterocycloalkyl, aryl, and heteroaryl are optionally substituted one, two, or three times with $R^6$;
each $R^5$ is independently, at each occurrence, selected from the group consisting of H, $C_{1-6}$ alkyl, $C_{1-3}$ haloalkyl, $C_{1-3}$ alkyl-O—$C_{1-3}$ alkyl, $C_{1-6}$ alkyl-OH, $C_{1-3}$ alkyl-$NH_2$, $C_{1-3}$ alkyl-$N(C_{1-3}$ alkyl$)_2$, $C_{3-10}$ cycloalkyl, 3-10 membered heterocycloalkyl, $NH_2$, $NH(C_{1-3}$ alkyl), $N(C_{1-3}$ alkyl$)_2$, $C_{6-10}$ aryl, and 5-10 membered heteroaryl, wherein alkyl, cycloalkyl, heterocycloalkyl, aryl, and heteroaryl are optionally substituted one, two, or three times with $R^6$;
each $R^6$ is independently, at each occurrence, selected from the group consisting of halo, OH, $NH_2$, $NH(C_{1-3}$ alkyl), $N(C_{1-3}$ alkyl$)_2$, $NO_2$, $COR^8$, $CO_2R^6$, $OSO_3H$, $C_{1-3}$ alkyl, $C_{1-3}$ alkoxy, $C_{1-3}$ haloalkyl, $C_{1-3}$ alkyl-O—$C_{1-3}$ alkyl, $C_{1-3}$ alkyl-$NH_2$, $C_{1-3}$ alkyl-$N(C_{1-3}$ alkyl$)_2$, and 3-10 membered heterocycloalkyl;
each $R^7$ is independently, at each occurrence, selected from the group consisting of $C_{1-3}$ alkyl, $C_{1-3}$ alkyl-OH, $C_{1-3}$ alkyl-phenyl-$R^9$, $C_{1-3}$ alkoxy, $C_{1-3}$ alkyl-O—$C_{1-3}$ alkyl, $C_{1-3}$ haloalkyl, $C_{3-10}$ cycloalkyl, 3-10 membered heterocycloalkyl, $C_{6-10}$ aryl, and 5-10 membered heteroaryl, =O, halo, OH, $NH_2$, $NHR^9$, $NHC(O)R^9$, $NO_2$, $COR^9$, and $CO_2R^9$;
each $R^8$ is independently, at each occurrence, selected from the group consisting of H, $NH_2$, $NH(C_{1-3}$ alkyl), $N(C_{1-3}$ alkyl$)_2$, $C_{1-3}$ alkyl, $C_{1-3}$ alkoxy, $C_{1-3}$ alkyl-OH, $C_{1-3}$ alkyl-O—$C_{1-3}$ alkyl, $C_{3-10}$ cycloalkyl, $C_{6-10}$ aryl, $C(O)C_{1-3}$ alkyl, and 5-10 membered heteroaryl;
each $R^9$ is independently, at each occurrence, selected from the group consisting of H, $NH_2$, $NH(C_{1-3}$ alkyl), $N(C_{1-3}$ alkyl$)_2$, $C_{1-3}$ alkyl, $C_{1-3}$ alkoxy, $C_{1-3}$ alkyl-OH, $C_{1-3}$ alkyl-O—$C_{1-3}$ alkyl, $C_{3-10}$ cycloalkyl, $C_{6-10}$ aryl, $C(O)C_{1-3}$ alkyl, and 5-10 membered heteroaryl; and
$R^{10}$ is selected from the group consisting of $C_{1-3}$ alkyl, $C_{1-6}$ alkyl-OH, $C_{1-3}$ haloalkyl, halo, $C_{3-10}$ cycloalkyl, 3-10 membered heterocycloalkyl, 5-10 membered heteroaryl, OH, $NH_2$, $NO_2$, $COR^{11}$, and $CO_2R^{11}$, wherein heterocycloalkyl is optionally substituted with $C_{1-3}$ alkyl;

alternatively, when B is $CR^{10}$, and D is $CR^{10}$, two $R^{10}$, together with the atoms to which they are attached, are optionally combined to form a 4-10 membered ring that is fused to the adjacent ring, wherein the 4-10 membered ring optionally contains one, two, or three heteroatoms; and $R^{11}$ is selected from the group consisting of H, $C_{1-3}$ alkyl, $NH_2$, $NH(C_{1-3}$ alkyl), and $N(C_{1-3}$ alkyl)$_2$.

In an embodiment, the compound of Formula I is a compound of Formula II

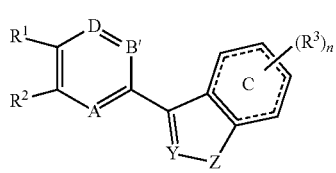

(II)

or a pharmaceutically acceptable salt thereof;
wherein
 ---- is an optional double bond;
A is N or CH;
B' is N, CH, or $CR^{10}$;
D is N, CH, or $CR^{10}$;
Y is CH or N;
Z is NH or $NR^{10}$;
Ring C is a 6-membered ring that optionally contains one, two, or three heteroatoms;

$R^1$ is selected from the group consisting of H, halo, $N(R^5)_2$, $OR^5$, $SR^5$, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, 3-10 membered heterocycloalkyl, $C_{6-10}$ aryl, 5-10 membered heteroaryl, CN, $NO_2$, $N(R^5)C(O)R^5$, $COR^5$, and $SO_2R^5$, wherein alkyl, alkenyl, alkynyl, cycloalkyl, heterocycloalkyl, aryl, and heteroaryl are optionally substituted one, two, or three times with $R^6$;

$R^2$ is selected from the group consisting of H, halo, $N(R^5)_2$, $OR^5$, $SR^5$, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, 3-10 membered heterocycloalkyl, $C_{6-10}$ aryl, 5-10 membered heteroaryl, CN, $NO_2$, and $SO_2R^5$, wherein alkyl, alkenyl, alkynyl, cycloalkyl, heterocycloalkyl, aryl, and heteroaryl are optionally substituted one, two, or three times with $R^6$;

alternatively, $R^1$ and $R^2$, together with the atoms to which they are attached, are optionally combined to form a 4-10 membered ring that is fused to the adjacent ring, wherein the 4-10 membered ring optionally contains one, two, or three heteroatoms, and the 4-10 membered ring is optionally substituted one, two, three, or four times with $R^7$;

each $R^3$ is independently, at each occurrence, selected from the group consisting of CN, OH, $SO_2C_{1-3}$ alkyl, $NH_2$, $NH(C_{1-3}$ alkyl), $N(C_{1-3}$ alkyl)$_2$, $NO_2$, $COR^9$, $CO_2R^9$, $OSO_3H$, halo, $C_{1-3}$ alkyl, $C_{1-3}$ alkoxy, $C_{1-3}$ haloalkyl, $C_{1-3}$ alkyl-$NH_2$, $C_{1-3}$ alkyl-NH—$C_{1-3}$ alkyl, $C_{3-10}$ cycloalkyl, 3-10 membered heterocycloalkyl, $C_{6-10}$ aryl, 5-10 membered heteroaryl, and $C_{1-3}$ haloalkyl; each $R^5$ is independently, at each occurrence, selected from the group consisting of H, $C_{1-6}$ alkyl, $C_{1-3}$ haloalkyl, $C_{1-3}$ alkyl-O—$C_{1-3}$ alkyl, $C_{1-6}$ alkyl-OH, $C_{1-3}$ alkyl-$NH_2$, $C_{1-3}$ alkyl-$N(C_{1-3}$ alkyl)$_2$, $C_{3-10}$ cycloalkyl, 3-10 membered heterocycloalkyl, $NH_2$, $NH(C_{1-3}$ alkyl), $N(C_{1-3}$ alkyl)$_2$, $C_{6-10}$ aryl, and 5-10 membered heteroaryl, wherein alkyl, cycloalkyl, heterocycloalkyl, aryl, and heteroaryl are optionally substituted one, two, or three times with $R^6$;

each $R^6$ is independently, at each occurrence, selected from the group consisting of halo, OH, $NH_2$, $NH(C_{1-3}$ alkyl), $N(C_{1-3}$ alkyl)$_2$, $COR^8$, $CO_2R^6$, $C_{1-3}$ alkyl, $C_{1-3}$ alkoxy, $C_{1-3}$ haloalkyl, $C_{1-3}$ alkyl-O—$C_{1-3}$ alkyl, $C_{1-3}$ alkyl-$NH_2$, $C_{1-3}$ alkyl-$N(C_{1-3}$ alkyl)$_2$, and 3-10 membered heterocycloalkyl;

each $R^7$ is independently, at each occurrence, selected from the group consisting of $C_{1-3}$ alkyl, $C_{1-3}$ alkyl-OH, $C_{1-3}$ alkoxy, $C_{1-3}$ alkyl-O—$C_{1-3}$ alkyl, $C_{1-3}$ haloalkyl, $C_{3-10}$ cycloalkyl, 3-10 membered heterocycloalkyl, $C_{6-10}$ aryl, and 5-10 membered heteroaryl, =O, halo, OH, $NH_2$, $NHC(O)R^9$, $NO_2$, $COR^9$, and $CO_2R^9$;

each $R^8$ is independently, at each occurrence, selected from the group consisting of H, $NH_2$, $NH(C_{1-3}$ alkyl), $N(C_{1-3}$ alkyl)$_2$, $C_{1-3}$ alkyl, $C_{1-3}$ alkoxy, $C_{1-3}$ alkyl-OH, $C_{1-3}$ alkyl-O—$C_{1-3}$ alkyl, $C_{3-10}$ cycloalkyl, $C_{6-10}$ aryl, $C(O)C_{1-3}$ alkyl, and 5-10 membered heteroaryl;

each $R^9$ is independently, at each occurrence, selected from the group consisting of H, $NH_2$, $NH(C_{1-3}$ alkyl), $N(C_{1-3}$ alkyl)$_2$, $C_{1-3}$ alkyl, $C_{1-3}$ alkyl-OH, $C_{1-3}$ alkyl-O—$C_{1-3}$ alkyl, $C_{3-10}$ cycloalkyl, $C_{6-10}$ aryl, $C(O)C_{1-3}$ alkyl, and 5-10 membered heteroaryl;

$R^{10}$ is selected from the group consisting of $C_{1-3}$ alkyl, $C_{1-6}$ alkyl-OH, $C_{1-3}$ haloalkyl, halo, $C_{3-10}$ cycloalkyl, 3-10 membered heterocycloalkyl, 5-10 membered heteroaryl, OH, $NH_2$, $NO_2$, $COR^{11}$, and $CO_2R^{11}$, wherein heterocycloalkyl is optionally substituted with $C_{1-3}$ alkyl;

$R^{11}$ is selected from the group consisting of H, $C_{1-3}$ alkyl, $NH_2$, $NH(C_{1-3}$ alkyl), and $N(C_{1-3}$ alkyl)$_2$; and n is 0, 1, 2, or 3.

In another aspect of Formula II, Z is O, S, NH, or $NR^{10}$; wherein the remaining variables are defined above.

In another embodiment, the compound of Formula I is a compound of Formula III:

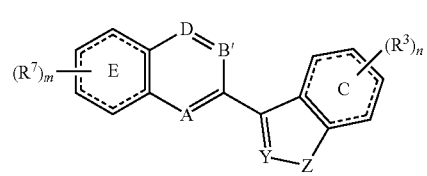

(III)

or a pharmaceutically acceptable salt thereof;
wherein
 ---- is an optional double bond;
A is N or CH;
B' is N, CH, or $CR^{10}$;
D is N, CH, or $CR^{10}$;
Y is CH or N;
Z is NH or $NR^{10}$;
Ring C is a 6-membered ring that optionally contains one, two, or three heteroatoms;
Ring E is a 6-membered ring that optionally contains one, two, or three heteroatoms;

each $R^3$ is independently, at each occurrence, selected from the group consisting of CN, OH, $SO_2C_{1-3}$ alkyl, $NH_2$, $NH(C_{1-3}$ alkyl), $N(C_{1-3}$ alkyl)$_2$, $NO_2$, $COR^9$, $CO_2R^9$, $OSO_3H$, halo, $C_{1-3}$ alkyl, $C_{1-3}$ alkoxy, $C_{1-3}$ haloalkyl, $C_{1-3}$ alkyl-$NH_2$, $C_{1-3}$ alkyl-NH—$C_{1-3}$ alkyl, $C_{3-10}$ cycloalkyl, 3-10 membered heterocycloalkyl, $C_{6-10}$ aryl, 5-10 membered heteroaryl, and $C_{1-3}$ haloalkyl;

each $R^7$ is independently, at each occurrence, selected from the group consisting of $C_{1-3}$ alkyl, $C_{1-3}$ alkyl-OH, $C_{1-3}$ alkoxy, $C_{1-3}$ alkyl-O—$C_{1-3}$ alkyl, $C_{1-3}$ haloalkyl, $C_{3-10}$ cycloalkyl, 3-10 membered heterocycloalkyl, $C_{6-10}$ aryl, and 5-10 membered heteroaryl, =O, halo, OH, $NH_2$, NHC(O)$R^9$, $NO_2$, $COR^9$, and $CO_2R^9$;

each $R^9$ is independently, at each occurrence, selected from the group consisting of H, $NH_2$, $NH(C_{1-3}$ alkyl), $N(C_{1-3}$ alkyl$)_2$, $C_{1-3}$ alkyl, $C_{1-3}$ alkyl-OH, $C_{1-3}$ alkyl-O—$C_{1-3}$ alkyl, $C_{3-10}$ cycloalkyl, $C_{6-10}$ aryl, $C(O)C_{1-3}$ alkyl, and 5-10 membered heteroaryl;

$R^{10}$ is selected from the group consisting of $C_{1-3}$ alkyl, $C_{1-6}$ alkyl-OH, $C_{1-3}$ haloalkyl, halo, $C_{3-10}$ cycloalkyl, 3-10 membered heterocycloalkyl, 5-10 membered heteroaryl, OH, $NH_2$, $NO_2$, $COR^{11}$, and $CO_2R^{11}$, wherein heterocycloalkyl is optionally substituted with $C_{1-3}$ alkyl;

$R^{11}$ is selected from the group consisting of H, $C_{1-3}$ alkyl, $NH_2$, $NH(C_{1-3}$ alkyl), and $N(C_{1-3}$ alkyl$)_2$;

m is 0, 1, 2, 3, or 4; and n is 0, 1, 2, or 3.

In yet another embodiment, the compound of Formula I is a compound of Formula IV:

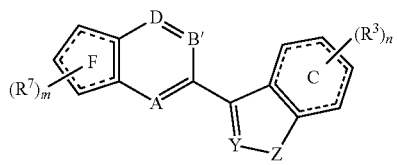

or a pharmaceutically acceptable salt thereof;
wherein
==== is an optional double bond;
A is N or CH;
B' is N, CH, or $CR^{10}$;
D is N, CH, or $CR^{10}$;
Y is CH or N;
Z is NH or $NR^{10}$;
Ring C is a 6-membered ring that optionally contains one, two, or three heteroatoms;
Ring F is a a 5-membered ring that optionally contains one or two heteroatoms;
each $R^3$ is independently, at each occurrence, selected from the group consisting of CN, OH, $SO_2C_{1-3}$ alkyl, $NH_2$, $NH(C_{1-3}$ alkyl), $N(C_{1-3}$ alkyl$)_2$, $NO_2$, $COR^9$, $CO_2R^9$, $OSO_3H$, halo, $C_{1-3}$ alkyl, $C_{1-3}$ alkoxy, $C_{1-3}$ haloalkyl, $C_{1-3}$ alkyl-$NH_2$, $C_{1-3}$ alkyl-NH—$C_{1-3}$ alkyl, $C_{3-10}$ cycloalkyl, 3-10 membered heterocycloalkyl, $C_{6-10}$ aryl, 5-10 membered heteroaryl, and $C_{1-3}$ haloalkyl;

each $R^7$ is independently, at each occurrence, selected from the group consisting of $C_{1-3}$ alkyl, $C_{1-3}$ alkyl-OH, $C_{1-3}$ alkoxy, $C_{1-3}$ alkyl-O—$C_{1-3}$ alkyl, $C_{1-3}$ haloalkyl, $C_{3-10}$ cycloalkyl, 3-10 membered heterocycloalkyl, $C_{6-10}$ aryl, and 5-10 membered heteroaryl, =O, halo, OH, $NH_2$, NHC(O)$R^9$, $NO_2$, $COR^9$, and $CO_2R^9$;

each $R^9$ is independently, at each occurrence, selected from the group consisting of H, $NH_2$, $NH(C_{1-3}$ alkyl), $N(C_{1-3}$ alkyl$)_2$, $C_{1-3}$ alkyl, $C_{1-3}$ alkyl-OH, $C_{1-3}$ alkyl-O—$C_{1-3}$ alkyl, $C_{3-10}$ cycloalkyl, $C_{6-10}$ aryl, $C(O)C_{1-3}$ alkyl, and 5-10 membered heteroaryl;

$R^{10}$ is selected from the group consisting of $C_{1-3}$ alkyl, $C_{1-6}$ alkyl-OH, $C_{1-3}$ haloalkyl, halo, $C_{3-10}$ cycloalkyl, 3-10 membered heterocycloalkyl, 5-10 membered heteroaryl, OH, $NH_2$, $NO_2$, $COR^{11}$, and $CO_2R^{11}$, wherein heterocycloalkyl is optionally substituted with $C_{1-3}$ alkyl;

$R^{11}$ is selected from the group consisting of H, $C_{1-3}$ alkyl, $NH_2$, $NH(C_{1-3}$ alkyl), and $N(C_{1-3}$ alkyl$)_2$;

m is 0, 1, 2, or 3; and n is 0, 1, 2, or 3.

In still another embodiment, the compound of Formula I is a compound of Formula V:

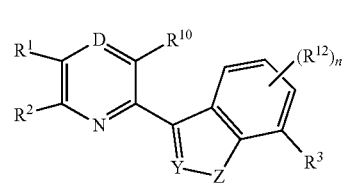

or a pharmaceutically acceptable salt thereof;
wherein
D is CH or N;
Y is CH or N;
Z is O or NH;
$R^1$ is selected from the group consisting of halo, $N(R^5)_2$, $OR_5$, $SR^5$, $C_{1-6}$ alkyl, $C_{2-6}$ alkenyl, $C_{2-6}$ alkynyl, $C_{3-10}$ cycloalkyl, 3-10 membered heterocycloalkyl, $C_{6-10}$ aryl, 5-10 membered heteroaryl, CN, $NO_2$, and $SO_2R^5$, wherein alkyl, alkenyl, alkynyl, cycloalkyl, heterocycloalkyl, aryl, and heteroaryl are optionally substituted one, two, or three times with $R^6$;

$R^2$ is selected from the group consisting of H, halo, $N(R^6)_2$, $OR^5$, $SR^5$, $C_{1-6}$ alkyl, $C_{2-6}$ alkenyl, $C_{2-6}$ alkynyl, $C_{1-6}$ haloalkyl, $C_{3-10}$ cycloalkyl, 3-10 membered heterocycloalkyl, $C_{6-10}$ aryl, 5-10 membered heteroaryl, CN, $NO_2$, and $SO_2R^6$, wherein alkyl, alkenyl, alkynyl, cycloalkyl, heterocycloalkyl, aryl, and heteroaryl are optionally substituted one, two, or three times with $R^6$;

alternatively, $R^1$ and $R^2$, together with the atoms to which they are attached, are optionally combined to form a 4-10 membered ring that is fused to the adjacent ring, wherein the 4-10 membered ring optionally contains one, two, or three heteroatoms, and the 4-10 membered ring is optionally substituted one, two, three, or four times with $R^7$;

$R^3$ is selected from the group consisting of CN, $NH_2$, Cl, Br, $C_{2-3}$ alkenyl, $C_{2-3}$ alkynyl, and $C_{1-3}$ haloalkyl;

each $R^5$ is independently, at each occurrence, selected from the group consisting of H, $C_{1-6}$ alkyl, $C_{1-6}$ alkyl-O—$C_{1-3}$ alkyl, $C_{1-6}$ alkyl-OH, $C_{3-10}$ cycloalkyl, 3-10 membered heterocycloalkyl, $C_{1-3}$ haloalkyl, $C_{6-10}$ aryl, and 5-10 membered heteroaryl, wherein alkyl, cycloalkyl, heterocycloalkyl, aryl, and heteroaryl are optionally substituted one, two, or three times with $R^6$;

each $R^6$ is independently, at each occurrence, selected from the group consisting of halo, OH, $NH_2$, $NO_2$, $COR^8$, $CO_2R^8$, $OSO_3H$, $C_{1-3}$ alkyl, $C_{1-3}$ alkoxy, $C_{1-3}$ haloalkyl, $NH(C_{1-3}$ alkyl), $N(C_{1-3}$ alkyl$)_2$, $C_{1-6}$ alkyl-O—$C_{1-3}$ alkyl, and 3-10 membered heterocycloalkyl;

each $R^7$ is independently, at each occurrence, selected from the group consisting of $C_{1-3}$ alkyl, $C_{1-6}$ alkyl-OH, $C_{1-3}$ haloalkyl, =O, halo, OH, $NH_2$, $NO_2$, and $COR^9$; each $R^9$ is independently, at each occurrence, selected from the group consisting of H, $C_{1-6}$ alkyl, $C_{3-10}$ cycloalkyl, $C_{6-10}$ aryl, $C(O)C_{1-3}$ alkyl, and 5-10 membered heteroaryl;

each $R^8$ is independently, at each occurrence, selected from the group consisting of H, $NH_2$, $NH(C_{1-3}$ alkyl), $N(C_{1-3}$ alkyl$)_2$, $C_{1-3}$ alkyl, $C_{1-3}$ alkoxy, $C_{1-3}$ alkyl-OH, $C_{1-3}$ alkyl-O—$C_{1-3}$ alkyl, $C_{3-10}$ cycloalkyl, $C_{6-10}$ aryl, $C(O)C_{1-3}$ alkyl, and 5-10 membered heteroaryl;

$R^{10}$ is selected from the group consisting of H, $C_{1-3}$ alkyl, $C_{1-6}$ alkyl-OH, $C_{1-3}$ haloalkyl, halo, OH, $NH_2$, $NO_2$, $COR^{11}$, and $CO_2R^{11}$;

R¹¹ is selected from the group consisting of H, $C_{1-3}$ alkyl, $NH_2$, $NH(C_{1-3}$ alkyl), and $N(C_{1-3}$ alkyl$)_2$;

each $R^{12}$ is independently, at each occurrence, selected from the group consisting of halo, OH, $NH_2$, $NO_2$, $COR^9$, $CO_2R^9$, $OSO_3H$ $C_{1-3}$ alkyl, $C_{1-3}$ alkoxy, $C_{1-3}$ haloalkyl, $NH(C_{1-3}$ alkyl), $N(C_{1-3}$ alkyl$)_2$, $C_{3-10}$ cycloalkyl, 3-10 membered heterocycloalkyl, $C_{6-10}$ aryl, and 5-10 membered heteroaryl; and n is 0, 1, or 2.

In an embodiment of Formula V,

D is CH or N;

Y is CH or N;

Z is O or NH;

$R^1$ is selected from the group consisting of halo, $N(R^5)_2$, $OR^5$, $C_{3-10}$ cycloalkyl, 3-10 membered heterocycloalkyl, wherein cycloalkyl and heterocycloalkyl are optionally substituted one, two, or three times with $R^6$;

$R^2$ is selected from the group consisting of H, $OR^5$, $C_{1-6}$ alkyl, $C_{1-6}$ haloalkyl, $C_{2-6}$ alkenyl, $C_{2-6}$ alkynyl, and halo, wherein alkyl, alkenyl, and alkynyl are optionally substituted one, two, or three times with $R^6$;

alternatively, $R^1$ and $R^2$, together with the atoms to which they are attached, are optionally combined to form a 4-10 membered ring that is fused to the adjacent ring, wherein the 4-10 membered ring optionally contains one, two, or three heteroatoms, and the 4-10 membered ring is optionally substituted one, two, or three times with $R^7$, provided that $R^1$ and $R^2$, together with the atoms to which they are attached are not phenyl or substituted phenyl;

$R^3$ is selected from the group consisting of CN, Cl, and $CF_3$;

each $R^5$ is independently, at each occurrence, selected from the group consisting of H, $C_{1-6}$ alkyl, 3-6 membered heterocycloalkyl, $C_{1-3}$ alkyl-O—$C_{1-3}$ alkyl, $C_{1-3}$ haloalkyl, and $C_{1-3}$ alkyl-OH, wherein alkyl and heterocycloalkyl are optionally substituted one, two, or three times with $R^6$;

each $R^6$ is independently, at each occurrence, selected from the group consisting of halo, OH, $NH_2$, $COR^8$, $C_{1-3}$ alkyl, $C_{1-3}$ alkoxy, $C_{1-3}$ haloalkyl, $N(R^8)_2$, $C_{1-6}$ alkyl-O—$C_{1-3}$ alkyl, and 3-10 membered heterocycloalkyl;

each $R^7$ is independently, at each occurrence, selected from the group consisting of $C_{1-3}$ alkyl, $C_{1-3}$ haloalkyl, =O, $C_{1-6}$ alkyl-OH, and halo;

each $R^8$ is independently, at each occurrence, selected from the group consisting of H, $C_{1-6}$ alkyl, $C_{3-10}$ cycloalkyl, $C_{6-10}$ aryl, $C(O)C_{1-3}$ alkyl, and 5-10 membered heteroaryl;

$R^{10}$ is selected from the group consisting of H, $C_{1-3}$ alkyl, $C_{1-3}$ haloalkyl, halo, $COR^8$, and $CO_2R^8$;

each $R^{12}$ is independently, at each occurrence, selected from the group consisting of H, halo, OH, $NH_2$, $NO_2$, $CO_2R^8$, $C_{1-3}$ alkyl, and $C_{1-3}$ alkoxy; and n is 1.

In another embodiment, the compound of Formula V is a compound of Formula Va:

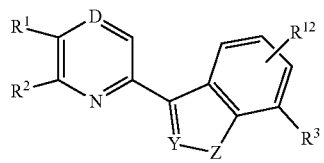

(Va)

or a pharmaceutically acceptable salt thereof.

In yet another embodiment, the compound of Formula V is a compound of Formula Vb:

(Vb)

or a pharmaceutically acceptable salt thereof.

In an embodiment of Formula V, $R^1$ and $R^2$, together with the atoms to which they are attached, form a ring of formula:

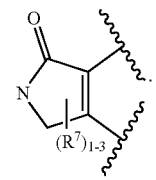

In still another embodiment, the compound of Formula I is a compound of Formula VI:

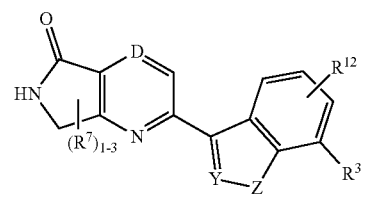

(VI)

or a pharmaceutically acceptable salt thereof.

In another embodiment, the compound of Formula I is a compound of Formula VIa:

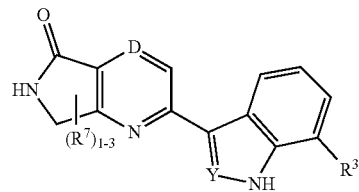

(VIa)

or a pharmaceutically acceptable salt thereof.

In an aspect, provided herein is a compound of Formula X:

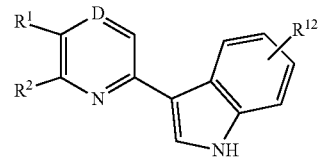

(X)

or a pharmaceutically acceptable salt thereof;

wherein
D is CH or N;
R$^1$ is selected from the group consisting of C$_{1-6}$ alkyl, OC$_{1-6}$ alkyl, and NH (3-7 membered heterocycloalkyl), all of which are optionally independently substituted with OH or C(O)C$_{1-6}$ alkyl;
R$^2$ is selected from the group consisting of H, C$_{1-6}$ alkyl, and OC$_{1-6}$ alkyl;
alternatively, R$^1$ and R$^2$, together with the atoms to which they are attached, are optionally combined to form a 4-7 membered ring that is fused to the adjacent ring, wherein the 4-7 membered ring optionally contains one, two, or three heteroatoms, and the 4-7 membered ring is optionally independently substituted one, two, or three times with a substituent selected from C$_{1-3}$ alkyl, C$_{1-3}$ haloalkyl, C$_{1-6}$ alkyl-OH, =O, and halo, provided that R$^1$ and R$^2$, together with the atoms to which they are attached, are not phenyl or substituted phenyl; and
R$^3$ is selected from the group consisting of CN, halo, and C$_{1-3}$ haloalkyl.

In an embodiment of the formulae provided herein, when R$^1$ and R$^2$, together with the atoms to which they are attached, combine to form a 4-7 membered ring that is fused to the adjacent ring, the 4-7 membered ring is not aromatic.

In another embodiment, of the formulae provided herein, when R$^1$ is methyl, R$^3$ is not chloro. In another embodiment, of the formulae provided herein, R$^1$ is OC$_{1-6}$ alkyl or NH (3-7 membered heterocycloalkyl), both of which are optionally independently substituted with OH or C(O)C$_{1-6}$ alkyl; and R$^3$ is selected from the group consisting of CN, halo, and C$_{1-3}$ haloalkyl.

In an embodiment, the compound of Formula X is a compound of Formula VII:

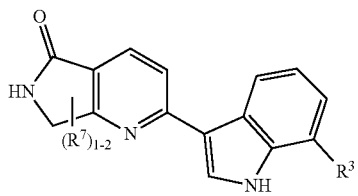

(VII)

or a pharmaceutically acceptable salt thereof;
wherein
R$^3$ is selected from the group consisting of CN, halo, and C$_{1-3}$ haloalkyl; and
each R$^7$ is independently, at each occurrence, selected from the group consisting of C$_{1-3}$ alkyl, C$_{1-3}$ haloalkyl, C$_{1-6}$ alkyl-OH, and halo.

In another embodiment, the compound of Formula X is a compound of Formula VII':

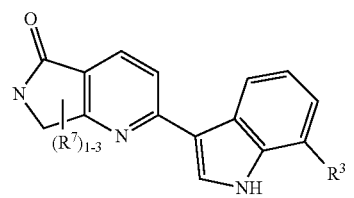

(VII')

or a pharmaceutically acceptable salt thereof;

wherein
R$^3$ is selected from the group consisting of CN, halo, and C$_{1-3}$ haloalkyl; and
each R$^7$ is independently, at each occurrence, selected from the group consisting of C$_{1-3}$ alkyl, C$_{1-3}$ haloalkyl, C$_{1-6}$ alkyl-OH, and halo;
wherein when the nitrogen atom in the lactam ring is not substituted by R$^7$, it is substituted with H.

In yet another embodiment, each R$^7$ is independently C$_{1-3}$ alkyl.

In another embodiment, the compound of Formula X is a compound of Formula VIII:

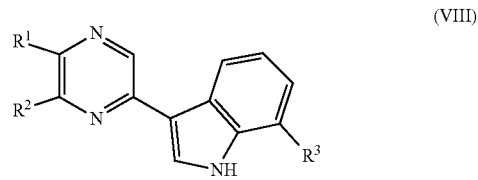

(VIII)

or a pharmaceutically acceptable salt thereof;
wherein
R$^1$ is selected from the group consisting of C$_{1-6}$ alkyl, OC$_{1-6}$ alkyl, and NH (3-7 membered heterocycloalkyl), all of which are optionally independently substituted with OH or C(O)C$_{1-6}$ alkyl;
R$^2$ is selected from the group consisting of H, C$_{1-6}$ alkyl, and OC$_{1-6}$ alkyl; and
R$^3$ is selected from the group consisting of CN, halo, and C$_{1-3}$ haloalkyl.

In an embodiment of the above formulae, Y is CH. In another embodiment, Y is N. In yet another embodiment, Z is NH. In still another embodiment, Z is NR$^{10}$. In an embodiment, B' is N. In another embodiment, B' is CH. In yet another embodiment, B' is CR$^{10}$. In still another embodiment, A is N. In an embodiment, A is CH. In another embodiment, D is N. In yet another embodiment, D is CH. In still another embodiment, D is CR$^{10}$.

In an embodiment of the above formulae, Ring C is phenyl. In another embodiment, Ring C is pyridine. In yet another embodiment, Ring E is phenyl. In still another embodiment, Ring E is pyridine. In an embodiment, Ring E is a 6-membered ring that contains one nitrogen atom. In another embodiment, Ring E is a 6-membered ring that contains one nitrogen atom and one oxygen atom. In yet another embodiment, Ring E is a 6-membered ring that does not contain a heteroatom.

In an embodiment of the above formulae, Ring F is a 5-membered ring that contains one or two heteroatoms. In another embodiment, Ring F is a 5-membered ring that contains one heteroatom. In yet another embodiment, Ring F is a 5-membered ring that contains no heteroatoms.

In an embodiment, of the above formulae R$^1$ is selected from the group consisting of H, N(R$^5$)$_2$, OR$^5$, C$_{1-3}$ alkyl, CF$_3$, halo, C$_{3-6}$ cycloalkyl, 4-6 membered heterocycloalkyl, CN, N(R$^5$)C(O)R$^5$, and COR$_5$, wherein alkyl and heterocycloalkyl are optionally substituted with one R$^6$. In another embodiment, R$^1$ is selected from the group consisting of halo, N(R$^5$)$_2$, OR$^5$, C$_{3-10}$ cycloalkyl, 3-10 membered heterocycloalkyl, wherein cycloalkyl and heterocycloalkyl are optionally substituted one, two, or three times with R$^6$. In yet another embodiment, R$^1$ is selected from the group consisting of N(R$^5$)$_2$, OR$^5$, and 3-10 membered heterocycloalkyl, wherein heterocycloalkyl is optionally substituted one, two, or three times with R$^6$.

In yet another embodiment of the formulae above, $R^3$ is selected from the group consisting of CN, Cl, and $CF_3$.

In another embodiment of the above formulae, each $R^5$ is independently selected from the group consisting of $C_{1-6}$ alkyl, 3-6 membered heterocycloalkyl, $C_{1-3}$ alkyl-O—$C_{1-3}$ alkyl, $C_{1-3}$ haloalkyl, and $C_{1-3}$ alkyl-OH, wherein alkyl and heterocycloalkyl are optionally substituted one, two, or three times with $R^6$.

In still another embodiment of the above formulae, each $R^6$ is independently selected from the group consisting of halo, 3-7 membered heterocycloalkyl, $N(R^8)_2$, $COR^8$, $NH_2$, $C_{1-6}$ alkyl-O—$C_{1-3}$ alkyl, and $C_{1-3}$ alkyl. In another embodiment, $R^8$ is independently selected from the group consisting of $C_{1-6}$ alkyl and $C(O)C_{1-3}$ alkyl.

In another embodiment of the above formulae, $R^2$ is selected from the group consisting of H, halo, $N(R^5)_2$, $OR^5$, $C_{1-3}$ alkyl, $CF_3$, $C_{1-3}$ alkoxy, $C_{3-6}$ cycloalkyl, 4-6 membered heterocycloalkyl, wherein heterocycloalkyl is optionally substituted with one $R^6$.

In yet another embodiment, $R^2$ is selected from the group consisting of H, OW, $C_{1-6}$ alkyl, $C_{1-6}$ haloalkyl, and halo, wherein alkyl is optionally substituted one, two, or three times with $R^6$. In still another embodiment, $R^2$ is $C_{1-3}$ alkyl. In an embodiment, $R^2$ is $C_{1-3}$ haloalkyl. In another embodiment, $R^2$ is halo. In yet another embodiment, $R^2$ is $OR^5$.

In an embodiment of the above formulae, $R^1$ and $R^2$, together with the atoms to which they are attached, are combined to form a 4-10 membered ring that is fused to the adjacent ring, wherein the 4-10 membered ring optionally contains one, two, or three heteroatoms, and the 4-10 membered ring is optionally substituted one, two, or three times with $R^7$, with the proviso that $R^1$ and $R^2$, together with the atoms to which they are attached are not phenyl or substituted phenyl.

In another embodiment, $R^1$ and $R^2$, together with the atoms to which they are attached, are combined to form a 4-7 membered ring that is fused to the adjacent ring, wherein the 4-7 membered ring contains one, two, or three heteroatoms, and the 4-7 membered ring is optionally substituted one, two, or three times with $R^7$, with the proviso that $R^1$ and $R^2$, together with the atoms to which they are attached are not phenyl or substituted phenyl.

In yet another embodiment, $R^1$ and $R^2$, together with the atoms to which they are attached, are combined to form a 4-7 membered ring that is fused to the adjacent ring, wherein the 4-7 membered ring optionally contains one, two, or three heteroatoms, and the 4-7 membered ring is optionally independently substituted one, two, or three times with a substituent selected from $C_{1-3}$ alkyl, $C_{1-3}$ haloalkyl, $C_{1-6}$ alkyl-OH, =O, and halo, provided that $R^1$ and $R^2$, together with the atoms to which they are attached, are not phenyl or substituted phenyl.

In still another embodiment, $R^1$ and $R^2$, together with the atoms to which they are attached, are combined to form a 4-7 membered ring that is fused to the adjacent ring, wherein the 4-7 membered ring optionally contains one, two, or three heteroatoms, and the 4-7 membered ring is optionally independently substituted one, two, or three times with $C_{1-3}$ alkyl, provided that $R^1$ and $R^2$, together with the atoms to which they are attached, are not phenyl or substituted phenyl.

In yet another embodiment, $R^1$ and $R^2$, together with the atoms to which they are attached, are not phenyl or substituted phenyl. In another embodiment, $R^1$ is not $NH_2$. In yet another embodiment, when $R^3$ is chloro, then $R^1$ is not —$CH_2NH_2$.

In an embodiment, $R^1$ is $OC_{1-6}$ alkyl or NH (3-7 membered heterocycloalkyl), wherein alkyl and heterocycloalkyl are optionally substituted with OH or $C(O)C_{1-6}$ alkyl. In another embodiment, $R^1$ is $OC_{1-6}$ alkyl substituted with OH. In yet another embodiment, $R^1$ is NH (4-6 membered heterocycloalkyl) substituted with $C(O)C_{1-6}$ alkyl.

In still another embodiment, $R^1$ is selected from the group consisting of:

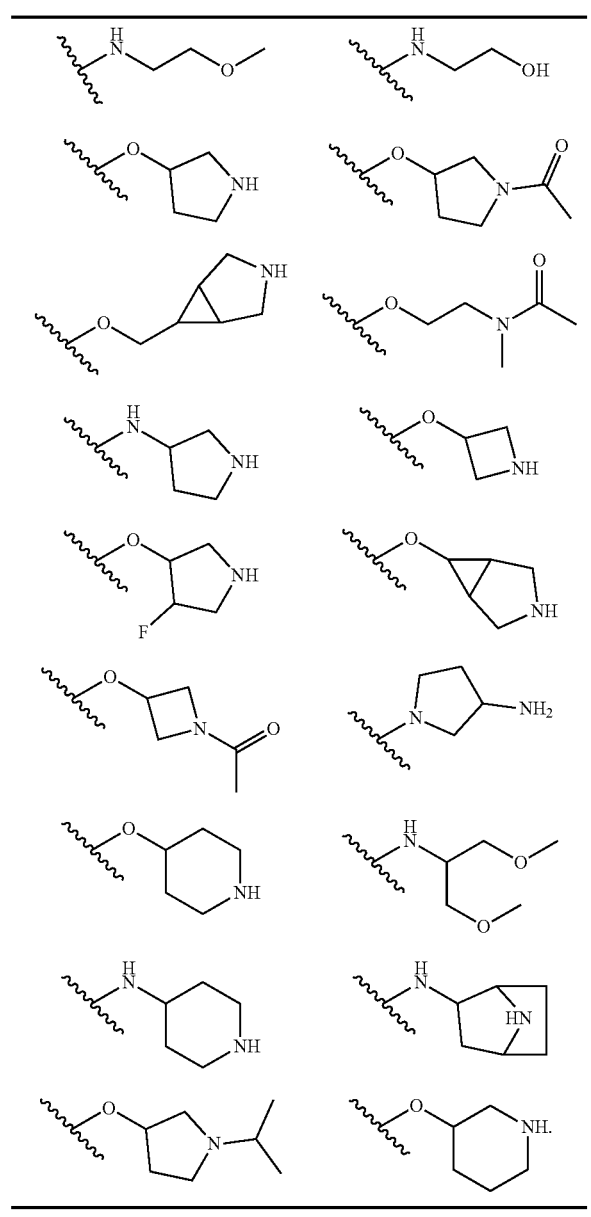

In another embodiment, $R^1$ is

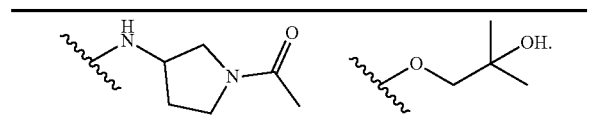

In an embodiment, $R^2$ is $C_{1-6}$ alkyl or $OC_{1-6}$ alkyl. In another embodiment, $R^3$ is CN or halo.

In yet another embodiment of the above formulae, $R^{3'}$ is H or $C_{1-3}$ alkyl.

In still another embodiment of the above formulae, $R^4$ is selected from the group consisting of pyridine, phenyl, and $C_{1-3}$ alkyl.

In an embodiment of the above formulae, each $R^3$ is independently, at each occurrence, selected from the group consisting of H, $NH_2$, $NH(C_{1-3}$ alkyl), $N(C_{1-3}$ alkyl$)_2$, $C_{1-3}$ alkyl, $C_{1-3}$ alkyl-OH, $C_{1-3}$ alkyl-O—$C_{1-3}$ alkyl, $C_{3-7}$ cycloalkyl, $C_{6-10}$ aryl, and 5-10 membered heteroaryl. In another embodiment, $R^3$ is absent. In yet another embodiment, $R^3$ is CN, Cl or $CF_3$.

In another embodiment, $R^7$ is independently, at each occurrence, selected from the group consisting of $C_{1-3}$ alkyl, $C_{1-3}$ haloalkyl, and $C_{1-6}$ alkyl-OH.

In an embodiment of the above formulae, each $R^8$ is independently, at each occurrence, selected from the group consisting of H, $NH_2$, $NH(C_{1-3}$ alkyl), $N(C_{1-3}$ alkyl$)_2$, $C_{1-3}$ alkyl, $C_{1-3}$ alkyl-OH, $C_{1-3}$ alkyl-O—$C_{1-3}$ alkyl, $C_{3-7}$ cycloalkyl, $C_{6-10}$ aryl, and 5-10 membered heteroaryl.

In another embodiment of the above formulae, $R^{10}$ is H or $C_{1-3}$ alkyl.

In an embodiment of the above formulae,
A is N;
A' is C;
B is C;
B' is CH;
C is CH;
D is N or CH;
X is C;
Y is CH or N;
Z is NH;
$R^1$ is selected from the group consisting of halo, $N(R^5)_2$, $OR^5$, $C_{1-6}$ alkyl, $C_{3-10}$ cycloalkyl, 3-10 membered heterocycloalkyl, $C_{6-10}$ aryl, 5-10 membered heteroaryl, and CN, wherein alkyl, cycloalkyl, heterocycloalkyl, aryl, and heteroaryl are optionally substituted one, two, or three times with $C_{1-3}$ alkyl;
$R^2$ is selected from the group consisting of H, halo, $N(R^5)_2$, $OR^5$, $C_{1-6}$ alkyl, $C_{1-6}$ haloalkyl, $C_{1-6}$ alkoxy, $C_{3-10}$ cycloalkyl, and 3-10 membered heterocycloalkyl, wherein alkyl, cycloalkyl, and heterocycloalkyl are optionally substituted one, two, or three times with $C_{1-3}$ alkyl;
alternatively, $R^1$ and $R^2$, together with the atoms to which they are attached, are optionally combined to form a 5-6 membered ring that is fused to the adjacent ring, wherein the 5-6 membered ring optionally contains one, two, or three heteroatoms, and the 5-6 membered ring is optionally substituted one, two, three, or four times with $C_{1-3}$ alkyl, $C_{1-3}$ alkyl-OH, $C_{1-3}$ alkoxy, $C_{1-3}$ alkyl-O—$C_{1-3}$ alkyl, $C_{1-3}$ haloalkyl, =O, halo, or CO($C_{1-3}$ alkyl);
$R^3$ and $R^4$ are each independently selected from the group consisting of H, $C_{1-3}$ alkyl, $C_{6-10}$ aryl, and 5-10 membered heteroaryl;
wherein when $R^3$ is H, $R^4$ is not H, and when $R^4$ is H, $R^3$ is not H;
alternatively, $R^3$ and $R^4$, together with the atoms to which they are attached, are optionally combined to form a 5-6 membered ring that is fused to the adjacent ring, wherein the 5-6 membered ring optionally contains one, two, or three heteroatoms, and the 5-6 membered ring is optionally substituted one, two, or three times with $C_{1-3}$ alkyl, halo, CN, or $C_{1-3}$ haloalkyl; and
each $R^5$ is independently, at each occurrence, selected from the group consisting of H, $C_{1-6}$ alkyl, $C_{1-3}$ haloalkyl, $C_{1-3}$ alkyl-O—$C_{1-3}$ alkyl, $C_{1-6}$ alkyl-OH, $C_{1-3}$ alkyl-$NH_2$, $C_{1-3}$ alkyl-N($C_{1-3}$ alkyl$)_2$, $C_{3-10}$ cycloalkyl, 3-10 membered heterocycloalkyl, $NH_2$, $NH(C_{1-3}$ alkyl), $N(C_{1-3}$ alkyl$)_2$, $C_{6-10}$ aryl, and 5-10 membered heteroaryl, wherein alkyl, cycloalkyl, heterocycloalkyl, aryl, and heteroaryl are optionally substituted one, two, or three times with halo, OH, $NH_2$, $NH(C_{1-3}$ alkyl), $N(C_{1-3}$ alkyl$)_2$, CO($C_{1-6}$ alkyl), $C_{1-3}$ alkyl, $C_{1-3}$ alkoxy, or $C_{1-3}$ haloalkyl.

In an embodiment, provided herein are the compounds of Table 1, or a pharmaceutically acceptable salt thereof.

In an embodiment, the compound of Formula X is selected from the group consisting of

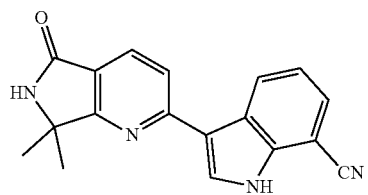 [SMILES: CC1(C)NC(=O)c2ccc(-c3c[nH]c4c(C#N)cccc34)nc21]

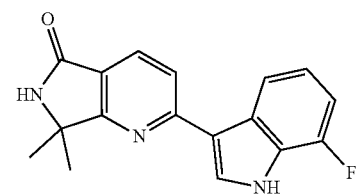 [SMILES: CC1(C)NC(=O)c2ccc(-c3c[nH]c4c(F)cccc34)nc21]

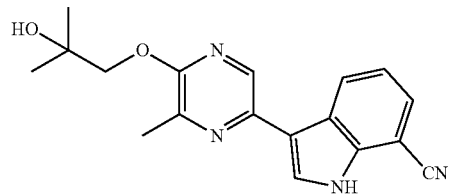 [SMILES: Cc1nc(-c2c[nH]c3c(C#N)cccc23)cnc1OCC(C)(C)O]

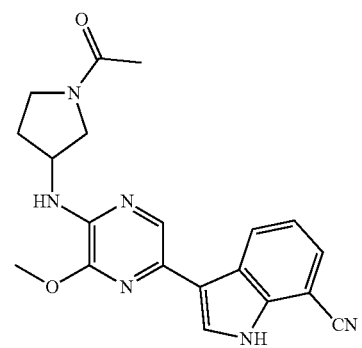 [SMILES: COc1nc(-c2c[nH]c3c(C#N)cccc23)cnc1NC1CCN(C(C)=O)C1]

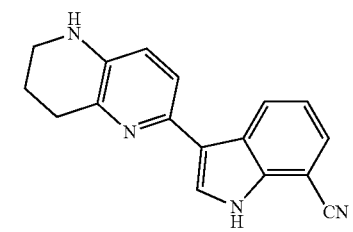 [SMILES: N#Cc1cccc2c(-c3ccc4c(n3)CCCN4)c[nH]c12]

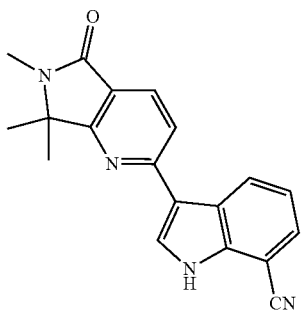 [SMILES: CN1C(=O)c2ccc(-c3c[nH]c4c(C#N)cccc34)nc2C1(C)C]
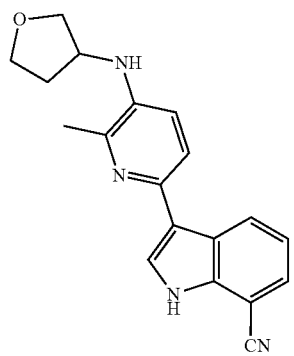 [SMILES: Cc1nc(-c2c[nH]c3c(C#N)cccc23)ccc1NC1CCOC1]
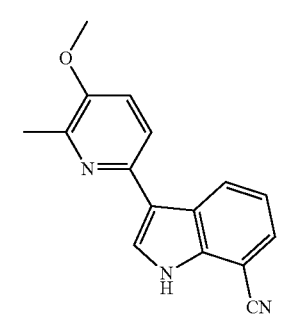 [SMILES: COc1ccc(-c2c[nH]c3c(C#N)cccc23)nc1C]
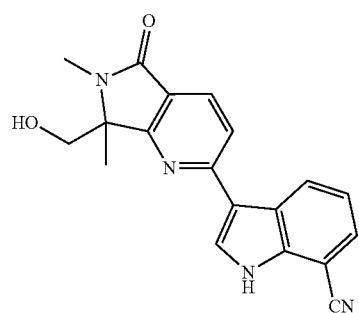 [SMILES: CN1C(=O)c2ccc(-c3c[nH]c4c(C#N)cccc34)nc2C1(C)CO]
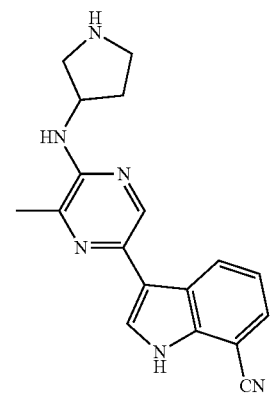 [SMILES: Cc1nc(-c2c[nH]c3c(C#N)cccc23)cnc1NC1CCNC1]
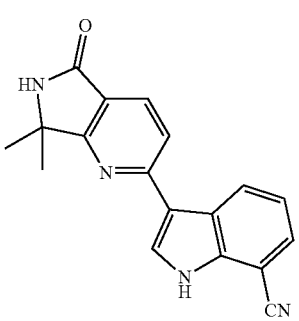 [SMILES: CC1(C)NC(=O)c2ccc(-c3c[nH]c4c(C#N)cccc34)nc21]
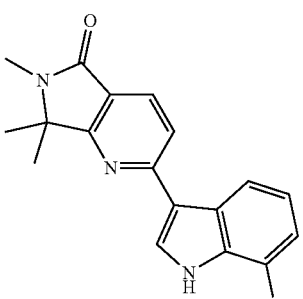
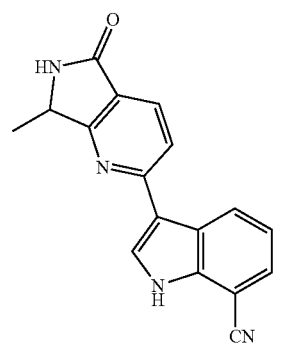 [SMILES: CC1NC(=O)c2ccc(-c3c[nH]c4c(C#N)cccc34)nc21]

-continued
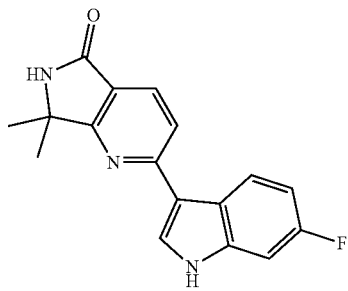 [SMILES: CC1(C)NC(=O)c2ccc(-c3c[nH]c4cc(F)ccc34)nc21]
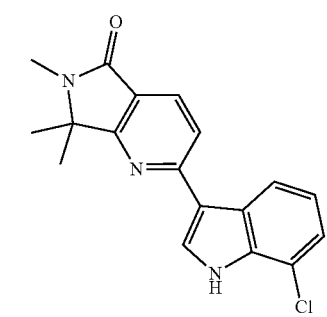 [SMILES: CN1C(=O)c2ccc(-c3c[nH]c4c(Cl)cccc34)nc2C1(C)C]
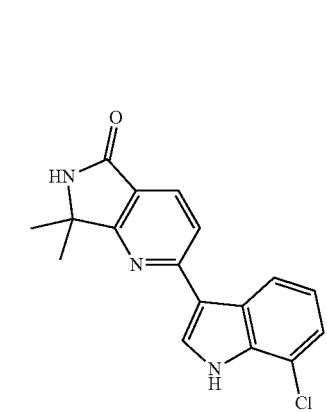 [SMILES: CC1(C)NC(=O)c2ccc(-c3c[nH]c4c(Cl)cccc34)nc21]
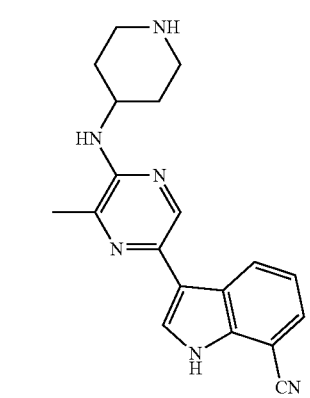 [SMILES: Cc1nc(-c2c[nH]c3c(C#N)cccc23)cnc1NC1CCNCC1]
-continued
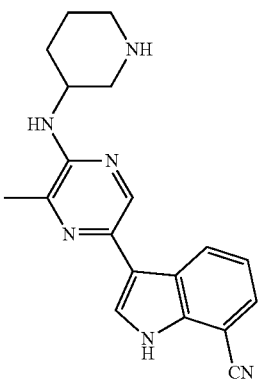 [SMILES: Cc1nc(-c2c[nH]c3c(C#N)cccc23)cnc1NC1CCCNC1]
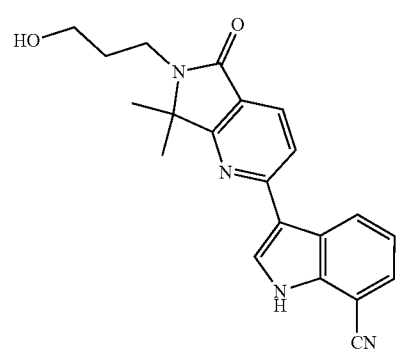 [SMILES: CC1(C)c2nc(-c3c[nH]c4c(C#N)cccc34)ccc2C(=O)N1CCCO]
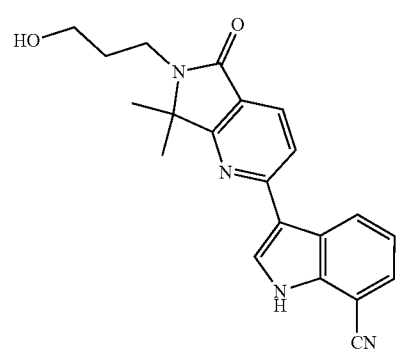 [SMILES: CC1(C)c2nc(-c3c[nH]c4c(C#N)cccc34)ccc2C(=O)N1CCCO]
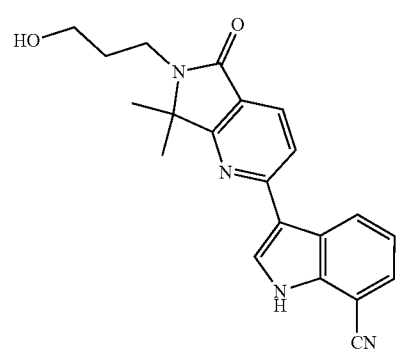 [SMILES: CC1(C)c2nc(-c3c[nH]c4c(C#N)cccc34)ccc2C(=O)N1CCCO]

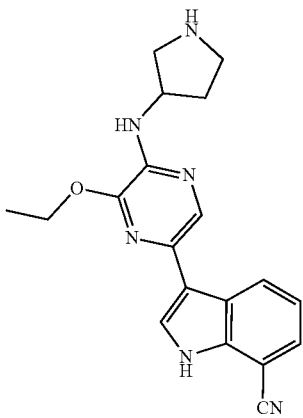 [SMILES: CCOc1nc(-c2c[nH]c3c(C#N)cccc23)cnc1NC1CCNC1]

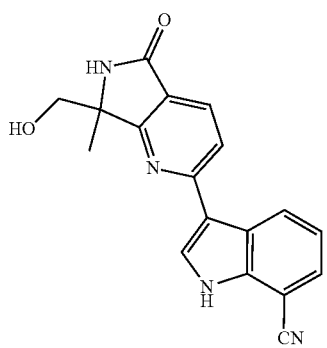 [SMILES: CC1(CO)NC(=O)c2ccc(-c3c[nH]c4c(C#N)cccc34)nc21]

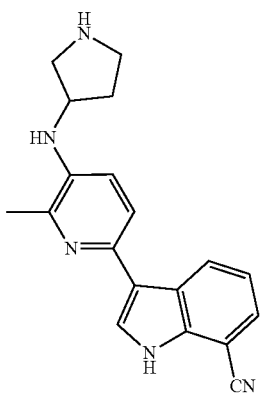 [SMILES: Cc1nc(-c2c[nH]c3c(C#N)cccc23)ccc1NC1CCNC1]

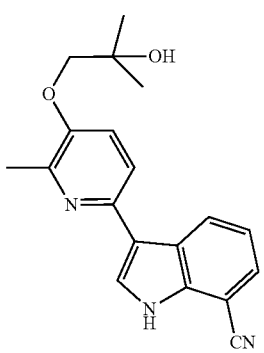 [SMILES: Cc1nc(-c2c[nH]c3c(C#N)cccc23)ccc1OCC(C)(C)O]

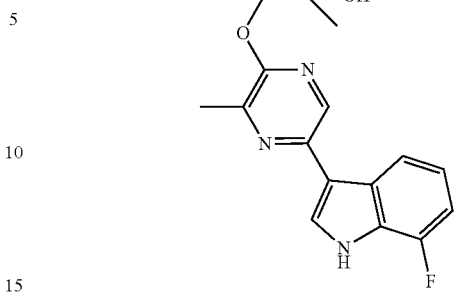

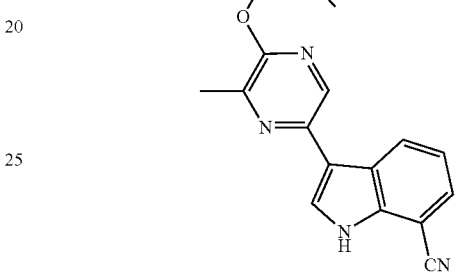

or a pharmaceutically acceptable salt thereof.

In an aspect, provided herein is a pharmaceutical composition comprising a compound provided herein, or a pharmaceutically acceptable salt thereof, and a pharmaceutically acceptable carrier.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In another embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, the compounds described herein include a 2H (i.e., deuterium) isotope.

In still another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the Formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds disclosed herein can be used in a method of treating a disease or condition in a subject, said method comprising administering to the subject a compound provided herein, or a pharmaceutical composition comprising the compound, and a pharmaceutically acceptable carrier.

In still another aspect, provided herein is a method of treating cancer in a subject in need thereof, comprising administering to the subject a therapeutically effective amount of a compound of Formula I or a pharmaceutical composition comprising a compound of Formula I.

In an embodiment, the cancer is selected from hematological cancers, sarcomas, lung cancers, gastrointestinal cancers, genitourinary tract cancers, liver cancers, bone cancers, nervous system cancers, gynecological cancers, and skin cancers.

In another embodiment, the lung cancer is selected from non-small cell lung cancer (NSCLC), small cell lung cancer, bronchogenic carcinoma, squamous cell bronchogenic carcinoma, undifferentiated small cell bronchogenic carcinoma, undifferentiated large cell bronchogenic carcinoma, adenocarcinoma, bronchogenic carcinoma, alveolar carcinoma, bronchiolar carcinoma, bronchial adenoma, chondromatous hamartoma, mesothelioma, pavicellular and non-pavicellular carcinoma, bronchial adenoma, and pleuropulmonary blastoma.

In yet another embodiment, the lung cancer is non-small cell lung cancer (NSCLC). In still another embodiment, the lung cancer is adenocarcinoma.

In an embodiment, the gastrointestinal cancer is selected from esophagus squamous cell carcinoma, esophagus adenocarcinoma, esophagus leiomyosarcoma, esophagus lymphoma, stomach carcinoma, stomach lymphoma, stomach leiomyosarcoma, exocrine pancreatic carcinoma, pancreatic ductal adenocarcinoma, pancreatic insulinoma, pancreatic glucagonoma, pancreatic gastrinoma, pancreatic carcinoid tumors, pancreatic vipoma, small bowel adenocarcinoma, small bowel lymphoma, small bowel carcinoid tumors, Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma, colorectal cancer, gall bladder cancer, and anal cancer.

In an embodiment, the gastrointestinal cancer is colorectal cancer.

In another embodiment, the cancer is a carcinoma. In yet another embodiment, the carcinoma is selected from pancreatic carcinoma, colorectal carcinoma, lung carcinoma, bladder carcinoma, gastric carcinoma, esophageal carcinoma, breast carcinoma, head and neck carcinoma, cervical skin carcinoma, and thyroid carcinoma.

In still another embodiment, the cancer is a hematopoietic malignancy. In an embodiment, the hematopoietic malignancy is selected from multiple myeloma, acute myelogenous leukemia, and myeloproliferative neoplasms.

In another embodiment, the cancer is a neoplasm. In yet another embodiment, the neoplasm is glioblastoma or sarcomas.

In an embodiment, the cancer is selected from the group consisting of hematological cancers, sarcomas, lung cancers, gastrointestinal cancers, genitourinary tract cancers, liver cancers, bone cancers, nervous system cancers, gynecological cancers, and skin cancers.

In an embodiment, the cancer is selected from the group consisting of pancreatic cancer, cervical cancer, colon cancer, ovarian cancer, breast cancer, pancreatic cancer, carcinoma, and adenocarcinoma.

In another embodiment, the cancer is pancreatic cancer. In yet another embodiment, the cancer is a solid tumor.

In an aspect, provided herein is a method of treating a neurodegenerative disorder in a subject in need thereof comprising administering to the subject a therapeutically effective amount of a compound of Formula I, or a pharmaceutically acceptable salt thereof.

In an embodiment, the neurodegenerative disorder is an x-linked recessive disorder. In another embodiment, the neurodegenerative disorder is spinal bulbar muscular atrophy (SBMA).

In another aspect, provided herein is a method of modulating androgen receptor (AR) activity in a subject in need thereof comprising administering to the subject a therapeutically effective amount of a compound of Formula I, or a pharmaceutically acceptable salt thereof.

In an embodiment, the androgen receptor (AR) undergoes allosteric modulation. In another embodiment, modulating androgen receptor (AR) activity treats spinal bulbar muscular atrophy (SBMA) in the subject.

In an embodiment of the methods, the subject is human.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Administration/Dosage/Formulations

In another aspect, provided herein is a pharmaceutical composition comprising at least one compound provided herein, together with a pharmaceutically acceptable carrier.

Actual dosage levels of the active ingredients in the pharmaceutical compositions discussed herein may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds provided herein are formulated as pharmaceutical compositions using one or more pharmaceutically acceptable excipients or carriers. In one embodiment, the pharmaceutical compositions comprise a therapeutically effective amount of a disclosed compound and a pharmaceutically acceptable carrier.

Routes of administration of any of the compositions disclosed herein include oral, nasal, rectal, intravaginal, parenteral, buccal, sublingual or topical. The compounds disclosed herein may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present application as set forth.

EXAMPLES

Example A: Synthetic Procedures

Intermediate A1

6-chloro-1H-1,5-naphthyridin-2-one

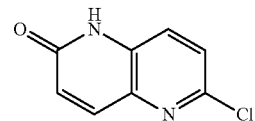 [SMILES: O=c1ccc2nc(Cl)ccc2[nH]1]

Step-1: To a solution of 6-chloropyridin-3-amine (10.00 g, 78.12 mmol) and silver sulfate (12.20 g, 39.22 mmol) in ethanol (200 mL) was added iodine (23.80 g, 94.07 mmol). The mixture was stirred at room temperature for 16 h. The mixture was concentrated under vacuum. The residue was diluted with water and extracted with ethyl acetate. The combined organic layers were washed with brine, dried over anhydrous sodium sulfate, filtered and concentrated under vacuum. The residue was purified by flash column chromatography with 0~60% ethyl acetate in petroleum ether to afford to afford 6-chloro-2-iodopyridin-3-amine (18.00 g, 90%) as a brown solid. MS m/z 254.9 [M+1]$^+$.

Step-2: To a degassed solution of 6-chloro-2-iodopyridin-3-amine obtained in the previous step (6.00 g, 23.52 mmol), ethyl acrylate (4.10 g, 41.00 mmol), tris(2-methylphenyl)phosphane (0.71 g, 1.73 mmol) and N,N-diisopropylethylamine (9.10 g, 70.54 mmol) in N,N-dimethylformamide (20 mL) was added palladium acetate (0.53 g, 2.35 mmol) under nitrogen atmosphere. The mixture was stirred at 100° C. for 16 h. The reaction mixture was diluted with water and extracted with ethyl acetate. The combined organic layers were washed with brine, dried over anhydrous sodium sulfate, filtered and concentrated under vacuum. The residue was purified by flash column chromatography with 0~60% ethyl acetate in petroleum ether to afford ethyl (2E)-3-(3-amino-6-chloropyridin-2-yl)prop-2-enoate (4.90 g, 91%) as a brown solid. MS m/z 227.1 [M+1]$^+$.

Step-3: A mixture of ethyl (2E)-3-(3-amino-6-chloropyridin-2-yl)prop-2-enoate prepared in the previous step (1.00 g, 4.40 mmol) and 1,8-diazabicyclo[5.4.0]undec-7-ene (1.30 g, 8.55 mmol) in ethanol (30 mL) was stirred at 100° C. for 24 h. The mixture was concentrated under vacuum. The residue was purified by flash column chromatography with 0~20% methanol in dichloromethane to afford 6-chloro-1H-1,5-naphthyridin-2-one (A1) (0.50 g, 62%) as a light yellow solid. MS m/z 181.0 [M+1]$^+$. $^1$H NMR (300 MHz, DMSO-d$_6$) δ 10.84 (bs, 1H), 7.86 (d, J=9.9 Hz, 1H), 7.74 (d, J=8.7 Hz, 1H), 7.58 (d, J=8.7 Hz, 1H), 6.79 (d, J=9.9 Hz, 1H).

Intermediate A2

5-methoxy-1,6-naphthyridin-2-yl trifluoromethanesulfonate

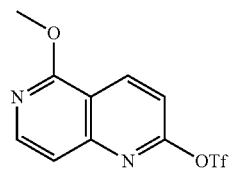 [SMILES: COc1nccc2nc(OS(=O)(=O)C(F)(F)F)ccc12]

Step 1: To a solution of methyl 2-methylnicotinate (9.00 g, 59.54 mmol) and 1,3,5-triazine (5.30 g, 65.37 mmol) in anhydrous methyl sulfoxide (50 mL) was added potassium tert-butoxide (8.00 g, 71.29 mmol) in portions at room temperature. After stirring at room temperature for 20 min, the mixture was heated at 80° C. for 1 h. The reaction was quenched by water (5 mL). The mixture was purified directly by reverse phase flash column chromatography with 5-20% acetonitrile in water to afford 1,6-naphthyridin-5(6H)-one (2.40 g, 27%) as a yellow solid. MS m/z 147.0 [M+1]$^+$.

Step 2: A mixture of 1,6-naphthyridin-5(6H)-one (820 mg, 5.61 mmol) and phosphorus oxychloride (15 mL) was heated at 80° C. for 5 h. The mixture was concentrated under vacuum. The residue was diluted with ice/water and basified using aqueous saturated sodium bicarbonate solution to pH 8. The mixture was extracted with ethyl acetate. The organic layer was dried over anhydrous sodium sulfate, filtered and concentrated under vacuum to afford 5-chloro-1,6-naphthyridine (720 mg, crude) as a yellow solid. MS m/z 164.1 [M+1]$^+$.

Step 3: To a solution of 5-chloro-1,6-naphthyridine (710 mg, 4.32 mmol) in dichloromethane (10 mL) was added 3-chloroperoxybenzoic acid (1200 mg, 5.93 mmol, 85%) at 0° C. The mixture was warmed to room temperature for 3 h, and then concentrated under vacuum. The residue was purified by flash column chromatography with 0~10% methanol in ethyl acetate to afford 5-chloro-1,6-naphthyridine 1-oxide (600 mg, 31% over 2 steps) as a yellow solid. MS m/z 181.1 [M+1]$^+$.

Step 4: A mixture of 5-chloro-1,6-naphthyridine 1-oxide (550 mg, 3.05 mmol) and sodium methylate (10 mL, 30% in methanol) was heated to 70° C. for 3 h. The mixture was concentrated under vacuum. The residue was purified by flash column chromatography with 0-15% methanol in ethyl acetate to afford 5-methoxy-1,6-naphthyridine 1-oxide (378 mg, 70%) as a yellow solid. MS m/z 177.1 [M+1]$^+$.

Step 5: To a solution of 5-methoxy-1,6-naphthyridine 1-oxide (300 mg, 1.70 mmol) in water (3 mL) was added methanesulfonyl chloride (390 mg, 3.41 mmol) slowly at 0° C. The mixture was stirred at room temperature for 2 h. The mixture was extracted with ethyl acetate. The organic layer was dried over anhydrous sodium sulfate, filtered and concentrated under vacuum to afford 5-methoxy-1,6-naphthyridin-2-ol (360 mg, crude) as a yellow oil. MS m/z 177.1 [M+1]$^+$. $^1$H NMR (300 MHz, Methanol-d$_4$) δ 8.19 (d, J=9.9 Hz, 1H), 8.12 (d, J=7.2 Hz, 1H), 7.21 (d, J=7.2 Hz, 1H), 6.76 (d, J=9.9 Hz, 1H), 4.38 (s, 3H).

Step 6: To a solution of 5-methoxy-1,6-naphthyridin-2-ol (360 mg, crude product from step 5) and pyridine (269 mg, 3.41 mmol) in dichloromethane (5 mL) was added trifluoromethanesulfonic anhydride (720 mg, 2.55 mmol) slowly at 0° C. The mixture was stirred at room temperature overnight. The reaction mixture was quenched with water and extracted with dichloromethane. The organic layer was dried over anhydrous sodium sulfate, filtered and concentrated under vacuum. The residue was purified by flash column chromatography with 0~50% ethyl acetate in petroleum ether to afford 5-methoxy-1,6-naphthyridin-2-yl trifluoromethanesulfonate (A2) (200 mg, 38% over 2 steps) as a yellow oil. MS m/z 309.0 [M+1]$^+$.

Intermediate A3

2-chloro-5,6,7,8-tetrahydro-1,5-naphthyridine

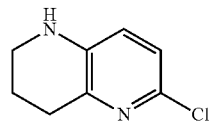

Step 1: To a stirred solution of ethyl (2E)-3-(3-amino-6-chloropyridin-2-yl)prop-2-enoate (from Intermediate A1) (2.00 g, 8.84 mmol) and cobaltous chloride hexahydrate (0.43 g, 3.34 mmol) in ethanol (40 mL) was added sodium borohydride (0.64 g, 16.86 mmol) in portions at 0° C. The resulting mixture was stirred at room temperature overnight. The mixture was concentrated under vacuum and diluted with water. The aqueous phase was extracted with ethyl acetate. The combined organic layers were washed with brine, dried over anhydrous sodium sulfate, filtered and concentrated under vacuum to afford ethyl 3-(3-amino-6-chloropyridin-2-yl)propanoate (1.80 g, crude) as a brown solid. MS m/z 229.0 [M+1]⁺.

Step 2: To a stirred mixture of ethyl 3-(3-amino-6-chloropyridin-2-yl)propanoate (1.80 g, 7.86 mmol) in ethanol (30 mL) was added acetic acid (3 mL). The mixture was stirred at 70° C. overnight. The reaction mixture was concentrated under vacuum to afford 6-chloro-3,4-dihydro-1H-1,5-naphthyridin-2-one (1.30 g, crude) as a brown solid. MS m/z 183.2 [M+1]⁺.

Step 3: To a stirred solution of 6-chloro-3,4-dihydro-1H-1,5-naphthyridin-2-one (5.10 g, crude product from step 2) in tetrahydrofuran (100 mL) was added lithium aluminium hydride (2.15 g, 56.64 mmol) slowly at 0° C. The mixture was heated at 60° C. for 14 h. The reaction was quenched with ice water. The resulting mixture was extracted with ethyl acetate. The combined organic layers were washed with water, dried over anhydrous sodium sulfate, filtered and concentrated under reduced pressure. The residue was purified by flash column chromatography with 0~50% ethyl acetate in petroleum ether to afford 2-chloro-5,6,7,8-tetrahydro-1,5-naphthyridine (A3) (2.90 g, 54% over 3 steps) as a yellow solid. MS m/z 169.1 [M+1]⁺. ¹H NMR (400 MHz, DMSO-d₆) δ 6.92 (d, J=8.4 Hz, 1H), 6.82 (d, J=8.4 Hz, 1H), 6.02 (s, 1H), 3.17-3.14 (m, 2H), 2.72 (t, J=6.5 Hz, 2H), 1.89-1.79 (m, 2H).

Intermediate A4 tert-butyl N-(2-chloro-5,6,7,8-tetrahydroquinolin-5-yl)carbamate

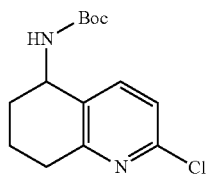 [SMILES: CC(C)(C)OC(=O)NC1CCCc2nc(Cl)ccc21]

Step 1: To a mixture of 2-chloro-7,8-dihydro-6H-quinolin-5-one (2.00 g, 11.01 mmol) and ammonium acetate (4.30 g, 55.94 mmol) in methanol was added sodium cyanoborohydride (1.40 g, 22.24 mmol) slowly at room temperature. After stirring at room temperature for 20 h, the mixture was concentrated under reduced pressure. The residue was diluted with ethyl acetate and washed with water. The organic layer was dried over anhydrous sodium sulfate, filtered and concentrated under reduced pressure to afford 2-chloro-5,6,7,8-tetrahydroquinolin-5-amine (2.00 g, crude). MS m/z 183.1 [M+1]⁺.

Step 2: To a stirred solution of 2-chloro-5,6,7,8-tetrahydroquinolin-5-amine (2.00 g, crude from step 1) in ethyl acetate (150 mL) and water (100 mL) were added sodium bicarbonate (6.20 g, 73.80 mmol) and di(tert-butyl) carbonate (3.80 g, 17.64 mmol) at room temperature. The mixture was stirred at room temperature for 14 h. The reaction mixture was washed with water. The organic layer was dried over anhydrous sodium sulfate, filtered and concentrated under vacuum. The residue was purified by flash column chromatography with 0~20% ethyl acetate in petroleum ether to afford tert-butyl N-(2-chloro-5,6,7,8-tetrahydroquinolin-5-yl)carbamate (A4) (0.25 g, 8% over 2 steps) as a colorless oil. MS m/z 283.1 [M+1]⁺.

Intermediate A5

2-chloro-1,5-naphthyridine

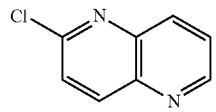 [SMILES: Clc1ccc2ncccc2n1]

Step 1: To a solution of 1,5-naphthyridine (5.00 g, 38.42 mmol) in dichloromethane (200 mL) was added 3-chloroperoxybenzoic acid (14.00 g, 81.12 mmol, 85%) at room temperature. The mixture was stirred at room temperature for 16 h. The reaction mixture was washed with sodium hydroxide (2N, aq.) and then dried over anhydrous sodium sulfate, filtered and concentrated under vacuum. The residue was purified by flash column chromatography with 0~15% methanol in ethyl acetate to afford 1-lambda-5-1,5-naphthyridin-1-one (0.81 g, 14%) as a white solid. MS m/z 147.1 [M+1]⁺.

Step 2: A mixture of 1-lambda5-1,5-naphthyridin-1-one (810 mg, 5.51 mmol) and phosphorus oxychloride (10 mL) was heated at 90° C. for 1 h. The mixture was concentrated under vacuum. The residue was diluted with water and basified using saturated sodium bicarbonate aqueous solution to pH 8. The mixture was extracted with ethyl acetate. The organic layer was dried over anhydrous sodium sulfate, filtered and concentrated under vacuum. The residue was purified by flash column chromatography with 0~40% ethyl acetate in petroleum ether to afford 2-chloro-1,5-naphthyridine (A5) (260 mg, 28%) as a white solid. MS m/z 165.0 [M+1]⁺. ¹H NMR (300 MHz, Chloroform-d) δ 8.99-8.89 (m, 1H), 8.41-8.29 (m, 2H), 7.68-7.60 (m, 2H).

Intermediate A6

4-chloro-1,5-naphthyridine

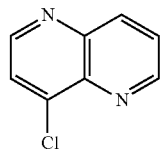 [SMILES: Clc1ccnc2cccnc12]

Purification of the reaction mixture of step 2 (Intermediate A5) described above also afforded 4-chloro-1,5-naphthyridine (A6) (320 mg, 35%) as a white solid. MS m/z 165.0 [M+1]⁺. ¹H NMR (300 MHz, Chloroform-d) δ 9.09-9.07 (m, 1H), 8.85 (d, J=5.1 Hz, 1H), 8.44 (d, J=8.1 Hz, 1H), 7.77-7.70 (m, 2H).

Intermediate A7 tert-butyl 2-(trifluoromethanesulfonyloxy)-7,8-di-hydro-5H-1,6-naphthyridine-6-carboxylate

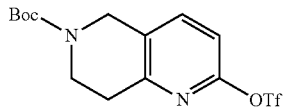 [SMILES: CC(C)(C)OC(=O)N1CCc2nc(OS(=O)(=O)C(F)(F)F)ccc2C1]

Step 1: To a stirred solution of methyl 2-methylpyridine-3-carboxylate (5.50 g, 36.40 mmol) in carbon tetrachloride (50 mL) were added N-bromosuccinimide (9.10 g, 51.12 mmol) and azodiisobutyronitrile (1.70 g, 10.36 mmol). The mixture was heated to 90° C. for 14 h under nitrogen atmosphere. The solid was filtered off. The filtrate was concentrated under reduced pressure. The residue was purified by flash column chromatography with 0~20% ethyl acetate in petroleum ether to afford methyl 2-(bromomethyl)pyridine-3-carboxylate (3.00 g, 35%) as an orange solid, MS m/z 230.1 [M+1]$^+$.

Step 2: To a stirred mixture of methyl 2-(bromomethyl)pyridine-3-carboxylate (3.00 g, 13.04 mmol) and tetrabutylammonium fluoride (5.00 g, 19.15 mmol) in acetonitrile was added trimethylsilyl cyanide (2.50 g, 25.62 mmol) dropwise at 0° C. The reaction mixture was warmed to room temperature for 16 h. The mixture was diluted with dichloromethane and washed with brine. The organic layers were dried over anhydrous sodium sulfate, filtered and concentrated under reduced pressure. The residue was purified by flash column chromatography with 0~30% ethyl acetate in petroleum ether to afford methyl 2-(cyanomethyl)pyridine-3-carboxylate (2.20 g, 97%) as a white solid. MS m/z 177.1 [M+1]$^+$.

Step 3: A mixture of methyl 2-(cyanomethyl)pyridine-3-carboxylate (2.20 g, 12.42 mmol) and Raney Ni (0.10 g) in methanol was stirred at room temperature under hydrogen atmosphere for 6 h. The solids were filtered off. The filtrate was concentrated under reduced pressure. The residue was purified by flash column chromatography with 0~20% methanol in dichloromethane to afford 7,8-dihydro-6H-1,6-naphthyridin-5-one (1.30 g, 69%) as a yellow solid. MS m/z 149.1 [M+1]$^+$. $^1$H NMR (300 MHz, DMSO-$d_6$) δ 8.58 (dd, J=6.8, 1.8 Hz, 1H), 8.13 (dd, J=7.8, 1.8 Hz, 1H), 8.08 (s, 1H), 7.43-7.32 (m, 1H), 3.50-3.39 (m, 2H), 3.02 (t, J=6.6 Hz, 2H).

Step 4: A mixture of 7,8-dihydro-6H-1,6-naphthyridin-5-one (0.50 g, 3.35 mmol) and lithium aluminum hydride (0.25 g, 6.40 mmol) in tetrahydrofuran was stirred at 60° C. for 16 h. The reaction was quenched with water at 0° C. The mixture was concentrated under reduced pressure. The residue was purified by flash column chromatography with 0~30% methanol in dichloromethane to afford 5,6,7,8-tetrahydro-1,6-naphthyridine (0.43 g, 95%) as a yellow solid. MS m/z 135.2 [M+1]$^+$.

Step 5: To a mixture of 5,6,7,8-tetrahydro-1,6-naphthyridine (1.20 g, 8.88 mmol) and triethylamine (2.60 g, 25.74 mmol) in dichloromethane (10 mL) was added di(tert-butyl) carbonate (6.20 g, 28.70 mmol). The mixture was stirred at 60° C. for 8 h. The mixture was concentrated under reduced pressure. The residue was purified by flash column chromatography with 0~80% ethyl acetate in petroleum ether to afford tert-butyl 7,8-dihydro-5H-1,6-naphthyridine-6-carboxylate (0.23 g, 11%) as a yellow oil. MS m/z 235.1 [M+1]$^+$.

Step 6: A mixture of tert-butyl 7,8-dihydro-5H-1,6-naphthyridine-6-carboxylate (0.31 g, 1.31 mmol) and 3-chloroperoxybenzoic acid (457 mg, 2.65 mmol) in dichloromethane (10 mL) was stirred at room temperature for 8 h. The reaction mixture was washed with potassium carbonate aqueous solution. The organic layer was washed dried over anhydrous sodium sulfate, filtered and concentrated under reduced pressure to afford tert-butyl 1-oxo-7,8-dihydro-5H-1lambda5-1,6-naphthyridine-6-carboxylate (0.30 g, crude) as a yellow solid. MS m/z 251.1 [M+1]$^+$.

Step 7: To a mixture of tert-butyl 1-oxo-7,8-dihydro-5H-1lambda5-1,6-naphthyridine-6-carboxylate (0.30 g, crude product from step 6) in water was added Methanesulfonyl chloride (0.27 g, 2.35 mmol). The mixture was stirred at room temperature for 2 h. The reaction mixture was extracted with dichloromethane. The combined organic layers were washed with water, then dried over anhydrous sodium sulfate, filtered and concentrated under reduced pressure to afford tert-butyl 2-oxo-1,5,7,8-tetrahydro-1,6-naphthyridine-6(2H)-carboxylate (0.26 g, crude) as a brown solid. MS m/z 251.2 [M+1]$^+$.

Step 8: To a mixture of tert-butyl 2-oxo-1,5,7,8-tetrahydro-1,6-naphthyridine-6-carboxylate (0.26 g, 1.03 mmol) and pyridine (0.16 g, 2.22 mmol) in dichloromethane (5 mL) was added trifluoromethanesulfonic anhydride (0.44 g, 1.56 mmol). The mixture was stirred at room temperature for 3 h. The reaction mixture was washed with water. The organic layer was dried over anhydrous sodium sulfate, filtered and concentrated under reduced pressure to afford tert-butyl 2-(trifluoromethanesulfonyloxy)-7,8-dihydro-5H-1,6-naphthyridine-6-carboxylate (A7) (320 mg, crude) as a brown oil, which was used directly without purification. MS m/z 383.2 [M+1]$^+$.

Intermediate A8 tert-butyl 2-chloro-6,8-dihydro-5H-1,7-naphthyridine-7-carboxylate

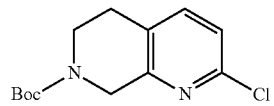 [SMILES: CC(C)(C)OC(=O)N1CCc2ccc(Cl)nc2C1]

Step 1: A mixture of methyl 6-chloro-3-methylpyridine-2-carboxylate (5.00 g, 27.02 mmol), N-bromosuccinimide (7.20 g, 40.44 mmol) and azodiisobutyronitrile (0.88 g, 5.36 mmol) in carbon tetrachloride was stirred at 80° C. for 8 h under nitrogen atmosphere. The solids were filtered off. The filtrate was concentrated under reduced pressure. The residue was purified by flash column chromatography with 0~50% ethyl acetate in petroleum ether to afford methyl 3-(bromomethyl)-6-chloropyridine-2-carboxylate (5.10 g, 72%) as a white solid. MS m/z 263.9 [M+1]$^+$.

Step 2: To a solution of methyl 3-(bromomethyl)-6-chloropyridine-2-carboxylate (3.90 g, 14.77 mmol) and tetrabutylammonium fluoride (5.80 g, 22.13 mmol) in acetonitrile was added trimethylsilyl cyanide (2.90 g, 29.00 mmol) slowly at 0° C. After stirring at room temperature for 16 h, the mixture was diluted with dichloromethane and washed with brine. The organic layer was dried over anhydrous sodium sulfate, filtered and concentrated under reduced pressure. The residue was purified by flash column chromatography with 0~70% ethyl acetate in petroleum ether to afford methyl 6-chloro-3-(cyanomethyl)pyridine-2-carboxylate (1.60 g, 52%) as a light yellow solid. MS m/z 211.1 [M+1]$^+$. $^1$H NMR (300 MHz, DMSO-d$_6$) δ 8.08 (d, J=8.4 Hz, 1H), 7.82 (d, J=8.4 Hz, 1H), 4.28 (s, 2H), 3.89 (s, 3H).

Step 3: A solution of methyl 6-chloro-3-(cyanomethyl)pyridine-2-carboxylate (1.60 g, 7.58 mmol) and Raney-Ni (0.06 g) in methanol was stirred at room temperature for 6 h under hydrogen atmosphere. The solids were filtered off. The filtrate was concentrated under reduced pressure. The residue was purified by flash column chromatography with 0~100% ethyl acetate in petroleum ether to afford 2-chloro-6,7-dihydro-5H-1,7-naphthyridin-8-one (0.57 g, 41%) as a yellow solid. MS m/z 183.1 [M+1]$^+$.

Step 4: To a mixture of 2-chloro-6,7-dihydro-5H-1,7-naphthyridin-8-one (0.42 g, 2.29 mmol) and sodium borohydride (0.52 g, 13.68 mmol) in tetrahydrofuran was added boron trifluoride ether complex (2.00 g, 13.51 mmol) at 0° C. The mixture was stirred at room temperature for 8 h. The reaction was quenched with water and acidified with HCl (aq., 2N) to pH 5. The mixture was extracted with ethyl acetate. The aqueous phase was collected and basified using saturated sodium bicarbonate aqueous solution to pH 8. The mixture was extracted with ethyl acetate. The organic layer was collected and dried over anhydrous sodium sulfate, filtered and concentrated under reduced pressure to afford 2-chloro-5,6,7,8-tetrahydro-1,7-naphthyridine (0.31 g, 80%) as a white solid. MS m/z 169.0 [M+1]$^+$. $^1$H NMR (300 MHz, DMSO-d$_6$) δ 7.68 (d, J=8.1 Hz, 1H), 7.35 (d, J=8.1 Hz, 1H), 6.72 (s, 1H), 3.90 (dd, J=17.1, 3.9 Hz, 1H), 3.67 (dd, J=17.1, 9.3 Hz, 1H), 3.27-3.13 (m, 1H), 3.03-2.63 (m, 3H).

Step 5: To a mixture of 2-chloro-5,6,7,8-tetrahydro-1,7-naphthyridine (0.10 g, 0.59 mmol) and triethylamine (0.18 g, 1.78 mmol) in dichloromethane (2 mL) was added di(tert-butyl) carbonate (0.42 g, 1.94 mmol). The mixture was stirred at 60° C. for 8 h. The mixture was concentrated under reduced pressure. The residue was purified by flash column chromatography with 0~80% ethyl acetate in petroleum ether to afford tert-butyl 2-chloro-6,8-dihydro-5H-1,7-naphthyridine-7-carboxylate (A7) (0.056 g, 35%) as a yellow oil. MS m/z 269.1 [M+1]$^+$.

Intermediate A9

6-fluoro-5-(1,3,4-oxadiazol-2-yl)quinolin-2-yl trifluoromethanesulfonate

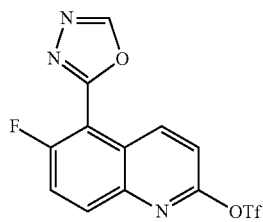 [SMILES: O=S(=O)(Oc1ccc2c(-c3nnco3)c(F)ccc2n1)C(F)(F)F]

Step 1: To a solution of 3-bromo-4-fluoroaniline (10.00 g, 52.63 mmol) in tetrahydrofuran (200 mL) was added lithium bis(trimethylsilyl)amide (78.90 mL, 78.90 mmol, 1M in tetrahydrofuran) slowly at −78° C. After stirring at −78° C. for 10 min, a solution of ethyl 3,3-diethoxypropanoate (12.00 g, 63.15 mmol) in tetrahydrofuran (50 mL) was added slowly to the above mixture at 0° C. The mixture was warmed slowly to room temperature and stirred at room temperature for 16 h. The reaction was quenched using citric acid (aq., 20%) at 5° C. The organic solvent was removed under reduced pressure. The remaining aqueous phase was extracted with dichloromethane. The organic layer was washed with water and then dried over anhydrous sodium sulfate, filtered and concentrated to dryness under reduced pressure to afford N-(3-bromo-4-fluorophenyl)-3,3-diethoxypropanamide (19.00 g, crude) as a brown solid. MS m/z 334.0 [M+1]$^+$.

Step 2: A mixture of N-(3-bromo-4-fluorophenyl)-3,3-diethoxypropanamide (3.00 g, 8.98 mmol) and sulfuric acid (13.20 g, 134.69 mmol) in dichloromethane (50 mL) heated to reflux for 0.5 h. The mixture was treated with ice water and extracted with dichloromethane. The combined organic layers were washed with water, dried over anhydrous sodium sulfate, filtered and concentrated under reduced pressure. The residue was purified by flash column chromatography 0~100% ethyl acetate in petroleum ether to afford a mixture of 5-bromo-6-fluoro-1H-quinolin-2-one and 7-bromo-6-fluoroquinolin-2(1H)-one (0.24 g, 11%) as a yellow solid. MS m/z 242.0 [M+1]$^+$.

Step 3: A mixture of 5-bromo-6-fluoro-1H-quinolin-2-one and 7-bromo-6-fluoroquinolin-2(1H)-one (1.00 g, 4.11 mmol), [1,1'-bis(diphenylphosphino)ferrocene]dichloropalladium(II) (0.30 g, 0.41 mmol) and triethylamine (0.84 g, 8.36 mmol) in methanol was stirred at 60° C. for 16 h under carbon monoxide atmosphere. The mixture was concentrated under vacuum. The residue was purified by flash column chromatography 0~100% ethyl acetate in petroleum ether to afford a mixture of methyl 6-fluoro-2-oxo-1H-quinoline-5-carboxylate and methyl 6-fluoro-2-oxo-1,2-dihydroquinoline-7-carboxylate (0.80 g, 88%) as a brown solid. MS m/z 222.1 [M+1]$^+$.

Step 4: A mixture of methyl 6-fluoro-2-oxo-1H-quinoline-5-carboxylate and methyl 6-fluoro-2-oxo-1,2-dihydroquinoline-7-carboxylate (5.00 g, 22.52 mmol) and lithium hydroxide (1.90 g, 79.16 mmol) in tetrahydrofuran (50 mL) and water (50 mL) was stirred at room temperature for 8 h. The organic solvent was removed under reduced pressure. The aqueous phase was acidified with HCl (aq., 2N) to pH 5. The aqueous phase was purified directly by reverse phase flash column chromatography 5~50% acetonitrile in water over 30 min to afford a mixture of methyl 6-fluoro-2-oxo-1H-quinoline-5-carboxylic acid and 6-fluoro-2-oxo-1,2-dihydroquinoline-7-carboxylic acid (2.20 g, 47%) as a brown solid. MS m/z 208.1 [M+1]$^+$.

Step 5: To a mixture of 6-fluoro-2-oxo-1H-quinoline-5-carboxylic acid (1.20 g, 5.76 mmol), tert-butoxycarbohydrazide (1.20 g, 9.09 mmol), N-(3-dimethylaminopropyl)-N'-ethylcarbodiimide hydrochloride (1.70 g, 8.85 mmol) and 1-hydroxybenzotriazole (1.20 g, 8.88 mmol) in N,N-dimethylformamide (15 mL) was added triethylamine (1.70 g, 16.83 mmol). The mixture was stirred at 30° C. for 8 h. The mixture was diluted with water and extracted with ethyl acetate. The combined organic layers were washed with water, dried over anhydrous sodium sulfate, filtered and concentrated under reduced pressure. The residue was purified by flash column chromatography to afford a mixture of N-(tert-butoxycarbonyl)-6-fluoro-2-oxo-1H-quinoline-5-carbohydrazide and tert-butyl 2-(6-fluoro-2-oxo-1,2-dihydroquinoline-7-carbonyl)hydrazine-1-carboxylate (1.10 g, 61%) as a brown solid. MS m/z 322.1 [M+1]$^+$.

Step 6: To a mixture of N-(tert-butoxycarbonyl)-6-fluoro-2-oxo-1H-quinoline-5-carbohydrazide tert-butyl 2-(6-fluoro-2-oxo-1,2-dihydroquinoline-7-carbonyl)hydrazine- 1-carboxylate (1.10 g, 3.31 mmol) in dichloromethane (20 mL) was added trifluoroacetic acid (11 mL). The mixture was stirred at room temperature for 3 h. The mixture was concentrated under reduced pressure to afford a mixture of 6-fluoro-2-oxo-1H-quinoline-5-carbohydrazide and 6-fluoro-2-oxo-1,2-dihydroquinoline-7-carbohydrazide (0.69 g, crude) as a yellow solid. MS m/z 222.2 [M+1]$^+$.

Step 7: A mixture of 6-fluoro-2-oxo-1H-quinoline-5-carbohydrazide and 6-fluoro-2-oxo-1,2-dihydroquinoline-7-carbohydrazide (1.40 g, 6.30 mmol) and trimethyl orthoformate (15 mL) was stirred at 120° C. for 3 h. The mixture was concentrated under reduced pressure to afford a mixture of 6-fluoro-5-(1,3,4-oxadiazol-2-yl)-1H-quinolin-2-one and 6-fluoro-7-(1,3,4-oxadiazol-2-yl)quinolin-2(1H)-one (0.96 g, crude) as a brown solid, which was used in the next step directly without further purification. MS m/z 232.0 [M+1]$^+$.

Step 8: To a mixture of 6-fluoro-5-(1,3,4-oxadiazol-2-yl)-1H-quinolin-2-one and 6-fluoro-7-(1,3,4-oxadiazol-2-yl)quinolin-2(1H)-one (0.30 g, 1.35 mmol), pyridine (0.20 g, 2.77 mmol) in dichloromethane was added trifluoromethanesulfonic anhydride (0.55 g, 1.94 mmol) slowly at 0° C. The mixture was stirred at room temperature for 3 h. The reaction was quenched by water and extracted with dichloromethane. The combined organic layers were dried over anhydrous sodium sulfate, filtered and concentrated under reduced pressure to afford a mixture of 6-fluoro-5-(1,3,4-oxadiazol-2-yl)quinolin-2-yl trifluoromethanesulfonate (A8) and 6-fluoro-7-(1,3,4-oxadiazol-2-yl)quinolin-2-yl trifluoromethanesulfonate (0.38 g, crude) as a brown solid, which was used in the next step directly without further purification. MS m/z 364.1 [M+1]$^+$.

Intermediate A10

5-(1,3,4-oxadiazol-2-yl)quinolin-2-yl trifluoromethanesulfonate

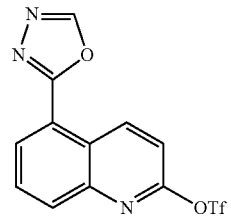 [SMILES: O=S(=O)(Oc1ccc2c(-c3nnco3)cccc2n1)C(F)(F)F]

Step 1: A solution of 5-quinolinecarboxylic acid (5.00 g, 28.87 mmol) and 1,1'-carbonyldiimidazole (5.20 g, 31.76 mmol) in tetrahydrofuran (40 mL) was stirred at room temperature for 2 h. Then hydrazine hydrate (2.90 g, 57.74 mmol, 80% in water) was added to the above mixture. The reaction mixture was stirred at room temperature for 2 h. The solids were collected by filtration and dried over vacuum to afford quinoline-5-carbohydrazide (2.50 g, 46%) as a grey solid. MS m/z 188.1 [M+1]$^+$.

Step 2: A mixture of quinoline-5-carbohydrazide (2.30 g, 12.28 mmol) and trimethyl orthoformate (10 mL) was stirred at 120° C. for 4 h. The mixture was concentrated under vacuum to afford 5-(1,3,4-oxadiazol-2-yl)quinoline (2.30 g, crude) as a brown solid. MS m/z 198.2 [M+1]$^+$.

Step 3: To a solution of 5-(1,3,4-oxadiazol-2-yl)quinoline (2.2 g, crude from step 2) in dichloromethane (20 mL) was added 3-chloroperoxybenzoic acid (3.80 g, 22.31 mmol). The mixture was stirred at room temperature for 5 h. The reaction mixture was basified using saturated sodium bicarbonate aqueous solution and extracted with dichloromethane. The organic layer was dried over anhydrous sodium sulfate, filtered and concentrated under vacuum to afford 5-(1,3,4-oxadiazol-2-yl)quinolin-1-ium-1-olate (2.3 g, crude) as a yellow solid. MS m/z 214.1 [M+1]$^+$.

Step 4: To a suspension of 5-(1,3,4-oxadiazol-2-yl)quinolin-1-ium-1-olate (0.63 g, 2.95 mmol) in water (8 mL) was added methanesulfonyl chloride (0.68 g, 5.91 mmol). The mixture was stirred at room temperature for 20 min. The solids were collected by filtration and dried over vacuum to afford 5-(1,3,4-oxadiazol-2-yl)-1H-quinolin-2-one (0.56 mg, 88%) as a yellow solid. MS m/z 214.1 [M+1]$^+$. $^1$H NMR (300 MHz, DMSO-d$_6$) δ 12.07 (s, 1H), 9.45 (s, 1H), 9.00-8.84 (m, 1H), 7.78 (dd, J=7.5, 1.3 Hz, 1H), 7.70 (t, J=7.8 Hz, 1H), 7.56 (dt, J=8.1, 1.2 Hz, 1H), 6.72 (d, J=9.9 Hz, 1H).

Step 5: To a solution of 5-(1,3,4-oxadiazol-2-yl)-1H-quinolin-2-one (0.26 g, 1.22 mmol) and pyridine (0.19 g, 2.44 mmol) in dichloromethane (2 mL) was added trifluoromethanesulfonic anhydride (0.51 g, 1.83 mmol) at 0° C. The mixture was stirred at room temperature for 2 h. The reaction mixture was washed with water. The organic layer was dried over anhydrous sodium sulfate, filtered and concentrated to afford 5-(1,3,4-oxadiazol-2-yl)quinolin-2-yl trifluoromethanesulfonate (A9) (404 mg, crude) as a red solid. MS m/z 346.1 [M+1]$^+$.

Intermediate A11

2-chloro-6-methyl-7H-pyrrolo[3,4-b]pyridin-5-one

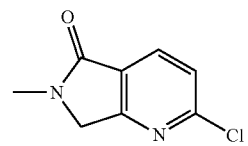

Step 1: To a solution of methyl 6-chloro-2-methylpyridine-3-carboxylate (200 mg, 1.08 mmol) and azodiisobutyronitrile (35 mg, 0.2 mmol) in carbon tetrachloride (10 mL) was added N-bromosuccinimide (153 mg, 0.88 mmol) under nitrogen atmosphere. The mixture was stirred at 80° C. overnight. The solids were filtered off. The filtrate was concentrated under vacuum. The residue was purified by flash column chromatography with 0~80% ethyl acetate in petroleum ether to afford methyl 2-(bromomethyl)-6-chloropyridine-3-carboxylate (260 mg, 91%) as a brown oil. MS m/z 264.2 [M+1]$^+$.

Step 2: A mixture of methyl 2-(bromomethyl)-6-chloropyridine-3-carboxylate (260 mg, 0.98 mmol) and methylamine (10 mL, 2M in tetrahydrofuran) was stirred at room temperature overnight. The mixture was concentrated under vacuum. The residue was purified by flash column chromatography with 0~70% ethyl acetate in petroleum ether to afford 2-chloro-6-methyl-7H-pyrrolo[3,4-b]pyridin-5-one (A11) (100 mg, 55%) as a light yellow solid. MS m/z 183.2 [M+1]$^+$. $^1$H NMR (300 MHz, DMSO-d$_6$) δ 8.09 (d, J=8.1 Hz, 1H), 7.60 (d, J=8.1 Hz, 1H), 4.52 (s, 2H), 3.07 (s, 3H).

Intermediate A12

6-chloro-4-methyl-1-(4-methylbenzenesulfonyl)-3,4-dihydro-2H-1,5-naphthyridine

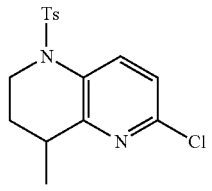 [SMILES: Cc1ccc(S(=O)(=O)N2CCC(C)c3nc(Cl)ccc32)cc1]

Step 1: To a solution of N-(6-chloropyridin-3-yl)-4-methylbenzenesulfonamide (3.00 g, 10.63 mmol), triphenylphosphine (4.20 g, 16.03 mmol) and 3-buten-1-ol (0.77 g, 10.69 mmol) in tetrahydrofuran (30 mL) was added diisopropyl azodiformate (3.20 g, 15.84 mmol) dropwise at 0° C. under nitrogen atmosphere. The mixture was stirred at room temperature for 2 h. The resulting mixture was concentrated under vacuum. The residue was purified by flash column chromatography with 0~80% ethyl acetate in petroleum ether to afford N-(but-3-en-1-yl)-N-(6-chloropyridin-3-yl)-4-methylbenzenesulfonamide (3.50 g, 97%) as a light-yellow oil. MS m/z 337.1 [M+1]$^+$.

Step-2: A mixture of N-(but-3-en-1-yl)-N-(6-chloropyridin-3-yl)-4-methylbenzenesulfonamide (1.40 g, 4.17 mmol) and trifluoroacetic acid (0.96 g, 9.90 mmol) in ethanol (10 mL) was stirred at room temperature for 10 min. Then ferric acetylacetonate (0.75 g, 2.12 mmol), phenylsilane (1.20 g, 10.65 mmol) and di-tert-butyl peroxide (1.90 g, 12.74 mmol) were added to above mixture at room temperature. The mixture was stirred at 60° C. overnight. The mixture was diluted with water and extracted with ethyl acetate. The combined organic layers were washed with brine, dried over anhydrous sodium sulfate, filtered and concentrated under vacuum. The residue was purified by reverse phase flash column chromatography with 40-60% acetonitrile in water to afford 6-chloro-4-methyl-1-(4-methylbenzenesulfonyl)-3,4-dihydro-2H-1,5-naphthyridine (A11) (0.30 g, 20%) as an off-white solid. MS m/z 337.1 [M+1]$^+$. $^1$H NMR (300 MHz, DMSO-d$_6$) δ 8.03 (d, J=8.7 Hz, 1H), 7.51 (d, J=8.4 Hz, 1H), 7.46-7.32 (m, 4H), 3.87-3.83 (m, 1H), 3.73-3.55 (m, 1H), 2.71-2.64 (m, 1H), 2.35 (s, 3H), 1.77-1.66 (m, 1H), 1.30-1.07 (m, 1H), 0.98 (d, J=7.2 Hz, 3H).

Intermediate A13

6-chloro-4-methyl-1-(4-methylbenzenesulfonyl)-3,4-dihydro-2H-1,7-naphthyridine

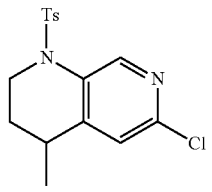 [SMILES: Cc1ccc(S(=O)(=O)N2CCC(C)c3cc(Cl)ncc32)cc1]

Purification of the reaction mixture of step 2 (A12) also afforded 6-chloro-4-methyl-1-(4-methylbenzenesulfonyl)-3,4-dihydro-2H-1,7-naphthyridine (0.20 g, 14%) as a yellow oil. MS m/z 337.1 [M+1]$^+$. $^1$H NMR (300 MHz, DMSO-d$_6$) δ 8.57 (s, 1H), 7.51 (d, J=8.4 Hz, 2H), 7.40-7.37 (m, 3H), 3.86-3.59 (m, 2H), 2.77-2.53 (m, 1H), 2.35 (s, 3H), 1.72-1.52 (m, 1H), 1.29-1.04 (m, 1H), 0.96 (d, J=7.0 Hz, 3H).

Intermediate A14

6-chloro-4,4-dimethyl-1-(4-methylbenzenesulfonyl)-2,3-dihydro-1,5-naphthyridine

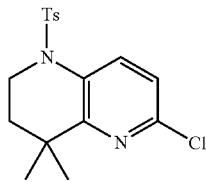 [SMILES: Cc1ccc(S(=O)(=O)N2CCC(C)(C)c3nc(Cl)ccc32)cc1]

Step 1: To a mixture of 6-chloropyridin-3-amine (5.00 g, 38.89 mmol) and pyridine (50 mL) was added p-toluenesulfonyl chloride (8.90 g, 46.68 mmol) in portions at 0~5° C. The mixture was heated to 60° C. for 2 h. The mixture was concentrated under vacuum. The residue was purified by flash column chromatography with 0~40% ethyl acetate in petroleum ether to afford N-(6-chloropyridin-3-yl)-4-methylbenzenesulfonamide (9.10 g, 82%) as a light yellow solid. MS m/z 283.0 [M+1]$^+$.

Step 2: To a solution of N-(6-chloropyridin-3-yl)-4-methylbenzenesulfonamide (1.00 g, 3.53 mmol), 3-methyl-3-buten-1-ol (0.31 g, 3.60 mmol) and triphenylphosphine (1.40 g, 5.34 mmol) in tetrahydrofuran (10 mL) was added diisopropyl azodiformate (1.10 g, 5.44 mmol) dropwise at 0° C. under nitrogen atmosphere. The mixture was warmed to room temperature for 3 h. The mixture was concentrated under vacuum. The residue was purified by flash column chromatography with 0~20% ethyl acetate in petroleum ether to afford N-(6-chloropyridin-3-yl)-4-methyl-N-(3-methylbut-3-en-1-yl)benzenesulfonamide (1.10 g, 88%) as a colorless oil. MS m/z 351.1 [M+1]$^+$. $^1$H NMR (300 MHz, Chloroform-0 δ 7.95 (d, J=1.5 Hz, 1H), 7.47-7.44 (m, 3H), 7.33-7.27 (m, 3H), 4.78 (s, 1H), 4.59 (s, 1H), 3.66 (t, J=7.2 Hz, 2H), 2.43 (s, 3H), 2.13 (t, J=7.2 Hz, 2H), 1.70 (s, 3H).

Step 3: To a solution of N-(6-chloropyridin-3-yl)-4-methyl-N-(3-methylbut-3-en-1-yl)benzenesulfonamide (2.00 g, 5.70 mmol) in ethanol (20 mL) was added trifluoroacetic acid (1.40 g, 12.27 mmol). The mixture was stirred at room temperature for 10 mins. This was followed by the addition of ferric acetylacetonate (1.00 g, 2.83 mmol), phenylsilane (1.60 g, 14.82 mmol) and di-tert-butyl peroxide (2.60 g, 17.81 mmol) at room temperature. The mixture was heated to 60° C. for 16 h. The mixture was diluted with water and basified by potassium carbonate. The mixture was extracted with ethyl acetate. The organic layer was dried over anhydrous sodium sulfate, filtered and concentrated under vacuum. The residue was purified by flash column chromatography with 0~20% ethyl acetate in petroleum ether to afford 6-chloro-4,4-dimethyl-1-(4-methylbenzenesulfonyl)-2,3-dihydro-1,5-naphthyridine (260 mg, 13%) as a white solid. MS m/z 351.1 [M+1]$^+$. $^1$H NMR (300 MHz, Chloroform-d) δ 8.12 (d, J=8.7 Hz, 1H), 7.47 (d, J=8.7 Hz, 2H), 7.25 (d, J=8.7 Hz, 2H), 7.12 (d, J=8.7 Hz, 1H), 3.83-3.73 (m, 2H), 2.40 (s, 3H), 1.42-1.32 (m, 2H), 1.06 (s, 6H).

Intermediate A15

6-chloro-4,4-dimethyl-1-(4-methylbenzenesulfonyl)-2,3-dihydro-1,7-naphthyridine

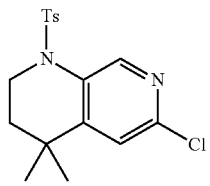 [SMILES: Cc1ccc(S(=O)(=O)N2CCC(C)(C)c3cc(Cl)ncc32)cc1]

Purification of the reaction mixture of step 2 (A14) also afforded 6-chloro-4,4-dimethyl-1-tosyl-1,2,3,4-tetrahydro-1,7-naphthyridine (A15) (170 mg, 8%) as a light yellow oil. MS m/z 337.1 [M+1]$^+$. $^1$H NMR (300 MHz, Chloroform-d) δ 8.82 (s, 1H), 7.46 (d, J=8.7 Hz, 1H), 7.22 (d, J=8.7 Hz, 1H), 7.15 (s, 1H), 3.84-3.74 (m, 2H), 2.39 (s, 3H), 1.43-1.33 (m, 2H), 1.04 (s, 6H).

Intermediate A16

2-chloro-6-[(4-methoxyphenyl)methyl]-7-methyl-7H-pyrrolo[3,4-b]pyridin-5-one

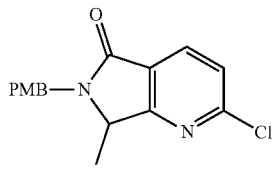

Step 1: To a solution of methyl 3-oxopentanoate (18.00 g, 138.30 mmol) in methanol (300 mL) was added ammonium acetate (56.00 g, 726.49 mmol). The mixture was stirred at room temperature for 48 h. The mixture was concentrated under vacuum. The residue was diluted with dichloromethane and washed with water. The organic layer was dried over anhydrous sodium sulfate, filtered and concentrated under vacuum to afford methyl (2Z)-3-aminopent-2-enoate (17.8 g, 99%) as a yellow oil. $^1$H NMR (400 MHz, Chloroform-d) δ 4.58 (s, 1H), 3.67 (s, 3H), 2.19 (q, J=7.6 Hz, 2H), 1.17 (t, J=7.6 Hz, 3H).

Step 2: A mixture of methyl (2Z)-3-aminopent-2-enoate (8.00 g, 61.93 mmol) and ethyl propiolate (7.40 g, 75.43 mmol) in toluene (150 mL) was heated to reflux for 48 h. The mixture was concentrated under vacuum to afford 1-ethyl 5-methyl (2E,4Z)-4-(1-aminopropylidene)pent-2-enedioate (17 g, crude) as a yellow semi-solid. MS m/z 228.1 [M+1]$^+$.

Step 3: To a solution of 1-ethyl 5-methyl (2E,4Z)-4-(1-aminopropylidene)pent-2-enedioate (17.00 g, 74.80 mmol) in methyl sulfoxide (100 mL) was added sodium tert-butoxide (0.50 g, 5.20 mmol). The mixture was heated at 150° C. for 1 h. The mixture was diluted with water and acidified with HCl (aq.) to pH 5-6. The mixture was extracted with ethyl acetate. The organic layer was dried over anhydrous sodium sulfate, filtered and concentrated under vacuum. The residue was purified by flash column chromatography with 0~80% ethyl acetate in petroleum ether to afford methyl 2-ethyl-6-oxo-1H-pyridine-3-carboxylate (5.00 g, 44% over 2 steps) as a yellow solid. MS m/z 182.1 [M+1]$^+$.

Step 4: A mixture of methyl 2-ethyl-6-oxo-1H-pyridine-3-carboxylate (4.40 g, 24.28 mmol) and phosphorus oxychloride (100 mL) was heated at reflux for 16 h. The mixture was concentrated under vacuum. The residue was diluted with water and basified with saturated sodium bicarbonate aqueous solution. The mixture was extracted with ethyl acetate. The organic layer was dried over anhydrous sodium sulfate, filtered and concentrated under vacuum. The residue was purified by flash column chromatography with 0~20% ethyl acetate in petroleum ether to afford methyl 6-chloro-2-ethylpyridine-3-carboxylate (3.60 g, 74%) as a yellow oil. MS m/z 199.9 [M+1]$^+$. $^1$H NMR (400 MHz, Chloroform-d) δ 8.14 (d, J=8.2 Hz, 1H), 7.24 (d, J=8.2 Hz, 1H), 3.18 (q, J=7.4 Hz, 2H), 1.32 (t, J=7.4 Hz, 3H).

Step 5: A mixture of methyl 6-chloro-2-ethylpyridine-3-carboxylate (2.00 g, 10.02 mmol), N-bromosuccinimide (2.10 g, 11.79 mmol) and azodiisobutyronitrile (0.16 g, 1.02 mmol) in Carbon tetrachloride (20 mL) was heated at reflux for 16 h. The solids were filtered off. The filtrate was concentrated under vacuum to afford methyl 2-(1-bromoethyl)-6-chloropyridine-3-carboxylate (2.60 g, crude) as a yellow oil. MS m/z 279.9 [M+1]$^+$.

Step 6: A mixture of methyl 2-(1-bromoethyl)-6-chloropyridine-3-carboxylate (2.60 g, 9.33 mmol) and (4-methoxyphenyl)methanamine (2.50 g, 18.22 mmol) in tetrahydrofuran (50 mL) was stirred at 60° C. for 16 h. The mixture was concentrated under vacuum. The residue was purified by flash column chromatography with 0~60% ethyl acetate in petroleum ether to afford 2-chloro-6-[(4-methoxyphenyl)methyl]-7-methyl-7H-pyrrolo[3,4-b]pyridin-5-one (A16) (2.60 g, 85% over 2 steps) as a yellow solid. MS m/z 303.0 [M+1]$^+$. $^1$H NMR (400 MHz, DMSO-d$_6$) δ 8.18 (d, J=8.0 Hz, 1H), 7.65 (d, J=8.0 Hz, 1H), 7.26 (d, J=8.8 Hz, 2H), 6.90 (d, J=8.8 Hz, 2H), 4.94 (d, J=15.2 Hz, 1H), 4.54-4.37 (m, 2H), 3.74 (s, 3H), 1.41 (d, J=6.8 Hz, 3H).

Intermediate A17

2-chloro-7-methyl-6H,7H-pyrrolo[3,4-b]pyridin-5-one

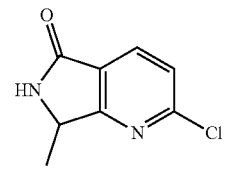

To a solution of 2-chloro-6-[(4-methoxyphenyl)methyl]-7-methyl-7H-pyrrolo[3,4-b]pyridin-5-one (300 mg, 0.99 mmol) in trifluoroacetic acid (3 mL) was added trifluoromethanesulfonic acid (0.2 mL). The mixture was stirred to 75° C. for 2 h. The mixture was concentrated under vacuum. The residue was diluted by water and basified using Sodium bicarbonate to pH 8. The mixture was extracted with dichloromethane. The organic layer was died over anhydrous sodium sulfate, filtered and concentrated under vacuum. The residue was purified by flash column chromatography with 0~60% ethyl acetate in petroleum ether to afford 2-chloro- 7-methyl-6H,7H-pyrrolo[3,4-b]pyridin-5-one (A17) (150 mg, 82.%) as a yellow solid. MS m/z 183.0 [M+1]⁺.

Intermediate A18

2-chloro-6-[(4-methoxyphenyl)methyl]-7,7-dimethylpyrrolo[3,4-b]pyridin-5-one

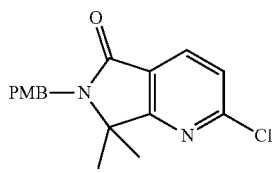

Step 1: To a mixture of methyl 2-methylpyridine-3-carboxylate (26.90 g, 0.18 mol) in dichloromethane (300 mL) was added 3-chloroperoxybenzoic acid (43.00 g, 0.21 mol, 85%) in portions at 0° C. The mixture was warmed to room temperature for 3 h. The reaction mixture was washed with saturated sodium thiosulfate aqueous solution and saturated sodium bicarbonate aqueous solution twice. The organic layer was washed with brine, dried over anhydrous sodium sulfate, filtered and concentrated under vacuum to afford methyl 2-methyl-1-oxo-1lambda5-pyridine-3-carboxylate (19.00 g, crude) as a yellow solid. MS m/z 168.0 [M+1]⁺.

Step 2: A mixture of methyl 2-methyl-1-oxo-1lambda5-pyridine-3-carboxylate (19.00 g, 113.66 mmol) and phosphorus oxychloride (150 mL) was heated to 90° C. for 6 h. The mixture was concentrated under vacuum. The residue was diluted with ice water and basified with saturated sodium bicarbonate aqueous solution to pH 8. The mixture was extracted with ethyl acetate. The organic layer was dried over anhydrous sodium sulfate, filtered and concentrated under vacuum to afford methyl 2-(chloromethyl)pyridine-3-carboxylate (18.00 g, crude) as a brown oil. MS m/z 186.0 [M+1]⁺.

Step 3: To a solution of methyl 2-(chloromethyl)pyridine-3-carboxylate (18.00 g, 96.97 mmol) in dichloromethane (150 mL) was added 3-chloroperoxybenzoic acid (21.00 g, 121.69 mmol, 85%) in portions at 0~10° C. The mixture was stirred at room temperature for 16 h. The reaction was quenched with saturated sodium bicarbonate aqueous solution and saturated sodium thiosulfate aqueous solution and extracted with dichloromethane. The organic layer was dried over anhydrous sodium sulfate, filtered and concentrated under vacuum to afford methyl 2-(chloromethyl)-1-oxo-1lambda5-pyridine-3-carboxylate (18.90 g, crude) as a brown oil. MS m/z 202.0 [M+1]⁺.

Step 4: A mixture of methyl 2-(chloromethyl)-1-oxo-1lambda5-pyridine-3-carboxylate (18.90 g, 93.74 mmol) and phosphorus oxychloride (200 mL) was heated to 90° C. for 16 h. The mixture was concentrated under vacuum. The residue was diluted with ice/water and basified with Sodium bicarbonate to pH 8. The mixture was extracted with ethyl acetate. The organic layer was dried over anhydrous sodium sulfate, filtered and concentrated under vacuum. The residue was purified by flash column chromatography with 0~30% ethyl acetate in petroleum ether to afford methyl 6-chloro-2-(chloromethyl)pyridine-3-carboxylate (8.50 g, 21% over 4 steps) as an orange oil. MS m/z 219.0 [M+1]⁺. ¹H NMR (400 MHz, Chloroform-d) δ 8.26 (d, J=8.4 Hz, 1H), 7.41 (d, J=8.4 Hz, 1H), 5.07 (s, 2H), 3.99 (s, 3H).

Step 5: To a solution of (4-methoxyphenyl)methanamine (2.49 g, 18.15 mmol) in tetrahydrofuran (50 mL) was added methyl 6-chloro-2-(chloromethyl) pyridine-3-carboxylate (4.0 g, 18.17 mmol). The mixture was stirred at room temperature for 4 h. The mixture was concentrated under vacuum. The residue was purified by flash column chromatography with 0~25% ethyl acetate in petroleum ether to afford 2-chloro-6-[(4-methoxyphenyl)methyl]-7H-pyrrolo[3,4-b]pyridin-5-one (2.90 g, 55%) as a yellow solid. MS m/z 289.0 [M+1]⁺.

Step 6: To a solution of 2-chloro-6-[(4-methoxyphenyl)methyl]-7H-pyrrolo[3,4-b]pyridin-5-one (5.30 g, 18.35 mmol) in tetrahydrofuran (100 mL) was added sodium hydride (1.08 g, 44.97 mmol, 60% in mineral oil) in portion at room temperature. After stirring at room temperature for 1 h, iodomethane (5.80 g, 40.93 mmol) was added slowly to above mixture. The mixture was stirred at room temperature for 16 h. The reaction mixture was diluted with ice water and extracted with ethyl acetate. The combined organic layers were washed with brine, dried over anhydrous sodium sulfate, filtered and concentrated under vacuum. The residue was purified by flash column chromatography with 0~40% ethyl acetate in petroleum ether to afford 2-chloro-6-[(4-methoxyphenyl)methyl]-7,7-dimethylpyrrolo[3,4-b]pyridin-5-one (A18) (4.30 g, 73%) as a yellow oil. MS m/z 371.0 [M+1]⁺. ¹H NMR (400 MHz, Chloroform-d) δ 8.10 (d, J=8.0 Hz, 1H), 7.43 (d, J=8.0 Hz, 1H), 7.32 (d, J=8.4 Hz, 2H), 6.86 (d, J=8.8 Hz, 2H), 4.72 (s, 2H), 3.80 (s, 3H), 1.44 (s, 6H).

Intermediate A19

2-chloro-7,7-dimethyl-6H-pyrrolo[3,4-b]pyridin-5-one

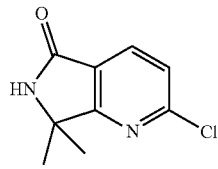

A mixture of 2-chloro-6-[(4-methoxyphenyl)methyl]-7,7-dimethylpyrrolo[3,4-b]pyridin-5-one (A18) (4.00 g, 12.62 mmol) in trifluoroacetic acid (25 mL) was stirred at 75° C. for 2 h. The mixture was concentrated under vacuum. The residue was diluted with water and basified with Sodium bicarbonate to pH 7. The mixture was extracted with dichloromethane. The combined organic layers were washed with brine, dried over anhydrous sodium sulfate, filtered and concentrated under vacuum. The residue was purified by flash column chromatography with 0~40% ethyl acetate in dichloromethane to afford 2-chloro-7,7-dimethyl-6H-pyrrolo[3,4-b]pyridin-5-one (A19) (2.10 g, 84%) as a brown solid. MS MS m/z 197.0 [M+1]⁺.

Intermediate A20

6-chloro-2-ethylpyridin-3-amine

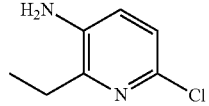

To a solution of 3-amino-2,6-dichloropyridine (300 mg, 1.85 mmol) in dioxane (3 mL) were added palladium(0) tetrakis(triphenylphosphine) (43 mg, 0.04 mmol) and aluminum triethyl (1.8 ml, 1 M in toluene). The mixture was stirred at 100° C. for 3 h under nitrogen atmosphere. The reaction was quenched by the addition of HCl (aq., 2M) and extracted with ethyl acetate. The organic layer was dried over anhydrous sodium sulfate, filtered and concentrated under vacuum. The residue was purified by flash column chromatography with 0~25% ethyl acetate in petroleum ether to afford 6-chloro-2-ethylpyridin-3-amine (A20) (70 mg, 24%) as a yellow solid. MS m/z 157.1 [M+1]$^+$.

Intermediate A21

2-chloropyrido[3,2-d]pyrimidine

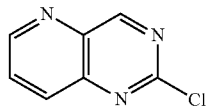 [SMILES: Clc1ncc2ncccc2n1]

To a solution of 2,4-dichloropyrido[3,2-d]pyrimidine (400 mg, 2.04 mmol) in toluene (4 mL) was added tri-n-butyltin hydride (642 mg, 2.20 mmol) at room temperature under nitrogen atmosphere. After stirring at room temperature for 30 min, Pd(triphenylphosphine)$_4$ (115 mg, 0.09 mmol) was added to above mixture. The mixture was stirred at 100° C. for 1 h. The mixture was concentrated under vacuum. The residue was purified by flash column chromatography with 0~50% ethyl acetate in petroleum ether to afford 2-chloropyrido[3,2-d]pyrimidine (A21) (300 mg, 90%) as an orange solid. MS m/z 166.0 [M+1]$^+$.

Intermediate A22

6-chloro-1,2,3,4-tetrahydro-1,7-naphthyridine

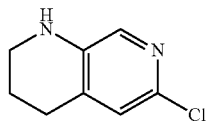 [SMILES: Clc1cc2c(cn1)NCCC2]

Step 1: To a solution of tert-butyl N-(6-chloro-4-iodopyridin-3-yl)carbamate (3.50 g, 9.87 mmol) in N,N-dimethylformamide (50 mL) were added N,N-diisopropylethylamine (0.38 g, 29.61 mmol), tri-tolylphosphine (0.30 g, 0.98 mmol), palladium acetate (0.22 g, 0.98 mmol) and ethyl acrylate (1.20 g, 11.89 mmol). The mixture was stirred at 100° C. for 16 h under nitrogen atmosphere. The reaction mixture was diluted with water and extracted with ethyl acetate. The combined organic layers were washed with brine, dried over anhydrous sodium sulfate, filtered and concentrated under reduced pressure. The residue was purified by flash column chromatography with 0~20% ethyl acetate in petroleum ether to afford ethyl (2E)-3-[5-[(tert-butoxycarbonyl)amino]-2-chloropyridin-4-yl]prop-2-enoate (0.90 g, 27%) as a yellow solid. MS m/z 327.1 [M+1]$^+$.

Step 2: To a solution of ethyl (2E)-3-[5-[(tert-butoxycarbonyl)amino]-2-chloropyridin-4-yl]prop-2-enoate (0.90 g, 2.75 mmol) in ethanol (36 mL) were added cobaltous chloride hexahydrate (0.07 g, 0.55 mmol) and sodium borohydride (0.21 g, 5.51 mmol). The mixture was stirred at room temperature for 2 h. The mixture was concentrated under vacuum. The residue was diluted with water and extracted with ethyl acetate. The combined organic layers were washed with brine, dried over anhydrous sodium sulfate, filtered and concentrated under reduced pressure. The residue was purified by flash column chromatography with 0~20% ethyl acetate in petroleum ether to afford ethyl 3-[5-[(tert-butoxycarbonyl)amino]-2-chloropyridin-4-yl]propanoate (0.80 g, 88%) as yellow solid. MS m/z 329.1 [M+1]$^+$.

Step 3: To a solution of ethyl 3-[5-[(tert-butoxycarbonyl)amino]-2-chloropyridin-4-yl]propanoate (1.00 g, 2.63 mmol) in dichloromethane (15 mL) was added trifluoroacetic acid (8 mL). The mixture was stirred at room temperature for 2 h. The mixture was concentrated under vacuum. The residue was diluted with water and basified with saturated sodium bicarbonate aqueous solution. The mixture was extracted with dichloromethane. The combined organic layers were washed with brine, dried over anhydrous sodium sulfate, filtered and concentrated under reduced pressure. The residue was purified by flash column chromatography with 0~10% methanol in dichloromethane to afford 6-chloro-3,4-dihydro-1H-1,7-naphthyridin-2-one (0.42 g, 73%) as a yellow solid. MS m/z 183.0 [M+1]$^+$.

Step 4: To a solution of 6-chloro-3,4-dihydro-1H-1,7-naphthyridin-2-one (0.20 g, 1.09 mmol) in tetrahydrofuran (5 mL) was added lithium aluminum hydride (83 mg, 2.19 mmol) slowly at 0° C. The mixture was stirred at 50° C. for 2 h. The reaction was quenched with ice water. The mixture was extracted with ethyl acetate. The combined organic layers were washed with water, dried over anhydrous sodium sulfate, filtered and concentrated under reduced pressure to afford 6-chloro-1,2,3,4-tetrahydro-1,7-naphthyridine (A22) (180, crude) as a yellow solid. MS m/z 169.0 [M+1]$^+$ Intermediate A23

1-benzyl-7-bromo-3,4-dihydro-2H-1,5-naphthyridine

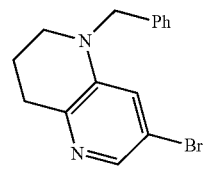 [SMILES: Brc1cnc2c(c1)N(Cc1ccccc1)CCC2]

Step 1: A mixture of 3-bromo-1,5-naphthyridine (1.00 g, 4.78 mmol) and benzyl bromide (0.82 g, 4.78 mmol) in acetonitrile was stirred at 90° C. for 16 h. The reaction mixture was concentrated under reduced pressure. The residue was purified by trituration with dichloromethane to afford 1-benzyl-7-bromo-1,5-naphthyridin-1-ium bromide (1.20 g, 66%) as a brown solid. MS m/z 379.0 [M+1]$^+$.

Step 2: To a solution of 1-benzyl-7-bromo-1,5-naphthyridin-1-ium bromide (0.40 g, 1.05 mmol) in acetic acid (5 mL) was added sodium cyanoborohydride (0.26 g, 4.21 mmol) slowly at room temperature. The mixture was stirred at room temperature for 16 h. The mixture was concentrated under reduced pressure. The residue was purified by flash column chromatography with 0~50% ethyl acetate in petroleum ether to afford 1-benzyl-7-bromo-3,4-dihydro-2H-1,5-naphthyridine (A23) (180 mg, 56%) as a yellow oil. MS m/z 303.1 [M+1]+.

Intermediate A24

2-chloropyrido[2,3-b]pyrazine

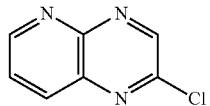 [SMILES: Clc1cnc2ncccc2n1]

Step 1: A mixture of pyridine-2,3-diamine (1.10 g, 9.98 mmol) in dioxane (10 mL) was added ethyl glyoxylate (2.04 g, 9.98 mmol, 50% in toluene). The mixture was stirred at 110° C. for 1 h. The reaction mixture was concentrated under reduced pressure. The residue was purified by flash column chromatography with 0~50% ethyl acetate in petroleum ether to afford 1H-pyrido[2,3-b]pyrazin-2-one (0.25 g, 17%) as a brown solid. MS m/z 148.0 [M+1]+. $^1$H NMR (300 MHz, DMSO-$d_6$) δ 12.87 (s, 1H), 8.54 (s, 1H), 8.22-8.18 (m, 2H), 7.38-7.34 (m, 1H).

Step 2: A mixture of 1H-pyrido[2,3-b]pyrazin-2-one (0.25 g, 1.69 mmol) in phosphorus oxychloride (5 mL) was stirred at 90° C. for 2 h. The reaction mixture was quenched with ice water. The mixture was extracted with dichloromethane. The organic layer was dried over anhydrous sodium sulfate, filtered and concentrated under vacuum to afford 2-chloropyrido[2,3-b]pyrazine (A24) (260 mg, 92%) as a brown solid. MS m/z 166.0 [M+1]+. $^1$H NMR (400 MHz, DMSO-$d_6$) δ 9.21-9.20 (m, 1H), 9.16 (s, 1H), 8.66-8.63 (m, 1H), 7.97-7.94 (m, 1H).

Intermediate A25

2-chloro-4-methyl-5,6,7,8-tetrahydro-1,5-naphthyridine

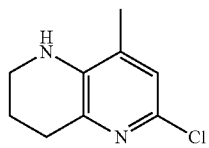

Step 1: To a solution of 6-chloro-4-methylpyridin-3-amine (5.00 g, 35.06 mmol) in N,N-dimethylformamide (50 mL) was added N-iodosuccinimide (9.47 g, 42.07 mmol) slowly at 0° C. The mixture was stirred at room temperature for 16 h. The reaction mixture was diluted with water and extracted with ethyl acetate. The combined organic layers were washed with brine, dried over anhydrous sodium sulfate, filtered and concentrated under vacuum to afford 6-chloro-2-iodo-4-methylpyridin-3-amine (7.00 g, 74%) as a brown solid. MS m/z 269.1 [M+1]+.

Step 2: To a solution of 6-chloro-2-iodo-4-methylpyridin-3-amine (7.00 g, 26.00 mmol) in N,N-dimethylformamide (120 mL) were added palladium acetate (0.60 g, 2.68 mmol), ethyl acrylate (5.37 g, 53.63 mmol), trio-tolylphosphine (0.82 g, 2.68 mmol) and N,N-diisopropylethylamine (10.36 g, 80.31 mmol). The mixture was stirred at 100° C. for 16 h under nitrogen atmosphere. The reaction mixture was diluted with water and extracted with ethyl acetate. The combined organic layers were washed with brine, dried over anhydrous sodium sulfate, filtered and concentrated under vacuum. The residue was purified by flash column chromatography with 0~80% ethyl acetate in petroleum ether to afford ethyl (2E)-3-(3-amino-6-chloro-4-methylpyridin-2-yl)prop-2-enoate (3.70 g, 57%) as a red solid. MS m/z 241.1 [M+1]+.

Step 3: To a solution of ethyl (2E)-3-(3-amino-6-chloro-4-methylpyridin-2-yl)prop-2-enoate (2.40 g, 9.97 mmol) and cobaltous chloride hexahydrate (0.47 g, 1.99 mmol) in ethanol (20 mL) was added sodium borohydride (0.76 g, 20.04 mmol) at 0° C. The mixture was stirred at room temperature for 16 h. The reaction mixture was diluted with water and extracted with ethyl acetate. The combined organic layers were washed with brine, dried over anhydrous sodium sulfate, filtered and concentrated under vacuum. The residue was purified by flash column chromatography with 0~50% ethyl acetate in petroleum ether to afford ethyl 3-(3-amino-6-chloro-4-methylpyridin-2-yl)propanoate (1.80 g, 74%) as a red solid. MS m/z 243.1 [M+1]+. $^1$H NMR (300 MHz, DMSO-$d_6$) δ 6.91 (s, 1H), 5.00 (s, 1H), 4.03 (q, J=7.2 Hz, 2H), 2.80 (t, J=7.2 Hz, 2H), 2.71-2.58 (m, 2H), 2.07 (s, 3H), 1.16 (t, J=7.2 Hz, 3H).

Step 4: A mixture of ethyl 3-(3-amino-6-chloro-4-methylpyridin-2-yl)propanoate (1.80 g, 7.41 mmol) in ethanol (20 mL) was stirred at 80° C. for 4 h. The reaction mixture was concentrated under vacuum to afford 6-chloro-8-methyl-3,4-dihydro-1H-1,5-naphthyridin-2-one (1.10 g, crude) as a red solid. MS m/z 197.2 [M+1]+.

Step 5: To a solution of 6-chloro-8-methyl-3,4-dihydro-1H-1,5-naphthyridin-2-one (100 mg, 0.50 mmol) in tetrahydrofuran (5 mL) was added lithium aluminum hydride (38 mg, 1.00 mmol) slowly at 0° C. The mixture was stirred at 50° C. for 2 h. The reaction was quenched with ice water at 0° C. The mixture was extracted with ethyl acetate. The combined organic layers were washed with water, dried over anhydrous sodium sulfate, filtered and concentrated under reduced pressure to afford 2-chloro-4-methyl-5,6,7,8-tetrahydro-1,5-naphthyridine (A24) (90 mg, crude) as a red solid. MS m/z 183.1 [M+1]+. $^1$H NMR (400 MHz, DMSO-$d_6$) δ 6.88 (s, 1H), 5.43 (s, 1H), 3.22-3.19 (m, 2H), 2.73 (t, J=6.5 Hz, 2H), 2.01 (s, 3H), 1.87-1.81 (m, 2H).

Intermediate A26 tert-butyl 4-(6-chloropyridin-3-yl)piperazine-1-carboxylate

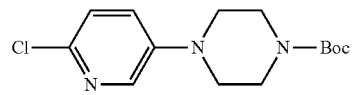 [SMILES: CC(C)(C)OC(=O)N1CCN(c2ccc(Cl)nc2)CC1]

To a solution of 5-bromo-2-chloropyridine (1.00 g, 5.20 mmol) in toluene (10 mL) were added tert-butyl piperazine-1-carboxylate (1.20 g, 6.24 mmol), tris(dibenzylideneacetone)dipalladium (0.48 g, 0.52 mmol), 9,9-dimethyl-4,5-bis(diphenylphosphino)xanthene (0.30 g, 0.52 mmol) and sodium tert-butoxide (1.00 g, 10.40 mmol). The resulting solution was stirred at 100° C. for 4 h under nitrogen atmosphere. The mixture was concentrated under vacuum. The residue was purified by flash column chromatography with 0~25% ethyl acetate in petroleum ether to afford tert-butyl 4-(6-chloropyridin-3-yl)piperazine-1-carboxylate (A26) (1.00 g, 65%) as an orange solid. MS m/z 298.1 [M+1]+.

Intermediate A27 tert-butyl 4-(2-chloropyridin-4-yl)piperazine-1-carboxylate

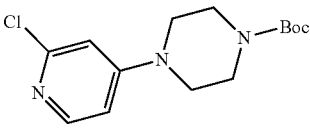 [SMILES: CC(C)(C)OC(=O)N1CCN(c2ccnc(Cl)c2)CC1]

To a solution of 2-chloro-4-fluoropyridine (1.00 g, 7.60 mmol) in N,N-dimethylformamide (8 mL) were added N,N-diisopropylethylamine (2.50 g, 19.00 mmol) and tert-butyl piperazine-1-carboxylate (1.7 g, 9.12 mmol). The mixture was stirred at 80° C. for 3 h. The reaction mixture was diluted with water and extracted with ethyl acetate. The combined organic layers were washed with brine, dried over anhydrous sodium sulfate, filtered and concentrated under vacuum. The residue was purified by trituration with petroleum ether/ethyl acetate (20/1) to afford tert-butyl 4-(2-chloropyridin-4-yl)piperazine-1-carboxylate (A27) (2.20 g, 97%) as a white solid. MS m/z 298.1 [M+1]$^+$.

Intermediate A28

1-(6-chloropyridin-2-yl)-4-methylpiperazine

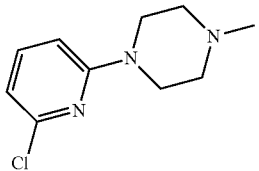

To a solution of 2-chloro-6-fluoropyridine (3.00 g, 22.81 mmol) in N,N-dimethylformamide (10 mL) were added N,N-diisopropylethylamine (8.80 g, 68.42 mmol) and 1-methylpiperazine (2.70 g, 27.37 mmol) at room temperature. The resulting solution was stirred at 100° C. overnight. The reaction mixture was diluted with water and extracted with ethyl acetate. The combined organic layers were washed with brine, dried over anhydrous sodium sulfate, filtered and concentrated under vacuum. The residue was purified by flash column chromatography with 0~10% methanol in dichloromethane to afford 1-(6-chloropyridin-2-yl)-4-methyl-piperazine (A28) (4.20 g, 87%) as a brown solid. MS m/z 212.1 [M+1]$^+$.

Intermediate A29

6-chloro-1H,2H,3H-pyrido[2,3-b][1,4]oxazine

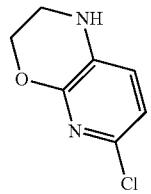 [SMILES: Clc1ccc2c(n1)OCCN2]

Step 1: To a solution of 2,6-dichloro-3-nitropyridine (5.00 g, 25.91 mmol) and ethyl 2-hydroxyacetate (2.70 g, 25.91 mmol) in N,N-dimethylformamide (100 mL) was added sodium hydride (1.24 g, 31.09 mmol, 60% in mineral oil) at 0~10° C. under nitrogen atmosphere. The reaction solution was stirred at room temperature for 5 hours. The reaction was quenched with saturated ammonium chloride aqueous solution at 0~10° C. The aqueous solution was extracted with ethyl acetate. The combined organic layers were washed with brine, dried over anhydrous sodium sulfate, filtered and concentrated under vacuum to afford ethyl 2-[(6-chloro-3-nitropyridin-2-yl)oxy]acetate (3.00 g, crude) as a brown oil. MS m/z 261.1 [M+1]$^+$.

Step 2: To a solution of ethyl 2-[(6-chloro-3-nitropyridin-2-yl)oxy]acetate (3.00 g, crude from step 1) in methanol (100 mL) and water (50 mL) were added ammonium chloride (3.69 g, 69.06 mmol) and iron powder (1.90 g, 33.92 mmol). The mixture was heated to 70° C. and stirred for 10 hours. The solids were filtered off. The filtrate was diluted by ethyl acetate and then washed with brine. The organic layer was dried over anhydrous sodium sulfate, filtered and concentrated under vacuum. The residue was purified by flash column chromatography with 0~100% ethyl acetate in petroleum ether to afford 6-chloro-1H,3H-pyrido[2,3-b][1,4]oxazin-2-one (1.30 g, 27% over 2 steps) as a grey solid. MS m/z 185.2 [M+1]$^+$. $^1$H NMR (400 MHz, DMSO-d$_6$) δ 10.95 (s, 1H), 7.26 (d, J=8.0 Hz, 1H), 7.10 (d, J=8.0 Hz, 1H), 4.82 (s, 2H).

Step 3: To a solution of 6-chloro-1H,3H-pyrido[2,3-b][1,4]oxazin-2-one (1.20 g, 6.50 mmol) in tetrahydrofuran (20 mL) were added boron trifluoride ether complex (2.77 g, 19.50 mmol) and sodium borohydride (0.74 g, 19.50 mmol) at 0~5° C. The mixture was stirred at room temperature for 3 hours. The reaction mixture was quenched with water and extracted with ethyl acetate. The combined organic layers were washed with brine, dried over anhydrous sodium sulfate, filtered and concentrated under vacuum to afford 6-chloro-1H,2H,3H-pyrido[2,3-b][1,4]oxazine (A29) (1.00 g, 90%) as a white solid. MS m/z 171.2 [M+1]$^+$.

Intermediate A30

6-chloro-3-methyl-1H,2H,3H-pyrido[2,3-b][1,4]oxazine

Followed the procedure of Intermediate A29 described above to afford 6-chloro-3-methyl-1H,2H,3H-pyrido[2,3-b][1,4]oxazine (A30) (0.54 g, 32% over 3 steps) as an off-white solid from 2,6-dichloro-3-nitro-pyridine. MS m/z 185.0 [M+1]$^+$.

Intermediate A31

2-(6-chloropyridin-3-yl)propan-2-ol

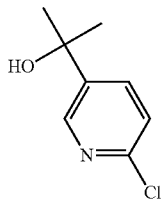

To a solution of ethyl 6-chloropyridine-3-carboxylate (2.00 g, 10.78 mmol) in tetrahydrofuran (30 mL) was added methylmagnesium bromide (20 mL, 40.00 mmol, 2M in tetrahydrofuran) dropwise at −30° C. under nitrogen atomosphere. The resulting solution was stirred at −30° C. for 4 h. The reaction was quenched with water. The aqueous phase was extracted with ethyl acetate. The combined organic layers were washed with brine, dried over anhydrous sodium sulfate, filtered and concentrated under vacuum. The residue was purified by flash column chromatography with 0~80% ethyl acetate in petroleum ether to afford 2-(6-chloropyridin-3-yl)propan-2-ol (A31) (0.70 g, 37%) as a white solid. MS m/z 172.0 [M+1]$^+$. $^1$H NMR (400 MHz, DMSO-d$_6$) δ 8.50 (dd, J=2.4, 0.8 Hz, 1H), 7.91 (dd, J=8.4, 2.4 Hz, 1H), 7.44 (dd, J=8.4, 0.8 Hz, 1H), 5.32 (s, 1H), 1.45 (s, 6H).

Intermediate A32

6-chloro-2H,3H,4H-pyrido[3,2-b][1,4]oxazine

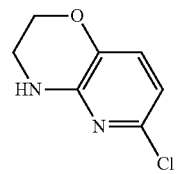

Step 1: A mixture of 3-bromo-6-chloro-2-fluoropyridine (3.00 g, 14.26 mmol), ethanolamine (0.96 g, 15.68 mmol) and N,N-diisopropylethylamine (3.69 g, 28.51 mmol) in N,N-dimethylformamide (30 ml) was stirred at room temperature for 16 h. The mixture was diluted with water and extracted with ethyl acetate. The organic layer was washed by water. The organic layer was dried over anhydrous sodium sulfate, filtered and concentrated under vacuum. The residue was purified by flash column chromatography with 0~80% ethyl acetate in petroleum ether to afford 2-[(3-bromo-6-chloropyridin-2-yl)amino]ethanol (3.00 g, 83%) as a yellow solid. MS m/z 251.0 [M+1]$^+$. $^1$H NMR (400 MHz, DMSO-d$_6$) δ 7.74 (d, J=8.0 Hz, 1H), 6.54-6.48 (m, 2H), 4.78 (t, J=5.4 Hz, 1H), 3.53 (q, J=6.0 Hz, 2H), 3.40-3.28 (m, 2H).

Step 2: A mixture of 2-[(3-bromo-6-chloropyridin-2-yl) amino]ethanol (0.50 g, 1.99 mmol), [1,1-biphenyl]-2-yldi-tert-butyl)phosphane (0.06 g, 0.20 mmol), palladium acetate (0.04 g, 0.20 mmol) and cesium carbonate (1.30 g, 3.98 mmol) in toluene (6 ml) was heated to 110° C. and stirred for 16 h under nitrogen atmosphere. The resulting mixture was concentrated under reduced pressure. The residue was purified by flash column chromatography with 0~100% ethyl acetate in petroleum ether to afford 6-chloro-2H,3H,4H-pyrido[3,2-b][1,4]oxazine (A32) (170 mg, 50%) as a light yellow solid. MS m/z 171.0 [M+1]$^+$.

Intermediate A33

6-chloro-4-methyl-2H,3H-pyrido[3,2-b][1,4]oxazine

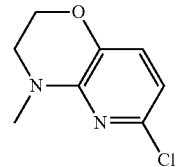

Followed the procedure of Intermediate A32 described above to afford 6-chloro-4-methyl-2H,3H-pyrido-[3,2-b][1,4]oxazine (A33) (200 mg, 27% over 2 steps) as a yellow oil from 3-bromo-6-chloro-2-fluoropyridine. MS m/z 185.1 [M+1]$^+$.

Intermediate A34

6-chloro-4-isopropyl-2H,3H-pyrido[3,2-b][1,4]oxazine

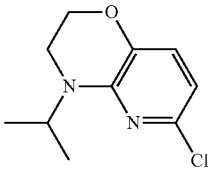

To a mixture of 6-chloro-2H,3H,4H-pyrido[3,2-b][1,4] oxazine (230 mg, 1.35 mmol) in N,N-dimethylformamide (5 mL) was added sodium hydride (49 mg, 1.22 mmol, 60% in mineral oil) at 0° C. After stirring at 0° C. for 30 min, 2-iodopropane (344 mg, 2.00 mmol) was added to the above mixture. The mixture was stirred at room temperature for 16 h. The reaction was quenched with water and extracted with ethyl acetate. The combined organic layers were washed with water, dried over anhydrous sodium sulfate. After filtration, the filtrate was concentrated under reduced pressure. The residue was purified by flash column chromatography with 0~100% ethyl acetate in petroleum ether to afford 6-chloro-4-isopropyl-2H,3H-pyrido[3,2-b][1,4]oxazine (A34) (210 mg, 73%) as a yellow solid. MS m/z 213.2 [M+1]$^+$.

Intermediate A35 tert-butyl N-[6-chloro-2-(prop-1-en-2-yl)pyridin-3-yl]carbamate

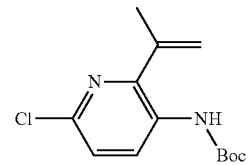

Step 1: To a solution of 6-chloropyridin-3-amine (10.00 g, 77.79 mmol) in ethanol (100 mL) were added iodine (29.61 g, 116.68 mmol) and silver sulfate (12.13 g, 38.89 mmol). The mixture was stirred at room temperature for 16 h. The aqueous solution was diluted with water and extracted with ethyl acetate. The combined organic layers were washed with brine, dried over anhydrous sodium sulfate, filtered and concentrated under vacuum. The residue was purified by flash column chromatography with 0~30% ethyl acetate in petroleum ether to afford 6-chloro-2-iodopyridin-3-amine (8.00 g, 40%) as a red solid. MS m/z 254.9 [M+1]$^+$. $^1$H NMR (400 MHz, Methanol-d$_4$) δ 7.15-7.08 (m, 1H), 7.04 (d, J=8.4 Hz, 1H).

Step 2: To a solution of 6-chloro-2-iodopyridin-3-amine (3.00 g, 11.79 mmol) in tetrahydrofuran (15 mL) were added triethylamine (1.19 g, 11.79 mmol), 4-dimethylaminopyridine (0.14 g, 1.18 mmol) and di(tert-butyl) carbonate (3.86 g, 17.69 mmol) at room temperature. The mixture was stirred at room temperature for 16 h. The mixture was concentrated under vacuum. The residue was purified by flash column chromatography with 0~40% ethyl acetate in petroleum ether to afford tert-butyl N-(6-chloro-2-iodopyridin-3-yl)carbamate (2.70 g, 64%) as a white solid. MS m/z 354.9 [M+1]$^+$.

Step 3: To a solution of tert-butyl N-(6-chloro-2-iodopyridin-3-yl)carbamate (0.50 g, 1.41 mmol) in dioxane (4 mL) and water (0.4 mL) were added 4,4,5,5-tetramethyl-2-(prop-1-en-2-yl)-1,3,2-dioxaborolane (0.24 g, 1.41 mmol), [1,1'-bis(diphenylphosphino)ferrocene]-dichloropalladium(II) (0.10 g, 0.14 mmol) and potassium carbonate (0.39 g, 2.80 mmol) at room temperature. The mixture was heated to 80° C. and stirred for 5 h. The mixture was concentrated under vacuum. The residue was purified by flash column chromatography with 0~50% ethyl acetate in petroleum ether to afford tert-butyl N-[6-chloro-2-(prop-1-en-2-yl)pyridin-3-yl]carbamate (A35) (0.14 mg, 37%) as a yellow oil. MS m/z 269.1 [M+1]$^+$.

Intermediate A36

6-chloro-2-isopropoxy-3-nitropyridine

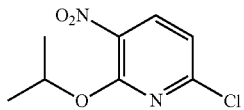

To a solution of propan-2-ol (234 mg, 3.89 mmol) in tetrahydrofuran (4 mL) was added sodium hydride (155 mg, 3.89 mmol, 60% in mineral oil). After stirring at room temperature for 1 h, 2,6-dichloro-3-nitropyridine (500 mg, 2.59 mmol) was added to above mixture. The mixture was stirred at room temperature for 5 h. The reaction was quenched using saturated ammonium chloride aqueous solution and extracted with ethyl acetate. The organic layer was dried over anhydrous sodium sulfate, filtered and concentrated under vacuum. The residue was purified by flash column chromatography with 0~50% ethyl acetate in petroleum ether to afford 6-chloro-2-isopropoxy-3-nitropyridine (A36) (325 mg, 58%) as a white solid. MS m/z 217.1 [M+1]$^+$. $^1$H NMR (400 MHz, DMSO-d$_6$) δ 8.47 (d, J=8.0 Hz, 1H), 7.30 (d, J=8.0 Hz, 1H), 5.48-5.27 (m, 1H), 1.42-1.31 (d, J=7.2 Hz, 6H).

Intermediate A37

6-chloro-2-ethoxy-3-nitropyridine

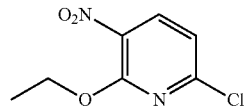

A solution of 2,6-dichloro-3-nitropyridine (1.00 g, 5.18 mmol) and sodium ethoxide (0.35 g, 5.18 mmol) in tetrahydrofuran (10 mL) was stirred at room temperature for 13 h. The mixture was diluted with water and extracted with ethyl acetate. The combined organic layers were washed with brine, dried over anhydrous sodium sulfate, filtered and concentrated under vacuum. The residue was purified by flash column chromatography with 0~30% ethyl acetate in petroleum ether to afford 6-chloro-2-ethoxy-3-nitropyridine (A37) (845 mg, 80%) as a yellow oil. MS m/z 203.6 [M+1]$^+$. $^1$H NMR (400 MHz, DMSO-d$_6$) δ 8.48 (d, J=8.4 Hz, 1H), 7.30 (d, J=8.4 Hz, 1H), 4.48 (q, J=7.0 Hz, 2H), 1.37 (t, J=7.0 Hz, 3H).

Intermediate A38

6-chloro-2-methoxy-3-nitropyridine

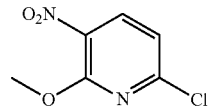

To a solution of 2,6-dichloro-3-nitropyridine (3.00 g, 15.55 mmol) in tetrahydrofuran (30 mL) was added sodium methylate (0.84 g, 15.55 mmol). The mixture was stirred at room temperature for 13 h. The mixture was diluted with water and extracted with ethyl acetate. The combined organic layers were washed with brine, dried over anhydrous sodium sulfate, filtered and concentrated under vacuum. The residue was purified by flash column chromatography with 0~30% ethyl acetate in petroleum ether to afford 6-chloro-2-methoxy-3-nitropyridine (A38) (1.20 g, 41%) as a white solid. MS m/z 189.0 [M+1]$^+$. $^1$H NMR (400 MHz, DMSO-d6) δ 8.51 (d, J=8.4 Hz, 1H), 7.36 (d, J=8.4 Hz, 1H), 4.04 (s, 3H).

Intermediate A39

N-(6-chloro-2-methylpyridin-3-yl)acetamide

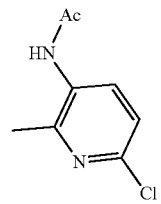

To a solution of 6-chloro-2-methylpyridin-3-amine (500 mg, 3.51 mmol) and triethylamine (710 mg, 7.01 mmol) in dichloromethane (5 mL) was added acetic anhydride (430 mg, 4.21 mmol) at 0° C. The mixture was stirred at 0° C. for 5 h. The mixture was concentrated under vacuum. The residue was purified by flash column chromatography with 0~70% ethyl acetate in petroleum ether to afford N-(6-chloro-2-methylpyridin-3-yl)-acetamide (A39) (600 mg, 92%) as a white solid. MS m/z 184.1 [M+1]$^+$.

Intermediate A40

N-(6-chloro-2-methylpyridin-3-yl)-N-methylacetamide

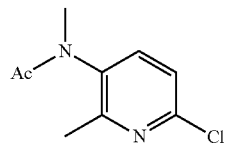

Step 1: A mixture of 6-chloro-2-methylpyridin-3-amine (1.00 g, 7.01 mmol) in trimethyl orthoformate (1.86 g, 17.53 mmol) was stirred at 145° C. for 30 min. The mixture was cooled to room temperature and concentrated under vacuum. The residue was dissolved in ethanol (10 mL). sodium borohydride (265 mg, 7.01 mmol) was added to above mixture at room temperature. The mixture was heated to 80° C. and stirred for 1 h. The mixture was diluted with water and extracted with ethyl acetate. The combined organic layers were washed with brine, dried over anhydrous sodium sulfate, filtered and concentrated under vacuum. The residue was purified by flash column chromatography with 0~50% ethyl acetate in petroleum ether to afford 6-chloro-N,2-dimethylpyridin-3-amine (820 mg, 74%) as a yellow oil. MS m/z 157.1 [M+1]$^+$.

Step 2: To a solution of 6-chloro-N,2-dimethylpyridin-3-amine (400 mg, 2.55 mmol) and triethylamine (516 mg, 5.10 mmol) in dichloromethane (4 mL) was added acetic anhydride (312 mg, 3.06 mmol) at 0° C. The mixture stirred at 0° C. for 2 h. The mixture was concentrated under vacuum. The residue was purified by flash column chromatography with 0~5% ethyl acetate in petroleum ether to afford N-(6-chloro-2-methylpyridin-3-yl)-N-methylacetamide (270 mg, 53%) as a light yellow oil. MS m/z 199.1 [M+1]$^+$. $^1$H NMR (400 MHz, DMSO-d$_6$) δ 7.83 (d, J=8.4 Hz, 1H), 7.47 (d, J=8.2 Hz, 1H), 3.05 (s, 3H), 2.37 (s, 3H), 1.68 (s, 3H).

Intermediate A41

6-bromo-N,N,2-trimethylpyridin-3-amine

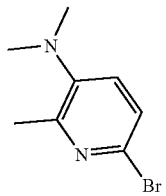

To a solution of 6-bromo-2-methylpyridin-3-amine (500 mg, 2.67 mmol) in tetrahydrofuran (5 mL) was added lithium bis(trimethylsilyl)amide (5.8 mL, 5.80 mmol, 1M in tetrahydrofuran) at −78° C. After stirring at −78° C. for 20 min, iodomethane (948 mg, 6.68 mmol) was added slowly to above mixture at −78° C. The mixture was warmed up to room temperature for 1 h. The reaction was quenched with water/ice and extracted with ethyl acetate. The combined organic layers were washed with water, dried over anhydrous sodium sulfate. After filtration, the filtrate was concentrated under reduced pressure. The residue was purified by flash column chromatography with 0~60% ethyl acetate in petroleum ether to afford 6-bromo-N,N,2-trimethylpyridin-3-amine (A41) (400 mg, 69%) as a white solid. MS m/z 215.1 [M+1]$^+$. $^1$H NMR (400 MHz, DMSO-d$_6$) δ 7.35 (d, J=1.2 Hz, 2H), 2.64 (s, 6H), 2.41 (s, 3H).

Intermediate A42

2-chloro-6-[(4-methoxyphenyl)methyl]-7-methyl-7H-pyrrolo[3,4-b]pyridin-5-one

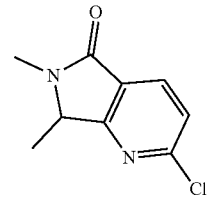

A mixture of methyl 2-(1-bromoethyl)-6-chloropyridine-3-carboxylate (830 mg, 2.98 mmol) and MeNH$_2$ (10 mL, 2M in tetrahydrofuran) was stirred at room temperature for 16 h. The mixture was diluted by ethyl acetate and washed with water. The organic layer was dried over anhydrous sodium sulfate, filtered and concentrated under vacuum to afford 2-chloro-6-[(4-methoxyphenyl)methyl]-7-methyl-7H-pyrrolo[3,4-b]pyridin-5-one (A42) (480 mg, 53%) as a yellow solid. MS m/z 197.0 [M+1]$^+$.

Intermediate A43

5-bromo-3-methyl-2,3-dihydroisoindol-1-one

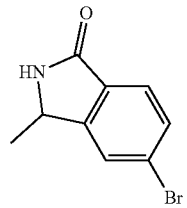

Step 1: To a solution of 4-bromo-2-ethylbenzoic acid (1.00 g, 4.36 mmol) in dichloromethane (10 mL) and methanol (1 mL) was added (trimethylsilyl)diazomethane (0.8 mL, 2.0 M in hexane) under nitrogen atmosphere at 0° C. The resulting solution was stirred at 0° C. for 2 h. The reaction was quenched by the addition of water at room temperature. The mixture was extracted with ethyl acetate. The organic layer was dried over anhydrous sodium sulfate, filtered and concentrated under vacuum. The residue was purified by flash column chromatography with 0~10% ethyl acetate in petroleum ether to afford to afford methyl 4-bromo-2-ethylbenzoate (950 mg, 89%) as yellow oil. MS m/z 243.0 [M+1]$^+$.

Step 2: To a solution of methyl 4-bromo-2-ethylbenzoate (300 mg, 1.23 mmol) in carbon tetrachloride (6 mL) were added azodiisobutyronitrile (40 mg, 0.2 mmol) and N-bromosuccinimide (219 mg, 1.2 mmol). The mixture was stirred at 80° C. overnight. The solids were filtered off. The filtrate was concentrated under vacuum to afford 4-bromo-2-(1-bromoethyl)benzoate (390 mg, curde) as a yellow oil. MS m/z 320.9 [M+1]$^+$. $^1$H NMR (400 MHz, Chloroform-d) δ 7.96 (d, J=2.0 Hz, 1H), 7.74 (d, J=8.4 Hz, 1H), 7.48 (dd, J=8.4, 2.0 Hz, 1H), 6.28 (q, J=6.8 Hz, 1H), 3.94 (s, 3H), 2.04 (d, J=6.8 Hz, 3H).

Step 3: A mixture of methyl 4-bromo-2-(1-bromoethyl)benzoate (300 mg, 0.93 mmol) and ammonia (7M in methanol) (8 mL) was stirred at 50° C. for 2 h. The mixture was concentrated under vacuum. The residue was purified by flash column chromatography with 0~50% ethyl acetate in petroleum ether to afford 5-bromo-3-methyl-2,3-dihydroisoindol-1-one (A43) (210 mg, 75% over 2 steps) as a yellow solid. MS m/z 226.0 [M+1]$^+$.

Intermediate A44 tert-butyl 6-bromo-1,1-dimethyl-3-oxoisoindole-2-carboxylate

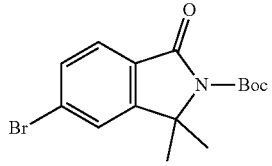 [SMILES: CC(C)(C)OC(=O)N1C(=O)c2ccc(Br)cc2C1(C)C]

Step-1: A mixture of methyl 4-bromo-2-(bromomethyl)benzoate (5.00 g, 16.34 mmol) and ammonia (g) (7M in methanol) (20 mL) was stirred at 50° C. for 2 h. The resulting mixture was concentrated under vacuum. The residue was purified by flash column chromatography with 0~10% methanol in dichloromethane to afford 5-bromo-2,3-dihydroisoindol-1-one (3.40 g, 98%) as a yellow solid. MS m/z 212.0 [M+1]$^+$.

Step-2: To a solution of 5-bromo-2,3-dihydroisoindol-1-one (3.40 g, 16.03 mmol) in dichloromethane (20 mL) were added di(tert-butyl) carbonate (4.20 g, 19.24 mmol), triethylamine (4.87 g, 48.10 mmol) and 4-dimethylaminopyridine (0.19 g, 1.60 mmol). The resulting solution was stirred at 50° C. overnight. The mixture was concentrated under vacuum. The residue was purified by flash column chromatography with 0~25% ethyl acetate in petroleum ether to afford tert-butyl 5-bromo-1-oxo-3H-isoindole-2-carboxylate (3.00 g, 60%) as a white solid. MS m/z 312.0 [M+1]$^+$.

Step-3: To a degassed solution of tert-butyl 5-bromo-1-oxo-3H-isoindole-2-carboxylate (0.40 g, 1.28 mmol) in tetrahydrofuran (4 mL) was added lithium bis(trimethylsilyl)amide (1.9 mL, 3.80 mmol, 2 M in tetrahydrofuran) under nitrogen atmosphere at −78° C. After stirring at −78° C. for 1 h, iodomethane (400 mg, 2.81 mmol) was added to above mixture. The resulting solution was stirred at −78° C. for 2 h. The reaction was then quenched using water and extracted with ethyl acetate. The organic layer was dried over anhydrous sodium sulfate, filtered and concentrated under vacuum. The residue was purified by flash column chromatography with 0~20% ethyl acetate in petroleum ether to afford tert-butyl 6-bromo-1,1-dimethyl-3-oxoisoindole-2-carboxylate (A44) (170 mg, 39%) as a yellow solid. MS m/z 340.0 [M+1]$^+$. $^1$H NMR (400 MHz, DMSO-d$_6$) δ 8.11 (d, J=1.6 Hz, 1H), 7.74 (dd, J=8.0, 1.6 Hz, 1H), 7.68 (d, J=8.0 Hz, 1H), 1.69 (s, 6H), 1.54 (s, 9H).

Intermediate A45

2-chloro-5-(oxetan-3-yl)pyridine

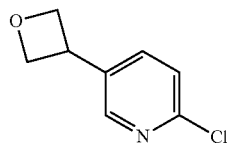 [SMILES: Clc1ccc(C2COC2)cn1]

A mixture of 6-chloropyridin-3-ylboronic acid (300 mg, 1.91 mmol), 3-iodooxetane (175 mg, 0.95 mmol), nickel(II) iodide (18 mg, 0.06 mmol), (1S,2S)-2-aminocyclohexan-1-ol (7 mg, 0.06 mmol) and lithium bis(trimethylsilyl)amide (1.9 mL, 3.80 mmol, 2M in tetrahydrofuran) in 2-propanol was stirred at 100° C. for 16 h under nitrogen atmosphere. The resulting mixture was diluted with water and extracted with ethyl acetate. The organic layer was dried over anhydrous sodium sulfate, filtered and concentrated under reduced pressure. The residue was purified by flash column chromatography with 0~100% ethyl acetate in petroleum ether to afford 2-chloro-5-(oxetan-3-yl)pyridine (A45) (90 mg, 27%) as a light yellow oil. MS m/z 170.0 [M+1]$^+$.

Intermediate A46 tert-butyl N-(6-chloro-2-cyclopropylpyridin-3-yl)carbamate

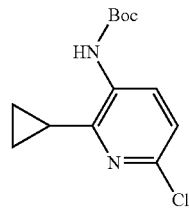 [SMILES: CC(C)(C)OC(=O)Nc1ccc(Cl)nc1C1CC1]

Step 1: To a solution of 6-chloro-2-iodopyridin-3-amine (1.00 g, 3.93 mmol), di(tert-butyl) carbonate (1.79 g, 7.86 mmol) and triethylamine (1.19 g, 11.79 mmol) in dichloromethane (10 mL) was added 4-dimethylaminopyridine (0.05 g, 0.39 mmol). The resulting solution was stirred at room temperature overnight. The mixture was concentrated under vacuum. The residue was purified by flash column chromatography with 0~60% ethyl acetate in petroleum ether to afford tert-butyl N-(6-chloro-2-iodopyridin-3-yl)carbamate (0.67 g, 49%) as a light yellow solid. MS m/z 354.9 [M+1]$^+$.

Step 2: To a degassed solution of tert-butyl N-(6-chloro-2-iodopyridin-3-yl)carbamate (0.67 g, 1.89 mmol), cyclopropylboronic acid (0.16 g, 1.89 mmol) and potassium carbonate (0.52 g, 3.78 mmol) in dioxane (5 mL) and water (0.5 mL) was added [1,1′-bis(diphenylphosphino)ferrocene]

dichloropalladium(II) (0.14 g, 0.19 mmol). The resulting solution was stirred at 100° C. overnight. The mixture was concentrated under vacuum. The residue was purified by flash column chromatography with 0~70% ethyl acetate in petroleum ether to afford tert-butyl N-(6-chloro-2-cyclopropylpyridin-3-yl)carbamate (A46) (300 mg, 59%) as a light yellow solid. MS m/z 269.1 [M+1]$^+$. $^1$H NMR (400 MHz, DMSO-d$_6$) δ 9.06 (s, 1H), 7.73 (d, J=8.4 Hz, 1H), 7.19 (d, J=8.4 Hz, 1H), 2.27-2.23 (m, 1H), 1.47 (s, 9H), 1.04-0.76 (m, 4H).

Intermediate A47

6-chloro-N-ethyl-2-methylpyridin-3-amine

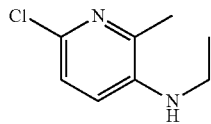

A mixture of 6-chloro-2-methylpyridin-3-amine (500 mg, 3.51 mmol), acetaldehyde (185 mg, 4.20 mmol) and acetic acid (21 mg, 0.35 mmol) in tetrahydrofuran was stirred at 60° C. for 3 h. The mixture was cooled down to room temperature and sodium borohydride (133 mg, 3.51 mmol) was added. The mixture was stirred at room temperature for 16 h. The reaction was quenched with water and extracted with ethyl acetate. The combined organic layers were washed with brine, dried over anhydrous sodium sulfate, filtered and concentrated under vacuum. The residue was purified by flash column chromatography with 0~100% ethyl acetate in petroleum ether to afford 6-chloro-N-ethyl-2-methylpyridin-3-amine (A47) (70 mg, 11%) as a yellow solid. MS m/z 171.1 [M+1]$^+$.

Intermediate A48 tert-butyl 3-bromo-7-cyano-2-methylindole-1-carboxylate

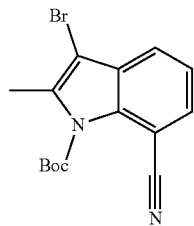 [SMILES: Cc1c(Br)c2cccc(C#N)c2n1C(=O)OC(C)(C)C]

Step 1: To a solution of 1H-indole-7-carbonitrile (1.00 g, 7.03 mmol) in dichloromethane (20 mL) were added triethylamine (1.50 g, 14.82 mmol), 4-dimethylaminopyridine (0.06 g, 0.49 mmol) and di(tert-butyl) carbonate (3.10 g, 14.20 mmol) at room temperature. The mixture was stirred at room temperature for 16 h. The reaction mixture was concentrated under vacuum. The residue was purified by flash column chromatography with 0~20% ethyl acetate in petroleum ether to afford tert-butyl 7-cyanoindole-1-carboxylate (1.60 g, 93%) as a white solid. MS m/z 243.2 [M+1]$^+$ Step 2: To a solution of tert-butyl 7-cyanoindole-1-carboxylate (1.20 g, 4.95 mmol) in tetrahydrofuran (20 mL) was added butyl lithium (2 mL, 5.00 mmol, 2.5M in hexane) slowly at −78° C. After stirring at −78° C. for 1 h, iodomethane (1.10 g, 7.75 mmol) was added slowly to above mixture. The mixture was warmed slowly at room temperature for 2 h. The reaction mixture was quenched using saturated ammonium chloride aqueous solution and extracted with ethyl acetate. The organic layer was dried over anhydrous sodium sulfate, filtered and concentrated under vacuum. The residue was purified by flash column chromatography with 0~20% ethyl acetate in petroleum ether to afford tert-butyl 7-cyano-2-methylindole-1-carboxylate (0.6 g, 48%) as a yellow oil. MS m/z 257.1 [M+1]$^+$. $^1$H NMR (400 MHz, DMSO-d$_6$) δ 7.85 (dd, J=7.8, 1.2 Hz, 1H), 7.68 (dd, J=7.8, 1.2 Hz, 1H), 7.33 (t, J=7.8 Hz, 1H), 6.60 (d, J=1.2 Hz, 1H), 2.52 (s, 3H), 1.65 (s, 9H).

Step 3: To a solution of tert-butyl 7-cyano-2-methylindole-1-carboxylate (0.60 g, 2.34 mmol) in dichloromethane (5 mL) was added trifluoroacetic acid (1 mL) at room temperature. The mixture was stirred at room temperature for 3 h. The reaction mixture was concentrated under vacuum. The residue was basified with saturated sodium bicarbonate aqueous solution and extracted with ethyl acetate. The organic layer was dried over anhydrous sodium sulfate, filtered and concentrated under vacuum to afford 2-methyl-1H-indole-7-carbonitrile (0.38 g, crude) yellow solid. MS m/z 157.0 [M+1]$^+$ Step 4: To a solution of 2-methyl-1H-indole-7-carbonitrile (0.38 g, 2.43 mmol) in tetrahydrofuran (5 mL) was added N-bromosuccinimide (0.43 g, 2.45 mmol). The mixture was stirred at room temperature for 4 h. The reaction mixture was diluted with water and extracted with ethyl acetate. The organic layer was dried over anhydrous sodium sulfate, filtered and concentrated under vacuum to afford 3-bromo-2-methyl-1H-indole-7-carbonitrile (470 mg, crude) as a yellow solid. MS m/z 235.0 [M+1]$^+$.

Step 5: To a solution of 3-bromo-2-methyl-1H-indole-7-carbonitrile (0.47 g, 1.99 mmol) in dichloromethane (10 mL) were added triethylamine (0.63 g, 6.25 mmol), 4-dimethylaminopyridine (0.03 g, 0.21 mmol) and di(tert-butyl) carbonate (0.91 g, 4.17 mmol). The mixture was stirred at room temperature for 16 h. The reaction mixture was concentrated under vacuum. The residue was purified by flash column chromatography with 0-15% ethyl acetate in petroleum ether to afford tert-butyl 3-bromo-7-cyano-2-methylindole-1-carboxylate (A48) (0.26 g, 33% over 3 steps) as a white solid. MS m/z 335.0 [M+1]$^+$. $^1$H NMR (400 MHz, DMSO-d$_6$) δ 7.84 (dd, J=7.8, 1.2 Hz, 1H), 7.78 (dd, J=7.8, 1.2 Hz, 1H), 7.47 (t, J=7.8 Hz, 1H), 2.57 (s, 3H), 1.66 (s, 9H).

Intermediate A49

2-chloro-6,7,7-trimethylpyrrolo[3,4-b]pyridin-5-one

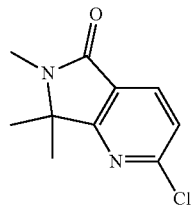

To a solution of 2-chloro-7,7-dimethyl-6H-pyrrolo[3,4-b]pyridin-5-one (50 mg, 0.25 mmol) in tetrahydrofuran (2 mL) was added sodium hydride (9 mg, 0.38 mmol, 60% in mineral oil) at 0° C. After stirring at 0° C. for 0.5 h, iodomethane (54 mg, 0.38 mmol) was added to above mixture. The reaction solution was stirred at room temperature for 2 h. The reaction mixture was quenched using water and extracted with ethyl acetate. The combined organic layers were washed with brine, dried over anhydrous sodium sulfate, filtered and concentrated under vacuum. The residue was purified by flash column chromatography with 0~20% ethyl acetate in petroleum ether to afford 2-chloro-6,7,7-trimethylpyrrolo[3,4-b]pyridin-5-one (A49) (50 mg, 93%) as a yellow solid. MS m/z 211.0 [M+1]$^+$.

Intermediate A50

2-chloro-6-(2-methoxyethyl)-7,7-dimethylpyrrolo[3,4-b]pyridin-5-one

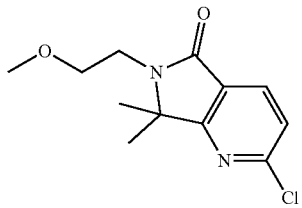 [SMILES: COCCN1C(=O)c2ccc(Cl)nc2C1(C)C]

To a solution of 2-chloro-7,7-dimethyl-6H-pyrrolo[3,4-b]pyridin-5-one (200 mg, 1.02 mmol) in tetrahydrofuran (3 mL) was added sodium hydride (120 mg, 5.00 mmol, 60% in mineral oil) slowly at room temperature. After stirring at room temperature for 30 min, 2-bromoethyl methyl ether (212 mg, 1.53 mmol) was added. The mixture was stirred at 55° C. overnight. The reaction was quenched using water and extracted with ethyl acetate. The combined organic layers were washed with brine, dried over anhydrous sodium sulfate, filtered and concentrated under vacuum. The residue was purified by flash column chromatography with 0~50% ethyl acetate in petroleum ether to afford 2-chloro-6-(2-methoxyethyl)-7,7-dimethylpyrrolo[3,4-b]-pyridin-5-one (A50) (100 mg, 39%) as yellow oil. MS m/z 254.1 [M+1]$^+$.

Intermediate A51

2-chloro-7,7-dimethyl-6-(oxolan-3-yl)pyrrolo[3,4-b]pyridin-5-one

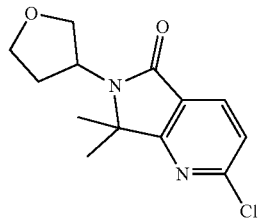 [SMILES: CC1(C)c2nc(Cl)ccc2C(=O)N1C1CCOC1]

Step 1: A mixture of methyl 6-chloro-2-(chloromethyl)pyridine-3-carboxylate (1.00 g, 4.54 mmol) and oxolan-3-amine (0.59 mg, 6.84 mmol 4) in tetrahydrofuran (5 ml) was stirred for 16 h at 50° C. The resulting mixture was concentrated under reduced pressure. The residue was purified by flash column chromatography with 0~100% ethyl acetate in petroleum ether to afford 2-chloro-6-(oxolan-3-yl)-7H-pyrrolo[3,4-b]pyridin-5-one (0.62 g, 57%) as a yellow solid. MS m/z 239.1 [M+1]$^+$.

Step 2: To a mixture of 2-chloro-6-(oxolan-3-yl)-7H-pyrrolo[3,4-b]pyridin-5-one (0.25 g, 1.05 mmol) in tetrahydrofuran (5 mL) was added sodium hydride (63 mg, 2.62 mmol, 60% in mineral oil). After stirring at room temperature for 0.5 h, iodomethane (0.33 g, 2.30 mmol) was added at room temperature. The mixture was stirred at room temperature for 16 h. The reaction was quenched using water and extracted with ethyl acetate. The combined organic layers were washed with brine, dried over anhydrous sodium sulfate, filtered and concentrated under vacuum. The residue was purified by flash column chromatography with 0~80% ethyl acetate in petroleum ether to afford 2-chloro-7,7-dimethyl-6-(oxolan-3-yl)pyrrolo[3,4-b]pyridin-5-one (A51) (0.25 g, 89%) as a light yellow solid. MS m/z 267.1 [M+1]$^+$.

Intermediate A52 tert-butyl 7-acetyl-3-bromoindole-1-carboxylate

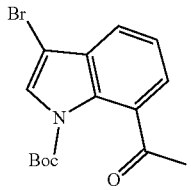 [SMILES: CC(=O)c1cccc2c(Br)cn(C(=O)OC(C)(C)C)c12]

Step 1: A mixture of 1H-indole-7-carbonitrile (1.00 g, 7.03 mmol) and N-bromosuccinimide (1.30 g, 7.02 mmol) in tetrahydrofuran (10 ml) was stirred for 16 h at room temperature. The resulting mixture was concentrated under reduced pressure. The residue was purified by flash column chromatography with 0~80% ethyl acetate in petroleum ether to afford 3-bromo-1H-indole-7-carbonitrile (1.40 g, 94%) as a white solid. MS m/z 221.0 [M+1]$^+$.

Step 2: To a mixture of 3-bromo-1H-indole-7-carbonitrile (1.00 g, 4.52 mmol) in tetrahydrofuran (10 ml) was added and methylmagnesium bromide (13.6 mL, 13.60 mmol, 1M in tetrahydrofuran) at 0° C. The mixture was warmed slowly to room temperature for 16 h. The reaction was quenched using water and extracted with ethyl acetate. The organic layer was dried over anhydrous sodium sulfate, filtered and concentrated under reduced pressure. The residue was purified by flash column chromatography with 0~100% ethyl acetate in petroleum ether to afford 1-(3-bromo-1H-indol-7-yl)ethanone (1.00 g, 92%) as a yellow solid. MS m/z 238.0 [M+1]$^+$. $^1$H NMR (400 MHz, DMSO-d$_6$) δ 11.66 (s, 1H), 7.96 (dt, J=7.6, 1.2 Hz, 1H), 7.75 (d, J=7.8 Hz, 1H), 7.53 (d, J=2.4 Hz, 1H), 7.28 (td, J=7.8, 1.2 Hz, 1H), 2.68 (s, 3H).

Step 3: A mixture of 1-(3-bromo-1H-indol-7-yl)ethanone (1.40 g, 6.01 mmol), di(tert-butyl) carbonate (4.30 g, 19.82 mmol), triethylamine (1.80 g, 18.03 mmol) and 4-dimethylaminopyridine (0.07 g, 0.60 mmol) in dichloromethane (15 ml) was stirred at room temperature for 16 h. The resulting mixture was concentrated under reduced pressure. The residue was purified by flash column chromatography with 0~70% ethyl acetate in petroleum ether to afford tert-butyl 7-acetyl-3-bromoindole-1-carboxylate (A52)

(1.80 g, 92%) as a brown solid. MS m/z 338.0 [M+1]⁺. ¹H NMR (400 MHz, DMSO-d₆) δ 7.98 (s, 1H), 7.66 (dd, J=7.8, 1.2 Hz, 1H), 7.58 (dd, J=7.8, 1.2 Hz, 1H), 7.46 (t, J=7.6 Hz, 1H), 2.50 (s, 3H), 1.57 (s, 9H).

Intermediate A53 tert-butyl 3-bromo-5-cyanoindole-1-carboxylate

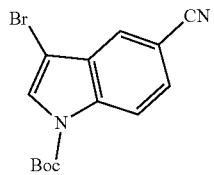 [SMILES: CC(C)(C)OC(=O)n1cc(Br)c2cc(C#N)ccc21]

Step 1: To a solution of 1H-indole-5-carbonitrile (2.00 g, 14.07 mmol) in tetrahydrofuran (20 mL) was added N-bromosuccinimide (2.50 g, 14.07 mmol). The mixture was stirred at room temperature for 3 h. The reaction mixture was diluted using water and extracted with ethyl acetate. The combined organic layers were washed with brine, dried over anhydrous sodium sulfate, filtered and concentrated under vacuum to afford 3-bromo-1H-indole-5-carbonitrile (1.80 g, crude) as a white solid. MS m/z 221.0 [M+1]⁺.

Step 2: To a solution of 3-bromo-1H-indole-5-carbonitrile (3.00 g, 13.57 mmol) in dichloromethane (30 mL) were added triethylamine (2.75 g, 27.14 mmol) and di(tert-butyl) carbonate (4.44 g, 20.36 mmol). Then the mixture was stirred at room temperature for 2 h. The mixture was concentrated under vacuum. The residue was purified by flash column chromatography with 0~50% ethyl acetate in petroleum ether to afford tert-butyl 3-bromo-5-cyanoindole-1-carboxylate (A53) (1.30 g, 30%) as a white solid. MS m/z 321.0 [M+1]⁺. ¹H NMR (400 MHz, DMSO-d₆) δ 8.29-8.19 (m, 1H), 8.12 (s, 1H), 8.09-7.99 (m, 1H), 7.89-7.79 (m, 1H), 1.64 (s, 9H).

Intermediate A54

6-bromo-N-(2-methoxyethyl)-2-methylpyridin-3-amine

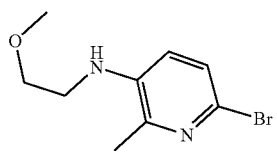

Step 1: A mixture of 6-bromo-2-methylpyridin-3-amine (1000 mg, 5.35 mmol) and triethylamine (1100 mg, 10.69 mmol) in dichloromethane (20 ml) was added methoxyacetyl chloride (580 mg, 5.35 mmol) at 0° C. The mixture was stirred at room temperature for 16 h. The mixture was concentrated under reduced pressure. The residue was purified by flash column chromatography with 0~100% ethyl acetate in petroleum ether to afford N-(6-bromo-2-methylpyridin-3-yl)-2-methoxyacetamide (1300 mg, 91%) as a yellow solid. MS m/z 259.0 [M+1]⁺.

Step 2: To a mixture of N-(6-bromo-2-methylpyridin-3-yl)-2-methoxyacetamide (600 mg, 2.32 mmol), in tetrahydrofuran (10 ml) were added sodium borohydride (175 mg, 4.64 mmol) and boron trifluoride ether complex (657 mg, 4.64 mmol). The mixture was stirred at room temperature for 16 h. The reaction was quenched with water/ice and then extracted with ethyl acetate. The combined organic layers were washed with brine, dried over anhydrous sodium sulfate, filtered and concentrated under vacuum. The residue was purified by flash column chromatography with 0~80% ethyl acetate in petroleum ether to afford 6-bromo-N-(2-methoxyethyl)-2-methylpyridin-3-amine (A53) (455 mg, 80%) as a yellow oil. MS m/z 245.0 [M+1]⁺.

Intermediate A55

6-bromo-2-methyl-N-(oxolan-3-yl)pyridin-3-amine

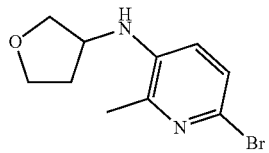

A mixture of 6-bromo-2-methylpyridin-3-amine (1.00 g, 5.35 mmol), dihydrofuran-3-one (0.92 g, 10.69 mmol), acetic acid (0.03 g, 0.53 mmol) and sodium triacetoxyborohydride (2.30 g, 10.60 mmol) in dichloroethane (15 ml) was stirred at 60° C. for 16 h. The reaction was quenched using water and extracted with ethyl acetate. The combined organic layers were washed with brine, dried over anhydrous sodium sulfate, filtered and concentrated under vacuum. The residue was purified by flash column chromatography with 0~100% ethyl acetate in petroleum ether to afford 6-bromo-2-methyl-N-(oxolan-3-yl)pyridin-3-amine (A55) (0.10 g, 7%) as a light yellow solid. MS m/z 257.0 [M+1]⁺.

Intermediate A56

6-bromo-3-(2-methoxyethoxy)-2-methylpyridine

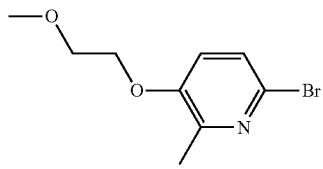

To a solution of 6-bromo-2-methylpyridin-3-ol (300 mg, 1.60 mmol) in N,N-dimethylformamide (3 mL) was added sodium hydride (144 mg, 3.60 mmol, 60% in mineral oil) at 0° C. After stirring at 0° C. for 30 min, 2-bromoethyl methyl ether (332 mg, 2.41 mmol) was added to above mixture. The mixture was stirred at room temperature for 2 h. The mixture was diluted with water and extracted with ethyl acetate. The organic layer was dried over anhydrous sodium sulfate, filtered and concentrated under vacuum. The residue was purified by flash column chromatography with 0~70% ethyl acetate in petroleum ether to afford 6-bromo-3-(2-methoxyethoxy)-2-methylpyridine (A56) (270 mg, 68%) as an off-white oil. MS m/z 246.0 [M+1]⁺.

Intermediate A57

2-bromo-6-(2-methoxyethoxy)pyridine

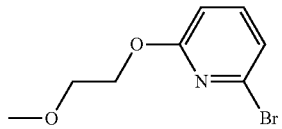

To a solution of 2-methoxyethanol (0.65 g, 8.54 mmol) in N,N-dimethylformamide (10 ml) was added sodium hydride (273 mg, 6.83 mmol, 60% in mineral oil) at 0° C. The mixture solution was stirred at 0° C. for 30 min under nitrogen atmosphere. 2-bromo-6-fluoropyridine (1.00 g, 5.71 mmol) was added at 0° C. The mixture was stirred at room temperature for 16 h. The reaction was quenched with water/ice and extracted with ethyl acetate. The combined organic layers were washed with brine, dried over anhydrous sodium sulfate, filtered and concentrated under vacuum. The residue was purified by flash column chromatography with 0~30% ethyl acetate in petroleum ether to afford 2-bromo-6-(2-methoxyethoxy)pyridine (A56) (1.20 g, 91%) as a colorless oil. MS m/z 232.0 [M+1]$^+$.

Intermediate A58 tert-butyl 3-[(6-bromopyridin-2-yl)oxy]pyrrolidine-1-carboxylate

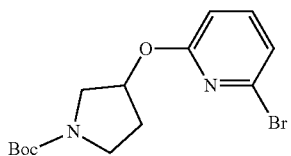

To a solution of tert-butyl 3-hydroxypyrrolidine-1-carboxylate (1.30 g, 6.95 mmol) in N,N-dimethylformamide (15 mL) was added sodium hydride (0.27 g, 6.75 mmol, 60% in mineral oil) at 0° C. After stirring at 0° C. for 30 min, 2-bromo-6-fluoropyridine (1.00 g, 5.71 mmol) was added to above mixture at 0° C. The mixture was stirred at room temperature for 16 h. The reaction was quenched with water/ice and extracted with ethyl acetate. The combined organic layers were washed with water, dried over anhydrous sodium sulfate, filtered and concentrated under reduced pressure. The residue was purified by flash column chromatography with 0~30% ethyl acetate in petroleum ether to afford tert-butyl 3-[(6-bromopyridin-2-yl)oxy]pyrrolidine-1-carboxylate (A57) (1.80 g, 92%) as a colorless oil. MS m/z 343.1 [M+1]$^+$.

Intermediate A59

2-bromo-6-[(1-methylpyrrolidin-3-yl)oxy]pyridine

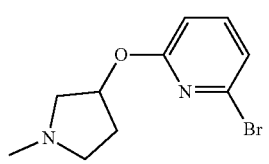

Step 1: To a mixture of tert-butyl 3-[(6-bromopyridin-2-yl)oxy]pyrrolidine-1-carboxylate (A58) (500 mg, 1.46 mmol) in dichloromethane (3 mL) was added trifluoroacetic acid (3 mL). The mixture was stirred at room temperature for 16 h. The mixture was concentrated under reduced pressure to afford 2-bromo-6-(pyrrolidin-3-yloxy)pyridine (280 mg, crude) as a yellow oil. MS m/z 243.1 [M+1]$^+$.

Step 2: A mixture of 2-bromo-6-(pyrrolidin-3-yloxy)pyridine (620 mg, 2.56 mmol), formaldehyde (384 mg, 3.71 mmol, 30% in water) and sodium cyanoborohydride (321 mg, 5.10 mmol) in tetrahydrofuran (10 mL) was stirred at room temperature for 16 h. The reaction was quenched with water/ice and extracted with ethyl acetate. The combined organic layers were washed with water, dried over anhydrous sodium sulfate, filtered and concentrated under reduced pressure. The residue was purified by flash column chromatography with 0~80% ethyl acetate in petroleum ether to afford 2-bromo-6-[(1-methylpyrrolidin-3-yl)oxy]pyridine (A59) (360 mg, 54%) as a light yellow oil. MS m/z 257.0 [M+1]$^+$.

Intermediate A60

6-chloro-2-(2-methoxyethoxy)pyridin-3-amine

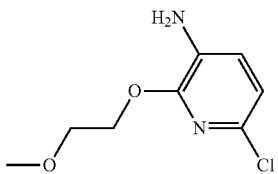

Step 1: To a solution of 2-methoxyethanol (946 mg, 12.45 mmol) in N,N-dimethylformamide (10 ml) was added sodium hydride (497 mg, 12.43 mmol, 60% in mineral oil) at 0° C. After stirring at 0° C. for 30 min, a solution of 2,6-dichloro-3-nitropyridine (2000 mg, 10.42 mmol) in tetrahydrofuran (10 mL) was added dropwise to above mixture at 0° C. The mixture was stirred at room temperature for 16 h. The reaction was quenched with water/ice and extracted with ethyl acetate. The combined organic layers were washed with brine, dried over anhydrous sodium sulfate, filtered and concentrated under vacuum. The residue was purified by flash column chromatography with 0~50% ethyl acetate in petroleum ether to afford 6-chloro-2-(2-methoxyethoxy)-3-nitropyridine (655 mg, 27%) as a yellow oil. MS m/z 233.0 [M+1]$^+$.

Step 2: To a solution of 6-chloro-2-(2-methoxyethoxy)-3-nitropyridine (600 mg, 2.59 mmol) in methanol (6 mL) and water (2 mL) were added Fe (432 mg, 7.71 mmol) and ammonium chloride (828 mg, 15.62 mmol). The resulting solution was stirred at 70° C. for 16 h. The mixture was filtered. The filtrate was diluted using ethyl acetate and washed with water. The organic layer was dried over anhydrous sodium sulfate, filtered and concentrated under reduced pressure. The residue was purified by flash column chromatography with 0~90% ethyl acetate in petroleum ether to afford 6-chloro-2-(2-methoxyethoxy)pyridin-3-amine (A60) (500 mg, 95%) as a brown solid. MS m/z 203.1 [M+1]$^+$.

Intermediate A661 tert-butyl (5-chloro-2-(difluoromethoxy)pyridin-3-yl)carbamate

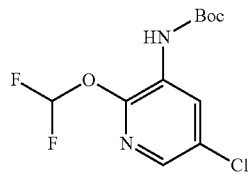 [SMILES: CC(C)(C)OC(=O)Nc1cc(Cl)cnc1OC(F)F]

Step 1: To a solution of 3-amino-5-chloropyridin-2(1H)-one (2.00 g, 13.89 mmol) in dichloromethane (15 mL) were added di(tert-butyl) carbonate (4.53 g, 20.78 mmol), triethylamine (4.20 g, 41.58 mmol), 4-dimethylaminopyridine (0.17 g, 1.39 mmol). The resulting solution was stirred at room temperature for 2 h. The mixture was concentrated under vacuum. The residue was purified by flash column chromatography with 0-35% ethyl acetate in petroleum ether to afford tert-butyl (5-chloro-2-oxo-1,2-dihydropyridin-3-yl)carbamate (1.00 g, 29%) as a white solid. MS m/z 245.1 [M+1]$^+$. $^1$H NMR (400 MHz, DMSO-d$_6$) δ 12.21 (s, 1H), 7.88 (s, 1H), 7.79 (d, J=2.8 Hz, 1H), 7.26 (d, J=2.8 Hz, 1H), 1.46 (s, 9H).

Step 2: To a solution of tert-butyl (5-chloro-2-oxo-1,2-dihydropyridin-3-yl)carbamate (200 mg, 0.82 mmol) in N,N-dimethylformamide (4 mL) were added 2-chloro-2,2-difluoroacetic acid (128 mg, 0.98 mmol) and potassium carbonate (339 mg, 2.46 mmol). The mixture was stirred at 50° C. for 16 h. The reaction mixture was diluted with ethyl acetate and washed with water and brine. The organic layer was dried over anhydrous sodium sulfate, filtered and concentrated under vacuum. The residue was purified by flash column chromatography with 0~20% ethyl acetate in petroleum ether to afford tert-butyl (5-chloro-2-(difluoromethoxy)pyridin-3-yl)carbamate (A61) (130 mg, 53%) as a colorless oil. MS m/z 295.1 [M+1]$^+$.

Intermediate A62 tert-butyl N-[6-chloro-2-(difluoromethoxy)pyridin-3-yl]carbamate

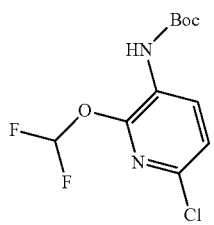 [SMILES: CC(C)(C)OC(=O)Nc1ccc(Cl)nc1OC(F)F]

Followed the procedure of Intermediate A61 described above to afford tert-butyl N-[6-chloro-2-(difluoromethoxy)pyridin-3-yl]carbamate (220 mg, 4% over 2 steps) as yellow oil from 3-amino-6-chloro-1H-pyridin-2-one (A62) (1.00 g, 6.92 mmol). MS m/z 295.0 [M+1]$^+$.

Intermediate A63

N-[5-bromo-3-(difluoromethoxy)pyrazin-2-yl]acetamide

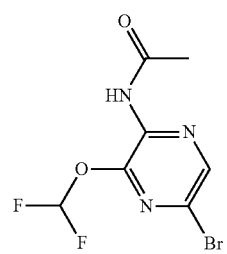

Step 1: To a mixture of 3,5-dibromopyrazin-2-amine (5.00 g, 19.92 mmol) and anise alcohol (2.70 g, 19.57 mmol) in dioxane (50 mL) was added potassium tert-butoxide (6.60 g, 58.92 mmol). The mixture was stirred at 100° C. for 1 h. The mixture was diluted using water and extracted with ethyl acetate. The organic layer was dried over anhydrous sodium sulfate, filtered and concentrated under vacuum. The residue was purified by flash column chromatography with 0~80% ethyl acetate in petroleum ether to afford 5-bromo-3-[(4-methoxyphenyl)methoxy]pyrazin-2-amine (5.10 g, 83%) as a yellow solid. MS m/z 310.0 [M+1]$^+$. $^1$H NMR (400 MHz, DMSO-d$_6$) δ 7.60 (s, 1H), 7.54-7.37 (m, 2H), 6.94 (d, J=8.8 Hz, 2H), 6.51 (s, 2H), 5.27 (s, 2H), 3.75 (s, 3H).

Step 2: A mixture of 5-bromo-3-[(4-methoxyphenyl)methoxy]pyrazin-2-amine (5.10 g, 16.45 mmol) in acetic anhydride (20 mL) was stirred at 100° C. for 1 h. The mixture was concentrated under vacuum. The residue was purified by flash column chromatography with 0~80% ethyl acetate in petroleum ether to afford N-[5-bromo-3-[(4-methoxyphenyl) methoxy]pyrazin-2-yl]acetamide (2.70 g, 46%) as an off-white solid. MS m/z 352.2 [M+1]$^+$.

Step 3: To a solution of N-[5-bromo-3-[(4-methoxyphenyl)methoxy]pyrazin-2-yl]acetamide (1.00 g, 2.85 mmol) in dichloromethane (6 mL) was added trifluoroacetic acid (4 mL). The resulting solution was stirred at room temperature for 16 h. The mixture was concentrated under vacuum. The residue was purified by flash column chromatography with 0-90% ethyl acetate in petroleum ether to afford N-(5-bromo-3-hydroxypyrazin-2-yl)acetamide (0.60 g, 91%) as a white solid. MS m/z 232.0 [M+1]$^+$.

Step 4: A mixture of N-(5-bromo-3-hydroxypyrazin-2-yl)acetamide (0.80 g, 3.46 mmol), 2-chloro-2,2-difluoroacetic acid (0.69 g, 5.36 mmol) and potassium carbonate (1.40 g, 10.14 mmol) in N,N-dimethylformamide (5 mL) was stirred at 50° C. for 16 h. The mixture was diluted with water and extracted with ethyl acetate. The combined organic layers were washed with brine, dried over anhydrous sodium sulfate, filtered and concentrated under vacuum. The residue was purified by flash column chromatography with 0~60% ethyl acetate in petroleum ether to afford N-[5-bromo-3-(difluoromethoxy)pyrazin-2-yl]acetamide (A63) (0.30 g, 30%) as a white solid. MS m/z 282.0 [M+1]$^+$. $^1$H NMR (400 MHz, DMSO-d$_6$) δ 10.44 (s, 1H), 8.53 (s, 1H), 7.64 (t, J=71.2 Hz, 1H), 2.11 (s, 3H).

Intermediate A64

2-chloro-7-(hydroxymethyl)-6,7-dimethylpyrrolo[3,4-b]pyridin-5-one

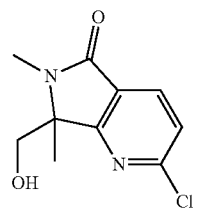

To a mixture of 2-chloro-6,7-dimethyl-7H-pyrrolo[3,4-b]pyridin-5-one (A42) (940 mg, 4.80 mmol) and paraformaldehyde (517 mg, 17.23 mmol) in N,N-dimethylformamide (10 mL) was added sodium hydride (288 mg, 7.20 mmol, 60% in mineral oil). The mixture was stirred at room temperature for 30 min. The reaction was quenched using water/ice and extracted with ethyl acetate. The combined organic layers were washed with brine, dried over anhydrous sodium sulfate, filtered and concentrated under vacuum. The residue was purified by reverse flash chromatography with 10% to 80% in acetonitrile in water in 30 min to afford 2-chloro-7-(hydroxymethyl)-6,7-dimethylpyrrolo[3,4-b]pyridin-5-one (A64) (300 mg, 27%) as a white solid. MS m/z 227.1 [M+1]$^+$. $^1$H NMR (400 MHz, DMSO-d$_6$) δ 8.08 (d, J=8.0 Hz, 1H), 7.59 (d, J=8.0 Hz, 1H), 4.90 (br, 1H), 3.76 (s, 2H), 2.93 (s, 3H), 1.34 (s, 3H).

Intermediate A65

6-bromo-N-(2-methoxyethyl)-N-methylpyrazin-2-amine

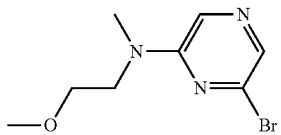

A mixture of 2,6-dibromopyrazine (1000 mg, 4.24 mmol), (2-methoxyethyl)(methyl)amine (377 mg, 4.24 mmol) and triethylamine (851 mg, 8.43 mmol) in methanol (10 mL) was stirred at room temperature for 4 h. The mixture was concentrated under vacuum. The residue was purified by flash column chromatography with 0~70% ethyl acetate in petroleum ether to afford 6-bromo-N-(2-methoxyethyl)-N-methylpyrazin-2-amine (A65) (250 mg, 24%) as a yellow oil. MS m/z 246.0 [M+1]$^+$.

Intermediate A66

2-(azetidin-1-yl)-6-bromopyridine

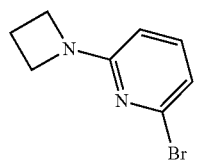 [SMILES: Brc1cccc(N2CCC2)n1]

To a solution of 2-bromo-6-fluoropyridine (1.00 g, 5.71 mmol) in N,N-dimethylformamide (8 mL) were added azetidine hydrochloride (0.63 g, 6.86 mmol) and potassium carbonate (2.40 g, 17.39 mmol). The mixture was stirred at 80° C. for 3 h. The mixture was diluted water and extracted with ethyl acetate. The combined organic layers were washed with brine, dried over anhydrous sodium sulfate, filtered and concentrated under vacuum. The residue was purified by flash column chromatography with 0~20% ethyl acetate in petroleum ether to afford 2-(azetidin-1-yl)-6-bromopyridine (A66) (0.87 g, 71%) as a white solid. MS m/z 213.0 [M+1]$^+$. $^1$H NMR (400 MHz, DMSO-d$_6$) δ 7.39 (dd, J=8.2, 7.6 Hz, 1H), 6.75 (dd, J=7.6, 0.6 Hz, 1H), 6.30 (dd, J=8.2, 0.6 Hz, 1H), 4.04-3.80 (m, 4H), 2.35-2.27 (m, 2H).

Intermediate A67 tert-butyl 3-[(5-bromo-3-methylpyrazin-2-yl)amino]pyrrolidine-1-carboxylate

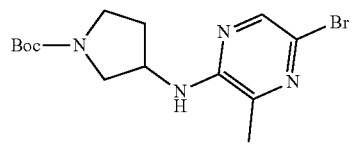

Step 1: To a solution of 2-bromo-3-methylpyrazine (1.00 g, 5.81 mmol) in dioxane (10 mL) were added tert-butyl 3-aminopyrrolidine-1-carboxylate (1.10 g, 5.91 mmol), tris(dibenzylideneacetone)dipalladium (0.53 g, 0.58 mmol), (±)-2,2'-Bis(diphenylphosphino)-1,1'-binaphthalene (0.36 g, 0.58 mmol) and sodium tert-butoxide (1.10 g, 11.46 mmol). The mixture was stirred at 100° C. for 16 h. The resulting mixture was concentrated under vacuum. The residue was purified by flash column chromatography with 0-90% ethyl acetate in petroleum ether to afford tert-butyl 3-[(3-methylpyrazin-2-yl)amino]pyrrolidine-1-carboxylate (0.60 g, 37%) as a yellow oil. MS m/z 279.0 [M+1]$^+$. $^1$H NMR (400 MHz, DMSO-d$_6$) δ 7.86 (d, J=2.8 Hz, 1H), 7.63 (d, J=2.8 Hz, 1H), 6.36 (d, J=6.0 Hz, 1H), 4.51-4.29 (m, 1H), 3.63-3.59 (m, 1H), 3.47-3.40 (m, 1H), 3.29-3.25 (m, 1H), 3.17-3.13 (m, 1H), 2.31 (s, 3H), 2.15-2.11 (m, 1H), 2.01-1.78 (m, 1H), 1.40 and 1.39 (s, 9H).

Step 2: To a solution of tert-butyl 3-[(3-methylpyrazin-2-yl)amino]pyrrolidine-1-carboxylate (0.50 g, 1.80 mmol) in dichloromethane (10 mL) was added Br$_2$ (0.31 g, 1.97 mmol) dropwise at 0° C. The mixture was stirred at room temperature for 16 h. The mixture was diluted with water and extracted with dichloromethane. The combined organic layers were washed with brine, dried over anhydrous sodium sulfate, filtered and concentrated under vacuum. The residue was purified by flash column chromatography with 0~70% ethyl acetate in petroleum ether to afford tert-butyl 3-[(5-bromo-3-methylpyrazin-2-yl)amino]pyrrolidine-1-carboxylate (A67) (0.42 g, 65%) as an off-white solid. MS m/z 357.0 [M+1]$^+$. $^1$H NMR (400 MHz, DMSO-d$_6$) δ 8.02 (s, 1H), 6.61 (d, J=6.0 Hz, 1H), 4.48-4.26 (m, 1H), 3.61-3.57 (m, 1H), 3.49-3.40 (m, 1H), 3.29-3.27 (m, 1H), 3.20-3.16 (m, 1H), 2.31 (s, 3H), 2.14-2.11 (m, 1H), 1.92-1.90 (m, 1H), 1.40 and 1.39 (s, 9H).

Intermediate A68

5-bromo-3-methyl-N-(1-methylpyrrolidin-3-yl)pyrazin-2-amine

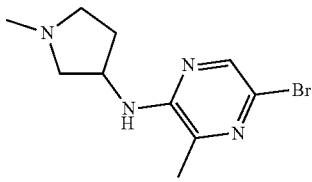

Step 1: To a solution of tert-butyl 3-[(5-bromo-3-methylpyrazin-2-yl)amino]pyrrolidine-1-carboxylate (200 mg, 0.56 mmol) in dichloromethane (3 mL) was added trifluoroacetic acid (2 mL). The mixture was stirred at room temperature overnight. The mixture was concentrated under vacuum to afford 5-bromo-3-methyl-N-(pyrrolidin-3-yl)pyrazin-2-amine (120 mg, crude) as a yellow oil. MS m/z 257.0 [M+1]$^+$.

Step 2: To a solution of 5-bromo-3-methyl-N-(pyrrolidin-3-yl)pyrazin-2-amine (180 mg, 0.70 mmol) in methanol (5 mL) were added formaldehyde (30% in water) (1 mL) and sodium cyanoborohydride (88 mg, 1.40 mmol). The mixture was stirred at room temperature for 16 h. The reaction mixture was quenched by water and extracted with ethyl acetate. The combined organic layers were washed with brine, dried over anhydrous sodium sulfate, filtered and concentrated under vacuum. The residue was purified by flash column chromatography with 0-80% ethyl acetate in petroleum ether to afford 5-bromo-3-methyl-N-(1-methylpyrrolidin-3-yl)pyrazin-2-amine (A68) (160 mg, 84%) as a light yellow solid. MS m/z 271.2 [M+1]$^+$.

Intermediate A69 tert-butyl 3-[(5-bromo-3-methylpyrazin-2-yl)oxy]pyrrolidine-1-carboxylate

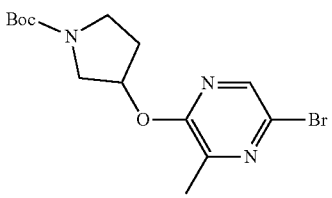 [SMILES: Cc1nc(Br)cnc1OC1CCN(C(=O)OC(C)(C)C)C1]

To a solution of 5-bromo-3-methylpyrazin-2-ol (500 mg, 2.65 mmol), triphenylphosphine (1041 mg, 3.97 mmol) and tert-butyl 3-hydroxypyrrolidine-1-carboxylate (495 mg, 2.65 mmol) in tetrahydrofuran (5 mL) was added diisopropyl azodiformate (802 mg, 3.97 mmol) at 0° C. under nitrogen atmosphere. The mixture was stirred at 0° C. for 4 h. The mixture was concentrated under vacuum. The residue was purified by flash column chromatography with 0~50% ethyl acetate in petroleum ether to afford tert-butyl 3-[(5-bromo-3-methylpyrazin-2-yl)oxy]pyrrolidine-1-carboxylate (A69) (450 mg, 47%) as a colorless oil. MS m/z 358.1 [M+1]$^+$. $^1$H NMR (400 MHz, DMSO-d$_6$) δ 8.23 (s, 1H), 5.43-5.42 (m, 1H), 3.64-3.56 (m, 1H), 3.51-3.37 (m, 3H), 2.35 (s, 3H), 2.23-1.96 (m, 2H), 1.40 and 1.39 (s, 9H).

Intermediate A70

5-bromo-3-methyl-2-[(1-methylpyrrolidin-3-yl)oxy]pyrazine

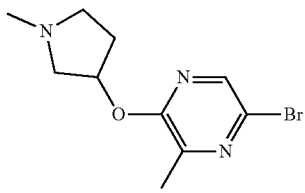

Step 1: To a solution of tert-butyl 3-[(5-bromo-3-methylpyrazin-2-yl)oxy]pyrrolidine-1-carboxylate (500 mg, 1.39 mmol) in dichloromethane (5 mL) was added trifluoroacetic acid (2 mL). The mixture was stirred at room temperature for 2 h. The mixture was concentrated under vacuum. The residue was basified with saturated sodium bicarbonate aqueous solution and extracted with dichloromethane. The combined organic layers were dried over anhydrous sodium sulfate, filtered and concentrated under vacuum to afford 5-bromo-3-methyl-2-(pyrrolidin-3-yloxy)pyrazine (300 mg, crude) as light yellow oil. MS m/z 258.0 [M+1]$^+$.

Step 2: To a solution of 5-bromo-3-methyl-2-(pyrrolidin-3-yloxy)pyrazine (200 mg, 0.38 mmol), formaldehyde (0.5 mL, 13.65 mmol, 30% in water) in methanol (2 mL) was added sodium cyanoborohydride (97 mg, 1.55 mmol). The mixture was stirred at room temperature for 2 h. The reaction mixture was quenched using water and extracted with ethyl acetate. The organic layer was dried over anhydrous sodium sulfate, filtered and concentrated under reduced pressure. The residue was purified by flash column chromatography 0~50% ethyl acetate in dichloromethane to afford 5-bromo-3-methyl-2-[(1-methylpyrrolidin-3-yl)oxy]pyrazine (A70) (85 mg, 27% over 2 steps) as colorless oil. MS m/z 272.0 [M+1]$^+$.

Intermediate A71

1-[3-[(5-bromo-3-methylpyrazin-2-yl)oxy]pyrrolidin-1-yl]ethanone

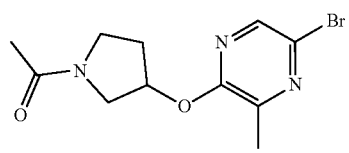 [SMILES: CC(=O)N1CCC(Oc2ncc(Br)nc2C)C1]

To a solution of 5-bromo-3-methyl-2-(pyrrolidin-3-yloxy)pyrazine (100 mg, 0.38 mmol) and triethylamine (117 mg, 1.16 mmol) in dichloromethane (2 mL) was added acetic anhydride (59 mg, 0.58 mmol). The mixture was stirred at room temperature for 2 h. The mixture was washed with water. The organic layer was dried over anhydrous sodium sulfate, filtered and concentrated under vacuum. The residue was purified by flash column chromatography with 0~20% methanol in dichloromethane to afford 1-[3-[(5-bromo-3-methylpyrazin-2-yl)oxy]pyrrolidin-1-yl]ethanone (A71) (58 mg, 49%) as a yellow oil. MS m/z 300.0 [M+1]$^+$.

Intermediate A72

2-[(6-bromo-2-methylpyridin-3-yl)amino]ethanol

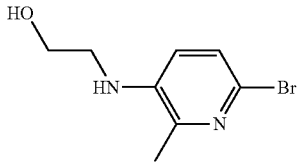

Step 1: A mixture of 6-bromo-2-methylpyridin-3-amine (1.00 g, 5.35 mmol), ethyl bromoacetate (1.79 g, 10.71 mmol) and potassium carbonate (1.48 g, 10.69 mmol) in N,N-dimethylformamide (20 mL) was stirred at 80° C. for 16 h. The reaction mixture was diluted using water and extracted with ethyl acetate. The combined organic layers were dried over anhydrous sodium sulfate, filtered and concentrated under reduced pressure. The residue was purified by flash column chromatography with 0~70% ethyl acetate in petroleum ether to afford ethyl 2-[(6-bromo-2-methylpyridin-3-yl)amino]acetate (1.45 g, 99%) as a light yellow solid. MS m/z 273.1 [M+1]$^+$.

Step 2: To a mixture of ethyl 2-[(6-bromo-2-methylpyridin-3-yl)amino]acetate (300 mg, 1.09 mmol), methanol (0.3 mL) in tetrahydrofuran (9 mL) was added lithium borohydride (36 mg, 1.64 mmol). The mixture was stirred at room temperature for 16 h. The reaction was quenched with water and extracted with ethyl acetate. The organic layers were dried over anhydrous sodium sulfate, filtered and concentrated under reduced pressure to afford 2-[(6-bromo-2-methylpyridin-3-yl)amino]ethanol (A72) (180 mg, crude) as a colorless oil. MS m/z 230.9 [M+1]$^+$.

Intermediate A73

2-[(6-bromo-2-methylpyridin-3-yl)amino]-N,N-dimethylpropanamide

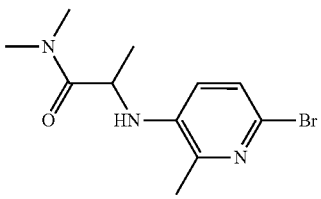 [SMILES: Cc1nc(Br)ccc1NC(C)C(=O)N(C)C]

Step 1: 2-Bromopropanoyl bromide (5.00 g, 23.16 mmol) was added slowly to a solution of dimethylamine (17 mL, 2M in tetrahydrofuran) in tetrahydrofuran (40 mL) at 0° C. The mixture was stirred at 0° C. for 30 min. The mixture was concentrated under vacuum. The residue was diluted using water and extracted with ethyl acetate. The combined organic layers were washed with brine, dried over anhydrous sodium sulfate, filtered and concentrated under vacuum to afford 2-bromo-N,N-dimethylpropanamide (2.60 g, 62%) as light yellow oil. $^1$H NMR (400 MHz, DMSO-d$_6$) δ 5.02-4.99 (m, 1H), 2.86 (s, 3H), 1.80-1.62 (m, 6H).

Step 2: To a solution of 2-bromo-N,N-dimethylpropanamide (0.50 g, 2.78 mmol) and potassium carbonate (1.15 g, 8.33 mmol) in N,N-dimethylformamide (2 mL) was added 6-bromo-2-methylpyridin-3-amine (1.03 g, 5.55 mmol). The resulting solution was stirred at 100° C. overnight. The mixture was diluted with water and extracted with ethyl acetate. The combined organic layers were washed with brine, dried over anhydrous sodium sulfate, filtered and concentrated under vacuum. The residue was purified by flash column chromatography with 0~50% ethyl acetate in dichloromethane to afford 2-[(6-bromo-2-methylpyridin-3-yl)amino]-N,N-dimethylpropanamide (A73) (0.10 g, 13%) as yellow oil. MS m/z 286.0 [M+1]$^+$.

Intermediate A74

6-bromo-N-(2-methoxypropyl)-2-methylpyridin-3-amine

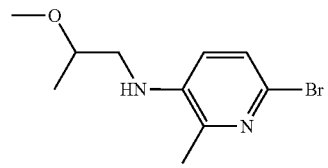

Step 1: To a solution of 2-methoxypropanol (240 mg, 2.67 mmol) and triethylamine (541 mg, 5.34 mmol) in dichloromethane (3 mL) was added Methanesulfonyl chloride (459 mg, 4.01 mmol) at 0° C. The mixture was stirred at 0° C. for 1 h. The resulting mixture was washed with water. The organic layer was dried over anhydrous sodium sulfate, filtered and concentrated under vacuum to afford 2-methoxypropyl methanesulfonate (370 mg, crude). $^1$H NMR (400 MHz, Methanol-d$_4$) δ 4.26 (dd, J=10.8, 3.4 Hz, 1H), 4.14 (dd, J=10.8, 5.8 Hz, 1H), 3.69-3.62 (m, 1H), 3.41 (s, 3H), 3.10 (s, 3H), 1.20 (d, J=6.4 Hz, 3H).

Step 2: To a solution of 6-bromo-2-methylpyridin-3-amine (500 mg, 2.67 mmol) in N,N-dimethylformamide (5 mL) was added sodium hydride (107 mg, 2.67 mmol, 60% in mineral oil). After stirring at 0° C. for 20 min, 2-methoxypropyl methanesulfonate (370 mg, crude from step 1) was added to above mixture at 0° C. The mixture was stirred at room temperature for 10 h. The reaction was quenched using water and extracted with ethyl acetate, the organic layer was washed by brine, then dried over anhydrous sodium sulfate, filtered and concentrated under vacuum. The residue was purified by flash column chromatography with 0-80% ethyl acetate in petroleum ether to afford 6-bromo-N-(2-methoxypropyl)-2-methylpyridin-3-amine (A74) (120 mg, 17%) as a yellow oil. MS m/z 259.3 [M+1]$^+$.

Intermediate A75

2-[(6-bromo-2-methylpyridin-3-yl)amino]-N,N-dimethylacetamide

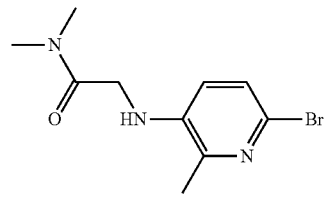

To a mixture of 6-bromo-2-methylpyridin-3-amine (500 mg, 2.69 mmol) and potassium carbonate (739 mg, 5.35 mmol) in N,N-dimethylformamide (5 mL) was added 2-bromo-N,N-dimethylacetamide (888 mg, 4.85 mmol). The mixture was stirred at 80° C. overnight. The reaction mixture was diluted with water and extracted with ethyl acetate. The combined organic layers were washed with brine, dried over anhydrous sodium sulfate, filtered and concentrated under vacuum. The residue was purified by flash column chromatography with 0-65% ethyl acetate in petroleum ether to afford 2-[(6-bromo-2-methylpyridin-3-yl)amino]-N,N-dimethylacetamide (A75) (400 mg, 54%) as a light yellow solid. MS m/z 272.0 [M+1]$^+$. $^1$H NMR (400 MHz, DMSO-d$_6$) δ 7.21 (dd, J=8.4, 0.8 Hz, 1H), 6.83 (d, J=8.4 Hz, 1H), 3.94 (s, 2H), 3.02 (s, 3H), 2.87 (s, 3H), 2.30 (s, 3H).

Intermediate A76

6-bromo-N-[2-(dimethylamino)ethyl]-2-methylpyridin-3-amine

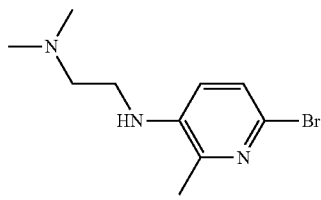

To a solution of 2-[(6-bromo-2-methylpyridin-3-yl)amino]-N,N-dimethylacetamide (500 mg, 1.84 mmol) in tetrahydrofuran (10 mL) were added sodium borohydride (347 mg, 9.19 mmol) and boron trifluoride ether complex (1303 mg, 9.19 mmol). The mixture was stirred at room temperature overnight. The reaction was quenched using water and extracted with ethyl acetate. The combined organic layers were washed with brine, dried over anhydrous sodium sulfate, filtered and concentrated under vacuum. The residue was purified by flash column chromatography with 0~100% ethyl acetate in petroleum ether to afford 6-bromo-N-[2-(dimethylamino)ethy]-2-methylpyridin-3-amine (A76) (350 mg, 73%) as an off-white solid. MS m/z 258.2 [M+1]$^+$. $^1$H NMR (400 MHz, DMSO-d$_6$) δ 7.22 (d, J=8.4 Hz, 1H), 6.92 (d, J=8.4 Hz, 1H), 5.47 (t, J=5.8 Hz, 1H), 3.50-3.45 (m, 2H), 2.97-2.81 (m, 2H), 2.58 (s, 6H), 2.26 (s, 3H).

Intermediate A77

3-[(6-bromo-2-methylpyridin-3-yl)oxy]pyrrolidin-2-one

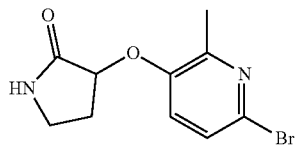

Step 1: To a solution of tert-butyl 3-hydroxypyrrolidine-1-carboxylate (1.00 g, 5.34 mmol), 4-dimethylaminopyridine (0.06 g, 0.52 mmol) and triethylamine (1.08 g, 10.68 mmol) in dichloromethane (10 mL) was added p-toluenesulfonyl chloride (1.12 g, 5.88 mmol) at 0° C. The mixture was stirred at room temperature for 16 h. The mixture was diluted with water and extracted with dichloromethane. The combined organic layers were washed with HCl (aq, 0.5N), dried over anhydrous sodium sulfate, filtered and concentrated under vacuum to afford tert-butyl 3-[(4-methylbenzenesulfonyl)oxy]pyrrolidine-1-carboxylate (1.81 g, 99%) as a brown solid. MS m/z 342.1 [M+1]$^+$.

Step 2: To a solution of tert-butyl 3-[(4-methylbenzenesulfonyl)oxy]pyrrolidine-1-carboxylate (1.30 g, 3.81 mmol) and 6-bromo-2-methylpyridin-3-ol (0.48 g, 2.53 mmol) in N,N-dimethylformamide (20 mL) was added potassium carbonate (0.70 g, 5.08 mmol). The mixture was stirred at 80° C. overnight. The mixture was diluted with water and extracted with ethyl acetate. The combined organic layers were washed with brine, dried over anhydrous sodium sulfate, filtered and concentrated under vacuum. The residue was purified by flash column chromatography with 0~80% ethyl acetate in petroleum ether to afford to afford tert-butyl 3-[(6-bromo-2-methylpyridin-3-yl)oxy]pyrrolidine-1-carboxylate (0.48 g, 35%) as a white solid. MS m/z 357.3 [M+1]$^+$. $^1$H NMR (400 MHz, DMSO-d$_6$) δ 7.42 (s, 2H), 5.07-5.03 (m, 1H), 3.55-3.39 (m, 4H), 2.29 (s, 3H), 2.10-1.99 (m, 2H), 1.41 and 1.39 (s, 9H).

Step 3: To a solution of tert-butyl 3-[(6-bromo-2-methylpyridin-3-yl)oxy]pyrrolidine-1-carboxylate (470 mg, 1.32 mmol) in ethyl acetate (5 mL) were added a solution of sodium periodate (1406 mg, 6.58 mmol) in water (15 mL) and ruthenium(III) chloride hydrate (89 mg, 0.40 mmol). The mixture was stirred at room temperature overnight. The reaction mixture was washed with water. The organic layer was dried over anhydrous sodium sulfate, filtered and concentrated under vacuum. The residue was purified by reverse phase flash column chromatography with 30-80% acetonitrile in water to afford tert-butyl 3-[(6-bromo-2-methylpyridin-3-yl)oxy]-2-oxopyrrolidine-1-carboxylate (100 mg, 20%) as a yellow solid. MS m/z 371.2 [M+1]$^+$. 1H NMR (400 MHz, DMSO-d$_6$) δ 7.56-7.30 (m, 2H), 5.26-5.22 (m, 1H), 3.85-3.69 (m, 1H), 3.57-3.50 (m, 1H), 2.62-2.53 (m, 2H), 2.34 (s, 3H), 1.47 (s, 9H).

Step 3: To a solution of tert-butyl 3-[(6-bromo-2-methylpyridin-3-yl)oxy]-2-oxopyrrolidine-1-carboxylate (100 mg, 0.27 mmol) in dichloromethane (3 mL) was added trifluoroacetic acid (2 mL). The resulting solution was stirred at room temperature for 2 h. The mixture was concentrated under vacuum to afford 3-[(6-bromo-2-methylpyridin-3-yl)oxy]pyrrolidin-2-one (A77) (80 mg, crude) as a yellow solid. MS m/z 271.0 [M+1]$^+$.

Intermediate A78

6-chloro-1H,2H,3H-4lambda6-pyrido[2,3-b][1,4]thiazine-4,4-dione

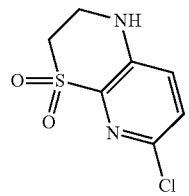 [SMILES: O=S1(=O)CCNc2ccc(Cl)nc21]

Step 1: To a solution of 2,6-dichloro-3-nitropyridine (5.00 g, 25.91 mmol) and ethyl thioglycolate (3.10 g, 25.91 mmol) in tetrahydrofuran (50 mL) was added sodium hydride (0.93 g, 23.25 mmol, 60% in mineral) in portions at 0° C. The mixture was stirred at room temperature for 2 h. The reaction mixture was diluted with water and extracted with ethyl acetate. The combined organic layers were washed with brine, dried over anhydrous sodium sulfate, filtered and concentrated under vacuum to afford ethyl 2-[(6-chloro-3-nitropyridin-2-yl)sulfanyl]acetate (6.59 g, crude) as a yellow oil. MS m/z 263.0 [M+1]$^+$.

Step 2: To a solution of ethyl 2-[(6-chloro-3-nitropyridin-2-yl)sulfanyl]acetate (6.59 g, 23.82 mmol) and iron powder (3.99 g, 71.45 mmol) in methanol (20 mL) and water (10 mL) was added ammonium chloride (7.64 g, 142.90 mmol). The mixture was heated to 70° C. and stirred for 16 h. The solids were filtered off. The filtrate was concentrated under vacuum. The residue was diluted with ethyl acetate and washed by water. The organic layer was dried over anhydrous sodium sulfate, filtered and concentrated under vacuum. The residue was purified by flash column chromatography with 0~70% ethyl acetate in petroleum ether to afford 6-chloro-1H,3H-pyrido[2,3-b][1,4]thiazin-2-one (1.04 g, 20% over 2 steps) as a yellow solid. MS m/z 201.0 [M+1]$^+$.

Step 3: To a solution of 6-chloro-1H,3H-pyrido[2,3-b][1,4]thiazin-2-one (0.78 g, 3.89 mmol) in dichloromethane (7 mL) was added 3-chloroperoxybenzoic acid (3.35 g, 19.44 mmol). The mixture was stirred at room temperature overnight. The mixture was concentrated under vacuum. The residue was purified by reverse phase flash column chromatography with 0~50% acetonitrile in water to afford 6-chloro-1H,3H-4lambda6-pyrido[2,3-b][1,4]thiazine-2,4,4-trione (290 mg, 29%) as a yellow solid. MS m/z 233.0 [M+1]$^+$.

Step 4: To a solution of 6-chloro-1H,3H-4lambda6-pyrido[2,3-b][1,4]thiazine-2,4,4-trione (290 mg, 1.25 mmol) and boron trifluoride ether complex (354 mg, 2.49 mmol) in tetrahydrofuran (4 mL) was added sodium borohydride (94.57 mg, 2.5 mmol). The mixture was stirred at room temperature for 16 h. The reaction mixture was diluted with water and extracted with ethyl acetate. The combined organic layers were washed with brine, dried over anhydrous sodium sulfate, filtered and concentrated under vacuum. The residue was purified by reverse phase flash column chromatography with 0~40% acetonitrile in water to afford 6-chloro-1H,2H,3H-4lambda6-pyrido[2,3-b][1,4]thiazine-4,4-dione (A78) (230 mg, 84%) as a yellow solid. MS m/z 219.0 [M+1]$^+$. $^1$H NMR (400 MHz, DMSO-d$_6$) δ 7.41 (d, J=8.8 Hz, 1H), 7.38 (s, 1H), 7.31 (d, J=8.8 Hz, 1H), 3.72-3.70 (m, 2H), 3.58-3.47 (m, 2H).

Intermediate A79 tert-butyl 3-bromo-7-cyano-6-fluoroindole-1-carboxylate

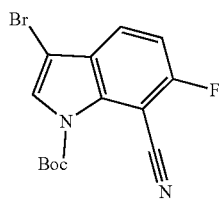 [SMILES: CC(C)(C)OC(=O)n1cc(Br)c2ccc(F)c(C#N)c21]

Step 1: To a degassed solution of 7-bromo-6-fluoro-1H-indole (700 mg, 3.27 mmol) in N,N-dimethylformamide (8 mL) were added zinc cyanide (1152 mg, 9.81 mmol) and palladium(0)tetrakis(triphenylphosphine) (378 mg, 0.32 mmol) under nitrogen atmosphere. The resulting solution was stirred at 140° C. for 4 h. The solids were filtered off. The filtrate was diluted with water and extracted with ethyl acetate. The combined organic layers were washed with brine, dried over anhydrous sodium sulfate, filtered and concentrated under vacuum. The residue was purified by flash column chromatography with 0~20% ethyl acetate in petroleum ether to afford 6-fluoro-1H-indole-7-carbonitrile (470 mg, 89%) as a white solid. MS m/z 161.0 [M+1]$^+$.

Step 2: To a stirred solution of 6-fluoro-1H-indole-7-carbonitrile (470 mg, 2.93 mmol) in tetrahydrofuran (5 mL) was added N-bromosuccinimide (522 mg, 2.93 mmol) at room temperature. The resulting mixture was stirred at room temperature for 2 h. The mixture was diluted with water and extracted with ethyl acetate. The combined organic layers were washed with brine, dried over anhydrous sodium sulfate, filtered and concentrated under vacuum to afford 3-bromo-6-fluoro-1H-indole-7-carbonitrile (700 mg, crude) as a white solid. MS m/z 239.0 [M+1]$^+$.

Step 3: To a solution of 3-bromo-6-fluoro-1H-indole-7-carbonitrile (700 mg, 2.93 mmol) in dichloromethane (10 mL) were added di(tert-butyl) carbonate (958 mg, 4.39 mmol), triethylamine (889 mg, 8.78 mmol), 4-dimethylaminopyridine (36 mg, 0.29 mmol). The resulting solution was stirred at room temperature for 2 h. The residue was purified by flash column chromatography with 0~20% ethyl acetate in petroleum ether to afford tert-butyl 3-bromo-7-cyano-6-fluoroindole-1-carboxylate (A79) (800 mg, 80% over 2 steps) as a light yellow solid. MS m/z 339.0 [M+1]$^+$.

Intermediate A80 tert-butyl 3-bromo-7-cyano-6-methoxyindole-1-carboxylate

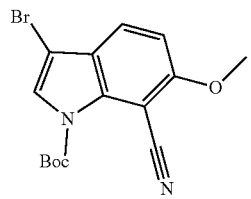 [SMILES: COc1ccc2c(Br)cn(C(=O)OC(C)(C)C)c2c1C#N]

Step 1: To a solution of 2-bromo-1-methoxy-3-nitrobenzene (10.00 g, 43.09 mmol) in tetrahydrofuran (100 mL) was added bromo(ethenyl)magnesium (130 mL, 130.00 mmol, 1 M in tetrahydrofuran) at −78° C. under nitrogen atmosphere. The resulting solution was stirred at −78° C. for 3 h. The reaction was then quenched with saturated ammonium chloride aqueous solution and extracted with ethyl acetate. The combined organic layers were washed with brine, dried over anhydrous sodium sulfate, filtered and concentrated under vacuum. The residue was purified by flash column chromatography with 0~20% ethyl acetate in petroleum ether to afford 7-bromo-6-methoxy-1H-indole (3.00 g, 31%) as a yellow solid. $^1$H NMR (400 MHz, DMSO-d$_6$) δ 11.02 (s, 1H), 7.50 (d, J=8.0 Hz, 1H), 7.26 (d, J=4.0 Hz, 1H), 6.90 (d, J=8.0 Hz, 1H), 6.48 (dd, J=4.0, 2.0 Hz, 1H), 3.86 (s, 3H).

Step 2: To a solution of 7-bromo-6-methoxy-1H-indole (3.00 g, 13.27 mmol) in DMF (15 mL) were added zinc cyanide (4.70 g, 39.81 mmol), palladium(0)tetrakis(triphenylphosphine) (1.50 g, 1.33 mmol) under nitrogen atmosphere. The resulting mixture was stirred at 140° C. for 4 h. The solids were filtered off. The filtrate was diluted with water and extracted with ethyl acetate. The organic layer was dried over anhydrous sodium sulfate, filtered and concentrated under vacuum. The residue was purified by flash column chromatography with 0~40% ethyl acetate in petroleum ether to afford 6-methoxy-1H-indole-7-carbonitrile (1.80 g, 79%) as a yellow solid. $^1$H NMR (400 MHz, DMSO-$d_6$) δ 11.69 (s, 1H), 7.83 (d, J=8.0 Hz, 1H), 7.33-7.30 (m, 1H), 6.94 (d, J=8.0 Hz, 1H), 6.53-6.51 (m, 1H), 3.93 (s, 3H).

Step 3: To a stirred solution of 6-methoxy-1H-indole-7-carbonitrile (1.80 g, 10.45 mmol) in tetrahydrofuran (10 mL) was added N-bromosuccinimide (1.90 g, 10.45 mmol). The mixture was stirred at room temperature for 2 h. The reaction mixture was diluted with water and extracted with ethyl acetate. The combined organic layers were washed with brine, dried over anhydrous sodium sulfate, filtered and concentrated under vacuum to afford 3-bromo-6-methoxy-1H-indole-7-carbonitrile (2.00 g, crude) as a yellow solid.

Step 4: To a solution of 3-bromo-6-methoxy-1H-indole-7-carbonitrile (2.50 g, 9.95 mmol) in dichloromethane (10 mL) was added di(tert-butyl) carbonate (3.30 g, 14.93 mmol), triethylamine (3.00 g, 29.87 mmol) and 4-dimethylaminopyridine (0.12 g, 0.99 mmol). The mixture was stirred at room temperature for 2 h. The mixture was concentrated under vacuum. The residue was purified by flash column chromatography with 0~25% ethyl acetate in petroleum ether to afford tert-butyl 3-bromo-7-cyano-6-methoxyindole-1-carboxylate (A80) (0.88 g, 24% over 2 steps) as a white solid. MS m/z 351.0 [M+1]$^+$. $^1$H NMR (400 MHz, DMSO-$d_6$) δ 7.88 (s, 1H), 7.75 (d, J=8.8 Hz, 1H), 7.31 (d, J=8.8 Hz, 1H), 3.99 (s, 3H), 1.62 (s, 9H).

Intermediate A81

2-(azetidin-1-yl)-6-bromopyrazine

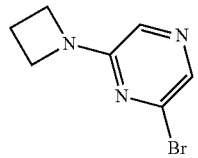 [SMILES: Brc1cncc(N2CCC2)n1]

To a solution of 2,6-dibromopyrazine (1.00 g, 4.20 mmol) and triethylamine (0.82 g, 8.11 mmol) in methanol (10 mL) was added azetidine (0.40 g, 6.94 mmol). The mixture was stirred at room temperature for 16 h. The mixture was concentrated under vacuum. The residue was purified by flash column chromatography with 0-55% ethyl acetate in petroleum ether to afford 2-(azetidin-1-yl)-6-bromopyrazine (A81) (0.64 g, 74%) as an off-white solid. MS m/z 214.0 [M+1]$^+$.

Intermediate A82

5-bromo-3-ethylpyrazin-2-amine

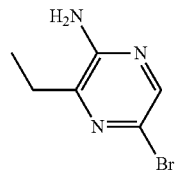

To a solution of 3-ethylpyrazin-2-amine (400 mg, 3.25 mmol) in dichloromethane (2 mL) was added N-bromosuccinimide (578 mg, 3.25 mmol). The resulting solution was then stirred at room temperature for 1.5 hours. The mixture was concentrated under vacuum. The resiudue was diluted with water and extracted with ethyl acetate. The combined organic layers were washed with brine, dried over anhydrous sodium sulfate, filtered and concentrated under vacuum to afford 5-bromo-3-ethylpyrazin-2-amine (A82) (450 mg, 69%) as a yellow solid. MS m/z 202.0 [M+1]$^+$. $^1$H NMR (400 MHz, DMSO-$d_6$) δ 7.89 (s, 1H), 6.44 (s, 2H), 2.57 (q, J=7.4 Hz, 2H), 1.15 (t, J=7.4 Hz, 3H).

Intermediate A83

1-[(6-bromo-2-methylpyridin-3-yl)amino]-2-methylpropan-2-ol

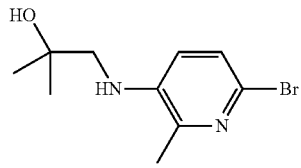

To a solution of ethyl 2-[(6-bromo-2-methylpyridin-3-yl)amino]acetate (300 mg, 1.09 mmol) in tetrahydrofuran was added methylmagnesium bromide (4.4 mL, 4.40 mmol, 1M in tetrahydrofuran) at −78° C. The mixture was stirred at −78° C. for 6 h under nitrogen atmosphere. The reaction was quenched with water/ice and extracted with ethyl acetate. The combined organic layers were washed with brine, dried over anhydrous sodium sulfate, filtered and concentrated under vacuum. The residue was purified by flash column chromatography with 0~70% ethyl acetate in petroleum ether to afford 1-[(6-bromo-2-methylpyridin-3-yl)amino]-2-methylpropan-2-ol (A83) (80 mg, 28%) as a yellow oil. MS m/z 259.0 [M+1]$^+$.

Intermediate A84 tert-butyl N-[2-[(6-bromo-2-methylpyridin-3-yl)amino]ethyl]carbamate

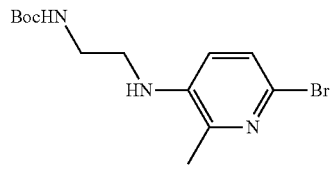 [SMILES: Cc1nc(Br)ccc1NCCNC(=O)OC(C)(C)C]

To a solution of 6-bromo-2-methylpyridin-3-amine (500 mg, 2.67 mmol) and tert-butyl N-(2-oxoethyl)carbamate (511 mg, 3.21 mmol) in dichloromethane (5 mL) were added sodium triacetoxyborohydride (1133 mg, 5.35 mmol) and glacial acetic acid (0.05 mL). The mixture was stirred at room temperature for 5 hours. The mixture was concentrated under vacuum. The resiudue was diluted with water and extracted with ethyl acetate. The combined organic layers were washed with brine, dried over anhydrous sodium sulfate, filtered and concentrated under vacuum. The residue was purified by reverse phase flash column chromatography with 0~60% acetonitrile in water to afford tert-butyl N-[2-[(6-bromo-2-methylpyridin-3-yl)amino]ethyl]carbamate (A84) (150 mg, 17%) as a yellow oil. MS m/z 330.1 [M+1]⁺.

Intermediate A85

6-bromo-N-(1-methoxypropan-2-yl)-2-methylpyridin-3-amine

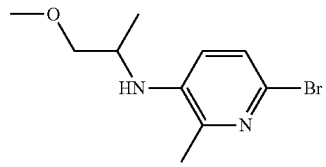

To a solution of 6-bromo-2-methylpyridin-3-amine (500 mg, 2.67 mmol) in dichloroethane (5 mL) were added glacial acetic acid (0.5 mL), 1-methoxy-2-propanone (2.35 g, 26.73 mmol) at room temperature. The mixture was stirred at 80° C. for 4 h. Then sodium triacetoxyborohydride (1.13 g, 5.34 mmol) was added to above mixture. The resulting solution was stirred at 80° C. for 4 h. The reaction was then quenched with water and extracted with dichloromethane. The combined organic layers were washed with brine, dried over anhydrous sodium sulfate, filtered and concentrated under vacuum. The residue was purified by flash column chromatography with 0~50% ethyl acetate in petroleum ether to afford 6-bromo-N-(1-methoxypropan-2-yl)-2-methylpyridin-3-amine (115 mg, 17%) as brown oil. MS m/z 259.0 [M+1]⁺.

Intermediate A86 tert-butyl 3-[(5-bromopyrazin-2-yl)oxy]pyrrolidine-1-carboxylate

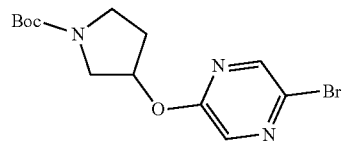 [SMILES: CC(C)(C)OC(=O)N1CCC(Oc2cnc(Br)cn2)C1]

To a solution of tert-butyl 3-hydroxypyrrolidine-1-carboxylate (472 mg, 2.52 mmol) in N,N-dimethylformamide (4 mL) were added sodium hydride (168 mg, 4.20 mmol, 60% in mineral oil). After stirring at room temperature for 30 min, 2,5-dibromopyrazine (500 mg, 2.10 mmol) was added to above mixture. The mixture was stirred at room temperature for 3 h. The mixture was diluted with water and extracted with ethyl acetate. The combined organic layers were washed with brine, dried over anhydrous sodium sulfate, filtered and concentrated under vacuum. The residue was purified by 0~25% ethyl acetate in petroleum ether to afford tert-butyl 3-[(5-bromopyrazin-2-yl)oxy]pyrrolidine-1-carboxylate (A86) (370 mg, 51%) as light yellow oil. MS m/z 344.1 [M+1]⁺. ¹H NMR (400 MHz, DMSO-d₆) δ 8.43 (d, J=1.2 Hz, 1H), 8.19 (d, J=1.2 Hz, 1H), 5.46-5.42 (m, 1H), 3.63-3.56 (m, 1H), 3.48-3.42 (m, 2H), 3.37-3.29 (m, 1H), 2.22-2.06 (m, 2H), 1.40 and 1.49 (s, 9H).

Intermediate A87 tert-butyl (1R,2S,4S)-2-((5-bromo-3-methylpyrazin-2-yl)oxy)-7-azabicyclo[2.2.1]heptane-7-carboxylate

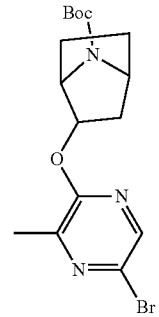 [SMILES: Cc1nc(Br)cnc1OC1CC2CCC1N2C(=O)OC(C)(C)C]

Step 1: To a solution of tert-butyl (1R,4S)-2-oxo-7-azabicyclo[2.2.1]heptane-7-carboxylate (300 mg, 1.42 mmol) in methanol (3 mL) was added sodium borohydride (107 mg, 2.84 mmol). The mixture was stirred at room temperature for 2 h. The mixture was quenched with water and extracted with dichloromethane. The combined organic layers was washed with brine, dried over anhydrous sodium sulfate, filtered and concentrated under vacuum. The residue was purified by flash column chromatography with 0~100% ethyl acetate in petroleum ether to afford tert-butyl (1R,4S)-2-oxo-7-azabicyclo[2.2.1]heptane-7-carboxylate (330 mg, 94%) as a yellow oil. MS m/z 241.1 [M+1]⁺.

Step 2: To a stirred solution of 5-bromo-3-methylpyrazin-2-ol (220 mg, 1.16 mmol), tert-butyl (1R,2S,4S)-2-hydroxy-7-azabicyclo[2.2.1]heptane-7-carboxylate (248 mg, 1.16 mmol) and triphenylphosphine (457 mg, 1.74 mmol) in tetrahydrofuran (3 mL) was added diisopropyl azodiformate (353 mg, 1.74 mmol) at room temperature under nitrogen atmosphere. The mixture was stirred at room temperature for 16 h. The reaction was quenched using water and extracted with ethyl acetate. The combined organic layers was washed with brine, dried over anhydrous sodium sulfate, filtered and concentrated under vacuum. The residue was purified by flash column chromatography with 0~50% ethyl acetate in petroleum ether to afford tert-butyl (1R,2S,4S)-2-((5-bromo-3-methylpyrazin-2-yl)oxy)-7-azabicyclo[2.2.1]heptane-7-carboxylate (A87) (120 mg, 24%) as a yellow oil. MS m/z 384.1, 386.1 [M+1]⁺. ¹H NMR (400 MHz, Methanol-d₄) δ 8.11 (s, 1H), 5.06-4.95 (m, 1H), 4.47-4.37 (m, 1H), 4.34-4.32 (m, 1H), 2.40 (s, 3H), 2.12-2.03 (m, 1H), 1.96-1.67 (m, 3H), 1.59-1.21 (m, 11H).

Intermediate A88 and A89 tert-butyl 6-((5-bromo-3-methylpyrazin-2-yl)oxy)-3-azabicyclo[3.1.0]hexane-3-carboxylate and tert-butyl 6-((5-chloro-6-methylpyrazin-2-yl)oxy)-3-azabicyclo[3.1.0]hexane-3-carboxylate

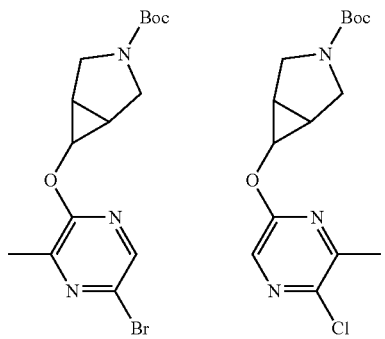 [SMILES: Cc1nc(Br)cnc1OC1C2CN(C(=O)OC(C)(C)C)CC21 ; Cc1nc(OC2C3CN(C(=O)OC(C)(C)C)CC32)cnc1Cl]

Step 1: To a stirred mixture of 5-bromo-3-methylpyrazin-2-amine (500 mg, 2.66 mmol), cuprous chloride (395 mg, 3.99 mmol) and cupric chloride (536 mg, 3.99 mmol) in acetonitrile (5 mL) was added t-butyl nitrite (630 mg, 6.12 mmol) dropwise at −10° C. under nitrogen atmosphere. The mixture was heated to 65° C. for 16 h with stirring. The reaction mixture was concentrated under vacuum. The residue was purified by flash column chromatography with 0~70% ethyl acetate in petroleum ether to afford 5-bromo-2-chloro-3-methylpyrazine (220 mg, 40%) as a yellow oil. MS m/z 206.9 [M+1]$^+$. $^1$H NMR (400 MHz, methyl sulfoxide-d$_6$) δ 8.58 (s, 1H), 2.58 (s, 3H).

Step 2: A mixture of 5-bromo-2-chloro-3-methylpyrazine (200 mg, 0.96 mmol), tert-butyl 6-hydroxy-3-azabicyclo [3.1.0]hexane-3-carboxylate (192 mg, 0.96 mmol) and cesium fluoride (440 mg, 2.89 mmol) in methyl sulfoxide (2 mL) was stirred at 100° C. for 16 h under nitrogen atmosphere. The reaction mixture was diluted with water and extracted with ethyl acetate. The combined organic layers was washed with brine, dried over anhydrous sodium sulfate, filtered and concentrated under vacuum. The residue was purified by flash column chromatography with 0~60% ethyl acetate in petroleum ether to afford a mixture of tert-butyl 6-((5-bromo-3-methylpyrazin-2-yl)oxy)-3-azabicyclo[3.1.0]hexane-3-carboxylate (A88) and tert-butyl 6-((5-chloro-6-methylpyrazin-2-yl)oxy)-3-azabicyclo[3.1.0]hexane-3-carboxylate (A89) (85 mg, 14%) as a yellow oil. Intermediate A87: MS m/z 370.1 [M+1]$^+$, Intermediate A88: MS m/z 326.1 [M+1]+

Intermediate A90 tert-butyl 3-((5-bromo-3-(difluoromethoxy)pyrazin-2-yl)amino)pyrrolidine-1-carboxylate

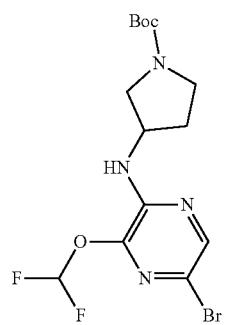 [SMILES: CC(C)(C)OC(=O)N1CCC(Nc2ncc(Br)nc2OC(F)F)C1]

Step 1: To a solution of 2,5-dibromopyrazine (6.00 g, 25.22 mmol) and tert-butyl 3-aminopyrrolidine-1-carboxylate (5.20 g, 27.76 mmol) in 1-methyl-2-pyrrolidinone (30 mL) was added N,N-diisopropylethylamine (9.80 g, 75.67 mmol). The mixture was then stirred at 150° C. for 2 h. The mixture was diluted with water and extracted with ethyl acetate. The combined organic layers was washed with brine, dried over anhydrous sodium sulfate, filtered and concentrated under vacuum. The residue was purified by flash column chromatography with 0~50% ethyl acetate in petroleum ether to afford tert-butyl 3-((5-bromopyrazin-2-yl)amino)pyrrolidine-1-carboxylate (3.50 g, 40%) as a yellow solid. MS m/z 343.1, 345.1 [M+1]$^+$.

Step 2: To a solution of tert-butyl 3-[(5-bromopyrazin-2-yl)amino]pyrrolidine-1-carboxylate (3.50 g, 10.20 mmol) in acetonitrile (30 mL) was added N-bromosuccinimide (2.20 g, 12.25 mmol). The mixture was stirred at room temperature for 2 h. The mixture was diluted with water and extracted with ethyl acetate. The combined organic layers was washed with brine, dried over anhydrous sodium sulfate, filtered and concentrated under vacuum. The residue was purified by flash column chromatography with 0~60% ethyl acetate in petroleum ether to afford tert-butyl 3-((3,5-dibromopyrazin-2-yl)amino)pyrrolidine-1-carboxylate (3.50 g, 81%) as a yellow oil. MS m/z 421.0, 423.0 [M+1]$^+$. $^1$H NMR (400 MHz, methyl sulfoxide-d$_6$) δ 8.26 (s, 1H), 6.96 (d, J=6.4 Hz, 1H), 4.48-4.27 (m, 1H), 3.60-3.55 (m, 1H), 3.51-3.40 (m, 1H), 3.31-3.16 (m, 2H), 2.13-1.96 (m, 2H), 1.40 and 1.39 (s, 9H).

Step 3: To a solution of tert-butyl 3-[(3,5-dibromopyrazin-2-yl)amino]pyrrolidine-1-carboxylate (1.50 g, 3.55 mmol) in water (45 mL) was added potassium hydroxide (1.00 g, 17.80 mmol). The mixture was stirred at 100° C. for 16 h. The reaction mixture was purified directly by reverse phase flash column chromatography with 5-70% acetonitrile in water to afford 6-bromo-3-(pyrrolidin-3-ylamino)pyrazin-2-ol (0.80 g, 87%) as a pink solid. MS m/z 259.1, 261.1 [M+1]$^+$.

Step 4: To a solution of 6-bromo-3-(pyrrolidin-3-ylamino)pyrazin-2-ol (1.00 g, 3.86 mmol) and triethylamine (1.20 g, 11.58 mmol) in dichloromethane (10 mL) was added di(tert-butyl) carbonate (2.50 g, 11.58 mmol). The mixture was stirred at room temperature for 2 h. The mixture was concentrated under vacuum. The residue was purified by flash column chromatography with 0~20% methanol in dichloromethane to afford tert-butyl 3-((5-bromo-3-hydroxypyrazin-2-yl)amino)pyrrolidine-1-carboxylate (0.70 g, 50%) as a brown oil. MS m/z 359.1, 361.1 [M+1]$^+$.

Step 5: To a solution of tert-butyl 3-[(5-bromo-3-hydroxypyrazin-2-yl)amino]pyrrolidine-1-carboxylate (900 mg, 2.51 mmol) in N,N-dimethylformamide (9 mL) were added 2-chloro-2,2-difluoroacetic acid (507 mg, 3.88 mmol) and potassium carbonate (1039 mg, 7.52 mmol). The mixture was stirred at 50° C. for 16 h. The mixture was diluted with water and extracted with ethyl acetate. The combined organic layers was washed with brine, dried over anhydrous sodium sulfate, filtered and concentrated under vacuum. The residue was purified by flash column chromatography with 0~60% ethyl acetate in petroleum ether to afford tert-butyl 3-((5-bromo-3-(difluoromethoxy)pyrazin-2-yl)amino)pyrrolidine-1-carboxylate (A90) (284 mg, 28%) as a yellow oil. MS m/z 408.9, 410.9 [M+1]$^+$. $^1$H NMR (400 MHz, methyl sulfoxide-d$_6$) δ 8.02 (s, 1H), 7.62 (t, J=71.4 Hz, 1H), 7.32 (d, J=6.4 Hz, 1H), 4.44-4.34 (m, 1H), 3.65-3.50 (m, 1H), 3.45-3.39 (m, 1H), 3.29-3.06 (m, 2H), 2.20-1.83 (m, 2H), 1.40 and 1.39 (s, 9H).

Intermediate A91 tert-butyl N-[1-(5-bromo-3-methylpyrazin-2-yl)pyrrolidin-3-yl]carbamate

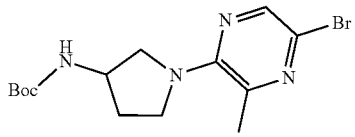 [SMILES: Cc1nc(Br)cnc1N1CCC(NC(=O)OC(C)(C)C)C1]

Step 1: To a solution of 2-chloro-3-methylpyrazine (1.0 g, 7.78 mmol) in methyl sulfoxide (10 mL) was added tert-butyl N-(pyrrolidin-3-yl)carbamate (1.7 g, 9.33 mmol) and N,N-diisopropylethylamine (3.0 g, 23.34 mmol) at room temperature. The mixture was stirred at 100° C. for 2 h. The mixture was cooled and diluted with water. The mixture was extracted with ethyl acetate. The combined organic layers was washed with brine, dried over anhydrous sodium sulfate, filtered and concentrated under vacuum. The residue was purified by flash column chromatography with 0~50% ethyl acetate in petroleum ether to afford tert-butyl N-[1-(3-methylpyrazin-2-yl)pyrrolidin-3-yl]carbamate (1.2 g, 57%) as a yellow oil. MS m/z 279.1 [M+1]$^+$.

Step 2: To a solution of tert-butyl N-[1-(3-methylpyrazin-2-yl)pyrrolidin-3-yl]carbamate (600 mg, 2.16 mmol) in acetonitrile (6 mL) was added N-bromosuccinimide (460 mg, 2.59 mmol). The mixture was stirred at room temperature for 2 h. The mixture was concentrated under vacuum. The residue was purified by flash column chromatography with 0~60% ethyl acetate in petroleum ether to afford tert-butyl N-[1-(5-bromo-3 methylpyrazin-2-yl)pyrrolidin-3-yl]carbamate (A91) (519 mg, 66%) as a yellow oil. MS m/z 357.1, 359.1 [M+1]$^+$. $^1$H NMR (400 MHz, methyl sulfoxide-d$_6$) δ 8.02 (s, 1H), 7.15 (d, J=6.4 Hz, 1H), 4.07-4.04 (m, 1H), 3.73-3.59 (m, 2H), 3.56-3.51 (m, 1H), 3.39-3.33 (m, 1H), 2.53 (s, 3H), 2.09-2.01 (m, 1H), 1.87-1.79 (m, 1H), 1.39 (s, 9H).

Intermediate A92

5-bromo-N-(1,3-dimethoxypropan-2-yl)-3-methylpyrazin-2-amine

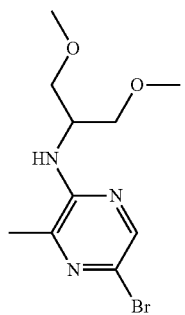

Step 1: A mixture of 2-chloro-3-methylpyrazine (500 mg, 3.89 mmol), sodium tert-butoxide (747 mg, 7.77 mmol) and 1,3-dimethoxypropan-2-amine (510 mg, 4.28 mmol) in toluene (5 mL) was stirred at 100° C. for 16 h. The mixture was diluted with ethyl acetate and washed by brine. The organic layer was dried over anhydrous sodium sulfate, filtered and concentrated under vacuum. The residue was purified by flash column chromatography with 0~100% ethyl acetate in petroleum ether to afford N-(1,3-dimethoxypropan-2-yl)-3-methylpyrazin-2-amine (530 mg, 65%) as a pink solid. MS m/z 212.1 [M+1]$^+$.

Step 2: To a solution of N-(1,3-dimethoxypropan-2-yl)-3-methylpyrazin-2-amine (250 mg, 1.18 mmol) in acetonitrile (3 mL) was added N-bromosuccinimide (253 mg, 1.42 mmol). The mixture was stirred at room temperature for 2 h. The reaction mixture was diluted with water. The aqueous solution was extracted with ethyl acetate. The combined organic layers was washed with brine, dried over anhydrous sodium sulfate, filtered and concentrated under vacuum. The residue was purified by flash column chromatography with 0~100% ethyl acetate in petroleum ether to afford 5-bromo-N-(1,3-dimethoxypropan-2-yl)-3-methylpyrazin-2-amine (A92) (95 mg, 28%) as a brown solid. MS m/z 290.0, 292.0 [M+1]$^+$.

Intermediate A93 tert-butyl 3-(4-bromo-2-fluorophenoxy)pyrrolidine-1-carboxylate

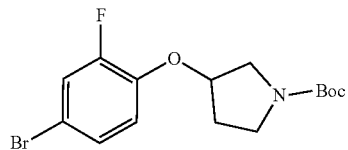 [SMILES: CC(C)(C)OC(=O)N1CCC(Oc2ccc(Br)cc2F)C1]

To a solution of 4-bromo-2-fluorophenol (500 mg, 2.62 mmol), tert-butyl 3-hydroxypyrrolidine-1-carboxylate (490 mg, 2.62 mmol) and triphenylphosphine (1030 mg, 3.93 mmol) in tetrahydrofuran (5 mL) was added diisopropyl azodiformate (794 mg, 3.93 mmol) slowly at room temperature under nitrogen atmosphere. The mixture was stirred at room temperature for 6 h. The mixture was diluted with water and extracted with ethyl acetate. The combined organic layers was washed with brine, dried over anhydrous sodium sulfate, filtered and concentrated under vacuum. The residue was purified by flash column chromatography with 0~50% ethyl acetate in petroleum ether to afford tert-butyl 3-(4-bromo-2-fluorophenoxy)pyrrolidine-1-carboxylate (A93) (330 mg, 35%) as a yellow solid. MS m/z 360.0, 362.0 [M+1]$^+$. $^1$H NMR (400 MHz, methyl sulfoxide-d$_6$) δ 7.56 (dd, J=10.8, 2.4 Hz, 1H), 7.35 (dt, J=8.8, 2.0 Hz, 1H), 7.20 (t, J=8.8 Hz, 1H), 5.07-5.02 (m, 1H), 3.60-3.37 (m, 4H), 2.18-2.01 (m, 2H), 1.41 and 1.39 (s, 9H).

Intermediate A94 tert-butyl 4-((5-bromo-3-methylpyrazin-2-yl)amino)piperidine-1-carboxylate

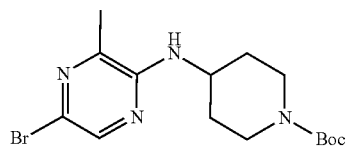 [SMILES: Cc1nc(Br)cnc1NC1CCN(C(=O)OC(C)(C)C)CC1]

Step 1: A solution of 2-chloro-3-methylpyrazine (500 mg, 3.81 mmol), tert-butyl 4-aminopiperidine-1-carboxylate (856 mg, 4.2 mmol), tris(dibenzylideneacetone)dipalladium (178 mg, 0.19 mmol), (±)-2,2'-bis(diphenylphosphino)-1,1'-binaphthalene (242 mg, 0.38 mmol) and sodium tert-butoxide (747 mg, 7.78 mmol) in toluene (5 mL) was stirred at 100° C. for 16 h under nitrogen atmosphere. The mixture was diluted with water and extracted with ethyl acetate. The combined organic layers was washed with brine, then dried over anhydrous sodium sulfate, filtered and concentrated under vacuum. The residue was purified by flash column chromatography with 0~70% ethyl acetate in petroleum ether to afford tert-butyl 4-[(3-methylpyrazin-2-yl)amino]piperidine-1-carboxylate (450 mg, 39%) as a yellow solid. MS m/z 293.2 [M+1]+.

Step 2: To a solution of tert-butyl 4-((3-methylpyrazin-2-yl)amino)piperidine-1-carboxylate (420 mg, 1.44 mmol) in acetonitrile (5 mL) was added N-bromosuccinimide (306 mg, 1.72 mmol). The mixture was stirred at room temperature for 2 h. The reaction mixture was diluted with water and extracted with ethyl acetate. The combined organic layers was washed with brine, dried over anhydrous sodium sulfate, filtered and concentrated under vacuum. The residue was purified by flash column chromatography with 0~100% ethyl acetate in petroleum ether to afford tert-butyl 4-((5-bromo-3-methylpyrazin-2-yl)amino)piperidine-1-carboxylate (A94) (370 mg, 67%) as a light yellow solid. MS m/z 371.1, 373.1 [M+1]+. 1H NMR (400 MHz, methyl sulfoxide-d6) δ 7.97 (d, J=0.8 Hz, 1H), 6.35 (d, J=7.6 Hz, 1H), 3.96 (s, 2H), 2.82 (s, 3H), 2.28 (d, J=0.8 Hz, 3H), 1.83 (d, J=11.2 Hz, 2H), 1.48-1.34 (m, 2H), 1.41 (s, 9H).

Intermediate A95 tert-butyl 3-[(5-bromo-3-methylpyrazin-2-yl)amino]piperidine-1-carboxylate

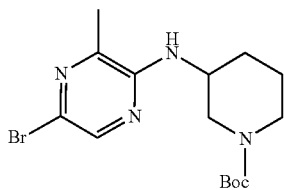 [SMILES: Cc1nc(Br)cnc1NC1CCCN(C(=O)OC(C)(C)C)C1]

Step 1: A degassed mixture of 2-chloro-3-methylpyrazine (500 mg, 4.00 mmol), (±)-2,2'-bis(diphenylphosphino)-1,1'-binaphthalene (242 mg, 0.4 mmol), tris(dibenzylideneacetone)dipalladium (178 mg, 0.2 mmol), sodium tert-butoxide (747 mg, 7.78 mmol) and tert-butyl 3-aminopiperidine-1-carboxylate (857 mg, 4.27 mmol) in toluene (5 mL) was stirred at 100° C. for 16 h. The mixture was diluted with water and extracted with ethyl acetate. The combined organic layers was washed with brine, then dried over anhydrous sodium sulfate, filtered and concentrated under vacuum. The residue was purified by flash column chromatography with 0~100% ethyl acetate petroleum ether to afford tert-butyl 3-[(3-methylpyrazin-2-yl)amino] piperidine-1-carboxylate (650 mg, 53%) as a yellow oil. MS m/z 293.2 [M+1]+.

Step 2: To a solution of tert-butyl 3-[(3-methylpyrazin-2-yl)amino]piperidine-1-carboxylate (300 mg, 1.02 mmol) in acetonitrile (3 mL) was added N-bromosuccinimide (219 mg, 1.23 mmol). The mixture was stirred at room temperature for 2 h. The reaction mixture was diluted with water and extracted with ethyl acetate. The combined organic layers was washed with brine, dried over anhydrous sodium sulfate, filtered and concentrated under vacuum. The residue was purified by flash column chromatography with 0~100% ethyl acetate in petroleum ether to afford tert-butyl 3-[(5-bromo-3-methylpyrazin-2-yl)amino]piperidine-1-carboxylate (A95) (240 mg, 63%) as a yellow oil. MS m/z 371.1, 373.1 [M+1]+. 1H NMR (400 MHz, methyl sulfoxide-d6) δ 7.99 (s, 1H), 6.24 (d, J=7.0 Hz, 1H), 3.92-3.53 (m, 3H), 3.16-2.64 (m, 2H), 2.30 (s, 3H), 1.97-1.45 (s, 4H), 1.43-1.13 (m, 9H).

Intermediate A96 tert-butyl 4-((5-bromo-3-methylpyrazin-2-yl)oxy)piperidine-1-carboxylate

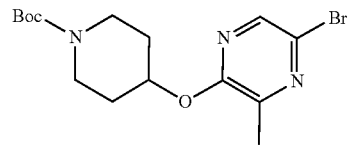 [SMILES: Cc1nc(Br)cnc1OC1CCN(C(=O)OC(C)(C)C)CC1]

To a stirred solution of 5-bromo-3-methylpyrazin-2-ol (300 mg, 1.59 mmol), tert-butyl 4-hydroxypiperidine-1-carboxylate (319 mg, 1.58 mmol) and triphenylphosphine (624 mg, 2.38 mmol) in tetrahydrofuran (10 mL) was added diisopropyl azodiformate (481 mg, 2.38 mmol) at room temperature under nitrogen atmosphere. The mixture was stirred at room temperature for 16 h. The reaction mixture was diluted with water and extracted with ethyl acetate. The organic layer was washed with brine, dried over anhydrous sodium sulfate, filtered and concentrated under vacuum. The residue was purified by flash column chromatography with 0~100% ethyl acetate in petroleum ether to afford tert-butyl 4-((5-bromo-3-methylpyrazin-2-yl)oxy)piperidine-1-carboxylate (A96) (400 mg, 64%) as a colorless oil. MS m/z 372.1, 374.1 [M+1]+. 1H NMR (400 MHz, methyl sulfoxide-d6) δ 8.21 (d, J=0.8 Hz, 1H), 5.28-5.07 (m, 1H), 3.64-3.50 (m, 2H), 3.31-3.18 (m, 2H), 2.38 (d, J=0.8 Hz, 3H), 1.96-1.81 (m, 2H), 1.74-1.53 (m, 2H), 1.41 (s, 9H).

Intermediate A97 tert-butyl 3-[(5-bromo-3-methylpyrazin-2-yl)oxy]piperidine-1-carboxylate

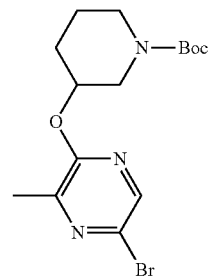 [SMILES: Cc1nc(Br)cnc1OC1CCCN(C(=O)OC(C)(C)C)C1]

To a solution of 5-bromo-3-methylpyrazin-2-ol (500 mg, 2.64 mmol), triphenylphosphine (1040 mg, 3.96 mmol) and tert-butyl 3-hydroxypiperidine-1-carboxylate (532 mg, 2.64 mmol) in tetrahydrofuran (5 mL) was added diisopropyl azodiformate (802 mg, 3.96 mmol) at 5° C. under nitrogen atmosphere. The reaction mixture was stirred at room temperature for 16 h. The reaction mixture was diluted with water and extracted with ethyl acetate. The combined organic layers was washed with brine, dried over anhydrous sodium sulfate, filtered and concentrated under vacuum. The residue was purified by flash column chromatography with 0~100% ethyl acetate in petroleum ether to afford tert-butyl 3-[(5-bromo-3-methylpyrazin-2-yl)oxy]piperidine-1-carboxylate (A97) (300 mg, 30%) as a colorless oil. MS m/z 372.1, 374.1 [M+1]$^+$.

Intermediate A98

6-(3-((tert-butyldimethylsilyl)oxy)propyl)-2-chloro-7,7-dimethyl-6,7-dihydro-5H-pyrrolo[3,4-b]pyridin-5-one

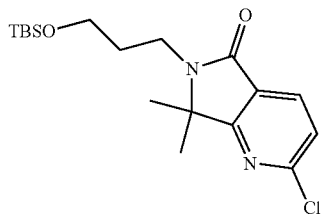 [SMILES: CC1(C)c2nc(Cl)ccc2C(=O)N1CCCO[Si](C)(C)C(C)(C)C]

To a stirred solution of 2-chloro-7,7-dimethyl-6,7-dihydro-5H-pyrrolo[3,4-b]pyridin-5-one (250 mg, 1.37 mmol) in N,N-dimethylformamide (3 mL) was added sodium hydride (99 mg, 2.47 mmol, 60% in mineral oil) at 5° C. After stirring for 30 min, (3-bromopropoxy)(tert-butyl)dimethylsilane (69 mg, 0.27 mmol) was added to above mixture. The mixture was stirred at room temperature for 3 h. The reaction was quenched with saturated ammonium chloride aqueous solution at 5° C. The mixture was extracted with ethyl acetate. The combined organic layers was washed with brine, dried over anhydrous sodium sulfate, filtered and concentrated under vacuum. The residue was purified by flash column chromatography with 0~50% ethyl acetate in petroleum ether to afford 6-(3-((tert-butyldimethylsilyl)oxy)propyl)-2-chloro-7,7-dimethyl-6,7-dihydro-5H-pyrrolo[3,4-b]pyridin-5-one (A98) (228 mg, 45%) as a yellow oil. MS m/z 369.2 [M+1]$^+$. $^1$H NMR (400 MHz, methyl sulfoxide-d$_6$) δ 8.11 (d, J=8.0 Hz, 1H), 7.62 (d, J=8.0 Hz, 1H), 3.68 (t, J=6.4 Hz, 2H), 3.51-3.42 (m, 2H), 1.90-1.79 (m, 2H), 1.47 (s, 6H), 0.89 (s, 9H), 0.06 (s, 6H).

Intermediate A99

6-(4-((tert-butyldimethylsilyl)oxy)butyl)-2-chloro-7,7-dimethyl-6,7-dihydro-5H-pyrrolo[3,4-b]pyridin-5-one

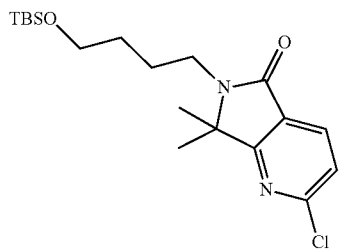 [SMILES: CC1(C)c2nc(Cl)ccc2C(=O)N1CCCCO[Si](C)(C)C(C)(C)C]

Step-1: To a stirred solution of 2-chloro-7,7-dimethyl-6H-pyrrolo[3,4-b]pyridin-5-one (250 mg, 1.25 mmol) in N,N-dimethylformamide (5 mL) was added sodium hydride (92 mg, 2.30 mmol, 60% in mineral oil) at 0~5° C. After stirring at 0~5° C. for 30 min, (4-bromobutoxy)(tert-butyl)dimethylsilane (410 mg, 1.55 mmol) was added to above mixture. The mixture was stirred at room temperature for 3 h. The reaction was quenched with saturated ammonium chloride aqueous solution at 5° C. The mixture was extracted with ethyl acetate. The combined organic layers was washed with brine, dried over anhydrous sodium sulfate, filtered and concentrated under vacuum. The residue was purified by flash column chromatography with 0~50% ethyl acetate in petroleum ether to afford 6-(4-((tert-butyldimethylsilyl)oxy)butyl)-2-chloro-7,7-dimethyl-6,7-dihydro-5H-pyrrolo[3,4-b]pyridin-5-one (A99) (370 mg, 76%) as a yellow oil. MS m/z 383.2 [M+1]$^+$. $^1$H NMR (400 MHz, methyl sulfoxide-d$_6$) δ 8.11 (d, J=8.0 Hz, 1H), 7.61 (d, J=8.0 Hz, 1H), 3.63 (t, J=6.2 Hz, 2H), 3.47-3.39 (m, 2H), 1.75-1.60 (m, 2H), 1.53 (dt, J=8.4, 6.4 Hz, 2H), 1.47 (s, 6H), 0.86 (s, 9H), 0.06 (s, 6H).

Intermediate A100 tert-butyl 3-[(2-chloro-6-iodopyridin-3-yl)oxy]pyrrolidine-1-carboxylate

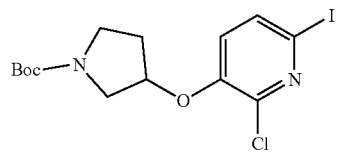 [SMILES: CC(C)(C)OC(=O)N1CCC(Oc2ccc(I)nc2Cl)C1]

To a stirred mixture of 2-chloro-6-iodopyridin-3-ol (500 mg, 1.95 mmol), tert-butyl 3-hydroxypyrrolidine-1-carboxylate (403 mg, 2.15 mmol) and triphenylphosphine (770 mg, 2.94 mmol) in tetrahydrofuran (10 mL) was added diisopropyl azodiformate (594 mg, 2.94 mmol) at 5° C. under nitrogen atmosphere. The mixture was stirred at room temperature for 16 h. The reaction mixture was diluted with water and extracted with ethyl acetate. The combined organic layers was washed with brine, dried over anhydrous sodium sulfate, filtered and concentrated under vacuum. The residue was purified by flash column chromatography with 0~100% ethyl acetate petroleum ether in to afford tert-butyl 3-[(2-chloro-6-iodopyridin-3-yl)oxy]pyrrolidine-1-carboxylate (A100) (500 mg, 60%) as a white solid. MS m/z 425.0 [M+1]$^+$. $^1$H NMR (400 MHz, methyl sulfoxide-d$_6$) 7.80 (d, J=8.4 Hz, 1H), 7.45 (d, J=8.4 Hz, 1H), 5.13 (d, J=5.0 Hz, 1H), 3.63-3.36 (m, 4H), 2.25-1.95 (m, 2H), 1.40 (s, 9H).

Intermediate A101 tert-butyl 3-((6-bromo-2-methylpyridin-3-yl)oxy)pyrrolidine-1-carboxylate

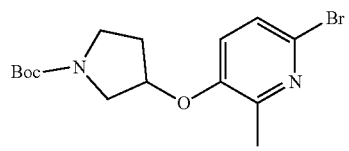 [SMILES: Cc1nc(Br)ccc1OC1CCN(C(=O)OC(C)(C)C)C1]

To a solution of 6-bromo-2-methylpyridin-3-ol (1.00 g, 5.32 mmol) and tert-butyl 3-hydroxypyrrolidine-1-carboxylate (1.00 g, 5.32 mmol) and triphenylphosphine (2.10 g, 7.98 mmol) in tetrahydrofuran (10 mL) was added diisopropyl azodiformate (1.60 g, 7.98 mmol) at 5° C. under nitrogen atmosphere. The mixture was then stirred at room temperature for 4 h under nitrogen atmosphere. The mixture was diluted with ethyl acetate, washed with brine, dried over anhydrous sodium sulfate, filtered and concentrated under vacuum. The residue was purified by reverse phase flash column chromatography with 5-70% acetonitrile in water to afford tert-butyl 3-((6-bromo-2-methylpyridin-3-yl)oxy) pyrrolidine-1-carboxylate (A101) (842 mg, 39%) as a yellow solid. MS m/z 357.3 [M+1]+. 1H NMR (400 MHz, methyl sulfoxide-d6) δ 7.41 (s, 2H), 5.05 (s, 1H), 3.60-3.34 (m, 4H), 2.29 (s, 3H), 2.13-2.04 (m, 2H), 1.40 (d, J=8.4 Hz, 9H).

Intermediate A102 tert-butyl 3-((5-bromo-3-methylpyrazin-2-yl)oxy) azetidine-1-carbonylate

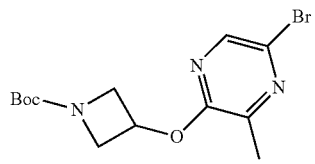 [SMILES: Cc1nc(Br)cnc1OC1CN(C(=O)OC(C)(C)C)C1]

To a stirred mixture of 5-bromo-3-methylpyrazin-2-ol (300 mg, 1.58 mmol), tert-butyl 3-hydroxyazetidine-1-carboxylate (274 mg, 1.58 mmol) and triphenylphosphine (624 mg, 2.38 mmol) in tetrahydrofuran (5 mL) was added diisopropyl azodiformate (481 mg, 2.38 mmol) at 5° C. under nitrogen atmosphere. The mixture was stirred at room temperature for 16 h. The reaction mixture was diluted with water and extracted with ethyl acetate. The organic layers were washed with brine, dried over anhydrous sodium sulfate, filtered and concentrated under vacuum. The residue was purified by flash column chromatography with 0~60% ethyl acetate in petroleum ether to afford tert-butyl 3-((5-bromo-3-methylpyrazin-2-yl)oxy)azetidine-1-carboxylate (A102) (300 mg, 65%) as a yellow oil. MS m/z 344.1, 346.1 [M+1]+. 1H NMR (400 MHz, methyl sulfoxide-d6) δ 8.20 (d, J=1.2 Hz, 1H), 5.27 (tt, J=6.4, 4.0 Hz, 1H), 4.26 (dd, J=9.6, 6.8 Hz, 2H), 3.88 (dd, J=9.6, 3.6 Hz, 2H), 2.42 (d, J=0.8 Hz, 3H), 1.39 (s, 9H).

Intermediate A103

1-[3-[(5-bromo-3-methylpyrazin-2-yl)oxy]azetidin-1-yl]ethanone

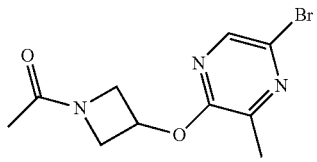 [SMILES: CC(=O)N1CC(Oc2ncc(Br)nc2C)C1]

To a solution of 5-bromo-3-methylpyrazin-2-ol (300 mg, 1.44 mmol), 1-(3-hydroxyazetidin-1-yl)ethan-1-one (183 mg, 1.59 mmol) and triphenylphosphine (568 mg, 2.16 mmol) in tetrahydrofuran (5 mL) was added diisopropyl azodiformate (438 mg, 2.16 mmol) at 5° C. under nitrogen atmosphere. The mixture was stirred at room temperature for 16 h. The mixture was diluted with ethyl acetate and washed with brine. The organic layer was dried over anhydrous sodium sulfate, filtered and concentrated under vacuum. The residue was purified by flash column chromatography with 0~70% ethyl acetate in n-hexane to afford 1-[3-[(5-bromo-3-methylpyrazin-2-yl)oxy]azetidin-1-yl]ethenone (A103) (200 mg, 43%) as a white solid. MS m/z 286.0, 288.0 [M+1]+. 1H NMR (400 MHz, methyl sulfoxide-d6) δ 8.22 (d, J=0.8 Hz, 1H), 5.31 (tt, J=6.4, 4.0 Hz, 1H), 4.59-4.45 (m, 1H), 4.29-4.20 (m, 1H), 4.19-4.10 (m, 1H), 3.90-3.82 (m, 1H), 2.43 (d, J=0.8 Hz, 3H), 1.79 (s, 3H).

Intermediate A104 tert-butyl 3-(4-bromo-2-chlorophenoxy)pyrrolidine-1-carboxylate

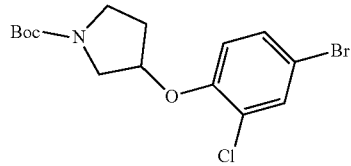 [SMILES: CC(C)(C)OC(=O)N1CCC(Oc2ccc(Br)cc2Cl)C1]

To a solution of 4-bromo-2-chlorophenol (200 mg, 0.96 mmol), tert-butyl 3-hydroxypyrrolidine-1-carboxylate (180 mg, 0.96 mmol) and triphenylphosphine (379 mg, 1.44 mmol) in tetrahydrofuran (5 mL) was added diisopropyl azodiformate (292 mg, 1.44 mmol) at 5° C. under nitrogen atmosphere. The mixture was stirred at room temperature for 16 h. The mixture was diluted with ethyl acetate and washed with brine. The organic layer was dried over anhydrous sodium sulfate, filtered and concentrated under vacuum. The residue was purified by flash column chromatography with 0~70% ethyl acetate in petroleum ether to afford tert-butyl 3-(4-bromo-2-chlorophenoxy)pyrrolidine-1-carboxylate (A104) (350 mg, 87%) as a yellow oil. MS m/z 376.0, 378.0 [M+1]+. 1H NMR (400 MHz, methyl sulfoxide-d6) δ 7.69 (d, J=2.4 Hz, 1H), 7.50 (dd, J=8.8, 2.4 Hz, 1H), 7.20 (d, J=8.8 Hz, 1H), 5.10 (s, 1H), 3.65-3.36 (m, 4H), 2.24-2.01 (m, 1H), 1.40 (d, J=6.8 Hz, 9H).

Intermediate A105 tert-butyl (3R,4R and 3S,4S)-3-((5-bromo-3-methylpyrazin-2-yl)oxy)-4-fluoropyrrolidine-1-carboxylate

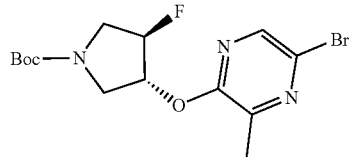 [SMILES: Cc1nc(Br)cnc1O[C@@H]1CN(C(=O)OC(C)(C)C)C[C@H]1F]

To a stirred solution of 5-bromo-3-methylpyrazin-2-ol (250 mg, 1.32 mmol), tert-butyl (3R,4S)-3-fluoro-4-hydroxypyrrolidine-1-carboxylate (298 mg, 1.46 mmol) and triphenylphosphine (520 mg, 1.98 mmol) in tetrahydrofuran (5 mL) was added diisopropyl azodiformate (401 mg, 1.98 mmol) dropwise at room temperature under nitrogen atmosphere. The mixture was stirred at room temperature for 16 h. The mixture was diluted with water and extracted with ethyl acetate. The combined organic layers was washed with brine, dried over anhydrous sodium sulfate, filtered and concentrated under vacuum. The residue was purified by flash column chromatography with 0~60% ethyl acetate in petroleum ether to afford tert-butyl (3R,4R and 3S,4S)-3-((5-bromo-3-methylpyrazin-2-yl)oxy)-4-fluoropyrrolidine-1-carboxylate (A105) (450 mg, 88%) as a white solid. MS m/z 376.1, 378.1 [M+1]$^+$. $^1$H NMR (400 MHz, methyl sulfoxide-d$_6$) δ 8.28 (s, 1H), 5.48-5.42 (br, 1H), 5.38-5.11 (m, 1H), 3.73-3.66 (m, 2H), 3.61-3.52 (m, 2H), 2.36 (s, 3H), 1.42 (s, 9H).

Intermediate A106 tert-butyl 3-((5-bromo-3-(difluoromethoxy)pyrazin-2-yl)oxy)pyrrolidine-1-carboxylate

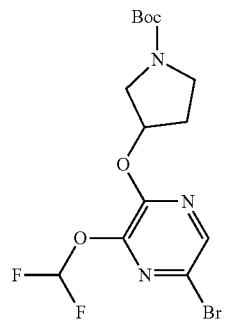 [SMILES: CC(C)(C)OC(=O)N1CCC(Oc2ncc(Br)nc2OC(F)F)C1]

Step 1: To a solution of 3,5-dibromopyrazin-2-amine (4.50 g, 17.79 mmol) in tetrahydrofuran (50 mL) was added sodium hydride (1.50 g, 37.50 mmol, 60% in mineral oil) in portions at 0° C. After stirring at 0° C. for 30 min, benzyl alcohol (4.80 g, 44.49 mmol) was added to above mixture. The mixture was stirred at room temperature for 3 h. The reaction mixture was quenched using saturated ammonium chloride aqueous solution at room temperature. The aqueous solution was extracted with ethyl acetate. The combined organic layers was washed with brine, dried over anhydrous sodium sulfate, filtered and concentrated under vacuum. The residue was purified by flash column chromatography with 0-70% ethyl acetate in petroleum ether to afford 3-(benzyloxy)-5-bromopyrazin-2-amine (7.00 g, 70%) as a yellow solid. MS m/z 280.0, 282.0 [M+1]$^+$. $^1$H NMR (400 MHz, methyl sulfoxide-d$_6$) δ 7.63 (s, 1H), 7.57-7.48 (m, 2H), 7.43-7.37 (m, 2H), 7.37-7.32 (m, 1H), 6.57 (s, 2H), 5.37 (s, 2H).

Step 2: To a stirred mixture of 3-(benzyloxy)-5-bromopyrazin-2-amine (5.00 g, 17.85 mmol) and cuprous chloride (2.70 g, 26.77 mmol), cupric chloride (3.60 g, 26.77 mmol) in acetonitrile (50 mL) was added tert-butyl nitrite (4.20 g, 41.05 mmol) dropwise at −10° C. under nitrogen atmosphere. After stirring at room temperature for 30 min, the mixture was stirred at 65° C. for 16 h. The mixture was diluted with saturated ammonium chloride aqueous solution and extracted with ethyl acetate. The combined organic layers was washed with brine, dried over anhydrous sodium sulfate, filtered and concentrated under vacuum. The residue was purified by flash column chromatography with 0-70% ethyl acetate in petroleum ether to afford 3-(benzyloxy)-5-bromo-2-chloropyrazine (2.00 g, 36%) as a yellow oil. MS m/z 299.0, 301.0 [M+1]$^+$. $^1$H NMR (400 MHz, methyl sulfoxide-d$_6$) δ 8.30 (s, 1H), 7.52-7.49 (m, 2H), 7.45-7.35 (m, 3H), 5.44 (s, 2H).

Step 3: To a solution of tert-butyl 3-hydroxypyrrolidine-1-carboxylate (2.00 g, 6.68 mmol) in tetrahydrofuran (20 mL) was added sodium hydride (0.56 g, 14.00 mmol, 60% in mineral oil) at 0° C. After stirring at 0° C. for 1 h, 3-(benzyloxy)-5-bromo-2-chloropyrazine (2.00 g, 6.68 mmol) was added dropwise to above mixture at room temperature. The resulting mixture was stirred at room temperature for 3 h. The reaction was quenched with saturated ammonium chloride aqueous solution and extracted with ethyl acetate. The combined organic layers was washed with brine, dried over anhydrous sodium sulfate, filtered and concentrated under vacuum. The residue was purified by flash column chromatography with 0~70% ethyl acetate in petroleum ether to afford tert-butyl 3-[[3-(benzyloxy)-5-bromopyrazin-2-yl]oxy]pyrrolidine-1-carboxylate (1.20 g, 40%) as a yellow oil. MS m/z 450.1, 452.1 [M+1]$^+$.

Step 4: To a solution of tert-butyl 3-[[3-(benzyloxy)-5-bromopyrazin-2-yl]oxy]pyrrolidine-1-carboxylate (690 mg, 1.53 mmol) in dichloromethane (5 mL) was added boron trichloride (7.6 mL, 7.60 mmol, 1M in dichloromethane) slowly at 0° C. The mixture was stirred at room temperature for 5 h under nitrogen atmosphere. The reaction was quenched with methanol. The mixture was concentrated under vacuum to afford 6-bromo-3-(pyrrolidin-3-yloxy)pyrazin-2-ol (600 mg, crude) as a yellow oil. MS m/z 260.1, 262.1 [M+1]$^+$.

Step 5: To a mixture of 6-bromo-3-(pyrrolidin-3-yloxy)pyrazin-2-ol (600 mg, crude from previous step) and triethylamine (404 mg, 4.00 mmol) in tetrahydrofuran (5 mL) was added di(tert-butyl) carbonate (582 mg, 2.66 mmol). The mixture was stirred at room temperature for 3 h under nitrogen atmosphere. The mixture was concentrated under vacuum. The residue was purified by flash column chromatography with 0~50% ethyl acetate in petroleum ether to afford tert-butyl 3-((5-bromo-3-((tert-butoxycarbonyl)oxy)pyrazin-2-yl)oxy)pyrrolidine-1-carboxylate (330 mg, 46% over 2 steps) as a yellow oil. MS m/z 460.1, 462.1 [M+1]$^+$.

Step 6: A mixture of tert-butyl 3-[(5-bromo-3-hydroxypyrazin-2-yl)oxy]pyrrolidine-1-carboxylate (330 mg, 0.92 mmol), 2-chloro-2,2-difluoroacetic acid (239 mg, 1.83 mmol) and potassium carbonate (380 mg, 2.75 mmol) in N,N-dimethylformamide (3 mL) was stirred at 50° C. for 16 h under nitrogen atmosphere. The mixture was diluted with water and extracted with ethyl acetate. The organic layer was dried over anhydrous sodium sulfate, filtered and concentrated under vacuum. The residue was purified by flash column chromatography with 0-60% ethyl acetate in petroleum ether to afford tert-butyl 3-((5-bromo-3-(difluoromethoxy)pyrazin-2-yl)oxy)pyrrolidine-1-carboxylate (A106) (160 mg, 42%) as a yellow oil. MS m/z 410.0, 412.0 [M+1]$^+$. $^1$H NMR (400 MHz, methyl sulfoxide-d$_6$) δ 8.24 (s, 1H), 7.62 (t, J=71.2 Hz, 1H), 5.52-5.47 (m, 1H), 3.65-3.59 (m, 1H), 3.49-3.44 (m, 3H), 2.26-2.04 (m, 2H), 1.40 (s, 9H).

Intermediate A107 tert-butyl 3-((5-bromo-3-(trifluoromethyl)pyrazin-2-yl)oxy)pyrrolidine-1-carboxylate

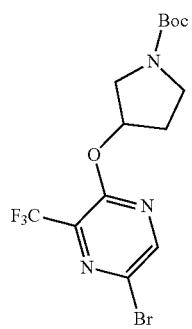

Step 1: To a stirred solution of 5-bromopyrazin-2-ol (6.00 g, 34.29 mmol) and sodium carbonate (7.30 g, 68.58 mmol) in water (50 mL) was added iodine (8.70 g, 34.29 mmol) in portions at room temperature. The mixture was stirred at room temperature for 16 h. The reaction mixture was acidified with hydrochloric acid (aq., 1 N) to pH 7. The aqueous solution was extracted with ethyl acetate. The combined organic layers was washed with ammonium hydroxide, hydrochloric acid (aq., 1 N), saturated sodium bicarbonate aqueous solution and brine. The organic layer was dried over anhydrous sodium sulfate, filtered and concentrated under vacuum. The residue was purified by reverse phase flash column chromatography with 5-100% acetonitrile in water to afford 5-bromo-3-iodopyrazin-2-ol (450 mg, 4%) as a yellow solid. MS m/z 300.8, 302.8 [M+1]$^+$.

Step 2: To a stirred mixture of 5-bromo-3-iodopyrazin-2-ol (430 mg, 1.42 mmol), tert-butyl 3-hydroxypyrrolidine-1-carboxylate (267 mg, 1.42 mmol) and triphenylphosphine (562 mg, 2.14 mmol) in tetrahydrofuran (5 mL) was added diisopropyl azodiformate (433 mg, 2.14 mmol) dropwise at 0° C. under nitrogen atmosphere. The mixture was stirred at room temperature for 16 h under nitrogen atmosphere. The mixture was concentrated under vacuum. The residue was purified by flash column chromatography with 0~60% ethyl acetate in petroleum ether to afford tert-butyl 3-((5-bromo-3-iodopyrazin-2-yl)oxy)pyrrolidine-1-carboxylate (550 mg, 57%) as a yellow oil. MS m/z 469.9, 471.9 [M+1]$^+$.

Step 3: To a stirred mixture of potassium fluoride (75 mg, 1.28 mmol) and copper(I) iodide (245 mg, 1.29 mmol) in 1-methyl-2-pyrrolidinone (4 mL) and N,N-dimethylformamide (4 mL) was added tert-butyl 3-((5-bromo-3-iodopyrazin-2-yl)oxy)pyrrolidine-1-carboxylate (550 mg, 1.17 mmol) and (trifluoromethyl)trimethylsilane (166 mg, 1.17 mmol) at room temperature under nitrogen atmosphere. The mixture was stirred at 70° C. for 3 h under nitrogen atmosphere. The mixture was diluted with water and extracted with ethyl acetate. The combined organic layers was washed with brine, dried over anhydrous sodium sulfate, filtered and concentrated under vacuum to afford tert-butyl 3-((5-bromo-3-(trifluoromethyl)pyrazin-2-yl)oxy)pyrrolidine-1-carboxylate (A107) (320 mg, crude) as a yellow solid. MS m/z 412.0, 414.0 [M+1]$^+$. $^1$H NMR (400 MHz, methyl sulfoxide-d$_6$) δ 8.37 (s, 1H), 5.45-5.39 (m, 1H), 3.68-3.35 (m, 4H), 2.24-2.02 (m, 2H), 1.42 and 1.40 (s, 9H).

Intermediate A108 tert-butyl 6-[[(5-bromo-3-methylpyrazin-2-yl)oxy]methyl]-3-azabicyclo[3.1.0]hexane-3-carboxylate

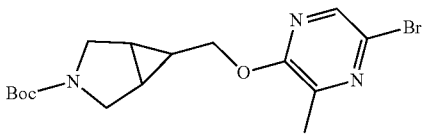 [SMILES: Cc1nc(Br)cnc1OCC1C2CN(C(=O)OC(C)(C)C)CC12]

Step 1: To a solution of ethyl 3-azabicyclo[3.1.0]hexane-6-carboxylate hydrochloride (400 mg, 2.09 mmol) in tetrahydrofuran (4 mL) were added di(tert-butyl) carbonate (634 mg, 6.26 mmol) and triethylamine (79 mg, 0.78 mmol). The mixture was then stirred at room temperature for 4 hours. The reaction mixture was concentrated under vacuum. The residue was purified by flash column chromatography with 0~50% ethyl acetate in petroleum ether to afford 3-tert-butyl 6-ethyl 3-azabicyclo[3.1.0]hexane-3,6-dicarboxylate (460 mg, 86%) as a yellow solid. MS m/z 256.1 [M+1]$^+$.

Step 2: To a solution of 3-tert-butyl 6-ethyl 3-azabicyclo[3.1.0]hexane-3,6-dicarboxylate (460 mg, 1.79 mmol) in tetrahydrofuran (5 mL) was added lithium aluminium hydride (70 mg, 1.84 mmol) at 0° C. The mixture was stirred at 0° C. for 2 h. The reaction mixture was quenched with ice/water and extracted with ethyl acetate. The combined organic layers was washed with brine, dried over anhydrous sodium sulfate, filtered and concentrated under vacuum. The residue was purified by flash column chromatography with 0-60% ethyl acetate in petroleum ether to afford tert-butyl 6-(hydroxymethyl)-3-azabicyclo[3.1.0]hexane-3-carboxylate (240 mg, 61%) as a yellow solid. MS m/z 214.0 [M+1]$^+$.

Step 3: To a solution of 5-bromo-3-methylpyrazin-2-ol (210 mg, 1.11 mmol), tert-butyl 6-(hydroxymethyl)-3-azabicyclo[3.1.0]hexane-3-carboxylate (237 mg, 1.11 mmol) and triphenylphosphine (437 mg, 1.67 mmol) in tetrahydrofuran (3 mL) was added diisopropyl azodiformate (794 mg, 3.93 mmol) slowly at 0° C. under nitrogen atmosphere. The mixture was stirred at room temperature for 8 h. The reaction mixture was diluted with water and extracted with ethyl acetate. The combined organic layers was washed with brine, dried over anhydrous sodium sulfate, filtered and concentrated under vacuum. The residue was purified by flash column chromatography with 0-80% ethyl acetate in petroleum ether to afford tert-butyl 6-[[(5-bromo-3-methylpyrazin-2-yl)oxy]methyl]-3-azabicyclo[3.1.0]hexane-3-carboxylate (A108) (230 mg, 54%) as a light yellow oil. MS m/z 384.0, 386.0 [M+1]$^+$. $^1$H NMR (400 MHz, methyl sulfoxide-d$_6$) δ 8.20-8.18 (m, 1H), 4.31-4.05 (m, 2H), 3.46-3.43 (m, 3H), 3.20-3.15 (m, 1H), 2.41-2.39 (m, 3H), 1.83-1.77 (m, 1H), 1.67-1.63 (m, 1H), 1.38 and 1.30 (s, 9H), 1.04-0.99 (m, 1H).

Intermediate A109 tert-butyl 3-[(5-bromo-3-ethylpyrazin-2-yl)oxy]pyrrolidine-1-carboxylate

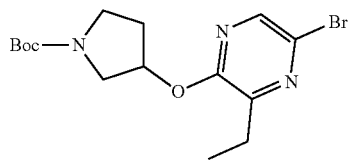 [SMILES: CCc1nc(Br)cnc1OC1CCN(C(=O)OC(C)(C)C)C1]

To a stirred mixture of 5-bromo-3-ethylpyrazin-2-ol (260 mg, 1.28 mmol), tert-butyl 3-hydroxypyrrolidine-1-carboxylate (240 mg, 1.28 mmol) and triphenylphosphine (504 mg, 1.92 mmol) in tetrahydrofuran (10 mL) was added diisopropyl azodiformate (388 mg, 1.92 mmol) dropwise at 0° C. under nitrogen atmosphere. The mixture was stirred at room temperature for 16 h. The reaction mixture was diluted with water and then extracted with ethyl acetate. The combined organic layers was washed with brine, dried over anhydrous sodium sulfate, filtered and concentrated under vacuum. The residue was purified by flash column chromatography with 0-50% ethyl acetate in petroleum ether to afford tert-butyl 3-[(5-bromo-3-ethylpyrazin-2-yl)oxy]pyrrolidine-1-carboxylate (A109) (290 mg, 61%) as a yellow oil. MS m/z 372.3, 374.3 [M+1]$^+$. $^1$H NMR (400 MHz, methyl sulfoxide-d$_6$) δ 8.24 (s, 1H), 5.49-5.42 (m, 1H), 3.63-3.55 (m, 1H), 3.50-3.32 (m, 3H), 2.71 (q, J=7.6 Hz, 2H), 2.18-2.10 (m, 2H), 1.40 and 1.39 (s, 9H), 1.16 (t, J=7.6 Hz, 3H).

Intermediate A110

3-(5-bromo-3-methoxypyrazin-2-ylamino)pyrrolidine-1-carboxylate

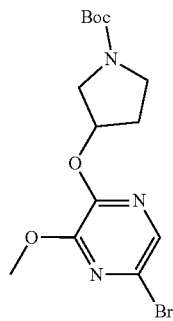 [SMILES: COc1nc(Br)cnc1OC1CCN(C(=O)OC(C)(C)C)C1]

Followed the procedure of Intermediate A96 described above to afford 3-(5-bromo-3-methoxypyrazin-2-ylamino) pyrrolidine-1-carboxylate (0.70 g, 27% over two steps) as a yellow oil from 2-chloro-3-methoxypyrazine (1.00 g, 6.92 mmol) and tert-butyl 3-aminopyrrolidine-1-carboxylate (A110) (1.30 g, 6.92 mmol). MS m/z 373.1, 375.1 [M+1]$^+$.

Intermediate A111 tert-butyl 3-[(5-bromo-3-ethoxypyrazin-2-yl)amino]pyrrolidine-1-carboxylate

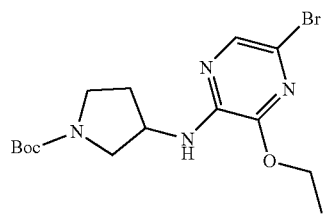 [SMILES: CCOc1nc(Br)cnc1NC1CCN(C(=O)OC(C)(C)C)C1]

Followed the procedure of Intermediate A96 described above to afford tert-butyl 3-[(5-bromo-3-ethoxypyrazin-2-yl)amino]pyrrolidine-1-carboxylate (0.52 g, 10% over 2 steps) as a brown solid from 2-chloro-3-ethoxypyrazine (1.70 g, 10.72 mmol), tert-butyl 3-aminopyrrolidine-1-carboxylate (A111) (2.20 g, 11.80 mmol). MS m/z 387.1, 389.1 [M+1]$^+$.

Intermediate A112 tert-butyl 3-((6-chloro-2-(trifluoromethyl)pyridin-3-yl)oxy)pyrrolidine-1-carboxylate

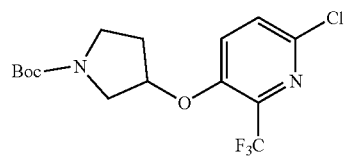 [SMILES: CC(C)(C)OC(=O)N1CCC(Oc2ccc(Cl)nc2C(F)(F)F)C1]

Step 1: To a stirred solution of 6-chloropyridin-3-ol (2.00 g, 15.44 mmol) in water (20 mL) were added sodium carbonate (3.30 g, 30.88 mmol) and iodine (3.90 g, 15.44 mmol) at room temperature under nitrogen atmosphere. The resulting mixture was stirred at room temperature for 2 h. The mixture was extracted with ethyl acetate. The combined organic layers was washed with brine, dried over anhydrous sodium sulfate, filtered and concentrated under vacuum to afford 6-chloro-2-iodopyridin-3-ol (4.10 g, crude) as a yellow solid. MS m/z 255.9 [M+1]$^+$.

Step 2: To a mixture of 6-chloro-2-iodopyridin-3-ol (2.00 g, 7.83 mmol), tert-butyl 3-hydroxypyrrolidine-1-carboxylate (1.60 g, 8.61 mmol) and triphenylphosphine (3.10 g, 11.74 mmol) in tetrahydrofuran (15 mL) was added diisopropyl azodiformate (2.40 g, 11.74 mmol) at 0° C. under nitrogen atmosphere. The resulting mixture was stirred at room temperature for 16 h. The reaction mixture was concentrated under vacuum. The residue was purified by reverse phase flash column chromatography with 5-90% acetonitrile in water to afford tert-butyl 3-((6-chloro-2-iodopyridin-3-yl)oxy)pyrrolidine-1-carboxylate (1.50 g, 22% over 2 steps) as a white solid. MS m/z 425.0 [M+1]$^+$.

Step 3: To a mixture of potassidium fluoride (0.15 g, 2.59 mmol) and copper(I) iodide (0.49 g, 2.59 mmol) in 1-Methyl-2-pyrrolidinone (10 mL) and N,N-dimethylformamide (10 mL) were added tert-butyl 3-((6-chloro-2-iodopyridin-3-yl)oxy)pyrrolidine-1-carboxylate (1.00 g, 2.36 mmol) and (trifluoridemethyl)trimethylsilane (0.33 g, 2.36 mmol) at room temperature under nitrogen atmosphere. The mixture was stirred at 70° C. for 3 h. The reaction mixture was diluted with water and treated with ammonium hydroxide. The mixture was extracted with ethyl acetate. The combined organic layers was washed with brine, dried over anhydrous $Na_2SO_4$. After filtration, the filtrate was concentrated under vacuum to afford tert-butyl 3-((6-chloro-2-(trifluoromethyl)pyridin-3-yl)oxy)pyrrolidine-1-carboxylate (A112) (800 mg, crude) as a yellow solid. MS m/z 367.1 [M+1]$^+$. $^1$H NMR (400 MHz, methyl sulfoxide-$d_6$) δ 8.01 (d, J=8.8 Hz, 1H), 7.84 (d, J=8.8 Hz, 1H), 5.30-5.28 (m, 1H), 3.60-3.38 (m, 3H), 3.31-3.23 (m, 1H), 2.29-2.01 (m, 2H), 1.39 and 1.37 (s, 9H).

Intermediate A113 tert-butyl 3-(4-bromo-2-fluorophenoxy)pyrrolidine-1-carboxylate

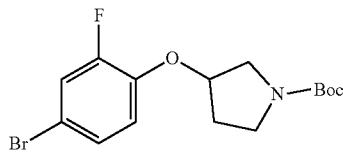 [SMILES: CC(C)(C)OC(=O)N1CCC(Oc2ccc(Br)cc2F)C1]

To a solution of 4-bromo-2-fluorophenol (500 mg, 2.62 mmol), tert-butyl 3-hydroxypyrrolidine-1-carboxylate (490 mg, 2.62 mmol) and triphenylphosphine (1030 mg, 3.93 mmol) in tetrahydrofuran (5 mL) was added diisopropyl azodiformate (794 mg, 3.93 mmol) at 0° C. under nitrogen atmosphere. The mixture was stirred at room temperature for 4 h. The mixture was diluted with ethyl acetate, washed with brine. The organic layer was dried over anhydrous sodium sulfate, filtered and concentrated under vacuum. The residue was purified by flash column chromatography with 0-30% ethyl acetate in petroleum ether to afford tert-butyl 3-(4-bromo-2-fluorophenoxy)pyrrolidine-1-carboxylate (A113) (855 mg, 90%) as an off-white oil. MS m/z 360.2, 362.2 [M+1]$^+$.

Intermediate A114

1-[3-[(5-bromo-3-chloropyrazin-2-yl)oxy]pyrrolidin-1-yl]ethanone

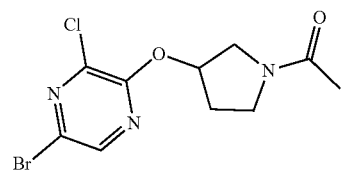 [SMILES: CC(=O)N1CCC(Oc2ncc(Br)nc2Cl)C1]

Step 1: To a solution of 3-chloropyrazin-2-amine (5.00 g, 38.60 mmol) in acetonitrile (50 mL) was added N-bromosuccinimide (10.30 g, 57.89 mmol). The mixture was stirred at room temperature for 2 h. The mixture was diluted with water and extracted with ethyl acetate. The organic layer was dried over anhydrous sodium sulfate, filtered and concentrated under vacuum. The residue was purified by flash column chromatography with 0-80% ethyl acetate in petroleum ether to afford 5-bromo-3-chloropyrazin-2-amine (2.10 g, 10.70%) as a yellow solid. MS m/z 208.1, 210.1 [M+1]$^+$.

Step 2: To a mixture of 5-bromo-3-chloropyrazin-2-amine (5.00 g, 23.99 mmol) in sulfuric acid (50 mL) was added a solution of sodium nitrite (1.80 g, 26.38 mmol) in water (15 mL) slowly at 0° C. The mixture was warmed slowly to room temperature for 16 h. The mixture was extracted with ethyl acetate. The organic layer was washed with brine. The organic layer was dried over anhydrous sodium sulfate, filtered and concentrated under vacuum to afford 5-bromo-3-chloropyrazin-2-ol (2.10 g, 42%) as a yellow solid. MS m/z 208.9, 310.9 [M+1]$^+$. $^1$H NMR (400 MHz, methyl sulfoxide-$d_6$) δ 13.09 (s, 1H), 7.93 (s, 1H).

Step 3: To a stirred mixture of 5-bromo-3-chloropyrazin-2-ol (0.80 g, 3.82 mmol), tert-butyl 3-hydroxypyrrolidine-1-carboxylate (0.71 g, 3.82 mmol) and triphenylphosphine (1.50 g, 5.73 mmol) in tetrahydrofuran (10 mL) was added diisopropyl azodiformate (1.20 g, 5.73 mmol) dropwise at 0° C. under nitrogen atmosphere. The mixture was stirred at room temperature for 16 h under nitrogen atmosphere. The mixture was concentrated under vacuum. The residue was purified by flash column chromatography with 0~50% ethyl acetate in petroleum ether to afford tert-butyl 3-[(5-bromo-3-chloropyrazin-2-yl)oxy]pyrrolidine-1-carboxylate (0.35 g, 24%) as an off-white solid. MS m/z 378.0, 380.0 [M+1]$^+$.

Step 4: To a solution of tert-butyl 3-[(5-bromo-3-chloropyrazin-2-yl)oxy]pyrrolidine-1-carboxylate (450 mg, 1.19 mmol) in dichloromethane (8 mL) was added trifluoroacetic acid (4 mL). Then the mixture was mixed at room temperature for 2 h. The mixture was concentrated under vacuum to afford 5-bromo-3-chloro-2-(pyrrolidin-3-yloxy)pyrazine (350 mg, crude) as a yellow oil. MS m/z 278.1, 280.1 [M+1]$^+$.

Step 5: To a solution of 5-bromo-3-chloro-2-(pyrrolidin-3-yloxy)pyrazine (331 mg, 1.19 mmol) and triethylamine (241 mg, 2.38 mmol) in acetonitrile (4 mL) was added acetic anhydride (146 mg, 1.43 mmol). The mixture was stirred at room temperature for 2 h. The mixture was concentrated under vacuum. The residue was purified by flash column chromatography with 0-15% methanol in methylene chloride to afford 1-[3-[(5-bromo-3-chloropyrazin-2-yl)oxy]pyrrolidin-1-yl]ethanone (A114) (342 mg, 89% over 2 steps) as a yellow oil. MS m/z 320.1, 322.1 [M+1]$^+$. $^1$H NMR (400 MHz, methyl sulfoxide-$d_6$) δ 8.47 and 8.46 (s, 1H), 5.61-5.48 (m, 1H), 3.84-3.80 (m, 1H), 3.74-3.49 (m, 3H), 2.31-2.13 (m, 2H), 1.92 and 1.91 (s, 3H).

Intermediate A115

1-[3-[(6-bromo-2-methylpyridin-3-yl)oxy]pyrrolidin-1-yl]ethanone

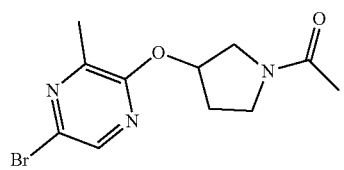 [SMILES: CC(=O)N1CCC(Oc2ncc(Br)nc2C)C1]

Step 1: To a solution of 6-bromo-2-methylpyridin-3-ol (500 mg, 2.66 mmol), tert-butyl 3-hydroxypyrrolidine-1-carboxylate (498 mg, 2.66 mmol) and triphenylphosphine (1046 mg, 3.99 mmol) in tetrahydrofuran (10 mL) was added diisopropyl azodiformate (806 mg, 3.99 mmol) slowly at 0° C. The mixture was stirred at room temperature for 4 h under nitrogen atmosphere. The mixture was concentrated under vacuum. The residue was purified by flash column chromatography with 0~50% ethyl acetate in petroleum ether to afford tert-butyl 3-[(6-bromo-2-methylpyridin-3-yl)oxy]pyrrolidine-1-carboxylate (900 mg, 95%) as a yellow oil. MS m/z 357.3, 359.3 [M+1]$^+$.

Step 2: To a solution of tert-butyl 3-[(6-bromo-2-methylpyridin-3-yl)oxy]pyrrolidine-1-carboxylate (500 mg, 1.40 mmol) in dichloromethane (6 mL) was added trifluoroacetic acid (2 mL). The mixture was stirred at room temperature for 2 h. The mixture was concentrated under vacuum to afford 6-bromo-2-methyl-3-(pyrrolidin-3-yloxy)pyridine (700 mg, crude) as a yellow oil. MS m/z 257.1, 259.1 [M+1]$^+$.

Step 3: To a solution of 6-bromo-2-methyl-3-(pyrrolidin-3-yloxy)pyridine (360 mg, 1.40 mmol) and triethylamine (283 mg, 2.80 mmol) in acetonitrile (4 mL) was added acetic anhydride (172 mg, 1.68 mmol). The mixture was stirred at room temperature for 2 h. The mixture was concentrated under vacuum. The residue was purified by flash column chromatography with 0-15% methanol in methylene chloride to afford 1-[3-[(6-bromo-2-methylpyridin-3-yl)oxy]pyrrolidin-1-yl]ethanone (A115) (415 mg, 99% over 2 steps) as a yellow oil. MS m/z 299.2, 301.2 [M+1]$^+$. 1H NMR (400 MHz, methyl sulfoxide-d$_6$) δ 7.43-7.41 (m, 2H), 5.14-5.05 (m, 1H), 3.82-3.53 (m, 4H), 2.30 and 2.29 (s, 3H), 2.25-2.02 (m, 2H), 1.93 and 1.91 (s, 3H).

Intermediate A116

1-[3-[(2-chloro-6-iodopyridin-3-yl)oxy]pyrrolidin-1-yl]ethanone

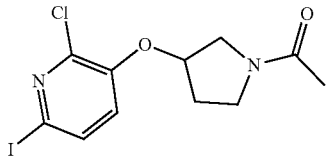 [SMILES: CC(=O)N1CCC(Oc2ccc(I)nc2Cl)C1]

Step 1: To a solution of tert-butyl 3-(2-chloro-6-iodopyridin-3-yloxy)pyrrolidine-1-carboxylate (300 mg, 0.70 mmol) in dichloromethane (3 mL) was added trifluoroacetic acid (1 mL). The mixture was stirred at room temperature for 1 h. The mixture was concentrated under reduced pressure to afford 2-chloro-6-iodo-3-(pyrrolidin-3-yloxy)pyridine (220 mg, crude) as a yellow solid. MS m/z 325.0 [M+1]$^+$.

Step 2: To a solution of 2-chloro-6-iodo-3-(pyrrolidin-3-yloxy)pyridine (210 mg, 0.65 mmol) and triethylamine (196 mg, 1.94 mmol) in acetonitrile (2 mL) was added acetic anhydride (132 mg, 1.30 mmol). The mixture was stirred at room temperature for 3 h. The reaction mixture was concentrated under vacuum. The residue was purified by flash column chromatography with 0-90% ethyl acetate in petroleum ether to afford 1-[3-[(2-chloro-6-iodopyridin-3-yl)oxy] pyrrolidin-1-yl]ethanone (A116) (150 mg, 58% over 2 steps) as a yellow oil. MS m/z 367.0 [M+1]$^+$. $^1$H NMR (400 MHz, methyl sulfoxide-d$_6$) δ 7.81 and 7.80 (d, J=8.4 Hz, 1H), 7.47 and 7.46 (d, J=8.4 Hz, 1H), 5.29-4.98 (m, 1H), 3.89-3.46 (m, 4H), 2.25-2.01 (m, 2H), 1.98 and 1.93 (s, 3H).

Intermediate A117

1-(3-((6-chloro-2-(trifluoromethyl)pyridin-3-yl)oxy) pyrrolidin-1-yl)ethan-1-one

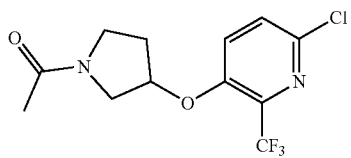 [SMILES: CC(=O)N1CCC(Oc2ccc(Cl)nc2C(F)(F)F)C1]

Followed the procedure of Intermediate A116 described above to afford 1-(3-((6-chloro-2-(trifluoromethyl)pyridin-3-yl)oxy)pyrrolidin-1-yl)ethan-1-one (A117) (270 mg, 74% over 2 steps) as a yellow oil from tert-butyl 3-((6-chloro-2-(trifluoromethyl)pyridin-3-yl)oxy)pyrrolidine-1-carboxylate. MS m/z 309.1 [M+1]$^+$.

Intermediate A118

N-[2-[(5-bromo-3-methylpyrazin-2-yl)oxy]ethyl]-N-methylacetamide

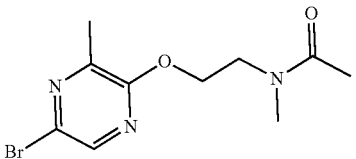 [SMILES: CC(=O)N(C)CCOc1ncc(Br)nc1C]

Step 1: To a solution of 5-bromo-3-methylpyrazin-2-ol (500 mg, 2.65 mmol), tert-butyl N-(2-hydroxyethyl)-N-methylcarbamate (464 mg, 2.65 mmol) and triphenylphosphine (1040 mg, 3.97 mmol) in tetrahydrofuran (10 mL) was added diisopropyl azodiformate (802 mg, 3.97 mmol) at 0° C. under nitrogen atmosphere. The mixture was stirred at room temperature for 4 h. The mixture was diluted with ethyl acetate and washed with brine. The organic layer was dried over anhydrous sodium sulfate, filtered and concentrated under vacuum. The residue was purified by flash column chromatography with 0~50% ethyl acetate in petroleum ether to afford tert-butyl N-[2-[(5-bromo-3-methylpyrazin-2-yl)oxy]ethyl]-N-methylcarbamate (626 mg, 68%) as a yellow oil. MS m/z 346.2, 348.2 [M+1]$^+$.

Step 2: To a solution of tert-butyl N-[2-[(5-bromo-3-methylpyrazin-2-yl)oxy]ethyl]-N-methylcarbamate (600 mg, 1.73 mmol) in dichloromethane (6 mL) was added trifluoroacetic acid (3 mL). Then the mixture was stirred at room temperature for 2 h. The mixture was concentrated under vacuum to afford [2-[(5-bromo-3-methylpyrazin-2-yl)oxy]ethyl](methyl)amine (750 mg, crude) as a yellow oil. MS m/z 246.1, 248.1 [M+1]$^+$. Step 3: To a solution of [2-[(5-bromo-3-methylpyrazin-2-yl)oxy]ethyl](methyl) amine (426 mg, 1.73 mmol) and triethylamine (350 mg, 3.46 mmol) in acetonitrile (5 mL) was added acetic anhydride (212 mg, 2.08 mmol). The mixture was stirred at room temperature for 2 h. The mixture was concentrated under vacuum. The residue was purified by flash column chromatography with 0-15% methanol in methylene chloride to afford N-[2-[(5-bromo-3-methylpyrazin-2-yl)oxy]ethyl]-N-methylacetamide (A118) (490 mg, 98% over 2 steps) as a yellow oil. MS m/z 288.2, 290.2 [M+1]⁺. $^1$H NMR (400 MHz, methyl sulfoxide-d$_6$) δ 8.23 and 8.21 (s, 1H), 4.43 (t, J=5.4 Hz, 1H), 4.38 (t, J=5.4 Hz, 1H), 3.73 (t, J=5.4 Hz, 1H), 3.65 (t, J=5.4 Hz, 1H), 3.04 and 2.85 (s, 3H), 2.37 and 2.36 (s, 3H), 2.05 and 1.97 (s, 3H).

Intermediate A119

5-bromo-3,3-dimethyl-2H-isoindol-1-one

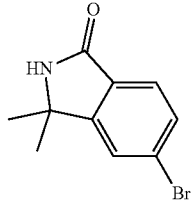

Step 1: To a solution of methyl 4-bromo-2-methylbenzoate (5.00 g, 21.83 mmol) in carbon tetrachloride (50 mL) were added N-bromosuccinimide (3.90 g, 21.83 mmol) and azodiisobutyronitrile (0.36 g, 2.18 mmol). The mixture was stirred at 80° C. for 16 h. The solids were filtered off. The filtrate was concentrated under vacuum. The residue was purified by flash column chromatography with 0-60% ethyl acetate in petroleum ether to afford methyl 4-bromo-2-(bromomethyl)benzoate (4.50 g, 67%) as a white solid. MS m/z 307.2, 309.2 [M+1]⁺.

Step 2: To a solution of methyl 4-bromo-2-(bromomethyl)benzoate (4.50 g, 14.60 mmol) in tetrahydrofuran (100 mL) was added (4-methoxyphenyl)methanamine (2.20 g, 16.06 mmol). The mixture was stirred at 80° C. for 2 h. The mixture was concentrated under vacuum. The residue was purified by flash column chromatography with 0~50% ethyl acetate in petroleum ether to afford 5-bromo-2-[(4-methoxyphenyl)methyl]-3H-isoindol-1-one (2.70 g, 56%) as a white solid. MS m/z 332.4, 334.4 [M+1]⁺. $^1$H NMR (400 MHz, methyl sulfoxide-d$_6$) δ 7.81 (d, J=1.8 Hz, 1H), 7.72-7.61 (m, 2H), 7.25-7.17 (m, 2H), 6.95-6.86 (m, 2H), 4.64 (s, 2H), 4.32 (s, 2H), 3.73 (s, 3H).

Step 3: To a solution of 5-bromo-2-[(4-methoxyphenyl)methyl]-3H-isoindol-1-one (500 mg, 1.51 mmol) in tetrahydrofuran (5 mL) was added sodium hydride (108 mg, 2.70 mmol, 60% in mineral oil) at 0° C. After stirring at 0° C. for 30 min, iodomethane (641 mg, 4.52 mmol) was added to above mixture at 0° C. Then the mixture was heated to 70° C. for 16 h. The reaction was quenched using water and extracted with ethyl acetate. The organic layer was dried over anhydrous sodium sulfate, filtered and concentrated under vacuum. The residue was purified by flash column chromatography with 0-50% ethyl acetate in petroleum ether to afford 5-bromo-2-[(4-methoxyphenyl)methyl]-3,3-dimethylisoindol-1-one (470 mg, 87%) as a yellow oil. MS m/z 360.3, 362.3 [M+1]⁺.

Step 4: To a solution of 5-bromo-2-[(4-methoxyphenyl)methyl]-3,3-dimethylisoindol-1-one (500 mg, 1.39 mmol) in trifluoroacetic acid (5 mL) was added trifluoromethanesulfonic acid (0.50 mL). The mixture was stirred at 60° C. for 16 h. The mixture was concentrated under vacuum. The residue was purified by flash column chromatography with 0~40% ethyl acetate in petroleum ether to afford 5-bromo-3,3-dimethyl-2H-isoindol-1-one (A119) (230 mg, 69%) as a yellow solid. MS m/z 240.1, 242.1 [M+1]⁺.

Intermediate A120

1-(3-((5-bromo-3-methoxypyrazin-2-yl)amino)pyrrolidin-1-yl)ethan-1-one

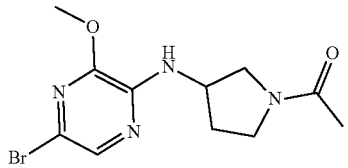 [SMILES: COc1nc(Br)cnc1NC1CCN(C(C)=O)C1]

Followed the procedure of Intermediate A116 described above to afford 1-(3-((5-bromo-3-methoxypyrazin-2-yl)amino)pyrrolidin-1-yl)ethan-1-one (A120) (200 mg, 29% over 2 steps) as a yellow oil from tert-butyl 3-[(5-bromo-3-methoxypyrazin-2-yl)amino]pyrrolidine-1-carboxylate (800 mg, 2.14 mmol). MS m/z 315.0, 317.0 [M+1]⁺. $^1$H NMR (400 MHz, methyl sulfoxide-d$_6$) δ 7.71 and 7.70 (s, 1H), 7.06 and 7.02 (d, J=6.4 Hz, 1H), 4.47-4.31 (m, 1H), 3.92 and 3.91 (s, 3H), 3.74-3.72 (m, 1H), 3.66-3.54 (m, 1H), 3.50-3.36 (m, 1H), 3.28-3.23 (m, 1H), 2.23-1.95 (m, 2H), 1.93 and 1.90 (s, 3H).

Intermediate A121 tert-butyl N-[2-[(5-bromo-3-ethylpyrazin-2-yl)oxy]ethyl]carbamate

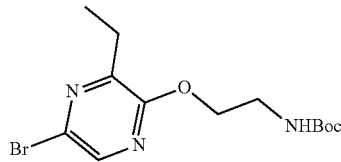 [SMILES: CCc1nc(Br)cnc1OCCNC(=O)OC(C)(C)C]

To a solution of 5-bromo-3-ethylpyrazin-2-ol (300 mg, 1.48 mmol), tert-butyl N-(2-hydroxyethyl)carbamate (238 mg, 1.48 mmol) and triphenylphosphine (581 mg, 2.22 mmol) in tetrahydrofuran (3 mL) was added diisopropyl azodiformate (448 mg, 2.22 mmol) at 0° C. under nitrogen atmosphere. The mixture was stirred at room temperature for 3 h. The mixture was concentrated under vacuum. The residue was purified by flash column with 0~30% ethyl acetate in petroleum ether to afford tert-butyl N-[2-[(5-bromo-3-ethylpyrazin-2-yl)oxy]ethyl]carbamate (A121) (200 mg, 39%) as a yellow solid. MS m/z 346.2, 348.2 [M+1]⁺.

Intermediate A122

1-[3-[(5-bromo-3-ethylpyrazin-2-yl)oxy]pyrrolidin-1-yl]ethanone

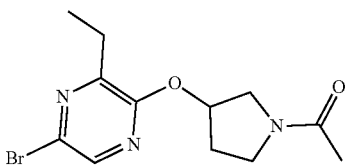 [SMILES: CCc1nc(Br)cnc1OC1CCN(C(C)=O)C1]

Step 1: To a solution of tert-butyl 3-[(5-bromo-3-ethylpyrazin-2-yl)oxy]pyrrolidine-1-carboxylate (730 mg, 1.96 mmol) in dichloromethane (14 mL) was added trifluoroacetic acid (7 mL). The mixture was stirred at room temperature for 1 h. The mixture was concentrated under vacuum to afford 5-bromo-3-ethyl-2-(pyrrolidin-3-yloxy)pyrazine (533 mg, crude) as a yellow oil. MS m/z 272.2, 274.2 [M+1]$^+$.

Step 2: To a solution of 5-bromo-3-ethyl-2-(pyrrolidin-3-yloxy)pyrazine (533 mg, 1.96 mmol) and triethylamine (396 mg, 3.92 mmol) in acetonitrile (6 mL) was added acetic anhydride (240 mg, 2.35 mmol) at room temperature. The mixture was stirred at room temperature for 3 h. The mixture was concentrated under vacuum. The residue was purified by flash column chromatography with 0-15% methanol in methylene chloride to afford 1-[3-[(5-bromo-3-ethylpyrazin-2-yl)oxy]pyrrolidin-1-yl]ethanone (A122) (580 mg, 94% over 2 steps) as a yellow oil. MS m/z 314.2, 316.2 [M+1]$^+$. HNMR $^1$H NMR (400 MHz, methyl sulfoxide-d$_6$) δ 8.25 (s, 1H), 5.60-5.41 (m, 1H), 3.87-3.47 (m, 4H), 2.72 (q, J=7.6 Hz, 2H), 2.34-2.05 (m, 2H), 2.03-1.89 (s, 3H), 1.17 (t, J=7.6 Hz, 3H).

Intermediate A123

1-(3-(5-bromo-3-(trifluoromethyl)pyrazin-2-yloxy)pyrrolidin-1-yl)ethanone

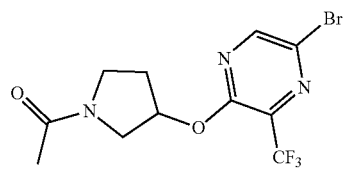 [SMILES: CC(=O)N1CCC(Oc2ncc(Br)nc2C(F)(F)F)C1]

Step 1: To a solution of tert-butyl 3-(5-bromo-3-(trifluoromethyl)pyrazin-2-yloxy)pyrrolidine-1-carboxylate (200 mg, 0.49 mmol) in dichloromethane (2 mL) was added trifluoroacetic acid (0.5 mL). The mixture was stirred at room temperature for 2 h. The mixture was concentrated under vacuum to afford 5-bromo-2-(pyrrolidin-3-yloxy)-3-(trifluoromethyl)pyrazine (150 mg, crude) as a brown oil. MS m/z 312.0, 314.0 [M+1]$^+$.

Step 2: To a solution of 5-bromo-2-(pyrrolidin-3-yloxy)-3-(trifluoromethyl)pyrazine (210 mg, 0.67 mmol) and triethylamine (204 mg, 2.02 mmol) in acetonitrile (3 mL) was added acetic anhydride (137 mg, 1.4 mmol). The mixture was stirred at room temperature for 2 h. The reaction mixture was diluted with ethyl acetate and washed with brine. The organic layer was dried over anhydrous sodium sulfate, filtered and concentrated under vacuum. The residue was purified by flash column chromatography with 0~80% ethyl acetate in petroleum ether to afford 1-(3-(5-bromo-3-(trifluoromethyl)pyrazin-2-yloxy)pyrrolidin-1-yl)ethanone (A123) (120 mg, 50%) as a yellow oil. MS m/z 354.0, 356.0 [M+1]$^+$.

Intermediate A124

1-(3-(5-bromo-3-(trifluoromethyl)pyrazin-2-yloxy)pyrrolidin-1-yl)ethenone

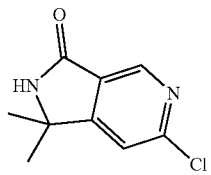

Step 1: To a solution of methyl 4-chloro-2-methylbenzoate (1.00 g, 5.42 mmol) in carbon tetrachloride (10 mL) were added N-bromosuccinimide (1.10 g, 5.96 mmol) and azodiisobutyronitrile (0.09 g, 0.54 mmol). The mixture was stirred at 80° C. for 2 h. The solids were filtered off. The filtrate was concentrated under vacuum. The residue was purified by flash column chromatography with 0~50% ethyl acetate in petroleum ether to afford methyl 2-(bromomethyl)-4-chlorobenzoate (470 mg, 33%) as a white solid. MS m/z 264.1, 266.1 [M+1]$^+$.

Step 2: A mixture of methyl 4-(bromomethyl)-6-chloropyridine-3-carboxylate (480 mg, 1.82 mmol) and (4-methoxyphenyl)methanamine (498 mg, 3.63 mmol) in tetrahydrofuran (5 mL) was stirred at 80° C. for 3 h. The mixture was concentrated under vacuum. The residue was purified by flash column chromatography with 0~60% ethyl acetate in petroleum ether to afford 6-chloro-2-[(4-methoxyphenyl)methyl]-1H-pyrrolo[3,4-c]pyridin-3-one (450 mg, 86%) as a white solid. MS m/z 289.1 [M+1]$^+$. $^1$H NMR (400 MHz, methyl sulfoxide-d$_6$) δ 8.76 (d, J=1.2 Hz, 1H), 7.78 (d, J=1.2 Hz, 1H), 7.28-7.20 (m, 2H), 6.96-6.88 (m, 2H), 4.65 (s, 2H), 4.41 (s, 2H), 3.74 (s, 3H).

Step 3: To a mixture of 6-chloro-2-[(4-methoxyphenyl)methyl]-1H-pyrrolo[3,4-c]pyridin-3-one (290 mg, 1.00 mmol) in tetrahydrofuran (3 mL) was added sodium hydride (72 mg, 1.80 mmol, 60% in mineral oil) at 0° C. After stirring at 0° C. for 1 h, iodomethane (214 mg, 1.51 mmol) was added to above mixture at room temperature. The mixture was stirred at room temperature for 2 h. The mixture was quenched using water and extracted with ethyl acetate. The organic layer was dried over anhydrous sodium sulfate, filtered and concentrated under vacuum. The residue was purified by flash column chromatography with 0~30% ethyl acetate in petroleum ether to afford 6-chloro-2-[(4-methoxyphenyl)methyl]-1,1-dimethylpyrrolo[3,4-c]pyridin-3-one (140 mg, 44%) as a white solid. MS m/z 317.1 [M+1]$^+$.

Step 4: A mixture of 6-chloro-2-[(4-methoxyphenyl)methyl]-1,1-dimethylpyrrolo[3,4-c]pyridin-3-one (120 mg, 0.38 mmol) in trifluoroacetic acid (2 mL) and trifluoromethanesulfonic acid (1 mL) was stirred at 80° C. for 4 h. The mixture was concentrated under vacuum. The residue was basified by saturated sodium bicarbonate aqueous solution and extracted with ethyl acetate. The organic layer was dried over anhydrous sodium sulfate, filtered and concentrated under vacuum. The residue product was purified by flash with 0-20% methanol in methylene chloride to afford 6-chloro-1,1-dimethyl-2H-pyrrolo[3,4-c]pyridin-3-one (A124) (60 mg, 81%) as a brown solid. MS m/z 197.0 [M+1]$^+$.

Intermediate A125

3-bromo-5,5-dimethyl-6H-pyrrolo[3,4-b]pyridin-7-one

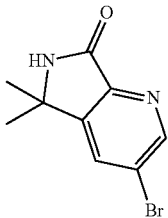

Step 1: To a stirred mixture of methyl 5-bromo-3-methylpyridine-2-carboxylate (2.00 g, 8.69 mmol) and azodiisobutyronitrile (0.14 g, 0.86 mmol) in carbon tetrachloride (20 mL) was added N-bromosuccinimide (1.90 g, 10.43 mmol). The mixture was stirred at 80° C. for 16 h. The solids were filtered off. The filtrate was concentrated under vacuum. The residue was purified by flash column chromatography with 0~30% ethyl acetate in petroleum ether to afford methyl 5-bromo-3-(bromomethyl)pyridine-2-carboxylate (1.90 g, 71%) as a white solid. MS m/z 310.0 [M+1]+.

Step 2: A mixture of methyl 5-bromo-3-(bromomethyl)pyridine-2-carboxylate (1.90 g, 6.21 mmol) and (4-methoxyphenyl)methanamine (1.70 g, 12.43 mmol) in tetrahydrofuran (20 mL) was stirred at 80° C. for 16 h. The mixture was concentrated under vacuum. The residue was purified by flash column chromatography with 0~70% ethyl acetate in petroleum ether to afford 3-bromo-6-[(4-methoxyphenyl)methyl]-5H-pyrrolo[3,4-b]pyridin-7-one (1.50 g, 72%) as a yellow solid. MS m/z 333.2, 335.2 [M+1]+. $^1$H NMR (400 MHz, methyl sulfoxide-$d_6$) δ 8.84 (d, J=2.0 Hz, 1H), 8.35-8.29 (m, 1H), 7.29-7.21 (m, 2H), 7.02-6.88 (m, 2H), 4.69 (s, 2H), 4.35 (s, 2H), 3.74 (s, 3H).

Step 3: To a solution of 3-bromo-6-[(4-methoxyphenyl)methyl]-5H-pyrrolo[3,4-b]pyridin-7-one (500 mg, 1.50 mmol) in tetrahydrofuran (5 mL) was added sodium hydride (144 mg, 3.60 mmol, 60% in mineral oil) at 5° C. After stirring for 30 min, iodomethane (1.30 g, 9.00 mmol) was added to above mixture. The mixture was stirred at 70° C. for 5 h. The mixture was quenched using water and extracted with ethyl acetate. The organic layer was dried over anhydrous sodium sulfate, filtered and concentrated under vacuum. The residue was purified by flash column chromatography with 0~100% ethyl acetate in petroleum ether to afford 3-bromo-6-[(4-methoxyphenyl)methyl]-5,5-dimethylpyrrolo[3,4-b]pyridin-7-one (0.53 g, 98%) as a yellow oil. MS m/z 361.2, 363.2 [M+1]+.

Step 4: A solution of 3-bromo-6-[(4-methoxyphenyl)methyl]-5,5-dimethylpyrrolo[3,4-b]pyridin-7-one (570 mg, 1.58 mmol) in trifluoroacetic acid (6 mL) and trifluoromethanesulfonic acid (0.60 mL) was stirred at 80° C. for 4 h. The mixture was concentrated under vacuum. The residue was purified by flash column with 0~10% methanol in methylene chloride to afford 3-bromo-5,5-dimethyl-6H-pyrrolo[3,4-b]pyridin-7-one (A125) (360 mg, 95%) as a brown solid. MS m/z 241.1, 243.1 [M+1]+. $^1$H NMR (400 MHz, methyl sulfoxide-$d_6$) δ 9.15 (s, 1H), 8.81 (d, J=2.0 Hz, 1H), 8.55 (d, J=2.0 Hz, 1H), 1.47 (s, 6H).

Intermediate A126

1-[(3R,4R and 3S,4S)-3-[(5-bromo-3-methylpyrazin-2-yl)oxy]-4-fluoropyrrolidin-1-yl]ethanone

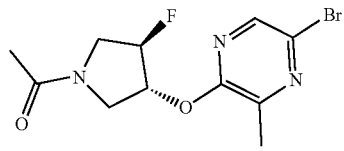 [SMILES: CC(=O)N1C[C@@H](F)[C@H](Oc2ncc(Br)nc2C)C1]

Step 1: To a solution of 5-bromo-3-methylpyrazin-2-ol (200 mg, 1.06 mmol), tert-butyl (3R,4S and 3S,4R)-3-fluoro-4-hydroxypyrrolidine-1-carboxylate (239 mg, 1.16 mmol) and triphenylphosphine (416 mg, 1.58 mmol) in tetrahydrofuran (5 mL) was added diisopropyl azodiformate (321 mg, 1.59 mmol) at 5° C. The mixture was stirred at room temperature for 16 h under nitrogen atmosphere. The reaction mixture was diluted with water and extracted with ethyl acetate. The organic layer was dried over anhydrous sodium sulfate, filtered and concentrated under vacuum. The residue was purified by flash column chromatography with 0-100% ethyl acetate in petroleum ether to afford tert-butyl (3R,4R and 3S,4S)-3-[(5-bromo-3-methylpyrazin-2-yl)oxy]-4-fluoropyrrolidine-1-carboxylate (300 mg, 75%) as a colorless oil. MS m/z 376.1, 378.1 [M+1]+.

Step 2: To a solution of tert-butyl (3R,4R and 3S,4S)-3-[[5-(7-chloro-1H-indol-3-yl)-3-methylpyrazin-2-yl]oxy]-4-fluoropyrrolidine-1-carboxylate (210 mg, 0.55 mmol) in dichloromethane (3 mL) was added trifluoroacetic acid (1 mL). The mixture was stirred at room temperature for 2 h. The mixture was concentrated under vacuum to afford 7-chloro-3-(5-[[(3R,4R and 3S,4S)-4-fluoropyrrolidin-3-yl]oxy]-6-methylpyrazin-2-yl)-1H-indole (230 mg, crude) as a yellow oil. MS m/z 276.0, 278.0 [M+1]+.

Step 3: To a solution of 5-bromo-2-[[(3R,4R and 3S,4S)-4-fluoropyrrolidin-3-yl]oxy]-3-methylpyrazine (150 mg, 0.54 mmol) and triethylamine (165 mg, 1.63 mmol) in acetonitrile (1 mL) was added acetic anhydride (111 mg, 1.09 mmol) at room temperature. The mixture was stirred at room temperature for 2 h. The mixture was concentrated under reduced pressure. The residue was purified by flash column chromatography with 0-100% ethyl acetate in petroleum ether to afford 1-[(3R,4R and 3S,4S)-3-[(5-bromo-3-methylpyrazin-2-yl)oxy]-4-fluoropyrrolidin-1-yl]ethanone (A126) (75 mg, 36%) as a colorless oil. MS m/z 318.0, 320.0 [M+1]+. $^1$H NMR (400 MHz, methyl sulfoxide-$d_6$) δ 8.30 (s, 1H), 5.64-5.18 (m, 2H), 4.09-3.50 (m, 4H), 2.43-2.32 (m, 3H), 2.03 and 2.01 (s, 3H).

Intermediate A127 tert-butyl N-[3-[(5-bromo-3-methylpyrazin-2-yl)oxy]cyclobutyl]carbamate

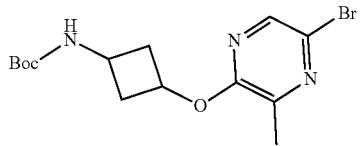 [SMILES: Cc1nc(Br)cnc1OC1CC(NC(=O)OC(C)(C)C)C1]

To a solution of 5-bromo-3-methylpyrazin-2-ol (200 mg, 1.06 mmol), triphenylphosphine (416 mg, 1.59 mmol) and tert-butyl N-(3-hydroxycyclobutyl)carbamate (218 mg, 1.16 mmol) in tetrahydrofuran (5 mL) was added diisopropyl azodiformate (321 mg, 1.59 mmol) at room temperature. The mixture was stirred at room temperature for 4 h. The reaction mixture was diluted with water and extracted with ethyl acetate. The organic layer was dried over anhydrous sodium sulfate, filtered and concentrated under vacuum. The residue was purified by flash column chromatography with 0~100% ethyl acetate in petroleum ether to afford tert-butyl N-[3-[(5-bromo-3-methylpyrazin-2-yl)oxy]cyclobutyl]carbamate (A127) (230 mg, 52%) as a white solid. MS m/z 358.1, 360.1 [M+1]$^+$. $^1$H NMR (400 MHz, methyl sulfoxide-d$_6$) δ 8.20 (t, J=1.2 Hz, 1H), 7.45-7.09 (m, 1H), 4.86-4.74 (m, 1H), 3.88-3.59 (m, 1H), 2.80-2.55 (m, 3H), 2.43-2.33 (m, 3H), 2.10-1.98 (m, 1H), 1.39 (d, J=3.2 Hz, 9H).

Intermediate A128 tert-butyl 3-(5-bromo-3-methylpyrazin-2-yloxy) cyclopentylcarbamate

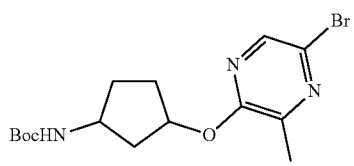 [SMILES: Cc1nc(Br)cnc1OC1CCC(NC(=O)OC(C)(C)C)C1]

To a solution of 5-bromo-3-methylpyrazin-2-ol (300 mg, 1.59 mmol), tert-butyl 3-hydroxycyclopentylcarbamate (351 mg, 1.75 mmol) and triphenylphosphine (624 mg, 2.38 mmol) in tetrahydrofuran (10 mL) was added diisopropyl azodiformate (481 mg, 2.38 mmol) at 5° C. The mixture was stirred at room temperature for 16 h. The reaction mixture was diluted with water and extracted with ethyl acetate. The organic layer was dried over anhydrous sodium sulfate, filtered and concentrated under vacuum. The residue was purified by flash column chromatography with 0~60% ethyl acetate in petroleum ether to afford tert-butyl 3-(5-bromo-3-methylpyrazin-2-yloxy)cyclopentylcarbamate (A128) (200 mg, 27%) as a yellow solid. MS m/z 372.1, 374.1 [M+1]$^+$. $^1$H NMR (400 MHz, methyl sulfoxide-d$_6$) δ 8.19 (s, 1H), 6.97 (d, J=7.6 Hz, 1H), 5.35-5.31 (m, 1H), 4.06-3.96 (m, 1H), 2.35 (s, 3H), 2.19-2.11 (m, 1H), 2.06-1.92 (m, 2H), 1.87-1.80 (m, 1H), 1.71-1.67 (m, 1H), 1.53-1.41 (m, 1H), 1.38 (s, 9H).

Intermediate A129

1-[3-[(5-bromo-3-methoxypyrazin-2-yl)oxy]pyrrolidin-1-yl]ethanone

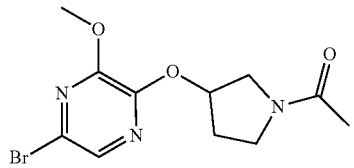 [SMILES: COc1nc(Br)cnc1OC1CCN(C(C)=O)C1]

Step 1: To a solution of 3-methoxypyrazin-2-amine (4.00 g, 31.97 mmol) in acetonitrile (40 mL) was added N-bromosuccinimide (5.69 g, 31.97 mmol). The mixture was stirred at room temperature for 2 h. The mixture was diluted with water and extracted with ethyl acetate. The organic layer was washed with brine, dried over anhydrous sodium sulfate, filtered and concentrated under vacuum. The residue was purified by flash column chromatography with 0~50% ethyl acetate in petroleum ether to afford 5-bromo-3-methoxypyrazin-2-amine (3.50 g, 54%) as a yellow solid. MS m/z 204.0, 206.0 [M+1]$^+$.

Step 2: To a mixture of 5-bromo-3-methoxypyrazin-2-amine (3.50 g, 17.30 mmol) in sulfuric acid (50 mL, 5% in water) was added a solution of sodium nitrite (1.30 g, 19.03 mmol) in water (2 mL) at 0~5° C. The mixture was stirred at 0~5° C. for 2 h. The mixture was extracted with ethyl acetate. The organic layers were washed with brine, dried over anhydrous sodium sulfate, filtered and concentrated under vacuum. The residue was purified by flash column chromatography with 0~50% ethyl acetate in petroleum ether to afford 5-bromo-3-methoxypyrazin-2-ol (2.10 g, 59%) as a yellow solid. MS m/z 205.0, 207.0 [M+1]$^+$. $^1$H NMR (400 MHz, methyl sulfoxide-d$_6$) δ 12.26 (s, 1H), 7.26 (s, 1H), 3.83 (s, 3H).

Step 3: To a solution of 5-bromo-3-methoxypyrazin-2-ol (1.00 g, 4.88 mmol), tert-butyl 3-hydroxypyrrolidine-1-carboxylate (0.90 g, 4.88 mmol) and triphenylphosphine (1.90 g, 7.32 mmol) in tetrahydrofuran (10 mL) was added diisopropyl azodiformate (1.50 g, 7.32 mmol) at 5° C. under nitrogen atmosphere. The mixture was stirred at room temperature for 16 h. The reaction mixture was diluted with water and extracted with ethyl acetate. The organic layer was dried over anhydrous sodium sulfate, filtered and concentrated under vacuum. The residue was purified by flash column chromatography with 0-50% ethyl acetate in petroleum ether to afford tert-butyl 3-[(5-bromo-3-methoxypyrazin-2-yl)oxy]pyrrolidine-1-carboxylate (1.80 g, 98%) as a yellow oil. MS m/z 374.2, 376.2 [M+1]$^+$.

Step 4: To a solution of tert-butyl 3-[(5-bromo-3-methoxypyrazin-2-yl)oxy]pyrrolidine-1-carboxylate (1.00 g, 2.67 mmol) dichloromethane (15 mL) was added trifluoroacetic acid (5 mL). The mixture was stirred at room temperature for 2 h. The mixture was concentrated under vacuum to afford 5-bromo-3-methoxy-2-(pyrrolidin-3-yloxy)pyrazine (700 mg, crude) as a yellow solid. MS m/z 274.1, 276.1 [M+1]$^+$.

Step 5: To a solution of 5-bromo-3-methoxy-2-(pyrrolidin-3-yloxy)pyrazine (732 mg, 2.67 mmol) and triethylamine (540 mg, 5.34 mmol) in acetonitrile (8 mL) was added acetic anhydride (327 mg, 3.20 mmol). The mixture was stirred at room temperature for 3 h. The mixture was diluted with water and extracted with ethyl acetate. The organic layer was washed with brine, dried over anhydrous sodium sulfate, filtered and concentrated under vacuum. The residue was purified by flash column chromatography with 0-50% ethyl acetate in petroleum ether to afford 1-[3-[(5-bromo-3-methoxypyrazin-2-yl)oxy]pyrrolidin-1-yl]ethanone (A129) (800 mg, 94% over 2 steps) as a yellow oil. MS m/z 316.2, 318.2 [M+1]$^+$. $^1$H NMR (400 MHz, methyl sulfoxide-d$_6$) δ 7.89 (s, 1H), 5.56-5.45 (m, 1H), 3.92 (s, 3H), 3.84-3.80 (m, 1H), 3.71-3.45 (m, 2H), 3.34-3.27 (m, 1H), 2.36-2.04 (m, 2H), 1.93 and 1.92 (s, 3H).

Intermediate A130

1-[(5-bromo-3-methylpyrazin-2-yl)amino]-2-methyl-propan-2-ol

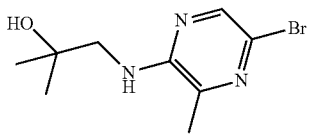

Step 1: A mixture of 2-chloro-3-methylpyrazine (200 mg, 1.56 mmol), 1-amino-2-methylpropan-2-ol (208 mg, 2.33 mmol), tris(dibenzylideneacetone)dipalladium (142 mg, 0.16 mmol), 2-dicyclohexylphosphino-2',4',6'-triisopropyl-1,1'-biphenyl (74 mg, 0.16 mmol) and sodium tert-butoxide (299 mg, 3.11 mmol) in toluene (2 mL) was stirred at 100° C. for 16 h under nitrogen atmosphere. The mixture was concentrated under vacuum. The residue was purified by flash column chromatography with 0~50% ethyl acetate in petroleum ether to afford 2-methyl-1-[(3-methylpyrazin-2-yl)amino]propan-2-ol (230 mg, 81%) as a yellow oil. MS m/z 182.2 [M+1]$^+$.

Step 2: To a solution of 2-methyl-1-[(3-methylpyrazin-2-yl)amino]propan-2-ol (210 mg, 1.16 mmol) in acetonitrile (2 mL) was added N-bromosuccinimide (206 mg, 1.16 mmol). The mixture was stirred at room temperature for 2 h. The mixture was diluted with ethyl acetate and washed with saturated sodium bicarbonate aqueous solution and brine. The organic layer was dried over anhydrous sodium sulfate, filtered and concentrated under vacuum. The residue was purified by flash column with 0-70% ethyl acetate in petroleum ether to afford 1-[(5-bromo-3-methylpyrazin-2-yl)amino]-2-methylpropan-2-ol (A130) (190 mg, 63%) as a yellow oil. MS m/z 260.1, 262.1 [M+1]$^+$. $^1$H NMR (400 MHz, methyl sulfoxide-d$_6$) δ 7.94 (s, 1H), 6.23 (t, J=6.0 Hz, 1H), 4.58 (s, 1H), 3.33 (d, J=6.0 Hz, 2H), 2.33 (s, 4H), 1.10 (s, 6H).

Intermediate A131

1-((5-bromo-3-methoxypyrazin-2-yl)amino)-2-methylpropan-2-ol

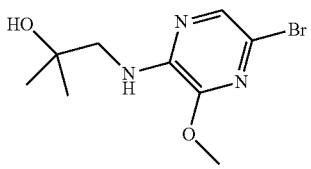

Step 1: A mixture of 2-chloro-3-methoxypyrazine (1.00 g, 6.92 mmol), 1-amino-2-methylpropan-2-ol (0.62 g, 6.96 mmol) and cesium fluoride (2.20 g, 13.84) in methyl sulfoxide (10 mL) was heated to 75° C. for 16 h. The mixture was diluted with water and extracted with ethyl acetate. The organic layer was dried over anhydrous sodium sulfate, filtered and concentrated under vacuum. The residue was purified by flash column chromatography with 0-80% ethyl acetate in petroleum ether to afford 1-((3-methoxypyrazin-2-yl)amino)-2-methylpropan-2-ol (0.20 g, 14%) as a yellow oil. MS m/z 198.1 [M+1]$^+$.

Step 2: To a solution of 1-((3-methoxypyrazin-2-yl)amino)-2-methylpropan-2-ol (170 mg, 0.85 mmol) in acetonitrile (2 mL) was added N-bromosuccinimide (150 mg, 0.85 mmol). The mixture was stirred at room temperature for 2 h. The mixture was diluted with ethyl acetate and washed with saturated sodium bicarbonate aqueous solution and brine. The organic layer was dried over anhydrous sodium sulfate, filtered and concentrated under vacuum. The residue was purified by flash column with 0-100% ethyl acetate in petroleum ether to afford 1-((5-bromo-3-methoxypyrazin-2-yl)amino)-2-methylpropan-2-ol (A131) (140 mg, 59%) as a yellow oil. MS m/z 276.0, 278.0 [M+1]$^+$. $^1$H NMR (400 MHz, methyl sulfoxide-d$_6$) δ 7.65 (s, 1H), 6.26 (t, J=6.0 Hz, 1H), 4.65 (s, 1H), 3.94 (s, 3H), 3.30 (d, J=6.0 Hz, 2H), 1.10 (s, 6H).

Intermediate A132 tert-butyl 3-[(5-bromo-3-methylpyrazin-2-yl)sulfanyl]pyrrolidine-1-carboxylate

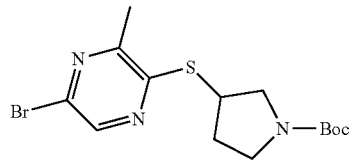 [SMILES: Cc1nc(Br)cnc1SC1CCN(C(=O)OC(C)(C)C)C1]

A mixture of 5-bromo-2-chloro-3-methylpyrazine (150 mg, 0.72 mmol), tert-butyl 3-sulfanylpyrrolidine-1-carboxylate (118 mg, 0.58 mmol) and potassium carbonate (150 mg, 1.09 mmol) in N,N-dimethylformamide (2 mL) was stirred at room temperature for 16 h. The mixture was diluted with water and extracted with ethyl acetate. The organic layer was dried over anhydrous sodium sulfate, filtered and concentrated under vacuum. The residue was purified by flash column chromatography with 0~100% ethyl acetate in petroleum ether to afford tert-butyl 3-[(5-bromo-3-methylpyrazin-2-yl)sulfanyl]pyrrolidine-1-carboxylate (A132) (61 mg, 22%) as a colorless oil. MS m/z 374.0, 376.0 [M+1]$^+$.

Intermediate A133 tert-butyl 3-[(5-chloro-3-cyclopropylpyrazin-2-yl)oxy]pyrrolidine-1-carboxylate

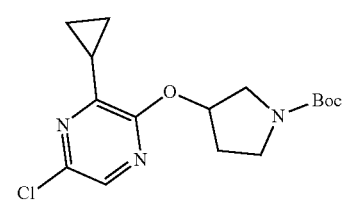 [SMILES: CC(C)(C)OC(=O)N1CCC(Oc2ncc(Cl)nc2C2CC2)C1]

Step 1: A degassed mixture of 3-bromo-5-chloropyrazin-2-amine (1.00 g, 4.80 mmol), cyclopropylboronic acid (0.401 g, 4.80 mmol), [1,1'-bis(diphenylphosphino)ferrocene]-dichloropalladium(II) (0.35 g, 0.48 mmol) and potassium carbonate (1.30 g, 9.60 mmol) in dioxane (10 mL) and water (1 mL) was stirred at 100° C. for 16 h. The mixture was concentrated under vacuum. The residue was purified by flash column chromatography with 0~40% ethyl acetate in petroleum ether to afford 5-chloro-3-cyclopropylpyrazin-2-amine (0.20 g, 25%) as a red oil. MS m/z 170.1 [M+1]$^+$. $^1$H NMR (400 MHz, methyl sulfoxide-d$_6$) δ 7.76 (s, 1H), 6.57 (s, 2H), 2.15-2.08 (m, 1H), 0.99-0.92 (m, 2H), 0.90-0.78 (m, 2H).

Step 2: To a mixture of 5-chloro-3-cyclopropylpyrazin-2-amine (740 mg, 4.36 mmol) in sulfuric acid (7 mL, 5% in water) was added a solution of sodium nitrite (331 mg, 4.80 mmol) in water (3 mL) at 0° C. The mixture was stirred at room temperature for 16 h. The reaction mixture was extracted with ethyl acetate. The combined organic layers was washed with brine, dried over anhydrous sodium sulfate, filtered and concentrated under vacuum to afford 5-chloro-3-cyclopropylpyrazin-2-ol (710 mg, crude) as a yellow solid. MS m/z 171.1 [M+1]$^+$.

Step 3: To a solution of 5-chloro-3-cyclopropylpyrazin-2-ol (760 mg, 4.46 mmol), tert-butyl 3-hydroxypyrrolidine-1-carboxylate (834 mg, 4.46 mmol) and triphenylphosphine (1753 mg, 6.68 mmol) in tetrahydrofuran (10 mL) was added diisopropyl azodiformate (1351 mg, 6.68 mmol) at 0° C. The mixture was stirred at room temperature for 16 h. The mixture was diluted with water and extracted with ethyl acetate. The organic layer was dried over anhydrous sodium sulfate, filtered and concentrated under vacuum. The residue was purified by flash column chromatography with 0~40% ethyl acetate in petroleum ether to afford tert-butyl 3-[(5-chloro-3-cyclopropylpyrazin-2-yl)oxy]pyrrolidine-1-carboxylate (A133) (518 mg, 34%) as a green solid. MS m/z 340.3 [M+1]$^+$. $^1$H NMR (400 MHz, methyl sulfoxide-d$_6$) δ 8.06 (s, 1H), 5.50-5.44 (m, 1H), 3.65-3.59 (m, 1H), 3.53-3.37 (m, 3H), 2.32-2.27 (m, 1H), 2.26-2.10 (m, 2H), 1.41 and 1.39 (s, 9H), 1.16-1.03 (m, 2H), 1.06-0.91 (m, 2H).

Intermediate A134 tert-butyl 3-[(5-iodo-3-methylpyrazin-2-yl)oxy]-2,2-dimethylpyrrolidine-1-carboxylate

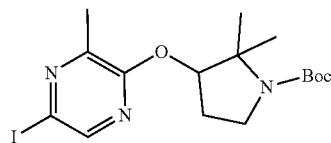 [SMILES: Cc1nc(I)cnc1OC1CCN(C(=O)OC(C)(C)C)C1(C)C]

Step 1: A solution of 3-methylpyrazin-2-amine (1.00 g, 9.16 mmol) and iodine (2.80 g, 11.00 mmol) in methyl sulfoxide (10 mL) was stirred at room temperature for 16 h. The mixture was diluted with water and extracted with ethyl acetate. The combined organic layers was washed with brine, dried over anhydrous sodium sulfate, filtered and concentrated under vacuum. to afford 5-iodo-3-methylpyrazin-2-amine (1.30 g, 60%) as a brown solid. MS m/z 236.0 [M+1]$^+$.

Step 2: A mixture of 5-iodo-3-methylpyrazin-2-amine (1.50 g, 6.38 mmol), cuprous chloride (0.95 g, 9.60 mmol) and cupric chloride (1.30 g, 9.60 mmol) in acetonitrile (15 mL) was stirred at −10° C. for 30 min under nitrogen atmosphere. Then a solution of tert-butyl nitrite (1.40 g, 14.67 mmol) was added to above mixture at −10° C. The mixture was heated to 65° C. for 16 h. The mixture was diluted with water and extracted with EA. The combined organic layers was washed with brine, dried over anhydrous sodium sulfate, filtered and concentrated under vacuum. The residue was purified by flash column chromatography with 0-40% ethyl acetate in petroleum ether to afford 2-chloro-5-iodo-3-methylpyrazine (391 mg, 24%) as a white solid. MS m/z 255.0 [M+1]$^+$.

Step 3: To a solution of tert-butyl 3-hydroxy-2,2-dimethylpyrrolidine-1-carboxylate (203 mg, 0.94 mmol) in tetrahydrofuran (3 mL) was added sodium hydride (56 mg, 1.40 mmol, 60% in mineral oil) at 0° C. After stirring at 5° C. for 30 min, 2-chloro-5-iodo-3-methylpyrazine (200 mg, 0.79 mmol) was added to above mixture. The mixture was stirred at room temperature for 4 h. The mixture was diluted with water and extracted with ethyl acetate. The organic layer was dried over anhydrous sodium sulfate, filtered and concentrated under vacuum. The residue was purified by flash column chromatography with 0-70% ethyl acetate in petroleum ether to afford tert-butyl 3-[(5-iodo-3-methylpyrazin-2-yl)oxy]-2,2-dimethylpyrrolidine-1-carboxylate (A134) (170 mg, 80%) as a yellow oil. MS m/z 434.1 [M+1]$^+$. $^1$H NMR (400 MHz, methyl sulfoxide-d$_6$) δ 8.31 (s, 1H), 5.12-5.09 (m, 1H), 3.44-3.38 (m, 2H), 2.37 (s, 3H), 2.30-2.24 (m, 1H), 1.86-1.79 (m, 1H), 1.43 and 1.41 (s, 9H), 1.36 (s, 6H).

Intermediate A135 tert-butyl 4-[(5-bromo-3-methylpyrazin-2-yl)oxy]-2,2-dimethylpyrrolidine-1-carboxylate

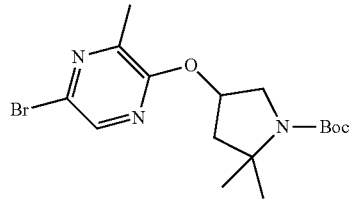 [SMILES: Cc1nc(Br)cnc1OC1CN(C(=O)OC(C)(C)C)C(C)(C)C1]

To a solution of 5-bromo-3-methylpyrazin-2-ol (175 mg, 0.93 mmol), tert-butyl 4-hydroxy-2,2-dimethylpyrrolidine-1-carboxylate (199 mg, 0.93 mmol) and triphenylphosphine (364 mg, 1.39 mmol) in tetrahydrofuran (5 mL) was added diisopropyl azodiformate (281 mg, 1.39 mmol) at room temperature. The mixture was stirred at room temperature for 16 h. The mixture was diluted with water and extracted with ethyl acetate. The organic layer was dried over anhydrous sodium sulfate, filtered and concentrated under vacuum. The residue was purified by flash column chromatography with 0~50% ethyl acetate in petroleum ether to afford tert-butyl 4-[(5-bromo-3-methylpyrazin-2-yl)oxy]-2,2-dimethylpyrrolidine-1-carboxylate (A135) (310 mg, 87%) as a white solid. MS m/z 386.1, 388.1 [M+1]$^+$. $^1$H NMR (400 MHz, methyl sulfoxide-d$_6$) δ 8.24 (s, 1H), 5.35-5.31 (m, 1H), 3.82-3.67 (m, 1H), 3.57-3.50 (m, 1H), 2.38 (s, 3H), 2.31-2.01 (m, 2H), 1.51-1.32 (m, 15H).

Intermediate A136 tert-butyl (2R,3S and 2S,3R)-3-((5-bromo-3-methylpyrazin-2-yl)oxy)-2-methylpyrrolidine-1-carboxylate

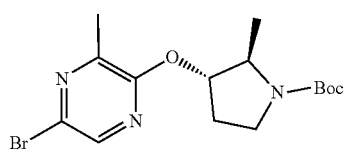 [SMILES: Cc1nc(Br)cnc1O[C@H]1CCN(C(=O)OC(C)(C)C)[C@@H]1C]

A mixture of 5-bromo-3-methylpyrazin-2-ol (417 mg, 2.21 mmol), trans-tert-butyl 3-hydroxy-2-methylpyrrolidine-1-carboxylate (488 mg, 2.40 mmol) and triphenylphosphine (868 mg, 3.31 mmol) in tetrahydrofuran (10 mL) was added diisopropyl azodiformate (669 mg, 3.31 mmol) dropwise at 0° C. The mixture was stirred at room temperature for 16 h. The mixture was diluted with water and extracted with ethyl acetate. The organic layer was dried over anhydrous sodium sulfate, filtered and concentrated under vacuum. The residue was purified by flash column chromatography with 0-100% ethyl acetate in petroleum ether to afford tert-butyl (2R,3S and 2S,3R)-3-((5-bromo-3-methylpyrazin-2-yl)oxy)-2-methylpyrrolidine-1-carboxylate (A136) (420 mg, 51%) as a colorless oil. MS m/z 372.1, 374.1 [M+1]$^+$.

Intermediate A137 tert-butyl N-[1-[(5-iodo-3-methylpyrazin-2-yl)oxy]-2-methylpropan-2-yl]carbamate

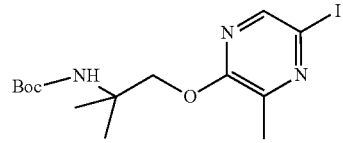 [SMILES: Cc1nc(I)cnc1OCC(C)(C)NC(=O)OC(C)(C)C]

A solution of 2-chloro-5-iodo-3-methylpyrazine (1.00 g, 3.93 mmol), tert-butyl N-(1-hydroxy-2-methylpropan-2-yl) carbamate (0.70 g, 3.93 mmol) and cesium fluoride (1.80 g, 11.79 mmol) in methyl sulfoxide (10 mL) was heated to 100° C. for 2 h. The mixture was diluted with water and extracted with ethyl acetate. The organic layer was dried over anhydrous sodium sulfate, filtered and concentrated under vacuum. The residue product was purified by flash column chromatography with 0-30% ethyl acetate in petroleum ether to afford tert-butyl N-[1-[(5-iodo-3-methylpyrazin-2-yl)oxy]-2-methylpropan-2-yl]carbamate (A137) (1.10 g, 67%) as an off-white oil. MS m/z 408.1 [M+1]$^+$. $^1$H NMR (400 MHz, methyl sulfoxide-d$_6$) δ 8.27 (s, 1H), 6.74-6.68 (m, 1H), 4.31 (s, 2H), 2.39 (s, 3H), 1.33 (s, 9H), 1.28 (s, 6H).

Intermediate A138 tert-butyl 2-(5-bromo-3-methylpyrazin-2-yloxy)propylcarbamate

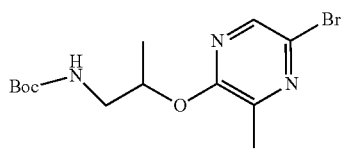 [SMILES: Cc1nc(Br)cnc1OC(C)CNC(=O)OC(C)(C)C]

To a solution of 5-bromo-3-methylpyrazin-2-ol (300 mg, 1.59 mmol), tert-butyl N-(2-hydroxypropyl)carbamate (417 mg, 2.38 mmol) and triphenylphosphine (624 mg, 2.381 mmol) in tetrahydrofuran (10 mL) was added diisopropyl azodiformate (481 mg, 2.38 mmol) at 0° C. The mixture was stirred at room temperature for 16 h. The mixture was diluted with water and extracted with ethyl acetate. The organic layer was dried over anhydrous sodium sulfate, filtered and concentrated under vacuum. The residue was purified by flash column chromatography with 0-60% ethyl acetate in petroleum ether to afford tert-butyl 2-(5-bromo-3-methylpyrazin-2-yloxy)propylcarbamate (A138) (398 mg, 72%) as a colorless oil. MS m/z 346.1, 348.1 [M+1]$^+$. $^1$H NMR (400 MHz, methyl sulfoxide-d$_6$) δ 8.18 (s, 1H), 7.02 (t, J=6.0 Hz, 1H), 5.19-4.99 (m, 1H), 3.31-3.02 (m, 2H), 2.35 (s, 3H), 1.35 (s, 9H), 1.25 (d, J=6.4 Hz, 3H).

Intermediate A139

1-[(3S)-3-[(5-bromo-3-methoxypyrazin-2-yl)amino]pyrrolidin-1-yl]ethanone

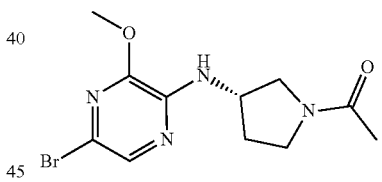

Step 1: A mixture of 2-chloro-3-methoxypyrazine (1.00 g, 6.92 mmol), tripotassium orthophosphate (2.30 g, 1.08 mmol), 2-dicyclohexylphosphino-2',4',6'-triisopropyl-1,1'-biphenyl (0.33 g, 0.69 mmol), tris(dibenzylideneacetone)dipalladium (0.63 g, 0.69 mmol), sodium tert-butoxide (1.30 g, 13.84 mmol) and (S)-tert-butyl 3-aminopyrrolidine-1-carboxylate (1.90 g, 10.38 mmol) in dioxane (10 mL) was stirred at 100° C. for 16 h under nitrogen atmosphere. The mixture was diluted with ethyl acetate and washed with brine. The organic layer was dried over anhydrous sodium sulfate, filtered and concentrated under vacuum. The residue was purified by flash column chromatography with 0-70% ethyl acetate in petroleum ether to afford (S)-tert-butyl 3-(3-methoxypyrazin-2-ylamino)pyrrolidine-1-carboxylate (2.00 g, 97%) brown oil. MS m/z 295.2 [M+1]$^+$.

Step 2: To a mixture of (S)-tert-butyl 3-(3-methoxypyrazin-2-ylamino)pyrrolidine-1-carboxylate (2.00 g, 6.70 mmol) in acetonitrile (20 mL) was added N-bromosuccinimide (1.40 g, 8.03 mmol) at 0° C. The mixture was stirred at room temperature for 2 h. The mixture was diluted with brine and extracted with ethyl acetate. The organic layers were dried over anhydrous sodium sulfate, filtered and concentrated under vacuum. The residue was purified by flash column chromatography with 0-85% ethyl acetate in petroleum ether to afford (S)-tert-butyl 3-(5-bromo-3-methoxypyrazin-2-ylamino)pyrrolidine-1-carboxylate (1.20 g, 48%) as a brown oil. MS m/z 373.1, 375.1 [M+1]$^+$. $^1$H NMR (400 MHz, methyl sulfoxide-d$_6$) δ 7.71 (s, 1H), 7.02 (d, J=6.4 Hz, 1H), 4.35 (dt, J=11.6, 6.4 Hz, 1H), 3.92 (s, 3H), 3.74-3.08 (m, 4H), 2.09-1.91 (m, 2H), 1.40 and 1.39 (s, 9H).

Step 3: To a solution of (S)-tert-butyl 3-(5-bromo-3-methoxypyrazin-2-ylamino)pyrrolidine-1-carboxylate (1.20 g, 3.20 mmol) in dichloromethane (10 mL) was added trifluoroacetic acid (1 mL). The mixture was stirred at room temperature for 1 h. The mixture was concentrated under vacuum to afford 5-bromo-3-methoxy-N-[(3S)-pyrrolidin-3-yl]pyrazin-2-amine (1.00 g, crude) as a brown oil. MS m/z 273.0, 275.0 [M+1]$^+$.

Step 4: To a solution of (S)-5-bromo-3-methoxy-N-(pyrrolidin-3-yl)pyrazin-2-amine (1.00 g, 3.66 mmol) and triethylamine (0.74 g, 7.32 mmol) in acetonitrile (10 mL) was added acetic anhydride (0.45 g, 4.39 mmol) at 0° C. The mixture was stirred at room temperature for 2 h. The mixture was diluted with brine and extracted with ethyl acetate. The organic layer was dried over anhydrous sodium sulfate, filtered and concentrated under vacuum. The residue was purified by flash column chromatography with 0-30% methanol in dichloromethane to afford 1-[(3S)-3-[(5-bromo-3-methoxypyrazin-2-yl)amino]pyrrolidin-1-yl]ethanone (A139) (0.90 g, 89% over 2 steps) as a brown oil. MS m/z 315.0, 317.0 [M+1]$^+$. $^1$H NMR (400 MHz, methyl sulfoxide-d$_6$) δ 7.71 and 7.70 (s, 1H), 7.16-6.94 (m, 1H), 4.44-4.22 (m, 1H), 3.92 (s, 3H), 3.79-3.21 (m, 4H), 2.33-1.97 (m, 2H), 1.93 and 1.91 (s, 3H).

Intermediate A140

1-[(3R)-3-[(5-bromo-3-methoxypyrazin-2-yl)amino]pyrrolidin-1-yl]ethanone

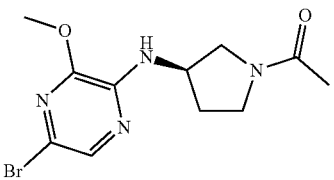 [SMILES: COc1nc(Br)cnc1N[C@@H]1CCN(C(C)=O)C1]

Followed the procedure of Intermediate A138 described above to afford 1-[(3R)-3-[(5-bromo-3-methoxypyrazin-2-yl)amino]pyrrolidin-1-yl]ethenone (A140) (0.60 g, 28% over 4 steps) as a yellow oil. MS m/z 315.1, 317.1 [M+1]$^+$ from 2-chloro-3-methoxypyrazine (1.00 g, 6.91 mmol).

Intermediate A141

1-[3-[(5-bromopyrazin-2-yl)oxy]pyrrolidin-1-yl]ethanone

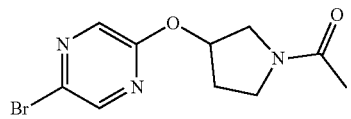 [SMILES: CC(=O)N1CCC(Oc2cnc(Br)cn2)C1]

To a solution of 1-(3-hydroxypyrrolidin-1-yl)ethanone (0.90 g, 6.98 mmol) in N,N-dimethylformamide (9 mL) was added sodium hydride (0.83 g, 20.94 mmol, 60% in mineral oil) at 0° C. After stirring at 0° C. for 30 min, 2,5-dibromopyrazine (2.40 g, 10.17 mmol) was added to above mixture. The mixture was stirred at room temperature for 2 h. The mixture was quenched using water and extracted with ethyl acetate. The organic layer was dried over anhydrous sodium sulfate, filtered and concentrated under vacuum. The residue was purified by flash column chromatography with 0-70% ethyl acetate in petroleum ether to afford 1-[3-[(5-bromopyrazin-2-yl)oxy]pyrrolidin-1-yl]ethanone (A141) (1.00 g, 50%) as a brown oil. MS m/z 286.0, 288.0 [M+1]$^+$. $^1$H NMR (400 MHz, methyl sulfoxide-d$_6$) δ 8.46 (d, J=1.2 Hz, 1H), 8.20 (d, J=1.2 Hz, 1H), 5.65-5.37 (m, 1H), 3.90-3.48 (m, 4H), 2.35-2.06 (m, 2H), 2.03-1.88 (m, 3H).

Intermediate A142

1-[3-[(5-bromo-3-methoxypyrazin-2-yl)(methyl)amino]pyrrolidin-1-yl]ethanone

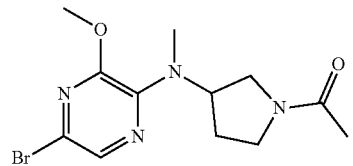 [SMILES: COc1nc(Br)cnc1N(C)C1CCN(C(C)=O)C1]

Followed the procedure of Intermediate A138 described above to afford 1-[3-[(5-bromo-3-methoxypyrazin-2-yl)(methyl)amino]pyrrolidin-1-yl]ethanone (A142) (252 mg, 15% over 4 steps) as a yellow oil from 2-chloro-3-methoxypyrazine (720 mg, 4.98 mmol) and tert-butyl 3-(methylamino)pyrrolidine-1-carboxylate (1.00 g, 4.99 mmol). MS m/z 329.0, 331.0 [M+1]$^+$. $^1$H NMR (400 MHz, methyl sulfoxide-d$_6$) δ 7.87 (d, J=1.2 Hz, 1H), 4.84-4.50 (m, 1H), 3.92 and 3.91 (s, 3H), 3.74-3.12 (m, 4H), 2.89 and 2.87 (s, 3H), 2.16-1.99 (m, 2H), 1.94 and 1.93 (s, 3H).

Intermediate A143 tert-butyl (3R,4S and 3S,4R)-3-[(5-bromo-3-methylpyrazin-2-yl)oxy]-4-fluoropyrrolidine-1-carboxylate

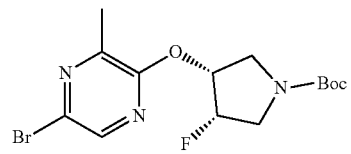 [SMILES: Cc1nc(Br)cnc1O[C@@H]1CN(C(=O)OC(C)(C)C)C[C@@H]1F]

Step 1: To a solution of 5-bromo-3-methylpyrazin-2-ol (500 mg, 2.65 mmol), tert-butyl (3S,4S and 3R,4R)-3-fluoro-4-hydroxypyrrolidine-1-carboxylate (545 mg, 2.66 mmol) and triphenylphosphine (1045 mg, 3.99 mmol) in tetrahydrofuran (5 mL) was added diisopropyl azodiformate (806 mg, 3.99 mmol) slowly at room temperature under nitrogen atmosphere. The resulting solution was stirred at 0° C. for 16 h. The mixture was diluted with water and extracted with ethyl acetate. The combined organic layers was washed with brine, dried over anhydrous sodium sulfate, filtered and concentrated under vacuum. The residue was purified by flash column chromatography with 0-5% ethyl acetate in petroleum ether to afford tert-butyl (3R,4S and 3S,4R)-3-[(5-bromo-3-methylpyrazin-2-yl)oxy]-4-fluoropyrrolidine-1-carboxylate (A143) (450 mg, 45%) as a yellow oil. MS m/z 376.1, 378.1 [M+1]+.

Intermediate A144 tert-butyl 3-[(6-bromo-2-methylpyridin-3-yl)amino]pyrrolidine-1-carboxylate

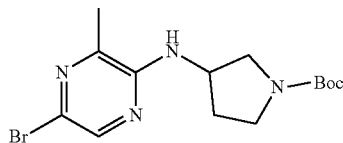 [SMILES: Cc1nc(Br)cnc1NC1CCN(C(=O)OC(C)(C)C)C1]

To a solution of 6-bromo-2-methylpyridin-3-amine (500 mg, 2.67 mmol) and tert-butyl 3-oxopyrrolidine-1-carboxylate (990 mg, 5.35 mmol) in dichloroethane (5 mL) was added glacial acetic acid (0.20 mL). The mixture was stirred at 90° C. for 3 h. Then sodium triacetoxyborohydride (1133 mg, 5.35 mmol) was added to above mixture. The mixture was stirred at 70° C. for 16 h. The mixture was concentrated under vacuum. The resiudue was diluted with water and extracted with ethyl acetate. The combined organic layers was washed with brine, dried over anhydrous sodium sulfate, filtered and concentrated under vacuum. The residue was purified by reverse phase flash column chromatography with 10-80% acetonitrile in water to afford tert-butyl 3-[(6-bromo-2-methylpyridin-3-yl)amino]pyrrolidine-1-carboxylate (A144) (320 mg, 34%) as a dark yellow solid. MS m/z 356.1, 358.1 [M+1]+.

Intermediate A145

3-[(6-bromo-2-methylpyridin-3-yl)oxy]pyrrolidin-2-one

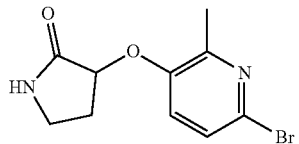

Step 1: To a solution of tert-butyl 3-hydroxypyrrolidine-1-carboxylate (1.00 g, 5.34 mmol), 4-dimethylaminopyridine (0.06 g, 0.52 mmol) and triethylamine (1.08 g, 10.68 mmol) in dichloromethane (10 mL) was added p-toluenesulfonyl chloride (1.12 g, 5.88 mmol) at 0° C. The mixture was stirred at room temperature for 16 h. The mixture was diluted with water and extracted with dichloromethane. The combined organic layers was washed with brine, dried over anhydrous sodium sulfate, filtered and concentrated under vacuum to afford tert-butyl 3-[(4-methylbenzenesulfonyl)oxy]pyrrolidine-1-carboxylate (1.81 g, crude) as a brown solid. MS m/z 342.1 [M+1]+.

Step 2: To a solution of tert-butyl 3-[(4-methylbenzenesulfonyl)oxy]pyrrolidine-1-carboxylate (1.30 g, 3.81 mmol) and 6-bromo-2-methylpyridin-3-ol (0.48 g, 2.53 mmol) in N,N-dimethylformamide (20 mL) was added potassium carbonate (0.70 g, 5.08 mmol). The mixture was stirred at 80° C. for 16 h. The mixture was diluted with water and extracted with ethyl acetate. The combined organic layers was washed with brine, dried over anhydrous sodium sulfate, filtered and concentrated under vacuum. The residue was purified by flash column chromatography with 0-80% ethyl acetate in petroleum ether to afford to afford tert-butyl 3-[(6-bromo-2-methylpyridin-3-yl)oxy]pyrrolidine-1-carboxylate (0.48 g, 35%) as a white solid. MS m/z 357.3, 359.3 [M+1]+. 1H NMR (400 MHz, DMSO-d6) δ 7.41 (s, 2H), 5.06-5.03 (m, 1H), 3.58-3.28 (m, 4H), 2.29 (s, 3H), 2.18-1.95 (m, 2H), 1.41 and 1.38 (s, 9H).

Step 3: To a solution of tert-butyl 3-[(6-bromo-2-methylpyridin-3-yl)oxy]pyrrolidine-1-carboxylate (470 mg, 1.32 mmol) in ethyl acetate (5 mL) were added a solution of sodium periodate (1406 mg, 6.58 mmol) in water (15 mL) and ruthenium(III) chloride hydrate (89 mg, 0.40 mmol). The mixture was stirred at room temperature for 16 h. The mixture was extracted with ethyl acetate. The combined organic layers was washed with brine, dried over anhydrous sodium sulfate, filtered and concentrated under vacuum. The residue was purified by reverse phase flash column chromatography with 30-80% acetonitrile in water to afford tert-butyl 3-[(6-bromo-2-methylpyridin-3-yl)oxy]-2-oxopyrrolidine-1-carboxylate (100 mg, 20%) as a yellow solid. MS m/z 371.2, 373.2 [M+1]+. 1H NMR (400 MHz, DMSO-d6) δ 7.49 (d, J=8.8 Hz, 1H), 7.44 (d, J=8.8 Hz, 1H), 5.24 (dd, J=9.8, 8.0 Hz, 1H), 3.82-3.71 (m, 1H), 3.57-3.50 (m, 1H), 2.57-2.53 (m, 1H), 2.34 (s, 3H), 2.12-1.96 (m, 1H), 1.47 (s, 9H).

Step 4: To a solution of tert-butyl 3-[(6-bromo-2-methylpyridin-3-yl)oxy]-2-oxopyrrolidine-1-carboxylate (100 mg, 0.27 mmol) in dichloromethane (3 mL) was added trifluoroacetic acid (2 mL). The mixture was stirred at room temperature for 2 h. The reaction mixture was concentrated under vacuum to afford 3-[(6-bromo-2-methylpyridin-3-yl)oxy]pyrrolidin-2-one (A145) (80 mg, crude) as a yellow solid. MS m/z 271.0, 273.0 [M+1]+.

Intermediate A146 tert-butyl 3-bromo-6-methyl-7-oxo-6,7-dihydro-1H-pyrrolo[2,3-c]pyridine-1-carboxylate

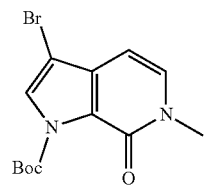 [SMILES: Cn1ccc2c(Br)cn(C(=O)OC(C)(C)C)c2c1=O]

Step 1: To a stirred solution of 6-methyl-1,6-dihydro-7H-pyrrolo[2,3-c]pyridin-7-one (0.50 g, 3.38 mmol) in tetrahydrofuran (5 mL) was added N-bromosuccinimide (0.57 g, 3.21 mmol) at 0° C. under nitrogen atmosphere. The mixture was stirred at room temperature for 3 h. The mixture was diluted with water and extracted with ethyl acetate. The combined organic layers was washed with brine, dried over anhydrous sodium sulfate, filtered and concentrated under vacuum to afford 3-bromo-6-methyl-1,6-dihydro-7H-pyrrolo[2,3-c]pyridin-7-one (0.95 g, crude) as a white solid. MS m/z 227.0, 229.0 [M+1]+.

Step 2: To a stirred solution of 3-bromo-6-methyl-1H-pyrrolo[2,3-c]pyridin-7-one (0.60 g, 2.64 mmol), triethylamine (0.80 g, 7.93 mmol) and 4-dimethylaminopyridine (0.06 g, 0.53 mmol) in tetrahydrofuran (10 mL) was added di(tert-butyl) carbonate (1.44 g, 6.61 mmol) at room temperature. The mixture was stirred at room temperature for 3 h. The mixture was concentrated under vacuum. The residue was purified by flash column chromatography with 0-80% ethyl acetate in petroleum ether to afford tert-butyl 3-bromo-6-methyl-7-oxo-6,7-dihydro-1H-pyrrolo[2,3-c]pyridine-1-carboxylate (A146) (0.65 g, 75%) as a yellow solid. MS m/z 327.0, 329.0 [M+1]$^+$. $^1$H NMR (400 MHz, DMSO-d$_6$) δ 7.96 (s, 1H), 7.56 (d, J=7.0 Hz, 1H), 6.35 (d, J=7.0 Hz, 1H), 3.50 (s, 3H), 1.58 (s, 9H).

Intermediate A147

5-iodo-3-methyl-2-[2-methyl-2-(oxan-2-yloxy)propoxy] pyrazine

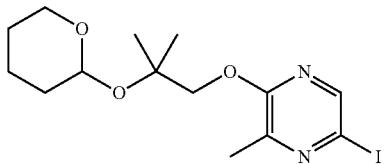 [SMILES: Cc1nc(I)cnc1OCC(C)(C)OC1CCCCO1]

Step 1: To a solution of methyl 2-hydroxy-2-methylpropanoate (5.00 g, 42.33 mmol) and dihydropyran (5.34 g, 63.57 mmol) in dichloromethane (50 mL) was added p-toluenesulfonic acid monohydrate (0.53 g, 2.11 mmol) at room temperature. The mixture was stirred at room temperature for 2 hours. The reaction mixture was washed by water. The organic layer was dried over anhydrous sodium sulfate, filtered and concentrated under vacuum to afford methyl 2-methyl-2-(oxan-2-yloxy)propanoate (6.94 g, 81%) as a yellow oil. MS m/z 203.1 [M+1]$^+$.

Step 2: To a solution of methyl 2-methyl-2-(oxan-2-yloxy)propanoate (6.94 g, 34.31 mmol) in tetrahydrofuran (70 mL) was added lithium aluminium hydride (1.30 g, 34.31 mmol) slowly at 0° C. under nitrogen atmosphere. The mixture was stirred at 0° C. for 2 hours. The reaction was quenched using ice water. The mixture was extracted with ethyl acetate. The combined organic layers was washed with brine, dried over anhydrous sodium sulfate, filtered and concentrated under vacuum to afford 2-methyl-2-(oxan-2-yloxy)propan-1-ol (5.25 g, 87%) as a yellow oil. MS m/z 175.1 [M+1]$^+$. $^1$H NMR (400 MHz, methyl sulfoxide-d$_6$) δ 4.79-4.76 (m, 1H), 3.44 (t, J=6.4 Hz, 1H), 3.85-3.79 (m, 1H), 3.42-3.37 (m, 1H), 3.29-3.33 (m, 2H), 1.58-1.33 (m, 6H), 1.11 (s, 6H).

Step 3: To a solution of 2-methyl-2-(oxan-2-yloxy)propan-1-ol (255 mg, 1.47 mmol) in N,N-dimethylformamide (10 mL) was added sodium hydride (75 mg, 1.87 mmol, 65% in mineral oil) at 0° C. After stirring at 0° C. for 40 minutes, a solution of 2-chloro-5-iodo-3-methylpyrazine (266 mg, 1.05 mmol) in N,N-dimethylformamide (2 mL) was added to above mixture at 0° C. The mixture was stirred at 0° C. for 2 hours. The reaction was quenched by water and extracted with ethyl acetate. The combined organic layers was washed with brine and dried over anhydrous sodium sulfate, filtered and concentrated under vacuum. The residue was purified by flash column chromatography with 0-35% ethyl acetate in petroleum ether to afford 5-iodo-3-methyl-2-[2-methyl-2-(oxan-2-yloxy)propoxy]pyrazine (A146) (190 mg, 46%) as a yellow oil. MS m/z 393.0 [M+1]$^+$.

Intermediate A148

3-bromo-6-fluoro-2,3-dihydro-1-benzofuran

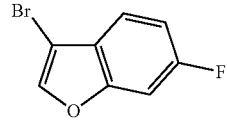 [SMILES: Fc1ccc2c(Br)coc2c1]

Step 1: To a mixture of 6-fluoro-2H-1-benzofuran-3-one (700.0 mg, 4.6 mmol) in MeOH (20 mL) was added NaBH$_4$ (692.8 mg, 18.31 mmol) at room temperature. The resulting mixture was stirred for 1 h under nitrogen atmosphere. To the above mixture was added acetone (10 mL) and HCl (10 mL, 3 mol/L) at room temperature for 1 h. The aqueous layer was extracted with ethyl acetate. The combined organic solution was dried over sodium sulfate, filtered, and concentrated under vacuum to afford 6-fluoro-1-benzofuran (100.0 mg, 14%) as a colorless oil. GCMS (EI) [M]$^+$, 136.0

Step 2: To a mixture of 6-fluoro-1-benzofuran (600 mg, 4.4 mmol) in CS$_2$ (10 mL) was added Br$_2$ (1.056 g, 6.61 mmol) at -10° C. The resulting mixture was stirred for 1 h at 0° C. under nitrogen atmosphere. The aqueous layer was extracted with Dichloromethane (3×40 mL). The combined organic solution was dried over sodium sulfate, filtered, and concentrated under vacuum. The solution was purified by silica gel column chromatography, eluted with 0-10% ethyl acetate in petroleum ether to afford 2,3-dibromo-6-fluoro-2,3-dihydro-1-benzofuran (200 mg, 15%) as a red solid.

Step 3: To a mixture of 2,3-dibromo-6-fluoro-2,3-dihydro-1-benzofuran (200.0 mg, 0.67 mmol) in ethyl alcohol (10.0 mL) was added Potassium hydroxide (75.84 mg, 1.35 mmol). The resulting mixture was stirred at 80° C. for 2 h under nitrogen atmosphere. The aqueous layer was extracted with ethyl acetate. The combined organic solution was dried over sodium sulfate, filtered, and concentrated under vacuum to afford 3-bromo-6-fluoro-2,3-dihydro-1-benzofuran (200.0 mg, crude) as a red solid. GCMS (EI) [M]$^+$, 214.0

Intermediate A149

3-bromobenzofuran-7-carbonitrile

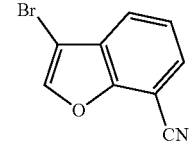

Step 1: A solution of 2-iodophenol (10.0 g, 45.45 mmol), 2-bromo-1,1-diethoxyethane (15.4 g, 90.9 mmol) and K$_2$CO$_3$ (12.56 g, 90.9 mmol) in DMF (100 mL) was stirred at 100° C. for 16 h. The reaction was quenched with water. The aqueous solution was extracted with ethyl acetate. The combined organic layers were washed with brine, dried over anhydrous sodium sulfate, filtered, and concentrated under vacuum. The residue was purified by flash column chromatography with 0-100% ethyl acetate in petroleum ether to afford 1-(2,2-diethoxyethoxy)-2-iodobenzene (7.31 g, 52.2%) as a yellow oil. MS m/z 337.1 [M+1]⁺

Step 2: A mixture of 1-(2,2-diethoxyethoxy)-2-iodobenzene (19 g, 56.51 mmol) and PPA (13 g) in toluene (200 mL) was stirred at 100° C. for 16 h. The mixture was diluted with ethyl acetate and washed with brine. The organic layer was dried over Na₂SO₄ and concentrated under vacuum. The residue was purified by flash column chromatography with 0~100% ethyl acetate in petroleum ether to afford 7-iodo-1-benzofuran (6.5 g, 42.41%) as a red oil. MS m/z 245.0 [M+1]⁺

Step 3: To a stirred solution of 7-iodo-1-benzofuran (4 g, 16.39 mmol) in CHCl₃ (40 mL) was added Br₂ (3.14 g, 19.67 mmol) dropwise at −10° C. The mixture was then stirred at −10° C. for 1 hour. The residue was stirred with ethanol and then filtered. The solid material is washed with diethyl ether. The mixture was concentrated under vacuum to afford 2,3-dibromo-7-iodo-2,3-dihydro-1-benzofuran (5.5 g, crude) as a yellow oil. MS m/z 402.9 [M+1]⁺

Step 4: A solution of 2,3-dibromo-7-iodo-2,3-dihydro-1-benzofuran (5.5 g, 13.62 mmol) and KOH (1.5 g, 27.24 mmol) in EtOH (60 mL) was stirred at 80° C. for 2 hours. The aqueous layer was extracted with ethyl acetate. The combined organic fractions are washed with brine. The mixture was concentrated under vacuum to afford 3-bromo-7-iodo-1-benzofuran (3.9 g, crude) as a white solid. MS m/z 322.9 [M+1]⁺

Step 5: A solution of 3-bromo-7-iodo-1-benzofuran (2 g, 6.19 mmol), Zn(CN)₂ (360 mg, 3.1 mmol) and Pd(PPh₃)₄ (720 g, 0.62 mmol) in DMF (200 mL) was stirred at 100° C. for 16 h under nitrogen atmosphere. The aqueous solution was extracted with ethyl acetate. The combined organic layers were washed with brine, dried over anhydrous sodium sulfate, filtered, and concentrated under vacuum. The residue was purified by flash column chromatography with 0-10% ethyl acetate in petroleum ether to afford 3-bromobenzofuran-7-carbonitrile (1.5 g, 82.9%) as a yellow solid. MS m/z 221.9 [M+1]⁺

Intermediate A150

3-bromo-7-chloro-1-benzofuran

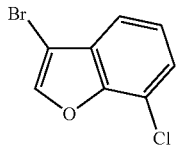 [SMILES: Clc1cccc2c(Br)coc12]

Step 1: To a mixture of 7-chloro-1-benzofuran (1 g, 6.554 mmol) in CHCl₃ (10 mL) was added Br₂ (1.26 g, 7.865 mmol) at −10° C. The resulting mixture was stirred at −10° C. for 20 min. Then the resulting mixture was stirred at 0° C. for additional 1 h. The resulting mixture was concentrated under vacuum. The residue was dissolved in EtOH. The precipitated solids were collected by filtration and washed with Et₂O. This resulted in 2,3-dibromo-7-chloro-2,3-dihydro-1-benzofuran (1.6 g, 78.15%) as a white solid.

Step 2: To a mixture of 2,3-dibromo-7-chloro-2,3-dihydro-1-benzofuran (1.6 g, 5.122 mmol) in EtOH (10 mL) and H₂O (2 mL) was added KOH (575 mg, 10.244 mmol) at 0° C. The resulting mixture was stirred at 80° C. for 2 h. The resulting mixture was extracted with EtOAc. The combined organic layers was washed with brine, dried over anhydrous Na₂SO₄. After filtration, the filtrate was concentrated under reduced pressure. This resulted in 3-bromo-7-chloro-1-benzofuran (1.1 g, 92.78%) as a yellow oil.

Intermediate A151

1-[(5-chloro-3-cyclopropylpyrazin-2-yl)oxy]-2-methylpropan-2-ol

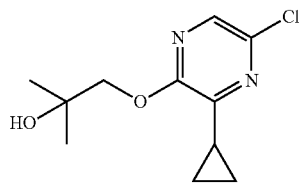 [SMILES: CC(C)(O)COc1ncc(Cl)nc1C1CC1]

To a mixture of 5-chloro-3-cyclopropylpyrazin-2-ol (530 mg, 3.107 mmol) in DMF (10 mL) was added K₂CO₃ (858 mg, 6.214 mmol) and 2-propanol 1-chloro-2-methyl-(404.75 mg, 3.728 mmol). The resulting mixture was stirred at 80° C. overnight. The resulting mixture was extracted with EtOAc. The combined organic layers were washed with brine, dried over anhydrous Na₂SO₄. After filtration, the filtrate was concentrated under reduced pressure. The residue was purified by flash column chromatography with 0-50% ethyl acetate in PE to afford 1-[(5-chloro-3-cyclopropylpyrazin-2-yl)oxy]-2-methylpropan-2-ol (437 mg, 57.96%) as a colorless oil. MS m/z 243.0 [M+1]⁺

Intermediate A160 tert-butyl 3-[[5-bromo-3-(methylthio)pyrazin-2-yl]oxy]pyrrolidine-1-carboxylate

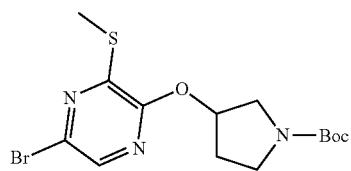 [SMILES: CSc1nc(Br)cnc1OC1CCN(C(=O)OC(C)(C)C)C1]

Step-1: A mixture of 5-bromo-3-chloropyrazin-2-amine (500 mg, 2.40 mmol) and CH₃SNa (202 mg, 2.88 mmol) in MeOH (5 mL) was stirred at 65° C. for 3 h. The mixture was diluted with ethyl acetate, washed with brine, dried over anhydrous sodium sulfate, filtered, and concentrated under vacuum. The residue was purified by flash column chromatography with 0-100% ethyl acetate in petroleum ether to afford 5-bromo-3-(methylthio)pyrazin-2-amine (430 mg, 73.30%) as a white solid. MS m/z 219.9 [M+1]⁺.

Step-2: A mixture of 5-bromo-3-(methylthio)pyrazin-2-amine (380 mg, 1.73 mmol) and NaNO₂ (131 mg, 1.90 mmol) in H₂SO₄ (5% in H₂O) (4 mL) was stirred at room temperature for 2 h. The mixture was diluted with ethyl acetate, washed with brine, dried over anhydrous sodium sulfate, filtered, and concentrated under vacuum. The residue was purified by flash column chromatography with 0-100% ethyl acetate in petroleum ether to afford 5-bromo- 3-(methylthio)pyrazin-2-ol (258 mg, 60.83%) as a white solid. MS m/z 220.9 [M+1]+.

Step-3: To a mixture of 5-bromo-3-(methylthio)pyrazin-2-ol (200 mg, 0.91 mmol), tert-butyl 3-hydroxypyrrolidine-1-carboxylate (254 mg, 1.36 mmol) and PPh$_3$ (356 mg, 1.36 mmol) in THF (2 mL) were added DIAD (274 mg, 1.36 mmol). The mixture was stirred at room temperature for 16 h. The mixture was diluted with ethyl acetate, washed with brine, dried over anhydrous sodium sulfate, filtered, and concentrated under vacuum. The residue was purified by flash column chromatography with 0-100% ethyl acetate in petroleum ether to afford tert-butyl 3-[[5-bromo-3-(methylthio)pyrazin-2-yl]oxy]pyrrolidine-1-carboxylate (300 mg, 82.41%) as a colorless oil. MS m/z 390.0 [M+1]+.

Intermediate A161 tert-butyl 3-((5-iodo-3-methylpyrazin-2-yl)oxy)-3-methylpyrrolidine-1-carboxylate

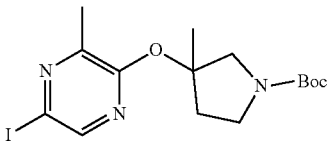 [SMILES: Cc1nc(I)cnc1OC1(C)CCN(C(=O)OC(C)(C)C)C1]

To a solution of 2-chloro-5-iodo-3-methylpyrazine (733 mg, 2.88 mmol) in toluene (8 mL) were added tert-butyl 3-hydroxy-3-methylpyrrolidine-1-carboxylate (579 mg, 2.88 mmol) and t-BuOK (646 mg, 5.76 mmol). Then the mixture was stirred at 120° C. for 16 h. The mixture was diluted with ethyl acetate, washed with brine, dried over anhydrous sodium sulfate, filtered, and concentrated under vacuum. The residue was purified by flash column chromatography with 0-50% ethyl acetate in petroleum ether to afford tert-butyl 3-((5-iodo-3-methylpyrazin-2-yl)oxy)-3-methylpyrrolidine-1-carboxylate (150 mg, 12.42%) as a yellow oil. MS m/z 420.1 [M+1]+.

Intermediate A162

1-[(6-bromo-2-methylpyridin-3-yl)oxy]-2-methyl-propan-2-amine

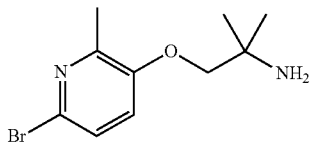

To a mixture of 2-amino-2-methyl-1-propanol (1 g, 11.21 mmol) in DMF (5 mL) were added NaH (0.36 g, 14.946 mmol) at 0° C. The resulting mixture was stirred at 0° C. for 30 min under nitrogen atmosphere. To the above mixture was added 6-bromo-3-fluoro-2-methylpyridine (1.42 g, 7.473 mmol). The resulting mixture was stirred at room temperature for 16 h. The reaction was then quenched by the addition of water. The resulting mixture was extracted with EtOAc (3×20 mL). The combined organic layers were washed with brine (1×5 mL), dried over anhydrous Na$_2$SO$_4$. After filtration, the filtrate was concentrated under reduced pressure. The residue was purified by flash column chromatography with 0-50% ethyl acetate in PE to afford 1-[(6-bromo-2-methylpyridin-3-yl)oxy]-2-methylpropan-2-amine (170 mg, 8.78%) as a yellow oil. MS m/z 259.1 [M+1]+.

Intermediate A163

6-chloro-2-methoxypyridine-3-carboxamide

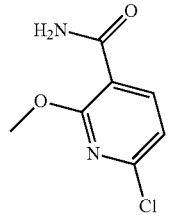

To a mixture of 6-chloro-2-methoxypyridine-3-carboxylic acid (200.0 mg, 1.06 mmol) in DCM (5.0 mL) and DMF (0.2 mL) was added (COCl)$_2$ (202.9 mg, 1.59 mmol) dropwise. The resulting mixture was stirred at room temperature for 3 h. The resulting mixture was concentrated under vacuum. To the above mixture was added NH$_3$.H$_2$O (15.0 mL) dropwise, the resulting mixture was stirred at room temperature for 10 min. The resulting mixture was filtered, the filter cake was washed with ethyl acetate. The filter cake is product. The product is 6-chloro-2-methoxypyridine-3-carboxamide (190.0 mg, 95%) as a white solid. MS m/z 186.9 [M+1]+.

Intermediate A164

5-bromo-2-((1-(2-methoxyethyl)pyrrolidin-3-yl)oxy)-3-methylpyrazine

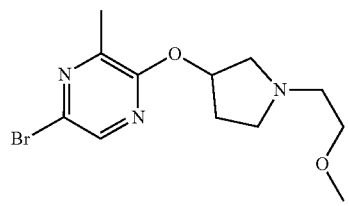 [SMILES: COCCN1CCC(Oc2ncc(Br)nc2C)C1]

To a solution of 5-bromo-3-methyl-2-(pyrrolidin-3-yloxy)pyrazine (600 mg, 2.32 mmol) in ACN (6 mL) was added K$_2$CO$_3$ (535 mg, 3.87 mmol). The mixture was stirred at room temperature for 20 min, this was followed by the addition of 1-bromo-2-methoxyethane (484 mg, 3.48 mmol) at room temperature. Then the mixture was heated at 80° C. for 16 h. The residue was purified by flash column chromatography with 0-55% ethyl acetate in petroleum ether to afford 5-bromo-2-((1-(2-methoxyethyl)pyrrolidin-3-yl)oxy)-3-methylpyrazine (300 mg, 40.82%) as an off-white oil. MS m/z 316.1 [M+1]+.

Intermediate A165

1-[3-[(5-bromo-3-methylpyrazin-2-yl)oxy]pyrrolidin-1-yl]-2-methoxyethanone

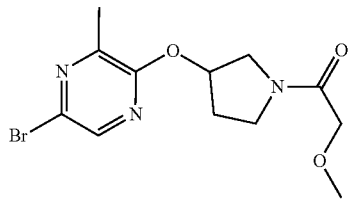 [SMILES: COCC(=O)N1CCC(Oc2ncc(Br)nc2C)C1]

To a mixture of 5-bromo-3-methyl-2-(pyrrolidin-3-yloxy)pyrazine (200 mg, 0.76 mmol) and TEA (549 mg, 5.42 mmol) in DCM (2 mL) were added methoxyacetyl chloride (126 mg, 1.16 mmol) in portions at room temperature. The mixture was stirred at room temperature for 2 h. The residue product was purified by flash with 0-30% ethyl acetate in petroleum ether to afford 1-[3-[(5-bromo-3-methylpyrazin-2-yl)oxy]pyrrolidin-1-yl]-2-methoxyethanone (198 mg, 77.39%) as a yellow oil. MS m/z 330.2 [M+1]$^+$.

Intermediate A166

2-chloro-N-isopropylquinoline-5-carboxamide

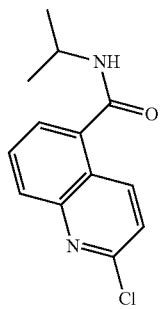 [SMILES: CC(C)NC(=O)c1cccc2nc(Cl)ccc12]

Step-1: To a mixture of 5-bromoquinoline (10 g, 48.064 mmol) in MeOH (50 mL) was added Pd(dppf)Cl$_2$ (3.52 g, 4.806 mmol) and TEA (14.59 g, 144.192 mmol). The resulting mixture was stirred at 65° C. for 16 h under CO atmosphere. The residue was purified by flash column chromatography with 0-60% ethyl acetate in petroleum ether to afford methyl quinoline-5-carboxylate (9.5 g, 89.75%) as a yellow oil. MS m/z 188.1 [M+1]$^+$ Step-2: To a mixture of methyl quinoline-5-carboxylate (1 g, 5.342 mmol) in DCM (20 mL) was added m-CPBA (1.155 g, 6.677 mmol). The resulting mixture was stirred at room temperature overnight. The resulting mixture was concentrated under vacuum. This resulted in methyl 1-oxo-1lambda5-quinoline-5-carboxylate (1.4 g, crude) as a yellow solid. MS m/z 204.1 [M+1]$^+$ Step-3: To a mixture of methyl 1-oxo-1lambda5-quinoline-5-carboxylate (1.4 g, 6.890 mmol) in POCl$_3$ (10 g, 65.218 mmol). The resulting mixture was stirred at 90° C. overnight. The reaction was quenched with water/ice at 0° C. The mixture was basified to pH 8 with saturated NaHCO$_3$ (aq.). The resulting mixture was extracted with EtOAc. The combined organic layers were washed with brine, dried over anhydrous Na$_2$SO$_4$. After filtration, the filtrate was concentrated under reduced pressure. The residue was purified by flash column chromatography with 0-50% ethyl acetate in petroleum ether to afford methyl 2-chloroquinoline-5-carboxylate (630 mg, 41.26%) as a yellow solid. MS m/z 222.0 [M+1]$^+$ Step-4: To a mixture of methyl 2-chloroquinoline-5-carboxylate (300 mg, 1.354 mmol) in THF (2 mL) and H$_2$O (2 mL) was added LiOH (97 mg, 4.060 mmol) at 0° C. The resulting mixture was stirred at room temperature for 2 h. The resulting mixture was concentrated under vacuum This resulted in 2-chloroquinoline-5-carboxylic acid (280 mg, crude) as a white solid. MS m/z 208.0 [M+1]$^+$ Step-5: To a mixture of 2-chloroquinoline-5-carboxylic acid (280 mg, 1.417 mmol) in DMF (3 mL) was added DIEA (549 mg, 4.251 mmol) and HATU (808 mg, 2.125 mmol). The resulting mixture was stirred at room temperature for 30 min. To the above mixture was added isopropylamine (251 mg, 4.251 mmol). The resulting mixture was stirred at room temperature for 2 h. The resulting mixture was extracted with EtOAc. The combined organic layers were washed with brine, dried over anhydrous Na$_2$SO$_4$. After filtration, the filtrate was concentrated under reduced pressure. The residue was purified by flash column chromatography with 0-50% ethyl acetate in PE to afford 2-chloro-N-isopropylquinoline-5-carboxamide (150 mg, 42.57%) as a white solid. MS m/z 249.0 [M+1]$^+$

Intermediate A167 tert-butyl N-[2-[(5-bromo-3-methylpyrazin-2-yl)oxy]propyl]carbamate

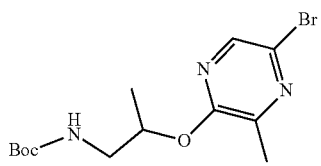 [SMILES: Cc1nc(Br)cnc1OC(C)CNC(=O)OC(C)(C)C]

To a mixture of of 5-bromo-3-methylpyrazin-2-ol (300 mg, 1.587 mmol) and tert-butyl N-(2-hydroxypropyl)carbamate (306 mg, 1.746 mmol) in THF (5 mL) was added PPh$_3$ (624 mg, 2.381 mmol) and DIAD (481 mg, 2.381 mmol) at 0° C. The resulting mixture was stirred at room temperature overnight under nitrogen atmosphere. The resulting mixture was concentrated under vacuum. The residue was purified by flash column chromatography with 0-40% ethyl acetate in PE to afford tert-butyl N-[2-[(5-bromo-3-methylpyrazin-2-yl)oxy]propyl]carbamate (400 mg, 72.79%) as a white oil. MS m/z 346.0 [M+1]$^+$.

Intermediate A168 tert-butyl 3,3-difluoro-4-[(5-iodo-3-methylpyrazin-2-yl)oxy]pyrrolidine-1-carboxylate

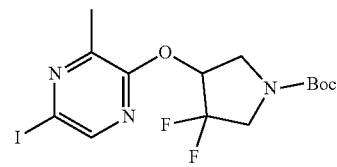 [SMILES: Cc1nc(I)cnc1OC1CN(C(=O)OC(C)(C)C)CC1(F)F]

To a mixture of tert-butyl 3,3-difluoro-4-hydroxypyrrolidine-1-carboxylate (88 mg, 0.393 mmol) in DMF (4 mL) were added NaH (19 mg, 0.786 mmol) at 0° C. The resulting mixture was stirred at 0° C. for 30 min under nitrogen atmosphere. To the above mixture was added 2-chloro-5-iodo-3-methylpyrazine (100 mg, 0.393 mmol). The resulting mixture was stirred at room temperature for 1 h. The reaction was then quenched by the addition of water. The resulting mixture was extracted with EtOAc (3×20 mL). The combined organic layers were washed with brine (1×5 mL), dried over anhydrous $Na_2SO_4$. After filtration, the filtrate was concentrated under reduced pressure. The residue was purified by flash column chromatography with 0-50% ethyl acetate in PE to afford tert-butyl 3,3-difluoro-4-[(5-iodo-3-methylpyrazin-2-yl)oxy]pyrrolidine-1-carboxylate (100 mg, 57.67%) as a light yellow oil. MS m/z 442.0 $[M+1]^+$.

Intermediate A169

1-[3,3-difluoro-4-[(5-iodo-3-methylpyrazin-2-yl)oxy]pyrrolidin-1-yl]ethanone

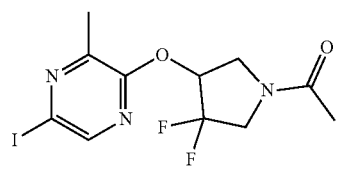 [SMILES: CC(=O)N1CC(Oc2ncc(I)nc2C)C(F)(F)C1]

Step-1: A mixture of tert-butyl 3,3-difluoro-4-[(5-iodo-3-methylpyrazin-2-yl)oxy]pyrrolidine-1-carboxylate (50 mg, 0.113 mmol) in HCl in 1,4-dioxane (5 mL, 4N) was stirred at room temperature for 1 h. The resulting mixture was concentrated under vacuum to afford 2-[(4,4-difluoropyrrolidin-3-yl)oxy]-5-iodo-3-methylpyrazine (35 mg, 90.55%) as a yellow oil. MS m/z 341.9 $[M+1]^+$.

Step-2: To a mixture of 2-[(4,4-difluoropyrrolidin-3-yl)oxy]-5-iodo-3-methylpyrazine (80 mg, 0.235 mmol) in DCM (3 mL) were added TEA (72 mg, 0.704 mmol) and acetyl chloride (21 mg, 0.258 mmol) dropwise at 0° C. The resulting mixture was stirred at 0° C. for 1 h. The reaction was quenched with MeOH at 0° C. The resulting mixture was concentrated under vacuum. The residue was purified by flash column chromatography with 0-50% ethyl acetate in PE to afford 1-[3,3-difluoro-4-[(5-iodo-3-methylpyrazin-2-yl)oxy]pyrrolidin-1-yl]ethanone (80 mg, 89.03%) as a yellow oil. MS m/z 384.0 $[M+1]^+$.

Intermediate A170

6-bromo-2-methyl-3-[2-methyl-2-(oxan-2-yloxy)propoxy]pyridine

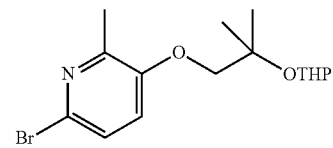

To a mixture of 2-methyl-2-(oxan-2-yloxy)propan-1-ol (1.29 g, 7.36 mmol) in DMF (5 mL) were added NaH (252 mg, 10.525 mmol) at 0° C. The resulting mixture was stirred at 0° C. for 30 min under nitrogen atmosphere. To the above mixture was added 6-bromo-3-fluoro-2-methylpyridine (1 g, 5.263 mmol). The resulting mixture was stirred at room temperature for 16 h. The reaction was then quenched by the addition of water. The resulting mixture was extracted with EtOAc. The combined organic layers were washed with brine, dried over anhydrous $Na_2SO_4$. After filtration, the filtrate was concentrated under reduced pressure. The residue was purified by flash column chromatography with 0-40% ethyl acetate in PE to afford 6-bromo-2-methyl-3-[2-methyl-2-(oxan-2-yloxy)propoxy]pyridine (1 g, 55.20%) as a colorless oil. MS m/z 344.0 $[M+1]^+$.

Intermediate A171

5-iodo-3-methyl-2-[(3-methyloxetan-3-yl)methoxy]pyrazine

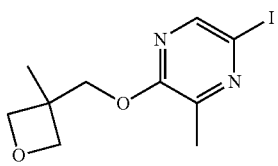

To a mixture of (3-methyloxetan-3-yl)methanol (81 mg, 0.786 mmol) in DMF (4 mL) were added NaH (63 mg, 1.572 mmol) at 0° C. The resulting mixture was stirred at 0° C. for 30 min under nitrogen atmosphere. To the above mixture was added 2-chloro-5-iodo-3-methylpyrazine (200 mg, 0.786 mmol). The resulting mixture was stirred at room temperature for 16 h. The reaction was then quenched by the addition of water. The resulting mixture was extracted with EtOAc (3×20 mL). The combined organic layers were washed with brine (1×5 mL), dried over anhydrous $Na_2SO_4$. After filtration, the filtrate was concentrated under reduced pressure. The residue was purified by flash column chromatography with 0-40% ethyl acetate in PE to afford 5-iodo-3-methyl-2-[(3-methyloxetan-3-yl)methoxy]pyrazine (120 mg, 47.69%) as a light yellow oil. MS m/z 321.0 $[M+1]^+$.

Intermediate A172

1-[(5-bromo-3-methylpyrazin-2-yl)(methyl)amino]-2-methylpropan-2-ol

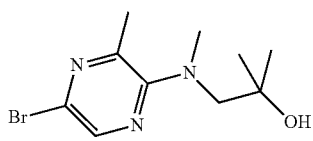

Step-1: To a mixture of 2-chloro-3-methylpyrazine (300 mg, 2.334 mmol) and 2-methyl-1-(methylamino)propan-2-ol (289 mg, 2.801 mmol) in toluene (5 mL) were added $Pd_2(dba)_3$ (214 mg, 0.233 mmol), XPhos (111 mg, 0.233 mmol) and t-BuONa (448 mg, 4.668 mmol). The resulting mixture was stirred at 100° C. overnight under nitrogen atmosphere. The resulting mixture was concentrated under vacuum. The residue was purified by flash column chromatography with 0-50% ethyl acetate in PE to afford 2-methyl- 1-[methyl(3-methylpyrazin-2-yl)amino]propan-2-ol (200 mg, 43.89%) as a yellow solid. MS m/z 196.1 [M+1]⁺.

Step-2: To a mixture of 2-methyl-1-[methyl(3-methylpyrazin-2-yl)amino]propan-2-ol (200 mg, 1.104 mmol) in ACN (5 mL) was added NBS (196 mg, 1.104 mmol). The resulting mixture was stirred at room temperature for 1 h. The resulting mixture was extracted with EtOAc. The combined organic layers were washed with brine, dried over anhydrous Na₂SO₄. After filtration, the filtrate was concentrated under reduced pressure. The residue was purified by flash column chromatography with 0-50% ethyl acetate in petroleum ether to afford 1-[(5-bromo-3-methylpyrazin-2-yl)(methyl)amino]-2-methylpropan-2-ol (90 mg, 32.05%) as a yellow solid. MS m/z 274.1 [M+1]⁺

Intermediate A173

1-[(5-bromo-3-methylpyrazin-2-yl)(ethyl)amino]-2-methylpropan-2-ol

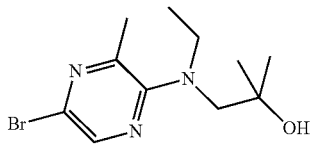 [SMILES: CCN(CC(C)(C)O)c1ncc(Br)nc1C]

Step-1: To a mixture of 2-chloro-3-methylpyrazine (250 mg, 1.945 mmol) and 1-(ethylamino)-2-methylpropan-2-ol (273 mg, 2.334 mmol) in dioxane (3 mL) was added Pd-PEPPSI-IHeptCl 3-chloropyridine (189 mg, 0.194 mmol) and Cs₂CO₃ (1.90 g, 5.834 mmol). The resulting mixture was stirred at 90° C. overnight under nitrogen atmosphere. The mixture was concentrated under vacuum. The residue was purified by flash column chromatography with 0-40% ethyl acetate in PE to afford 1-[ethyl(3-methylpyrazin-2-yl)amino]-2-methylpropan-2-ol (295 mg, 72.70%) as a brown oil. MS m/z 210.1 [M+1]⁺.

Step-2: To a mixture of 1-[ethyl(3-methylpyrazin-2-yl)amino]-2-methylpropan-2-ol (255 mg, 1.218 mmol) in ACN (3 mL) were added NBS (217 mg, 1.218 mmol). The resulting mixture was stirred at room temperature for 2 h. The resulting mixture was extracted with EtOAc. The combined organic layers were washed with brine, dried over anhydrous Na₂SO₄. After filtration, the filtrate was concentrated under reduced pressure. This resulted in 1-[(5-bromo-3-methylpyrazin-2-yl)(ethyl)amino]-2-methylpropan-2-ol (330 mg, 93.98%) as a yellow solid. MS m/z 288.1 [M+1]⁺.

Intermediate A174

5-iodo-3-methyl-2-[[1-(oxan-2-yloxy)cyclopropyl]methoxy]pyrazine

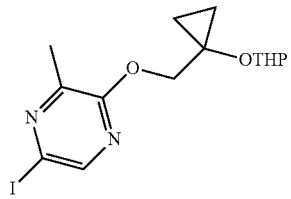

Step-1: To a mixture of methyl 1-hydroxycyclopropane-1-carboxylate (1 g, 8.612 mmol) in DCM (10 mL) were added DHP (1.09 g, 12.958 mmol) and PPTS (0.11 g, 0.438 mmol) at 0° C. The resulting mixture was stirred at room temperature for 4 h. The resulting mixture was extracted with EtOAc. The combined organic layers were washed with brine, dried over anhydrous Na₂SO₄. After filtration, the filtrate was concentrated under reduced pressure. This resulted in methyl 1-(oxan-2-yloxy)cyclopropane-1-carboxylate (1.8 g, crude) as a yellow oil. ¹H NMR (400 MHz, DMSO-d₆) δ 4.87-4.75 (m, 1H), 3.80-3.70 (m, 1H), 3.64 (s, 3H), 3.49-3.37 (m, 1H), 1.70-1.65 (m, 1H), 1.73-1.64 (m, 2H), 1.58-1.48 (m, 1H), 1.48-1.37 (m, 1H), 1.42 (s, 1H), 1.24-1.15 (m, 2H), 1.19-1.10 (m, 2H).

Step-2: To a mixture of methyl 1-(oxan-2-yloxy)cyclopropane-1-carboxylate (1.8 g, 8.989 mmol) in THF (20 mL) was added LAH (0.34 g, 8.958 mmol) at 0° C. under nitrogen atmosphere. The resulting mixture was stirred at 0° C. for 4 h. The resulting mixture was extracted with EtOAc. The combined organic layers were washed with brine, dried over anhydrous Na₂SO₄. After filtration, the filtrate was concentrated under reduced pressure. This resulted in [1-(oxan-2-yloxy)cyclopropyl]methanol (1.6 g, crude) as a yellow oil. ¹H NMR (400 MHz, DMSO-d₆) δ 4.86-4.76 (m, 1H), 4.58-4.51 (m, 1H), 3.86-3.76 (m, 1H), 3.64-3.53 (m, 1H), 3.51-3.43 (m, 1H), 3.47-3.35 (m, 1H), 3.17 (d, J=5.2 Hz, 1H), 1.77-1.63 (m, 1H), 1.67-1.52 (m, 1H), 1.55-1.42 (m, 1H), 1.46-1.30 (m, 2H), 0.90-0.79 (m, 1H), 0.71-0.60 (m, 1H), 0.63-0.42 (m, 2H).

Step-3: To a mixture of [1-(oxan-2-yloxy)cyclopropyl]methanol (666 mg, 3.871 mmol) in DMF (5 mL) was added NaH (186 mg, 7.742 mmol) at 0° C. The resulting mixture was stirred for 30 min at 0° C. To the above mixture was added 2-chloro-5-iodo-3-methylpyrazine (985.00 mg, 3.871 mmol). The resulting mixture was stirred at room temperature overnight. The resulting mixture was extracted with EtOAc. The combined organic layers were washed with brine, dried over anhydrous Na₂SO₄. After filtration, the filtrate was concentrated under reduced pressure. The residue was purified by flash column chromatography with 0-50% ethyl acetate in PE to afford 5-iodo-3-methyl-2-[[1-(oxan-2-yloxy)cyclopropyl]methoxy]pyrazine (430 mg, 28.47%) as a yellow oil. MS m/z 391.0 [M+1]+

Intermediate A175

(2R,3R)-3-[(5-iodo-3-methylpyrazin-2-yl)oxy]butan-2-ol

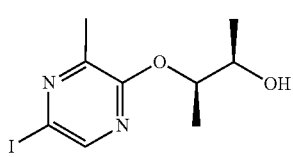

To a mixture of (R,R)-butane-2,3-diol (106 mg, 1.179 mmol) in DMF (1 mL) was added NaH (57 mg, 2.358 mmol). The resulting mixture was stirred at 0° C. for 30 min under nitrogen atmosphere. To the above mixture was added 2-chloro-5-iodo-3-methylpyrazine (300 mg, 1.179 mmol). The resulting mixture was stirred at room temperature for 1 h. The resulting mixture was extracted with EtOAc. The combined organic layers were washed with brine, dried over anhydrous Na₂SO₄. After filtration, the filtrate was concentrated under reduced pressure. The residue was purified by flash column chromatography with 0-40% ethyl acetate in PE to afford (2R,3R)-3-[(5-iodo-3-methylpyrazin-2-yl)oxy]butan-2-ol (224 mg, 55.99%) as a brown oil. MS m/z 309.0 [M+1]+.

Intermediate A176

1-[(5-iodo-3-methylpyrazin-2-yl)oxy]propan-2-ol

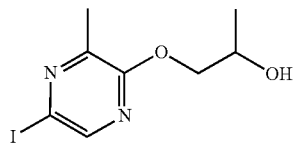

Step-1: To a mixture of 2-methoxypropanol (128 mg, 1.415 mmol) in DMF (5 mL) were added NaH (57 mg, 2.358 mmol) at 0° C. The resulting mixture was stirred at 0° C. for 30 min under nitrogen atmosphere. To the above mixture was added 2-chloro-5-iodo-3-methylpyrazine (300 mg, 1.179 mmol). The resulting mixture was stirred at room temperature for 16 h. The reaction was then quenched by the addition of water. The resulting mixture was extracted with EtOAc (3×20 mL). The combined organic layers were washed with brine (1×5 mL), dried over anhydrous $Na_2SO_4$. After filtration, the filtrate was concentrated under reduced pressure. The residue was purified by flash column chromatography with 0-10% ethyl acetate in PE to afford 5-iodo-2-(2-methoxypropoxy)-3-methylpyrazine (160 mg, 44.05%) as a light yellow oil. MS m/z 309.0 [M+1]+.

Step-2: To a mixture of 5-iodo-2-(2-methoxypropoxy)-3-methylpyrazine (140 mg, 0.454 mmol) in DCM (3 mL) was added $BBr_3$ in DCM (0.9 mL, 0.90 mmol, 1 moL/L) dropwise at 0° C. The resulting mixture was stirred at 0° C. for 1 h. The residue was quenched with EtOH (10 mL). The resulting mixture was concentrated under vacuum. The resulting mixture was extracted with EtOAc (3×20 mL). The combined organic layers were washed with brine (1×5 mL), dried over anhydrous $Na_2SO_4$. After filtration, the filtrate was concentrated under reduced pressure. This resulted in 1-[(5-iodo-3-methylpyrazin-2-yl)oxy]propan-2-ol (80 mg, 59.87%) as a yellow oil. MS m/z 294.9 [M+1]+.

Intermediate B1

4-(1-(tetrahydro-2H-pyran-2-yl)-3-(4,4,5,5-tetramethyl-1,3,2-dioxaborolan-2-yl)-1H-indazol-5-yl)morpholine

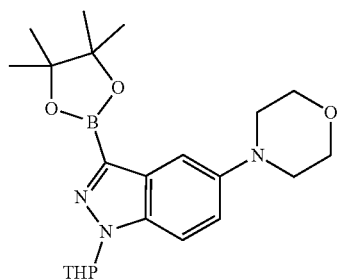

Step 1: To a solution of 5-bromo-1H-indazole (5.00 g, 25.3 mmol) and dihydropyran (6.40 g, 76.10 mmol) in dichloromethane (30 mL) was added p-toluenesulfonic acid monohydrate (440 mg, 2.31 mmol). The mixture was stirred at room temperature overnight. The mixture was washed with saturated sodium bicarbonate aqueous solution and brine. The organic layer was dried over anhydrous sodium sulfate, filtered and concentrated under reduced pressure. The residue was purified by flash column chromatography with 0~40% ethyl acetate in petroleum ether to afford 5-bromo-1-(oxan-2-yl)indazole (6.70 g, 94%) as a colorless oil. MS m/z 281.0 [M+1]+.

Step-2: To a degassed mixture of 5-bromo-1-(oxan-2-yl)indazole (3.00 g, 10.67 mmol), palladium acetate (0.24 g, 1.09 mmol), (±)-2,2'-bis(diphenylphosphino)-1,1'-binaphthalene (1.33 g, 2.13 mmol) and sodium tert-butoxide (2.06 g, 21.45 mmol) in toluene (30 mL) was added morpholine (1.39 g, 15.97 mmol). The mixture was stirred at 100° C. for 16 h. The mixture was concentrated under reduced pressure. The crude product was purified by flash column chromatography with 0~50% ethyl acetate in petroleum ether to afford 5-(morpholin-4-yl)-1-(oxan-2-yl)indazole (1.60 g, 54%) as a pink solid. MS m/z 288.1 [M+1]+. $^1$H NMR (300 MHz, DMSO-$d_6$) δ 7.93 (s, 1H), 7.60 (d, J=9.0 Hz, 1H), 7.25 (dd, J=9.0, 2.4 Hz, 1H), 7.10 (d, J=2.1 Hz, 1H), 5.78-5.74 (m, 1H), 3.92-3.81 (m, 1H), 3.78-3.64 (m, 5H), 3.10-3.01 (m, 4H), 2.44-2.31 (m, 1H), 2.09-1.87 (m, 2H), 1.79-1.63 (m, 1H), 1.61-1.52 (m, 2H).

Step-3: To a solution of 5-(morpholin-4-yl)-1-(oxan-2-yl)indazole (500 mg, 1.73 mmol) and bis(pinacolato)diboron (221 mg, 0.87 mmol) in methyl tert-butyl ether (8.5 mL) were added (1,5-cyclooctadiene)(methoxy)iridium(I) dimer (62 mg, 0.09 mmol) and 4,4-di-tert-butyl bipyridine (47 mg, 0.13 mmol). The mixture was stirred at 60° C. for 16 h. The mixture was concentrated under reduced pressure. The residue was purified by flash column chromatography with 0~70% ethyl acetate in petroleum ether to afford 4-(1-(tetrahydro-2H-pyran-2-yl)-3-(4,4,5,5-tetramethyl-1,3,2-dioxaborolan-2-yl)-1H-indazol-5-yl)morpholine (B1) (163 mg, 22%) as a yellow solid. MS m/z 414.2 [M+1]+.

Intermediate B2

4-(1-(tetrahydro-2H-pyran-2-yl)-3-(4,4,5,5-tetramethyl-1,3,2-dioxaborolan-2-yl)-1H-indazol-6-yl)morpholine

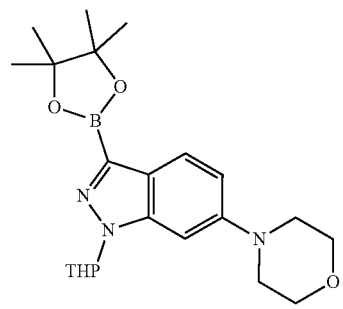

Following the procedure of intermediate B1 described above to afford 4-(1-(tetrahydro-2H-pyran-2-yl)-3-(4,4,5,5-tetramethyl-1,3,2-dioxaborolan-2-yl)-1H-indazol-6-yl)morpholine (B2) (175 mg, 13% over 3 steps) as a brown solid from starting material 6-bromo-1H-indazole. MS m/z 414.2 [M+1]+.

143

Intermediate B3

N,N-dimethyl-1-(tetrahydro-2H-pyran-2-yl)-3-(4,4,5,5-tetramethyl-1,3,2-dioxaborolan-2-yl)-1H-indazol-5-amine

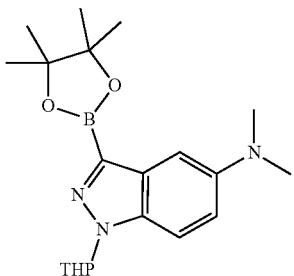

Following the procedure of intermediate B1 described above to afford N,N-dimethyl-1-(tetrahydro-2H-pyran-2-yl)-3-(4,4,5,5-tetramethyl-1,3,2-dioxaborolan-2-yl)-1H-indazol-5-amine (B3) (503 mg, 53% over 2 steps) as yellow oil from starting material 5-bromo-1-(tetrahydro-2H-pyran-2-yl)-1H-indazole. MS m/z 372.2 [M+1]$^+$.

Intermediate B4

N,N-dimethyl-1-(oxan-2-yl)-3-(4,4,5,5-tetramethyl-1,3,2-dioxaborolan-2-yl)indazol-6-amine

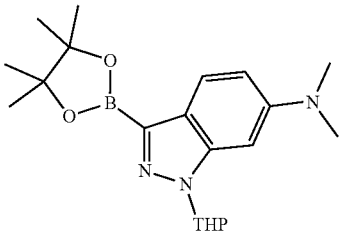

Following the procedure of intermediate B1 described above to afford N,N-dimethyl-1-(oxan-2-yl)-3-(4,4,5,5-tetramethyl-1,3,2-dioxaborolan-2-yl)indazol-6-amine (B4) (543 mg, 82% over 2 steps) as yellow oil from starting material 6-bromo-1-(oxan-2-yl)indazole. MS m/z 372.2 [M+1]$^+$.

Intermediate B5

1-(oxan-2-yl)-3-(4,4,5,5-tetramethyl-1,3,2-dioxaborolan-2-yl)indazole

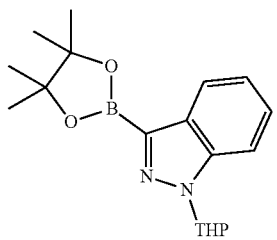

144

Step 1: To a solution of 3-bromo-1H-indazole (5.00 g, 25.38 mmol) and dihydropyran (6.40 g, 76.19 mmol) in dichloromethane (30 mL) was added p-toluenesulfonic acid monohydrate (0.43 g, 2.28 mmol). The mixture was stirred at room temperature overnight. The reaction mixture was washed with saturated sodium bicarbonate aqueous solution and brine. The organic layer was dried over anhydrous sodium sulfate, filtered and concentrated under reduced pressure. The residue was purified by flash column chromatography with 0~40% ethyl acetate in petroleum ether to afford 3-bromo-1-(oxan-2-yl)indazole (7.12 g, 99%) as a white solid. MS m/z 281.0 [M+1]$^+$.

Step 2: To a mixture of 3-bromo-1-(oxan-2-yl)indazole (6.51 g, 23.16 mmol) and bis(pinacolato)diboron (12.21 g, 48.03 mmol) in dioxane (60 mL) were added [1,1'-bis(diphenylphosphino)ferrocene]dichloro-palladium(II) (1.70 g, 2.29 mmol) and potassium acetate (4.57 g, 46.66 mmol). The mixture was stirred at 80° C. for 16 h. The mixture was concentrated under reduced pressure. The crude product was purified by flash column chromatography with 0~10% ethyl acetate in petroleum ether to afford 1-(oxan-2-yl)-3-(4,4,5,5-tetramethyl-1,3,2-dioxaborolan-2-yl)indazole (B5) (7.20 g, 94%) as green solid. MS m/z 329.1 [M+1]$^+$. $^1$H NMR (300 MHz, DMSO-d$_6$) δ 7.92-7.89 (m, 1H), 7.76-7.73 (m, 1H), 7.42-7.37 (m, 1H), 7.24-7.19 (m, 1H), 5.91-5.87 (m, 1H), 3.90-3.86 (m, 1H), 3.78-3.71 (m, 1H), 2.48-2.34 (m, 1H), 2.08-1.86 (m, 2H), 1.78-1.66 (m, 1H), 1.60-1.57 (m, 2H), 1.34 (s, 12H).

Intermediate B6

5,6-difluoro-1-(oxan-2-yl)-3-(4,4,5,5-tetramethyl-1,3,2-dioxaborolan-2-yl)indazole

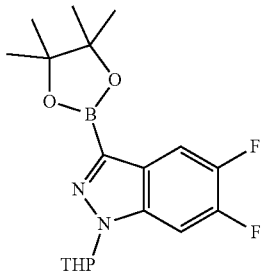

Step 1: To a solution of 5,6-difluoro-1H-indazole (11.40 g, 73.96 mmol) in N,N-dimethylformamide (200 mL) was added N-bromosuccinimide (13.20 g, 74.16 mmol) in portions at 0° C. The mixture was stirred at 0° C. for 2 h. The mixture was diluted with water and extracted with ethyl acetate. The organic layer was dried over anhydrous sodium sulfate, filtered and concentrated under vacuum. The residue was purified by flash column chromatography with 0~30% ethyl acetate in petroleum ether to afford 3-bromo-5,6-difluoro-1H-indazole (12.60 g, 73%) as a white solid. MS m/z 233.0 [M+1]$^+$.

Step 2: To a solution of 3-bromo-5,6-difluoro-1H-indazole (14.00 g, 60.08 mmol) and dihydropyran (7.60 g, 90.34 mmol) in dichloromethane (200 mL) was added p-toluenesulfonic acid monohydrate (0.52 g, 3.02 mmol). The mixture was stirred at room temperature for 16 h. The mixture was concentrated under vacuum. The residue was purified by flash column chromatography with 0~20% ethyl acetate in petroleum ether to afford 3-bromo-5,6-difluoro-1-(oxan-2-yl)indazole (16.40 g, 86%) as a colorless syrup. MS m/z 317.0 [M+1]+

Step 3: A mixture of 3-bromo-5,6-difluoro-1-(oxan-2-yl)indazole (4.20 g, 13.24 mmol), bis(pinacolato)-diboron (6.70 g, 26.38 mmol), [1,1'-bis(diphenylphosphino)ferrocene]dichloropalladium(II) (0.62 g, 0.84 mmol) and potassium acetate (3.80 g, 38.71 mmol) in dioxane (50 mL) was heated at 90° C. for 4 h. The mixture was concentrated under vacuum. The residue was purified by flash column chromatography with 0~30% ethyl acetate in petroleum ether to afford 5,6-difluoro-1-(oxan-2-yl)-3-(4,4,5,5-tetramethyl-1,3,2-dioxaborolan-2-yl)indazole (B6) (3.60 g, 74%) as a yellow syrup. MS m/z 365.1 [M+1]+. 1H NMR (300 MHz, DMSO-d6) δ 7.94 (dd, J=10.8, 6.6 Hz, 1H), 7.70 (dd, J=10.2, 7.8 Hz, 1H), 5.89-5.85 (m, 1H), 3.90-3.85 (m, 1H), 3.76-3.70 (m, 1H), 2.43-2.27 (m, 1H), 2.10-1.87 (m, 2H), 1.82-1.49 (m, 3H), 1.33 (s, 12H).

Intermediate B7

5,6-difluoro-1-(oxan-2-yl)indazol-3-ylboronic acid

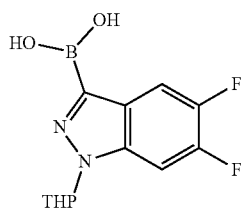

A degassed mixture of 3-bromo-5,6-difluoro-1-(oxan-2-yl)indazole (11.00 g, 34.68 mmol), bis-(pinacolato)diboron (17.60 g, 69.30 mmol), potassium acetate (6.80 g, 69.28 mmol) and [1,1'-bis(diphenyl-phosphino)ferrocene]dichloropalladium(II) (2.50 g, 3.41 mmol) in dioxane (100 mL) was heated at 85° C. for 16 h. The mixture was concentrated under vacuum. The residue was diluted with water and extracted with ethyl acetate. The organic layer was dried over anhydrous sodium sulfate, filtered and concentrated under vacuum. The residue was purified by reverse phase flash column chromatography with 10~80% acetonitrile in water over 50 min to afford 5,6-difluoro-1-(oxan-2-yl)indazol-3-ylboronic acid (B7) (5.9 g, 60%) as a brown solid. MS m/z 283.0 [M+1]+. 1H NMR (400 MHz, DMSO-d6) δ 8.46 (s, 2H), 7.91-7.81 (m, 2H), 5.85 (dd, J=10.2, 2.4 Hz, 1H), 3.96-3.84 (m, 1H), 3.83-3.69 (m, 1H), 2.18-1.88 (m, 2H), 1.86-1.51 (m, 4H).

Intermediate B8

7-methyl-1-(oxan-2-yl)indazol-3-ylboronic acid

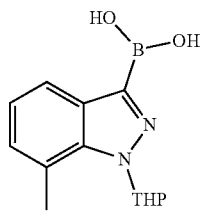

Followed the procedure of Intermediate B7 described above to afford 7-methyl-1-(oxan-2-yl)indazol-3-yl-boronic acid (B8) (120 mg, 24% over 2 steps) as a light yellow oil from 3-bromo-7-methyl-1H-indazole. MS m/z 261.0 [M+1]+.

Intermediate B9

1-(oxan-2-yl)pyrazolo[4,3-b]pyridin-3-ylboronic acid

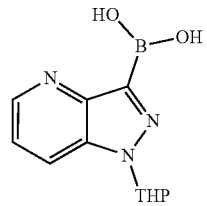

Followed the procedure of Intermediate B7 described above to afford 1-(oxan-2-yl)pyrazolo[4,3-b]pyridin-3-ylboronic acid (B9) (350 mg, 64% over 2 steps) as a brown solid from 3-bromo-1H-pyrazolo[4,3-b]pyridine (1.00 g, 5.05 mmol). MS m/z 248.1 [M+1]+.

Intermediate B10

5,6-difluoro-1-(oxan-2-yl)indazol-3-ylboronic acid

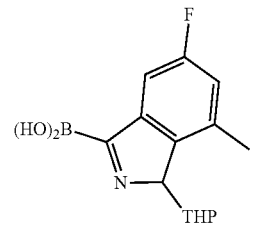

Step 1: A mixture of 7-bromo-5-fluoro-1H-indazole (2.50 g, 11.62 mmol) and dihydropyran (1.50 g, 17.85 mmol) in dichloromethane (30 mL) was added p-toluenesulfonic acid monohydrate (0.10 g, 0.52 mmol). The mixture was stirred at room temperature for 8 h. The reaction mixture was concentrated under reduced pressure. The residue was purified by flash column chromatography with 0~70% ethyl acetate in petroleum ether to afford 7-bromo-5-fluoro-1-(oxan-2-yl)indazole (2.00 g, 58%) as a white solid. MS m/z 299.1 [M+1]+.

Step 2: A mixture of 7-bromo-5-fluoro-1-(oxan-2-yl)indazole (1.40 g, 4.66 mmol), palladium(0)tetrakis-(triphenylphosphine) (0.54 g, 0.47 mmol), methylboronic acid (0.84 g, 14.00 mmol) and potassium carbonate (1.3 g, 9.42 mmol) in dioxane was stirred for 4 h at 100° C. under nitrogen atmosphere. The mixture was concentrated under reduced pressure. The residue was purified by flash column chromatography with 0~80% ethyl acetate in petroleum ether to afford 5-fluoro-7-methyl-1-(oxan-2-yl)indazole (1.00 g, 91%) as a white solid. MS m/z 235.2 [M+1]+.

Step 3: A degassed mixture of 5-fluoro-6-methyl-1-(oxan-2-yl)indazole (0.50 g, 2.12 mmol), bis(pinacolato)diboron (1.10 g, 4.33 mmol), (1,5-cyclooctadiene)(methoxy)iridium (I) dimer (0.14 g, 0.21 mmol) and 4,4-di-tert-butyl bipyridine (0.11 g, 0.32 mmol) in methyl tert-butyl ether (10 mL) was stirred at 55° C. for 16 h. The mixture was concentrated under vacuum. The residue was purified by reverse flash chromatography with 10% to 70% acetonitrile in water over 30 min to afford 5-fluoro-6-methyl-1-(oxan-2-yl)indazol-3-ylboronic acid (B10) (0.28 g, 47%) as a light yellow solid. MS m/z 279.2 [M+1]$^+$. $^1$H NMR (400 MHz, DMSO-d$_6$) δ 8.31 (s, 2H), 7.50 (dd, J=8.8, 2.4 Hz, 1H), 7.08 (dd, J=8.8, 2.4 Hz, 1H), 6.04-5.81 (m, 1H), 3.97-3.85 (m, 1H), 3.80-3.63 (m, 1H), 2.71 (s, 3H), 2.25-1.94 (m, 2H), 1.87-1.67 (m, 2H), 1.60-1.55 (m, 2H).

Intermediate B11

5-fluoro-1-(oxan-2-yl)indazol-3-ylboronic acid

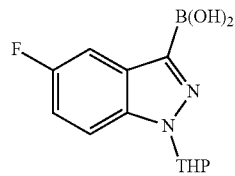

Followed the procedure of Intermediate B8 described above to afford 5-fluoro-1-(oxan-2-yl)indazol-3-ylboronic acid (B11) (151 mg, 33% over 2 steps) as a yellow oil from 5-fluoro-1H-indazole. MS m/z 265.1 [M+1]$^+$.

Intermediate B12

5-fluoro-6-methyl-1-(oxan-2-yl)indazol-3-ylboronic acid

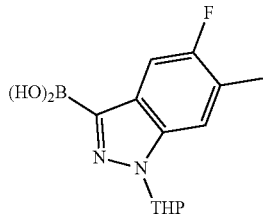

Followed the procedure of Intermediate B8 described above to afford 5-fluoro-6-methyl-1-(oxan-2-yl)indazol-3-ylboronic acid (B12) (0.90 g, 68% over 3 steps) as a yellow oil from 6-bromo-5-fluoro-1H-indazole (1.00 g, 4.65 mmol). MS m/z 279.1 [M+1]$^+$.

Intermediate B13

6-fluoro-5-methyl-1-(oxan-2-yl)indazol-3-ylboronic acid

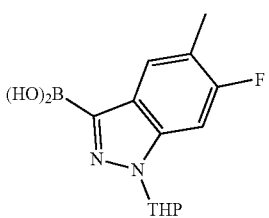

Followed the procedure of Intermediate B8 described above to afford 6-fluoro-5-methyl-1-(oxan-2-yl)indazol-3-ylboronic acid (B13) (0.20 g, 53% over 3 steps) as a brown solid from 5-bromo-6-fluoro-1H-indazole (1.00 g, 4.65 mmol). MS m/z 279.1 [M+1]$^+$ Intermediate B14

6-fluoro-1-(oxan-2-yl) indazol-3-ylboronic acid

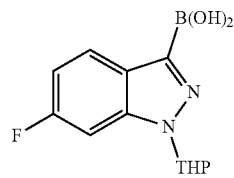

Followed the procedure of Intermediate B8 described above to afford 6-fluoro-1-(oxan-2-yl) indazol-3-ylboronic acid (B14) (200 mg, 38% over 2 steps) as a light-yellow oil from 6-fluoro-1H-indazole. MS m/z 265.1 [M+1]$^+$.

Intermediate B15 tert-butyl 7-cyano-3-(4,4,5,5-tetramethyl-1,3,2-dioxaborolan-2-yl)indole-1-carboxylate

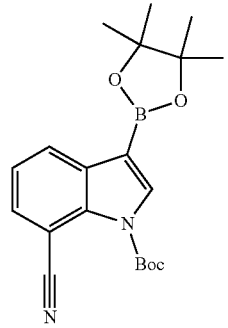 [SMILES: CC(C)(C)OC(=O)n1cc(B2OC(C)(C)C(C)(C)O2)c2cccc(C#N)c21]

Step 1: To a solution of 1H-indole-7-carbonitrile (15.00 g, 105.51 mmol) in tetrahydrofuran (147 mL) was added N-bromosuccinimide (18.78 g, 105.51 mmol). The mixture was stirred at room temperature for 4 h. The mixture was concentrated under vacuum to afford 3-bromo-1H-indole-7-carbonitrile (20.00 g, crude) as a light yellow solid. MS m/z 221.0. [M+1]$^+$.

Step 2: To a solution of 3-bromo-1H-indole-7-carbonitrile (13.13 g, 59.39 mmol), 4-dimethylaminopyridine (1.45 g, 11.87 mmol) and triethylamine (12.00 g, 0.12 mmol) in dichloromethane (150 mL) was added di(tert-butyl) carbonate (26.25 g, 0.12 mmol). The mixture was stirred at room temperature for 16 h. The mixture was concentrated under vacuum. The residue was purified by flash column chromatography with 0~20% ethyl acetate in petroleum ether to afford tert-butyl 7-cyanoindole-1-carboxylate (12.8 g, 56% over 2 steps) as a yellow solid. MS m/z 321.1 [M+1]$^+$.

Step 3: To a solution of tert-butyl 3-bromo-7-cyanoindole-1-carboxylate (5.00 g, 15.56 mmol) and bis(pinacolato)diboron (12.49 g, 49.35 mmol) in dioxane (50 mL) were added [1,1'-bis(diphenylphosphino)-ferrocene]dichloropalladium(II) (1.14 g, 1.55 mmol) and potassium acetate (3.06 g, 31.13 mmol) under nitrogen atmosphere. The mixture was heated at 80° C. for 2 h. The mixture was concentrated under vacuum. The residue was purified by flash column chromatography with 0~50% ethyl acetate in petroleum ether to afford tert-butyl 7-cyano-3-(4,4,5,5-tetramethyl-1,3,2-dioxaborolan-2-yl)indole-1-carboxylate (B15) (2.55 g, 44%) as an off-white solid. MS m/z 369.2 [M+1]⁺. ¹H NMR (400 MHz, DMSO-d₆) δ 8.18 (dd, J=8.0, 1.2 Hz, 1H), 7.99 (s, 1H), 7.83 (dd, J=7.6, 1.2 Hz, 1H), 7.47 (t, J=7.6 Hz, 1H), 1.65 (s, 9H), 1.33 (s, 12H).

Intermediate B16

1-(oxan-2-yl)-3-(4,4,5,5-tetramethyl-1,3,2-dioxaborolan-2-yl)indazole-7-carbonitrile

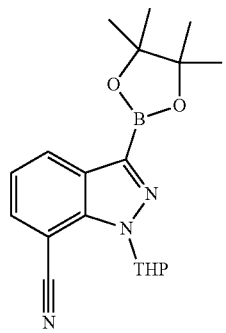

Step 1: To a solution of 1H-indazole-7-carbonitrile (1.00 g, 6.98 mmol) in N,N-dimethylformamide (10 mL) was added N-bromosuccinimide (1.24 g, 6.98 mmol) at room temperature. The mixture was stirred at room temperature for 2 h. The mixture was diluted with water. The solids were collected by filtration and dried under vacuum to afford 3-bromo-1H-indazole-7-carbonitrile (1.30 g, 83%) as a white solid. MS m/z 222.0 [M+1]⁺.

Step 2: To a solution of 3-bromo-1H-indazole-7-carbonitrile (1.00 g, 4.50 mmol) and 3,4-dihydro-2H-pyran (0.75 g, 9.00 mmol) in dichloromethane (10 mL) was added p-toluenesulfonic acid monohydrate (77 mg, 0.40 mmol). The mixture was stirred at room temperature for 3 h. The reaction mixture was concentrated under vacuum. The residue was purified by flash column chromatography with 0~25% ethyl acetate in petroleum ether to afford 3-bromo-1-(oxan-2-yl)indazole-7-carbonitrile (1.30 g, 94%) as a white solid. MS m/z 306.0 [M+1]⁺.

Step 3: To a solution of 3-bromo-1-(oxan-2-yl)indazole-7-carbonitrile (1.00 g, 3.26 mmol) in dioxane (10 mL) were added potassium acetate (0.96 g, 9.79 mmol), [1,1'-bis(diphenylphosphino)ferrocene]dichloro-palladium(II) (0.24 g, 0.33 mmol) and bis(pinacolato)diboron (1.66 g, 6.53 mmol). The mixture was stirred at 90° C. for 4 h under nitrogen atmosphere. The reaction mixture was concentrated under vacuum. The residue was purified by flash column chromatography with 0~5% MeOH in dichloromethane to afford 1-(oxan-2-yl)-3-(4,4,5,5-tetramethyl-1,3,2-dioxaborolan-2-yl)indazole-7-carbonitrile (B16) (0.80 g, 69%) as a light yellow solid. MS m/z 354.2 [M+1]⁺.

Intermediate B17 tert-butyl 5,6-difluoro-3-(4,4,5,5-tetramethyl-1,3,2-dioxaborolan-2-yl)indole-1-carboxylate

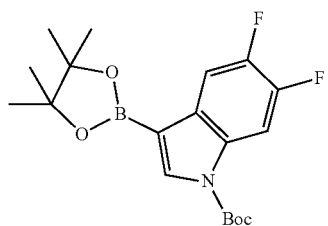 [SMILES: CC(C)(C)OC(=O)n1cc(B2OC(C)(C)C(C)(C)O2)c2cc(F)c(F)cc21]

Step 1: To a solution of 5,6-difluoro-1H-indole (2.00 g, 13.06 mmol) in N,N-dimethylformamide (20 mL) was added N-bromosuccinimide (2.32 g, 13.06 mmol). The mixture was stirred at 0° C. for 1 h. The mixture was diluted with water and extracted with ethyl acetate. The combined organic layers were washed with brine, dried over anhydrous sodium sulfate, filtered and concentrated under vacuum. The residue was purified by flash column chromatography with 0-50% ethyl acetate in petroleum ether to afford 3-bromo-5,6-difluoro-1H-indole (2.00 g, 66%) as a white solid.

Step 2: To a solution of 3-bromo-5,6-difluoro-1H-indole (2.00 g, 8.62 mmol) in dichloromethane (30 mL) were added 4-dimethylaminopyridine (0.53 g, 4.31 mmol) and triethylamine (0.87 g, 8.62 mmol). Then di(tert-butyl) carbonate (2.82 g, 12.92 mmol) was added to above mixture. The mixture was stirred at room temperature for 16 hours. The mixture was concentrated under vacuum. The residue was purified by flash column chromatography with 0~40% ethyl acetate in petroleum ether to afford tert-butyl 3-bromo-5,6-difluoroindole-1-carboxylate (800 mg, 26%) as a yellow oil. ¹H NMR (400 MHz, Chroloform-d) δ 8.06-8.02 (m, 1H), 7.06 (s, 1H), 7.32-7.28 (m, 1H), 1.67 (s, 9H).

Step 3: A degassed mixture of tert-butyl 3-bromo-5,6-difluoroindole-1-carboxylate (800 mg, 2.41 mmol), bis(pinacolato)diboron (1200 mg, 4.72 mmol), [1,1'-bis(diphenylphosphino)ferrocene]dichloropalladium(II) (170 mg, 0.23 mmol), and potassium acetate (512 mg, 5.21 mmol) in dioxane (10 mL) was heated at 85° C. for 16 h. The mixture was concentrated under vacuum. The residue was purified by flash column chromatography with 0-15% ethyl acetate in petroleum ether to afford tert-butyl 5,6-difluoro-3-(4,4,5,5-tetramethyl-1,3,2-dioxaborolan-2-yl)indole-1-carboxylate (B17) (280 mg, 18%) as a white solid. ¹H NMR (400 MHz, Chroloform-d) δ 8.06-8.00 (m, 2H), 7.78-7.73 (m, 1H), 1.59 (s, 9H), 1.14 (s, 12H).

Intermediate B18 tert-butyl 7-fluoro-3-(4,4,5,5-tetramethyl-1,3,2-dioxaborolan-2-yl)indole-1-carboxylate

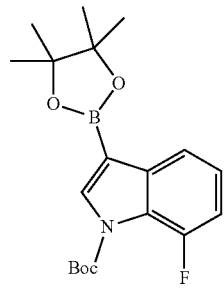 [SMILES: CC(C)(C)OC(=O)n1cc(B2OC(C)(C)C(C)(C)O2)c2cccc(F)c21]

Followed the procedure of Intermediate B14 described above to afford tert-butyl 7-fluoro-3-(4,4,5,5-tetramethyl-1,3,2-dioxaborolan-2-yl)indole-1-carboxylate (B18) (0.40 g, 16% over 3 steps) as a yellow solid from 7-fluoro-1H-indole. MS m/z 362.2 [M+1]$^+$. $^1$H NMR (400 MHz, DMSO-d6) δ 7.92 (s, 1H), 7.69-7.67 (m, 1H), 7.231-7.26 (m, 1H), 7.18-7.13 (m, 1H), 1.61 (s, 9H), 1.33 (s, 12H).

Intermediate B19 tert-butyl 6-cyano-3-(4,4,5,5-tetramethyl-1,3,2-dioxaborolan-2-yl)indole-1-carboxylate

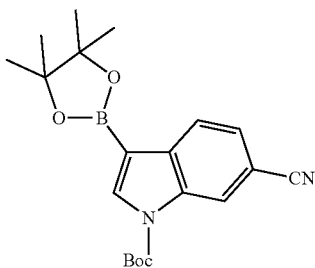 [SMILES: CC(C)(C)OC(=O)n1cc(B2OC(C)(C)C(C)(C)O2)c2ccc(C#N)cc21]

Followed the procedure of Intermediate B14 described above to afford tert-butyl 6-cyano-3-(4,4,5,5-tetramethyl-1,3,2-dioxaborolan-2-yl)indole-1-carboxylate (B19) (460 mg, 17% over 3 steps) as a white solid from 1H-indole-6-carbonitrile. MS m/z 369.2 [M+1]$^+$.

Intermediate B20 tert-butyl 7-cyano-6-fluoro-3-(4,4,5,5-tetramethyl-1,3,2-dioxaborolan-2-yl)-1H-indole-1-carbon/late

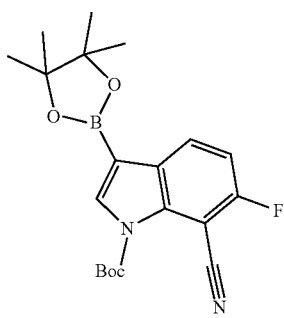 [SMILES: CC(C)(C)OC(=O)n1cc(B2OC(C)(C)C(C)(C)O2)c2ccc(F)c(C#N)c21]

Followed the procedure of Intermediate B14 described above to afford tert-butyl 7-cyano-6-fluoro-3-(4,4,5,5-tetramethyl-1,3,2-dioxaborolan-2-yl)-1H-indole-1-carbonylate (B20) (170 mg, 74%) as a white solid from 6-fluoro-1H-indole-7-carbonitrile. MS m/z 387.0 [M+1]$^+$.

Intermediate B21

2-(oxan-2-yl)-5-phenylpyrazol-3-ylboronic acid

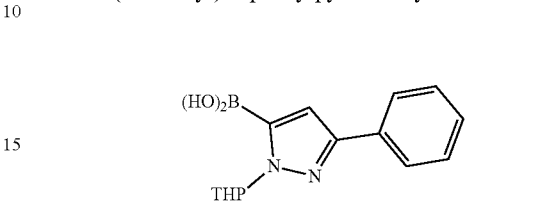

Step 1: A mixture of 3-phenyl-2H-pyrazole (5.00 g, 34.68 mmol), p-toluenesulfonic acid monohydrate (0.30 g, 1.73 mmol) and 3,4-dihydro-2H-pyran (5.83 g, 69.31 mmol) in toluene was stirred at room temperature for 6 h. The mixture was concentrated under reduced pressure. The residue was purified by flash column chromatography with 0~80% ethyl acetate in petroleum ether to afford 1-(oxan-2-yl)-3-phenylpyrazole (7.00 g, 88%) as a yellow oil. MS m/z 229.2 [M+1]$^+$. $^1$H NMR (400 MHz, DMSO-d$_6$) δ 7.93 (d, J=2.4 Hz, 1H), 7.86-7.76 (m, 2H), 7.43-7.39 (m, 2H), 7.34-7.24 (m, 1H), 6.77 (d, J=2.4 Hz, 1H), 5.44 (dd, J=10.2, 2.4 Hz, 1H), 3.95-3.92 (m, 1H), 3.75-3.57 (m, 1H), 2.24-2.06 (m, 1H), 1.96-1.95 (m, 2H), 1.78-1.62 (m, 1H), 1.60-1.49 (m, 2H).

Step 2: To a stirred mixture of 1-(oxan-2-yl)-3-phenylpyrazole (1.00 g, 4.38 mmol) in tetrahydrofuran (10 mL) was added butyl lithium (1.8 mL, 4.50 mmol, 2.5M in hexane) dropwise at −78° C. under nitrogen atmosphere. The mixture was stirred at −78° C. for 0.5 h, triisopropyl borate (0.99 g, 5.26 mmol) was added to the above mixture dropwise at −78° C. The reaction mixture was stirred at −78° C. for additional 2 h. The reaction was quenched with saturated ammonium chloride aqueous solution at −78° C. The mixture was acidified with HCl (aq.) to pH 5. The mixture was extracted with ethyl acetate. The combined organic layers were washed with water, dried over anhydrous sodium sulfate. After filtration, the filtrate was concentrated under reduced pressure. The residue was purified by reverse flash chromatography with 10% to 60% acetonitrile in water in 30 min to afford 2-(oxan-2-yl)-5-phenylpyrazol-3-ylboronic acid (B21) (640 mg, 53%) as a yellow oil. MS m/z 273.2 [M+1]$^+$.

Intermediate B22

1-(tert-butoxycarbonyl)-4,5-dimethylpyrazol-3-ylboronic acid

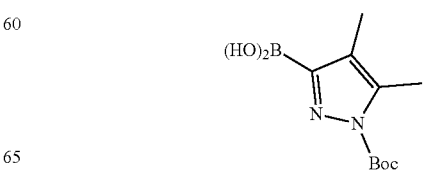

Step 1: To a solution of 3,4-dimethyl-2H-pyrazole (2.00 g, 20.81 mmol) in dichloromethane (15 mL) were added di(tert-butyl) carbonate (5.45 g, 24.97 mmol) and 4-dimethylaminopyridine (7.62 g, 62.37 mmol). The resulting solution was stirred at room temperature for 2 h. The mixture was concentrated under vacuum. The residue was purified by flash column chromatography with 0~25% ethyl acetate in petroleum ether to afford tert-butyl 4,5-dimethylpyrazole-1-carboxylate (4.00 g, 97%) as colorless oil. MS m/z 197.1 [M+1]$^+$.

Step 2: To a solution of tert-butyl 4,5-dimethylpyrazole-1-carboxylate (2.0 g, 10.19 mmol) in tetrahydrofuran (10 mL) was added butyl lithium (8.0 mL, 20.00 mmol, 2.5M in hexane) dropwise at −78° C. under nitrogen atmosphere. After stirring at −78° C. for 30 min, triisopropyl borate (2.30 g, 12.23 mmol) was added slowly to above mixture. The mixture was stirred at −78° C. for 4 h. The reaction was then quenched using saturated ammonium chloride aqueous solution. The mixture was extracted with ethyl acetate. The organic layer was dried over anhydrous sodium sulfate, filtered and concentrated under vacuum. The residue was purified by reverse phase flash column chromatography with 5-25% acetonitrile in water to afford 1-(tert-butoxycarbonyl)-4,5-dimethylpyrazol-3-ylboronic acid (B22) (200 mg, 8%) as yellow oil. MS m/z 241.1 [M+1]$^+$.

Intermediate B23

1-(oxan-2-yl)-4H,6H,7H-pyrano[4,3-c]pyrazol-3-ylboronic acid

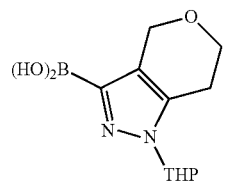

Step 1: To a solution of 1H,4H,6H,7H-pyrano[4,3-c]pyrazole (400 mg, 3.22 mmol) in dichloromethane (6 mL) were added p-toluenesulfonic acid monohydrate (55 mg, 0.29 mmol) and 3,4-dihydro-2H-pyran (542 mg, 6.44 mmol). The resulting solution was stirred at room temperature for 2 h. The mixture was concentrated under vacuum. The residue was purified by flash column chromatography with 0~50% ethyl acetate in petroleum ether to afford 1-(oxan-2-yl)-4H,6H,7H-pyrano[4,3-c]pyrazole (370 mg, 55%) as yellow oil. MS m/z 209.1 [M+1]$^+$.

Step 2: To a solution of 1-(oxan-2-yl)-4H,6H,7H-pyrano[4,3-c]pyrazole (370 mg, 1.78 mmol) in methyl tert-butyl ether (5 mL) were added bis(pinacolato)diboron (902 mg, 3.55 mmol), (1,5-cyclooctadiene)-(methoxy)iridium(I) dimer (59 mg, 0.09 mmol) and 4,4-di-tert-butyl bipyridine (47 mg, 0.18 mmol) under nitrogen atmosphere. The resulting solution was stirred at 55° C. for 2 h. The mixture was concentrated under vacuum. The residue was purified by reverse phase flash column chromatography with 5-20% acetonitrile in water to afford 1-(oxan-2-yl)-4H,6H,7H-pyrano[4,3-c]pyrazol-3-ylboronic acid (B23) (430 mg, 96%) as brown oil. MS m/z 253.1 [M+1]$^+$.

Intermediate B24

2-[1-[(4-methoxyphenyl)methyl]-5-(4,4,5,5-tetramethyl-1,3,2-dioxaborolan-2-yl)pyrazol-3-yl]pyridine

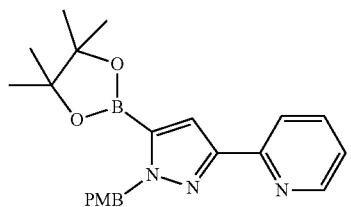

Step 1: A mixture of ethyl 3-oxo-3-(pyridin-2-yl)propanoate (5.00 g, 25.9 mmol) and [(4-methoxyphenyl)methyl]hydrazine hydrochloride (4.9 g, 25.9 mmol) in ethanol was stirred at 80° C. for 16 h. The mixture was concentrated under reduced pressure. The residue was purified by reverse phase flash column chromatography with 10-80% acetonitrile in water in 30 min to afford 2-[(4-methoxyphenyl)methyl]-5-(pyridin-2-yl)-4H-pyrazol-3-one (2.00 g, 27%) as a brown solid. MS m/z 282.2. [M+1]$^+$.

Step 2: To a stirred mixture of 2-[(4-methoxyphenyl)methyl]-5-(pyridin-2-yl)-4H-pyrazol-3-one (1.40 g, 4.98 mmol) in tetrahydrofuran (20 mL) was added lithium bis(trimethylsilyl)-amide (5.5 mL, 5.50 mmol, 1M in tetrahydrofuran) dropwise at −78° C. under nitrogen atmosphere. After stirring at −78° C. for 0.5 h, perfluorobutanesulfonyl fluoride (1.70 g, 5.47 mmol) was added dropwise to above mixture at −78° C. The mixture was stirred at room temperature for 16 h. The reaction was quenched using water and extracted with ethyl acetate. The organic layer was dried over anhydrous sodium sulfate, filtered and concentrated under vacuum. The residue was purified by reverse phase flash column chromatography with 10-70% acetonitrile in water in 30 min to afford 2-[(4-methoxyphenyl)methyl]-5-(pyridin-2-yl)pyrazol-3-yl 1,1,2,2,3,3,4,4,4-nonafluorobutane-1-sulfonate (2.40 g, 85%) as a yellow solid. MS m/z 564.1 [M+1]$^+$. $^1$H NMR (400 MHz, DMSO-d$_6$) δ 8.62-8.60 (m, 1H), 7.97-7.96 (m, 1H), 7.89-7.88 (m, J=7.8, 1.8 Hz, 1H), 7.41-7.39 (m, 1H), 7.28-7.19 (m, 2H), 6.98-6.91 (m, 2H), 6.88-6.87 (m, 1H), 5.37 (s, 2H), 3.74 (s, 3H).

Step 3: A degassed mixture of 2-[(4-methoxyphenyl)methyl]-5-(pyridin-2-yl)pyrazol-3-yl 1,1,2,2,3,3,4,4,4-nonafluorobutane-1-sulfonate (2.40 g, 4.26 mmol), [1,1'-bis(diphenylphosphino)ferrocene]dichloro-palladium(II) (0.31 mg, 0.43 mmol), bis(pinacolato)diboron (2.16 g, 8.52 mmol) and potassium acetate (0.84 g, 8.52 mmol) in dioxane was stirred at 80° C. for 16 h. The resulting mixture was concentrated under reduced pressure. The reaction mixture was diluted using water and extracted with ethyl acetate. The organic layer was dried over anhydrous sodium sulfate, filtered and concentrated under vacuum. The residue was purified by reverse phase flash column chromatography with 10-70% acetonitrile in water in 30 min to afford 2-[1-[(4-methoxyphenyl)methyl]-5-(4,4,5,5-tetramethyl-1,3,2-dioxaborolan-2-yl)pyrazol-3-yl]pyridine (B24) (150 mg, 9%) as a yellow solid. MS m/z 392.3 [M+1]$^+$.

Intermediate B25 tert-butyl 7-methyl-3-(4,4,5,5-tetramethyl-1,3,2-dioxaborolan-2-yl)indole-1-carboxylate

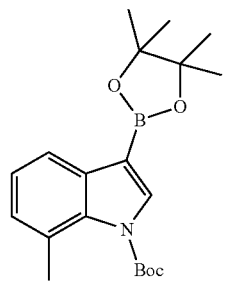 [SMILES: Cc1cccc2c(B3OC(C)(C)C(C)(C)O3)cn(C(=O)OC(C)(C)C)c12]

Step 1: A mixture of 7-methylindole (5.00 g, 38.11 mmol), di(tert-butyl) carbonate (9.15 g, 0.04 mmol), triethylamine (7.70 g, 0.07 mmol) and 4-dimethylaminopyridine (0.47 g, 0.004 mmol) in dichloromethane was stirred at room temperature for 8 h. The mixture was concentrated under reduced pressure. The residue was purified by flash column chromatography with 0~10% ethyl acetate in petroleum ether to afford tert-butyl 7-methylindole-1-carboxylate (7.80 g, 88%) as a colorless oil. $^1$H NMR (400 MHz, Chloroform-d) δ 7.68 (d, J=7.2 Hz, 1H), 7.55 (d, J=8.0 Hz, 1H), 7.31-7.25 (m, 2H), 6.68 (d, J=7.2 Hz, 1H), 2.84 (s, 3H), 1.78 (s, 9H).

Step 2: A mixture of tert-butyl 7-methylindole-1-carboxylate (2.00 g, 8.64 mmol) and N-bromosuccinimide (1.68 g, 9.55 mmol) in dichloromethane (20 mL) was heated to reflux and stirred for 2 h. The mixture was concentrated under vacuum. The residue was purified by flash column chromatography with 0~10% ethyl acetate in petroleum ether to afford tert-butyl 3-bromo-7-methylindole-1-carboxylate (2.8 g, 100%) as a colorless oil. MS m/z 310.1 $[M+1]^+$.

Step 3: A degassed mixture of tert-butyl 3-bromo-7-methylindole-1-carboxylate (0.50 g, 1.61 mmol), bis(pinacolato)diboron (0.56 g, 2.20 mmol), [1,1'-bis(diphenylphosphino)-ferrocene]dichloropalladium(II) (0.10 g, 0.13 mmol) and potassium acetate (0.32 g, 3.29 mmol) in dioxane (10 mL) was heated at 80° C. for 4 h. The mixture was concentrated under vacuum. The residue was purified by flash column chromatography with 0~10% ethyl acetate in petroleum ether to afford tert-butyl 7-methyl-3-(4,4,5,5-tetramethyl-1,3,2-dioxaborolan-2-yl)indole-1-carboxylate (B25) (0.20 g, 35%) as a white solid. $^1$H NMR (400 MHz, Chloroform-d) δ 7.95 (s, 1H), 7.87 (d, J=8.0 Hz, 1H), 7.22-7.18 (m, 1H), 7.11 (d, J=8.0 Hz, 1H), 2.63 (s, 3H), 1.68 (s, 9H), 1.42 (s, 12H).

Intermediate B26

5,6-difluoro-1-methylindazol-3-ylboronic acid

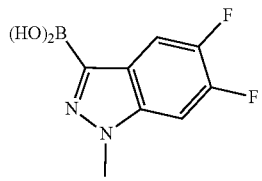

Step 1: To a solution of 5,6-difluoro-1H-indazole (500 mg, 3.24 mmol) in acetone (10 mL) was added potassium hydroxide (183 mg, 3.26 mmol) at 0° C. After stirring at 0° C. for 30 min, iodomethane (470 mg, 3.31 mmol) was added to above mixture. The mixture was stirred at room temperature for 16 h. The solids were filtered off. The filtrate was concentrated under vacuum. The residue was purified by flash column chromatography with 0~40% ethyl acetate in petroleum ether to afford 5,6-difluoro-1-methylindazole (340 mg, 62%) as an off-white solid. MS m/z 168.9 $[M+1]^+$. $^1$H NMR (400 MHz, DMSO-$d_6$) δ 8.06 (s, 1H), 7.86-7.77 (m, 2H), 4.03 (s, 3H).

Step 2: A degassed mixture of 5,6-difluoro-1-methylindazole (340 mg, 2.02 mmol), bis(pinacolato)diboron (306 mg, 1.20 mmol), (1,5-cyclooctadiene)(methoxy)iridium(I) dimer (61 mg, 0.092 mmol), 4,4-di-tert-butyl bipyridine (57 mg, 0.21 mmol) in methyl tert-butyl ether (5 mL) was heated to 55° C. for 2 h. The mixture was diluted with ethyl acetate and washed using HCl (aq. 1N), then dried over anhydrous sodium sulfate, filtered and concentrated under vacuum to afford 5,6-difluoro-1-methylindazol-3-ylboronic acid (B26) (460 mg, crude) as a brown oil. MS m/z 213.0 $[M+1]^+$.

Intermediate B27 tert-butyl 3-(4,4,5,5-tetramethyl-1,3,2-dioxaborolan-2-yl)pyrrolo[2,3-b]pyridine-1-carboxylate

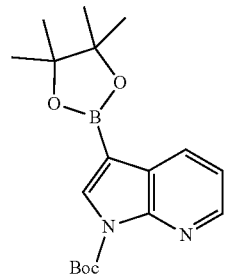 [SMILES: CC(C)(C)OC(=O)n1cc(B2OC(C)(C)C(C)(C)O2)c2cccnc21]

Step 1: A mixture of 3-bromo-1H-pyrrolo[2,3-b]pyridine (1.00 g, 5.07 mmol), di(tert-butyl) carbonate (3.66 g, 16.77 mmol), 4-dimethylaminopyridine (62 mg, 0.50 mmol) and triethylamine (1.54 g, 15.22 mmol) in dichloromethane (30 mL) was stirred at room temperature for 6 h. The resulting mixture was concentrated under reduced pressure. The residue was purified by flash column chromatography with 0~60% ethyl acetate in petroleum ether to afford tert-butyl 3-bromopyrrolo[2,3-b]pyridine-1-carboxylate (1.50 g, 99%) as a yellow oil. MS m/z 297.1 $[M+1]^+$.

Step 2: A degassed mixture of tert-butyl 3-bromopyrrolo[2,3-b]pyridine-1-carboxylate (1.20 g, 4.03 mmol), [1,1'-bis(diphenylphosphino)ferrocene]dichloropalladium(II) (295 mg, 0.40 mmol), bis(pinacolato)diboron (2.05 g, 8.07 mmol) and potassium acetate (793 mg, 8.07 mmol) in dioxane (20 mL) was stirred at 80° C. for 16 h. The resulting mixture was concentrated under reduced pressure. The residue was purified by flash column chromatography with 0~80% ethyl acetate in petroleum ether to afford tert-butyl 3-(4,4,5,5-tetramethyl-1,3,2-dioxaborolan-2-yl)pyrrolo[2,3-b]pyridine-1-carboxylate (B27) (1.30 g, 93%) as a yellow oil. MS m/z 345.3 $[M+1]^+$.

Intermediate B28 tert-butyl 3-(4,4,5,5-tetramethyl-1,3,2-dioxaborolan-2-yl)-1H-pyrrolo[3,2-b]pyridine-1-carboxylate

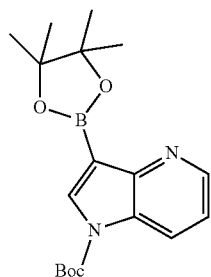 [SMILES: CC(C)(C)OC(=O)n1cc(B2OC(C)(C)C(C)(C)O2)c2ncccc21]

Followed the procedure of Intermediate B21 described above to afford tert-butyl 3-(4,4,5,5-tetramethyl-1,3,2-dioxaborolan-2-yl)-1H-pyrrolo[3,2-b]pyridine-1-carboxylate (B28) (470 mg, 16% over 2 steps) as a yellow solid from 3-bromo-1H-pyrrolo[3,2-b]pyridine (2.00 g, 10.20 mmol). MS m/z 345.2 [M+1]$^+$.

Intermediate B29 tert-butyl 7-cyano-5-fluoro-3-(4,4,5,5-tetramethyl-1,3,2-dioxaborolan-2-yl)indole-1-carboxylate

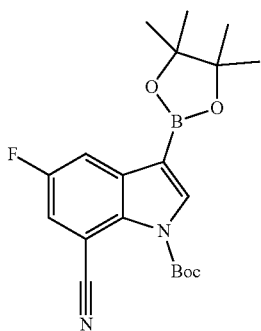 [SMILES: CC(C)(C)OC(=O)n1cc(B2OC(C)(C)C(C)(C)O2)c2cc(F)cc(C#N)c21]

Step 1: A mixture of 7-bromo-5-fluoro-1H-indole (1.00 g, 4.67 mmol), zinc cyanide (1.65 g, 14.04 mmol) and palladium(0)tetrakis(triphenylphosphine) (1.08 g, 0.93 mmol) in N,N-Dimethylformamide (15 mL) was stirred for 16 h at 120° C. under nitrogen atmosphere. The solids were filtered off. The filtrate was diluted with water and extracted with dichloromethane. The combined organic layers were washed with brine, dried over anhydrous sodium sulfate, filtered and concentrated under vacuum. The residue was purified by flash column chromatography with 0~70% ethyl acetate in petroleum ether to afford 5-fluoro-1H-indole-7-carbonitrile (680 mg, 90%) as a white solid. MS m/z 161.0 [M+1]$^+$. $^1$H NMR (400 MHz, DMSO-d$_6$) δ 12.13 (bs, 1H), 7.78 (dd, J=9.6, 2.4 Hz, 1H), 7.64-7.56 (m, 2H), 6.63 (dd, J=3.2, 1.6 Hz, 1H).

Step 2: A mixture of 5-fluoro-1H-indole-7-carbonitrile (0.66 g, 4.12 mmol), di(tert-butyl) carbonate (3.00 g, 13.60 mmol), triethylamine (1.25 g, 12.36 mmol) and 4-dimethylaminopyridine (0.05 g, 0.41 mmol) in dichloromethane (10 mL) was stirred for 16 h at room temperature. The resulting mixture was concentrated under reduced pressure. The residue was purified by flash column chromatography with 0~80% ethyl acetate in petroleum ether to afford tert-butyl 7-cyano-5-fluoroindole-1-carboxylate (1.00 g, 93%) as a light yellow solid. MS m/z 261.1 [M+1]$^+$. $^1$H NMR (400 MHz, DMSO-d$_6$) δ 7.91-7.83 (m, 2H), 7.78 (dd, J=9.2, 2.8 Hz, 1H), 6.83 (d, J=3.6 Hz, 1H), 1.64 (s, 9H).

Step 3: A mixture of tert-butyl 7-cyano-5-fluoroindole-1-carboxylate (300 mg, 1.15 mmol) and N-bromosuccinimide (205 mg, 1.15 mmol) in dichloromethane (5 mL) was stirred for 16 h at 50° C. The resulting mixture was concentrated under reduced pressure. The residue was purified by flash column chromatography with 0~60% ethyl acetate in petroleum ether to afford tert-butyl 3-bromo-7-cyano-5-fluoroindole-1-carboxylate (220 mg, 56%) as a light yellow solid. MS m/z 339.0 [M+1]$^+$.

Step 4: A mixture of tert-butyl 3-bromo-7-cyano-5-fluoroindole-1-carboxylate (200 mg, 0.59 mmol), [1,1'-bis(diphenylphosphino)ferrocene]dichloropalladium(II) (43 mg, 0.06 mmol), bis(pinacolato)diboron (299 mg, 1.18 mmol) and potassium acetate (115 mg, 1.18 mmol) in dioxane was stirred at 80° C. for 16 h under nitrogen atmosphere. The mixture was concentrated under reduced pressure. The residue was purified by by flash column chromatography with 0~10% ethyl acetate in petroleum ether to afford tert-butyl 7-cyano-5-fluoro-3-(4,4,5,5-tetramethyl-1,3,2-dioxaborolan-2-yl)indole-1-carboxylate (220 mg, 96%) as a white solid. MS m/z 387.2 [M+1]$^+$.

Intermediate B30

1-(oxan-2-yl)pyrazolo[3,4-b]pyridin-3-ylboronic acid

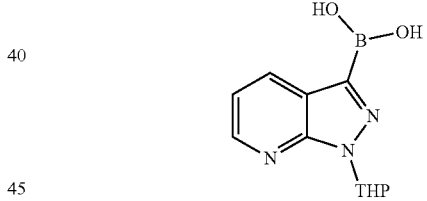

Step 1: To a solution of 3-bromo-1H-pyrazolo[3,4-b]pyridine (1.00 g, 5.08 mmol) and dihydropyran (425 mg, 5.06 mmol) in dichloromethane (10 mL) was added pyridinium p-toluenesulfonate (0.08 g, 0.51 mmol). The mixture was stirred at room temperature overnight. The mixture was concentrated under vacuum. The residue was purified by flash column chromatography with 0-80% ethyl acetate in petroleum ether to afford 3-bromo-1-(oxan-2-yl)pyrazolo[3,4-b]pyridine (1.10 g, 77%) as an off-white solid. MS m/z 281.9 [M+1]$^+$.

Step 2: To a solution of 3-bromo-1-(oxan-2-yl)pyrazolo[3,4-b]pyridine (0.56 g, 1.99 mmol), bis(pinacolato)diboron (1.00 g, 3.94 mmol) and potassium acetate (389 mg, 3.97 mmol) in dioxane (5 mL) was added [1,1'-bis(diphenylphosphino)ferrocene]dichloropalladium(II) (145 mg, 0.19 mmol). The resulting solution was heated to 80° C. stirred overnight under nitrogen atmosphere. The mixture was diluted with water and extracted with ethyl acetate. The combined organic layers were washed with brine, dried over anhydrous sodium sulfate, filtered and concentrated under vacuum to afford 1-(oxan-2-yl)pyrazolo[3,4-b]pyridin-3-yl-boronic acid (B30) (450 mg, crude) as a brown solid. MS m/z 248.1 [M+1]$^+$.

Intermediate B31

2-methyl-6-(tributylstannyl)pyridin-3-amine

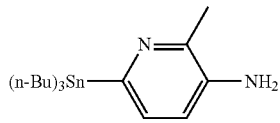

A degassed mixture of 6-bromo-2-methylpyridin-3-amine (1.00 g, 5.34 mmol), hexabutyldistannane (4.60 g, 7.92 mmol) and palladium(0)tetrakis(triphenylphosphine) (0.31 g, 0.27 mmol) in toluene (10 mL) was heated at 110° C. for 16 h. The solids were filtered off. The filtrate was concentrated under vacuum. The residue was purified by reverse phase flash column chromatography with 10~70% acetonitrile in water to afford 2-methyl-6-(tributylstannyl)pyridin-3-amine (B31) (765 mg, 36%) as a yellow syrup. MS m/z 399.1 [M+1]$^+$.

Intermediate B32

7-(1,3,4-oxadiazol-2-yl)-1-[[2-(trimethylsilyl)ethoxy]methyl]indol-3-ylboronic acid

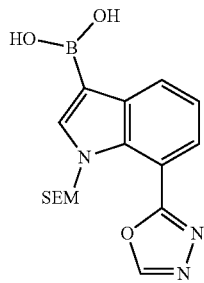 [SMILES: C[Si](C)(C)CCOCn1cc(B(O)O)c2cccc(-c3nnco3)c21]

Step 1: To a degassed solution of methyl 1H-indole-7-carboxylate (5.00 g, 28.54 mmol) in tetrahydrofuran (30 mL) was added N-bromosuccinimide (5.08 g, 28.54 mmol) slowly at 0° C. under nitrogen atmosphere. The resulting solution was stirred at room temperature overnight. The mixture was diluted with water and extracted with ethyl acetate. The combined organic layers were washed with brine, dried over anhydrous sodium sulfate, filtered and concentrated under vacuum. The residue was purified by flash column chromatography with 0~80% ethyl acetate in petroleum ether to afford methyl 3-bromo-1H-indole-7-carboxylate (6.40 g, 88%) as a white solid. MS m/z 254.1 [M+1]$^+$.

Step 2: To a solution of methyl 3-bromo-1H-indole-7-carboxylate (6.36 g, 25.03 mmol) in N,N-dimethylformamide (30 mL) was added sodium hydride (1.20 g, 30.04 mmol, 60% in mineral oil) in portions at 0° C. After stirring at 30 min, 2-chloroethoxy methyl trimethylsilane (5.01 g, 30.04 mmol) was added dropwise to above mixture at 0° C. The mixture was stirred at 0° C. for 1 h. The reaction mixture was quenched using water and extracted with ethyl acetate. The combined organic layers were washed with brine, dried over anhydrous sodium sulfate, filtered and concentrated under vacuum. The residue was purified by flash column chromatography with 0~40% ethyl acetate in petroleum ether to afford methyl 3-bromo-1-[[2-(trimethylsilyl)ethoxy]methyl]indole-7-carboxylate (8.50 g, 88%) as light yellow oil. MS m/z 384.1 [M+1]$^+$. $^1$H NMR (400 MHz, DMSO-d$_6$) δ 7.87 (s, 1H), 7.74-7.66 (m, 1H), 7.63 (dd, J=7.6, 1.4 Hz, 1H), 7.34-7.25 (m, 1H), 5.65 (s, 2H), 3.89 (s, 3H), 3.14 (t, J=8.0 Hz, 2H), 0.67 (t, J=8.0 Hz, 2H), −0.15 (s, 9H).

Step 3: A mixture of methyl 3-bromo-1-[[2-(trimethylsilyl)ethoxy]methyl]indole-7-carboxylate (2.00 g, 5.22 mmol) and hydrazine hydrate (2.60 g, 34.67 mmol, 80% in water) in ethanol (10 mL) was stirred at 70° C. overnight. The mixture was concentrated under vacuum. The residue was diluted with water and extracted with ethyl acetate. The combined organic layers were washed with brine, dried over anhydrous sodium sulfate, filtered and concentrated under vacuum to afford 3-bromo-1-[[2-(trimethylsilyl)ethoxy]methyl]indole-7-carbohydrazide (1.50 g, crude) as a yellow solid. MS m/z 384.1 [M+1]$^+$.

Step 4: A mixture of 3-bromo-1-[[2-(trimethylsilyl)ethoxy]methyl]indole-7-carbohydrazide (1.50 g, 3.91 mmol) and trimethyl orthoformate (20 mL) was stirred at 140° C. overnight. The reaction mixture was concentrated under vacuum. The residue was purified by flash column chromatography with 0~80% ethyl acetate in petroleum ether to afford 3-bromo-7-(1,3,4-oxadiazol-2-yl)-1-[[2-(trimethylsilyl)ethoxy]methyl]indole (0.80 g, 38% over 2 steps) as an off-white solid. MS m/z 394.1 [M+1]$^+$.

Step 5: To a degassed solution of 3-bromo-7-(1,3,4-oxadiazol-2-yl)-1-[[2-(trimethylsilyl)ethoxy]-methyl]indole (0.76 g, 1.92 mmol), bis(pinacolato)diboron (1.10 g, 4.49 mmol) and potassium acetate (0.38 g, 3.87 mmol) in dioxane (10 mL) was added [1,1'-bis(diphenylphosphino)ferrocene]dichloropalladium(II) (0.15 g, 0.21 mmol) under nitrogen atmosphere. The mixture was stirred at 80° C. overnight. The reaction mixture was diluted by water and extracted with ethyl acetate. The organic layer was dried over anhydrous sodium sulfate, filtered and concentrated under vacuum. The residue was purified by reverse phase flash column chromatography with 40-80% acetonitrile in water to afford 7-(1,3,4-oxadiazol-2-yl)-1-[[2-(trimethylsilyl)ethoxy]methyl]indol-3-ylboronic acid (B32) (100 mg, 14%) as colorless oil. MS m/z 360.1 [M+1]$^+$.

Intermediate B33

7-(methylcarbamoyl)-1-[[2-(trimethylsilyl)ethoxy]methyl]indol-3-ylboronic acid

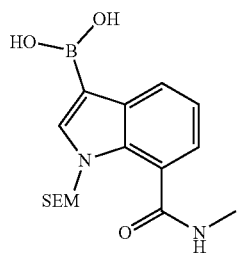 [SMILES: CNC(=O)c1cccc2c(B(O)O)cn(COCC[Si](C)(C)C)c12]

Step 1: To a solution of methyl 3-bromo-1-[[2-(trimethylsilyl)ethoxy]methyl]indole-7-carboxylate (1.00 g, 2.61 mmol) in ethanol (5 mL) and water (5 mL) was added sodium hydroxide (0.21 g, 5.20 mmol). The mixture was stirred at 70° C. for 1 h. The organic solvent was removed under vacuum. The aqueous phase was acidified with HCl (aq.) to pH 6. The aqueous solution was extracted with ethyl acetate. The combined organic layers were washed with brine, dried over anhydrous sodium sulfate, filtered and concentrated under vacuum to afford 3-bromo-1-[[2-(trimethylsilyl)ethoxy]methyl]indole-7-carboxylic acid (0.8 g, 83%) as a yellow solid. MS m/z 370.0 [M+1]$^+$.

Step 2: To a solution of 3-bromo-1-[[2-(trimethylsilyl)ethoxy]methyl]indole-7-carboxylic acid (0.76 g, 2.06 mmol), N-(3-dimethylaminopropyl)-N'-ethylcarbodiimide hydrochloride (0.59 g, 3.11 mmol) and 1-hydroxybenzotriazole (0.43 g, 3.21 mmol) in N,N-dimethylformamide (5 mL) were added triethylamine (1.10 g, 10.89 mmol) and methylamine hydrochloride (0.41 g, 6.18 mmol). The mixture was stirred at room temperature for 16 h. The reaction mixture was diluted with water and extracted with ethyl acetate. The combined organic layers were washed with brine, dried over anhydrous sodium sulfate, filtered and concentrated under vacuum. The residue was purified by flash column chromatography with 0~50% ethyl acetate in petroleum ether to afford 3-bromo-N-methyl-1-[[2-(trimethylsilyl)ethoxy]methyl]indole-7-carboxamide (0.60 g, 76%) as a colorless oil. MS m/z 383.0 [M+1]$^+$.

Step 3: To a degassed mixture of 3-bromo-N-methyl-1-[[2-(trimethylsilyl)ethoxy]methyl]indole-7-carboxamide (0.60 g, 1.56 mmol), bis(pinacolato)diboron (0.79 g, 3.12 mmol) and potassium acetate (0.31 g, 3.12 mmol) in dioxane (10 mL) was added [1,1'-bis(diphenylphosphino)ferrocene]dichloropalladium(II) (0.11 g, 0.15 mmol). The mixture was heated 80° C. stirred for 16. The reaction mixture was concentrated under vacuum. The residue was diluted with ethyl acetate and washed with water. The organic layer was dried over anhydrous sodium sulfate, filtered and concentrated under vacuum. The residue was purified by reverse phase flash column chromatography with 30-80% acetonitrile in water to afford 7-(methylcarbamoyl)-1-[[2-(trimethylsilyl)ethoxy]methyl]indol-3-ylboronic acid (B33) (120 mg, 21%) as a colorless oil. MS m/z 349.2 [M+1]$^+$.

Intermediate B34 tert-butyl 7-cyano-6-methyl-3-(4,4,5,5-tetramethyl-1,3,2-dioxaborolan-2-yl)indole-1-carboxylate

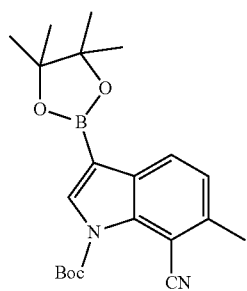

Step 1: To a solution of 2-bromo-1-methyl-3-nitrobenzene (5.00 g, 23.26 mmol) in tetrahydrofuran (100 mL) was added bromo(ethenyl)magnesium (70 mL) dropwise at −60° C. under nitrogen atmosphere. The mixture was stirred at −40° C. for 2 h under nitrogen atmosphere. The reaction mixture was quenched by saturated ammonium chloride aqueous solution and extracted with ethyl acetate. The combined organic layers were washed with brine, dried over anhydrous sodium sulfate, filtered and concentrated under vacuum. The residue was purified by flash column chromatography with 0~20% ethyl acetate in petroleum ether to afford 7-bromo-6-methyl-1H-indole (2.70 g, 55%) as a light yellow solid. MS m/z 208.0 [M−1]$^-$. $^1$H NMR (400 MHz, DMSO-d$_6$) δ 11.10 (s, 1H), 7.44 (d, J=8.0 Hz, 1H), 7.30 (d, J=3.2 Hz, 1H), 6.97 (d, J=8.0 Hz, 1H), 6.51-6.50 (m, 1H), 2.45 (s, 3H).

Step 2: To a solution of 7-bromo-6-methyl-1H-indole (1.00 g, 4.76 mmol) and zinc cyanide (1.70 g, 14.28 mmol) in N,N-dimethylformamide (5 mL) was added palladium(0) tetrakis(triphenylphosphine) (0.55 g, 0.48 mmol). The resulting solution was stirred at 140° C. for 16 h under nitrogen atmosphere. The mixture was diluted by water and extracted with ethyl acetate. The combined organic layers were washed with brine, dried over anhydrous sodium sulfate, filtered and concentrated under vacuum. The residue was purified by flash column chromatography with 0-50% ethyl acetate in petroleum ether to afford 6-methyl-1H-indole-7-carbonitrile (0.60 g, 81%) as an off-white solid. MS m/z 155.1 [M−1]$^-$.

Step 3: To a solution of 6-methyl-1H-indole-7-carbonitrile (0.60 g, 3.84 mmol) in tetrahydrofuran (10 mL) was added N-bromosuccinimide (0.68 g, 3.84 mmol). The resulting solution was stirred at room temperature for 2 h. The mixture was diluted with water and extracted with ethyl acetate. The combined organic layers were washed with brine, dried over anhydrous sodium sulfate, filtered and concentrated under vacuum to afford 3-bromo-6-methyl-1H-indole-7-carbonitrile (0.90 g, crude) as an off-white solid. MS m/z 233.0 [M−1]$^-$.

Step 4: To a solution of 3-bromo-6-methyl-1H-indole-7-carbonitrile (0.85 g, 3.62 mmol), di(tert-butyl) carbonate (1.60 g, 7.23 mmol) and triethylamine (1.10 g, 10.85 mmol) in dichloromethane (10 mL) was added 4-dimethylaminopyridine (0.04 g, 0.36 mmol). The resulting solution was stirred at room temperature for 16 h. The mixture was concentrated under vacuum. The residue was purified by flash column chromatography with 0-50% ethyl acetate in petroleum ether to afford tert-butyl 3-bromo-7-cyano-6-methylindole-1-carboxylate (0.85 g, 70%) as a white solid. MS m/z 335.0 [M+1]$^+$. $^1$H NMR (400 MHz, DMSO-d$_6$) δ 8.00 (s, 1H), 7.74 (d, J=8.0 Hz, 1H), 7.49 (d, J=8.0 Hz, 1H), 2.65 (s, 3H), 1.64 (s, 9H).

Step 5: To a solution of tert-butyl 3-bromo-7-cyano-6-methylindole-1-carboxylate (1.10 g, 3.28 mmol), bis(pinacolato)diboron (1.70 g, 6.56 mmol) and potassium acetate (0.65 g, 6.59 mmol) in dioxane (10 mL) was added [1,1'-bis(diphenylphosphino)ferrocene]dichloropalladium(II) (0.25 g, 0.36 mmol). The resulting solution was stirred at 80° C. for 16 h under nitrogen atmosphere. The mixture was concentrated under vacuum. The residue was purified by flash column chromatography with 0-80% ethyl acetate in petroleum ether to afford tert-butyl 7-cyano-6-methyl-3-(4,4,5,5-tetramethyl-1,3,2-dioxaborolan-2-yl)indole-1-carboxylate (B34) (0.80 g, 63%) as a white solid. MS m/z 383.2 [M+1]$^+$.

Intermediate B35 tert-butyl 6-chloro-7-cyano-3-(4,4,5,5-tetramethyl-1,3,2-dioxaborolan-2-yl)indole-1-carboxylate

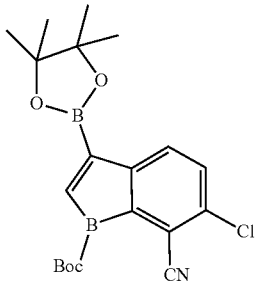 [SMILES: CC(C)(C)OC(=O)B1C=C(B2OC(C)(C)C(C)(C)O2)c2ccc(Cl)c(C#N)c21]

Followed the procedure of Intermediate B31 described above to afford 6-chloro-7-cyano-3-(4,4,5,5-tetramethyl-1,3,2-dioxaborolan-2-yl)indole-1-carboxylate (B35) (1.10 g, 24% over 5 steps) as a yellow solid from 2-bromo-1-chloro-3-nitrobenzene. MS m/z 403.2 [M+1]$^+$.

Intermediate B36 tert-butyl 7-cyano-5-methyl-3-(4,4,5,5-tetramethyl-1,3,2-dioxaborolan-2-yl)indole-1-carboxylate

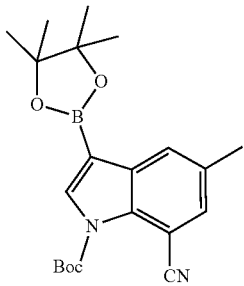

Followed the procedure of Intermediate B31 described above to afford tert-butyl 7-cyano-5-methyl-3-(4,4,5,5-tetramethyl-1,3,2-dioxaborolan-2-yl)indole-1-carboxylate (B36) (1.00 g, 18% over 5 steps) as a white solid from 2-bromo-4-methyl-1-nitrobenzene. MS m/z 383.2 [M+1]$^+$.

Intermediate B37 tert-butyl 5-chloro-7-cyano-3-(4,4,5,5-tetramethyl-1,3,2-dioxaborolan-2-yl)indole-1-carboxylate

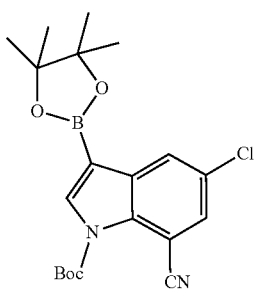 [SMILES: CC(C)(C)OC(=O)n1cc(B2OC(C)(C)C(C)(C)O2)c2cc(Cl)cc(C#N)c21]

Step 1: A mixture of 7-bromo-5-chloro-1H-indole (0.80 g, 3.60 mmol), zinc cyanide (1.20 g, 10.21 mmol), palladium (0)tetrakis(triphenylphosphine) (0.25 g, 0.21 mmol) in N,N-dimethylformamide (10 mL) was heated at 140° C. for 16 h. The reaction was diluted with water and extracted with ethyl acetate. The combined organic layers were washed with brine, dried over anhydrous sodium sulfate, filtered and concentrated under vacuum. The residue was purified by flash column chromatography with 0~20% ethyl acetate in petroleum ether to afford 5-chloro-1H-indole-7-carbonitrile (0.50 g, 81%) as a white solid. MS m/z 175.0 [M−1]$^+$. $^1$H NMR (400 MHz, Chloroform-d) δ 9.04 (s, 1H), 7.87 (d, J=2.0 Hz, 1H), 7.50 (d, J=2.0 Hz, 1H), 7.50 (t, J=2.8 Hz, 1H), 6.64-6.62 (m, 1H).

Step 2: To a solution of 5-chloro-1H-indole-7-carbonitrile (0.52 g, 2.94 mmol) in tetrahydrofuran (10 mL) was added N-bromosuccinimide (0.54 g, 3.01 mmol) at room temperature. The mixture was stirred at room temperature for 2 h. The reaction mixture was diluted by water and extracted with ethyl acetate. The organic layer was dried over anhydrous sodium sulfate, filtered and concentrated under vacuum to afford 3-bromo-5-chloro-1H-indole-7-carbonitrile (960 mg, crude) as an off-white solid. MS m/z 252.9 [M−1]$^+$.

Step 3: To a solution of 3-bromo-5-chloro-1H-indole-7-carbonitrile (0.96 g, 3.75 mmol) in dichloromethane (20 mL) were added triethylamine (0.74 g, 7.37 mmol), 4-dimethylaminopyridine (0.05 g, 0.45 mmol) and di(tert-butyl) carbonate (1.70 g, 7.78 mmol) at room temperature. The mixture was stirred at room temperature for 16 h. The reaction mixture was concentrated under vacuum. The residue was purified by flash column chromatography with 0-15% ethyl acetate in petroleum ether to afford tert-butyl 3-bromo-5-chloro-7-cyanoindole-1-carboxylate (0.70 g, 52%) as a yellow solid. MS m/z 355.0 [M+1]$^+$ Step 4: A mixture of bis(pinacolato)diboron (1.07 g, 4.24 mmol), tert-butyl 3-bromo-5-chloro-7-cyanoindole-1-carboxylate (700 mg, 1.96 mmol), [1,1'-bis(diphenylphosphino)ferrocene]dichloropalladium(II) (15\8 mg, 0.21 mmol) and potassium acetate (312 mg, 3.18 mmol) in dioxane (10 mL) was heated at 80° C. for 16 h. The reaction mixture was concentrated under vacuum. The residue was purified by flash column chromatography with 0-15% ethyl acetate in petroleum ether to afford tert-butyl 5-chloro-7-cyano-3-(4,4,5,5-tetramethyl-1,3,2-dioxaborolan-2-yl)indole-1-carboxylate (B37) (420 mg, 52%) as a white solid. MS m/z 403.2 [M+1]$^+$

Intermediate B38 tert-butyl 3-(4,4,5,5-tetramethyl-1,3,2-dioxaborolan-2-yl)-7-(trifluoromethyl)indole-1-carboxylate

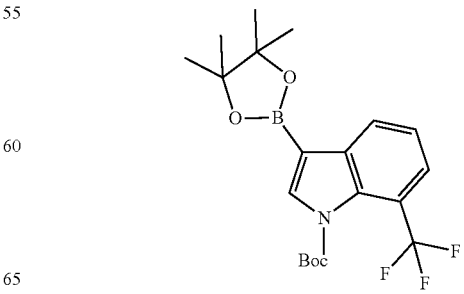

Followed the procedure of Intermediate B14 described above to afford tert-butyl 3-(4,4,5,5-tetramethyl-1,3,2-dioxaborolan-2-yl)-7-(trifluoromethyl)indole-1-carboxylate (B38) (340 mg, 42% over 3 steps) as a colorless solid from 7-(trifluoromethyl)-1H-indole. MS m/z 413.2 [M+1]⁺. $^1$H NMR (400 MHz, DMSO-$d_6$) δ 8.15 (d, J=7.8 Hz, 1H), 7.97 (s, 1H), 7.74-7.62 (m, 1H), 7.53-7.43 (m, 1H), 1.60 (s, 9H), 1.33 (s, 12H).

Intermediate B39 tert-butyl 3-(4,4,5,5-tetramethyl-1,3,2-dioxaborolan-2-yl)-1H-pyrrolo[2,3-c]pyridine-1-carboxylate

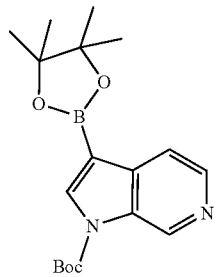 [SMILES: CC(C)(C)OC(=O)n1cc(B2OC(C)(C)C(C)(C)O2)c2ccncc21]

Step 1: To a solution of 3-bromo-1H-pyrrolo[2,3-c]pyridine (1.00 g, 5.08 mmol) and 4-dimethylaminopyridine (0.06 g, 0.51 mmol) in dichloromethane (20 mL) was added di(tert-butyl) carbonate (1.66 g, 7.64 mmol). The mixture was stirred at room temperature for 3 h. The mixture was concentrated under vacuum. The residue was purified by flash column chromatography with 0~70% ethyl acetate in petroleum ether to afford tert-butyl 3-bromopyrrolo[2,3-c]pyridine-1-carboxylate (1.40 g, 93%) as a pink solid. MS m/z 297.02 [M+1]⁺. $^1$H NMR (400 MHz, DMSO-$d_6$) δ 9.30 (d, J=1.2 Hz, 1H), 8.49 (d, J=5.4 Hz, 1H), 8.17 (s, 1H), 7.56 (dd, J=5.4, 1.2 Hz, 1H), 1.66 (s, 9H).

Step 2: To a solution of tert-butyl 3-bromopyrrolo[2,3-c]pyridine-1-carboxylate (1.20 g, 4.04 mmol) and [1,1'-bis(diphenylphosphino)ferrocene]dichloropalladium(II) (0.29 g, 0.40 mmol) in dioxane (10 mL) were added potassium acetate (0.79 g, 8.08 mmol) and bis(pinacolato)diboron (2.04 g, 8.08 mmol). The mixture was heated to 80° C. and stirred for 4 h under nitrogen atmosphere. The reaction mixture was diluted with water and extracted with ethyl acetate. The combined organic layers were washed with brine, dried over anhydrous sodium sulfate, filtered and concentrated under vacuum to afford tert-butyl 3-(4,4,5,5-tetramethyl-1,3,2-dioxaborolan-2-yl)-1H-pyrrolo[2,3-c]pyridine-1-carboxylate (B39) (935 mg, crude) as a yellow solid. MS m/z 345.2 [M+1]⁺.

Intermediate B40 tert-butyl 3-(4,4,5,5-tetramethyl-1,3,2-dioxaborolan-2-yl)pyrrolo[3,2-b]pyridine-1-carboxylate

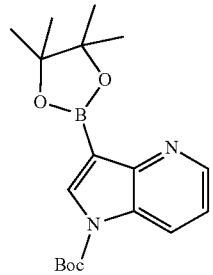 [SMILES: CC(C)(C)OC(=O)n1cc(B2OC(C)(C)C(C)(C)O2)c2ncccc21]

Step 1: To a solution of 3-bromo-1H-pyrrolo[3,2-b]pyridine (2.00 g, 10.15 mmol) in dichloromethane (15 mL) were triethylamine (3.08 g, 30.45 mmol), 4-dimethylaminopyridine (0.12 g, 1.01 mmol) and di(tert-butyl) carbonate (2.66 g, 12.18 mmol). The resulting solution was stirred at room temperature for 2 h. The mixture was concentrated under vacuum. The residue was purified by flash column chromatography with 0~25% ethyl acetate in petroleum ether to afford tert-butyl 3-bromopyrrolo[3,2-b]pyridine-1-carboxylate (3.00 g, 99%) as a white solid. MS m/z 297.0 [M+1]⁺.

Step 2: To a degassed solution of tert-butyl 3-bromopyrrolo[3,2-b]pyridine-1-carboxylate (200 mg, 0.67 mmol) in dioxane (3 mL) were added bis(pinacolato)diboron (342 mg, 1.34 mmol), [1,1'-bis(diphenyl-phosphino)ferrocene]dichloropalladium(II) (49 mg, 0.06 mmol) and potassium acetate (198 mg, 2.02 mmol) under nitrogen atmosphere. The mixture was stirred at 80° C. overnight. The mixture was concentrated under vacuum. The residue was purified by flash column chromatography with 0~25% ethyl acetate in petroleum ether to afford tert-butyl 3-(4,4,5,5-tetramethyl-1,3,2-dioxaborolan-2-yl)pyrrolo[3,2-b]pyridine-1-carboxylate (B40) (85 mg, 36%) as a brown solid. MS m/z 345.2 [M+1]⁺.

Intermediate B41 tert-butyl 6-fluoro-3-(4,4,5,5-tetramethyl-1,3,2-dioxaborolan-2-yl)pyrrolo[3,2-b]pyridine-1-carboxylate

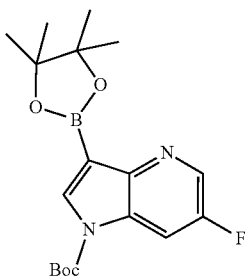 [SMILES: CC(C)(C)OC(=O)n1cc(B2OC(C)(C)C(C)(C)O2)c2ncc(F)cc21]

Step 1: To a solution of 6-fluoro-1H-pyrrolo[3,2-b]pyridine (1.00 g, 7.34 mmol) in THF (15 mL) was added N-bromosuccinimide (1.30 g, 7.30 mmol) at 0° C. The mixture was warmed at room temperature for 4 h. The mixture was concentrated under vacuum. The residue was purified by flash column chromatography with 0~80% EA in petroleum ether to afford 3-bromo-6-fluoro-1H-pyrrolo[3,2-b]pyridine (1.5 g, 94%) as a brown solid. MS m/z 216.9 [M+1]$^+$ Step 2: To a solution of 3-bromo-6-fluoro-1H-pyrrolo[3,2-b]pyridine (1.50 g, 6.97 mmol) in dichloromethane (30 mL) were added triethylamine (2.10 g, 20.75 mmol), 4-dimethylaminopyridine (0.12 g, 0.98 mmol) and di(tert-butyl) carbonate (2.90 g, 13.29 mmol). The mixture was stirred at room temperature for 16 h. The mixture was concentrated under vacuum, The residue was purified by flash column chromatography with 0~20% EA in petroleum ether to afford tert-butyl 3-bromo-6-fluoropyrrolo[3,2-b]pyridine-1-carboxylate (1.60 g, 72%) as a light yellow solid. MS m/z 316.9 [M+1]$^+$. $^1$H NMR (400 MHz, Chloroform-d) δ 8.53 (dd, J=2.4, 1.2 Hz, 1H), 8.18 (s, 1H), 7.90 (s, 1H), 1.70 (s, 9H).

Step 3: A degassed mixture of tert-butyl 3-bromo-6-fluoropyrrolo[3,2-b]pyridine-1-carboxylate (510 mg, 1.62 mmol), bis(pinacolato)diboron (888 mg, 3.49 mmol), [1,1'-bis(diphenylphosphino)ferrocene]-dichloropalladium(II) (0.11 g, 0.16 mmol) and potassium acetate (706 mg, 7.20 mmol) in dioxane (15 mL) was heated at 80° C. for 16 h. The mixture was concentrated under vacuum. The residue was purified by flash column chromatography with 0~40% EA in petroleum ether to afford tert-butyl 6-fluoro-3-(4,4,5,5-tetramethyl-1,3,2-dioxaborolan-2-yl)pyrrolo[3,2-b]pyridine-1-carboxylate (B41) (410 mg, ~40% purity, 27%) as a yellow oil. MS m/z 363.1 [M+1]+

Intermediate B42 tert-butyl 6-methyl-3-(4,4,5,5-tetramethyl-1,3,2-dioxaborolan-2-yl)pyrrolo[2,3-b]pyridine-1-carboxylate

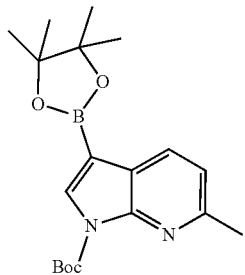

Followed the procedure of Intermediate B14 described above to afford tert-butyl 6-methyl-3-(4,4,5,5-tetramethyl-1,3,2-dioxaborolan-2-yl)pyrrolo[2,3-b]pyridine-1-carboxylate (B42) (400 mg, 32% over 3 steps) as yellow oil from 6-methyl-1H-pyrrolo[2,3-b]pyridine. MS m/z 359.2 [M+1]$^+$.

Intermediate B43 tert-butyl 7-chloro-3-(4,4,5,5-tetramethyl-1,3,2-dioxaborolan-2-yl)-1H-indole-1-carboxylate

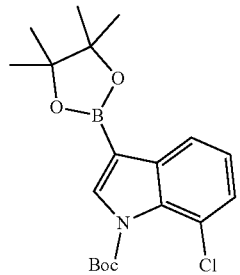 [SMILES: CC(C)(C)OC(=O)n1cc(B2OC(C)(C)C(C)(C)O2)c2cccc(Cl)c21]

Followed the procedure of Intermediate B14 described above to afford tert-butyl 7-chloro-3-(4,4,5,5-tetramethyl-1,3,2-dioxaborolan-2-yl)-1H-indole-1-carboxylate (B43) (0.60 g, 30% over 3 steps) as an off-white solid from indole-7-chloro. $^1$H NMR (400 MHz, DMSO-d$_6$) δ 7.92 (s, 1H), 7.43-7.36 (m, 2H), 7.30-7.27 (m, 1H), 1.61 (s, 9H), 1.25 (s, 12H).

Intermediate B44 tert-butyl 7-(methylsulfonyl)-3-(4,4,5,5-tetramethyl-1,3,2-dioxaborolan-2-yl)-1H-indole-1-carboxylate

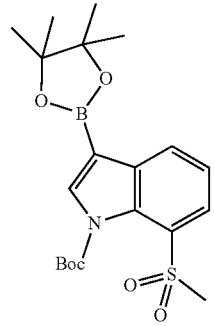 [SMILES: CC(C)(C)OC(=O)n1cc(B2OC(C)(C)C(C)(C)O2)c2cccc(S(C)(=O)=O)c21]

Step 1: To a solution of sodium methyl sulfinate (7.80 g, 76.41 mmol) in methyl sulfoxide (50 mL) was added a solution of o-chloronitrobenzene (10.00 g, 63.47 mmol) in methyl sulfoxide (20 mL) slowly at 80° C. After stirring at 80° C. for 16 h, the mixture was diluted with water. The solids were collected by filtration and then dried over vacuum to afford 1-methanesulfonyl-2-nitrobenzene (12.00 g, 94%) as a light brown solid. $^1$H NMR (400 MHz, DMSO-d$_6$) δ 8.15-8.04 (m, 2H), 7.99-7.95 (m, 2H), 3.49 (s, 3H).

Step 2: To a solution of 1-methanesulfonyl-2-nitrobenzene (3.00 g, 14.91 mmol) in tetrahydrofuran (30 ml) was added bromo(ethenyl)magnesium (50 mL, 50.00 mmol, 1M in tetrahydrofuran) slowly at −60° C. The mixture was stirred at −60° C. for 2 h. The reaction was quenched using saturated ammonium chloride aqueous solution and extracted with ethyl acetate. The organic layer was dried over anhydrous sodium sulfate, filtered and concentrated under vacuum. The residue was purified by flash column chromatography with 0–30% ethyl acetate in petroleum ether to afford 7-methanesulfonyl-1H-indole (1.60 g, 55%) as a white solid. $^1$H NMR (400 MHz, DMSO-$d_6$) δ 11.33 (s, 1H), 7.95 (dt, J=7.8, 1.2 Hz, 1H), 7.62 (dt, J=7.4, 1.2 Hz, 1H), 7.48 (t, J=2.8 Hz, 1H), 7.23 (t, J=7.6 Hz, 1H), 6.67-6.58 (m, 1H), 3.29 (s, 3H).

Step 3: To a solution of 7-methanesulfonyl-1H-indole (0.80 g, 4.10 mmol) in tetrahydrofuran (8 mL) was added N-bromosuccinimide (0.72 g, 4.08 mmol). The mixture was stirred at room temperature for 2 h. The mixture was concentrated under vacuum. The residue was diluted using water and extracted with ethyl acetate. The combined organic layers were dried over anhydrous sodium sulfate, filtered and concentrated under vacuum to afford 3-bromo-7-methanesulfonyl-1H-indole (1.54 g, crude) as a light yellow solid. MS m/z 274.0 [M+1]$^+$.

Step 4: To a solution of 3-bromo-7-methanesulfonyl-1H-indole (1.50 g, 5.62 mmol) and di(tert-butyl) carbonate (2.50 g, 11.24 mmol) in dichloromethane (10 mL) were added triethylamine (1.00 g, 11.24 mmol) and 4-dimethylaminopyridine (0.14 g, 1.12 mmol). The mixture was stirred at room temperature for 3 h. The mixture was concentrated under vacuum. the residue was purified by flash column chromatography with 0-80% ethyl acetate in petroleum ether to afford tert-butyl 3-bromo-7-methanesulfonylindole-1-carboxylate (1.44 g, 93% over 2 steps) as a yellow solid. MS m/z 374.0 [M+1]$^+$.

Step 5: To a solution of tert-butyl 3-bromo-7-methanesulfonylindole-1-carboxylate (700 mg, 1.87 mmol) and bis(pinacolato)diboron (946 mg, 3.74 mmol) in dioxane (7 mL) and were added [1,1'-bis(diphenylphosphino)ferrocene]dichloropalladium(II) (137 mg, 0.19 mmol) and potassium acetate (367 mg, 3.74 mmol). The mixture was stirred at 80° C. for 8 h under nitrogen atmosphere. The mixture was concentrated under vacuum. The residue was purified by flash column chromatography with 0-65% ethyl acetate in petroleum ether to afford tert-butyl 7-(methylsulfonyl)-3-(4,4,5,5-tetramethyl-1,3,2-dioxaborolan-2-yl)-1H-indole-1-carboxylate (B44) (520 mg, 82%) as a yellow solid. MS m/z 422.2 [M+1]$^+$. $^1$H NMR (400 MHz, DMSO-$d_6$) δ 8.19 (dd, J=7.8, 1.2 Hz, 1H), 8.00 (s, 1H), 7.87 (td, J=8.2, 1.2 Hz, 1H), 7.53 (t, J=7.8 Hz, 1H), 3.47 (s, 3H), 1.63 (s, 9H), 1.33 (s, 12H).

Intermediate B45 tert-butyl 6-fluoro-3-(4,4,5,5-tetramethyl-1,3,2-dioxaborolan-2-yl)-1H-indole-1-carboxylate

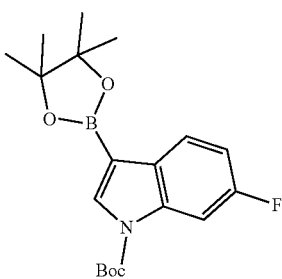 [SMILES: CC(C)(C)OC(=O)n1cc(B2OC(C)(C)C(C)(C)O2)c2ccc(F)cc21]

Followed the procedure of Intermediate B14 described above to afford tert-butyl 6-fluoro-3-(4,4,5,5-tetramethyl-1,3,2-dioxaborolan-2-yl)-1H-indole-1-carboxylate (B45) (0.56 g, 38% over 3 steps) as a yellow solid from 6-fluoro-1H-indole. MS m/z 362.2 [M+1]$^+$. $^1$H NMR (400 MHz, Chloroform-d) δ 7.99 (s, 1H), 7.93-7.89 (m, 2H), 7.06-7.01 (m, 1H), 1.68 (s, 9H), 1.39 (s, 12H).

Intermediate B46

5-amino-6-methylpyrazin-2-ylboronic acid

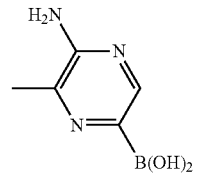

To a solution of 5-bromo-3-methylpyrazin-2-amine (500 mg, 2.66 mmol) in dioxane (10 mL) were added bis(pinacolato)diboron (675 mg, 2.66 mmol), tris(dibenzylideneacetone)dipalladium (122 mg, 0.13 mmol), potassium acetate (783 mg, 7.98 mmol) and tricyclohexylphosphane (52 mg, 0.19 mmol) at room temperature under nitrogen atmosphere. The mixture was stirred at 80° C. for 2 h. The mixture was diluted with water and extracted with ethyl acetate. The combined organic layers was washed with brine, dried over anhydrous sodium sulfate, filtered and concentrated under vacuum to afford 5-amino-6-methylpyrazin-2-ylboronic acid (B46) (400 mg, crude) as a light yellow oil. MS m/z 154.2 [M+1]$^+$.

Intermediate B47

7-chloro-1-(tetrahydro-2H-pyran-2-yl)-3-(4,4,5,5-tetramethyl-1,3,2-dioxaborolan-2-yl)-1H-indazole

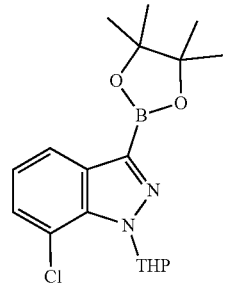

Step 1: To a mixture of 3-chloro-2-fluorobenzaldehyde (10.00 g, 63.07 mmol) and potassium carbonate (9.60 g, 69.39 mmol) in N,N-dimethylformamide (100 mL) was added hydrazine hydrate (60 mL, 80% in water). The mixture was heated to 120° C. for 16 h. The mixture was diluted with water and extracted with ethyl acetate. The combined organic layers was washed with brine, dried over anhydrous sodium sulfate, filtered and concentrated under vacuum to afford 7-chloro-1H-indazole (8.00 g, 83%) as a brown solid. MS m/z 152.6 [M+1]$^+$.

Step 2: To a solution of 7-chloro-1H-indazole (9.60 g, 62.92 mmol) in tetrahydrofuran (100 mL) was added N-bromosuccinimide (11.20 g, 62.92 mmol). The mixture was stirred at room temperature for 2 h. The mixture was diluted with water and extracted with ethyl acetate. The combined organic layers was washed with brine, dried over anhydrous sodium sulfate, filtered and concentrated under vacuum to afford 3-bromo-7-chloro-1H-indazole (8.40 g, crude) as a brown yellow oil. MS m/z 231.0, 232.0 [M+1]$^+$.

Step 3: To a solution of 3-bromo-7-chloro-1H-indazole (9.00 g, 38.88 mmol) and p-toluenesulfonic acid monohydrate (338 mg, 1.94 mmol) in dichloromethane (90 mL) was added dihydropyran (4.90 g, 58.32 mmol). The mixture was stirred at room temperature for 16 h. The mixture was concentrated under vacuum. The residue was purified by flash column chromatography with 0~5% ethyl acetate in petroleum ether to afford 3-bromo-7-chloro-1-(oxan-2-yl) indazole (6.00 g, 30% over 2 steps) as a red oil. MS m/z 315.1, 317.1 [M+1]$^+$.

Step 4: To a solution of 3-bromo-7-chloro-1-(oxan-2-yl) indazole (500 mg, 1.58 mmol) in dioxane (5 mL) were added bis(pinacolato)diboron (603 mg, 2.38 mmol), [1,1'-bis(diphenylphosphino)ferrocene]dichloropalladium(II) (116 mg, 0.16 mmol) and potassium acetate (311 mg, 3.17 mmol) at room temperature. The mixture was heated to 100° C. for 2 h under nitrogen atmosphere. The mixture was filtered. The filtrate was collected and concentrated under vacuum. The residue was purified by flash column chromatography with 0~30% ethyl acetate in petroleum ether to afford 7-chloro-1-(tetrahydro-2H-pyran-2-yl)-3-(4,4,5,5-tetramethyl-1,3,2-dioxaborolan-2-yl)-1H-indazole (B47) (460 mg, 80%) as a brown oil. MS m/z 363.2 [M+1]$^+$. $^1$H NMR (400 MHz, methyl sulfoxide-d$_6$) δ 7.93 (dd, J=8.0, 0.8 Hz, 1H), 7.52 (dd, J=7.6, 1.0 Hz, 1H), 7.25 (t, J=7.8 Hz, 1H), 6.31 (dd, J=10.2, 2.0 Hz, 1H), 3.93-3.91 (m, 1H), 3.77-3.66 (m, 1H), 2.57-2.54 (m, 1H), 2.11-1.99 (m, 2H), 1.78-1.73 (m, 1H), 1.58-1.56 (m, 2H), 1.36 (s, 12H).

Intermediate B48 tert-butyl 3-((2-methyl-6-(tributylstannyl)pyridin-3-yl)oxy)pyrrolidine-1-carboxylate

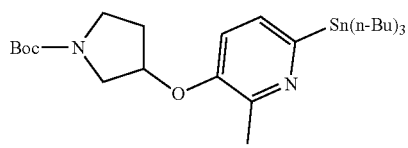

A degassed mixture of tert-butyl 3-((6-bromo-2-methylpyridin-3-yl)oxy)pyrrolidine-1-carboxylate (0.40 g, 1.12 mmol) and hexabutyldistannane (1.62 g, 2.80 mmol), palladium(0)tetrakis(triphenylphosphine) (129 mg, 0.11 mmol) in dioxane (5 mL) was stirred at 100° C. for 16 h. The mixture was concentrated under vacuum. The residue was purified by reverse phase flash column chromatography with 10-90% acetonitrile in water to afford tert-butyl 3-((2-methyl-6-(tributylstannyl)pyridin-3-yl)oxy)pyrrolidine-1-carboxylate (B48) (0.30 g, 40%) as a yellow oil. MS m/z 569.3 [M+1]$^+$.

Intermediate B49

2-(6-fluoro-1-benzothiophen-3-yl)-4,4,5,5-tetramethyl-1,3,2-dioxaborolane

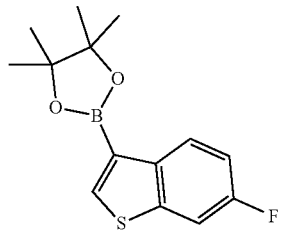 [SMILES: CC1(C)OB(c2csc3cc(F)ccc23)OC1(C)C]

Step 1: To a mixture of 3-chloro-6-fluoro-1-benzothiophene-2-carboxylic acid (800 mg, 3.469 mmol) in DMSO (8 mL) were added CuI (198 mg, 1.041 mmol) and TEA (184 mg, 1.822 mmol). The resulting mixture was stirred at 120° C. overnight under nitrogen atmosphere. The resulting mixture was extracted with EtOAc. The combined organic layers were washed with brine, dried over anhydrous Na$_2$SO$_4$. After filtration, the filtrate was concentrated under reduced pressure. The residue was purified by flash column chromatography with 0~50% ethyl acetate in PE to afford 3-chloro-6-fluoro-1-benzothiophene (500 mg, 77.24%) as a white solid. $^1$H NMR (400 MHz, DMSO-d$_6$) δ 8.06-7.99 (m, 1H), 7.94-7.87 (m, 1H), 7.85-7.77 (m, 1H), 7.48-7.36 (m, 1H).

Step 2: To a mixture of 3-chloro-6-fluoro-1-benzothiophene (460 mg, 2.465 mmol) and 4,4,5,5-tetramethyl-2-(tetramethyl-1,3,2-dioxaborolan-2-yl)-1,3,2-dioxaborolane (1.25 g, 4.930 mmol) in dioxane (8 mL) were added KOAc (726 mg, 7.395 mmol) and Xphos Pd G2 (388 mg, 0.493 mmol). The resulting mixture was stirred at 70° C. overnight under nitrogen atmosphere. The resulting mixture was concentrated under reduced pressure. The residue was purified by flash column chromatography with 0-50% ethyl acetate in PE to afford 2-(6-fluoro-1-benzothiophen-3-yl)-4,4,5,5-tetramethyl-1,3,2-dioxaborolane (417 mg, 60.82%) as a yellow solid. $^1$H NMR (400 MHz, DMSO-d$_6$) δ 8.25-8.17 (m, 2H), 7.99-7.92 (m, 1H), 7.37-7.27 (m, 1H), 1.34 (s, 12H).

Intermediate B50

3-methyl-2-[2-methyl-2-(oxan-2-yloxy) propoxy]-5-(4,4,5,5-tetramethyl-1,3,2-dioxaborolan-2-yl)pyrazine

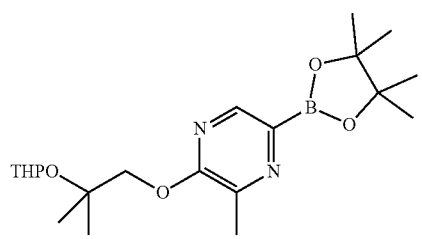

To a mixture of 5-iodo-3-methyl-2-[2-methyl-2-(oxan-2-yloxy)propoxy]pyrazine (150 mg, 0.382 mmol) and 4,4,5,5-tetramethyl-2-(tetramethyl-1,3,2-dioxaborolan-2-yl)-1,3,2-dioxaborolane (486 mg, 1.912 mmol) in dioxane (3 mL)

were added KOAc (76 mg, 0.765 mmol) and Pd(dppf)Cl$_2$ (28 mg, 0.038 mmol). The resulting mixture was stirred at 90° C. for 2 h under nitrogen atmosphere. The resulting mixture was used in the next step directly without further purification.

Intermediate B51

7-chloro-1H-pyrrolo[2,3-c]pyridin-3-ylboronic acid

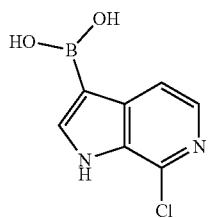 [SMILES: OB(O)c1c[nH]c2c(Cl)nccc12]

To a mixture of 7-chloro-1H-pyrrolo[2,3-c]pyridine (200 mg, 1.311 mmol) in MTBE (5 mL) were added 4,4,5,5-tetramethyl-2-(tetramethyl-1,3,2-dioxaborolan-2-yl)-1,3,2-dioxaborolane (666 mg, 2.622 mmol), Bis(1,5-cyclooctadiene)dimethoxydiiridium (17 mg, 0.026 mmol) and dtbpy (18 mg, 0.066 mmol). The resulting mixture was stirred at 80° C. for 1 h under nitrogen atmosphere. The reaction was quenched with MeOH at 0° C. The resulting mixture was concentrated under vacuum. This resulted in 7-chloro-1H-pyrrolo[2,3-c]pyridin-3-ylboronic acid (200 mg, crude) as a brown solid. MS m/z 197.0 [M+1]$^+$ Intermediate B52

7-cyano-1-(oxan-2-yl)indazol-3-ylboronic acid

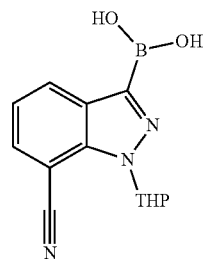

Step 1: To a solution of 1H-indazole-7-carbonitrile (1.0 g, 6.98 mmol) in DMF (10 mL) was added NBS (1.8 g, 6.98 mmol). The mixture was stirred at room temperature for 2 h. The aqueous solution was extracted with ethyl acetate. The combined organic layers were washed with brine, dried over anhydrous sodium sulfate, filtered, and concentrated under vacuum to afford 3-bromo-1H-indazole-7-carbonitrile (1.5 g, 96.70%) as a white solid. MS m/z 221.9 [M+1]$^+$.

Step 2: To a solution of 3-bromo-1H-indazole-7-carbonitrile (1.5 g, 6.75 mmol) in DCM (15 mL) was added TsOH (60 mg, 0.30 mmol) and dihydropyran (0.8 g, 10 mmol). The mixture was stirred at room temperature for 16 h. The mixture was concentrated under vacuum. The residue was purified by flash column chromatography with 0-30% ethyl acetate in petroleum ether to afford 3-bromo-1-(oxan-2-yl)indazole-7-carbonitrile (983 mg, 47.53%) as a white solid. MS m/z 306.0 [M+1]$^+$.

Step 3: To a solution of 3-bromo-1-(oxan-2-yl)indazole-7-carbonitrile (1.8 g, 5.87 mmol) in dioxane (20 mL) were added AcOK (1.7 g, 7.04 mmol), (Bpin)$_2$ (2.9 g, 2.94 mmol) and Pd(dppf)Cl$_2$ (0.4 g, 0.59 mmol). The mixture was stirred at 80° C. for 16 h under nitrogen. The aqueous solution was extracted with ethyl acetate. The combined organic layers were washed with brine, dried over anhydrous sodium sulfate, filtered, and concentrated under vacuum to afford 7-cyano-1-(oxan-2-yl)indazol-3-ylboronic acid (765 mg, crude) as a black oil. MS m/z 272.2[M+1]$^+$.

Intermediate B53 tert-butyl 7-methyl-3-(4,4,5,5-tetramethyl-1,3,2-dioxaborolan-2-yl)-1H-indole-1-carboxylate

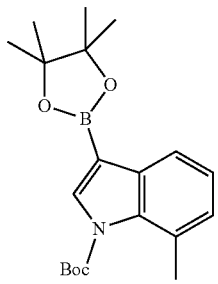 [SMILES: Cc1cccc2c(B3OC(C)(C)C(C)(C)O3)cn(C(=O)OC(C)(C)C)c12]

Step 1: A mixture of 7-methyl-1H-indole (15.0 g, 114.34 mmol), Boc$_2$O (27.4 g, 125.78 mmol), TEA (23.1 g, 228.69 mmol) and DMAP (1.4 g, 11.43 mmol) in DCM (200 mL) was stirred at room temperature for 16 h. The resulting mixture was concentrated under reduced pressure. The mixture was diluted with ethyl acetate, washed with brine, dried over anhydrous sodium sulfate, filtered, and concentrated under vacuum. The residue was purified by flash column chromatography with 0-50% ethyl acetate in petroleum ether to afford tert-butyl 7-methyl-1H-indole-1-carboxylate (24.5 g, 92.63%) as a colorless oil. MS m/z 232.1 [M+1]$^+$.

Step 2: A mixture of tert-butyl 7-methyl-1H-indole-1-carboxylate (30.0 g, 129.70 mmol) and NBS (25.4 g, 142.67 mmol) in DCM (300 mL) was stirred at 40° C. for 2 h. The mixture was diluted with ethyl acetate, washed with brine, dried over anhydrous sodium sulfate, filtered, and concentrated under vacuum. The residue was purified by flash column chromatography with 0~30% ethyl acetate in petroleum ether to afford tert-butyl 3-bromo-7-methyl-1H-indole-1-carboxylate (26.8 g, 66.61%) as a yellow oil. MS m/z 310.1 [M+1]$^+$.

Step 3: To a solution of tert-butyl 3-bromo-7-methyl-1H-indole-1-carboxylate (1.7 g, 5.48 mmol) in dioxane (20 mL) was added (Bpin)$_2$ (2.8 g, 10.96 mmol). The mixture was stirred at room temperature for 20 min, this was followed by the addition of Pd(dppf)Cl$_2$ (0.4 g, 0.55 mmol) and AcOK (1.1 g, 10.96 mmol) at room temperature. Then the mixture was stirred at 80° C. for 10 h. The residue was purified by flash column chromatography with 0-20% ethyl acetate in petroleum ether to afford tert-butyl 7-methyl-3-(4,4,5,5-tetramethyl-1,3,2-dioxaborolan-2-yl)-1H-indole-1-carboxylate (516 mg, 26.35%) as a yellow oil. MS m/z 358.0 [M+1]$^+$.

Intermediate B54

1-(tert-butoxycarbonyl)-5,6,7-trifluoroindol-3-ylboronic acid

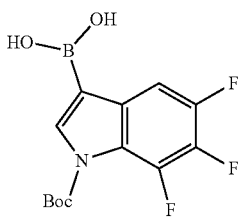

Step-1: To a mixture of 1,2,3-trifluoro-4-nitrobenzene (3 g, 16.941 mmol) in THF (30 mL) was added bromo(ethenyl)magnesium (84.7 mL, 84.707 mmol, 1 mol/L in THF) at −40° C. The mixture was stirred at −40° C. for 1 h. The reaction mixture was quenched by NH$_4$Cl solution. The resulting mixture was extracted with EtOAc. The combined organic layers were washed with brine, dried over anhydrous Na$_2$SO$_4$. After filtration, the filtrate was concentrated under reduced pressure. The residue was purified by flash column chromatography with 0-20% ethyl acetate in petroleum ether to afford 5,6,7-trifluoro-1H-indole (340 mg, 11.73%) as a yellow solid. $^1$H NMR (400 MHz, DMSO-d$_6$) δ 11.89 (s, 1H), 7.54-7.48 (m, 1H), 7.47-7.38 (m, 1H), 6.57-6.50 (m, 1H)

Step-2: To a mixture of 5,6,7-trifluoro-1H-indole (310 mg, 1.812 mmol) in acetonitrile (5 mL) was added NBS (322 mg, 1.812 mmol) at 0° C. The resulting mixture was stirred at room temperature for 2 h. The resulting mixture was extracted with EtOAc. The combined organic layers were washed with brine, dried over anhydrous Na$_2$SO$_4$. After filtration, the filtrate was concentrated under reduced pressure. This resulted in 3-bromo-5,6,7-trifluoro-1H-indole (400 mg, 88.31%) as a brown solid. GCMS (EI) [M]$^+$, 248.9

Step-3: To a mixture of 3-bromo-5,6,7-trifluoro-1H-indole (440 mg, 1.760 mmol) in DCM (5 mL) was added TEA (356 mg, 3.52 mmol), di-tert-butyl dicarbonate (768 mg, 3.52 mmol) and DMAP (65 mg, 0.528 mmol). The resulting mixture was stirred at room temperature overnight. The resulting mixture was concentrated under vacuum. The residue was purified by flash column chromatography with 0-50% ethyl acetate in petroleum ether to afford tert-butyl 3-bromo-5,6,7-trifluoroindole-1-carboxylate (240 mg, 38.95%) as a white solid. $^1$H NMR (400 MHz, DMSO-d$_6$) δ 8.08 (s, 1H), 7.46-7.37 (m, 1H), 1.61 (s, 9H).

Step-4: To a mixture of tert-butyl 3-bromo-5,6,7-trifluoroindole-1-carboxylate (100 mg, 0.286 mmol) in dioxane (5 mL) was added 4,4,5,5-tetramethyl-2-(tetramethyl-1,3,2-dioxaborolan-2-yl)-1,3,2-dioxaborolane (145 mg, 0.572 mmol), AcOK (84 mg, 0.858 mmol) and Pd(dppf)Cl$_2$ (21 mg, 0.029 mmol). The resulting mixture was stirred at 80° C. overnight under nitrogen atmosphere. The resulting mixture was extracted with EtOAc. The combined organic layers were washed with brine, dried over anhydrous Na$_2$SO$_4$. After filtration, the filtrate was concentrated under reduced pressure. This resulted in 1-(tert-butoxycarbonyl)-5,6,7-trifluoroindol-3-ylboronic acid (100 mg, crude) as a brown solid.

Example 1

2-[5-(morpholin-4-yl)-1H-indazol-3-yl]quinoline

Step 1: To a degassed mixture of 2-bromoquinoline (82 mg, 0.39 mmol) and 4-(1-(tetrahydro-2H-pyran-2-yl)-3-(4,4,5,5-tetramethyl-1,3,2-dioxaborolan-2-yl)-1H-indazol-5-yl)morpholine (B1) (163 mg, 0.39 mmol) in dioxane (5 mL) and water (0.5 mL) were added potassium carbonate (136 mg, 1.00 mmol) and [1,1'-bis(diphenylphosphino)ferrocene]-dichloropalladium(II) (36 mg, 0.04 mmol). The mixture was heated to 100° C. and stirred for 16 h. The reaction mixture was diluted with water and extracted with ethyl acetate. The combined organic layers were washed with brine, dried over anhydrous sodium sulfate, filtered and concentrated under reduced pressure. The residue was purified by flash column chromatography with 0~50% ethyl acetate in petroleum ether to afford 2-[5-(morpholin-4-yl)-1-(oxan-2-yl)indazol-3-yl]quinoline (93 mg, 56%) as a white solid. MS m/z 415.1 [M+1]$^+$.

Step 2: To a solution of 2-[5-(morpholin-4-yl)-1-(oxan-2-yl)indazol-3-yl]quinoline (93 mg, 0.22 mmol) in dichloromethane (5 mL) was added trifluoroacetic acid (1.5 mL). The mixture was stirred at room temperature for 16 h. The mixture was concentrated under vacuum. The residue was basified using saturated sodium bicarbonate aqueous solution. The mixture was extracted with ethyl acetate. The combined organic layers were washed was brine, dried over anhydrous sodium sulfate, filtered and concentrated under reduced pressure. The crude product was purified by Prep-HPLC (Method A) [Column: XBridge Shield RP18 OBD Column, 30150 mm, 5 um; Mobile Phase A: water (10 mmol/L ammonium bicarbonate), Mobile Phase B: acetonitrile; Flow rate: 60 mL/min; Gradient: 43% B to 59% B in 7 min] to afford 2-[5-(morpholin-4-yl)-1H-indazol-3-yl]quinoline (47.5 mg, 65%) as a white solid.

Example 2

2-[6-(morpholin-4-yl)-1H-indazol-3-yl]quinoline

Followed the procedure of example 1 described above and purified by Prep-HPLC (Method A) to afford 2-[6-(morpholin-4-yl)-1H-indazol-3-yl]quinoline (49 mg, 35% over 2 steps) as a white solid from 4-(1-(tetrahydro-2H-pyran-2-yl)-3-(4,4,5,5-tetramethyl-1,3,2-dioxaborolan-2-yl)-1H-indazol-6-yl)morpholine (175 mg, 0.42 mmol).

Example 3

N,N-dimethyl-3-(quinolin-2-yl)-1H-indazol-5-amine

Followed the procedure of example 1 described above purified by Prep-HPLC (Method A) to afford N,N-dimethyl-3-(quinolin-2-yl)-1H-indazol-5-amine (64.2 mg, 15% over 2 steps) as a yellow solid from N,N-dimethyl-1-(tetrahydro-2H-pyran-2-yl)-3-(4,4,5,5-tetramethyl-1,3,2-dioxaborolan-2-yl)-1H-indazol-5-amine (503 mg, 1.35 mmol).

Example 4

N,N-dimethyl-3-(quinolin-2-yl)-1H-indazol-6-amine

Followed the procedure of example 1 described above and purified by Prep-HPLC (Method A) to afford N,N-dimethyl-3-(quinolin-2-yl)-1H-indazol-6-amine (71.7 mg, 22% over 2 steps) as a yellow solid from N,N-dimethyl-1-(oxan-2-yl)-3-(4,4,5,5-tetramethyl-1,3,2-dioxaborolan-2-yl)indazol-6-amine (543 mg, 1.45 mmol).

Example 5

2-(1H-indazol-3-yl)-1,5-naphthyridine

Followed the procedure of example 1 described above and purified by Prep-HPLC (Method A) to afford 2-(1H-indazol- 3-yl)-1,5-naphthyridine (65.2 mg, 17% over 2 steps) as a white solid from 1-(oxan-2-yl)-3-(4,4,5,5-tetramethyl-1,3,2-dioxaborolan-2-yl)indazole (500 mg, 1.52 mmol).

Example 6

6-(1H-indazol-3-yl)-1H-1,5-naphthyridin-2-one

Followed the procedure of example 1 described above and purified by Prep-HPLC (Method A) to afford 6-(1H-indazol-3-yl)-1H-1,5-naphthyridin-2-one (5.9 mg, 7%) as a light yellow solid from 6-[1-(oxan-2-yl)indazol-3-yl]-1H-1,5-naphthyridin-2-one (from step 1 of example 7) (100 mg, 0.27 mmol).

Example 7

2-(1H-indazol-3-yl)-1,6-naphthyridine

Followed the procedure of example 1 described above and purified by Prep-HPLC (Method A) to afford 2-(1H-indazol-3-yl)-1,6-naphthyridine (64.6 mg, 23% over two steps) as a white solid from 1-(tetrahydro-2H-pyran-2-yl)-3-(4,4,5,5-tetramethyl-1,3,2-dioxaborolan-2-yl)-1H-indazole (367 mg, 1.11 mmol).

Example 8

2-(1H-indazol-3-yl)-1,7-naphthyridine

Followed the procedure of example 1 described above and purified by Prep-HPLC (Method B) to afford 2-(1H-indazol-3-yl)-1,7-naphthyridine (32 mg, 23% over 2 steps) as a white solid from 2-chloro-1,7-naphthyridine (100 mg, 0.60 mmol).

Example 9

2-(1H-indazol-3-yl)-5,6,7,8-tetrahydro-1,5-naphthyridine

Followed the procedure of example 1 described above and purified by Prep-HPLC (Method A) to afford 2-(1H-indazol-3-yl)-5,6,7,8-tetrahydro-1,5-naphthyridine (18.5 mg, 10% over 2 steps) as a white solid from 2-chloro-5,6,7,8-tetrahydro-1,5-naphthyridine (100 mg, 0.59 mmol).

Example 10

3-[1-methyl-2H,3H-pyrido[2,3-b][1,4]oxazin-6-yl]-1H-indazole

Followed the procedure of example 1 described above and purified by Prep-HPLC (Method A) to afford 3-[1-methyl-2H,3H-pyrido[2,3-b][1,4]oxazin-6-yl]-1H-indazole (20.8 mg, 20% over 2 steps) as a light yellow solid from 6-chloro-1-methyl-2H,3H-pyrido[2,3-b][1,4]oxazine (70 mg, 0.38 mmol).

Example 11

2-(1H-indazol-3-yl)-6H,7H-pyrrolo[3,4-b]pyridin-5-one

Followed the procedure of example 1 described above and purified by Prep-HPLC (Method B) to afford 2-(1H-indazol-3-yl)-6H,7H-pyrrolo[3,4-b]pyridin-5-one (7.1 mg, 11% over 2 steps) as a yellow solid from 5,6-difluoro-1-(oxan-2-yl)-3-(4,4,5,5-tetramethyl-1,3,2-dioxaborolan-2-yl)indazole (350 mg, 0.96 mmol).

Example 12

2-(1H-indazol-3-yl)-5-methoxy-1,6-naphthyridine

Followed the procedure of example 1 described above and purified by Prep-HPLC (Method B) to afford 2-(1H-indazol-3-yl)-5-methoxy-1,6-naphthyridine (27.9 mg, 38% over 2 steps) as a brown solid from 5-methoxy-1,6-naphthyridin-2-yl trifluoromethanesulfonate (80 mg, 0.26 mmol).

Example 13

5,6-difluoro-3-[1-methyl-2H,3H-pyrido[2,3-b][1,4]oxazin-6-yl]-1H-indazole

Followed the procedure of example 1 described above and purified by Prep-HPLC (Method A) to afford 5,6-difluoro-3-[1-methyl-2H,3H-pyrido[2,3-b][1,4]oxazin-6-yl]-1H-indazole (24.6 mg, 21% over 2 steps) as a white solid from 5,6-difluoro-1-(oxan-2-yl)-3-(4,4,5,5-tetramethyl-1,3,2-dioxaborolan-2-yl)indazole (207 mg, 0.56 mmol).

Example 14

3-(5,6-difluoro-1H-indazol-3-yl)cinnoline

Followed the procedure of example 1 described above and purified by Prep-HPLC (Method A) to afford 3-(5,6-difluoro-1H-indazol-3-yl)cinnoline (33.2 mg, 23% over 2 steps) as a white solid from 5,6-difluoro-1-(oxan-2-yl)-3-(4,4,5,5-tetramethyl-1,3,2-dioxaborolan-2-yl)indazole (209 mg, 0.57 mmol).

Example 15

2-(1H-indazol-3-yl)-6-methyl-1,5-naphthyridine

Step 1: To a degassed mixture of 6-chloro-1H-1,5-naphthyridin-2-one (750 mg, 4.16 mmol), 1-(oxan-2-yl)-3-(4,4,5,5-tetramethyl-1,3,2-dioxaborolan-2-yl)indazole (B5) (2000 mg, 6.09 mmol) and potassium carbonate (1700 mg, 12.31 mmol) in dioxane (30 mL)/water (3 mL) was added [1,1'-bis(diphenylphosphino)ferrocene]dichloropalladium (II) (304 mg, 0.41 mmol). The mixture was heated to 90° C. and stirred for 16 h. The reaction mixture was concentrated under vacuum. The residue was diluted with water and extracted with ethyl acetate. The combined organic layers were washed with brine, dried over anhydrous sodium sulfate, filtered and concentrated under vacuum. The residue was purified by flash column chromatography with 0~80% ethyl acetate in petroleum ether to afford 6-[1-(oxan-2-yl)indazol-3-yl]-1H-1,5-naphthyridin-2-one (500 mg, 34%) as a light yellow solid. MS m/z 347.1 [M+1]⁺.

Step 2: To a solution of 6-[1-(oxan-2-yl)indazol-3-yl]-1H-1,5-naphthyridin-2-one (300 mg, 0.86 mmol) and pyridine (136 mg, 1.72 mmol) in dichloromethane (10.00 mL) was added trifluoromethanesulfonic anhydride (359 mg, 1.27 mmol) slowly at 0° C. The mixture was stirred at room temperature for 16 h. The reaction was quenched with water at 0° C. The mixture was extracted with dichloromethane. The combined organic layers were washed with brine, dried over anhydrous sodium sulfate, filtered and concentrated under vacuum. The residue was purified by flash column chromatography with 0~80% ethyl acetate in petroleum ether to afford 6-[1-(oxan-2-yl)indazol-3-yl]-1,5-naphthyridin-2-yl trifluoromethanesulfonate (200 mg, 48%) as a light yellow solid. MS m/z 479.1 [M+1]$^+$.

Step 3: To a mixture of 6-[1-(oxan-2-yl)indazol-3-yl]-1,5-naphthyridin-2-yl trifluoromethanesulfonate (150 mg, 0.31 mmol), potassium carbonate (120 mg, 0.9 mmol) and methylboronic acid (38 mg, 0.60 mmol) in dioxane (5 mL) was added palladium(0)tetrakis(triphenylphosphine) (36 mg, 0.031 mmol) under nitrogen. The mixture was stirred at 90° C. for 16 h under nitrogen. The reaction mixture was concentrated under vacuum. The residue was purified by flash column chromatography with 0~80% ethyl acetate in petroleum ether to afford 2-methyl-6-[1-(oxan-2-yl)indazol-3-yl]-1,5-naphthyridine (60 mg, 55%) as a light yellow solid. MS m/z 345.2 [M+1]$^+$.

Step 4: To a solution of 2-methyl-6-[1-(oxan-2-yl)indazol-3-yl]-1,5-naphthyridine (60 mg, 0.17 mmol) in dichloromethane (3 mL) was added trifluoroacetic acid (2 mL) dropwise at 0° C. The mixture was stirred at room temperature for 16 h. The resulting mixture was concentrated under vacuum. The residue was diluted with water and basified with sodium bicarbonate to pH 7. The mixture was extracted with dichloromethane. The combined organic layers were washed with brine, dried over anhydrous sodium sulfate, filtered and concentrated under vacuum. The crude product was purified by Prep-HPLC [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 37% B to 53% B in 7 min] to afford 2-(1H-indazol-3-yl)-6-methyl-1,5-naphthyridine (22.9 mg, 50%) as an off-white solid.

Example 16

2-(1H-indazol-3-yl)-6-methoxy-1,5-naphthyridine

Step 1: To a mixture of 6-[1-(oxan-2-yl)indazol-3-yl]-1H-1,5-naphthyridin-2-one (380 mg, 1.10 mmol) and silver carbonate (303 mg, 1.10 mmol) in N,N-Dimethylformamide (5 mL) was added iodomethane (311 mg, 2.20 mmol) dropwise at 0° C. The mixture was stirred at 50° C. for overnight. The reaction mixture was diluted with water and extracted with ethyl acetate. The combined organic layers were washed with brine, dried over anhydrous sodium sulfate, filtered and concentrated under vacuum. The residue was purified by flash column chromatography with 0~100% ethyl acetate in petroleum ether to afford 2-methoxy-6-[1-(oxan-2-yl)indazol-3-yl]-1,5-naphthyridine (100 mg, 25%) as an off-white solid. MS m/z 361.1 [M+1]$^+$.

Step 2: To a solution of 2-methoxy-6-[1-(oxan-2-yl)indazol-3-yl]-1,5-naphthyridine (100 mg, 0.27 mmol) in dichloromethane (3 mL) was added trifluoroacetic acid (2 mL). The mixture was stirred at room temperature overnight and then was concentrated under vacuum. The residue was diluted with water and basified using sodium bicarbonate to pH 7. The mixture was extracted with dichloromethane. The combined organic layers were washed with brine, dried over anhydrous sodium sulfate, filtered and concentrated under vacuum. The crude product was purified by Prep-HPLC [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 5% B to 66% B in 7 min] to afford 2-(1H-indazol-3-yl)-6-methoxy-1,5-naphthyridine (7.7 mg, 10%) as a white solid.

Example 17

2-(1H-indazol-3-yl)-6-methoxy-1,5-naphthyridine

Step 1: Purification of the reaction mixture of step 1 described in example 7 also afforded 1-methyl-6-[1-(oxan-2-yl)indazol-3-yl]-1,5-naphthyridin-2-one (40 mg, 10%) as an brown solid. MS m/z 361.1 [M+1]$^+$.

Step 2: Followed the procedure described in step-2 of example 7 and purified by Prep-HPLC [Column: XBridge Shield RP18 OBD Column, 30150 mm, 5 um; Mobile Phase A: water (10 mmol/L ammonium bicarbonate), Mobile Phase B: acetonitrile; Flow rate: 60 mL/min; Gradient: 46% B to 76% B in 7 min] to afford 6-(1H-indazol-3-yl)-1-methyl-1,5-naphthyridin-2-one (6.6 mg, 21%) as an off-white solid.

Example 18

2-(1H-indazol-3-yl)-6-methyl-1,6-naphthyridin-5(6H)-one

Step 1: To a solution of methyl 6-chloro-2-methylnicotinate (1000 mg, 5.38 mmol) in dioxane (10 mL) and water (2 mL) were added 1-(oxan-2-yl)-3-(4,4,5,5-tetramethyl-1,3,2-dioxaborolan-2-yl)indazole (B5) (2600 mg, 8.08 mmol), potassium carbonate (2200 mg, 16.13 mmol) and [1,1'-bis(diphenylphosphino)ferrocene]dichloropalladium(II) (394 mg, 0.54 mmol) under nitrogen atmosphere. The mixture was heated at 100° C. for 16 h. The reaction mixture was concentrated under vacuum. The residue was purified by flash column chromatography with 0~20% ethyl acetate in petroleum ether to afford methyl 2-methyl-6-(1-(tetrahydro-2H-pyran-2-yl)-1H-indazol-3-yl)nicotinate (1800 mg, 95%) as a yellow solid. MS m/z 352.2 [M+1]$^+$.

Step 2: To a solution of methyl 2-methyl-6-(1-(tetrahydro-2H-pyran-2-yl)-1H-indazol-3-yl)nicotinate (1800 mg, 5.11 mmol) in N,N-Dimethylformamide (10 mL) was added sodium hydride (443 mg, 11.07 mmol, 60% in mineral oil) at 0° C. After stirring for 30 min, 1,3,5-triazine (876 mg, 10.81 mmol) was added to above mixture. The resulting solution was heated at 100° C. for 2 h with stirring. The reaction was quenched with ice-water and extracted with ethyl acetate. The organic layers were washed by brine, then dried over anhydrous sodium sulfate. The solids were filtered off. The filtrate was concentrated under reduced pressure to afford 2-[1-(oxan-2-yl)indazol-3-yl]-6H-1,6-naphthyridin-5-one (1800 mg, crude) as a yellow solid. MS m/z 347.1 [M+1]$^+$.

Step 3: To a solution of 2-[1-(oxan-2-yl)indazol-3-yl]-6H-1,6-naphthyridin-5-one (200 mg, crude from step 2) in N,N-Dimethylformamide (5 mL) was added silver carbonate (159 mg, 0.57 mmol). The mixture was stirred at 55° C. for 1 h. Then the mixture was cooled to room temperature and iodomethane (82 mg, 0.58 mmol) was added. The mixture was stirred at room temperature for 2 h. The reaction mixture was diluted with ethyl acetate and washed with water and brine. The organic layer was dried over anhydrous sodium sulfate, filtered and concentrated under vacuum. The residue was purified by flash column chromatography with 0~50% ethyl acetate in petroleum ether to afford 6-methyl-2-(1-(tetrahydro-2H-pyran-2-yl)-1H-indazol-3-yl)-1,6-naphthyridin-5(6H)-one (200 mg, 97% over 2 steps) as a yellow solid. MS m/z 361.2 [M+1]$^+$.

Step 4: To a solution of 6-methyl-2-(1-(tetrahydro-2H-pyran-2-yl)-1H-indazol-3-yl)-1,6-naphthyridin-5(6H)-one (100 mg, 0.28 mmol) in dichloromethane (2 mL) was added trifluoroacetic acid (3 mL). The resulting solution was stirred at room temperature for 2 h. The mixture was concentrated under vacuum. The residue was basified using saturated sodium bicarbonate aqueous solution to pH 8. The mixture was extracted with dichloromethane. The organic layer was dried over anhydrous sodium sulfate, filtered and concentrated under vacuum. The crude product was purified by Prep-HPLC (Method B) [Column: Xselect CSH OBD Column 30150 mm 5 um; Mobile Phase A: water (0.1% formic acid), Mobile Phase B: acetonitrile; Gradient: 24% B to 46% B in 7 min] to afford 2-(1H-indazol-3-yl)-6-methyl-1,6-naphthyridin-5(6H)-one (19.8 mg, 25%) as a white solid.

Example 19

2-(1H-indazol-3-yl)-5-methyl-1,6-naphthyridine

Step 1: To a solution of 2-[1-(oxan-2-yl)indazol-3-yl]-6H-1,6-naphthyridin-5-one (from step 2 of example 11) (200 mg, 0.57 mmol) and pyridine (91 mg, 1.15 mmol) in dichloromethane (5 mL) was added trifluoromethanesulfonic anhydride (244 mg, 0.86 mmol) slowly at 0° C. The mixture was stirred at room temperature for 2 h. The reaction was quenched with water and extracted with dichloromethane. The organic layers were dried over anhydrous sodium sulfate, filtered and concentrated under reduced pressure to afford 2-[1-(oxan-2-yl)indazol-3-yl]-1,6-naphthyridin-5-yl trifluoromethanesulfonate (100 mg, crude) as a brown solid. MS m/z 479.1 [M+1]$^+$.

Step 2: To a degassed solution of 2-[1-(oxan-2-yl)indazol-3-yl]-1,6-naphthyridin-5-yl trifluoromethanesulfonate (100 mg, crude product from step 1) in dioxane (4 mL) were added methylboronic acid (25 mg, 0.41 mmol), potassium carbonate (86 mg, 0.62 mmol) and palladium(0)tetrakis (triphenylphosphine) (24 mg, 0.021 mmol). The mixture was stirred at 90° C. overnight. The reaction mixture was diluted with water and extracted with ethyl acetate. The organic layers were dried over anhydrous sodium sulfate, filtered and concentrated under reduced pressure to afford 5-methyl-2-[1-(oxan-2-yl)indazol-3-yl]-1,6-naphthyridine (50 mg, crude) as a brown solid. MS m/z 345.2 [M+1]$^+$.

Step 3: To a solution of 5-methyl-2-[1-(oxan-2-yl)indazol-3-yl]-1,6-naphthyridine (50 mg, crude product from step 2) in dichloromethane (2 mL) was added trifluoroacetic acid (3 mL). The mixture was stirred at room temperature for 2 h. The resulting solution was stirred at room temperature for 2 h. The mixture was concentrated under vacuum. The residue was basified with saturated sodium bicarbonate aqueous solution to pH 8. The mixture was extracted with dichloromethane. The organic layer was dried over anhydrous sodium sulfate, filtered and concentrated under vacuum. The crude product was purified by Prep-HPLC (Method B) [Column: Xselect CSH OBD Column 30*150 mm 5 um; Mobile Phase A: water (0.1% formic acid), Mobile Phase B: acetonitrile; Flow rate: 60 mL/min; Gradient: 20% B to 70% B in 10 min] to afford 2-(1H-indazol-3-yl)-5-methyl-1,6-naphthyridine (7.9 mg, 5% over 3 steps) as a white solid.

Example 20

2-(1H-indazol-3-yl)-5,6,7,8-tetrahydro-1,7-naphthyridine

Step 1: To a mixture of 2-chloro-5,6,7,8-tetrahydro-1,7-naphthyridine (270 mg, 1.60 mmol) and triethylamine (486 mg, 4.85 mmol) in dichloromethane was added di(tert-butyl) carbonate (1200 mg, 5.55 mmol) at room temperature. The mixture was stirred at 60° C. for 4 h. The reaction mixture was concentrated under reduced pressure. The residue was purified by flash column chromatography with 0~50% ethyl acetate in petroleum ether to afford tert-butyl 2-chloro-6,8-dihydro-5H-1,7-naphthyridine-7-carboxylate (210 mg, 49%) as a colorless oil. MS m/z 269.1 [M+1]$^+$.

Step 2: A degassed mixture of tert-butyl 2-chloro-6,8-dihydro-5H-1,7-naphthyridine-7-carboxylate (90 mg, 0.33 mmol), 1-(tetrahydro-2H-pyran-2-yl)-3-(4,4,5,5-tetramethyl-1,3,2-dioxaborolan-2-yl)-1H-indazole (101 mg, 0.31 mmol), [1,1'-bis(diphenylphosphino)ferrocene]-dichloropalladium(II) (25 mg, 0.031 mmol) and potassium carbonate (93 mg, 0.67 mmol) in 1,4-dioxane (5 mL)/water (0.5 mL) was stirred at 100° C. for 16 h under nitrogen atmosphere. The reaction mixture was concentrated under reduced pressure. The residue was purified by flash column chromatography with 0~70% ethyl acetate in petroleum ether to afford tert-butyl 2-[1-(oxan-2-yl)indazol-3-yl]-6,8-dihydro-5H-1,7-naphthyridine-7-carboxylate (100 mg, 69%) as a colorless oil. MS m/z 435.3 [M+1]$^+$.

Step 3: To a solution of tert-butyl 2-[1-(oxan-2-yl)indazol-3-yl]-6,8-dihydro-5H-1,7-naphthyridine-7-carboxylate (100 mg, 0.23 mmol) in dichloromethane (3 mL) was added trifluoroacetic acid (1 mL). The mixture was stirred at room temperature for 16 h. The reaction mixture was concentrated under reduced pressure. The residue was basified with saturated sodium bicarbonate aqueous solution to pH 8. The mixture was extracted with dichloromethane. The organic layer was concentrated under vacuum. The residue was purified by reverse phase flash column chromatography with 10-50% acetonitrile in water to afford 2-(1H-indazol-3-yl)-5,6,7,8-tetrahydro-1,7-naphthyridine (33.4 mg, 58%) as a white solid.

Example 21

1-[2-(1H-indazol-3-yl)-6,8-dihydro-5H-1,7-naphthyridin-7-yl]ethanone

Step 1: To a mixture of 2-(1H-indazol-3-yl)-5,6,7,8-tetrahydro-1,7-naphthyridine (118 mg, 0.47 mmol) and triethylamine (143 mg, 1.41 mmol) in dichloromethane was added acetic anhydride (48 mg, 0.47 mmol) at 0° C. The mixture was stirred at 0° C. for 8 h. The mixture was concentrated under vacuum. The residue was purified by prep-HPLC (Method A) [Column: XBridge Prep OBD C18 Column, 30*150 mm 5 um; Mobile Phase A: water (10 mmol/L ammonium bicarbonate), Mobile Phase B: acetonitrile; Flow rate: 60 mL/min; Gradient: 37% B to 67% B in 7 min] to afford 1-[2-(1H-indazol-3-yl)-6,8-dihydro-5H-1,7-naphthyridin-7-yl]ethanone (22.8 mg, 17%) as a light yellow solid.

Example 22

2-(1H-indazol-3-yl)-5,6,7,8-tetrahydroquinolin-5-amine

Step 1: To a stirred solution of tert-butyl N-(2-chloro-5,6,7,8-tetrahydroquinolin-5-yl)carbamate (350 mg, 1.23 mmol) and 1-(oxan-2-yl)-3-(4,4,5,5-tetramethyl-1,3,2-dioxaborolan-2-yl)indazole (Intermediate B5) (500 mg, 1.52 mmol) in dioxane (10 mL) and water (1 mL) were added [1,1'-bis(diphenylphosphino)-ferrocene]dichloropalladium (II) (100 mg, 0.13 mmol) and potassium carbonate (370 mg, 2.67 mmol) at room temperature. The mixture was stirred at 90° C. under nitrogen atmosphere for 14 h. The mixture was concentrated under reduced pressure. The residue was purified by flash column chromatography with 0~40% ethyl acetate in petroleum ether to afford tert-butyl N-[2-[1-(oxan-2-yl)indazol-3-yl]-5,6,7,8-tetrahydroquinolin-5-yl]carbamate (370 mg, 66%) as a yellow solid. MS m/z 449.2 [M+1]$^+$.

Step 2: To a stirred solution of tert-butyl N-[2-[1-(oxan-2-yl)indazol-3-yl]-5,6,7,8-tetrahydroquinolin-5-yl]carbamate (482 mg, 1.07 mmol) in dichloromethane (15 mL) was added trifluoroacetic acid (5 mL) slowly at room temperature. The mixture was stirred at room temperature for 14 h. The mixture was concentrated under reduced pressure. The residue was purified by reverse flash chromatography with 10-50% acetonitrile in water over 50 min to afford 2-(1H-indazol-3-yl)-5,6,7,8-tetrahydroquinolin-5-amine (17.9 mg, 6%) as a white solid.

Example 23

N-[2-(1H-indazol-3-yl)-5,6,7,8-tetrahydroquinolin-5-yl]acetamide

Step 1: To a solution of 2-(1H-indazol-3-yl)-5,6,7,8-tetrahydroquinolin-5-amine (51 mg, 0.19 mmol) and triethylamine (42 mg, 0.41 mmol) in dichloromethane (5 mL) was added acetic anhydride (19 mg, 0.18 mmol) at 0° C. The mixture was stirred at 0° C. for 1 h. The mixture was concentrated under vacuum. The residue was purified by (Method A) Prep-HPLC [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 22% B to 57% B in 7 min] to afford N-[2-(1H-indazol-3-yl)-5,6,7,8-tetrahydroquinolin-5-yl]acetamide (29.1 mg, 49%) as a white solid.

Example 24

6-(5,6-difluoro-1H-indazol-3-yl)-1-methyl-1,2,3,4-tetrahydro-1,5-naphthyridine

Step 1: To a solution of 6-(5,6-difluoro-1H-indazol-3-yl)-1,2,3,4-tetrahydro-1,5-naphthyridine (Example 21) (90 mg, 0.31 mmol) in methanol (2 mL) were added sodium cyanoborohydride (40 mg, 0.63 mmol), glacial acetic acid (20 uL) and formaldehyde (0.1 mL, 33% in water). The reaction mixture was stirred at room temperature for 2 h. The reaction mixture was concentrated. The residue was purified by Prep-HPLC [Column: XBridge Shield RP18 OBD Column, 30150 mm, 5 um; Mobile Phase A: water (10 mmol/L ammonium bicarbonate), Mobile Phase B: acetonitrile; Flow rate: 60 mL/min; Gradient: 48% B to 76% B in 7 min] to afford 6-(5,6-difluoro-1H-indazol-3-yl)-1-methyl-1,2,3,4-tetrahydro-1,5-naphthyridine (6.8 mg, 7%) as a white solid. MS (ESI) calculated for ($C_{16}H_{14}F_2N_4$) [M+1]$^+$, 301.1; found, 301.1. $^1$H NMR (300 MHz, Methanol-$d_4$) δ 8.34-8.28 (m, 1H), 7.75 (d, J=8.7 Hz, 1H), 7.71-7.35 (m, 1H), 7.05 (d, J=8.7 Hz, 1H), 3.36-3.29 (m, 2H), 3.06-3.02 (m, 2H), 2.97 (s, 3H), 2.18-2.05 (m, 2H).

Example 25

1-[6-(5,6-difluoro-1H-indazol-3-yl)-3,4-dihydro-2H-1,5-naphthyridin-1-yl]ethanone Step 1: To a solution of 2-(5,6-difluoro-1H-indazol-3-yl)-5,6,7,8-tetrahydroquinolin-5-amine (80 mg, 0.28 mmol) and triethylamine (56 mg, 0.56 mmol) in dichloromethane (1 mL) was added acetic anhydride (28 mg, 0.28 mmol). The mixture was stirred at room temperature for 2 h. The mixture was concentrated under vacuum. The crude product was purified by (Method C) Prep-HPLC [Column: Xselect CSH OBD Column 30*150 mm 5 um; Mobile Phase A: water (0.1% formic acid), Mobile Phase B: acetonitrile; Flow rate: 60 mL/min; Gradient: 20% B to 60% B in 10 min] to afford 1-[6-(5,6-difluoro-1H-indazol-3-yl)-3,4-dihydro-2H-1,5-naphthyridin-1-yl]ethanone (24 mg, 24%) as a white solid.

Example 26

2-(5,6-difluoro-1H-indazol-3-yl)-1,5-naphthyridine

Step 1: A mixture of 5,6-difluoro-1-(oxan-2-yl)-3-(4,4,5,5-tetramethyl-1,3,2-dioxaborolan-2-yl)indazole (140 mg, 0.38 mmol), 2-chloro-1,5-naphthyridine (66 mg, 0.40 mmol), [1,1'-bis(diphenylphosphino)-ferrocene]dichloropalladium(II) (31 mg, 0.04 mmol) and potassium carbonate (121 mg, 0.87 mmol) in dioxane (5 mL)/water (0.2 mL) was heated at 100° C. for 5 h. The mixture was concentrated under vacuum. The residue was purified by flash column chromatography with 0~30% ethyl acetate in petroleum ether to afford 2-[5,6-difluoro-1-(oxan-2-yl)indazol-3-yl]-1,5-naphthyridine (85 mg, 60%) as a white solid. MS m/z 367.2 [M+1]$^+$.

Step 2: To a solution of 2-[5,6-difluoro-1-(oxan-2-yl)indazol-3-yl]-1,5-naphthyridine (85 mg, 0.23 mmol) in dichloromethane (3 mL) was added trifluoroacetic acid (1 mL). The mixture was stirred at room temperature for 16 h. The mixture was concentrated under vacuum. The residue was dissolved in N,N-Dimethylformamide (2 mL) and then basified with sodium hydroxide (aq., 2N) to pH 9. The mixture was purified by reverse phase flash column chromatography with 10-70% acetonitrile in water to afford 2-(5,6-difluoro-1H-indazol-3-yl)-1,5-naphthyridine (26.1 mg, 39%) as an off-white solid.

Example 27

4-(5,6-difluoro-1H-indazol-3-yl)-1,5-naphthyridine

Step 1: A degassed mixture of 4-chloro-1,5-naphthyridine (60 mg, 0.36 mmol), 5,6-difluoro-1-(oxan-2-yl)-3-(4,4,5,5-tetramethyl-1,3,2-dioxaborolan-2-yl)indazole (140 mg, 0.38 mmol), palladium(0)tetrakis(triphenyl-phosphine) (40 mg, 0.03 mmol) and potassium carbonate (146 mg, 1.05 mmol) in dioxane (2 mL) was heated at 100° C. for 16 h. The mixture was concentrated under vacuum. The residue was purified by flash column chromatography with 0~50% ethyl acetate in petroleum ether to afford 4-[5,6-difluoro-1-(oxan-2-yl)indazol-3-yl]-1,5-naphthyridine (130 mg, 97%) as a yellow syrup. MS m/z 367.1 [M+1]$^+$.

Step 2: To a solution of 4-[5,6-difluoro-1-(oxan-2-yl)indazol-3-yl]-1,5-naphthyridine (130 mg, 0.35 mmol) in dichloromethane (5 mL) was added trifluoroacetic acid (2 mL) at room temperature. The mixture was concentrated under vacuum. The mixture was dissolved in N,N-Dimethylformamide (2 mL) and basified with sodium hydroxide (2N, aq.) to pH 9. The mixture was purified by reverse phase flash column chromatography with 10~70% acetonitrile in water to afford 4-(5,6-difluoro-1H-indazol-3-yl)-1,5-naphthyridine (44.8 mg, 44%) as a yellow solid.

Example 28

2-(5,6-difluoro-1H-indazol-3-yl)-6H-1,6-naphthyridin-5-one

Step 1: A mixture of methyl 6-chloro-2-methylpyridine-3-carboxylate (200 mg, 1.08 mmol), 5,6-difluoro-1-(oxan-2-yl)-3-(4,4,5,5-tetramethyl-1,3,2-dioxaborolan-2-yl)indazole (471 mg, 1.29 mmol), [1,1'-bis(diphenyl-phosphino)ferrocene]dichloropalladium(II) (79 mg, 0.10 mmol) and potassium carbonate (298 mg, 2.16 mmol) in dioxane (10 mL)/water (1 mL) was stirred at 100° C. for 16 h. The mixture was concentrated under vacuum. The residue was purified by flash column chromatography with 0~70% ethyl acetate in petroleum ether to afford methyl 6-[5,6-difluoro-1-(oxan-2-yl)indazol-3-yl]-2-methylpyridine-3-carboxylate (400 mg, 96%) as a white solid. MS m/z 388.2 [M+1]$^+$.

Step 2: A mixture of methyl 6-[5,6-difluoro-1-(oxan-2-yl)indazol-3-yl]-2-methylpyridine-3-carboxylate (400 mg, 1.03 mmol), 1,3,5-triazine (92 mg, 1.13 mmol) and potassium tert-butoxide (139 mg, 1.24 mmol) in methyl sulfoxide was stirred at 80° C. for 1 h. The reaction mixture was diluted with water and extracted with ethyl acetate. The combined organic layers were dried over anhydrous sodium sulfate, filtered and concentrated under reduced pressure. The residue was purified by flash column chromatography with 0~80% ethyl acetate in petroleum ether to afford 2-[5,6-difluoro-1-(oxan-2-yl)indazol-3-yl]-6H-1,6-naphthyridin-5-one (390 mg, 99%) as a yellow solid. MS m/z 383.1 [M+1]$^+$.

Step 3: To a mixture of 2-[5,6-difluoro-1-(oxan-2-yl)indazol-3-yl]-6H-1,6-naphthyridin-5-one (100 mg, 0.26 mmol) in dichloromethane was added trifluoroacetic acid (2 mL). The mixture was stirred at room temperature for 16 h. The mixture was concentrated under reduced pressure. The residue was purified by reverse phase flash chromatography with 10~70% acetonitrile in water over 30 min to afford 2-(5,6-difluoro-1H-indazol-3-yl)-6H-1,6-naphthyridin-5-one (5.7 mg, 7%) as a light yellow solid.

Example 29

2-(5,6-difluoro-1H-indazol-3-yl)-6-methyl-1,6-naphthyridin-5-one

Step 1: To a mixture of 2-[5,6-difluoro-1-(oxan-2-yl)indazol-3-yl]-6H-1,6-naphthyridin-5-one (300 mg, 0.78 mmol) and silver carbonate (216 mg, 0.78 mmol) in N,N-dimethyl-formamide was added iodomethane (111 mg, 0.78 mmol) at room temperature. The mixture was stirred at room temperature for 1 h. The reaction mixture was concentrated under vacuum. The residue was purified by flash column chromatography with 0~70% ethyl acetate in petroleum ether to afford 2-[5,6-difluoro-1-(oxan-2-yl)indazol-3-yl]-6-methyl-1,6-naphthyridin-5-one (90 mg, 29%) as a white solid. MS m/z 397.1 [M+1]$^+$.

Step 2: To a mixture of 2-[5,6-difluoro-1-(oxan-2-yl)indazol-3-yl]-6-methyl-1,6-naphthyridin-5-one (90 mg, 0.22 mmol) in dichloromethane (3 mL) was added trifluoroacetic acid (1 mL). The mixture was stirred at room temperature for 16 h. The mixture was concentrated under reduced pressure. The residue was purified by prep-HPLC [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 28% B to 75% B in 7 min] to afford 2-(5,6-difluoro-1H-indazol-3-yl)-6-methyl-1,6-naphthyridin-5-one (39.9 mg, 56%) as a light yellow solid.

Example 30

2-(5,6-difluoro-1H-indazol-3-yl)-5,6,7,8-tetrahydro-1,6-naphthyridine

Followed the procedure of example 1 described above and purified by Prep-HPLC (Method A) to afford 2-(5,6-difluoro-1H-indazol-3-yl)-5,6,7,8-tetrahydro-1,6-naphthyridine (90 mg, 35% over 2 steps) as a light yellow solid from 5,6-difluoro-1-(oxan-2-yl)-3-(4,4,5,5-tetramethyl-1,3,2-dioxaborolan-2-yl)indazole (Intermediate B6) (366 mg, 1.01 mmol).

Example 31

1-[2-(5,6-difluoro-1H-indazol-3-yl)-7,8-dihydro-5H-1,6-naphthyridin-6-yl]ethanone Step 1: To a mixture of 2-(5,6-difluoro-1H-indazol-3-yl)-5,6,7,8-tetrahydro-1,6-naphthyridine (60 mg, 0.21 mmol) and triethylamine (64 mg, 0.63 mml) in dichloromethane (2 mL) was added acetic anhydride (21 mg, 0.21 mmol). The mixture was stirred at room temperature for 16 h. The mixture was concentrated under reduced pressure. The residue was purified by reverse phase flash chromatography with 10-60% acetonitrile in water over 30 min to afford 1-[2-(5,6-difluoro-1H-indazol-3-yl)-7,8-dihydro-5H-1,6-naphthyridin-6-yl]ethanone (17.4 mg, 25%) as a white solid.

Example 32

2-(5,6-difluoro-1H-indazol-3-yl)-5,6,7,8-tetrahydro-1,7-naphthyridine

Followed the procedure of example 1 described above and purified by Prep-HPLC (Method A) to afford 2-(5,6-difluoro-1H-indazol-3-yl)-5,6,7,8-tetrahydro-1,7-naphthyridine (14.8 mg, 24% over 2 steps) as a white solid. from tert-butyl 2-chloro-6,8-dihydro-5H-1,7-naphthyridine-7-carboxylate (Intermediate A8) (56 mg, 0.21 mmol).

Example 33

2-(5,6-difluoro-1H-indazol-3-yl)-6-fluoro-5-(1,3,4-oxadiazol-2-yl)quinoline

Followed the procedure of example 1 described above and purified by Prep-HPLC (Method A) to afford 2-(5,6-difluoro-1H-indazol-3-yl)-6-fluoro-5-(1,3,4-oxadiazol-2-yl)-quinoline (3.3 mg, 2% over 2 steps) as a white solid from 5,6-difluoro-1-(oxan-2-yl)-3-(4,4,5,5-tetramethyl-1,3,2-dioxaborolan-2-yl)indazole (Intermediate B6) (241 mg, 0.66 mmol) and Intermediate A9.

Example 34

2-(2-(5,6-difluoro-1H-indazol-3-yl)-6-fluoroquinolin-7-yl)-1,3,4-oxadiazole

Purification of the reaction mixture of Example 33 described above also afforded 2-(2-(5,6-difluoro-1H-indazol-3-yl)-6-fluoroquinolin-7-yl)-1,3,4-oxadiazole (4.1 mg, 2% over 2 steps) as a white solid.

Example 35

2-(2-(5,6-difluoro-1H-indazol-3-yl)quinolin-5-yl)-1,3,4-oxadiazole

Followed the procedure of example 1 described above and the crude product was purified by Prep-HPLC (Method A) to afford 2-(2-(5,6-difluoro-1H-indazol-3-yl)quinolin-5-yl)-1,3,4-oxadiazole (1.5 mg, 2% over 2 steps) as a white solid from 5,6-difluoro-1-(oxan-2-yl)-3-(4,4,5,5-tetramethyl-1,3,2-dioxaborolan-2-yl)indazole (Intermediate B6) (190 mg, 0.52 mmol) and Intermediate A10.

Example 36

1-(6-(5,6-difluoro-1H-indazol-3-yl)-3,4-dihydro-1,5-naphthyridin-1(2H)-yl)-2-hydroxyethan-1-one Step 1: To a solution of 5,6-difluoro-1-(oxan-2-yl)indazol-3-ylboronic acid (300 mg, 1.06 mmol) in dioxane (5 mL)/water (0.1 mL) were added 2-chloro-5,6,7,8-tetrahydro-1,5-naphthyridine (180 mg, 1.07 mmol), [1,1'-bis(diphenylphosphino)ferrocene]dichloro-palladium(II) (71 mg, 0.10 mmol) and potassium carbonate (460 mg, 3.33 mmol), under $N_2$. The mixture was stirred at 100° C. overnight. The mixture was concentrated under vacuum. The residue was purified by flash column chromatography with 0~40% ethyl acetate in petroleum ether to afford 2-[5,6-difluoro-1-(oxan-2-yl)indazol-3-yl]-5,6,7,8-tetrahydro-1,5-naphthyridine (220 mg, 55%) as a yellow solid. MS m/z 371.2 $[M+1]^+$.

Step 2: To a solution of 2-[5,6-difluoro-1-(oxan-2-yl)indazol-3-yl]-5,6,7,8-tetrahydro-1,5-naphthyridine (150 mg, 0.40 mmol) and triethylamine (131 mg, 1.30 mmol) in dichloromethane (5 mL) was added (benzyloxy)acetyl chloride (156 mg, 0.80 mmol) at 0° C. The mixture was stirred at room temperature for 2 h. The mixture was concentrated under vacuum. The residue was purified by flash column chromatography with 0~40% ethyl acetate in petroleum ether to afford 2-(benzyloxy)-1-[6-[5,6-difluoro-1-(oxan-2-yl)indazol-3-yl]-3,4-dihydro-2H-1,5-naphthyridin-1-yl]ethanone (200 mg, 57%) as a yellow oil. MS m/z 519.2 $[M+1]^+$.

Step 3: To a solution of 2-(benzyloxy)-1-[6-[5,6-difluoro-1-(oxan-2-yl)indazol-3-yl]-3,4-dihydro-2H-1,5-naphthyridin-1-yl]ethanone (90 mg, 0.17 mmol) in dichloromethane (2 mL) was added trifluoroacetic acid (3 mL). The mixture was stirred at room temperature for 2 h. The mixture was basified with saturated sodium bicarbonate aqueous solution and extracted with dichloromethane. The organic layer was dried over anhydrous sodium sulfate, filtered and concentrated under vacuum. The residue was dissolved in methanol (2 mL). Then Pd/C (20 mg, 10%) added to above mixture. The mixture was stirred at room temperature for 2 h under hydrogen atmosphere. The solids were filtered off. The filtrate was concentrated. The residue was purified by reverse phase flash column chromatography with 5~30% acetonitrile in water to afford 21-(6-(5,6-difluoro-1H-indazol-3-yl)-3,4-dihydro-1,5-naphthyridin-1(2H)-yl)-2-hydroxyethan-1-one (3 mg, 9%) as a white solid.

Example 37

1-(6-(5,6-difluoro-1H-indazol-3-yl)-3,4-dihydro-1,5-naphthyridin-1 (2H)-yl)-2-methoxyethan-1-one Step 1: To a solution of 6-(5,6-difluoro-1-(tetrahydro-2H-pyran-2-yl)-1H-indazol-3-yl)-1,2,3,4-tetrahydro-1,5-naphthyridine (60 mg, 0.16 mmol) and triethylamine (49 mg, 0.48 mmol). in dichloromethane (2 mL) was added 2-methoxyacetyl chloride (21 mg, 0.19 mmol) at 0° C. The mixture was stirred at room temperature for 2 h. The reaction mixture was diluted with water and extracted with ethyl acetate. The organic layer was dried over anhydrous sodium sulfate, filtered and concentrated under vacuum to afford 1-(6-(5,6-difluoro-1-(tetrahydro-2H-pyran-2-yl)-1H-indazol-3-yl)-3,4-dihydro-1,5-naphthyridin-1(2H)-yl)-2-methoxyethan-1-one (70 mg, crude) as a yellow solid. MS m/z 443.2 $[M+1]^+$.

Step 2: To a solution of 1-(6-(5,6-difluoro-1-(tetrahydro-2H-pyran-2-yl)-1H-indazol-3-yl)-3,4-dihydro-1,5-naphthyridin-1(2H)-yl)-2-methoxyethan-1-one (70 mg, crude from step 1) in dichloromethane (2 mL) was added trifluoroacetic acid (3 mL). The mixture was stirred at room temperature for 2 h. The mixture was concentrated under vacuum. The residue was diluted with water and basified with sodium bicarbonate to pH 8. The mixture was extracted with dichloromethane. The organic layer was dried over anhydrous sodium sulfate, filtered and concentrated under vacuum. The residue was purified by reverse phase flash column chromatography with 5~30% acetonitrile in water over 30 min to afford 1-(6-(5,6-difluoro-1H-indazol-3-yl)-3,4-dihydro-1,5-naphthyridin-1(2H)-yl)-2-methoxyethan-1-one (27 mg, 47% over 2 steps) as a white solid.

Example 38

6-(5,6-difluoro-1H-indazol-3-yl)-N-methyl-3,4-dihydro-2H-1,5-naphthyridine-1-carboxamide Step 1: To a solution of 2-[5,6-difluoro-1-(oxan-2-yl)indazol-3-yl]-5,6,7,8-tetrahydro-1,5-naphthyridine (60 mg, 0.16 mmol) in pyridine (1 mL) was added 2,5-dioxopyrrolidin-1-yl N-methylcarbamate (42 mg, 0.24 mmol). The mixture was stirred at 50° C. for 24 h. The reaction mixture was diluted with ethyl acetate and washed with HCl (aq., 1N). The organic layer was dried over anhydrous sodium sulfate, filtered and concentrated under vacuum to afford 6-[5,6-difluoro-1-(oxan-2-yl)indazol-3-yl]-N-methyl-3,4-dihydro-2H-1,5-naphthyridine-1-carboxamide (65 mg, crude) as a yellow solid. MS m/z 428.2 $[M+1]^+$.

Step 2: To a solution of 6-[5,6-difluoro-1-(oxan-2-yl)indazol-3-yl]-N-methyl-3,4-dihydro-2H-1,5-naphthyridine-1-carboxamide (60 mg, 0.14 mmol) in dichloromethane (2 mL) was added trifluoroacetic acid (3 mL). The mixture was stirred at room temperature for 2 h. The mixture was concentrated under vacuum. The residue was diluted with water and basified with sodium bicarbonate to pH 8. The mixture was extracted with dichloromethane. The organic layer was dried over anhydrous sodium sulfate, filtered and concentrated under vacuum. The crude product was purified by Prep-HPLC (Method A) [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 33% B to 49% B in 7 min] to afford 6-(5,6-difluoro-1H-indazol-3-yl)-N-methyl-3,4-dihydro-2H-1,5-naphthyridine-1-carboxamide (7.2 mg, 13% over 2 steps) as a white solid.

Example 39

5,6-difluoro-3-[5H,6H,8H-pyrano[3,4-b]pyridin-2-yl]-1H-indazole

Followed the procedure of example 1 described above and the crude product was purified by reverse phase flash column chromatography with 10~80% acetonitrile in water to afford 2-(2-(5,6-difluoro-1H-indazol-3-yl)quinolin-5-yl)-1,3,4-oxadiazole (47.3 mg, 45% over 2 steps) as a white solid from 5,6-difluoro-1-(oxan-2-yl)-3-(4,4,5,5-tetramethyl-1,3,2-dioxaborolan-2-yl)indazole (130 mg, 0.35 mmol).

Example 40

2-(5,6-difluoro-1H-indazol-3-yl)-7,8-dihydro-5H-pyrano[4,3-b]pyridine

Followed the procedure of example 1 described above and the crude product was purified by Prep-HPLC (Method B) to afford 2-(5,6-difluoro-1H-indazol-3-yl)-7,8-dihydro-5H-pyrano[4,3-b]pyridine (19 mg, 11% over 2 steps) as a white solid from 5,6-difluoro-1-(oxan-2-yl)-3-(4,4,5,5-tetramethyl-1,3,2-dioxaborolan-2-yl)indazole (257 mg, 0.71 mmol).

Example 41

2-(5,6-difluoro-1H-indazol-3-yl)-6H,7H-pyrrolo[3,4-b]pyridin-5-one

Followed the procedure of example 1 described above and the crude product was purified by Prep-HPLC (Method A) to afford 2-(5,6-difluoro-1H-indazol-3-yl)-6H,7H-pyrrolo[3,4-b]pyridin-5-one (2 mg, 3% over 2 steps) as a white solid from 5,6-difluoro-1-(oxan-2-yl)-3-(4,4,5,5-tetramethyl-1,3, 2-dioxaborolan-2-yl)indazole (130 mg, 0.36 mmol).

Example 42

2-(5,6-difluoro-1H-indazol-3-yl)-6-methyl-7H-pyrrolo[3,4-b]pyridin-5-one

Followed the procedure of example 1 described above and the crude product was purified by Prep-HPLC (Method A) to afford 2-(5,6-difluoro-1H-indazol-3-yl)-6-methyl-7H-pyrrolo[3,4-b]pyridin-5-one (24.9 mg, 20% over 2 steps) as a white solid from 2-chloro-6-methyl-7H-pyrrolo[3,4-b]pyridin-5-one (80 mg, 0.43 mmol).

Example 43

2-(5-fluoro-7-methyl-1H-indazol-3-yl)-5,6,7,8-tetrahydro-1,5-naphthyridine

Followed the procedure of example 1 described above and the crude product was purified by Prep-HPLC (Method A) to afford 2-(5-fluoro-7-methyl-1H-indazol-3-yl)-5,6,7,8-tetrahydro-1,5-naphthyridine (22.4 mg, 12% over 2 steps) as a light yellow solid from 5-fluoro-7-methyl-1-(oxan-2-yl)indazol-3-ylboronic acid (230 mg, 0.82 mmol).

Example 44

2-(5,6-difluoro-1H-indazol-3-yl)-6-fluoro-5-(1,3,4-oxadiazol-2-yl)quinoline

Followed the procedure of example 1 described above and the crude product was purified by Prep-HPLC (Method A) to afford 2-(5,6-difluoro-1H-indazol-3-yl)-6-fluoro-5-(1,3,4-oxadiazol-2-yl)quinoline (9.8 mg, 9% over 2 steps) as a light yellow solid from 5-fluoro-6-methyl-1-(oxan-2-yl)indazol-3-ylboronic acid (120 mg, 0.09 mmol).

Example 45

2-(6-fluoro-5-methyl-1H-indazol-3-yl)-5,6,7,8-tetrahydro-1,5-naphthyridine

Followed the procedure of example 1 described above and the crude product was purified by Prep-HPLC (Method A) to afford 2-(6-fluoro-5-methyl-1H-indazol-3-yl)-5,6,7,8-tetrahydro-1,5-naphthyridine (14.3 mg, 12% over 2 steps) as an off-white solid from 6-fluoro-5-methyl-1-(oxan-2-yl)indazol-3-ylboronic acid (100 mg, 0.36 mmol).

Example 46

2-(5,6-difluoro-1H-indazol-3-yl)-8-methyl-5,6,7,8-tetrahydro-1,5-naphthyridine

Step-1: To a solution of 6-chloro-4-methyl-1-(4-methylbenzenesulfonyl)-3,4-dihydro-2H-1,5-naphthyridine (300 mg, 0.89 mmol), 5,6-difluoro-1-(oxan-2-yl)indazol-3-ylboronic acid (251 mg, 0.89 mmol) and potassium carbonate (246 mg, 1.78 mmol) in dioxane (10 mL) and water (1 mL) was added palladium(0)tetrakis(triphenylphosphine) (103 mg, 0.09 mmol). The mixture was heated to 100° C. and stirred overnight under nitrogen atmosphere. The resulting mixture was concentrated under vacuum. The residue was purified by flash column chromatography with 0~80% ethyl acetate in petroleum ether to afford 6-[5,6-difluoro-1-(oxan-2-yl)indazol-3-yl]-4-methyl-1-(4-methylbenzenesulfonyl)-3,4-dihydro-2H-1,5-naphthyridine (400 mg, 83%) as a light yellow solid. MS m/z 539.2 [M+1]$^+$.

Step-2: To a mixture of 6-[5,6-difluoro-1-(oxan-2-yl)indazol-3-yl]-4-methyl-1-(4-methylbenzenesulfonyl)-3,4-dihydro-2H-1,5-naphthyridine (400 mg, 0.74 mmol) in dichloromethane (6 mL) was added trifluoroacetic acid (4 mL). After stirring at room temperature for 16 h, the mixture was concentrated under vacuum. The residue was dissolved in ethanol (2 mL). Then HCl (8 mL, conc.) was added. The mixture was heated to 80° C. and stirred for 16 h. The reaction mixture was concentrated under vacuum. The residue was purified by flash column chromatography with 0~20% methanol in dichloromethane. The product was further purified by Prep-HPLC [Column: XBridge Shield RP18 OBD Column, 30150 mm, 5 um; Mobile Phase A: water (10 mmol/L ammonium bicarbonate), Mobile Phase B: acetonitrile; Flow rate: 60 mL/min; Gradient: 48% B to 59% B in 7 min] to afford 2-(5,6-difluoro-1H-indazol-3-yl)-8-methyl-5,6,7,8-tetrahydro-1,5-naphthyridine (35 mg, 26%) as a white solid.

Example 47

(8S)-2-(5,6-difluoro-1H-indazol-3-yl)-8-methyl-5,6,7,8-tetrahydro-1,5-naphthyridine Racemate 2-(5,6-difluoro-1H-indazol-3-yl)-8-methyl-5,6,7,8-tetrahydro-1,5-naphthyridine (35 mg) was purified by Chiral-Prep-HPLC [Column: CHIRAL ART Cellulose-SB, 2*25 cm, 5 um; Mobile Phase A: hex (8 mmol/L ammonia in methanol)-HPLC, Mobile Phase B: ethanol-HPLC; Flow rate: 20 mL/min; Gradient: 15% B to 15% B in 15 min, RT1: 11.413 min; RT2: 13.314 min] to afford (8S)-2-(5,6-difluoro-1H-indazol-3-yl)-8-methyl-5,6,7,8-tetrahydro-1,5-naphthyridine (8.4 mg) as an off-white solid. The stereochemistry assignment is tentative.

Example 48

(8R)-2-(5,6-difluoro-1H-indazol-3-yl)-8-methyl-5,6,7,8-tetrahydro-1,5-naphthyridine Purification of racemate 2-(5,6-difluoro-1H-indazol-3-yl)-8-methyl-5,6,7,8-tetrahydro-1,5-naphthyridine by Chiral-Prep-HPLC described above also afforded (8R)-2-(5,6-difluoro-1H-indazol-3-yl)-8-methyl-5,6,7,8-tetrahydro-1,5-naphthyridine (10.5 mg) as a light yellow solid with longer retention time The stereochemistry assignment is tentative.

Example 49

6-(5,6-difluoro-1H-indazol-3-yl)-4-methyl-1,2,3,4-tetrahydro-1,7-naphthyridine

Followed the procedure of Example 46 described above and the crude product was purified by reverse phase flash column chromatography with 40~60% acetonitrile in water to afford 6-(5,6-difluoro-1H-indazol-3-yl)-4-methyl-1,2,3,4-tetrahydro-1,7-naphthyridine (18.1 mg, 34%) as an off-white solid from 6-chloro-4-methyl-1-(4-methylbenzenesulfonyl)-3,4-dihydro-2H-1,7-naphthyridine (80 mg, 0.24 mmol).

Example 50

2-(5,6-difluoro-1H-indazol-3-yl)-8,8-dimethyl-6,7-dihydro-5H-1,5-naphthyridine

Followed the procedure of Example 46 described above and the crude product was purified by reverse phase flash column chromatography with 10~70% acetonitrile in water to afford 2-(5,6-difluoro-1H-indazol-3-yl)-8,8-dimethyl-6,7-dihydro-5H-1,5-naphthyridine (24.7 mg, 22% over 2 steps) as a yellow solid from 6-chloro-4,4-dimethyl-1-(4-methylbenzene-sulfonyl)-2,3-dihydro-1,5-naphthyridine (120 mg, 0.34 mmol).

Example 51

2-(5,6-difluoro-1H-indazol-3-yl)-7-methyl-6H,7H-pyrrolo[3,4-b]pyridin-5-one

Step 1: To a solution 2-chloro-6-[(4-methoxyphenyl)methyl]-7-methyl-7H-pyrrolo[3,4-b]pyridin-5-one (50 mg, 0.16 mmol) in dioxane (5 mL) and water (0.5 mL) were added 5,6-difluoro-1-(oxan-2-yl)indazol-3-ylboronic acid (56 mg, 0.19 mmol), potassium carbonate (68 mg, 0.49 mmol) and [1,1'-bis(diphenylphosphino)ferrocene]dichloropalladium(II) (12 mg, 0.02 mmol). The mixture was heated to 100° C. for 4 h under nitrogen atmosphere. The resulting mixture was concentrated under vacuum. The residue was purified by flash column chromatography with 0~35% ethyl acetate in petroleum ether to afford 2-[5,6-difluoro-1-(oxan-2-yl)indazol-3-yl]-6-[(4-methoxyphenyl)methyl]-7-methyl-7H-pyrrolo[3,4-b]pyridin-5-one as (62 mg, 74%) as a yellow solid. MS m/z 505.2 [M+1]$^+$.

Step 2: To a solution of 2-[5,6-difluoro-1-(oxan-2-yl)indazol-3-yl]-6-[(4-methoxyphenyl)methyl]-7-methyl-7H-pyrrolo[3,4-b]pyridin-5-one (62 mg, 0.12 mmol) in trifluoroacetic acid (2 mL) was added trifluoromethanesulfonic acid (50 uL). The mixture was stirred at 70° C. for 2 h. The reaction mixture was concentrated under vacuum. The residue was basified with saturated sodium bicarbonate aqueous solution to pH 8 and extracted with dichloromethane. The organic layer was dried over anhydrous sodium sulfate, filtered and concentrated under vacuum. The crude product was purified by Prep-HPLC [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 30% to 46% in 7 min] to afford 2-(5,6-difluoro-1H-indazol-3-yl)-7-methyl-6H,7H-pyrrolo[3,4-b]pyridin-5-one (7.1 mg, 19%) as a white solid.

Example 52

2-(5,6-difluoro-1H-indazol-3-yl)-7,7-dimethyl-6H-pyrrolo[3,4-b]pyridin-5-one

Followed the procedure of Example 51 described above and the crude product was purified by Prep-HPLC (Method A) to afford 2-(5,6-difluoro-1H-indazol-3-yl)-7,7-dimethyl-6H-pyrrolo[3,4-b]pyridin-5-one (16.8 mg, 12% over 2 steps) as a white solid from 2-chloro-6-[(4-methoxyphenyl)methyl]-7,7-dimethylpyrrolo[3,4-b]pyridin-5-one (130 mg, 0.41 mmol).

Example 53

6-(5,6-difluoro-1H-indazol-3-yl)-2-methylpyridin-3-amine

Followed the procedure of Example 1 described above and the crude product was purified by Prep-HPLC (Method A) to afford 6-(5,6-difluoro-1H-indazol-3-yl)-2-methylpyridin-3-amine (11.1 mg, 30% over 2 steps) as a light yellow solid from 5,6-difluoro-1-(oxan-2-yl)-3-(4,4,5,5-tetramethyl-1,3,2-dioxaborolan-2-yl)indazole (61 mg, 0.17 mmol).

Example 54

6-(5,6-difluoro-1H-indazol-3-yl)-2-ethylpyridin-3-amine

Followed the procedure of Example 1 described above and the crude product was purified by reverse phase flash column chromatography with 5%~40% acetonitrile in water to afford 6-(5,6-difluoro-1H-indazol-3-yl)-2-ethylpyridin-3-amine (30.2 mg, 33% over 2 steps) as a light yellow solid from 6-chloro-2-ethylpyridin-3-amine (60 mg, 0.38 mmol).

Example 55

5,6-difluoro-3-[5H,6H,7H,8H-pyrido[3,2-d]pyrimidin-2-yl]-1H-indazole

Step 1: To a solution of 2-chloropyrido[3,2-d]pyrimidine (120 mg, 0.72 mmol) in dioxane (5 mL) and water (0.5 mL) were added 5,6-difluoro-1-(oxan-2-yl)indazol-3-ylboronic acid (245 mg, 0.87 mmol), [1,1'-bis(diphenylphosphino)ferrocene]dichloropalladium(II) (53 mg, 0.07 mmol) and potassium carbonate (300 mg, 2.17 mmol). The mixture was stirred at 100° C. overnight under nitrogen atmosphere. The mixture was concentrated under vacuum. The residue was purified by flash column chromatography with 0~20% ethyl acetate in petroleum ether to afford 5,6-difluoro-1-(oxan-2-yl)-3-[pyrido[3,2-d]pyrimidin-2-yl]indazole (250 mg, 93%) as an off-white solid. MS m/z 368.1 [M+1]$^+$.

Step 2: To a solution of 5,6-difluoro-1-(oxan-2-yl)-3-[pyrido[3,2-d]pyrimidin-2-yl]indazole (200 mg, 0.54 mmol) in methanol (4 mL) was added PtO$_2$ (50 mg, 0.22 mmol). The mixture was stirred at room temperature overnight under hydrogen atmosphere. The solids were filtered off. The filtrate was concentrated under vacuum to afford 5,6-difluoro-1-(oxan-2-yl)-3-[5H,6H,7H,8H-pyrido[3,2-d]pyrimidin-2-yl]indazole (80 mg, crude) as a yellow solid. MS m/z 372.2 [M+1]$^+$.

Step 3: To a solution of 5,6-difluoro-1-(oxan-2-yl)-3-[5H,6H,7H,8H-pyrido[3,2-d]pyrimidin-2-yl]indazole (80 mg, crude from step 2) in dichloromethane (2 mL) was added trifluoroacetic acid (3 mL). The resulting solution was stirred at room temperature for 2 h. The mixture was concentrated under vacuum. The residue was basified with saturated sodium bicarbonate aqueous solution to pH 8. The mixture was extracted with dichloromethane. The organic layer was dried over anhydrous sodium sulfate, filtered and concentrated under vacuum. The residue was purified by Prep-HPLC [Column, XBridge Prep OBD C18 Column, 30*150 mm 5 um; mobile phase, water (10 mmol/L ammonium bicarbonate) and methanol (60% to 80% in 7 min)] to afford 5,6-difluoro-3-[5H,6H,7H,8H-pyrido[3,2-d]pyrimidin-2-yl]-1H-indazole (13.5 mg, 8% over 2 steps) as a light yellow solid.

Example 56

6-(5,6-difluoro-1H-indazol-3-yl)-1,2,3,4-tetrahydro-1,7-naphthyridine

Followed the procedure of Example 1 described above and the crude product was purified by Prep-HPLC (Method A) to afford 6-(5,6-difluoro-1H-indazol-3-yl)-1,2,3,4-tetrahydro-1,7-naphthyridine (60.1 mg, 23% over 2 steps) as a light yellow solid from 6-chloro-1,2,3,4-tetrahydro-1,7-naphthyridine (180 mg, 1.06 mmol).

Example 57

3-(1H-indazol-3-yl)-5,6,7,8-tetrahydro-1,5-naphthyridine

Step 1: A mixture of 1-benzyl-7-bromo-3,4-dihydro-2H-1,5-naphthyridine (100 mg, 0.33 mmol), 1-(oxan-2-yl)-3-(4,4,5,5-tetramethyl-1,3,2-dioxaborolan-2-yl)indazole (130 mg, 0.39 mmol), [1,1'-bis(diphenyl-phosphino)ferrocene]dichloropalladium(II) (24 mg, 0.03 mmol) and potassium carbonate (91 mg, 0.66 mmol) in dioxane (2 mL) and water (0.2 mL) was stirred at 100° C. for 16 h under nitrogen atmosphere. The reaction mixture was concentrated under reduced pressure. The residue was purified by flash column chromatography with 0~70% ethyl acetate in petroleum ether to afford 1-benzyl-7-[1-(oxan-2-yl)indazol-3-yl]-3,4-dihydro-2H-1,5-naphthyridine (120 mg, 85%) as a brown oil. MS m/z 425.2 [M+1]$^+$.

Step 2: To a solution of 1-benzyl-7-[1-(oxan-2-yl)indazol-3-yl]-3,4-dihydro-2H-1,5-naphthyridine (120 mg, 0.28 mmol) in dichloromethane (10 mL) was added trifluoroacetic acid (2 mL) slowly at room temperature. The reaction mixture was stirred at room temperature for 16 h. The resulting mixture was concentrated under reduced pressure. The residue was dissolved in methanol. Then Pd/C (12 mg, 0.12 mmol, 10%) was added to the solution. The mixture was stirred at room temperature for 72 h under hydrogen atmosphere. The reaction mixture was filtered, the filter cake was washed with methanol. The filtrate was concentrated under reduced pressure. The residue was purified by Prep-HPLC [Column: XBridge Shield RP18 OBD Column, 19*150 mm, 5 um 13 nm; Mobile Phase A: water (10 mmol/L ammonium bicarbonate), Mobile Phase B: acetonitrile; Flow rate: 25 mL/min; Gradient: 50% B to 77% B in 8 min] to afford 3-(1H-indazol-3-yl)-5,6,7,8-tetrahydro-1,5-naphthyridine (7.9 mg, 11%) as a white solid.

Example 58

5,6-difluoro-3-[5H,6H,7H,8H-pyrido[2,3-b]pyrazin-2-yl]-1H-indazole

Step 1: To a solution of 2-chloropyrido[2,3-b]pyrazine (88 mg, 0.53 mmol) in dioxane (5 mL) and water (0.5 mL) were added [1,1'-bis(diphenylphosphino)ferrocene]dichloro-palladium(II) (39 mg, 0.05 mmol), 5,6-difluoro-1-(oxan-2-yl)indazol-3-ylboronic acid (150 mg, 0.53 mmol) and potassium carbonate (147 mg, 1.06 mmol). The mixture was stirred at 100° C. for 16 h under nitrogen atmosphere. The mixture was concentrated under vacuum. The residue was purified by flash column chromatography with 0~70% ethyl acetate in petroleum ether to afford 5,6-difluoro-1-(oxan-2-yl)-3-[pyrido[2,3-b]pyrazin-2-yl]indazole (100 mg, 51%) as an off-white solid. MS m/z 368.3 [M+1]$^+$.

Step 2: To a solution of 5,6-difluoro-1-(oxan-2-yl)-3-[pyrido[2,3-b]pyrazin-2-yl]indazole (100 mg, 0.27 mmol) in methanol (10 mL) was added PtO$_2$ (10 mg, 0.04 mmol). The mixture was stirred at room temperature for 16 h under hydrogen atmosphere. The reaction mixture was filtered. The filtrate was collected and concentrated under vacuum. The residue was purified by flash column chromatography with 0~80% ethyl acetate in petroleum ether to afford 5,6-difluoro-1-(oxan-2-yl)-3-[5H,6H,7H,8H-pyrido[2,3-b]pyrazin-2-yl]indazole (90 mg, 89%) as a white solid. MS m/z 372.2 [M+1]$^+$.

Step 3: To a solution of 5,6-difluoro-1-(oxan-2-yl)-3-[5H,6H,7H,8H-pyrido[2,3-b]pyrazin-2-yl]indazole (90 mg, 0.02 mmol) in dichloromethane (3 mL) was added trifluoroacetic acid (2 mL) at 0° C. The mixture was stirred at room temperature for 16 h. The reaction mixture was concentrated under vacuum. The residue was diluted with water extracted with dichloromethane. The combined organic layers were washed with brine, dried over anhydrous sodium sulfate, filtered and concentrated under vacuum. The residue was purified by Prep-HPLC [Column: Xselect CSH OBD Column 30*150 mm 5 um; Mobile Phase A: water (0.1% formic acid), Mobile Phase B: acetonitrile; Flow rate: 60 mL/min; Gradient: 24% B to 54% B in 7 min] to afford 5,6-difluoro-3-[5H,6H,7H,8H-pyrido[2,3-b]pyrazin-2-yl]-1H-indazole (22.2 mg, 31%) as a light yellow solid.

Example 59

2-(5,6-difluoro-1H-indazol-3-yl)-4-methyl-5,6,7,8-tetrahydro-1,5-naphthyridine

Followed the procedure of Example 1 described above and the crude product was purified by Prep-HPLC (Method A) to afford 2-(5,6-difluoro-1H-indazol-3-yl)-4-methyl-5,6,7,8-tetrahydro-1,5-naphthyridine (44.8 mg, 26% over 2 steps) as a light yellow solid from 2-chloro-4-methyl-5,6,7,8-tetrahydro-1,5-naphthyridine (100 mg, 0.35 mmol).

Example 60

6-(5,6-difluoro-1H-indazol-3-yl)-4,4-dimethyl-2,3-dihydro-1H-1,7-naphthyridine

Step 1: A mixture of 6-chloro-4,4-dimethyl-1-(4-methyl-benzenesulfonyl)-2,3-dihydro-1,7-naphthyridine (50 mg, 0.14 mmol), 5,6-difluoro-1-(oxan-2-yl)indazol-3-ylboronic acid (47 mg, 0.16 mmol), methane-sulfonato-2-dicyclohexylphosphino-3,6-dimethoxy-2'-4'-6'-tri-i-propyl-1,1'-bipheny)(2'-amino-1,1'-biphenyl-2-yl)-palladium(II) (10 mg, 0.01 mmol) and tripotassium orthophosphate (96 mg, 0.45 mmol) in dioxane (2 mL)/water (0.2 mL) was heated to 100° C. for 16 h. The mixture was concentrated under vacuum. The residue was purified by flash column chromatography with 0~30% ethyl acetate in petroleum ether to afford 6-[5,6-difluoro-1-(oxan-2-yl)indazol-3-yl]-4,4-dimethyl-1-(4-methylbenzenesulfonyl)-2,3-dihydro-1,7-naphthyridine (90 mg, ~80% purity, 92%) as a colorless syrup. MS m/z 553.3 [M+1]$^+$.

Step 2: To a mixture of 6-[5,6-difluoro-1-(oxan-2-yl)indazol-3-yl]-4,4-dimethyl-1-(4-methylbenzene-sulfonyl)-2,3-dihydro-1,7-naphthyridine (90 mg, 0.16 mmol) in ethanol (5 mL) was added HCl (conc.) (5 mL). The mixture was heated to 100° C. for 16 h, and then concentrated under vacuum. The residue was purified by reverse phase flash column chromatography with 10~60% acetonitrile in water to afford 6-(5,6-difluoro-1H-indazol-3-yl)-4,4-dimethyl-2,3-dihydro-1H-1,7-naphthyridine (6 mg, 11%) as an off-white solid.

Example 61

3-[5-(trifluoromethyl)pyridin-2-yl]-1H-indazole

Followed the procedure of Example 1 described above and the crude product was purified by Prep-HPLC (Method A) to afford 3-[5-(trifluoromethyl)pyridin-2-yl]-1H-indazole (19.9 mg, 7% over 2 steps) as a light yellow solid from 1-(oxan-2-yl)indazol-3-ylboronic acid (246 mg, 1.00 mmol).

Example 62

3-(5-fluoropyridin-2-yl)-1H-indazole

Followed the procedure of Example 1 described above and the crude product was purified by Prep-HPLC (Method A) to afford 3-(5-fluoropyridin-2-yl)-1H-indazole (56.4 mg, 25%) as a white solid from 1-(oxan-2-yl)indazol-3-ylboronic acid (246 mg, 1.00 mmol).

Example 63

3-(7-fluoroquinolin-2-yl)-1H-indazole-7-carbonitrile

Followed the procedure of Example 1 described above and the crude product was purified by reverse phase flash column chromatography with 5-30% acetonitrile in water to afford 3-(7-fluoroquinolin-2-yl)-1H-indazole-7-carbonitrile (16.3 mg, 17% over 2 steps) as a white solid from 1-(oxan-2-yl)-3-(4,4,5,5-tetramethyl-1,3,2-dioxaborolan-2-yl)indazole-7-carbonitrile (110 mg, 0.31 mmol).

Example 64

3-[5-(piperazin-1-yl)pyridin-2-yl]-1H-indazole

Followed the procedure of Example 1 described above to afford the crude product (500 mg) as a 2,2,2-trifluoroacetate from tert-butyl 4-(6-chloropyridin-3-yl)piperazine-1-carboxylate (500 mg, 1.68 mmol). ~100 mg of the crude product was diluted by water and basified by sodium bicarbonate. The aqueous phase was extracted with dichloromethane. The organic layer was dried over anhydrous sodium sulfate, filtered and concentrated under vacuum. The residue was purified by reverse phase flash column chromatography with 5~30% acetonitrile in water to afford 3-[5-(piperazin-1-yl)pyridin-2-yl]-1H-indazole (16.0 mg, 15% over 2 steps) as a light yellow solid.

Example 65

3-(5-(4-methylpiperazin-1-yl)pyridin-2-yl)-1H-indazole

To a solution of 3-[5-(piperazin-1-yl)pyridin-2-yl]-1H-indazole 2,2,2-trifluoroacetate (200 mg, 0.72 mmol) in methanol (4 mL) was added sodium cyanoborohydride (90 mg, 1.43 mmol) and formaldehyde (1 mL, 33% in water). The mixture was stirred at room temperature for 2 h. The mixture was concentrated under vacuum. The residue was purified by flash column chromatography with 5-35% acetonitrile in water to afford 3-(5-(4-methylpiperazin-1-yl)pyridin-2-yl)-1H-indazole (17.6 mg, 8%) as a brown solid.

Example 66

3-[4-(piperazin-1-yl)pyridin-2-yl]-1H-indazole

Step 1: To a solution of tert-butyl 4-(2-chloropyridin-4-yl)piperazine-1-carboxylate (400 mg, 1.34 mmol) in dioxane (5 mL) and water (1 mL) were added [1,1'-bis(diphenyl-phosphino)ferrocene]dichloropalladium(II) (98 mg, 0.13 mmol), potassium carbonate (557 mg, 4.03 mmol) and 1-(oxan-2-yl)-3-(4,4,5,5-tetramethyl-1,3,2-dioxaborolan-2-yl)indazole (529 mg, 1.61 mmol) under nitrogen atmosphere. The mixture was stirred at 100° C. for 4 h. The reaction mixture was concentrated under vacuum. The residue was purified by flash column chromatography with 0~50% ethyl acetate in petroleum ether to afford tert-butyl 4-[2-[1-(oxan-2-yl)indazol-3-yl]pyridin-4-yl]piperazine-1-carboxylate (520 mg, 84%) as yellow oil. MS m/z 464.3 [M+1]$^+$.

Step 2: To a solution of tert-butyl 4-[2-[1-(oxan-2-yl)indazol-3-yl]pyridin-4-yl]piperazine-1-carboxylate (300 mg, 0.65 mmol) in dichloromethane (2 mL) was added trifluoroacetic acid (4 mL). The resulting solution was stirred at room temperature for 2 h. The mixture was concentrated under vacuum. The residue was diluted with water and basified using saturated sodium bicarbonate aqueous solution. The mixture was extracted with dichloromethane. The combined organic layers were washed with brine, dried over anhydrous sodium sulfate, filtered and concentrated under vacuum. The crude product was purified by Prep-HPLC [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 13% B to 43% B in 8 min] to afford product 3-[4-(piperazin-1-yl)pyridin-2-yl]-1H-indazole (23 mg, 12%) as a light yellow solid.

Example 67

3-[4-(4-methylpiperazin-1-yl)pyridin-2-yl]-1H-indazole

To a solution of 3-[4-(piperazin-1-yl)pyridin-2-yl]-1H-indazole (Example 66) (80 mg, 0.29 mmol) in methanol (2 mL) were added sodium cyanoborohydride (36 mg, 0.57 mmol) and formaldehyde (0.2 mL, 33% in water). The mixture was stirred at room temperature for 2 h. The reaction mixture was concentrated under vacuum. The crude product was purified by Prep-HPLC [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 18% B to 48% B in 7 min] to afford product 3-[4-(4-methylpiperazin-1-yl) pyridin-2-yl]-1H-indazole (17.9 mg, 21%) as a white solid.

Example 68

3-[6-(4-methylpiperazin-1-yl)pyridin-2-yl]-1H-indazole formate

Followed the procedure of Example 1 described above and the crude product was purified by Prep-HPLC (Method C) to afford 3-[6-(4-methylpiperazin-1-yl)pyridin-2-yl]-1H-indazole formate (69.6 mg, 44% over 2 steps) as a green solid from 1-(6-chloropyridin-2-yl)-4-methylpiperazine (200 mg, 0.95 mmol).

Example 69

5,6-difluoro-3-[1H,2H,3H-pyrido[2,3-b][1,4]oxazin-6-yl]-1H-indazole

Followed the procedure of Example 1 described above and the crude product was purified by Prep-HPLC (Method B) to afford 5,6-difluoro-3-[1H,2H,3H-pyrido[2,3-b][1,4] oxazin-6-yl]-1H-indazole (7.8 mg, 5% over 2 steps) as a white solid from 6-chloro-1H,2H,3H-pyrido[2,3-b][1,4] oxazine (91 mg, 0.53 mmol).

Example 70

5,6-difluoro-3-[3-methyl-1H,2H,3H-pyrido[2,3-b][1,4]oxazin-6-yl]-1H-indazole

Step 1: A degassed mixture of 5,6-difluoro-1-(oxan-2-yl) indazol-3-ylboronic acid (150 mg, 0.53 mmol), 6-chloro-3-methyl-1H,2H,3H-pyrido[2,3-b][1,4]oxazine (94 mg, 0.51 mmol), 1,1'-bis (di-t-butylphosphino)-ferrocene palladium dichloride (36 mg, 0.05 mmol) and potassium carbonate (152 mg, 1.10 mmol) in dioxane (5 mL)/water (0.5 mL) was heated to 90° C. for 16 h. The mixture was concentrated under vacuum. The residue was purified by flash column chromatography with 0~50% ethyl acetate in petroleum ether to afford 5,6-difluoro-3-[3-methyl-1H,2H,3H-pyrido [2,3-b][1,4]oxazin-6-yl]-1-(oxan-2-yl)indazole (85 mg, 20%) as a yellow solid. MS m/z 387.1 [M+1]$^+$.

Step 2: To a solution of 5,6-difluoro-3-[3-methyl-1H,2H,3H-pyrido[2,3-b][1,4]oxazin-6-yl]-1-(oxan-2-yl)indazole (85 mg, 50% purity, 0.11 mmol) in dichloromethane (5 mL) was added trifluoroacetic acid (2 mL). The mixture was stirred at room temperature for 16 h. The mixture was concentrated under vacuum. The residue was purified by prep-HPLC [Column: XBridge Prep OBD C18 Column, 30×150 mm 5 um; Mobile Phase A: water (10 mM ammonium bicarbonate), Mobile Phase B: acetonitrile; Flow rate: 60 mL/min; Gradient: 32% B to 55% B in 8 min] to afford 5,6-difluoro-3-[3-methyl-1H,2H,3H-pyrido[2,3-b][1,4] oxazin-6-yl]-1H-indazole (4.0 mg, 12%) as a white solid.

Example 71

3-[7,7-dimethyl-5H,6H-pyrrolo[3,4-b]pyridin-2-yl]-5,6-difluoro-1H-indazole

Step 1: A degassed mixture of 2-chloro-6-[(4-methoxyphenyl)methyl]-7,7-dimethyl-pyrrolo[3,4-b]pyridin-5-one (120 mg, 0.37 mmol), 5,6-difluoro-1-(oxan-2-yl)indazol-3-ylboronic acid (112 mg, 0.39 mmol), [1,1'-bis(diphenylphosphino)ferrocene]dichloropalladium(II) (31 mg, 0.04 mmol) and potassium carbonate (107 mg, 0.77 mmol) in dioxane (5 mL)/water (0.5 mL) was heated to 90° C. for 16 h. The mixture was concentrated under vacuum. The mixture was purified by flash column chromatography with 0~40% ethyl acetate in petroleum ether to afford 2-[5,6-difluoro-1-(oxan-2-yl)indazol-3-yl]-6-[(4-methoxyphenyl)methyl]-7,7-dimethyl-pyrrolo[3,4-b]pyridin-5-one (85 mg, 43%) as a white solid. MS m/z 519.2 [M+1]$^+$.

Step 2: To a mixture of 2-[5,6-difluoro-1-(oxan-2-yl) indazol-3-yl]-6-[(4-methoxyphenyl)methyl]-7,7-dimethylpyrrolo[3,4-b]pyridin-5-one (65 mg, 0.12 mmol) and sodium borohydride (26 mg, 0.68 mmol) in tetrahydrofuran (2 mL) was added boron trifluoride ether complex (91 mg, 0.64 mmol) at room temperature. The mixture was heated to 50° C. for 16 h. The mixture was diluted with water and extracted with ethyl acetate. The organic layer was dried over anhydrous sodium sulfate, filtered and concentrated under vacuum to afford 5,6-difluoro-3-[6-[(4-methoxyphenyl)methyl]-7,7-dimethyl-5H-pyrrolo[3,4-b]pyridin-2-yl]-1-(oxan-2-yl)indazole (70 mg, crude) as a white solid. MS m/z 505.2 [M+1]$^+$.

Step 3: A solution of 5,6-difluoro-3-[6-[(4-methoxyphenyl)methyl]-7,7-dimethyl-5H-pyrrolo[3,4-b]pyridin-2-yl]-1-(oxan-2-yl)indazole (65 mg, 0.12 mmol) in trifluoroacetic acid (2 mL) was heated to reflux for 16 h. The mixture was concentrated under vacuum. The residue was purified by Prep-HPLC [Column: XBridge Shield RP18 OBD Column, 30*150 mm, 5 um; Mobile Phase A: water (10 mmol/L ammonium bicarbonate+0.1% NH$_3$.H$_2$O), Mobile Phase B: acetonitrile; Flow rate: 60 mL/min; Gradient: 35% B to 55% B in 8 min] to afford 3-[7,7-dimethyl-5H,6H-pyrrolo[3,4-b] pyridin-2-yl]-5,6-difluoro-1H-indazole (13.6 mg, 35%) as a white solid.

Example 72

2-[6-(5,6-difluoro-1H-indazol-3-yl)pyridin-3-yl] propan-2-ol

Followed the procedure of Example 1 described above and the crude product was purified by Prep-HPLC (Method A) to afford 2-[6-(5,6-difluoro-1H-indazol-3-yl)pyridin-3-yl]propan-2-ol (40.1 mg, 36% over 2 steps) as a light yellow solid from 2-(6-chloropyridin-3-yl)propan-2-ol (61 mg, 0.36 mmol).

Example 73

2-[5-(5,6-difluoro-1H-indazol-3-yl)pyridin-2-yl] propan-2-ol

Followed the procedure of Example 1 described above and the crude product was purified by Prep-HPLC (Method C) [Column: XBridge Shield RP18 OBD Column, 30150 mm, 5 um; Mobile Phase A: water, Mobile Phase B: acetonitrile; Flow rate: 60 mL/min; Gradient: 25% to 50% in 8 min] to afford 2-[5-(5,6-difluoro-1H-indazol-3-yl)pyridin-2-yl]propan-2-ol (40.6 mg, 37% over 2 steps) as a white solid from 5,6-difluoro-1-(oxan-2-yl)indazol-3-ylboronic acid (104 mg, 0.37 mmol).

Example 74

6-(5,6-difluoro-1H-indazol-3-yl)-3,4-dihydro-2H-pyrido[3,2-b][1,4]oxazine

Step 1: A mixture of 5,6-difluoro-1-(oxan-2-yl)indazol-3-ylboronic acid (100 mg, 0.36 mmol), 6-chloro-2H,3H,4H-pyrido[3,2-b][1,4]oxazine (36 mg, 0.21 mmol), tripotassium orthophosphate (151 mg, 0.71 mmol) and methanesulfonato 2-dicyclohexylphosphino-3,6-dimethoxy-2'-4'-6'-tri-i-propyl-1,1'-bipheny)(2'-amino-1,1'-biphenyl-2-yl)palladium(II) (32 mg, 0.04 mmol) in dioxane (2 ml) and water (0.1 ml) was stirred at 100° C. for 16 h under nitrogen atmosphere. The resulting mixture was concentrated under reduced pressure. The residue was purified by flash column chromatography with 0~80% ethyl acetate in petroleum ether to afford 5,6-difluoro-1-(oxan-2-yl)-3-[2H,3H,4H-pyrido[3,2-b][1,4]oxazin-6-yl]indazole (35 mg, 26%) as a yellow solid. MS m/z 373.1 [M+1]$^+$.

Step 2: To a mixture of 5,6-difluoro-1-(oxan-2-yl)indazol-3-ylboronic acid (35 mg, 0.09 mmol) in dichloromethane (3 mL) was added trifluoroacetic acid (1 mL). The mixture was stirred for 16 h at room temperature. The reaction mixture was concentrated under reduced pressure. The residue was purified by Prep-HPLC [Column: XBridge Shield RP18 OBD Column, 30150 mm, 5 um; Mobile Phase A: water (10 mmol/L ammonium bicarbonate), Mobile Phase B: acetonitrile; Flow rate: 60 mL/min; Gradient: 30% B to 48% B in 8 min] to afford 6-(5,6-difluoro-1H-indazol-3-yl)-3,4-dihydro-2H-pyrido[3,2-b][1,4]oxazine (11.2 mg, 40%) as a white solid.

Example 75

5,6-difluoro-3-[4-methyl-2H,3H-pyrido[3,2-b][1,4]oxazin-6-yl]-1H-indazole

Step 1: A mixture of 6-chloro-4-methyl-2H,3H-pyrido[3,2-b][1,4]oxazine (100 mg, 0.54 mmol), 5,6-difluoro-1-(oxan-2-yl)indazol-3-ylboronic acid (183 mg, 0.65 mmol), RuPhos Palladacycle Gen.3 (45 mg, 0.05 mmol) and tripotassium orthophosphate (230 mg, 1.08 mmol) in dioxane (5 mL) and water (0.5 mL) was stirred at 100° C. for 16 h under nitrogen atmosphere. The resulting mixture was concentrated under reduced pressure. The residue was purified by flash column chromatography with 0~80% ethyl acetate in petroleum ether to afford 5,6-difluoro-3-[4-methyl-2H,3H-pyrido[3,2-b][1,4]oxazin-6-yl]-1-(oxan-2-yl)indazole (200 mg, 95%) as a light yellow solid. MS m/z 387.3 [M+1]$^+$.

Step 2: To a mixture of 5,6-difluoro-3-[4-methyl-2H,3H-pyrido[3,2-b][1,4]oxazin-6-yl]-1-(oxan-2-yl)indazole (200 mg, 0.52 mmol) in dichloromethane (6 mL) was added trifluoroacetic acid (2 mL). The mixture was stirred at room temperature for 16 h. The mixture was concentrated under reduced pressure. The residue was purified by Prep-HPLC (Method A) to afford 5,6-difluoro-3-[4-methyl-2H,3H-pyrido[3,2-b][1,4]oxazin-6-yl]-1H-indazole (50.9 mg, 32%) as a white solid.

Example 76

5,6-difluoro-3-[4-isopropyl-2H,3H-pyrido[3,2-b][1,4]oxazin-6-yl]-1H-indazole

Followed the procedure of Example 1 described above and the crude product was purified by Prep-HPLC (Method A) to afford 5,6-difluoro-3-[4-isopropyl-2H,3H-pyrido[3,2-b][1,4]oxazin-6-yl]-1H-indazole (60.9 mg, 35% ober 2 steps) as a light yellow solid from 6-chloro-4-isopropyl-2H,3H-pyrido[3,2-b][1,4]oxazine (100 mg, 0.47 mmol).

Example 77

2-(1H-indazol-3-yl)-8,8-dimethyl-6,7-dihydro-5H-1,5-naphthyridine

Followed the procedure of Example 46 described above and the crude product was purified by Prep-HPLC (Method A) to afford 2-(1H-indazol-3-yl)-8,8-dimethyl-6,7-dihydro-5H-1,5-naphthyridine (6.4 mg, 8% over 2 steps) as a white solid from 6-chloro-4,4-dimethyl-1-(4-methylbenzenesulfonyl)-2,3-dihydro-1,5-naphthyridine (100 mg, 0.29 mmol).

Example 78

2-(5-fluoro-1H-indazol-3-yl)-8,8-dimethyl-6,7-dihydro-5H-1,5-naphthyridine

Followed the procedure of Example 46 described above and the crude product was purified by Prep-HPLC (Method B) to afford 2-(5-fluoro-1H-indazol-3-yl)-8,8-dimethyl-6,7-dihydro-5H-1,5-naphthyridine (9.2 mg, 4% over 2 steps) as a yellow green solid from 6-chloro-4,4-dimethyl-1-(4-methylbenzenesulfonyl)-2,3-dihydro-1,5-naphthyridine (151 mg, 0.43 mmol).

Example 79 ethyl 2-(7-methyl-1H-indazol-3-yl)-1,3-oxazole-4-carboxylate

Followed the procedure of Example 1 described above and the crude product was purified by Prep-HPLC (Method C) to afford ethyl 2-(7-methyl-1H-indazol-3-yl)-1,3-oxazole-4-carboxylate (16.1 mg, 11% over 2 steps) as a white solid from 7-methyl-1-(oxan-2-yl)indazol-3-ylboronic acid (100 mg, 0.46 mmol).

Example 80

6-(5,6-difluoro-1H-indazol-3-yl)-8-methyl-3,4-dihydro-1H-1,5-naphthyridin-2-one

Followed the procedure of Example 1 described above and the crude product was purified by reverse phase flash column chromatography with 40~60% acetonitrile in water to afford 6-(5,6-difluoro-1H-indazol-3-yl)-8-methyl-3,4-dihydro-1H-1,5-naphthyridin-2-one (19.8 mg, 10% over 2 steps) as a light yellow solid from 5,6-difluoro-1-(oxan-2-yl)indazol-3-ylboronic acid (115 mg, 0.41 mmol).

Example 81

2-(5-phenyl-1H-pyrazol-3-yl)-5,6,7,8-tetrahydro-1,5-naphthyridine

Followed the procedure of Example 75 described above and the crude product was purified by Prep-HPLC (Method A) to afford 2-(5-phenyl-1H-pyrazol-3-yl)-5,6,7,8-tetrahydro-1,5-naphthyridine (5.4 mg, 1% over 2 steps) as a white solid from 2-(oxan-2-yl)-5-phenylpyrazol-3-ylboronic acid (480 mg, 1.76 mmol).

Example 82

2-(4,5-dimethyl-1H-pyrazol-3-yl)-5,6,7,8-tetrahydro-1,5-naphthyridine

To a solution of 1-(tert-butoxycarbonyl)-4,5-dimethylpyrazol-3-ylboronic acid (110 mg, 0.46 mmol) in dioxane (2 mL) and water (0.5 mL) were added 2-chloro-5,6,7,8-tetrahydro-1,5-naphthyridine (69 mg, 0.41 mmol), [1,1'-bis(diphenylphosphino)ferrocene]dichloro-palladium(II) (33 mg, 0.04 mmol) and potassium carbonate (190 mg, 1.38 mmol) under nitrogen atmosphere. The mixture was stirred at 100° C. for 4 h. The reaction mixture was diluted with water and extracted with ethyl acetate. The organic layer was dried over anhydrous sodium sulfate, filtered and concentrated under vacuum. The crude product was purified by Prep-HPLC [Column: XBridge Prep Phenyl OBD Column, 19*100 mm 5 um 13 nm; Mobile Phase A: water (10 mmol/L ammonium bicarbonate), Mobile Phase B: acetonitrile; Flow rate: 60 mL/min; Gradient: 18% B to 37% B in 8 min] to afford product 2-(4,5-dimethyl-1H-pyrazol-3-yl)-5,6,7,8-tetrahydro-1,5-naphthyridine (8.3 mg, 8%) as a yellow solid.

Example 83

3-(5,6,7,8-tetrahydro-1,5-naphthyridin-2-yl)-1,4,6,7-tetrahydropyrano[4,3-c]pyrazole Followed the procedure of Example 1 described above and the crude product was purified by Prep-HPLC (Method B) to afford 3-(5,6,7,8-tetrahydro-1,5-naphthyridin-2-yl)-1,4,6,7-tetrahydropyrano[4,3-c]pyrazole (35.5 mg, 17% over 2steps) as a yellow solid from 1-(oxan-2-yl)-hexahydro-2H-pyrano[4,3-c]pyrazol-3-ylboronic acid.

Example 84

2-[5-(pyridin-2-yl)-1H-pyrazol-3-yl]-5,6,7,8-tetrahydro-1,5-naphthyridine

Followed the procedure of Example 1 described above and the crude product was purified by Prep-HPLC (Method A) to afford 2-[5-(pyridin-2-yl)-1H-pyrazol-3-yl]-5,6,7,8-tetrahydro-1,5-naphthyridine (7.0 mg, 6% over 2 steps) as a white solid from 2-[1-[(4-methoxyphenyl)methyl]-5-(4,4,5,5-tetramethyl-1,3,2-dioxaborolan-2-yl)pyrazol-3-yl]pyridine (150 mg, 0.38 mmol).

Example 85

3-(1,5-naphthyridin-2-yl)-1-(oxan-2-yl)indazole-7-carbonitrile

To a solution of 1-(oxan-2-yl)-3-(4,4,5,5-tetramethyl-1,3,2-dioxaborolan-2-yl)indazole-7-carbonitrile (700 mg, 1.98 mmol) in dioxane (5 mL) and water (0.5 mL) were added 2-chloro-1,5-naphthyridine (391 mg, 2.38 mmol), potassium carbonate (822 mg, 5.95 mmol) and [1,1'-bis(diphenylphosphino)ferrocene]-dichloropalladium(II) (145 mg, 0.20 mmol). The mixture was heated to 100° C. and stirred for 4 h. The reaction mixture was concentrated under vacuum. The residue was purified by flash column chromatography with 0~30% ethyl acetate in petroleum ether to afford 3-(1,5-naphthyridin-2-yl)-1-(oxan-2-yl)indazole-7-carbonitrile (250 mg, 35%) as an off-white solid.

Example 86

(3-(1,5-naphthyridin-2-yl)-1H-indazol-7-yl)methanamine

Step 1: To a mixture of 3-(1,5-naphthyridin-2-yl)-1-(oxan-2-yl)indazole-7-carbonitrile (Example 85) (100 mg, 0.28 mmol) and ammonia (2 mL, 7M in methanol) was added Raney-Ni (50 mg). The mixture was stirred at room temperature for 3 h under hydrogen atmosphere. The solids were filtered off. The filtrate was concentrated under vacuum to afford 1-[3-(1,5-naphthyridin-2-yl)-1-(oxan-2-yl)indazol-7-yl]methanamine (100 mg, 98%) as a light yellow solid. MS m/z 360.2 [M+1]$^+$.

Step 2: To a solution of 1-[3-(1,5-naphthyridin-2-yl)-1-(oxan-2-yl)indazol-7-yl]methanamine (70 mg, 0.20 mmol) in dichloromethane (1 mL) was added trifluoroacetic acid (2 mL). The resulting solution was stirred at room temperature for 2 h. The mixture was concentrated under vacuum. The residue was diluted by saturated sodium bicarbonate aqueous solution and extracted with dichloromethane. The organic layer was dried over anhydrous sodium sulfate, filtered and concentrated under vacuum. The residue was purified by Prep-HPLC (Method A) to afford (3-(1,5-naphthyridin-2-yl)-1H-indazol-7-yl)methanamine (10.9 mg, 20%) as a white solid.

Example 87

N-((3-(1,5-naphthyridin-2-yl)-1H-indazol-7-yl)methyl)propan-2-amine

To a solution of 1-[3-(1,5-naphthyridin-2-yl)-1H-indazol-7-yl]methanamine (Example 86) (50 mg, 0.18 mmol) in dichloromethane (2 mL) were added glacial acetic acid (0.1 mL), sodium triacetoxyborohydride (77 mg, 0.36 mmol) and acetone (0.1 mL). The mixture was stirred at room temperature for 2 h. The resulting mixture was concentrated under vacuum. The residue was diluted with saturated sodium bicarbonate aqueous solution and extracted with dichloromethane. The organic layer was dried over anhydrous sodium sulfate, filtered and concentrated under vacuum. The residue was purified by reverse phase flash column chromatography with 5-40% acetonitrile in water to afford N-((3-(1,5-naphthyridin-2-yl)-1H-indazol-7-yl)methyl)propan-2-amine (6.9 mg, 12%) as a white solid.

Example 88

6-(5,6-difluoro-1H-indazol-3-yl)-2-isopropylpyridin-3-amine

Step 1: To a solution of 5,6-difluoro-1-(oxan-2-yl)indazol-3-ylboronic acid (200 mg, 0.71 mmol) in dioxane (2 mL) and water (0.2 mL) were added tert-butyl N-[6-chloro-2-(prop-1-en-2-yl)pyridin-3-yl]carbamate (191 mg, 0.71 mmol), chloro(2-dicyclohexylphosphino-2',4',6'-triisopropyl-1,1'-biphenyl)[2-(2'-amino-1,1'-biphenyl)]palladium(II) (56 mg, 0.07 mmol) and tripotassium orthophosphate (301 mg, 1.42 mmol) at room temperature. The mixture was heated to 100° C. and stirred for 4 h. The mixture was concentrated under vacuum. The residue was purified by flash column chromatography with 0~70% ethyl acetate in petroleum ether to afford tert-butyl N-[6-[5,6-difluoro-1-(oxan-2-yl)indazol-3-yl]-2-(prop-1-en-2-yl)pyridin-3-yl] carbamate (170 mg, 51%) as a white solid. MS m/z 471.3 [M+1]$^+$.

Step 2: To a solution of tert-butyl N-[6-[5,6-difluoro-1-(oxan-2-yl)indazol-3-yl]-2-(prop-1-en-2-yl)pyridin-3-yl] carbamate (160 mg, 0.34 mmol) in methanol (2 mL) was added Pd/C (4 mg, 10%). The mixture was stirred at room temperature for 2 h under hydrogen atmosphere. The solids were filtered off. The filtrate was concentrated under vacuum to afford tert-butyl N-[6-[5,6-difluoro-1-(oxan-2-yl)indazol-3-yl]-2-isopropylpyridin-3-yl]carbamate (110 mg, crude) as a white solid. MS m/z 473.2 [M+1]$^+$.

Step 3: To a solution of tert-butyl N-[6-[5,6-difluoro-1-(oxan-2-yl)indazol-3-yl]-2-isopropylpyridin-3-yl]carbamate (110 mg, 0.23 mmol) in dichloromethane (2 mL) was added trifluoroacetic acid (1 mL). The mixture was stirred at room temperature for 10 h. The mixture was concentrated under vacuum. The residue was purified by Prep-HPLC [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 38% B to 57% B in 8 min] to afford 6-(5,6-difluoro-1H-indazol-3-yl)-2-isopropylpyridin-3-amine (3 mg, 3%) as a white solid.

Example 89

6-(5,6-difluoro-1H-indazol-3-yl)-2-isopropoxypyridin-3-amine

Step 1: To a solution of 5,6-difluoro-1-(oxan-2-yl)indazol-3-ylboronic acid (150 mg, 0.53 mmol) in dioxane (3 mL) and water (0.3 mL) were added 6-chloro-2-isopropoxy-3-nitropyridine (115 mg, 0.53 mmol), [1,1'-bis(diphenylphosphino)ferrocene]dichloro-palladium(II) (39 mg, 0.05 mmol) and potassium carbonate (147 mg, 1.06 mmol) at room temperature. The mixture was heated to 100° C. and stirred for 6 h. The mixture was concentrated under vacuum. The residue was purified by flash column chromatography with 0~60% ethyl acetate in petroleum ether to afford 5,6-difluoro-3-(6-isopropoxy-5-nitropyridin-2-yl)-1-(oxan-2-yl) indazole (141 mg, 63%) as a white solid. MS m/z 419.2 [M+1]$^+$.

Step 2: To a solution of 5,6-difluoro-3-(6-isopropoxy-5-nitropyridin-2-yl)-1-(oxan-2-yl)indazole (179 mg, 0.43 mmol) in methanol (10 mL, 0.09 mmol) was added Pd/C (20 mg, 10%). The mixture was stirred at room temperature for 2 h under hydrogen atmosphere. The solids were filtered off. The filtrate was concentrated under vacuum to afford 6-[5, 6-difluoro-1-(oxan-2-yl)indazol-3-yl]-2-isopropoxypyridin-3-amine (122 mg, 73%) as a white solid. MS m/z 389.2 [M+1]$^+$.

Step 3: To a solution of 6-[5,6-difluoro-1-(oxan-2-yl) indazol-3-yl]-2-isopropoxypyridin-3-amine (80 mg, 0.21 mmol) in dichloromethane (2 mL) was added trifluoroacetic acid (1 mL). The mixture was stirred at room temperature for 10 h. The mixture was concentrated under vacuum. The residue was purified by Prep-HPLC (Method C) [Column: XBridge Shield RP18 OBD Column, 30150 mm, 5 um; Mobile Phase A: water, Mobile Phase B: acetonitrile; Flow rate: 60 mL/min; Gradient: 40% B to 72% B in 8 min] to afford 6-(5,6-difluoro-1H-indazol-3-yl)-2-isopropoxypyridin-3-amine (11.6 mg, 18%) as a white solid.

Example 90

6-(5,6-difluoro-1H-indazol-3-yl)-2-ethoxypyridin-3-amine

Followed the procedure of Example 89 described above and the crude product was purified by Prep-HPLC (Method A) to afford 6-(5,6-difluoro-1H-indazol-3-yl)-2-ethoxypyridin-3-amine (7 mg, 4% over 3 steps) as a white solid from 6-chloro-2-ethoxy-3-nitropyridine (108 mg, 0.53 mmol).

Example 91

6-(5,6-difluoro-1H-indazol-3-yl)-2-methoxypyridin-3-amine

Step 1: To a solution of 6-chloro-2-methoxy-3-nitropyridine (500 mg, 0.27 mmol) in methanol (5 mL) was added Pd/C (50 mg, 10%). The mixture was stirred at room temperature for 2 h under hydrogen atmosphere. The solids were filtered off. The filtrate was concentrated under vacuum to afford 6-chloro-2-methoxypyridin-3-amine (312 mg, 74%) as a white solid. MS m/z 159.1 [M+1]$^+$.

Step 2: To a solution of 5,6-difluoro-1-(oxan-2-yl)indazol-3-ylboronic acid (150 mg, 0.53 mmol) in dioxane (2 mL) and water (0.2 mL) were added 6-chloro-2-methoxypyridin-3-amine (84 mg, 0.53 mmol), tripotassium orthophosphate (226 mg, 1.06 mmol) and chloro(2-dicyclohexylphosphino-2',4',6'-triisopropyl-1,1'-biphenyl)[2-(2'-amino-1,1'-biphenyl)]palladium(II) (45 mg, 0.05 mmol) at room temperature. Then the mixture was heated to 100° C. and stirred for 10 h. The residue was purified by flash column chromatography with 0~60% ethyl acetate in petroleum ether to afford 6-[5,6-difluoro-1-(oxan-2-yl)indazol-3-yl]-2-methoxypyridin-3-amine (80 mg, 41%) as a grey solid. MS m/z 361.2 [M+1]+.

Step 3: To a solution of 6-[5,6-difluoro-1-(oxan-2-yl) indazol-3-yl]-2-methoxypyridin-3-amine (80 mg, 0.22 mmol) in dichloromethane (1 mL) was added trifluoroacetic acid (0.7 mL). The mixture was stirred at room temperature for 10 h. The mixture was concentrated under vacuum. The residue was purified by reverse phase flash column chromatography with 10~70% acetonitrile in water. The product was further purified by prep-HPLC (Method C) [Column: XBridge Shield RP18 OBD Column, 30*150 mm, 5 um; Mobile Phase A: water, Mobile Phase B: acetonitrile; Flow rate: 60 mL/min; Gradient: 33% B to 65% B in 8 min] to afford 6-(5,6-difluoro-1H-indazol-3-yl)-2-methoxypyridin-3-amine (11.5 mg, 18%) as an off-white solid.

Example 92

6-(5,6-difluoro-1H-indazol-3-yl)-2-(trifluoromethyl)pyridin-3-amine

Followed the procedure of Example 27 described above and the crude product was purified by Prep-HPLC (Method C) to afford 6-(5,6-difluoro-1H-indazol-3-yl)-2-(trifluoromethyl)pyridin-3-amine (36.5 mg, 32% over 2 steps) as a white solid from 5,6-difluoro-1-(oxan-2-yl)indazol-3-ylboronic acid (100 mg, 0.36 mmol).

Example 93

2-chloro-6-(5,6-difluoro-1H-indazol-3-yl)pyridin-3-amine

Followed the procedure of Example 27 described above and the crude product was purified by Prep-HPLC (Method A) to afford 2-chloro-6-(5,6-difluoro-1H-indazol-3-yl)pyridin-3-amine (9 mg, 13% over 2 steps) as a white solid from 5,6-difluoro-1-(oxan-2-yl)indazol-3-ylboronic acid (200 mg, 0.71 mmol).

Example 94

6-(5,6-difluoro-1H-indazol-3-yl)-N,2-dimethylpyridin-3-amine

Step 1: To a solution of 5,6-difluoro-1-(oxan-2-yl)indazol-3-ylboronic acid (200 mg, 0.71 mmol) in dioxane (4 mL) and water (0.4 mL) were added tert-butyl N-(6-bromo-2-methyl-pyridin-3-yl)carbamate (204 mg, 0.71 mmol), 1,1'-bis (di-t-butylphosphino)ferrocene palladium dichloride (46 mg, 0.071 mmol) and potassium carbonate (196 mg, 1.42 mmol) at room temperature. The mixture was heated to 100° C. and stirred for 16 h. The mixture was concentrated under vacuum. The residue was purified by flash column chromatography with 0~50% ethyl acetate in petroleum ether to afford tert-butyl N-[6-[5,6-difluoro-1-(oxan-2-yl)indazol-3-yl]-2-methylpyridin-3-yl]carbamate (252 mg, 79%) as a yellow solid. MS m/z 445.2 [M+1]$^+$.

Step 2: To a solution of tert-butyl N-[6-[5,6-difluoro-1-(oxan-2-yl)indazol-3-yl]-2-methylpyridin-3-yl]carbamate (100 mg, 0.23 mmol) in N,N-Dimethylformamide (2 mL) was added sodium hydride (13 mg, 0.39 mmol, 60% in mineral oil). The mixture was stirred at 0° C. for 20 min, this was followed by the addition of iodomethane (48 mg, 0.38 mmol) at 0° C. The mixture was stirred at 0° C. for 5 h. The reaction was quenched with water and extracted with ethyl acetate. The combined organic layers were washed with brine, dried over anhydrous sodium sulfate, filtered and concentrated under vacuum. The residue was purified by flash column chromatography with 0-50% ethyl acetate in petroleum ether to afford tert-butyl N-[6-[5,6-difluoro-1-(oxan-2-yl)indazol-3-yl]-2-methylpyridin-3-yl]-N-methylcarbamate (80 mg, 77%) as a colorless oil. MS m/z 459.2 [M+1]$^+$.

Step 3: To a solution of tert-butyl N-[6-[5,6-difluoro-1-(oxan-2-yl)indazol-3-yl]-2-methylpyridin-3-yl]-N-methylcarbamate (80 mg, 0.17 mmol) in dichloromethane (1 mL) was added trifluoroacetic acid (0.5 mL). The mixture was stirred at room temperature for 16 h. The mixture was concentrated under vacuum. The residue was purified by Prep-HPLC (Method A) [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 30% B to 55% B in 8 min] to afford 6-(5,6-difluoro-1H-indazol-3-yl)-N,2-dimethylpyridin-3-amine (10.8 mg, 22%) as a white solid.

Example 95

6-(5,6-difluoro-1H-indazol-3-yl)-N-ethyl-2-methylpyridin-3-amine

Followed the procedure of Example 94 described above and the crude product was purified by Prep-HPLC (Method C) to afford 6-(5,6-difluoro-1H-indazol-3-yl)-N-ethyl-2-methylpyridin-3-amine (19.8 mg, 30% over 2 steps) as a white solid from tert-butyl N-[6-[5,6-difluoro-1-(oxan-2-yl)indazol-3-yl]-2-methylpyridin-3-yl]carbamate (100 mg, 0.23 mmol).

Example 96

N-[6-(5,6-difluoro-1H-indazol-3-yl)-2-methylpyridin-3-yl]acetamide

Followed the procedure of Example 1 described above and the crude product was purified by Prep-HPLC (Method B) to afford N-[6-(5,6-difluoro-1H-indazol-3-yl)-2-methylpyridin-3-yl]acetamide (7.9 mg, 14% over 2 steps) as a white solid from N-(6-chloro-2-methylpyridin-3-yl)acetamide (157 mg, 0.85 mmol).

Example 97

N-[6-(5,6-difluoro-1H-indazol-3-yl)-2-methylpyridin-3-yl]-N-methylacetamide

Followed the procedure of Example 1 described above and the crude product was purified by Prep-HPLC (Method A) to afford N-[6-(5,6-difluoro-1H-indazol-3-yl)-2-methylpyridin-3-yl]-N-methylacetamide (19.8 mg, 11% over 2 steps) as a white solid from N-(6-chloro-2-methylpyridin-3-yl)-N-methylacetamide (126 mg, 0.63 mmol).

Example 98

6-(5,6-difluoro-1H-indazol-3-yl)-N,N,2-trimethylpyridin-3-amine

Followed the procedure of Example 1 described above and the crude product was purified by Prep-HPLC (Method C) to afford 6-(5,6-difluoro-1H-indazol-3-yl)-N,N,2-trimethylpyridin-3-amine (54.5 mg, 30% over 2 steps) as a light brown solid from 6-bromo-N,N,2-trimethylpyridin-3-amine (114 mg, 0.53 mmol).

Example 99

5,6-difluoro-3-(5-methoxy-6-methylpyridin-2-yl)-1H-indazole

Step 1: To a solution of 6-bromo-3-methoxy-2-methylpyridine (71 mg, 0.35 mmol) and 5,6-difluoro-1-(oxan-2-yl)indazol-3-ylboronic acid (100 mg, 0.35 mmol) in dioxane (5 mL) and water (0.5 mL) were added chloro(2-dicyclohexylphosphino-2',4',6'-triisopropyl-1,1'-biphenyl)[2-(2'-amino-1,1'-biphenyl)]palladium(II) (28 mg, 0.03 mmol) and tripotassium orthophosphate (150 mg, 0.70 mmol). The mixture was heated to 100° C. under nitrogen atmosphere for 4 h. The mixture was concentrated under vacuum. The residue was purified by flash column chromatography with 0~50% ethyl acetate in petroleum ether to afford 5,6-difluoro-3-(5-methoxy-6-methylpyridin-2-yl)-1-(oxan-2-yl)indazole (70 mg, 55%) as a white solid. MS m/z 360.2 [M+1]$^+$.

Step 2: To a solution 5,6-difluoro-3-(5-methoxy-6-methylpyridin-2-yl)-1-(oxan-2-yl)indazole (70 mg, 0.19 mmol) in dichloromethane (3 mL) was added trifluoroacetic acid (2 mL). The mixture was stirred at room temperature for 4 h. The mixture was concentrated under vacuum. The residue was purified by Prep-HPLC [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 40% to 65% in 8 min] to afford 5,6-difluoro-3-(5-methoxy-6-methylpyridin-2-yl)-1H-indazole (33.4 mg, 62%) as a white solid.

Example 100

6-(5,6-difluoro-1H-indazol-3-yl)-N,2-dimethylpyridine-3-carboxamide

Step 1: To a mixture of 5,6-difluoro-1-(oxan-2-yl)indazol-3-ylboronic acid (100 mg, 0.35 mmol), 6-chloro-2-methylpyridine-3-carboxylic acid (61 mg, 0.35 mmol) and potassium carbonate (98 mg, 0.71 mmol) in dioxane (2 mL) and water (0.2 mL) was added [1,1'-bis(diphenylphosphino)ferrocene]dichloropalladium(II) (25 mg, 0.04 mmol) under nitrogen atmosphere. The mixture was stirred at 100° C. overnight. The mixture was concentrated under vacuum. The residue was purified by flash column chromatography with 0~100% ethyl acetate in petroleum ether to afford 6-[5,6-difluoro-1-(oxan-2-yl)indazol-3-yl]-2-methylpyridine-3-carboxylic acid (100 mg, 75%) as a brown solid. MS m/z 374.0 [M+1]$^+$.

Step 2: To a solution of 6-[5,6-difluoro-1-(oxan-2-yl)indazol-3-yl]-2-methylpyridine-3-carboxylic acid (100 mg, 0.26 mmol), triethylamine (81 mg, 0.80 mmol) and methylamine (2M in tetrahydrofuran) (0.3 mL) in dichloromethane (3 mL) was added 2,4,6-tripropyl-1,3,5,2,4,6-trioxatriphosphorinane-2,4,6-trioxide (340 mg, 0.53 mmol, 50% in ethyl acetate). The mixture was stirred at room temperature for 16 h. The reaction mixture was concentrated under vacuum. The residue was purified by flash column chromatography with 0~80% ethyl acetate in petroleum ether to afford 6-[5,6-difluoro-1-(oxan-2-yl)indazol-3-yl]-N,2-dimethylpyridine-3-carboxamide (60 mg, 57%) as a white solid. MS m/z 387.2 [M+1]$^+$.

Step 3: To a solution of 6-[5,6-difluoro-1-(oxan-2-yl)indazol-3-yl]-N,2-dimethylpyridine-3-carboxamide (60 mg, 0.15 mmol) in dichloromethane (3 mL) was added trifluoroacetic acid (2 mL). The mixture was stirred at room temperature for 16 h. The reaction mixture was concentrated under vacuum. The residue was purified by Prep-HPLC [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 20% B to 45% B in 8 min] to afford 6-(5,6-difluoro-1H-indazol-3-yl)-N,2-dimethylpyridine-3-carboxamide (25.8 mg, 54%) as a light yellow solid.

Example 101

6-(5,6-difluoro-1H-indazol-3-yl)-2-methylpyridine-3-carboxamide

Step 1: To a solution of 6-[5,6-difluoro-1-(oxan-2-yl)indazol-3-yl]-2-methylpyridine-3-carboxylic acid (from Example 98) (40 mg, 0.10 mmol), ammonium chloride (29 mg, 0.53 mmol), N-(3-dimethylaminopropyl)-N'-ethylcarbodiimide hydrochloride (31 mg, 0.16 mmol) and 1-hydroxybenzotriazole (22 mg, 0.16 mmol) in N,N-Dimethylformamide (5 mL) was added 4-dimethylaminopyridine (7 mg, 0.05 mmol). The mixture was stirred at room temperature overnight. The mixture was diluted with water and extracted with EA. The combined organic layers were washed with brine, dried over anhydrous sodium sulfate, filtered and concentrated under vacuum to afford 6-[5,6-difluoro-1-(oxan-2-yl)indazol-3-yl]-2-methylpyridine-3-carboxamide (35 mg, crude) as a brown solid. MS m/z 373.3 [M+1]$^+$.

Step 2: To a solution of 6-[5,6-difluoro-1-(oxan-2-yl)indazol-3-yl]-2-methylpyridine-3-carboxamide (60 mg, 0.16 mmol) in dichloromethane (3 mL) was added trifluoroacetic acid (2 mL). The resulting solution was stirred at room temperature overnight. The mixture was concentrated under vacuum. The crude product was purified by Prep-HPLC [Column: XBridge Shield RP18 OBD Column, 30*150 mm, 5 um; Mobile Phase A: water, Mobile Phase B: acetonitrile; Flow rate: 60 mL/min; Gradient: 22% B to 45% B in 8 min] to afford 6-(5,6-difluoro-1H-indazol-3-yl)-2-methylpyridine-3-carboxamide (14.2 mg, 30%) as a white solid.

Example 102

6-(5,6-difluoro-1H-indazol-3-yl)-N,N,2-trimethylpyridine-3-carboxamide

Step 1: To a solution of 6-[5,6-difluoro-1-(oxan-2-yl)indazol-3-yl]-2-methylpyridine-3-carboxylic acid (40 mg, 0.10 mmol), O-(7-Azabenzotriazol-1-yl)-N,N,N,N-tetramethyluronium hexafluorophosphate (61 mg, 0.16 mmol) and dimethylamine hydrochloride (26 mg, 0.32 mmol) in dichloromethane (5 mL) was added DIEA (69 mg, 0.53 mmol). The resulting solution was stirred at room temperature overnight. The mixture was concentrated under vacuum. The residue was purified by flash column chromatography with 0~70% ethyl acetate in petroleum ether to afford 6-[5,6-difluoro-1-(oxan-2-yl)indazol-3-yl]-N,N,2-trimethylpyridine-3-carboxamide (25 mg, 58%) as a white solid. MS m/z 401.1 [M+1]$^+$.

Step 2: To a solution of 6-[5,6-difluoro-1-(oxan-2-yl)indazol-3-yl]-N,N,2-trimethylpyridine-3-carboxamide (25 mg, 0.1 mmol) in dichloromethane (3 mL) was added trifluoroacetic acid (2 mL). The resulting solution was stirred at room temperature overnight. The mixture was concentrated under vacuum. The residue was purified by Prep-HPLC [Column: XBridge Shield RP18 OBD Column, 30150 mm, 5 um; Mobile Phase A: water, Mobile Phase B: acetonitrile; Flow rate: 60 mL/min; Gradient: 24% B to 53% B in 8 min] to afford 6-(5,6-difluoro-1H-indazol-3-yl)-N,N,2-trimethylpyridine-3-carboxamide (15.2 mg, 76%) as a white solid.

Example 103

6-(5,6-difluoro-1H-indazol-3-yl)-2-methylpyridine-3-carbonitrile

Followed the procedure of Example 1 described above and the crude product was purified by Prep-HPLC (Method C) to afford 6-(5,6-difluoro-1H-indazol-3-yl)-2-methylpyridine-3-carbonitrile (14.1 mg, 15% over 2 steps) as a white solid from 5,6-difluoro-1-(oxan-2-yl)indazol-3-ylboronic acid (100 mg, 0.35 mmol).

Example 104

2-(5,6-difluoro-1H-indazol-3-yl)-6,7-dimethyl-7H-pyrrolo[3,4-b]pyridin-5-one

Followed the procedure of Example 1 described above and the crude product was purified by Prep-HPLC (Method A) to afford 2-(5,6-difluoro-1H-indazol-3-yl)-6,7-dimethyl-7H-pyrrolo[3,4-b]pyridin-5-one (32.6 mg, 24% over 2 steps) as an off-white solid from 2-chloro-6,7-dimethyl-7H-pyrrolo[3,4-b]pyridin-5-one (86 mg, 0.43 mmol).

Example 105

2-(5,6-difluoro-1-methylindazol-3-yl)-7-methyl-6H, 7H-pyrrolo[3,4-b]pyridin-5-one Step 1: A degassed mixture of 5,6-difluoro-1-methylindazol-3-ylboronic acid (80 mg, 0.37 mmol), 2-chloro-6-[(4-methoxyphenyl)methyl]-7-methyl-7H-pyrrolo[3,4-b]pyridin-5-one (122 mg, 0.40 mmol), chloro(2-dicyclohexylphosphino-2',4',6'-triisopropyl-1,1'-biphenyl)[2-(2'-amino-1,1'-biphenyl)]palladium(II) (31 mg, 0.041 mmol) and tripotassium orthophosphate (160 mg, 0.75 mmol) in dioxane (2 mL)/water (0.2 mL) was heated to 100° C. for 16 h. The mixture was concentrated under vacuum. The residue was purified by flash column chromatography with 0~40% ethyl acetate in petroleum ether to afford 2-(5,6-difluoro-1-methyl-indazol-3-yl)-6-[(4-methoxyphenyl)methyl]-7-methyl-7H-pyrrolo[3,4-b]pyridin-5-one (60 mg, 36%) as a light yellow solid. MS m/z 435.1 [M+1]$^+$.

Step 2: A mixture of 2-(5,6-difluoro-1-methylindazol-3-yl)-6-[(4-methoxyphenyl)methyl]-7-methyl-7H-pyrrolo[3,4-b]pyridin-5-one (60 mg, 0.13 mmol) in trifluoroacetic acid (5 mL) was heated to reflux for 16 h. The mixture was concentrated under vacuum. The residue was purified by Prep-HPLC [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 25% B to 53% B in 8 min] to afford 2-(5,6-difluoro-1-methylindazol-3-yl)-7-methyl-6H,7H-pyrrolo[3,4-b]pyridin-5-one (6.6 mg, 15%) as a yellow solid.

Example 106

2-(5,6-difluoroindazol-1-yl)-6-[(4-methoxyphenyl)methyl]-7-methyl-7H-pyrrolo[3,4-b]pyridin-5-one A degassed mixture of 5,6-difluoro-1H-indazole (70 mg, 0.45 mmol), 2-chloro-6-[(4-methoxyphenyl)-methyl]-7-methyl-7H-pyrrolo[3,4-b]pyridin-5-one (136 mg, 0.45 mmol), methanesulfonato-2-dicyclohexyl-phosphino-3,6-dimethoxy-2'-4'-6'-tri-i-propyl-1,1'-bipheny)(2'-amino-1,1'-biphenyl-2-yl)-palladium(II) (47 mg, 0.052 mmol), 2-(dicyclohexylphosphino)-3,6-dimethoxy-2'-4'-6'-tri-i-propyl-1,1'-biphenyl (22 mg, 0.041 mmol) and caesium carbonate (310 mg, 0.95 mmol) in dioxane (5 mL) was heated to 90° C. for 16 h. The mixture was concentrated under vacuum. The residue was purified by flash column chromatography with 0~70% ethyl acetate in petroleum ether to afford 2-(5,6-difluoroindazol-1-yl)-6-[(4-methoxyphenyl)methyl]-7-methyl-7H-pyrrolo[3,4-b]pyridin-5-one (110 mg, 57%) as a white solid.

Example 107

2-(5,6-difluoroindazol-1-yl)-7-methyl-6H,7H-pyrrolo[3,4-b]pyridin-5-one

A mixture of 2-(5,6-difluoroindazol-1-yl)-6-[(4-methoxyphenyl)methyl]-7-methyl-7H-pyrrolo[3,4-b]pyridin-5-one (80 mg, 0.19 mmol) and trifluoromethanesulfonic acid (0.5 mL) in trifluoroacetic acid (2 mL) was stirred to 60° C. for 16 h. The mixture was concentrated under reduced pressure. The residue was purified by trituration with ethyl acetate and hexane (1/10) to afford 2-(5,6-difluoroindazol-1-yl)-7-methyl-6H,7H-pyrrolo[3,4-b]pyridin-5-one (9.2 mg, 16%) as a grey solid.

Example 108

2-(5,6-difluoro-1,3-benzodiazol-1-yl)-7-methyl-6H, 7H-pyrrolo[3,4-b]pyridin-5-one Step 1: A degassed mixture of 2-chloro-6-[(4-methoxyphenyl)methyl]-7-methyl-7H-pyrrolo[3,4-b]pyridin-5-one (150 mg, 0.49 mmol), 4,5-difluorobenzene-1,2-diamine (108 mg, 0.75 mmol), tris(dibenzylidene-acetone)dipalladium (54 mg, 0.059 mmol), 9,9-dimethyl-4,5-bis(diphenylphosphino)xanthene (58 mg, 0.10 mmol) and cesium carbonate (342 mg, 1.05 mmol) in dioxane (5 mL) was heated to 100° C. for 16 h. The mixture was concentrated under vacuum. The residue was purified by flash column chromatography with 0~5% methanol in dichloromethane to afford 2-[(2-amino-4,5-difluorophenyl)amino]-6-[(4-methoxyphenyl)-methyl]-7-methyl-7H-pyrrolo[3,4-b]pyridin-5-one (240 mg, 93%) as a brown syrup. MS m/z 411.1 [M+1]$^+$.

Step 2: To a solution of 2-[(2-amino-4,5-difluorophenyl)amino]-6-[(4-methoxyphenyl)-methyl]-7-methyl-7H-pyrrolo[3,4-b]pyridin-5-one (220 mg, 0.53 mmol) and trimethyl orthoformate (171 mg, 1.63 mmol) in toluene (5 mL) was added p-toluenesulfonic acid monohydrate (12 mg, 0.07 mmol). The mixture was heated to reflux for 16 h. The mixture was concentrated under vacuum. The residue was triturated with petroleum ether/ethyl acetate (10/1) to afford 2-(5,6-difluoro-1,3-benzodiazol-1-yl)-6-[(4-methoxyphenyl)methyl]-7-methyl-7H-pyrrolo[3,4-b]pyridin-5-one (120 mg, 53%) as a yellow solid. MS m/z 421.1 [M+1]$^+$.

Step 3: To a solution of 2-(5,6-difluoro-1,3-benzodiazol-1-yl)-6-[(4-methoxyphenyl)-methyl]-7-methyl-7H-pyrrolo[3,4-b]pyridin-5-one (120 mg, 0.28 mmol) in trifluoroacetic acid (5 mL) was added trifluoromethanesulfonic acid (0.2 mL). The mixture was heated to reflux for 7 h. The mixture was concentrated under vacuum. The residue was purified by reverse phase flash column chromatography with 10~55% acetonitrile in water (10 mmol/L ammonium bicarbonate) to afford 2-(5,6-difluoro-1,3-benzodiazol-1-yl)-7-methyl-6H,7H-pyrrolo[3,4-b]pyridin-5-one (5.7 mg, 6%) as a white solid.

Example 109

5-(1H-indazol-3-yl)-3-methylisoindolin-1-one

Followed the procedure of Example 1 described above and the crude product was purified by Prep-HPLC (Method C) to afford 5-(1H-indazol-3-yl)-3-methylisoindolin-1-one (45.3 mg, 38% over 2 steps) as a white solid from 5-bromo-3-methyl-2,3-dihydroisoindol-1-one (100 mg, 0.44 mmol).

Example 110

5-(5,6-difluoro-1H-indazol-3-yl)-3,3-dimethyl-2H-isoindol-1-one

Followed the procedure of Example 105 described above and the crude product was purified by reverse phase flash column chromatography with 5~50% acetonitrile in water to afford 5-(5,6-difluoro-1H-indazol-3-yl)-3,3-dimethyl-2H-isoindol-1-one (4.5 mg, 6% over 2 steps) as a white solid from 5,6-difluoro-1-(oxan-2-yl)indazol-3-ylboronic acid (49 mg, 0.12 mmol).

Example 111

6-fluoro-3-(5-fluoropyridin-2-yl)-1H-indazole

Followed the procedure of Example 1 described above and the crude product was purified by Prep-HPLC (Method A) to afford 6-fluoro-3-(5-fluoropyridin-2-yl)-1H-indazole (12.7 mg, 26% over 2 steps) as a white solid from 6-fluoro-1-(oxan-2-yl) indazol-3-ylboronic acid (180 mg, 0.68 mmol).

Example 112

5-fluoro-2-[1H-pyrazolo[4,3-b]pyridin-3-yl]pyridine

Followed the procedure of Example 75 described above and the crude product was purified by Prep-HPLC (Method A) to afford 5-fluoro-2-[1H-pyrazolo[4,3-b]pyridin-3-yl]pyridine (4.5 mg, 1% over 2 steps) as a light pink solid from 1-(oxan-2-yl)pyrazolo[4,3-b]pyridin-3-ylboronic acid (500 mg, 2.02 mmol).

Example 113

3-(4-fluorophenyl)-1H-pyrazolo[3,4-b]pyridine

Followed the procedure of Example 105 described above and the crude product was purified by Prep-HPLC (Method B) to afford 3-(4-fluorophenyl)-1H-pyrazolo[3,4-b]pyridine (80.3 mg, 18% over 2 steps) as a white solid from 1-(oxan-2-yl)pyrazolo[3,4-b]pyridin-3-ylboronic acid (500 mg, 2.02 mmol).

Example 114

2-(1H-indazol-3-yl)-6H,7H-pyrrolo[3,4-b]pyridin-5-one

Followed the procedure of Example 1 described above and the crude product was purified by Prep-HPLC (Method C) to afford 2-(1H-indazol-3-yl)-6H,7H-pyrrolo[3,4-b]pyridin-5-one (7.1 mg, 4% over 2 steps) as a yellow solid from 1-(oxan-2-yl)-3-(4,4,5,5-tetramethyl-1,3,2-dioxaborolan-2-yl)indazole (304 mg, 0.93 mmol).

Example 115

6-(5,6-difluoro-1H-indazol-3-yl)-2,3-dihydro-1H-pyrido[2,3-b][1,4]thiazine 4,4-dioxide Followed the procedure of Example 1 described above and the crude product was purified by Prep-HPLC (Method A) to afford 6-(5,6-difluoro-1H-indazol-3-yl)-1H,2H,3H-4lambda6-pyrido[2,3-b][1,4]thiazine-4,4-dione (10.9 mg, 4% over 2 steps) as a white solid from 5,6-difluoro-1-(oxan-2-yl)indazol-3-ylboronic acid (148 mg, 0.53 mmol).

Example 116

5-fluoro-2-[1H-pyrazolo[3,4-b]pyridin-3-yl]pyridine

Followed the procedure of Example 105 described above and the crude product was purified by Prep-HPLC (Method A) to afford 5-fluoro-2-[1H-pyrazolo[3,4-b]pyridin-3-yl]pyridine (19.4 mg, 24% over 2 steps) as a white solid from 1-(oxan-2-yl)pyrazolo[3,4-b]pyridin-3-ylboronic acid.

Example 117

2-(1H-indazol-3-yl)quinoline

Followed the procedure of Example 1 described above and the crude product was purified by reverse phase flash column chromatography with 5-50% acetonitrile in water to afford 2-(1H-indazol-3-yl)quinoline (42.3 mg, 35% over 2 steps) as a light brown solid from 2-bromoquinoline (100 mg, 0.48 mmol).

Example 118

3-[5-(trifluoromethyl)pyridin-2-yl]-1H-indole

Step 1: To a solution of 1-(tert-butoxycarbonyl)indol-3-ylboronic acid (100 mg, 0.38 mmol) in dioxane (5 mL) and water (0.5 mL) were added 2-chloro-5-(trifluoromethyl) pyridine (83 mg, 0.4 mmol), [1,1'-bis(diphenylphosphino) ferrocene]dichloropalladium(II) (28 mg, 0.04 mmol) and potassium carbonate (156 mg, 1.13 mmol). The mixture was stirred at 100° C. for 4 h under nitrogen atmosphere. The mixture was diluted with water and extracted with ethyl acetate. The organic layer was dried over anhydrous sodium sulfate, filtered and concentrated under vacuum. The residue was purified by flash column chromatography with 0~40% ethyl acetate in petroleum ether to afford tert-butyl 3-[5-(trifluoromethyl)pyridin-2-yl]indole-1-carboxylate (128 mg, 92%) as a brown solid. MS m/z 363.1 [M+1]$^+$.

Step 2: To a solution of tert-butyl 3-[5-(trifluoromethyl) pyridin-2-yl]indole-1-carboxylate (128 mg, 0.35 mmol) in dichloromethane (2 mL) was added trifluoroacetic acid (3 mL). The mixture was stirred at room temperature for 2 h. The mixture was concentrated under vacuum. The residue was diluted with water and basified with NaHCO$_3$. The aqueous phase was extracted with dichloromethane. The organic layer was dried over anhydrous sodium sulfate, filtered and concentrated under vacuum. The crude product was purified by Prep-HPLC (Method A) [Column, XBridge Shield RP18 OBD Column, 30*150 mm, 5 um; mobile phase A: water (10 mmol/L ammonium bicarbonate), mobile phase B: acetonitrile, Flow rate: 60 mL/min; Gradient: 48% B up to 71% in 7 min] to afford 3-[5-(trifluoromethyl) pyridin-2-yl]-1H-indole (38.8 mg, 41%) as an off-white solid.

Example 119

3-(5-fluoropyridin-2-yl)-1H-indole

Followed the procedure of Example 118 described above and purified by Prep-HPLC (Method A) to afford 3-(5-fluoropyridin-2-yl)-1H-indole (69.3 mg, 86% over 2 steps) as a white solid from 1-(tert-butoxycarbonyl)indol-3-ylboronic acid (100 mg, 0.38 mmol).

Example 120

3-(7-fluoroquinolin-2-yl)-1H-indole-7-carbonitrile

A mixture of tert-butyl 7-cyano-3-(4,4,5,5-tetramethyl-1,3,2-dioxaborolan-2-yl)indole-1-carboxylate (100 mg, 0.27 mmol), 2-bromo-7-fluoroquinoline (37 mg, 0.16 mmol), [1,1'-bis(diphenylphosphino)-ferrocene]dichloropalladium (II) (20 mg, 0.03 mmol) and potassium carbonate (75 mg, 0.55 mmol) in dioxane (5 mL)/water (0.5 mL) was stirred to 100° C. for 16 h. The mixture was concentrated under reduced pressure. The residue was diluted with ethyl acetate and washed with water. The organic layer was dried over anhydrous sodium sulfate, filtered and concentrated under vacuum. The residue was purified directly by Prep-HPLC (Method A) [Column: XBridge Prep OBD C18 Column, 30*150 mm 5 um; Mobile Phase A: water (10 mmol/L ammonium bicarbonate), Mobile Phase B: acetonitrile; Flow rate: 60 mL/min; Gradient: 50% B to 70% B in 8 min] to afford 3-(7-fluoroquinolin-2-yl)-1H-indole-7-carbonitrile (7.9 mg, 17%) as a white solid.

Example 121

3-(5,6,7,8-tetrahydro-1,5-naphthyridin-2-yl)-1H-indole-7-carbonitrile

A mixture of tert-butyl 7-cyano-3-(4,4,5,5-tetramethyl-1,3,2-dioxaborolan-2-yl)indole-1-carboxylate (300 mg, 0.81 mmol), 2-chloro-5,6,7,8-tetrahydro-1,5-naphthyridine (82 mg, 0.48 mmol), (2-dicyclohexyl-phosphino-2',6'-diisopropoxy-1,1'-biphenyl)[2-(2'-amino-1,1'-biphenyl)]palladium(II) methanesulfonate (68 mg, 0.08 mmol) and tripotassium orthophosphate (346 mg, 1.62 mmol) in dioxane (5 mL) and water (0.5 mL) was stirred at 100° C. for 16 h under nitrogen atmosphere. The reaction mixture was concentrated under reduced pressure. The residue was diluted with ethyl acetate and washed with water. The organic layer was dried over anhydrous sodium sulfate, filtered and concentrated under vacuum. The residue was purified directly by Prep-HPLC (Method A) [Column: XBridge Prep OBD C18 Column, 30*150 mm 5 um; Mobile Phase A: water (10 mmol/L ammonium bicarbonate), Mobile Phase B: acetonitrile; Flow rate: 60 mL/min; Gradient: 32% B to 60% B in 8 min] to afford 3-(5,6,7,8-tetrahydro-1,5-naphthyridin-2-yl)-1H-indole-7-carbonitrile (28 mg, 12%) as a light yellow solid.

Example 122

2-(5,6-difluoro-1H-indol-3-yl)-7,7-dimethyl-6H-pyrrolo[3,4-b]pyridin-5-one

Step 1: A degassed mixture of tert-butyl 5,6-difluoro-3-(4,4,5,5-tetramethyl-1,3,2-dioxaborolan-2-yl)indole-1-carboxylate (90 mg, 0.23 mmol), 2-chloro-6-[(4-methoxy-phenyl)methyl]-7,7-dimethylpyrrolo[3,4-b]pyridin-5-one (70 mg, 0.22 mmol), (2-dicyclohexyl-phosphino-2',6'-diisopropoxy-1,1'-biphenyl)[2-(2'-amino-1,1'-biphenyl)]palladium(II) methanesulfonate (22 mg, 0.03 mmol), tripotassium orthophosphate (107 mg, 0.50 mmol) in dioxane (5 mL)/water (0.2 mL) was heated to 100° C. for 16 h. The mixture was concentrated under vacuum. The residue was purified by flash column chromatography with 0~40% ethyl acetate in petroleum ether to afford tert-butyl 5,6-difluoro-3-[6-[(4-methoxyphenyl)methyl]-7,7-dimethyl-5-oxopyrrolo-[3,4-b]pyridin-2-yl]indole-1-carboxylate (65 mg, 51%) as a yellow oil. MS m/z 534.3 [M+1]$^+$.

Step 2: A mixture of tert-butyl 5,6-difluoro-3-[6-[(4-methoxyphenyl)methyl]-7,7-dimethyl-5-oxopyrrolo[3,4-b]pyridin-2-yl]indole-1-carboxylate (65 mg, 0.12 mmol) in trifluoroacetic acid (2 mL)/trifluoromethanesulfonic acid (0.20 mL) was heated at reflux for 24 h. The mixture was concentrated under vacuum. The residue was purified by Prep-HPLC (Method D) [Column: YMC-Actus Triart C18, 30*250, 5 um; Mobile Phase A: water (10 mmol/L ammonium bicarbonate+0.1% ammonium hydroxide), Mobile Phase B: acetonitrile; Flow rate: 50 mL/min; Gradient: 35% B to 55% B in 8 min] to afford 2-(5,6-difluoro-1H-indol-3-yl)-7,7-dimethyl-6H-pyrrolo[3,4-b]pyridin-5-one (10.5 mg, 27%) as a white solid.

Example 123 ethyl 2-(7-methyl-1H-indol-3-yl)-1,3-oxazole-4-carboxylate

Followed the procedure of Example 118 described above and purified by Prep-HPLC (Method A) to afford ethyl 2-(7-methyl-1H-indol-3-yl)-1,3-oxazole-4-carboxylate (13.6 mg, 17% over 2 steps) as a white solid from tert-butyl 7-methyl-3-(4,4,5,5-tetramethyl-1,3,2-dioxaborolan-2-yl) indole-1-carboxylate.

Example 124

6-(5,6-difluoro-1H-indol-3-yl)-2-methylpyridin-3-amine

Step 1: To a mixture of 1-(tert-butoxycarbonyl)-5,6-difluoroindol-3-ylboronic acid (100 mg, 0.34 mmol), 6-chloro-2-methylpyridin-3-amine (48 mg, 0.34 mmol) and tripotassium orthophosphate (143 mg, 0.67 mmol) in dioxane (2 mL) and water (0.2 mL) was added chloro(2-dicyclohexylphosphino-2',4',6'-triisopropyl-1,1'-biphenyl)[2-(2'-amino-1,1'-biphenyl)]palladium(II) (27 mg, 0.03 mmol). The mixture was stirred at 100° C. for 16 h under nitrogen atmosphere. The mixture was concentrated under vacuum. The residue was purified by Prep-TLC with petroleum ether/ethyl acetate (1:1) to afford tert-butyl 3-(5-amino-6-methylpyridin-2-yl)-5,6-difluoroindole-1-carboxylate (50 mg, 41%) as a white solid. MS m/z 360.0 [M+1]$^+$.

Step 1: To a solution of tert-butyl 3-(5-amino-6-methylpyridin-2-yl)-5,6-difluoroindole-1-carboxylate (50 mg, 0.14 mmol) in dichloromethane (3 mL) was added trifluoroacetic acid (2 mL). The mixture was stirred at room temperature overnight. The mixture was concentrated under vacuum. The residue was purified by Prep-HPLC (Method C) [Column: XBridge Shield RP18 OBD Column, 30*150 mm, 5 um; Mobile Phase A: water, Mobile Phase B: acetonitrile; Flow rate: 60 mL/min; Gradient: 30% B to 55% B in 8 min] to afford 6-(5,6-difluoro-1H-indol-3-yl)-2-methylpyridin-3-amine (14.7 mg, 40%) as a light yellow solid.

Example 125

3-(5-amino-6-methylpyridin-2-yl)-1H-indole-7-carbonitrile

A degassed mixture of tert-butyl 7-cyano-3-(4,4,5,5-tetramethyl-1,3,2-dioxaborolan-2-yl)indole-1-carboxylate (500 mg, 0.81 mmol), 6-bromo-2-methylpyridin-3-amine (154 mg, 0.82 mmol), chloro(2-dicyclo-hexylphosphino-2',4',6'-triisopropyl-1,1'-biphenyl)[2-(2'-amino-1,1'-biphenyl)] palladium(II) (56 mg, 0.074 mmol) and tripotassium orthophosphate (357 mg, 1.68 mmol) in dioxane (5 mL)/water (0.5 mL) was heated to 100° C. for 16 h. The mixture was concentrated under vacuum. The residue was purified by flash column chromatography with 0~80% ethyl acetate in petroleum ether, and then further purified by reverse phase flash column chromatography with 10-70% acetonitrile in water to afford 3-(5-amino-6-methylpyridin-2-yl)-1H-indole-7-carbonitrile (66.5 mg, 32%) as a light yellow solid.

Example 126

5-fluoro-2-[1H-pyrrolo[2,3-b]pyridin-3-yl]pyridine

Step 1: A mixture of tert-butyl 3-(4,4,5,5-tetramethyl-1,3,2-dioxaborolan-2-yl)pyrrolo[2,3-b]pyridine-1-carboxylate (100 mg, 0.29 mmol), 2-bromo-5-fluoropyridine (31 mg, 0.17 mmol), 2-dicyclohexylphosphino-3,6-dimethoxy-2'-4'-6'-tri-i-propyl-1,1'-bipheny)(2'-amino-1,1'-biphenyl-2-yl) palladium(II) methanesulfonate (26 mg, 0.029 mmol) and tripotassium orthophosphate (123 mg, 0.58 mmol) in dioxane (2 mL)/water (0.2 mL) was heated to 100° C. and stirred for 16 h under nitrogen atmosphere. The mixture was concentrated under reduced pressure. The residue was purified by flash column chromatography with 0~60% ethyl acetate in petroleum ether to afford tert-butyl 3-(5-fluoropyridin-2-yl)pyrrolo[2,3-b]pyridine-1-carboxylate (37 mg, 40%) as a yellow solid. MS m/z 314.2 [M+1]$^+$.

Step 2: To a solution of tert-butyl 3-(5-fluoropyridin-2-yl)pyrrolo[2,3-b]pyridine-1-carboxylate (37 mg, 0.11 mmol) in dichloromethane (3 mL) was added trifluoroacetic acid (1 mL). The mixture was stirred at room temperature for 16 h. The mixture was concentrated under reduced pressure. The residue was purified by Prep-HPLC [Column: XBridge Shield RP18 OBD Column, 30150 mm, 5 um; Mobile Phase A: water (10 mmol/L ammonium bicarbonate+0.1% ammonium hydroxide), Mobile Phase B: acetonitrile; Flow rate: 50 mL/min; Gradient: 40% B to 65% B in 8 min] to afford 5-fluoro-2-[1H-pyrrolo[2,3-b]pyridin-3-yl]pyridine (5.2 mg, 20%) as a white solid.

Example 127

3-(5-fluoropyridin-2-yl)-1H-indole-7-carbonitrile

Followed the procedure of Example 126 described above and purified by Prep-HPLC (Method D) to afford 3-(5-fluoropyridin-2-yl)-1H-indole-7-carbonitrile (11.4 mg, 17%) as a white solid from tert-butyl 7-cyano-3-(4,4,5,5-tetramethyl-1,3,2-dioxaborolan-2-yl)indole-1-carboxylate (100 mg, 0.27 mmol).

Example 128

5-cyclopropyl-2-[1H-pyrrolo[2,3-b]pyridin-3-yl]pyridine

Followed the procedure of Example 126 described above and purified by Prep-HPLC (Method A) to afford 5-cyclopropyl-2-[1H-pyrrolo[2,3-b]pyridin-3-yl]pyridine (6.4 mg, 4% over 2 steps) as a white solid from tert-butyl 3-(4,4,5,5-tetramethyl-1,3,2-dioxaborolan-2-yl)pyrrolo[2,3-b]pyridine-1-carboxylate (200 mg, 0.58 mmol).

Example 129

5-(oxetan-3-yl)-2-[1H-pyrrolo[2,3-b]pyridin-3-yl]pyridine

Followed the procedure of Example 124 described above and purified by Prep-HPLC (Method B) to afford 5-(oxetan-3-yl)-2-[1H-pyrrolo[2,3-b]pyridin-3-yl]pyridine (7.7 mg, 3%) as a light yellow solid from 2-chloro-5-(oxetan-3-yl)pyridine (150 mg, 0.88 mmol).

Example 130

3-(5-amino-6-methylpyridin-2-yl)-5-fluoro-1H-indole-7-carbonitrile

Followed the procedure of Example 125 described above and purified by Prep-HPLC (Method A) to afford 3-(5-amino-6-methylpyridin-2-yl)-5-fluoro-1H-indole-7-carbonitrile (10.1 mg, 14%) as a light yellow solid from tert-butyl 7-cyano-5-fluoro-3-(4,4,5,5-tetramethyl-1,3,2-dioxaborolan-2-yl)indole-1-carboxylate (100 mg, 0.26 mmol).

Example 131

5-fluoro-3-(5-fluoro-6-methylpyridin-2-yl)-1H-indole-7-carbonitrile

Followed the procedure of Example 125 described above and purified by Prep-HPLC (Method A) to afford 5-fluoro-3-(5-fluoro-6-methylpyridin-2-yl)-1H-indole-7-carbonitrile (15.3 mg, 21%) as a light yellow solid from tert-butyl 7-cyano-5-fluoro-3-(4,4,5,5-tetramethyl-1,3,2-dioxaborolan-2-yl)indole-1-carboxylate (100 mg, 0.26 mmol).

Example 132

3-(5-aminopyridin-2-yl)-1H-indole-7-carbonitrile

Followed the procedure of Example 124 described above and purified by reverse phase flash column chromatography with 5-40% acetonitrile in water to afford 3-(5-aminopyridin-2-yl)-1H-indole-7-carbonitrile (3.1 mg, 8%) as a white solid from tert-butyl 7-cyano-3-(4,4,5,5-tetramethyl-1,3,2-dioxaborolan-2-yl)indole-1-carboxylate (100 mg, 0.27 mmol).

Example 133

3-(6-methylpyridin-2-yl)-1H-indole-7-carbonitrile

Followed the procedure of Example 125 described above and purified by reverse phase flash column chromatography with 5-50% acetonitrile in water to afford 3-(6-methylpyridin-2-yl)-1H-indole-7-carbonitrile (8.1 mg, 11%) as a white solid from tert-butyl 7-cyano-3-(4,4,5,5-tetramethyl-1,3,2-dioxaborolan-2-yl)indole-1-carboxylate (100 mg, 0.27 mmol).

Example 134

2-methyl-6-[1H-pyrrolo[3,2-b]pyridin-3-yl]pyridin-3-amine

Followed the procedure of Example 124 described above and purified by Prep-HPLC (Method A) to afford 2-methyl-6-[1H-pyrrolo[3,2-b]pyridin-3-yl]pyridin-3-amine (19.6 mg, 5% over 2 steps) as a light yellow solid from tert-butyl 3-(4,4,5,5-tetramethyl-1,3,2-dioxaborolan-2-yl)-1H-pyrrolo[3,2-b]pyridine-1-carboxylate (470 mg, 1.36 mmol).

Example 135

2-methyl-6-[1H-pyrrolo[2,3-b]pyridin-3-yl]pyridin-3-amine

Followed the procedure of Example 125 described above and purified by Prep-HPLC (Method A) to afford 2-methyl- 6-[1H-pyrrolo[2,3-b]pyridin-3-yl]pyridin-3-amine (6.7 mg, 5%) as a light yellow solid from tert-butyl 3-(4,4,5,5-tetramethyl-1,3,2-dioxaborolan-2-yl)pyrrolo[2,3-b]pyridine-1-carboxylate (200 mg, 0.58 mmol).

Example 136

2-(5,6-difluoro-1H-indol-3-yl)-7-methyl-6H,7H-pyrrolo[3,4-b]pyridin-5-one

Step-1: A degassed mixture of tert-butyl 5,6-difluoro-3-(4,4,5,5-tetramethyl-1,3,2-dioxaborolan-2-yl)indole-1-carboxylate (140 mg, 0.37 mmol), 2-chloro-6-[(4-methoxyphenyl)-methyl]-7-methyl-7H-pyrrolo[3,4-b]pyridin-5-one (108 mg, 0.35 mmol), chloro(2-dicyclo-hexylphosphino-2',4',6'-triisopropyl-1,1'-biphenyl)[2-(2'-amino-1,1'-biphenyl)] palladium(II) (28 mg, 0.037 mmol) and tripotassium orthophosphate (162 mg, 0.76 mmol) in dioxane (3 mL)/water (0.2 mL) was heated to 100° C. and stirred for 4 h. The mixture was concentrated under vacuum. The residue was purified by flash column chromatography with 0~50% ethyl acetate in petroleum ether to afford tert-butyl 5,6-difluoro-3-[6-[(4-methoxyphenyl)methyl]-7-methyl-5-oxo-7H-pyrrolo[3,4-b]pyridin-2-yl]indole-1-carboxylate (40 mg, 20%) as a yellow solid. MS m/z 520.2 [M+1]$^+$.

Step-2: A mixture of tert-butyl 5,6-difluoro-3-[6-[(4-methoxyphenyl)methyl]-7-methyl-5-oxo-7H-pyrrolo[3,4-b]pyridin-2-yl]indole-1-carboxylate (70 mg, 0.13 mmol) and trifluoroacetic acid (5 mL) trifluoro-methanesulfonic acid (0.5 mL) was heated to reflux for 16 h. The mixture was concentrated under vacuum. The residue was basified using saturated sodium bicarbonate aqueous solution and extracted with ethyl acetate. The organic layer was dried over anhydrous sodium sulfate, filtered and concentrated under vacuum. The residue was purified by reverse phase flash column chromatography with 10~60% acetonitrile in water to afford 2-(5,6-difluoro-1H-indol-3-yl)-7-methyl-6H,7H-pyrrolo[3,4-b]pyridin-5-one (30.3 mg, 75%) as a white solid.

Example 137

3-(5-amino-6-chloropyridin-2-yl)-1H-indole-7-carbonitrile

Followed the procedure of Example 125 described above and purified by Prep-HPLC (Method C) to afford 3-(5-amino-6-chloropyridin-2-yl)-1H-indole-7-carbonitrile (4.2 mg, 5%) as a white solid from tert-butyl 7-cyano-3-(4,4,5,5-tetramethyl-1,3,2-dioxaborolan-2-yl)indole-1-carboxylate (100 mg, 0.27 mmol).

Example 138

3-(5-amino-4-methylpyridin-2-yl)-1H-indole-7-carbonitrile

Followed the procedure of Example 125 described above and purified by Prep-HPLC (Method C) to afford 3-(5-amino-4-methylpyridin-2-yl)-1H-indole-7-carbonitrile (10.8 mg, 5%) as a white solid from tert-butyl 7-cyano-3-(4,4,5,5-tetramethyl-1,3,2-dioxaborolan-2-yl)indole-1-carboxylate (300 mg, 0.81 mmol).

Example 139

3-(5-amino-6-cyclopropylpyridin-2-yl)-1H-indole-7-carbonitrile

Followed the procedure of Example 124 described above and purified by Prep-HPLC (Method C) to afford 3-(5-amino-6-cyclopropylpyridin-2-yl)-1H-indole-7-carbonitrile (10 mg, 6% over 2 steps) as a brown solid from tert-butyl N-(6-chloro-2-cyclopropylpyridin-3-yl)carbamate (150 mg, 0.54 mmol).

Example 140

2-methyl-6-(7-methyl-1H-indol-3-yl)pyridin-3-amine

Followed the procedure of Example 124 described above and purified by flash column chromatography with 10-70% acetonitrile in water to afford 2-methyl-6-(7-methyl-1H-indol-3-yl)pyridin-3-amine (6.4 mg, 8% over 2 steps) as a yellow green solid from tert-butyl 7-methyl-3-(4,4,5,5-tetramethyl-1,3,2-dioxaborolan-2-yl)indole-1-carboxylate (100 mg, 0.28 mmol).

Example 141

6-(7-fluoro-1H-indol-3-yl)-2-methylpyridin-3-amine

Followed the procedure of Example 124 described above and purified by Prep-HPLC (Method C) to afford 6-(7-fluoro-1H-indol-3-yl)-2-methylpyridin-3-amine (64 mg, 45% over 2 steps) as a white solid from tert-butyl 7-fluoro-3-(4,4,5,5-tetramethyl-1,3,2-dioxaborolan-2-yl)indole-1-carboxylate (200 mg, 0.55 mmol).

Example 142

6-(7-cyclopropyl-1H-indol-3-yl)-2-methylpyridin-3-amine

Step-1: To a solution of 7-cyclopropyl-1H-indole (500 mg, 3.18 mmol), di(tert-butyl) carbonate (1100 mg, 5.04 mmol) and triethylamine (965 mg, 9.55 mmol) in dichloromethane (5 mL) was added 4-dimethylaminopyridine (39 mg, 0.29 mmol). The resulting solution was stirred at room temperature overnight. The mixture was concentrated under vacuum. The residue was purified by flash column chromatography with 0-50% ethyl acetate in petroleum ether to afford tert-butyl 7-cyclopropylindole-1-carboxylate (750 mg, 91%) as colorless oil. MS m/z 258.1 [M+1]$^+$.

Step-2: A mixture of tert-butyl 7-cyclopropylindole-1-carboxylate (600 mg, 2.33 mmol) and N-bromosuccinimide (415 mg, 2.33 mmol) in dichloromethane (5 mL) was stirred at 40° C. for 2 h. The residue was diluted with water and extracted with ethyl acetate. The combined organic layers were washed with brine, dried over anhydrous sodium sulfate, filtered and concentrated under vacuum. The residue was purified by flash column chromatography with 0-50% ethyl acetate in petroleum ether to afford tert-butyl 3-bromo-7-cyclopropylindole-1-carboxylate (600 mg, 76%) as colorless oil. $^1$H NMR (400 MHz, DMSO-d$_6$) δ 7.91 (s, 1H), 7.38-7.32 (m, 1H), 7.31-7.25 (m, 1H), 7.24-7.16 (m, 1H), 2.45-2.40 (m, 1H) 1.61 (s, 9H), 0.89-0.79 (m, 2H), 0.52-0.48 (m, 2H).

Step-3: To a degassed solution of tert-butyl 3-bromo-7-cyclopropylindole-1-carboxylate (200 mg, 0.59 mmol), 2-methyl-6-(tributylstannyl)pyridin-3-amine (307 mg, 0.77 mmol) and cesium fluoride (271 mg, 1.78 mmol) in toluene (5 mL) was added bis(triphenylphosphine)palladium(II) chloride (42 mg, 0.06 mmol) under nitrogen atmosphere. The resulting solution was heated to 100° C. and stirred overnight. The mixture was concentrated under vacuum. The residue was purified by flash column chromatography with 0~80% ethyl acetate in petroleum ether to afford tert-butyl 3-(5-amino-6-methylpyridin-2-yl)-7-cyclopropylindole-1-carboxylate (120 mg, 55%) as an off-white solid. MS m/z 364.2 [M+1]$^+$.

Step-4: To a solution of tert-butyl 3-(5-amino-6-methylpyridin-2-yl)-7-cyclopropylindole-1-carboxylate (120 mg, 0.3 mmol) in dichloromethane (6 mL) was added trifluoroacetic acid (4 mL). The resulting solution was stirred at room temperature for 2 h. The residue was basified using saturated sodium bicarbonate aqueous solution to pH 8. The mixture was extracted with ethyl acetate. The organic layer was dried over anhydrous sodium sulfate, filtered and concentrated under vacuum. The crude product was purified by Prep-HPLC (Method D) [Column: XBridge Prep OBD C18 Column, 30×150 mm 5 um; Mobile Phase A: water (10 mmol/L ammonium bicarbonate+0.1% ammonium hydroxide), Mobile Phase B: acetonitrile; Flow rate: 60 mL/min; Gradient: 30% B to 55% B in 8 min] to afford 6-(7-cyclopropyl-1H-indol-3-yl)-2-methylpyridin-3-amine (30.2 mg, 34%) as a yellow solid.

Example 143

5-(5,6-difluoro-1H-indol-3-yl)-3,3-dimethylisoindolin-1-one

Followed the procedure of Example 124 described above and purified by Prep-HPLC (Method C) to afford 5-(5,6-difluoro-1H-indol-3-yl)-3,3-dimethylisoindolin-1-one (34.2 mg, 47% over 2 steps) as a white solid from tert-butyl 6-bromo-1,1-dimethyl-3-oxoisoindole-2-carboxylate (80 mg, 0.23 mmol).

Example 144

2-methyl-6-[7-(1,3,4-oxadiazol-2-yl)-1H-indol-3-yl] pyridin-3-amine

Followed the procedure of Example 124 described above and purified by reverse phase flash column chromatography with 30-70% acetonitrile in water to afford 2-methyl-6-[7-(1,3,4-oxadiazol-2-yl)-1H-indol-3-yl]pyridin-3-amine (17.2 mg, 24% over 2 steps) as a yellow solid from 7-(1,3,4-oxadiazol-2-yl)-1-[[2-(trimethylsilyl)ethoxy]methyl]indol-3-ylboronic acid (100 mg, 0.28 mmol).

Example 145

3-(5-amino-6-methylpyridin-2-yl)-N-methyl-1H-indole-7-carboxamide

Step 1: To a solution of 7-(methylcarbamoyl)-1-[[2-(trimethylsilyl)ethoxy]methyl]indol-3-ylboronic acid (120 mg, 0.34 mmol), 6-bromo-2-methylpyridin-3-amine (52 mg, 0.28 mmol) and potassium carbonate (78 mg, 0.56 mmol) in dioxane (2 mL) and water (0.2 mL) was added palladium (0)tetrakis(triphenylphosphine) (32 mg, 0.02 mmol). The mixture was stirred at 100° C. for 16 h under nitrogen atmosphere. The reaction mixture was concentrated under vacuum. The residue was purified by Prep-TLC with 50% ethyl acetate in petroleum ether to afford 3-(5-amino-6-methylpyridin-2-yl)-N-methyl-1-[[2-(trimethylsilyl)ethoxy] methyl]indole-7-carboxamide (100 mg, 70%) as a brown solid. MS m/z 411.2 [M+1]$^+$.

Step 2: To a solution of 3-(5-amino-6-methylpyridin-2-yl)-N-methyl-1-[[2-(trimethylsilyl)-ethoxy]-methyl]indole-7-carboxamide (80 mg, 0.19 mmol) in dichloromethane (3 mL) was added trifluoroacetic acid (2 mL). The mixture was stirred at room temperature for 16 h. The reaction mixture was concentrated under vacuum. The residue was purified by reverse phase flash column chromatography with 30-80% acetonitrile in water to afford 3-(5-amino-6-methylpyridin-2-yl)-N-methyl-1H-indole-7-carboxamide (14.9 mg, 24%) as an off-white solid.

Example 146

3-[6-methyl-5-(methylamino)pyridin-2-yl]-1H-indole-7-carbonitrile

Followed the procedure of Example 125 described above and purified by Prep-HPLC (Method A) to afford 3-[6-methyl-5-(methylamino)pyridin-2-yl]-1H-indole-7-carbonitrile (8.2 mg, 11%) as a light yellow solid from tert-butyl 7-cyano-3-(4,4,5,5-tetramethyl-1,3,2-dioxaborolan-2-yl)indole-1-carboxylate (100 mg, 0.27 mmol).

Example 147

3-[5-(ethylamino)-6-methylpyridin-2-yl]-1H-indole-7-carbonitrile

Followed the procedure of Example 125 described above and purified by Prep-HPLC (Method A) to afford 3-[5-(ethylamino)-6-methylpyridin-2-yl]-1H-indole-7-carbonitrile (6.3 mg, 11%) as a white solid from 6-chloro-N-ethyl-2-methylpyridin-3-amine (19 mg, 0.11 mmol).

Example 148

3-[5-(dimethylamino)-6-methylpyridin-2-yl]-1H-indole-7-carbonitrile

Followed the procedure of Example 125 described above and purified by Prep-HPLC (Method A) to afford 3-[5-(dimethylamino)-6-methylpyridin-2-yl]-1H-indole-7-carbonitrile (12.9 mg, 8%) as a white solid from tert-butyl 7-cyano-3-(4,4,5,5-tetramethyl-1,3,2-dioxaborolan-2-yl)indole-1-carboxylate (200 mg, 0.54 mmol).

Example 149

3-(5-amino-6-methylpyrazin-2-yl)-1H-indole-7-carbonitrile

Followed the procedure of Example 125 described above and purified by Prep-HPLC (Method A) to afford 3-(5-amino-6-methylpyrazin-2-yl)-1H-indole-7-carbonitrile (17.8 mg, 13%) as a light yellow solid from tert-butyl 7-cyano-3-(4,4,5,5-tetramethyl-1,3,2-dioxaborolan-2-yl)indole-1-carboxylate (200 mg, 0.54 mmol).

Example 150

3-(5-amino-6-methylpyridin-2-yl)-6-methyl-1H-indole-7-carbonitrile

Followed the procedure of Example 145 described above and purified by Prep-HPLC (Method A) to afford 3-(5- amino-6-methylpyridin-2-yl)-6-methyl-1H-indole-7-carbonitrile (12.3 mg, 9%) as an off-white solid from tert-butyl 7-cyano-6-methyl-3-(4,4,5,5-tetramethyl-1,3,2-dioxaborolan-2-yl)indole-1-carboxylate (200 mg, 0.52 mmol).

Example 151

3-(5-amino-6-methylpyridin-2-yl)-6-chloro-1H-indole-7-carbonitrile

Followed the procedure of Example 124 described above and purified by Prep-HPLC (Method C) to afford 3-(5-amino-6-methylpyridin-2-yl)-6-chloro-1H-indole-7-carbonitrile (22.1 mg, 27% over 2 steps) as a yellow solid from tert-butyl 6-chloro-7-cyano-3-(4,4,5,5-tetramethyl-1,3,2-dioxaborolan-2-yl)indole-1-carboxylate (100 mg, 0.24 mmol).

Example 152

3-(5-amino-6-methylpyridin-2-yl)-5-methyl-1H-indole-7-carbonitrile

Followed the procedure of Example 124 described above and purified by Prep-HPLC (Method C) to afford 3-(5-amino-6-methylpyridin-2-yl)-5-methyl-1H-indole-7-carbonitrile (22.7 mg, 12%) as a white solid from tert-butyl 7-cyano-5-methyl-3-(4,4,5,5-tetramethyl-1,3,2-dioxaborolan-2-yl)indole-1-carboxylate (200 mg, 0.52 mmol).

Example 153

3-(5-amino-6-methylpyridin-2-yl)-5-chloro-1H-indole-7-carbonitrile

Followed the procedure of Example 125 described above and purified by Prep-HPLC (Method A) to afford 3-(5-amino-6-methylpyridin-2-yl)-5-chloro-1H-indole-7-carbonitrile (17.0 mg, 12%) as a yellow solid from tert-butyl 5-chloro-7-cyano-3-(4,4,5,5-tetramethyl-1,3,2-dioxaborolan-2-yl)indole-1-carboxylate (200 mg, 0.49 mmol).

Example 154

1-[5-fluoro-3-(1,5-naphthyridin-2-yl)-1H-indol-7-yl]methanamine 2,2,2-trifluoroacetate Step 1: A degassed mixture of tert-butyl 7-cyano-5-fluoro-3-(4,4,5,5-tetramethyl-1,3,2-dioxaborolan-2-yl)indole-1-carboxylate (300 mg, 0.77 mmol), 2-chloro-1,5-naphthyridine (76 mg, 0.46 mmol), chloro(2-dicyclohexylphosphino-2',4',6'-triisopropyl-1,1'-biphenyl)[2-(2'-amino-1,1'-biphenyl)]palladium(II) (61 mg, 0.07 mmol) and tripotassium orthophosphate (329 mg, 1.55 mmol) in dioxane (5 mL) and water (0.5 mL) was stirred at 100° C. for 16 h under nitrogen atmosphere. The reaction mixture was diluted with water and extracted with ethyl acetate. The organic layer was dried over anhydrous sodium sulfate, filtered and concentrated under reduced pressure. The residue was purified by trituration with ethyl acetate and hexane to afford 5-fluoro-3-(1,5-naphthyridin-2-yl)-1H-indole-7-carbonitrile (90 mg, 39%) as a light yellow solid. MS m/z 289.0 [M+1]$^+$.

Step 2: A mixture of tert-butyl 7-cyano-5-fluoro-3-(1,5-naphthyridin-2-yl)indole-1-carboxylate (95 mg, 0.24 mmol)) and Raney Ni (9 mg, 0.48 mmol) in methanol (5 mL) was stirred at room temperature for 16 h under hydrogen atmosphere. The reaction mixture was filtered. The filtrate was concentrated under reduced pressure. The residue was purified by Prep-HPLC (Method F) [Column: XBridge Shield RP18 OBD Column, 30150 mm, 5 um; Mobile Phase A: water (0.05% trifluoroacetic acid), Mobile Phase B: acetonitrile; Flow rate: 60 mL/min; Gradient: 30% B to 75% B in 8 min] to afford 1-[5-fluoro-3-(1,5-naphthyridin-2-yl)-1H-indol-7-yl]methanamine 2,2,2-trifluoroacetate (5.4 mg, 7%) as a yellow solid.

Example 155

3-(5-amino-6-methylpyridin-2-yl)-2-methyl-1H-indole-7-carbonitrile

Step 1: To a solution of tert-butyl 3-bromo-7-cyano-2-methylindole-1-carboxylate (A47) (150 mg, 0.44 mmol) in toluene (3 mL) were added 2-methyl-6-(tributylstannyl)pyridin-3-amine (266 mg, 0.67 mmol), bis(triphenylphosphine)palladium(II) chloride (31 mg, 0.04 mmol) and cesium fluoride (203 mg, 1.34 mmol) at room temperature. The mixture was heated to 100° C. for 10 h. The reaction mixture was concentrated under vacuum. The residue was purified by flash column chromatography with 0-60% ethyl acetate in petroleum ether to afford tert-butyl 3-(5-amino-6-methylpyridin-2-yl)-7-cyano-2-methylindole-1-carboxylate (80 mg, 49%) as a white solid. MS m/z 363.2 [M+1]$^+$ Step 2: To a solution of tert-butyl 3-(5-amino-6-methylpyridin-2-yl)-7-cyano-2-methylindole-1-carboxylate (80 mg, 0.22 mmol) in dichloromethane (2 mL) was added trifluoroacetic acid (1 mL). The mixture was stirred at room temperature for 4 h. The reaction mixture was concentrated under vacuum. The residue was basified using saturated sodium bicarbonate aqueous solution to pH 8. The mixture was extracted with dichloromethane. The organic layer was dried over anhydrous sodium sulfate, filtered and concentrated under vacuum. The residue was purified by prep-HPLC [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 22% B to 45% B in 8 min] to afford 3-(5-amino-6-methylpyridin-2-yl)-2-methyl-1H-indole-7-carbonitrile (9.5 mg, 16%) as a white solid.

Example 156

3-[6,7,7-trimethyl-5-oxopyrrolo[3,4-b]pyridin-2-yl]-1H-indole-7-carbonitrile

Followed the procedure of Example 125 described above and purified by Prep-HPLC (Method C) to afford 3-[6,7,7-trimethyl-5-oxopyrrolo[3,4-b]pyridin-2-yl]-1H-indole-7-carbonitrile (6.1 mg, 8%) as a yellow solid from 2-chloro-6,7,7-trimethylpyrrolo[3,4-b]pyridin-5-one (A48) (50 mg, 0.23 mmol).

Example 157

3-(6-(2-methoxyethyl)-7,7-dimethyl-5-oxo-6,7-dihydro-5H-pyrrolo[3,4-b]pyridin-2-yl)-1H-indole-7-carbonitrile Followed the procedure of Example 125 described above and purified by reverse phase flash column chromatography with 5~45% acetonitrile in water to afford 3-(6-(2-methoxyethyl)-7,7-dimethyl-5-oxo-6,7-dihydro-5H-pyrrolo[3,4-b]pyridin-2-yl)-1H-indole-7-carbonitrile (30.6 mg, 21%) as a white solid from 2-chloro-6-(2-methoxyethyl)-7,7-dimethylpyrrolo[3,4-b]pyridin-5-one (A49) (100 mg, 0.39 mmol).

Example 158

3-[7,7-dimethyl-5-oxo-6-(oxolan-3-yl)pyrrolo[3,4-b]pyridin-2-yl]-1H-indole-7-carbonitrile Followed the procedure of Example 125 described above and purified by flash column chromatography with 0~100% ethyl acetate in petroleum ether and then triturated with ethyl acetate and hexane to afford 3-[7,7-dimethyl-5-oxo-6-(oxolan-3-yl)pyrrolo[3,4-b]pyridin-2-yl]-1H-indole-7-carbonitrile (24.8 mg, 12%) as a white solid from 2-chloro-7,7-dimethyl-6-(oxolan-3-yl)pyrrolo[3,4-b]pyridin-5-one (A50) (87 mg, 0.33 mmol).

Example 159

2-methyl-6-(7-(trifluoromethyl)-1H-indol-3-yl)pyridin-3-amine

Followed the procedure of Example 124 described above and purified by reverse phase FC with 5-50% acetonitrile in water to afford 2-methyl-6-(7-(trifluoromethyl)-1H-indol-3-yl)pyridin-3-amine (15 mg, 5% over 2 steps) as an off-white solid from tert-butyl 3-(4,4,5,5-tetramethyl-1,3,2-dioxaborolan-2-yl)-7-(trifluoromethyl)-indole-1-carboxylate (340 mg, 0.83 mmol).

Example 160

1-[3-(5-amino-6-methylpyridin-2-yl)-1H-indol-7-yl]ethanone

Followed the procedure of Example 155 described above and purified by Prep-HPLC (Method A) to afford 1-[3-(5-amino-6-methylpyridin-2-yl)-1H-indol-7-yl]ethanone (41.2 mg, 24% over 2 steps) as a yellow solid from tert-butyl 7-acetyl-3-bromoindole-1-carboxylate (200 mg, 0.59 mmol).

Example 161

3-(6-methylpyridin-2-yl)-1H-indole-6-carbonitrile

Followed the procedure of Example 125 described above and purified by Prep-HPLC (Method C) to afford 3-(6-methylpyridin-2-yl)-1H-indole-6-carbonitrile (17.4 mg, 13%) as a white solid from tert-butyl 6-cyano-3-(4,4,5,5-tetramethyl-1,3,2-dioxaborolan-2-yl)indole-1-carboxylate (200 mg, 0.54 mmol).

Example 162

3-(6-methylpyridin-2-yl)-1H-indole-5-carbonitrile

Followed the procedure of Example 155 described above and purified by flash column chromatography with 10-70% acetonitrile in water to afford 3-(6-methylpyridin-2-yl)-1H-indole-5-carbonitrile (22.5 mg, 31%) as a white solid from tert-butyl 3-bromo-5-cyanoindole-1-carboxylate (100 mg, 0.31 mmol).

Example 163

3-[5-[(2-methoxyethyl)amino]-6-methylpyridin-2-yl]-1H-indole-7-carbonitrile

Followed the procedure of Example 125 described above and purified by Prep-HPLC (Method A) to afford 3-[5-[(2-methoxyethyl)amino]-6-methylpyridin-2-yl]-1H-indole-7-carbonitrile (19.9 mg, 15%) as a light yellow solid from 6-bromo-N-(2-methoxyethyl)-2-methylpyridin-3-amine (60 mg, 0.24 mmol).

Example 164

3-[6-methyl-5-(oxolan-3-ylamino)pyridin-2-yl]-1H-indole-7-carbonitrile

Followed the procedure of Example 125 described above and purified by Prep-HPLC (Method B) to afford 3-[6-methyl-5-(oxolan-3-ylamino)pyridin-2-yl]-1H-indole-7-carbonitrile (5.4 mg, 4%) as a white solid from 6-bromo-2-methyl-N-(oxolan-3-yl)pyridin-3-amine (63 mg, 0.24 mmol).

Example 165

3-[5-(2-methoxyethoxy)-6-methylpyridin-2-yl]-1H-indole-7-carbonitrile

Followed the procedure of Example 125 described above and purified by Prep-HPLC (Method A) to afford 3-[5-(2-methoxyethoxy)-6-methylpyridin-2-yl]-1H-indole-7-carbonitrile (24.1 mg, 15%) as an off-white solid from 6-bromo-3-(2-methoxyethoxy)-2-methylpyridine (128 mg, 0.52 mmol).

Example 166

3-(5-methoxy-6-methyl pyridin-2-yl)-1H-indole-7-carbonitrile

Followed the procedure of Example 125 described above and purified by Prep-HPLC (Method A) to afford 3-(5-methoxy-6-methylpyridin-2-yl)-1H-indole-7-carbonitrile (21.5 mg, 49%) as an off-white solid from tert-butyl 7-cyano-3-(4,4,5,5-tetramethyl-1,3,2-dioxaborolan-2-yl)indole-1-carboxylate (150 mg, 0.48 mmol).

Example 167

3-[6-(2-methoxyethoxy)pyridin-2-yl]-1H-indole-7-carbonitrile

Followed the procedure of Example 125 described above and purified by Prep-HPLC (Method A) to afford 3-[6-(2-methoxyethoxy)pyridin-2-yl]-1H-indole-7-carbonitrile (13.5 mg, 11%) as a white solid from 2-bromo-6-(2-methoxyethoxy)pyridine (57 mg, 0.25 mmol).

Example 168

3-[6-(pyrrolidin-3-yloxy)pyridin-2-yl]-1H-indole-7-carbonitrile

Followed the procedure of Example 125 described above and purified by Prep-HPLC (Method A) to afford 3-[6-

(pyrrolidin-3-yloxy)pyridin-2-yl]-1H-indole-7-carbonitrile (11.6 mg, 21%) as a white solid from tert-butyl 3-[(6-bromopyridin-2-yl)oxy]pyrrolidine-1-carboxylate (45 mg, 0.13 mmol).

Example 169

3-[6-[(1-methylpyrrolidin-3-yl)oxy]pyridin-2-yl]-1H-indole-7-carbonitrile

Followed the procedure of Example 125 described above and purified by Prep-HPLC (Method A) to afford 3-[6-[(1-methylpyrrolidin-3-yl)oxy]pyridin-2-yl]-1H-indole-7-carbonitrile (6.8 mg, 26%) as a light yellow solid from 2-bromo-6-[(1-methylpyrrolidin-3-yl)oxy]pyridine (63 mg, 0.25 mmol).

3-[5-amino-6-(2-methoxyethoxy)pyridin-2-yl]-1H-indole-7-carbonitrile

Followed the procedure of Example 125 described above and purified by Prep-HPLC (Method B) to afford 3-[5-amino-6-(2-methoxyethoxy)pyridin-2-yl]-1H-indole-7-carbonitrile (16.9 mg, 13%) as a yellow solid from 6-chloro-2-(2-methoxyethoxy)pyridin-3-amine (50 mg, 0.25 mmol).

Example 171

3-(5-amino-6-(difluoromethoxy)pyridin-3-yl)-1H-indole-7-carbonitrile

Followed the procedure of Example 124 described above and purified by Prep-HPLC (Method D) to afford 3-(5-amino-6-(difluoromethoxy)pyridin-3-yl)-1H-indole-7-carbonitrile (25.9 mg, 18% over 2 steps) as a white solid from tert-butyl (5-chloro-2-(difluoromethoxy)pyridin-3-yl)carbamate (130 mg, 0.44 mmol).

Example 172

3-[5-amino-6-(difluoromethoxy)pyrazin-2-yl]-1H-indole-7-carbonitrile

Step 1: To a solution of N-[5-bromo-3-(difluoromethoxy)pyrazin-2-yl]acetamide (115 mg, 0.41 mmol) in dioxane (3 mL) and water (0.3 mL) were added tert-butyl 7-cyano-3-(4,4,5,5-tetramethyl-1,3,2-dioxaborolan-2-yl)indole-1-carboxylate (150 mg, 0.41 mmol), potassium carbonate (113 mg, 0.82 mmol) and [1,1'-bis(diphenylphosphino)ferrocene]dichloro-palladium(II) (33 mg, 0.045 mmol). The mixture was stirred at 100° C. for 16 h under nitrogen atmosphere. The reaction mixture was diluted with water and extracted with ethyl acetate. The combined organic layers were washed with brine, dried over anhydrous sodium sulfate, filtered and concentrated under vacuum. The residue was purified by reverse phase flash column chromatography with 10% to 70% acetonitrile in water in 30 min to afford tert-butyl 7-cyano-3-[6-(difluoromethoxy)-5-acetamidopyrazin-2-yl]indole-1-carboxylate (80 mg, 56%) as a brown solid. MS m/z 344.0 [M+1]$^+$.

Step 2: To a solution of tert-butyl 7-cyano-3-[6-(difluoromethoxy)-5-acetamidopyrazin-2-yl]indole-1-carboxylate (80 mg, 0.23 mmol) in dichloromethane (3 mL) was added trifluoroacetic acid (2 mL). The mixture was stirred at room temperature for 16 h. The reaction mixture was concentrated under vacuum. The residue was treated with sodium hydroxide (5 mL, 1M) and stirred at room temperature for 16 h. The mixture was extracted with ethyl acetate. The combined organic layers were washed with brine, dried over anhydrous sodium sulfate, filtered and concentrated under vacuum. The residue was purified by reverse phase flash column chromatography with 10% to 50% acetonitrile in water in 30 min and further purified by Prep-HPLC [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 35% B to 55% B in 8 min] to afford 3-[5-amino-6-(difluoromethoxy)pyrazin-2-yl]-1H-indole-7-carbonitrile (7.5 mg, 13%) as a brown solid.

Example 173

3-[7-(hydroxymethyl)-6,7-dimethyl-5-oxopyrrolo[3,4-b]pyridin-2-yl]-1H-indole-7-carbonitrile Followed the procedure of Example 125 described above and purified by reverse phase flash column chromatography with 10% to 70% acetonitrile in water in 30 min to afford 3-[7-(hydroxymethyl)-6,7-dimethyl-5-oxopyrrolo[3,4-b]pyridin-2-yl]-1H-indole-7-carbonitrile (15.2 mg, 11%) as a light yellow solid from 2-chloro-7-(hydroxymethyl)-6,7-dimethylpyrrolo[3,4-b]pyridin-5-one (55 mg, 0.22 mmol).

Example 174

3-(pyrazin-2-yl)-1H-indole-7-carbonitrile

Followed the procedure of Example 125 described above and purified by Prep-HPLC (Method D) to afford 3-(pyrazin-2-yl)-1H-indole-7-carbonitrile (13.8 mg, 11%) as a white solid from tert-butyl 7-cyano-3-(4,4,5,5-tetramethyl-1,3,2-dioxaborolan-2-yl)indole-1-carboxylate (200 mg, 0.54 mmol).

Example 175

3-(6-methylpyrazin-2-yl)-1H-indole-7-carbonitrile

Followed the procedure of Example 125 described above and purified by Prep-HPLC (Method D) to afford 3-(6-methylpyrazin-2-yl)-1H-indole-7-carbonitrile (25.7 mg, 26%) as a white solid from tert-butyl 7-cyano-3-(4,4,5,5-tetramethyl-1,3,2-dioxaborolan-2-yl)indole-1-carboxylate (150 mg, 0.41 mmol).

Example 176

3-(pyridin-2-yl)-1H-indole-7-carbonitrile

Followed the procedure of Example 125 described above and purified by Prep-HPLC (Method D) to afford 3-(pyridin-2-yl)-1H-indole-7-carbonitrile (20.9 mg, 23%) as a white solid from tert-butyl 7-cyano-3-(4,4,5,5-tetramethyl-1,3,2-dioxaborolan-2-yl)indole-1-carboxylate (150 mg, 0.41 mmol).

Example 177

3-[6-[(2-methoxyethyl)(methyl)amino]pyrazin-2-yl]-1H-indole-7-carbonitrile

Followed the procedure of Example 125 described above and purified by Prep-HPLC (Method D) to afford 3-[6-[(2-methoxyethyl)(methyl)amino]pyrazin-2-yl]-1H-indole-7- carbonitrile (21.3 mg, 12%) as a white solid from 6-bromo-N-(2-methoxyethyl)-N-methylpyrazin-2-amine (80 mg, 0.33 mmol).

Example 178

3-[6-(azetidin-1-yl)pyridin-2-yl]-1H-indole-7-carbonitrile

Followed the procedure of Example 125 described above and purified by reverse phase flash column chromatography with 5% to 55% acetonitrile in water in 30 min to afford 3-[6-(azetidin-1-yl)pyridin-2-yl]-1H-indole-7-carbonitrile (16.4 mg, 12.74%) as a white solid from 2-(azetidin-1-yl)-6-bromopyridine (100 mg, 0.47 mmol).

Example 179

3-(2-methyl-1,3-benzothiazol-6-yl)-1H-indole-7-carbonitrile

Followed the procedure of Example 125 described above and purified by Prep-HPLC (Method D) to afford 3-(2-methyl-1,3-benzothiazol-6-yl)-1H-indole-7-carbonitrile (7.5 mg, 6%) as a white solid from tert-butyl 7-cyano-3-(4,4,5,5-tetramethyl-1,3,2-dioxaborolan-2-yl)indole-1-carboxylate (150 mg, 0.41 mmol).

Example 180

3-(2-amino-1,3-benzothiazol-6-yl)-1H-indole-7-carbonitrile

Followed the procedure of Example 125 described above and purified by Prep-HPLC (Method C) to afford 3-(2-amino-1,3-benzothiazol-6-yl)-1H-indole-7-carbonitrile (8 mg, 6%) as a white solid from tert-butyl 7-cyano-3-(4,4,5,5-tetramethyl-1,3,2-dioxaborolan-2-yl)indole-1-carboxylate (150 mg, 0.41 mmol).

Example 181

3-[6-methyl-5-(pyrrolidin-3-ylamino)pyrazin-2-yl]-1H-indole-7-carbonitrile

Followed the procedure of Example 124 described above and purified by Prep-HPLC (Method A) to afford 3-[6-methyl-5-(pyrrolidin-3-ylamino)pyrazin-2-yl]-1H-indole-7-carbonitrile (20.0 mg, 11% over 2 steps) as a white solid from tert-butyl 3-[(5-bromo-3-methylpyrazin-2-yl)amino]pyrrolidine-1-carboxylate (200 mg, 0.56 mmol).

Example 182

3-[6-methyl-5-[(1-methylpyrrolidin-3-yl)amino]pyrazin-2-yl]-1H-indole-7-carbonitrile Followed the procedure of Example 122 described above and purified by Prep-HPLC (Method A) to afford 3-[6-methyl-5-[(1-methylpyrrolidin-3-yl)amino]pyrazin-2-yl]-1H-indole-7-carbonitrile (14 mg, 7%) as an off-white solid from 5-bromo-3-methyl-N-(1-methylpyrrolidin-3-yl)pyrazin-2-amine (150 mg, 0.56 mmol).

Example 183

3-[6-methyl-5-(pyrrolidin-3-yloxy)pyrazin-2-yl]-1H-indole-7-carbonitrile

Followed the procedure of Example 124 described above and purified by Prep-HPLC (Method A) to afford 3-[6-methyl-5-(pyrrolidin-3-yloxy)pyrazin-2-yl]-1H-indole-7-carbonitrile (15.8 mg, 12%) as a white solid from tert-butyl 3-[(5-bromo-3-methylpyrazin-2-yl)oxy]pyrrolidine-1-carboxylate (146 mg, 0.41 mmol).

Example 184

3-(7,7-dimethyl-5-oxo-6,7-dihydro-5H-pyrrolo[3,4-b]pyridin-2-yl)-6-fluoro-1H-indole-7-carbonitrile Followed the procedure of Example 125 described above and purified by Prep-HPLC (Method A) to afford 3-(7,7-dimethyl-5-oxo-6,7-dihydro-5H-pyrrolo[3,4-b]pyridin-2-yl)-6-fluoro-1H-indole-7-carbonitrile (18.2 mg, 18%) as a white solid from tert-butyl 7-cyano-6-fluoro-3-(4,4,5,5-tetramethyl-1,3,2-dioxaborolan-2-yl)indole-1-carboxylate (50 mg, 0.13 mmol).

Example 185

6-chloro-3-[7,7-dimethyl-5-oxo-6H-pyrrolo[3,4-b]pyridin-2-yl]-1H-indole-7-carbonitrile To a solution of tert-butyl 6-chloro-7-cyano-3-(4,4,5,5-tetramethyl-1,3,2-dioxaborolan-2-yl)indole-1-carboxylate (150 mg, 0.37 mmol) in dioxane (3 mL) and water (0.30 mL) were added 2-chloro-7,7-dimethyl-6H-pyrrolo[3,4-b]pyridin-5-one (73 mg, 0.37 mmol), palladium(0)tetrakis(triphenylphosphine) (43 mg, 0.037 mmol) and potassium carbonate (102 mg, 0.74 mmol) at room temperature. The mixture was heated to 100° C. for 1 h. The mixture was concentrated under vacuum. The residue was purified by flash column chromatography with 0-80% ethyl acetate in petroleum ether and further purified by prep-HPLC [Column: XBridge Prep OBD C18 Column, 30×150 mm 5 um; Mobile Phase A: water (10 mmol/L ammonium bicarbonate+0.1% ammonium hydroxide), Mobile Phase B: acetonitrile; Flow rate: 60 mL/min; Gradient: 30% B to 55% B in 8 min] to afford 6-chloro-3-[7,7-dimethyl-5-oxo-6H-pyrrolo[3,4-b]pyridin-2-yl]-1H-indole-7-carbonitrile (9.6 mg, 7%) as a white solid.

Example 186

3-methyl-5-[7-(trifluoromethyl)-1H-indol-3-yl]pyrazin-2-amine

Followed the procedure of Example 125 described above and purified by Prep-HPLC (Method D) to afford 3-methyl-5-[7-(trifluoromethyl)-1H-indol-3-yl]pyrazin-2-amine (9.6 mg, 11% over 2 steps) as a yellow solid from tert-butyl 3-(4,4,5,5-tetramethyl-1,3,2-dioxaborolan-2-yl)-7-(trifluoromethyl)indole-1-carboxylate (100 mg, 0.24 mmol).

Example 187

7,7-dimethyl-2-[7-(trifluoromethyl)-1H-indol-3-yl]-6H-pyrrolo[3,4-b]pyridin-5-one Followed the procedure of Example 124 described above and purified by reverse phase flash column chromatography with 10~80% acetonitrile in water to afford 7,7-dimethyl-2-[7-(trifluoromethyl)-1H-indol-3-yl]-6H-pyrrolo[3,4-b]pyridin-5-one (7.2 mg, 6% over 2 steps) as a white solid from tert-butyl 3-(4,4,5,5-tetramethyl-1,3,2-dioxaborolan-2-yl)-7-(trifluoromethyl)indole-1-carboxylate (100 mg, 0.24 mmol).

Example 188

6,7,7-trimethyl-2-[7-(trifluoromethyl)-1H-indol-3-yl]pyrrolo[3,4-b]pyridin-5-one Followed the procedure of Example 124 described above and purified by reverse phase flash column chromatography with 5-50% acetonitrile in water to afford 6,7,7-trimethyl-2-[7-(trifluoromethyl)-1H-indol-3-yl]pyrrolo[3,4-b]pyridin-5-one (16.3 mg, 8% over 2 steps) as a white solid from tert-butyl 3-(4,4,5,5-tetramethyl-1,3,2-dioxaborolan-2-yl)-7-(trifluoromethyl)indole-1-carboxylate (189 mg, 0.46 mmol).

Example 189

N-(2-methoxyethyl)-2-methyl-6-[7-(trifluoromethyl)-1H-indol-3-yl]pyridin-3-amine Followed the procedure of Example 124 described above and purified by reverse phase flash column chromatography with 5~70% acetonitrile in water to afford N-(2-methoxyethyl)-2-methyl-6-[7-(trifluoromethyl)-1H-indol-3-yl]pyridin-3-amine (6.4 mg, 7% over 2 steps) as a white solid from tert-butyl 3-(4,4,5,5-tetramethyl-1,3,2-dioxaborolan-2-yl)-7-(trifluoromethyl)indole-1-carboxylate (100 mg, 0.24 mmol).

Example 190

3-[5-[(2-hydroxyethyl)amino]-6-methylpyridin-2-yl]-1H-indole-7-carbonitrile

Followed the procedure of Example 125 described above and purified by Prep-HPLC (Method A) to afford 3-[5-[(2-hydroxyethyl)amino]-6-methylpyridin-2-yl]-1H-indole-7-carbonitrile (18.1 mg, 22%) as a light yellow solid from 2-[(6-bromo-2-methylpyridin-3-yl)amino]ethanol (38 mg, 0.16 mmol).

Example 191

2-[[6-(7-cyano-1H-indol-3-yl)-2-methylpyridin-3-yl]amino]-N,N-dimethylpropanamide Followed the procedure of Example 125 described above and purified by Prep-HPLC (Method D) to afford 2-[[6-(7-cyano-1H-indol-3-yl)-2-methylpyridin-3-yl]amino]-N,N-dimethyl-propanamide (17.2 mg, 19%) as a white solid from 2-[(6-bromo-2-methylpyridin-3-yl)amino]-N,N-dimethylpropanamide (75 mg, 0.26 mmol).

Example 192

3-[5-amino-6-(difluoromethoxy)pyridin-2-yl]-1H-indole-7-carbonitrile

Followed the procedure of Example 124 described above and purified by Prep-HPLC (Method A) to afford 3-[5-amino-6-(difluoromethoxy)pyridin-2-yl]-1H-indole-7-carbonitrile (16.5 mg, 10% over 2 steps) as a white solid from tert-butyl N-[6-chloro-2-(difluoromethoxy)pyridin-3-yl]carbamate (160 mg, 0.54 mmol).

Example 193

3-[6-methyl-5-[(1-methylpyrrolidin-3-yl)oxy]pyrazin-2-yl]-1H-indole-7-carbonitrile Followed the procedure of Example 124 described above and purified by Prep-HPLC (Method A) to afford 3-[6-methyl-5-[(1-methylpyrrolidin-3-yl)oxy]pyrazin-2-yl]-1H-indole-7-carbonitrile (11.4 mg, 8% over 2 steps) as a white solid from 5-bromo-3-methyl-2-[(1-methylpyrrolidin-3-yl)oxy]pyrazine (100 mg, 0.37 mmol).

Example 194

3-[5-[(1-acetylpyrrolidin-3-yl)oxy]-6-methylpyrazin-2-yl]-1H-indole-7-carbonitrile Followed the procedure of Example 125 described above and purified by Prep-HPLC (Method A) to afford 3-[5-[(1-acetylpyrrolidin-3-yl)oxy]-6-methylpyrazin-2-yl]-1H-indole-7-carbonitrile (4 mg, 9%) as a light yellow solid from 1-[3-[(5-bromo-3-methylpyrazin-2-yl)oxy]pyrrolidin-1-yl]ethenone (A72) (35 mg, 0.11 mmol).

Example 195

3-[5-[(2-methoxypropyl)amino]-6-methylpyridin-2-yl]-1H-indole-7-carbonitrile

Followed the procedure of Example 125 described above and purified by flash column chromatography with 10-80% acetonitrile in water in 30 mins to afford 3-[5-[(2-methoxypropyl)amino]-6-methylpyridin-2-yl]-1H-indole-7-carbonitrile (5.6 mg, 3%) as a light yellow solid from 6-bromo-N-(2-methoxypropyl)-2-methylpyridin-3-amine (150 mg, 0.579 mmol).

Example 196

3-(5-[[2-(dimethylamino)ethyl]amino]-6-methylpyridin-2-yl)-1H-indole-7-carbonitrile 2,2,2-trifluoroacetate To a mixture of 6-bromo-N-[2-(dimethylamino)ethyl]-2-methylpyridin-3-amine (100 mg, 0.39 mmol), tert-butyl 7-cyano-3-(4,4,5,5-tetramethyl-1,3,2-dioxaborolan-2-yl)indole-1-carboxylate (142 mg, 0.39 mmol) and tripotassium orthophosphate (164 mg, 0.78 mmol) in dioxane (10 mL) and water (1 mL) was added 1,1'-bis(di-t-butylphosphino)ferrocene palladium dichloride (25 mg, 0.04 mmol). The mixture was stirred at 90° C. overnight under nitrogen atmosphere. The reaction mixture was diluted with water and extracted with ethyl acetate. The organic layer was dried over anhydrous sodium sulfate, filtered and concentrated under vacuum. The residue was purified by Prep-HPLC (Method F) [Column: YMC-Actus Triart C18, 30*250, 5 um; Mobile Phase A: water (0.1% trifluoroacetic acid), Mobile Phase B: acetonitrile; Flow rate: 60 mL/min; Gradient: 4% B to 35% B in 7 min] to afford 3-(5-[[2-(dimethylamino)ethyl]amino]-6-methylpyridin-2-yl)-1H-indole-7-carbonitrile 2,2,2-trifluoroacetate (40 mg, 23%) as a white solid.

Example 197

2-[[6-(7-cyano-1H-indol-3-yl)-2-methylpyridin-3-yl]amino]-N,N-dimethylacetamide

To a solution of 2-[(6-bromo-2-methylpyridin-3-yl)amino]-N,N-dimethylacetamide (100 mg, 0.37 mmol) and tert-butyl 7-cyano-3-(4,4,5,5-tetramethyl-1,3,2-dioxaborolan-2-yl)indole-1-carboxylate (149 mg, 0.40 mmol) in dioxane (2 mL) and water (0.2 mL) were added potassium carbonate (102 mg, 0.74 mmol) and palladium(0)tetrakis(triphenylphosphine) (42 mg, 0.04 mmol). The mixture was stirred to 100° C. overnight under nitrogen atmosphere. The reaction mixture was diluted with water and extracted with ethyl acetate. The organic layer was dried over anhydrous sodium sulfate, filtered and concentrated under vacuum. The crude product was purified by Prep-HPLC [Column: XBridge Shield RP18 OBD Column, 30*150 mm, 5 um; Mobile Phase A: water (0.1% formic acid), Mobile Phase B: acetonitrile; Flow rate: 60 mL/min; Gradient: 15% B to 40% B in 8 min] to afford 2-[[6-(7-cyano-1H-indol-3-yl)-2-methylpyridin-3-yl]amino]-N,N-dimethylacetamide (6 mg, 5%) as a yellow solid.

Example 198

3-[6-methyl-5-(pyrrolidin-3-yloxy)pyrazin-2-yl]-7-(trifluoromethyl)-1H-indole

Followed the procedure of Example 124 described above and purified by Prep-HPLC (Method D) to afford 3-[6-methyl-5-(pyrrolidin-3-yloxy)pyrazin-2-yl]-7-(trifluoromethyl)-1H-indole (18.8 mg, 14% over 2 steps) as a yellow solid from tert-butyl 3-(4,4,5,5-tetramethyl-1,3,2-dioxaborolan-2-yl)-7-(trifluoromethyl)-indole-1-carboxylate (150 mg, 0.36 mmol).

Example 199

3-[6-methyl-5-[(2-oxopyrrolidin-3-yl)oxy]pyridin-2-yl]-1H-indole-7-carbonitrile

Followed the procedure of Example 125 described above and purified by Prep-HPLC (Method A) to afford 3-[6-methyl-5-[(2-oxopyrrolidin-3-yl)oxy]pyridin-2-yl]-1H-indole-7-carbonitrile (10.6 mg, 10%) as an off-white solid from 3-[(6-bromo-2-methylpyridin-3-yl)oxy]pyrrolidin-2-one (A76) (80 mg, 0.30 mmol).

Example 200

5-fluoro-2-[1H-pyrrolo[2,3-c]pyridin-3-yl]pyridine

Followed the procedure of Example 124 described above and purified by Prep-HPLC (Method A) to afford 5-fluoro-2-[1H-pyrrolo[2,3-c]pyridin-3-yl]pyridine (29.5 mg, 30% over 2 steps) as a white solid from tert-butyl 3-(4,4,5,5-tetramethyl-1,3,2-dioxaborolan-2-yl)-1H-pyrrolo[2,3-c]pyridine-1-carboxylate.

Example 201

5-fluoro-2-[1H-pyrrolo[3,2-b]pyridin-3-yl]pyridine

Followed the procedure of Example 5 described above and purified by Prep-HPLC (Method B) to afford 5-fluoro-2-[1H-pyrrolo[3,2-b]pyridin-3-yl]pyridine (10.3 mg, 30% over 2 steps) as a white solid from tert-butyl 3-(4,4,5,5-tetramethyl-1,3,2-dioxaborolan-2-yl)pyrrolo[3,2-b]pyridine-1-carboxylate (70 mg, 0.20 mmol).

Example 202

5-fluoro-2-[6-fluoro-1H-pyrrolo[3,2-b]pyridin-3-yl]pyridine

Followed the procedure of Example 124 described above and purified by purified by Prep-TLC with petroleum ether/ethyl acetate (1/1) to afford 5-fluoro-2-[6-fluoro-1H-pyrrolo[3,2-b]pyridin-3-yl]pyridine (12.3 mg, 12% over 2 steps) as a light yellow solid from tert-butyl 6-fluoro-3-(4,4,5,5-tetramethyl-1,3,2-dioxaborolan-2-yl)pyrrolo[3,2-b]pyridine-1-carboxylate (150 mg, 0.41 mmol).

Example 203

3-(4-fluorophenyl)-6-methyl-1H-pyrrolo[2,3-b]pyridine

Followed the procedure of Example 124 described above and purified by reverse phase flash column chromatography with 5-50% acetonitrile in water to afford 3-(4-fluorophenyl)-6-methyl-1H-pyrrolo[2,3-b]pyridine (31.8 mg, 24% over 2 steps) as a white solid from tert-butyl 6-methyl-3-(4,4,5,5-tetramethyl-1,3,2-dioxaborolan-2-yl)pyrrolo[2,3-b]pyridine-1-carboxylate (200 mg, 0.55 mmol).

Example 204

5-fluoro-3-(7-fluoroquinolin-2-yl)-1H-indole-7-carbonitrile

Followed the procedure of Example 123 described above and purified by Prep-HPLC (Method A) to afford 5-fluoro-3-(7-fluoroquinolin-2-yl)-1H-indole-7-carbonitrile (27.3 mg, 23%) as a white solid from tert-butyl 7-cyano-5-fluoro-3-(4,4,5,5-tetramethyl-1,3,2-dioxaborolan-2-yl)indole-1-carboxylate (150 mg, 0.38 mmol).

Example 205

3-(7-methyl-5-oxo-6,7-dihydro-5H-pyrrolo[3,4-b]pyridin-2-yl)-1H-indole-7-carbonitrile Followed the procedure of Example 125 described above and purified by Prep-HPLC (Method B) to afford 3-(7-methyl-5-oxo-6,7-dihydro-5H-pyrrolo[3,4-b]pyridin-2-yl)-1H-indole-7-carbonitrile (13.5 mg, 5%) as a white solid from tert-butyl 7-cyano-3-(4,4,5,5-tetramethyl-1,3,2-dioxaborolan-2-yl)indole-1-carboxylate (363 mg, 0.99 mmol).

Example 206

3-[7,7-dimethyl-5-oxo-6H-pyrrolo[3,4-b]pyridin-2-yl]-1H-indole-7-carbonitrile

Followed the procedure of Example 125 described above and purified by Prep-HPLC (Method B) to afford 3-[7,7- dimethyl-5-oxo-6H-pyrrolo[3,4-b]pyridin-2-yl]-1H-indole-7-carbonitrile (24.6 mg, 18%) as a white solid from 2-chloro-7,7-dimethyl-6H-pyrrolo[3,4-b]pyridin-5-one (90 mg, 0.45 mmol).

Example 207

6-(7-chloro-1H-indol-3-yl)-2-methylpyridin-3-amine

Followed the procedure of Example 124 described above and purified by Prep-HPLC (Method A) to afford 6-(7-chloro-1H-indol-3-yl)-2-methylpyridin-3-amine (19.7 mg, 10% over 2 steps) as a white solid from tert-butyl 7-chloro-3-(4,4,5,5-tetramethyl-1,3,2-dioxaborolan-2-yl)-1H-indole-1-carboxylate (200 mg, 0.68 mmol).

Example 208

6-(7-methanesulfonyl-1H-indol-3-yl)-2-methylpyridin-3-amine

Followed the procedure of Example 125 described above and purified by Prep-HPLC (Method A) to afford 6-(7-methanesulfonyl-1H-indol-3-yl)-2-methylpyridin-3-amine (30.2 mg, 7%) as an off-white solid from tert-butyl 7-(methylsulfonyl)-3-(4,4,5,5-tetramethyl-1,3,2-dioxaborolan-2-yl)-1H-indole-1-carboxylate (470 mg, 1.45 mmol).

Example 209

2-chloro-6-(5,6-difluoro-1H-indol-3-yl)pyridin-3-amine

Followed the procedure of Example 124 described above and purified by Prep-HPLC (Method B) to afford 2-chloro-6-(5,6-difluoro-1H-indol-3-yl)pyridin-3-amine (17.8 mg, 16% over 2 steps) as an off-white solid from tert-butyl 5,6-difluoro-3-(4,4,5,5-tetramethyl-1,3,2-dioxaborolan-2-yl)indole-1-carboxylate (150 mg, 0.40 mmol).

Example 210

3-(5-amino-6-methylpyridin-2-yl)-6-fluoro-1H-indole-7-carbonitrile

To a degassed solution of tert-butyl 3-bromo-7-cyano-6-fluoroindole-1-carboxylate (150 mg, 0.44 mmol) in toluene (3 mL) were added 2-methyl-6-(tributylstannyl)pyridin-3-amine (193 mg, 0.48 mmol), bis(triphenylphosphine)palladium(II) chloride (31 mg, 0.04 mmol), cesium fluoride (202 mg, 1.33 mmol) under nitrogen atmosphere. The mixture was stirred at 100° C. for 16 h. The mixture was diluted by ethyl acetate and washed by water and brine. The organic layer was dried over anhydrous sodium sulfate, filtered and concentrated under vacuum. The crude product was purified by Prep-HPLC [Column, XBridge Prep OBD C18 Column, 30*150 mm 5 um; mobile phase, water (10 mmol/L ammonium bicarbonate) and acetonitrile (30% B up to 55% in 7 min)] to afford 3-(5-amino-6-methylpyridin-2-yl)-6-fluoro-1H-indole-7-carbonitrile (9.7 mg, 6%) as a yellow solid.

Example 211

3-(5-amino-6-methylpyridin-2-yl)-6-methoxy-1H-indole-7-carbonitrile

Followed the procedure of Example 210 described above and purified by Prep-HPLC (Method B) to afford 3-(5-amino-6-methylpyridin-2-yl)-6-methoxy-1H-indole-7-carbonitrile (5.5 mg, 2%) as a white solid from tert-butyl 3-bromo-7-cyano-6-methoxyindole-1-carboxylate (350 mg, 0.99 mmol).

Example 212

7-chloro-3-(6-1methylpyrazin-2-yl)-H-indole

Followed the procedure of Example 125 described above and purified by Prep-HPLC (Method A) to afford 7-chloro-3-(6-1methylpyrazin-2-yl)-H-indole (16.2 mg, 12%) as an off-white solid from tert-butyl 7-chloro-3-(4,4,5,5-tetramethyl-1,3,2-dioxaborolan-2-yl)-1H-indole-1-carboxylate (200 mg, 0.53 mmol).

Example 213

3-[6-(azetidin-1-yl)pyrazin-2-yl]-1H-indole-7-carbonitrile

Followed the procedure of Example 125 described above and purified by Prep-HPLC (Method A) to afford 3-[6-(azetidin-1-yl)pyrazin-2-yl]-1H-indole-7-carbonitrile (6 mg, 5%) as an off-white solid from 2-(azetidin-1-yl)-6-bromopyrazine (87 mg, 0.41 mmol).

Example 214

3-(5-amino-6-ethylpyrazin-2-yl)-1H-indole-7-carbonitrile

Followed the procedure of Example 125 described above and purified by Prep-HPLC (Method A) to afford 3-(5-amino-6-ethylpyrazin-2-yl)-1H-indole-7-carbonitrile (14.6 mg, 7%) as a light yellow solid from 5-bromo-3-ethylpyrazin-2-amine (144 mg, 0.71 mmol).

Example 215

3-(6-methoxypyrazin-2-yl)-1H-indole-7-carbonitrile

Followed the procedure of Example 125 described above and purified by Prep-HPLC (Method A) to afford 3-(6-methoxypyrazin-2-yl)-1H-indole-7-carbonitrile (13 mg, 10%) as an off-white solid from 2-bromo-6-methoxypyrazine (99 mg, 0.52 mol).

Example 216

2-(6-fluoro-1H-indol-3-yl)-7,7-dimethyl-6H-pyrrolo[3,4-b]pyridin-5-one

Followed the procedure of Example 125 described above and purified by Prep-HPLC (Method A) to afford 2-(6-fluoro-1H-indol-3-yl)-7,7-dimethyl-6H-pyrrolo[3,4-b]pyridin-5-one (28.6 mg, 18%) as an off-white solid from tert-butyl 6-fluoro-3-(4,4,5,5-tetramethyl-1,3,2-dioxaborolan-2-yl)-1H-indole-1-carboxylate (150 mg, 0.41 mmol).

Example 217

2-(7-chloro-1H-indol-3-yl)-6,7,7-trimethylpyrrolo[3,4-b]pyridin-5-one

Followed the procedure of Example 125 described above and purified by Prep-HPLC (Method A) to afford 2-(7- chloro-1H-indol-3-yl)-6,7,7-trimethylpyrrolo[3,4-b]pyridin-5-one (17.2 mg, 10%) as a yellow solid from 2-chloro-6,7,7-trimethylpyrrolo[3,4-b]pyridin-5-one (110 mg, 0.52 mmol).

Example 218

2-(7-chloro-1H-indol-3-yl)-7,7-dimethyl-6H-pyrrolo [3,4-b]pyridin-5-one

Followed the procedure of Example 125 described above and purified by Prep-HPLC (Method A) to afford 2-(7-chloro-1H-indol-3-yl)-7,7-dimethyl-6H-pyrrolo[3,4-b]pyridin-5-one (11.5 mg, 7%) as an off-white solid from 2-chloro-7,7-dimethyl-6H-pyrrolo[3,4-b]pyridin-5-one (100 mg, 0.51 mmol).

Example 219

3-[5-[(2-hydroxy-2-methylpropyl)amino]-6-methylpyridin-2-yl]-1H-indole-7-carbonitrile Followed the procedure of Example 125 described above and purified by reverse phase flash column chromatography with 10-70% acetonitrile in water to afford 3-[5-[(2-hydroxy-2-methylpropyl)amino]-6-methylpyridin-2-yl]-1H-indole-7-carbonitrile (32 mg, 24%) as a yellow solid.

Example 220

3-[5-[(2-aminoethyl)amino]-6-methylpyridin-2-yl]-1H-indole-7-carbonitrile

Followed the procedure of Example 125 described above and purified by Prep-HPLC (Method A) to afford 3-[5-[(2-aminoethyl)amino]-6-methylpyridin-2-yl]-1H-indole-7-carbonitrile (15.2 mg, 15% over 2 steps) as a light yellow solid from tert-butyl N-[2-[(6-bromo-2-methylpyridin-3-yl)amino]ethyl]carbamate (100 mg, 0.30 mmol).

Example 221

3-[5-[(1-methoxypropan-2-yl)amino]-6-methylpyridin-2-yl]-1H-indole-7-carbonitrile Followed the procedure of Example 125 described above and purified by Prep-HPLC (Method D) to afford 3-[5-[(1-methoxypropan-2-yl)amino]-6-methylpyridin-2-yl]-1H-indole-7-carbonitrile (10.4 mg, 9%) as a white solid from 6-bromo-N-(1-methoxypropan-2-yl)-2-methylpyridin-3-amine (94 mg, 0.36 mmol).

Example 222

3-(5-(pyrrolidin-3-yloxy)pyrazin-2-yl)-1H-indole-7-carbonitrile 2,2,2-trifluoroacetate Step 1: To a solution of tert-butyl 3-[(5-bromopyrazin-2-yl)oxy]pyrrolidine-1-carboxylate (50 mg, 0.15 mmol), tert-butyl 7-cyano-3-(4,4,5,5-tetramethyl-1,3,2-dioxaborolan-2-yl)indole-1-carboxylate (59 mg, 0.16 mmol) and potassium carbonate (60 mg, 0.44 mmol) in dioxane (2 mL) and water (0.4 mL) was added [1,1'-bis(diphenylphosphino)ferrocene]dichloro-palladium(II) (11 mg, 0.02 mmol) under nitrogen atmosphere. The mixture was stirred at 100° C. overnight. The mixture was diluted with water and extracted with ethyl acetate. The combined organic layers were washed with brine, dried over anhydrous sodium sulfate, filtered and concentrated under vacuum. The residue product was purified by reverse phase flash column chromatography with 5-60% acetonitrile in water to afford tert-butyl 3-[[5-(7-cyano-1H-indol-3-yl)pyrazin-2-yl]oxy]pyrrolidine-1-carboxylate (63 mg, 53%) as colorless oil. MS m/z 406.2 [M+1]$^+$.

Step 2: To a solution of tert-butyl 3-[[5-(7-cyano-1H-indol-3-yl)pyrazin-2-yl]oxy]-pyrrolidine-1-carboxylate (100 mg, 0.25 mmol) in dichloromethane (2 mL) was added trifluoroacetic acid (1 mL) at room temperature for 2 h. The mixture was concentrated under vacuum. The residue was basified with saturated sodium bicarbonate aqueous solution. The mixture was extracted with ethyl acetate dried over anhydrous sodium sulfate. After filtration, the filtrate was concentrated under reduced pressure. The residue product was purified by reverse phase flash column chromatography with 5~60% acetonitrile in water to afford 3-(5-(pyrrolidin-3-yloxy)pyrazin-2-yl)-1H-indole-7-carbonitrile 2,2,2-trifluoroacetate (9.6 mg, 9%) as a white solid.

Example 223

3-(5-(((1R,2S,4S)-7-azabicyclo[2.2.1]heptan-2-yl) oxy)-6-methylpyrazin-2-yl)-1H-indole-7-carbonitrile 2,2,2-trifluoroacetate Step 3: A degassed mixture of tert-butyl (1R,2S,4S)-2-((5-bromo-3-methylpyrazin-2-yl)oxy)-7-azabicyclo[2.2.1] heptane-7-carboxylate (100 mg, 0.20 mmol), tert-butyl 7-cyano-3-(4,4,5,5-tetramethyl-1,3,2-dioxaborolan-2-yl)-1H-indole-1-carboxylate (76 mg, 0.20 mmol), [1,1'-bis(diphenylphosphino)ferrocene]dichloropalladium(II) (15 mg, 0.02 mmol) and potassium carbonate (86 mg, 0.62 mmol) in dioxane (1 mL) and water (0.1 mL) was stirred at 100° C. for 16 h. The mixture was diluted with water and extracted with ethyl acetate. The combined organic layers was washed with brine, dried over anhydrous sodium sulfate, filtered and concentrated under vacuum. The residue was purified by flash column chromatography with 0~100% ethyl acetate in petroleum ether to afford tert-butyl (1R,2S,4S)-2-((5-(7-cyano-1H-indol-3-yl)-3-methylpyrazin-2-yl)oxy)-7-azabicyclo[2.2.1]heptane-7-carboxylate (50 mg, 35%) as a colorless oil. MS m/z 446.2 [M+1]$^+$.

Step 4: To a solution of tert-butyl (1R,2S,4S)-24(5-(7-cyano-1H-indol-3-yl)-3-methylpyrazin-2-yl)oxy)-7-azabicyclo[2.2.1]heptane-7-carboxylate (40 mg, 0.09 mmol) in dichloromethane (0.9 mL) was added trifluoroacetic acid (0.3 mL). The mixture was stirred at room temperature for 30 min. The mixture was concentrated under vacuum. The residue was purified by Prep-HPLC (Method F) [Column: Xselect CSHOBD Column 30×150 mm 5 um; Mobile Phase A: water (0.05% trifluoroacetic acid), Mobile Phase B: acetonitrile; Flow rate: 60 mL/min; Gradient: 5% B to 40% B in 7 min] to afford 3-(5-(((1R,2S,4S)-7-azabicyclo[2.2.1] heptan-2-yl)oxy)-6-methylpyrazin-2-yl)-1H-indole-7-carbonitrile 2,2,2-trifluoroacetate (15 mg, 48%) as a yellow solid.

Example 224

3-(5((3-azabicyclo[3.1.0]hexan-6-yl)oxy)-6-methylpyrazin-2-yl)-1H-indole-7-carbonitrile Followed the procedure of Example 223 described above and purified by Prep-HPLC (Method A) to [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 30% B to 55% B in 8 min] to afford 3-(5-((3-azabicyclo[3.1.0]hexan-6-yl)oxy)-6-methylpyrazin-2-yl)-1H-indole-7-carbonitrile (5.3 mg, 17%) as a white solid from tert-butyl 7-cyano-3-(4,4,5,5-tetramethyl-1,3,2-dioxaborolan-2-yl)indole-1-carboxylate (93 mg, 0.25 mmol).

Example 225

3-(5((3-azabicyclo[3.1.0]hexan-6-yl)oxy)-3-methylpyrazin-2-yl)-1H-indole-7-carbonitrile Purification of the reaction mixture of Example 224 described above also afforded 3-(5-((3-azabicyclo[3.1.0]hexan-6-yl)oxy)-3-methylpyrazin-2-yl)-1H-indole-7-carbonitrile (5.0 mg, 16%) as a white solid.

Example 226

3-(6-(difluoromethoxy)-5-(pyrrolidin-3-ylamino)pyrazin-2-yl)-1H-indole-7-carbonitrile Followed the procedure of Example 223 described above and purified by Prep-HPLC (Method A) to afford 3-(6-(difluoromethoxy)-5-(pyrrolidin-3-ylamino)pyrazin-2-yl)-1H-indole-7-carbonitrile (18.8 mg, 10%) as a yellow solid from tert-butyl 3-[[5-bromo-3-(difluoromethoxy)-pyrazin-2-yl]amino]pyrrolidine-1-carboxylate (100 mg, 0.24 mmol).

Example 227

3-(5-(3-aminopyrrolidin-1-yl)-6-methylpyrazin-2-yl)-1H-indole-7-carbonitrile 2,2,2-trifluoroacetate Step 1: To a solution of tert-butyl N-[1-(5-bromo-3-methylpyrazin-2-yl)pyrrolidin-3-yl]carbamate (200 mg, 0.56 mmol) and tert-butyl 7-cyano-3-(4,4,5,5-tetramethyl-1,3,2-dioxaborolan-2-yl)indole-1-carboxylate (206 mg, 0.56 mmol) in water (0.5 mL) and dioxane (2.0 mL) were added 1,1'-bis (di-t-butylphosphino)ferrocene palladium dichloride (41 mg, 0.06 mmol), tripotassium orthophosphate (238 mg, 1.12 mmol). The mixture was stirred at 100° C. for 2 h under nitrogen atmosphere. The residue was purified by flash column chromatography with 0~50% ethyl acetate in petroleum ether to afford tert-butyl (1-(5-(7-cyano-1H-indol-3-yl)-3-methylpyrazin-2-yl)pyrrolidin-3-yl)carbamate (156 mg, 67%) as a yellow solid. MS m/z 419.2 [M+1]$^+$.

Step 2: To a solution of tert-butyl N-[1-[5-(7-cyano-1H-indol-3-yl)-3-methylpyrazin-2-yl]pyrrolidin-3-yl]carbamate (156 mg, 0.37 mmol) in dichloromethane (1.5 mL) was added trifluoroacetic acid (0.5 mL). The mixture was stirred at room temperature for 2 h. The mixture was concentrated under vacuum. The residue was purified by Prep-HPLC (Method F) [Column: Xselect CSH OBD Column 30×150 mm 5 um; Mobile Phase A: water (0.05% trifluoroacetic acid), Mobile Phase B: acetonitrile; Flow rate: 60 mL/min, Gradient: 5% B to 35% B in 7 min] to afford 3-(5-(3-aminopyrrolidin-1-yl)-6-methylpyrazin-2-yl)-1H-indole-7-carbonitrile 2,2,2-trifluoroacetate (40.8 mg, 34%) as a yellow solid.

Example 228

3-(5-(1,3-dimethoxypropan-2-ylamino)-6-methylpyrazin-2-yl)-1H-indole-7-carbonitrile Followed the procedure of Example 223 described above and purified by Prep-HPLC (Method A) [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 35% to 62% in 7 min] to afford 3-[5-[(1,3-dimethoxypropan-2-yl)amino]-6-methylpyrazin-2-yl]-1H-indole-7-carbonitrile (6.5 mg, 3%) as a white solid from 5-bromo-N-(1,3-dimethoxypropan-2-yl)-3-methylpyrazin-2-amine (180 mg, 0.62 mmol).

Example 229

3-(3-fluoro-4-(pyrrolidin-3-yloxy)phenyl)-1H-indole-7-carbonitrile formate

Step 1: To a solution of tert-butyl 3-(4-bromo-2-fluorophenoxy)pyrrolidine-1-carboxylate (120 mg, 0.33 mmol) and tert-butyl 7-cyano-3-(4,4,5,5-tetramethyl-1,3,2-dioxaborolan-2-yl)indole-1-carboxylate (123 mg, 0.33 mmol) in dioxane (1.5 mL) and water (0.15 mL) were added tripotassium orthophosphate (141 mg, 0.67 mmol) and chloro(2-dicyclohexylphosphino-2',4',6'-triisopropyl-1,1'-biphenyl)[2-(2'-amino-1,1'-biphenyl)]palladium(II) (26 mg, 0.03 mmol) at room temperature. The mixture was stirred at 100° C. for 6 h under nitrogen atmosphere. The mixture was concentrated under vacuum. The residue was purified by flash column chromatography with 0~80% ethyl acetate in petroleum ether to afford tert-butyl 3-[4-(7-cyano-1H-indol-3-yl)-2-fluorophenoxy]pyrrolidine-1-carboxylate (80 mg, 57%) as a yellow solid. MS m/z 422.2 [M+1]$^+$.

Step 2: To a solution of tert-butyl 3-[4-(7-cyano-1H-indol-3-yl)-2-fluorophenoxy]pyrrolidine-1-carboxylate (157 mg, 0.37 mmol) in dichloromethane (2 mL) was added trifluoroacetic acid (2 mL). The mixture was stirred at room temperature for 1 h. The mixture was concentrated under vacuum. The residue was purified by Prep-HPLC (Method B) [Column: Xselect CSH OBD Column 30×150 mm 5 um; Mobile Phase A: water (0.1% formic acid), Mobile Phase B: acetonitrile; Flow rate: 60 mL/min; Gradient: 10% B to 32% B in 7 min] to afford 3-(3-fluoro-4-(pyrrolidin-3-yloxy)phenyl)-1H-indole-7-carbonitrile formate (8.6 mg, 6%) as a light yellow solid.

Example 230

3-(6-methyl-5-(pyrrolidin-3-yloxy)pyridin-2-yl)-1H-indole-7-carbonitrile

Followed the procedure of Example 229 described above and purified by Prep-HPLC (Method B) 3-[6-methyl-5-(pyrrolidin-3-yloxy)pyridin-2-yl]-1H-indole-7-carbonitrile (12.1 mg, 20%) as an off-white solid from tert-butyl 3-[(6-bromo-2-methylpyridin-3-yl)oxy]pyrrolidine-1-carboxylate (150 mg, 0.42 mmol).

Example 231

3-(6-methyl-5-(piperidin-4-ylamino)pyrazin-2-yl)-1H-indole-7-carbonitrile 2,2,2-trifluoroacetate Followed the procedure of Example 223 described above and purified by Prep-HPLC (Method F) to afford 3-(6-methyl-5-(piperidin-4-ylamino)pyrazin-2-yl)-1H-indole-7-carbonitrile 2,2,2-trifluoroacetate (62.6 mg, 81%) as a yellow solid from tert-butyl 4-((5-bromo-3-methylpyrazin-2-yl)amino)piperidine-1-carboxylate (150 mg, 0.40 mmol).

Example 232

3-(6-methyl-5-(piperidin-3-ylamino)pyrazin-2-yl)-1H-indole-7-carbonitrile 2,2,2-trifluoroacetate Followed the procedure of Example 223 described above and purified by Prep-HPLC (Method F) to afford 3-(6-methyl-5-(piperidin-3-ylamino)pyrazin-2-yl)-1H-indole-7-carbonitrile 2,2,2-trifluoroacetate (14 mg, 38%) as a yellow solid from tert-butyl 3-[(5-bromo-3-methylpyrazin-2-yl)amino]piperidine-1-carboxylate (100 mg, 0.27 mmol).

Example 233

3-(6-methyl-5-(piperidin-4-yloxy)pyrazin-2-yl)-1H-indole-7-carbonitrile 2,2,2-trifluoroacetate Followed the procedure of Example 223 described above and purified by Prep-HPLC (Method F) to afford 3-(6-methyl-5-(piperidin-4-yloxy)pyrazin-2-yl)-1H-indole-7-carbonitrile 2,2,2-trifluoroacetate (23.8 mg, 62%) as an off-white solid from tert-butyl 4-((5-(7-cyano-1H-indol-3-yl)-3-methylpyrazin-2-yl)oxy)piperidine-1-carboxylate (100 mg, 0.27 mmol).

Example 234

3-(6-methyl-5-(piperidin-3-yloxy)pyrazin-2-yl)-1H-indole-7-carbonitrile 2,2,2-trifluoroacetate Followed the procedure of Example 223 described above and purified by Prep-HPLC (Method F) to afford 3-(6-methyl-5-(piperidin-3-yloxy)pyrazin-2-yl)-1H-indole-7-carbonitrile 2,2,2-trifluoroacetate (8.3 mg, 28%) as a yellow solid from tert-butyl 3-[(5-bromo-3-methylpyrazin-2-yl)oxy]piperidine-1-carboxylate (220 mg, 0.59 mmol).

Example 235

3-(6-(3-hydroxypropyl)-7,7-dimethyl-5-oxo-6,7-dihydro-5H-pyrrolo[3,4-b]pyridin-2-yl)-1H-indole-7-carbonitrile Step 1: A degassed mixture of 6-(3-((tert-butyldimethylsilyl)oxy)propyl)-2-chloro-7,7-dimethyl-6,7-dihydro-5H-pyrrolo[3,4-b]pyridin-5-one (150 mg, 0.41 mmol), tert-butyl 7-cyano-3-(4,4,5,5-tetramethyl-1,3,2-dioxaborolan-2-yl)-1H-indole-1-carboxylate (165 mg, 0.45 mmol), potassium carbonate (169 mg, 1.22 mmol) and [1,1'-bis(diphenylphosphino)ferrocene]dichloropalladium(II) (30 mg, 0.04 mmol) in dioxane (2 mL) and water (0.2 mL) was stirred at 100° C. for 16 h. The mixture was concentrated under vacuum. The residue was purified by flash column chromatography with 0~90% ethyl acetate in petroleum ether to afford 3-(6-(3-((tert-butyldimethylsilyl)oxy)propyl)-7,7-dimethyl-5-oxo-6,7-dihydro-5H-pyrrolo[3,4-b]pyridin-2-yl)-1H-indole-7-carbonitrile (130 mg, 67%) yellow oil. MS m/z 475.2 [M+1]$^+$.

Step 2: To a solution of 3-(6-(3-((tert-butyldimethylsilyl)oxy)propyl)-7,7-dimethyl-5-oxo-6,7-dihydro-5H-pyrrolo[3,4-b]pyridin-2-yl)-1H-indole-7-carbonitrile (100 mg, 0.21 mmol) in tetrahydrofuran (1 mL) was added tetrabutylammonium fluoride (61 mg, 0.23 mmol). The mixture was stirred at room temperature for 3 h. The mixture was concentrated under vacuum. The residue was purified by flash column chromatography by Prep-HPLC [Column: YMC-Actus Triart C18, 30×250 mm, 5 um; Mobile Phase A: water (10 mmol/L ammonium bicarbonate), Mobile Phase B: acetonitrile; Flow rate: 60 mL/min; Gradient: 32% B to 45% B in 8 min] to afford 3-(6-(3-hydroxypropyl)-7,7-dimethyl-5-oxo-6,7-dihydro-5H-pyrrolo[3,4-b]pyridin-2-yl)-1H-indole-7-carbonitrile (10.5 mg, 14%) as a white solid.

Example 236

3-(6-(4-hydroxybutyl)-7,7-dimethyl-5-oxo-6,7-dihydro-5H-pyrrolo[3,4-b]pyridin-2-yl)-1H-indole-7-carbonitrile Followed the procedure of Example 233 described above and purified by Prep-HPLC (Method A) to afford 3-(6-(4-hydroxybutyl)-7,7-dimethyl-5-oxo-6,7-dihydro-5H-pyrrolo[3,4-b]pyridin-2-yl)-1H-indole-7-carbonitrile (8.6 mg, 6% over 2 steps) as a white solid from 6-(4-((tert-butyldimethylsilyl)oxy)butyl)-2-chloro-7,7-dimethyl-6,7-dihydro-5H-pyrrolo[3,4-b]pyridin-5-one (150 mg, 0.39 mmol).

Example 237

3-(6-chloro-5-(pyrrolidin-3-yloxy)pyridin-2-yl)-1H-indole-7-carbonitrile

Followed the procedure of Example 223 described above and purified by Prep-HPLC (Method A) to afford 3-[6-chloro-5-(pyrrolidin-3-yloxy)pyridin-2-yl]-1H-indole-7-carbonitrile (22 mg, 12% over 2 steps) as a white solid from tert-butyl 3-(2-chloro-6-iodopyridin-3-yloxy)pyrrolidine-1-carboxylate (220 mg, 0.58 mmol).

Example 238

7-chloro-3-(6-methyl-5-(pyrrolidin-3-yloxy)pyridin-2-yl)-1H-indole

Followed the procedure of Example 223 described above and purified by Prep-HPLC (Method A) to afford 7-chloro-3-(6-methyl-5-(pyrrolidin-3-yloxy)pyridin-2-yl)-1H-indole (19.1 mg, 25% over 2 steps) as a white solid from tert-butyl 3-(2-chloro-6-iodopyridin-3-yloxy)pyrrolidine-1-carboxylate (120 mg, 0.34 mmol).

Example 239

3-(5-(azetidin-3-yloxy)-6-methylpyrazin-2-yl)-1H-indole-7-carbonitrile

Followed the procedure of Example 223 described above and purified by Prep-HPLC (Method A) to afford 3-[5-(azetidin-3-yloxy)-6-methylpyrazin-2-yl]-1H-indole-7-carbonitrile (12.4 mg, 15% over 2 steps) as a white solid from tert-butyl 3-((5-bromo-3-methylpyrazin-2-yl)oxy)azetidine-1-carboxylate (200 mg, 0.58 mmol).

Example 240

3-(5-((1-acetylazetidin-3-yl)oxy)-6-methylpyrazin-2-yl)-1H-indole-7-carbonitrile Followed the procedure of Example 223 described above and purified by Prep-HPLC (Method A) to afford 3-[5-(azetidin-3-yloxy)-6-methylpyrazin-2-yl]-1H-indole-7-carbonitrile (12.4 mg, 15% over 2 steps) as a white solid from tert-butyl 3-((5-bromo-3-methylpyrazin-2-yl)oxy)azetidine-1-carboxylate (200 mg, 0.58 mmol).

Example 241

3-(3-chloro-4-(pyrrolidin-3-yloxy)phenyl)-1H-indole-7-carbonitrile

Followed the procedure of Example 223 described above and purified by Prep-HPLC (Method A) to afford 3-(3-chloro-4-(pyrrolidin-3-yloxy)phenyl)-1H-indole-7-carbonitrile (13.3 mg, 12% over 2 steps) as a white solid from tert-butyl 3-(4-bromo-2-chlorophenoxy)pyrrolidine-1-carboxylate (200 mg, 0.53 mmol).

Example 242

3-(5-((1-isopropylpyrrolidin-3-yl)oxy)-6-methylpyrazin-2-yl)-1H-indole-7-carbonitrile Step 1: A degassed mixture of tert-butyl 3-[(5-bromo-3-methylpyrazin-2-yl)oxy]pyrrolidine-1-carboxylate (300 mg, 0.84 mmol), tert-butyl 7-cyano-3-(4,4,5,5-tetramethyl-1,3,2-dioxaborolan-2-yl)indole-1-carboxylate (308 mg, 0.84 mmol), [1,1'-bis(diphenylphosphino)ferrocene]dichloropalladium(II) (61 mg, 0.08 mmol) and potassium carbonate (231 mg, 1.68 mmol) in dioxane (3 mL) and water (0.3 mL) was stirred at 100° C. for 2 h. The mixture was concentrated under vacuum. The residue was purified by flash column chromatography with 0-80% ethyl acetate in petroleum ether to afford tert-butyl 3-((5-(7-cyano-1H-indol-3-yl)-3-methylpyrazin-2-yl)oxy)pyrrolidine-1-carboxylate (291 mg, 83%) as a white solid. MS m/z 420.4 [M+1]$^+$.

Step 2: To a solution of tert-butyl 3-[[5-(7-cyano-1H-indol-3-yl)-3-methylpyrazin-2-yl]oxy]pyrrolidine-1-carboxylate (291 mg, 0.69 mmol) in dichloromethane (1 mL) was added trifluoroacetic acid (2 mL). The mixture was stirred at room temperature for 2 h. The reaction mixture was concentrated under vacuum to afford 3-(6-methyl-5-(pyrrolidin-3-yloxy)pyrazin-2-yl)-1H-indole-7-carbonitrile (220 mg, crude) as a yellow oil. MS m/z 320.1 [M+1]$^+$.

Step 3: To a solution of 3-[6-methyl-5-(pyrrolidin-3-yloxy)pyrazin-2-yl]-1H-indole-7-carbonitrile (100 mg, 0.31 mmol) in dichloromethane (1 mL) was added triethylamine until pH 7~8. Then the mixture was acidified with glacial acetic acid to pH 5~6. This was followed by the addition of acetone (36 mg, 0.63 mmol) and sodium triacetoxyborohydride (134 mg, 0.63 mmol). The mixture was stirred at room temperature for 2 h. The mixture was diluted with water and extracted with dichloromethane. The organic layer was dried over anhydrous sodium sulfate, filtered and concentrated under vacuum. The residue was purified by Prep-HPLC (Method D) [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 45% B to 75% B in 8 min] to afford 3-(5-((1-isopropylpyrrolidin-3-yl)oxy)-6-methylpyrazin-2-yl)-1H-indole-7-carbonitrile (28.8 mg, 25% over 2 steps) as a white solid.

Example 243

3-(5-(((3R,4R and 3S,4S)-4-fluoropyrrolidin-3-yl)oxy)-6-methylpyrazin-2-yl)-1H-indole-7-carbonitrile Followed the procedure of Example 223 described above and purified by Prep-HPLC (Method A) to afford 3-(5-(((3R,4R)-4-fluoropyrrolidin-3-yl)oxy)-6-methylpyrazin-2-yl)-1H-indole-7-carbonitrile (17.6 mg, 10% over 2 steps) as a white solid from tert-butyl (3R,4R and 3S,4S)-3-((5-bromo-3-methylpyrazin-2-yl)oxy)-4-fluoropyrrolidine-1-carboxylate (200 mg, 0.53 mmol).

Example 244

3-(6-(difluoromethoxy)-5-(pyrrolidin-3-yloxy)pyrazin-2-yl)-1H-indole-7-carbonitrile Followed the procedure of Example 223 described above and purified by Prep-HPLC (Method A) to afford 3-(6-(difluoromethoxy)-5-(pyrrolidin-3-yloxy)pyrazin-2-yl)-1H-indole-7-carbonitrile (21.8 mg, 8% over 2 steps) as an off-white solid from tert-butyl 3-((5-bromo-3-(difluoromethoxy)pyrazin-2-yl)oxy)pyrrolidine-1-carboxylate (140 mg, 0.34 mmol).

Example 245

3-(5-(pyrrolidin-3-yloxy)-6-(trifluoromethyl)pyrazin-2-yl)-1H-indole-7-carbonitrile Followed the procedure of Example 223 described above and purified by Prep-HPLC (Method A) to afford 3-(5-(pyrrolidin-3-yloxy)-6-(trifluoromethyl)pyrazin-2-yl)-1H-indole-7-carbonitrile (6.3 mg, 4% over 2 steps) as a white solid from tert-butyl 3-((5-bromo-3-(trifluoromethyl)pyrazin-2-yl)oxy)pyrrolidine-1-carboxylate (200 mg, 0.49 mmol).

Example 246

3-(5-(((1R,5S,6r)-3-azabicyclo[3.1.0]hexan-6-yl)methoxy)-6-methylpyrazin-2-yl)-1H-indole-7-carbonitrile Followed the procedure of Example 223 described above and purified by Prep-HPLC (Method A), than further purified by Prep-Achiral SFC [Column: DAICEL DCpak P4VP (02), 30*250 mm, 5 um; Mobile Phase A: CO$_2$, Mobile Phase B: methanol (0.5% 2M ammonia-methanol)-HPLC; Flow rate: 60 mL/min; Gradient: 50% B] to afford 3-[5-[(1R,5S,6R)-3-azabicyclo[3.1.0]hexan-6-ylmethoxy]-6-methylpyrazin-2-yl]-1H-indole-7-carbonitrile (17.8 mg, 13% over 2 steps) as an off-white solid from tert-butyl 6-[[(5-bromo-3-methylpyrazin-2-yl)oxy]methyl]-3-azabicyclo[3.1.0]hexane-3-carboxylate (120 mg, 0.31 mmol).

Example 247

3-(5-(((1R,5S,6s)-3-azabicyclo[3.1.0]hexan-6-yl)methoxy)-6-methylpyrazin-2-yl)-1H-indole-7-carbonitrile Purification of the reaction mixture of Example 246 described above also afforded 3-[5-[(1R,5S,6R)-3-azabicyclo[3.1.0]hexan-6-ylmethoxy]-6-methylpyrazin-2-yl]-1H-indole-7-carbonitrile (13.7 mg, 10% over 2 steps) as an off-white solid.

Example 248

5-(7-chloro-1-benzofuran-3-yl)-3-methylpyrazin-2-amine

A degassed mixture of 5-amino-6-methylpyrazin-2-ylboronic acid (100 mg, 0.65 mmol), 3-bromo-7-chloro-1-benzofuran (151 mg, 0.65 mmol), [1,1'-bis(diphenylphosphino)-ferrocene]dichloropalladium(II) (48 mg, 0.07 mmol) and potassium carbonate (181 mg, 1.31 mmol) in dioxane (3 mL) and water (0.3 mL) was stirred at 100° C. for 16 h. The mixture was diluted with ethyl acetate and washed by water. The organic layer was dried over anhydrous sodium sulfate, filtered and concentrated under vacuum. The residue was purified by Prep-HPLC (Method B) [Column: Sunfire prep $C_{18}$ column, 30*150 mm, 5 um; Mobile Phase A: water (0.1% formic acid), Mobile Phase B: acetonitrile; Flow rate: 60 mL/min; Gradient: 40% B to 70% B in 8 min] to afford 5-(7-chloro-1-benzofuran-3-yl)-3-methylpyrazin-2-amine (7 mg, 4%) as a white solid.

Example 249

3-(6-ethyl-5-(pyrrolidin-3-yloxy)pyrazin-2-yl)-1H-indole-7-carbonitrile

Followed the procedure of Example 223 described above and purified by Prep-HPLC (Method A) to afford 3-[6-ethyl-5-(pyrrolidin-3-yloxy)pyrazin-2-yl]-1H-indole-7-carbonitrile (12.6 mg, 13% over 2 steps) as a white solid from tert-butyl 3-[(5-bromo-3-methylpyrazin-2-yl)oxy]pyrrolidine-1-carboxylate (100 mg, 0.28 mmol).

Example 250

3-(6-methoxy-5-(pyrrolidin-3-ylamino)pyrazin-2-yl)-1H-indole-7-carbonitrile

Followed the procedure of Example 223 described above and purified by Prep-HPLC (Method B) to afford 3-[6-methoxy-5-(pyrrolidin-3-ylamino)pyrazin-2-yl]-1H-indole-7-carbonitrile (6.8 mg, 5% over 2 steps) as a white solid from tert-butyl 3-[(5-bromo-3-methoxypyrazin-2-yl)amino]pyrrolidine-1-carboxylate (150 mg, 0.40 mmol).

Example 251

3-(6-ethoxy-5-(pyrrolidin-3-ylamino)pyrazin-2-yl)-1H-indole-7-carbonitrile formate Followed the procedure of Example 223 described above and purified by Prep-HPLC (Method B) to afford 3-(6-ethoxy-5-(pyrrolidin-3-ylamino)pyrazin-2-yl)-1H-indole-7-carbonitrile formate (30 mg, 13% over 2 steps) as a white solid from tert-butyl 3-[(5-bromo-3-ethoxypyrazin-2-yl)amino]pyrrolidine-1-carboxylate (131 mg, 0.34 mmol).

Example 252

3-(5-(pyrrolidin-3-yloxy)-6-(trifluoromethyl)pyridin-2-yl)-1H-indole-7-carbonitrile Followed the procedure of Example 223 described above and purified by Prep-HPLC (Method A) to afford 3-[5-(pyrrolidin-3-yloxy)-6-(trifluoromethyl)pyridin-2-yl]-1H-indole-7-carbonitrile (11.6 mg, 5% over 2 steps) as a white solid from tert-butyl 3-((6-chloro-2-(trifluoromethyl)pyridin-3-yl)oxy)pyrrolidine-1-carboxylate (180 mg, 0.49 mmol).

Example 253

7-chloro-3-(6-ethyl-5-(pyrrolidin-3-yloxy)pyrazin-2-yl)-1H-indole

Followed the procedure of Example 223 described above and purified by Prep-HPLC (Method A) to afford 7-chloro-3-[6-ethyl-5-(pyrrolidin-3-yloxy)pyrazin-2-yl]-1H-indole (23.6 mg, 17% over 2 steps) as a white solid from tert-butyl 3-[(5-bromo-3-ethylpyrazin-2-yl)oxy]pyrrolidine-1-carboxylate (150 mg, 0.40 mmol).

Example 254

7-chloro-3-(3-fluoro-4-(pyrrolidin-3-yloxy)phenyl)-1H-indole

Followed the procedure of Example 223 described above and purified by Prep-HPLC (Method A) to afford 7-chloro-3-[3-fluoro-4-(pyrrolidin-3-yloxy)phenyl]-1H-indole (10.9 mg, 10% over 2 steps) as a white solid from tert-butyl 3-(4-bromo-2-fluorophenoxy)pyrrolidine-1-carboxylate (80 mg, 0.22 mmol) and tert-butyl 7-chloro-3-(4,4,5,5-tetramethyl-1,3,2-dioxaborolan-2-yl)indole-1-carboxylate (84 mg, 0.22 mmol).

Example 255

5,6-difluoro-3-(6-methyl-5-(pyrrolidin-3-yloxy)pyridin-2-yl)-1H-indazole

Followed the procedure of Example 229 described above and purified by Prep-HPLC (Method A) to afford 5,6-difluoro-3-[6-methyl-5-(pyrrolidin-3-yloxy)pyridin-2-yl]-1H-indazole (20 mg, 6% over 2 steps) as a white solid from tert-butyl 3-[(6-bromo-2-methylpyridin-3-yl)oxy]pyrrolidine-1-carboxylate (300 mg, 0.84 mmol), 5,6-difluoro-1-(oxan-2-yl)indazol-3-ylboronic acid (237 mg, 0.84 mmol).

Example 256

7-chloro-3-(6-methyl-5-(pyrrolidin-3-yloxy)pyridin-2-yl)-1H-indazole

Followed the procedure of Example 223 described above and purified by Prep-HPLC (Method A) to afford 7-chloro-3-[6-methyl-5-(pyrrolidin-3-yloxy)pyridin-2-yl]-1H-indazole (13.7 mg, 10% over 2 steps) as a white solid from 7-chloro-1-(tetrahydro-2H-pyran-2-yl)-3-(4,4,5,5-tetramethyl-1,3,2-dioxaborolan-2-yl)-1H-indazole (158 mg, 0.41 mmol) and tert-butyl 3-[(6-bromo-2-methylpyridin-3-yl)oxy]pyrrolidine-1-carboxylate (201 mg, 0.56 mmol).

Example 257

1-(3-((5-(7-chloro-1H-indol-3-yl)-3-methylpyrazin-2-yl)oxy)pyrrolidin-1-yl)ethan-1-one Followed the procedure of Example 223 described above and purified by Prep-HPLC (Method A) to afford 1-(3-[[5-(7-chloro-1H-indol-3-yl)-3-methylpyrazin-2-yl]oxy]pyrrolidin-1-yl)ethanone (28.7 mg, 26%) as a white solid from 1-[3-[(5-bromo-3-methylpyrazin-2-yl)oxy]pyrrolidin-1-yl]ethanone (150 mg, 0.50 mmol) and tert-butyl 7-chloro-3-(4,4,5,5-tetramethyl-1,3,2-dioxaborolan-2-yl)indole-1-carboxylate (189 mg, 0.50 mmol).

Example 258

1-(3((3-methyl-5-(7-(trifluoromethyl)-1H-indol-3-yl)pyrazin-2-yl)oxy)pyrrolidin-1-yl)ethan-1-one Followed the procedure of Example 223 described above and purified by Prep-HPLC (Method A) to afford 1-(3-((3- methyl-5-(7-(trifluoromethyl)-1H-indol-3-yl)pyrazin-2-yl) oxy)pyrrolidin-1-yl)ethan-1-one (11.4 mg, 8%) as a white solid from tert-butyl 3-(4,4,5,5-tetramethyl-1,3,2-dioxaborolan-2-yl)-7-(trifluoromethyl)-1H-indole-1-carboxylate (150 mg, 0.36 mmol), 1-(3-((5-bromo-3-methylpyrazin-2-yl)oxy)pyrrolidin-1-yl)ethan-1-one (131 mg, 0.43 mmol).

Example 259

3-(5((1-acetylpyrrolidin-3-yl)oxy)-6-chloropyrazin-2-yl)-1H-indole-7-carbonitrile Followed the procedure of Example 223 described above and purified by Prep-HPLC (Method A) to afford 3-[5-[(1-acetylpyrrolidin-3-yl)oxy]-6-chloropyrazin-2-yl]-1H-indole-7-carbonitrile (20 mg, 13%) as a white solid from 1-[3-[(5-bromo-3-chloropyrazin-2-yl)oxy]pyrrolidin-1-yl]ethanone (130 mg, 0.41 mmol) and tert-butyl 7-chloro-3-(4,4,5,5-tetramethyl-1,3,2-dioxaborolan-2-yl)indole-1-carboxylate (149 mg, 0.40 mmol).

Example 260

3-(5((1-acetylpyrrolidin-3-yl)oxy)-6-methylpyridin-2-yl)-1H-indole-7-carbonitrile Followed the procedure of Example 223 described above and purified by Prep-HPLC (Method A) to afford 3-[5-[(1-acetylpyrrolidin-3-yl)oxy]-6-methylpyridin-2-yl]-1H-indole-7-carbonitrile (22.6 mg, 16%) as a white solid from 1-[3-[(6-bromo-2-methylpyridin-3-yl)oxy]pyrrolidin-1-yl]ethanone (121 mg, 0.40 mmol) and tert-butyl 7-chloro-3-(4,4,5,5-tetramethyl-1,3,2-dioxaborolan-2-yl)indole-1-carboxylate (149 mg, 0.40 mmol).

Example 261

3-(5-(1-acetylpyrrolidin-3-yloxy)-6-chloropyridin-2-yl)-1H-indole-7-carbonitrile A mixture of 1-[3-[(2-chloro-6-iodopyridin-3-yl)oxy]pyrrolidin-1-yl]ethanone (157 mg, 0.43 mmol), tert-butyl 7-cyano-3-(4,4,5,5-tetramethyl-1,3,2-dioxaborolan-2-yl)indole-1-carboxylate (158 mg, 0.43 mmol), tripotassium orthophosphate (182 mg, 0.86 mmol) and 1,1'-bis (di-t-butylphosphino)ferrocene palladium dichloride (28 mg, 0.04 mmol) in dioxane (2 mL) and water (0.2 mL) was stirred at 100° C. for 16 h under nitrogen atmosphere. The mixture was concentrated under vacuum. The residue was purified by flash column chromatography with 0-100% ethyl acetate in petroleum ether and further purified by Prep-HPLC (Method D) [Column: XBridge Prep OBD C18 Column, 30×150 mm 5 um; Mobile Phase A: Water (10 mmol/L ammonium bicarbonate+0.1% ammonium hydroxide), Mobile Phase B: acetonitrile; Flow rate: 60 mL/min; Gradient: 20% B to 55% B in 8 min] to afford 3-[5-[(1-acetylpyrrolidin-3-yl)oxy]-6-chloropyridin-2-yl]-1H-indole-7-carbonitrile (30 mg, 18%) as a white solid.

Example 262

3-(5-((1-acetylpyrrolidin-3-yl)oxy)-6-(trifluoromethyl)pyridin-2-yl)-1H-indole-7-carbonitrile Followed the procedure of Example 223 described above and purified by Prep-HPLC (Method A) to afford 3-(5-((1-acetylpyrrolidin-3-yl)oxy)-6-(trifluoromethyl)pyridin-2-yl)-1H-indole-7-carbonitrile (20.5 mg, 10%) as a white solid from 1-(3-((6-chloro-2-(trifluoromethyl)pyridin-3-yl)oxy)pyrrolidin-1-yl)ethan-1-one (150 mg, 0.48 mmol) and tert-butyl 7-cyano-3-(4,4,5,5-tetramethyl-1,3,2-dioxaborolan-2-yl)-1H-indole-1-carboxylate (214 mg, 0.58 mmol).

Example 263

N-(2-((5-(7-chloro-1H-indol-3-yl)-3-methylpyrazin-2-yl)oxy)ethyl)-N-methylacetamide Followed the procedure of Example 223 described above and purified by Prep-HPLC (Method A) to afford N-(2-[[5-(7-chloro-1H-indol-3-yl)-3-methylpyrazin-2-yl]oxy]ethyl)-N-methylacetamide (27.9 mg, 20% over 2 steps) as a white solid from N-[2-[(5-bromo-3-methylpyrazin-2-yl)oxy]ethyl]-N-methylacetamide (114 mg, 0.40 mmol) and tert-butyl 7-chloro-3-(4,4,5,5-tetramethyl-1,3,2-dioxaborolan-2-yl)indole-1-carboxylate (149 mg, 0.40 mmol).

Example 264

3-(3,3-dimethyl-1-oxo-2H-isoindol-5-yl)-1H-indole-7-carbonitrile

Followed the procedure of Example 223 described above and purified by Prep-HPLC (Method D) to afford 3-(3,3-dimethyl-1-oxo-2H-isoindol-5-yl)-1H-indole-7-carbonitrile (32.5 mg, 13%) as a white solid from 5-bromo-3,3-dimethyl-2H-isoindol-1-one (200 mg, 0.83 mmol) and tert-butyl 7-cyano-3-(4,4,5,5-tetramethyl-1,3,2-dioxaborolan-2-yl)indole-1-carboxylate (307 mg, 0.83 mmol).

Example 265

3-[5-[(1-acetylpyrrolidin-3-yl)amino]-6-methoxypyrazin-2-yl]-1H-indole-7-carbonitrile Followed the procedure of Example 223 described above and purified by Prep-HPLC (Method A) to afford 3-[5-[(1-acetylpyrrolidin-3-yl)amino]-6-methoxypyrazin-2-yl]-1H-indole-7-carbonitrile (33.8 mg, 12%) as a white solid from 1-(3-((5-bromo-3-methoxypyrazin-2-yl)-amino)pyrrolidin-1-yl)ethan-1-one (200 mg, 0.64 mmol) and tert-butyl 7-cyano-3-(4,4,5,5-tetramethyl-1,3,2-dioxaborolan-2-yl)-1H-indole-1-carboxylate (280 mg, 0.76 mmol).

Example 266

3-[7-(hydroxymethyl)-7-methyl-5-oxo-6H-pyrrolo[3,4-b]pyridin-2-yl]-1H-indole-7-carbonitrile Followed the procedure of Example 223 described above and purified by Prep-HPLC (Method D) to afford 3-[7-(hydroxymethyl)-7-methyl-5-oxo-6H-pyrrolo[3,4-b]pyridin-2-yl]-1H-indole-7-carbonitrile (18.3 mg, 61% over 2 steps) as a yellow solid from 2-chloro-7-(hydroxymethyl)-7-methyl-6H-pyrrolo[3,4-b]pyridin-5-one (20 mg, 0.094 mmol).

Example 267

3-(5-(2-aminoethoxy)-6-ethylpyrazin-2-yl)-1H-indole-7-carbonitrile

Followed the procedure of Example 223 described above and purified by Prep-HPLC (Method A) to afford 3-[5-(2- aminoethoxy)-6-ethylpyrazin-2-yl]-1H-indole-7-carbonitrile (9.1 mg, 8% over 2 steps) as a white solid from tert-butyl N-[2-[(5-bromo-3-ethylpyrazin-2-yl)oxy]ethyl]carbamate (130 mg, 0.38 mmol).

Example 268

3-(5-((1-acetylpyrrolidin-3-yl)oxy)-6-ethylpyrazin-2-yl)-1H-indole-7-carbonitrile Followed the procedure of Example 223 described above and purified by Prep-HPLC (Method A) to afford 3-[5-[(1-acetylpyrrolidin-3-yl)oxy]-6-ethylpyrazin-2-yl]-1H-indole-7-carbonitrile (41.5 mg, 14%) as a white solid from 1-[3-[(5-bromo-3-ethylpyrazin-2-yl)oxy]pyrrolidin-1-yl]ethanone (250 mg, 0.80 mmol).

Example 269

3-(5-(1-acetyl pyrrolidin-3-yloxy)-6-(trifluoromethyl)pyrazin-2-yl)-1H-indole-7-carbonitrile Followed the procedure of Example 223 described above and purified by Prep-HPLC (Method A) to afford 3-(5-(1-acetylpyrrolidin-3-yloxy)-6-(trifluoromethyl)pyrazin-2-yl)-1H-indole-7-carbonitrile (11 mg, 9%) as a white solid from 1-(3-(5-bromo-3-(trifluoromethyl)-pyrazin-2-yloxy)pyrrolidin-1-yl)ethanone (100 mg, 0.28 mmol).

Example 270

3-(1,1-dimethyl-3-oxo-2,3-dihydro-1H-pyrrolo[3,4-c]pyridin-6-yl)-1H-indole-7-carbonitrile Followed the procedure of Example 223 described above and purified by Prep-HPLC (Method A) to afford 3-[1,1-dimethyl-3-oxo-2H-pyrrolo[3,4-c]pyridin-6-yl]-1H-indole-7-carbonitrile (30.3 mg, 20%) as a white solid from 6-chloro-1,1-dimethyl-2H-pyrrolo[3,4-c]pyridin-3-one (100 mg, 0.51 mmol).

Example 271

3-(5,5-dimethyl-7-oxo-6,7-dihydro-5H-pyrrolo[3,4-b]pyridin-3-yl)-1H-indole-7-carbonitrile Followed the procedure of Example 223 described above and purified by Prep-HPLC (Method A) to afford 3-[5,5-dimethyl-7-oxo-6H-pyrrolo[3,4-b]pyridin-3-yl]-1H-indole-7-carbonitrile (103 mg, 33%) as a white solid from 3-bromo-5,5-dimethyl-6H-pyrrolo[3,4-b]pyridin-7-one (250 mg, 1.04 mmol).

Example 272

3-(5-[[(3R,4R and 3S,4S)-1-acetyl-4-fluoropyrrolidin-3-yl]oxy]-6-methylpyrazin-2-yl)-1H-indole-7-carbonitrile Followed the procedure of Example 223 described above and purified by Prep-HPLC (Method D) to afford 3-(5-[[(3R,4R and 3S,4S)-1-acetyl-4-fluoropyrrolidin-3-yl]oxy]-6-methylpyrazin-2-yl)-1H-indole-7-carbonitrile (19.1 mg, 21%) white solid from 1-[(3R,4R and 3S,4S)-3-[(5-bromo-3-methylpyrazin-2-yl)oxy]-4-fluoropyrrolidin-1-yl]ethanone (75 mg, 0.24 mmol).

Example 273

7-chloro-3-(5-((3R,4R and 3S,4S)-4-fluoropyrrolidin-3-yloxy)-6-methylpyrazin-2-yl)-1H-indole Followed the procedure of Example 227 described above and purified by Prep-HPLC (Method A) to afford 7-chloro-3-(5-((3R,4R)-4-fluoropyrrolidin-3-yloxy)-6-methylpyrazin-2-yl)-1H-indole (10.3 mg, 11%) as a white solid from tert-butyl (3R,4R and 3S,4S)-3-[(5-bromo-3-methylpyrazin-2-yl)oxy]-4-fluoropyrrolidine-1-carboxylate (150 mg, 0.40 mmol).

Example 274

3-[5-(3-aminocyclobutoxy)-6-methylpyrazin-2-yl]-1H-indole-7-carbonitrile

Followed the procedure of Example 223 described above and purified by Prep-HPLC (Method A) to afford 3-[5-(3-aminocyclobutoxy)-6-methylpyrazin-2-yl]-1H-indole-7-carbonitrile (20 mg, 19% over 2 steps) white solid from tert-butyl N-[3-[(5-bromo-3-methyl-pyrazin-2-yl)oxy]cyclobutyl]carbamate (150 mg, 0.42 mmol).

Example 275

3-(5-(3-aminocyclopentyloxy)-6-methylpyrazin-2-yl)-1H-indole-7-carbonitrile

Followed the procedure of Example 227 described above and purified by Prep-HPLC (Method A) to afford 3-(5-(3-aminocyclopentyloxy)-6-methylpyrazin-2-yl)-1H-indole-7-carbonitrile (31.3 mg, 11% over 2 steps) as a white solid from tert-butyl 3-(5-bromo-3-methylpyrazin-2-yloxy)cyclopentylcarbamate (150 mg, 0.40 mmol).

Example 276

1-(3-((5-(7-chloro-1H-indazol-3-yl)-3-methylpyrazin-2-yl)oxy)pyrrolidin-1-yl)ethan-1-one Followed the procedure of Example 227 described above and purified by Prep-HPLC (Method D) to afford 1-(3-[[5-(7-chloro-1H-indazol-3-yl)-3-methylpyrazin-2-yl]oxy]pyrrolidin-1-yl)ethanone (36.3 mg, 11% over 2 steps) as a yellow solid from 1-[3-[(5-bromo-3-methyl-pyrazin-2-yl)oxy]pyrrolidin-1-yl]ethenone (268 mg, 0.89 mmol).

Example 277

7-chloro-3-(6-methyl-5-(pyrrolidin-3-yloxy)pyrazin-2-yl)-1H-indazole

Followed the procedure of Example 223 described above and purified by Prep-HPLC (Method A) to afford 7-chloro-3-[6-methyl-5-(pyrrolidin-3-yloxy)pyrazin-2-yl]-1H-indazole (20.5 mg, 9% over 2 steps) as a white solid from tert-butyl 3-[(5-bromo-3-methylpyrazin-2-yl)oxy]pyrrolidine-1-carboxylate (250 mg, 0.70 mmol).

Example 278

3-(5((1-acetylpyrrolidin-3-yl)oxy)-6-methoxypyrazin-2-yl)-1H-indole-7-carbonitrile Followed the procedure of Example 223 described above and purified by Prep-HPLC (Method A) to afford 3-[5-[(1- acetylpyrrolidin-3-yl)oxy]-6-methoxypyrazin-2-yl]-1H-indole-7-carbonitrile (22.4 mg, 11%) as a white solid from 1-[3-[(5-bromo-3-methoxypyrazin-2-yl)oxy]pyrrolidin-1-yl]ethanone (171 mg, 0.54 mmol).

Example 279

3-(5-((2-hydroxy-2-methylpropyl)amino)-6-methylpyrazin-2-yl)-1H-indole-7-carbonitrile Followed the procedure of Example 223 described above and purified by Prep-HPLC (Method A) to afford 3-[5-[(2-hydroxy-2-methylpropyl)amino]-6-methylpyrazin-2-yl]-1H-indole-7-carbonitrile (81.7 mg, 37%) as a white solid from 1-[(5-bromo-3-methylpyrazin-2-yl)amino]-2-methylpropan-2-ol (180 mg, 0.69 mmol).

Example 280

3-(5-((2-hydroxy-2-methylpropyl)amino)-6-methoxypyrazin-2-yl)-1H-indole-7-carbonitrile Followed the procedure of Example 223 described above and purified by Prep-HPLC (Method A) to afford 3-[5-[(2-hydroxy-2-methylpropyl)amino]-6-methoxypyrazin-2-yl]-1H-indole-7-carbonitrile (19.2 mg, 16%) as a white solid from 1-[(5-bromo-3-methoxypyrazin-2-yl)amino]-2-methylpropan-2-ol (100 mg, 0.36 mmol).

Example 281

3-(6-methyl-5-(pyrrolidin-3-ylthio)pyrazin-2-yl)-1H-indole-7-carbonitrile hydrochloride Followed the procedure of Example 223 described above and purified by Prep-HPLC (Method E) [Column: Xselect CSH OBD Column 30*150 mm 5 um; Mobile Phase A: water (0.05% HCl), Mobile Phase B: acetonitrile; Flow rate: 60 mL/min; Gradient: 5% B to 30% B in 8 min] to afford 3-[6-methyl-5-(pyrrolidin-3-ylsulfanyl)pyrazin-2-yl]-1H-indole-7-carbonitrile hydrochloride (17.9 mg, 66%) as a yellow solid from tert-butyl 3-[(5-bromo-3-methylpyrazin-2-yl)sulfanyl]pyrrolidine-1-carboxylate (60 mg, 0.16 mmol).

Example 282

3-[6-cyclopropyl-5-(pyrrolidin-3-yloxy)pyrazin-2-yl]-1H-indole-7-carbonitrile

Followed the procedure of Example 223 described above and purified by Prep-HPLC (Method D) to afford 3-[6-cyclopropyl-5-(pyrrolidin-3-yloxy)pyrazin-2-yl]-1H-indole-7-carbonitrile (13.5 mg, 7% over 2 steps) as a white solid from tert-butyl 3-[(5-chloro-3-cyclopropylpyrazin-2-yl)oxy]pyrrolidine-1-carboxylate (200 mg, 0.60 mmol).

Example 283

3-(5((1-acetylpyrrolidin-3-yl)oxy)-6-methylpyridin-2-yl)-1H-indole-7-carbonitrile Followed the procedure of Example 223 described above and purified by Prep-HPLC (Method A) to afford 3-[5-[(2,2-dimethylpyrrolidin-3-yl)oxy]-6-methylpyrazin-2-yl]-1H-indole-7-carbonitrile (21 mg, 18% over 2 steps) as a white solid from tert-butyl 3-[(5-iodo-3-methylpyrazin-2-yl)oxy]-2,2-dimethylpyrrolidine-1-carboxylate (150 mg, 0.35 mmol).

Example 284

3-(5-((5,5-dimethylpyrrolidin-3-yl)oxy)-6-methylpyrazin-2-yl)-1H-indole-7-carbonitrile Followed the procedure of Example 223 described above and purified by Prep-HPLC (Method A) to afford 3-[5-[(5,5-dimethylpyrrolidin-3-yl)oxy]-6-methylpyrazin-2-yl]-1H-indole-7-carbonitrile (34.9 mg, 17% over 2 steps) as a white solid from tert-butyl 4-[(5-bromo-3-methylpyrazin-2-yl)oxy]-2,2-dimethylpyrrolidine-1-carboxylate (200 mg, 0.52 mmol).

Example 285

3-(6-methyl-5-((2R,3S and 2S,3R)-2-methylpyrrolidin-3-yloxy)pyrazin-2-yl)-1H-indole-7-carbonitrile Followed the procedure of Example 223 described above and purified by Prep-HPLC (Method D) to afford 3-(6-methyl-5-((2R,3S and 2S,3R)-2-methylpyrrolidin-3-yloxy)pyrazin-2-yl)-1H-indole-7-carbonitrile (39.6 mg, 18% over 2 steps) as a white solid from tert-butyl (2R,3S and 2S,3R)-3-((5-bromo-3-methylpyrazin-2-yl)oxy)-2-methylpyrrolidine-1-carboxylate (200 mg, 0.54 mmol).

Example 286

3-(5-(2-amino-2-methylpropoxy)-6-methylpyrazin-2-yl)-1H-indole-7-carbonitrile

Followed the procedure of Example 223 described above and purified by Prep-HPLC (Method A) to afford 3-[5-(2-amino-2-methylpropoxy)-6-methylpyrazin-2-yl]-1H-indole-7-carbonitrile (34.6 mg, 21% over 2 steps) as a white solid from tert-butyl N-[1-[(5-iodo-3-methylpyrazin-2-yl)oxy]-2-methylpropan-2-yl]carbamate (200 mg, 0.49 mmol).

Example 287

3-(5-(1-aminopropan-2-yloxy)-6-methylpyrazin-2-yl)-1H-indole-7-carbonitrile

Followed the procedure of Example 223 described above and purified by Prep-HPLC (Method A) to afford 3-(5-(1-aminopropan-2-yloxy)-6-methylpyrazin-2-yl)-1H-indole-7-carbonitrile (31.8 mg, 22% over 2 steps) as a white solid from tert-butyl N-[2-[(5-bromo-3-methylpyrazin-2-yl)oxy]propyl]carbamate (50 mg, 0.14 mmol).

Example 288

3-(5-[[(3S)-1-acetylpyrrolidin-3-yl]amino]-6-methoxypyrazin-2-yl)-1H-indole-7-carbonitrile Followed the procedure of Example 227 described above and purified by Prep-HPLC (Method A) to afford 3-(5-[[(3S)-1-acetylpyrrolidin-3-yl]amino]-6-methoxypyrazin-2-yl)-1H-indole-7-carbonitrile (83.1 mg, 23%) as a white solid from 1-[(3S)-3-[(5-bromo-3-methoxypyrazin-2-yl)amino]pyrrolidin-1-yl]ethenone (300 mg, 0.95 mmol).

Example 289

3-(5-[[(3R)-1-acetylpyrrolidin-3-yl]amino]-6-methoxypyrazin-2-yl)-1H-indole-7-carbonitrile Followed the procedure of Example 227 described above and purified by Prep-HPLC (Method A) to afford 3-(5-[[(3R)-1-acetylpyrrolidin-3-yl]amino]-6-methoxypyrazin-2-yl)-1H-indole-7-carbonitrile (68.3 mg, 22%) as a white solid from 1-[(3R)-3-[(5-bromo-3-methoxypyrazin-2-yl)amino]pyrrolidin-1-yl]ethanone (250 mg, 0.79 mmol).

Example 290

3-(5-(1-acetylpyrrolidin-3-yloxy)pyrazin-2-yl)-1H-indole-7-carbonitrile

Followed the procedure of Example 227 described above and purified by Prep-HPLC (Method A) to afford 3-[5-[(1-acetylpyrrolidin-3-yl)oxy]pyrazin-2-yl]-1H-indole-7-carbonitrile (50 mg, 27%) as a white solid from 1-[3-[(5-bromopyrazin-2-yl)oxy]pyrrolidin-1-yl]ethanone (150 mg, 0.52 mmol).

Example 291

1-(3-(5-(7-fluoro-1H-indol-3-yl)-3-methylpyrazin-2-yloxy)pyrrolidin-1-yl)ethanone Followed the procedure of Example 223 described above and purified by Prep-HPLC (Method A) to afford 1-(3-(5-(7-fluoro-1H-indol-3-yl)-3-methylpyrazin-2-yloxy)pyrrolidin-1-yl)ethanone (19.4 mg, 11%) as a white solid from 1-(3-(5-bromo-3-methylpyrazin-2-yloxy)pyrrolidin-1-yl)ethanone (150 mg, 0.50 mmol).

Example 292

1-(3-(3-methyl-5-(1H-pyrrolo[2,3-b]pyridin-3-yl)pyrazin-2-yloxy)pyrrolidin-1-yl)ethanone Followed the procedure of Example 223 described above and purified by Prep-HPLC (Method A) to afford 1-(3-(3-methyl-5-(1H-pyrrolo[2,3-b]pyridin-3-yl)pyrazin-2-yloxy)pyrrolidin-1-yl)ethanone (77.8 mg, 46%) as a white solid from 1-(3-(5-bromo-3-methylpyrazin-2-yloxy)pyrrolidin-1-yl)ethanone (150 mg, 0.50 mmol).

Example 293

1-(3-(3-methoxy-5-(1H-pyrrolo[2,3-b]pyridin-3-yl)pyrazin-2-ylamino)pyrrolidin-l-yl)ethanone Followed the procedure of Example 223 described above and purified by Prep-HPLC (Method A) to afford 1-(3-(3-methoxy-5-(1H-pyrrolo[2,3-b]pyridin-3-yl)pyrazin-2-ylamino)pyrrolidin-1-yl)ethanone (58 mg, 25% over 2 steps) as a white solid from 1-(3-(5-bromo-3-methoxypyrazin-2-ylamino)pyrrolidin-1-yl)ethanone (200 mg, 0.64 mmol).

Example 294

3-(5((1-acetylpyrrolidin-3-yl)(methyl)amino)-6-methoxypyrazin-2-yl)-1H-indole-7-carbonitrile Followed the procedure of Example 223 described above and purified by Prep-HPLC (Method A) to afford 3-(5-((1-acetylpyrrolidin-3-yl)(methyl)amino)-6-methoxypyrazin-2-yl)-1H-indole-7-carbonitrile (76.1 mg, 27%) as a white solid from 1-[3-[(5-bromo-3-methoxypyrazin-2-yl)(methyl)amino]pyrrolidin-1-yl]ethanone (242 mg, 0.74 mmol).

Example 295

2-(7-fluoro-1H-indol-3-yl)-7,7-dimethyl-6,7-dihydropyrrolo[3,4-b]pyridin-5-one

Step 1: A degassed mixture of 2-chloro-7,7-dimethyl-6,7-dihydropyrrolo[3,4-b]pyridin-5-one (100 mg, 0.51 mmol), tert-butyl 7-fluoro-3-(4,4,5,5-tetramethyl-1,3,2-dioxaborolan-2-yl)-1H-indole-1-carboxylate (193 mg, 0.56 mmol), 1,1'-bis(di-t-butylphosphino)ferrocene palladium dichloride (33 mg, 0.05 mmol) and tripotassium orthophosphate (216 mg, 1.02 mmol) in dioxane (2 mL) and water (0.1 mL) was stirred at 100° C. for 16 h. The reaction mixture was diluted using water and extracted with ethyl acetate. The combined organic layers was washed with brine, dried over anhydrous sodium sulfate, filtered and concentrated under vacuum to afford tert-butyl 3-(7,7-dimethyl-5-oxo-6,7-dihydro-5H-pyrrolo[3,4-b]pyridin-2-yl)-7-fluoro-1H-indole-1-carboxylate (130 mg, crude) as a yellow solid. MS m/z 396.1 [M+1]$^+$.

Step 2: A mixture of 2-(7-fluoro-1H-indol-3-yl)-7,7-dimethyl-6,7-dihydropyrrolo[3,4-b]pyridin-5-one (130 mg, 0.33 mmol) in dichloromethane (0.9 mL) was added trifluoroacetic acid (0.3 mL). The mixture was stirred at room temperature for 2 h. The mixture was concentrated under vacuum. The residue was purified by prep-HPLC with the following conditions [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 33% B to 42% B in 8 min] to afford 2-(7-fluoro-1H-indol-3-yl)-7,7-dimethyl-6,7-dihydropyrrolo[3,4-b]pyridin-5-one (33.3 mg, 22% over two steps) as a white solid.

Example 296

7-chloro-3-(6-methyl-5-(pyrrolidin-3-yloxy)pyrazin-2-yl)-1H-indole 2,2,2-trifluoroacetate Followed the procedure of Example 223 described above and purified by Prep-HPLC (Method F) to afford 7-chloro-3-(6-methyl-5-(pyrrolidin-3-yloxy)pyrazin-2-yl)-1H-indole 2,2,2-trifluoroacetate (6.9 mg, 6% over 2 steps) as a yellow solid from tert-butyl 7-chloro-3-(4,4,5,5-tetramethyl-1,3,2-dioxaborolan-2-yl)indole-1-carboxylate (80 mg, 0.21 mmol).

Example 297

3-(5-[[(3R,4S and 3S,4R)-4-fluoropyrrolidin-3-yl]oxy]-6-methylpyrazin-2-yl)-1H-indole-7-carbonitrile 2,2,2-trifluoroacetate Followed the procedure of Example 223 described above and purified by Prep-HPLC (Method F) to afford 3-(5-[[(3R,4S and 3S,4R)-4-fluoropyrrolidin-3-yl]oxy]-6-methylpyrazin-2-yl)-1H-indole-7-carbonitrile 2,2,2-trifluoroacetate (57.1 mg, 36% over 2 steps) as a light yellow solid from tert-butyl (3R,4S and 3S,4R)-3-[(5-bromo-3-methylpyrazin-2-yl)oxy]-4-fluoropyrrolidine-1-carboxylate (130 mg, 0.35 mmol).

Example 298

3-[6-methyl-5-(pyrrolidin-3-ylamino)pyridin-2-yl]-1H-indole-7-carbonitrile 2,2,2-trifluoroacetate Followed the procedure of Example 297 described above and purified by Prep-HPLC (Method F) to afford 3-[6-methyl-5-(pyrrolidin-3-ylamino)pyridin-2-yl]-1H-indole-7-carbonitrile 2,2,2-trifluoroacetate (14.8 mg, 9% over 2 steps) as an off-white solid from tert-butyl 3-[(6-bromo-2-methylpyridin-3-yl)amino]pyrrolidine-1-carboxylate (130 mg, 0.37 mmol).

Example 299

3-[6-methyl-5-[(2-oxopyrrolidin-3-yl)oxy]pyridin-2-yl]-1H-indole-7-carbonitrile

To a mixture of 3-[(6-bromo-2-methylpyridin-3-yl)oxy]pyrrolidin-2-one (80 mg, 0.30 mmol), tert-butyl 7-cyano-3-(4,4,5,5-tetramethyl-1,3,2-dioxaborolan-2-yl)indole-1-carboxylate (108 mg, 0.30 mmol) and tripotassium orthophosphate (125 mg, 0.59 mmol) in dioxane (2 mL) and water (0.2 mL) was added chloro(2-dicyclohexylphosphino-2',4',6'-triisopropyl-1,1'-biphenyl)[2-(2'-amino-1,1'-biphenyl)]palladium(II) (23 mg, 0.03 mmol) under nitrogen atmosphere. The resulting solution was stirred at 100° C. overnight. The mixture was diluted with water and extracted by ethyl acetate. The organic layer was dried over anhydrous sodium sulfate, filtered and concentrated under vacuum. The residue was purified by Prep-HPLC [Method A] to afford 3-[6-methyl-5-[(2-oxopyrrolidin-3-yl)oxy]pyridin-2-yl]-1H-indole-7-carbonitrile (10.6 mg, 10%) as an off-white solid.

Example 300

6-methyl-3-(6-methyl-5-(pyrrolidin-3-yloxy)pyridin-2-yl)-1,6-dihydro-7H-pyrrolo[2,3-c]pyridin-7-one Step 1: To a degassed mixture of tert-butyl 3-bromo-6-methyl-7-oxo-6,7-dihydro-1H-pyrrolo[2,3-c]pyridine-1-carboxylate (280 mg, 0.49 mmol) and tert-butyl 3-bromo-6-methyl-7-oxo-6,7-dihydro-1H-pyrrolo[2,3-c]pyridine-1-carboxylate (161 mg, 0.49 mmol) in dioxane (28 mL) were added bis(triphenylphosphine)palladium(II) chloride (35 mg, 0.05 mmol) and [1,1'-bis(diphenylphosphino)ferrocene]dichloropalladium(II) (36 mg, 0.05 mmol). The mixture was stirred at 110° C. for 16 h. The mixture was concentrated under vacuum. The residue was purified by flash column chromatography with 0-20% methanol in dichloromethane to afford tert-butyl 3-((2-methyl-6-(6-methyl-7-oxo-6,7-dihydro-1H-pyrrolo[2,3-c]pyridin-3-yl)pyridin-3-yl)oxy)pyrrolidine-1-carboxylate (110 mg, 52%) as a yellow oil. MS m/z 425.2 [M+1]$^+$.

Step 2: To a mixture of tert-butyl 3-((2-methyl-6-(6-methyl-7-oxo-6,7-dihydro-1H-pyrrolo[2,3-c]pyridin-3-yl)pyridin-3-yl)oxy)pyrrolidine-1-carboxylate (100 mg, 0.24 mmol) in dichloromethane (0.6 mL) was added trifluoroacetic acid (0.2 mL). The mixture was stirred at room temperature for 3 h. The mixture was concentrated under vacuum. The residue was purified by prep-HPLC [Method A] to afford 6-methyl-3-(6-methyl-5-(pyrrolidin-3-yloxy)pyridin-2-yl)-1,6-dihydro-7H-pyrrolo[2,3-c]pyridin-7-one (10.6 mg, 13%) as a white solid.

Example 301

3-[5-(2-hydroxy-2-methylpropoxy)-6-methylpyrazin-2-yl]-1H-indole-7-carbonitrile

Step 1: To a degassed mixture of 5-iodo-3-methyl-2-[2-methyl-2-(oxan-2-yloxy)propoxy]pyrazine (150 mg, 0.38 mmol) and tert-butyl 7-cyano-3-(4,4,5,5-tetramethyl-1,3,2-dioxaborolan-2-yl)indole-1-carboxylate (140 mg, 0.38 mmol) in dioxane (2 mL) and water (0.2 mL) were added potassium carbonate (105 mg, 0.76 mmol) and [1,1'-bis(diphenylphosphino)ferrocene]dichloropalladium(II) (27 mg, 0.04 mmol) at room temperature. The mixture was stirred at 100° C. for 2 hours. The reaction mixture was diluted using water and extracted with ethyl acetate. The organic combined layers was washed with brine, dried over anhydrous sodium sulfate, filtered and concentrated under vacuum. The residue was purified by flash column chromatography with 0-35% ethyl acetate in petroleum ether to afford 3-[6-methyl-5-[2-methyl-2-(oxan-2-yloxy)propoxy]pyrazin-2-yl]-1H-indole-7-carbonitrile (67 mg, 43%) as a white solid. MS m/z 407.1 [M+1]$^+$.

Step 2: To a solution of 3-[6-methyl-5-[2-methyl-2-(oxan-2-yloxy)propoxy]pyrazin-2-yl]-1H-indole-7-carbonitrile (62 mg, 0.15 mmol) in dichloromethane (2.1 mL) was added trifluoroacetic acid (0.7 mL) at room temperature. The mixture was stirred at room temperature for 3 hours. The mixture was concentrated under vacuum. The residue was purified by reverse phase flash column chromatography with 10-80% acetonitrile in water (10 mmol/L ammonium bicarbonate) to afford 3-[5-(2-hydroxy-2-methylpropoxy)-6-methylpyrazin-2-yl]-1H-indole-7-carbonitrile (21.3 mg, 43%) as a white solid.

Example 304 and Example 319

3-(5-[[(3R,4R)-1-acetyl-4-fluoropyrrolidin-3-yl]oxy]-6-methylpyrazin-2-yl)-1H-indole-7-carbonitrile and 3-(5-[[(3S,4S)-1-acetyl-4-fluoropyrrolidin-3-yl]oxy]-6-methylpyrazin-2-yl)-1H-indole-7-carbonitrile Followed the procedure of Example 270 described above and the residue was separated by prep-chiral-HPLC [Column: Repaired Chiral IC, 4.6*100 mm, 5 um; Mobile Phase A: Hex (0.2% DEA): (IPA:DCM=1:1)=80:20, Mobile Phase B; Flow rate: 1 mL/mina to afford product 3-(5-[[(3R,4R)-1-acetyl-4-fluoropyrrolidin-3-yl]oxy]-6-methylpyrazin-2-yl)-1H-indole-7-carbonitrile (43.5 mg, 13.59%) as a white solid and 3-(5-[[(3S,4S)-1-acetyl-4-fluoropyrrolidin-3-yl]oxy]-6-methylpyrazin-2-yl)-1H-indole-7-carbonitrile (45.8 mg, 14.31%) as a white solid.

Example 309

5-(6-fluoro-1-benzofuran-3-yl)-3-methylpyrazin-2-amine

A mixture of 3-bromo-6-fluoro-1-benzofuran (100 mg, 0.46 mmol), 5-amino-6-methylpyrazin-2-ylboronic acid (142.2 mg, 0.93 mmol), Pd(dppf)Cl$_2$ (68.06 mg, 0.093 mmol) and Potassium carbonate (128.5 mg, 0.93 mmol) in dioxane (10 mL) and water (2 mL) was stirred at 100° C. for 2 h under nitrogen atmosphere. The resulting mixture was concentrated under reduced pressure. The residue was purified by Prep-HPLC [Column: XBridge Prep OBD C18 Column, 30×150 mm 5 um; Mobile Phase A: Water (10 mmol/L NH$_4$HCO$_3$), Mobile Phase B: ACN; Flow rate: 60 mL/min; Gradient: 38 B to 52 B in 8 min; 254/220 nm] to afford 5-(6-fluoro-1-benzofuran-3-yl)-3-methylpyrazin-2-amine (8.7 mg, 7%) as a white solid.

Example 307

3-(6-(methylthio)-5-(pyrrolidin-3-yloxy)pyrazin-2-yl)-1H-indole-7-carbonitrile

Step-1: A mixture of tert-butyl 3-[[5-bromo-3-(methylthio)pyrazin-2-yl]oxy]pyrrolidine-1-carboxylate (100 mg, 0.26 mmol), tert-butyl 7-cyano-3-(4,4,5,5-tetramethyl-1,3,2-dioxaborolan-2-yl)indole-1-carboxylate (104 mg, 0.28 mmol), $K_3PO_4$ (109 mg, 0.51 mmol) and Pd(DtBPF)Cl$_2$ (17 mg, 0.03 mmol) in dioxane (1 mL) and H$_2$O (0.1 mL) was stirred at 100° C. for 16 h under N$_2$. The mixture was diluted with ethyl acetate, washed with brine, dried over anhydrous sodium sulfate, filtered, and concentrated under vacuum. The residue was purified by flash column chromatography with 0-100% ethyl acetate in petroleum ether to afford tert-butyl 3-[[5-(7-cyano-1H-indol-3-yl)-3-(methylthio)pyrazin-2-yl]oxy]pyrrolidine-1-carboxylate (64 mg, 55.32%) as a yellow solid. MS m/z 452.1 [M+1]$^+$.

Step-2: To a solution of tert-butyl 3-[[5-(7-cyano-1H-indol-3-yl)-3-(methylthio)pyrazin-2-yl]oxy]pyrrolidine-1-carboxylate (64 mg, 0.14 mmol) in DCM (1 mL) was added TFA (0.3 mL). The mixture was stirred at room temperature for 2 h. The mixture was concentrated under vacuum. The residue was purified by Prep-HPLC [Column: YMC-Pack Diol-120-NP, 20*150 mm, 5 pm; Flow rate: 60 mL/min; Gradient: 40% B to 63% B in 8 min;] to afford 3-(6-(methylthio)-5-(pyrrolidin-3-yloxy)pyrazin-2-yl)-1H-indole-7-carbonitrile (4.1 mg, 7.98%) as a white solid.

Example 308

3-(6-methyl-5-((3-methylpyrrolidin-3-yl)oxy)pyrazin-2-yl)-1H-indole-7-carbonitrile Step-1: To a solution of tert-butyl 3-((5-iodo-3-methylpyrazin-2-yl)oxy)-3-methylpyrrolidine-1-carboxylate (120 mg, 0.29 mmol) in dioxane (2 mL) and H$_2$O (0.2 mL) were added tert-butyl 7-cyano-3-(4,4,5,5-tetramethyl-1,3,2-dioxaborolan-2-yl)-1H-indole-1-carboxylate (105 mg, 0.29 mmol), Pd(dtbpf)Cl$_2$ (19 mg, 0.03 mmol) and K$_3$PO$_4$ (121 mg, 0.57 mmol) at room temperature. Then the mixture was stirred at 100° C. for 16 h under N$_2$. The mixture was concentrated under vacuum. The residue was purified by flash column chromatography with 0-40% ethyl acetate in petroleum ether to afford tert-butyl 3-((5-(7-cyano-1H-indol-3-yl)-3-methylpyrazin-2-yl)oxy)-3-methylpyrrolidine-1-carboxylate (120 mg, 96.71%) as an off-white oil. MS m/z 434.2 [M+1]$^+$.

Step-2: To a solution of tert-butyl 3-((5-(7-cyano-1H-indol-3-yl)-3-methylpyrazin-2-yl)oxy)-3-methylpyrrolidine-1-carboxylate (110 mg, 0.25 mmol) in DCM (2 mL) was added TFA (1 mL). The mixture was stirred at room temperature for 2 h. The mixture was concentrated under vacuum. The residue was purified by prep-HPLC [Column: Xselect CSH OBD Column 30.150 mm 5 um, Mobile Phase A: Water (0.05% HCl), Mobile Phase B: ACN; Flow rate: 60 mL/min; Gradient: 15 B to 40 B in 8 min;] to afford 3-(6-methyl-5-((3-methylpyrrolidin-3-yl)oxy)pyrazin-2-yl)-1H-indole-7-carbonitrile (25.6 mg, 29.43%) as a yellow solid.

Example 310

3-(5-amino-6-methylpyrazin-2-yl)-1-benzofuran-7-carbonitrile

A mixture of 3-bromobenzofuran-7-carbonitrile (500 mg, 2.25 mmol) and 5-amino-6-methylpyrazin-2-ylboronic acid (344 mg, 2.25 mmol) and Pd(dppf)Cl$_2$ (165 mg, 0.22 mmol) and K$_2$CO$_3$ (622 mg, 4.50 mmol) in dioxane (5 mL) and H$_2$O (0.5 mL) was stirred at 100° C. for 16 h under nitrogen atmosphere. The aqueous solution was extracted with ethyl acetate. The combined organic layers were washed with brine, dried over anhydrous sodium sulfate, filtered, and concentrated under vacuum. The residue was purified by Prep-HPLC [Column: Sunfire prep C18 column, 30*150, 5 um; Mobile Phase A: Water (0.1% FA), Mobile Phase B: ACN; Flow rate: 60 mL/min; Gradient: 20% B to 45% B in 11 min, 45% B;] to afford as 3-(5-amino-6-methylpyrazin-2-yl)-1-benzofuran-7-carbonitrile (24.7 mg, 4.37%) as a yellow solid.

Example 311

1-(3-((3-methyl-5-(1H-pyrrolo[3,2-b]pyridin-3-yl)pyrazin-2-yl)oxy)pyrrolidin-1-yl)ethan-1-one Step 1: A mixture of (1-(tert-butoxycarbonyl)-1H-pyrrolo[3,2-b]pyridin-3-yl)boronic acid (300 mg, 1.15 mmol) and 1-(3-((5-bromo-3-methylpyrazin-2-yl)oxy)pyrrolidin-1-yl)ethan-1-one (344 mg, 1.15 mmol), Pd(dppf)Cl$_2$ (83.76 mg, 0.115 mmol), K$_2$CO$_3$ (475 mg, 3.44 mmol), H$_2$O (0.1 mL) in dioxane (1 mL) was stirred at 100° C. for 16 h under nitrogen atmosphere. The resulting mixture was concentrated under vacuum. The residue was purified by flash column chromatography with 0-60% ethyl acetate in petroleum ether to afford tert-butyl 3-(5-((1-acetylpyrrolidin-3-yl)oxy)-6-methylpyrazin-2-yl)-1H-pyrrolo[3,2-b]pyridine-1-carboxylate (400 mg, 79.87%) as a brown oil. MS m/z 438.2 [M+1]$^+$.

Step 2: To a mixture of tert-butyl 3-(5-((1-acetylpyrrolidin-3-yl)oxy)-6-methylpyrazin-2-yl)-1H-pyrrolo[3,2-b]pyridine-1-carboxylate (400 mg, 0.91 mmol) in DCM (6 mL) was added TFA (2 mL). The mixture was stirred at room temperature for 1 h. The resulting mixture was concentrated under reduced pressure. The residue was purified by prep-HPLC [Column: XBridge Prep OBD C18 Column, 30×150 mm 5 um; Mobile Phase A: Water (10 mmol/L NH$_4$HCO$_3$), Mobile Phase B: ACN; Flow rate: 60 mL/min; Gradient: 20 B to 30 B in 8 min;] to afford 1-(3-((3-methyl-5-(1H-pyrrolo[3,2-b]pyridin-3-yl)pyrazin-2-yl)oxy)pyrrolidin-1-yl)ethan-1-one (110.5 mg, 35.80%) as a white solid.

Example 312

3-[5-[(1-acetylpyrrolidin-3-yl)oxy]-6-methylpyrazin-2-yl]-1H-indazole-7-carbonitrile Step 1: To a solution of 7-cyano-1-(oxan-2-yl)indazol-3-ylboronic acid (181 mg, 0.66 mmol) and 1-[3-[(5-bromo-3-methylpyrazin-2-yl)oxy]pyrrolidin-1-yl]ethanone (200 mg, 0.66 mmol) in dioxane (2 mL) and H$_2$O (0.2 mL) were added K$_2$CO$_3$ (184 mg, 1.33 mmol) and Pd(dppf)Cl$_2$ (48 mg, 0.06 mmol). The mixture was stirred at 100° C. for 16 h under nitrogen The aqueous solution was extracted with ethyl acetate. The combined organic layers were washed with brine, dried over anhydrous sodium sulfate, filtered, and concentrated under vacuum. The residue was purified by flash column chromatography with 0-25% ethyl acetate in petroleum ether to afford 3-[5-[(1-acetylpyrrolidin-3-yl)oxy]-6-methylpyrazin-2-yl]-1-(oxan-2-yl)indazole-7-carbonitrile (280 mg, 93.78%) as a brown solid. MS m/z 447.2 [M+1]$^+$.

Step 2: To a solution of 3-[5-[(1-acetylpyrrolidin-3-yl)oxy]-6-methylpyrazin-2-yl]-1-(oxan-2-yl)indazole-7-carbonitrile (370 mg, 0.82 mmol) in DCM (4 mL) was added TFA (2 mL). The mixture was stirred at room temperature for 2 h. The aqueous solution was concentrated under vacuum. The solid was purified by prep-HPLC [Column: YMC-Triart Diol Hilic, 20*150 mm 5 um; Mobile Phase A: H$_2$O, Mobile Phase B: acetonitrile; Flow rate: 60 mL/min; Gradient: 35 B to 44 B in 8 min;] to afford 3-[5-[(1-acetylpyrrolidin-3-yl)oxy]-6-methylpyrazin-2-yl]-1H-indazole-7-carbonitrile (42.1 mg, 14.02%) as a white solid.

Example 313

1-(3-((3-methyl-5-(7-methyl-1H-indol-3-yl)pyrazin-2-yl)oxy)pyrrolidin-1-yl)ethan-1-one Step 1: To a solution of tert-butyl 7-methyl-3-(4,4,5,5-tetramethyl-1,3,2-dioxaborolan-2-yl)-1H-indole-1-carboxylate (200 mg, 0.56 mmol) in dioxane (2 mL) and H$_2$O (0.2 mL) were added 1-(3-((5-bromo-3-methylpyrazin-2-yl)oxy)pyrrolidin-1-yl)ethan-1-one (168 mg, 0.56 mmol). The mixture was stirred at room temperature for 20 min, this was followed by the addition of K$_2$CO$_3$ (154 mg, 1.12 mmol) and Pd(dppf)Cl$_2$ (41 mg, 0.06 mmol) at room temperature. Then the mixture was stirred at 100° C. for 2 h. The residue was purified by flash column chromatography with 0-50% ethyl acetate in petroleum ether to afford tert-butyl 3-(5-((1-acetylpyrrolidin-3-yl)oxy)-6-methylpyrazin-2-yl)-7-methyl-1H-indole-1-carboxylate (100 mg, 39.65%) as a white solid. MS m/z 451.1 [M+1]$^+$.

Step 2: To a solution of tert-butyl 3-(5-((1-acetylpyrrolidin-3-yl)oxy)-6-methylpyrazin-2-yl)-7-methyl-1H-indole-1-carboxylate (100 mg, 0.23 mmol) in DCM (1 mL) was added TFA (2 mL). The mixture was stirred at room temperature for 2 h. The solid was purified by prep-HPLC [Column: XBridge Prep OBD C18 Column, 30*150 mm 5 um; Mobile Phase A: Water (10 mmol/L NH$_4$HCO$_3$), Mobile Phase B: ACN; Flow rate: 60 mL/min; Gradient: 37 B to 48 B in 8 min;] to afford 1-(3-((3-methyl-5-(7-methyl-1H-indol-3-yl)pyrazin-2-yl)oxy)pyrrolidin-1-yl)ethan-1-one (42.3 mg, 52.69%) as a white solid.

Example 314

7,7-dimethyl-2-(7-methyl-1H-indol-3-yl)-6,7-dihydropyrrolo[3,4-b]pyridin-5-one

Step 1: To a stirred solution of 2-chloro-7,7-dimethyl-6,7-dihydropyrrolo[3,4-b]pyridin-5-one (100 mg, 0.51 mmol), K$_3$PO$_4$ (216 mg, 1.02 mmol) and tert-butyl 7-methyl-3-(4,4,5,5-tetramethyl-1,3,2-dioxaborolan-2-yl)-1H-indole-1-carboxylate (200 mg, 0.56 mmol) in dioxane (1 mL) and H$_2$O (0.1 mL) was added Pd(DtBPF)Cl$_2$ (33 mg, 0.05 mmol) at room temperature. The resulting solution was then stirred at 100° C. for 16 h. The mixture was diluted with ethyl acetate, washed with brine, dried over anhydrous sodium sulfate, filtered, and concentrated under vacuum. The residue was purified by flash column chromatography with 0-60% ethyl acetate in petroleum ether to afford tert-butyl 3-(7,7-dimethyl-5-oxo-6,7-dihydro-5H-pyrrolo[3,4-b]pyridin-2-yl)-7-methyl-1H-indole-1-carboxylate (130 mg, 65.30%) as a brown solid. MS m/z 392.1 [M+1]$^+$.

Step 2: To a mixture of tert-butyl 3-(7,7-dimethyl-5-oxo-6,7-dihydro-5H-pyrrolo[3,4-b]pyridin-2-yl)-7-methyl-1H-indole-1-carboxylate (130 mg, 0.33 mmol) in DCM (1.2 mL) was added TFA (0.3 mL). The mixture was stirred room temperature for 2 h. The mixture was diluted with ethyl acetate, washed with brine, dried over anhydrous sodium sulfate, filtered, and concentrated under vacuum. The residue was purified by prep-HPLC [Column: YMC-Pack Diol-120-NP, 20*150 mm 5 um; Mobile Phase A: undefined, Mobile Phase B: undefined; Flow rate: 60 mL/min; Gradient: 35 B to 59 B in 8 min;] to afford 7,7-dimethyl-2-(7-methyl-1H-indol-3-yl)-6,7-dihydropyrrolo[3,4-b]pyridin-5-one (24.3 mg, 25.12%) as a white solid.

Example 315

7,7-dimethyl-2-[1H-pyrrolo[2,3-b]pyridin-3-yl]-6H-pyrrolo[3,4-b]pyridin-5-one

Step 1: To a stirred solution of 2-chloro-7,7-dimethyl-6,7-dihydropyrrolo[3,4-b]pyridin-5-one (100 mg, 0.51 mmol), K$_3$PO$_4$ (216 mg, 1.02 mmol) and tert-butyl 3-(4,4,5,5-tetramethyl-1,3,2-dioxaborolan-2-yl)-1H-pyrrolo[2,3-b]pyridine-1-carboxylate (193 mg, 0.56 mmol) in dioxane (1 mL) and H$_2$O (0.1 mL) was added Pd(DtBPF)Cl$_2$ (33.15 mg, 0.051 mmol) at room temperature. The resulting solution was then stirred at 100° C. for 16 h nuder nitrogen. The residue was purified by flash column chromatography with 0-100% ethyl acetate in petroleum ether to afford tert-butyl 3-(7,7-dimethyl-5-oxo-6,7-dihydro-5H-pyrrolo[3,4-b]pyridin-2-yl)-1H-pyrrolo[2,3-b]pyridine-1-carboxylate (110 mg, 77.72%) as a brown solid. MS m/z 379.1 [M+1]$^+$.

Step 2: A mixture of tert-butyl 3-(7,7-dimethyl-5-oxo-6,7-dihydro-5H-pyrrolo[3,4-b]pyridin-2-yl)-1H-pyrrolo[2,3-b]pyridine-1-carboxylate (100 mg, 0.26 mmol) in DCM (0.9 mL) and TFA (0.3 mL) was stirred at room temperature for 2 h. The mixture was diluted with ethyl acetate, washed with brine, dried over anhydrous sodium sulfate, filtered, and concentrated under vacuum. The residue was purified by prep-HPLC [Column: Xcelect CSH F-pheny OBD Column, 19*250 mm, 5 um; Mobile Phase A: Water (10 mmol/L NH$_4$HCO$_3$), Mobile Phase B: ACN; Flow rate: 60 mL/min; Gradient: 35 B to 50 B in 8 min;] to afford 7,7-dimethyl-2-[1H-pyrrolo[2,3-b]pyridin-3-yl]-6H-pyrrolo[3,4-b]pyridin-5-one (11.4 mg, 15.50%) as a white solid.

Example 316

6-(7-cyano-1H-indol-3-yl)-2-methoxypyridine-3-carboxamide

A mixture of 6-chloro-2-methoxypyridine-3-carboxamide (160.0 mg, 0.85 mmol), tert-butyl 7-cyano-3-(4,4,5,5-tetramethyl-1,3,2-dioxaborolan-2-yl)indole-1-carboxylate (631.4 mg, 1.71 mmol), Pd(dppf)Cl$_2$ (125.4 mg, 0.17 mmol) and potassium carbonate (237.0 mg, 1.71 mmol) in dioxane (10 mL) and water (2 mL) were stirred at 100° C. for 2 h under nitrogen atmosphere. The aqueous layer was extracted with ethyl acetate. The combined organic solution was dried over sodium sulfate, filtered, and concentrated under vacuum. The crude was purified by flash column chromatography with 0-50% ethyl acetate in petroleum ether and prep-HPLC [Column: XBridge Prep OBD C18 Column, 30×150 mm 5 um; Mobile Phase A: Water (10 mmoL/L NH$_4$HCO$_3$), Mobile Phase B: ACN; Flow rate: 60 mL/min;

Gradient: 20 B to 50 B in 7 min;] to afford 6-(7-cyano-1H-indol-3-yl)-2-methoxypyridine-3-carboxamide (48.9 mg, 19%) as a white solid.

Example 317

3-(5-[[1-(2-methoxyethyl)pyrrolidin-3-yl]oxy]-6-methylpyrazin-2-yl)-1H-indole-7-carbonitrile To a solution of 5-bromo-2-[[1-(2-methoxyethyl)pyrrolidin-3-yl]oxy]-3-methylpyrazine (283 mg, 0.89 mmol) and tert-butyl 7-cyano-3-(4,4,5,5-tetramethyl-1,3,2-dioxaborolan-2-yl)indole-1-carboxylate (329 mg, 0.89 mmol) in dioxane (3 mL) and $H_2O$ (0.3 mL) was added $K_2CO_3$ (247 mg, 1.79 mmol) and Pd(dppf)$Cl_2$ (65 mg, 0.09 mmol). The mixture was stirred at 100° C. for 16 h under nitrogen. The residue was purified by flash column chromatography with 0-50% ethyl acetate in petroleum ether and prep-HPLC [Column: XBridge Prep OBD C18 Column, 30*150 mm 5 um; Mobile Phase A: Water (10 mmoL/L $NH_4HCO_3$), Mobile Phase B: ACN; Flow rate: 60 mL/min; Gradient: 42 B to 53 B in 8 min;] to afford 3-(5-[[1-(2-methoxyethyl)pyrrolidin-3-yl]oxy]-6-methylpyrazin-2-yl)-1H-indole-7-carbonitrile (97 mg, 28.77%) as a white solid.

Example 318

3-(5-[[1-(2-methoxyacetyl)pyrrolidin-3-yl]oxy]-6-methylpyrazin-2-yl)-1H-indole-7-carbonitrile To a mixture of 1-[3-[(5-bromo-3-methylpyrazin-2-yl)oxy]pyrrolidin-1-yl]-2-methoxyethanone (178 mg, 0.54 mmol) and tert-butyl 7-cyano-3-(4,4,5,5-tetramethyl-1,3,2-dioxaborolan-2-yl)indole-1-carboxylate (198 mg, 0.54 mmol) in $H_2O$ (0.2 mL) and dioxane (2 mL) was added Pd(dppf)$Cl_2$ (39 mg, 0.05 mmol), $K_2CO_3$ (149 mg, 1.08 mmol). Then the mixture was stirred at 100° C. for 16 h under nitrogen. The residue product was purified by Prep-HPLC [Column: Xselect CSH OBD Column 30*150 mm 5 um, n; Mobile Phase A: Water (0.1% FA), Mobile Phase B: ACN; Flow rate: 60 mL/min; Gradient: 25 B to 55 B in 8 min;] to afford 3-(5-[[1-(2-methoxyacetyl)pyrrolidin-3-yl]oxy]-6-methylpyrazin-2-yl)-1H-indole-7-carbonitrile (70.8 mg, 33.55%) as a white solid.

Example 321

3-[5-[(1-aminopropan-2-yl)oxy]-6-methylpyrazin-2-yl]-1H-indazole-7-carbonitrile

Step-1: To a mixture of tert-butyl N-[2-[(5-bromo-3-methylpyrazin-2-yl)oxy]propyl]carbamate (140 mg, 0.404 mmol) and 7-cyano-1-(oxan-2-yl)indazol-3-ylboronic acid (219 mg, 0.808 mmol) in dioxane (5 mL) and $H_2O$ (0.5 mL) were added $K_2CO_3$ (112 mg, 0.808 mmol) and Pd(dppf)$Cl_2$ (30 mg, 0.04 mmol). The resulting mixture was stirred at 100° C. overnight under nitrogen atmosphere. The mixture was concentrated under vacuum. The residue was purified by flash column chromatography with 0-50% ethyl acetate in PE to afford tert-butyl N-[2-([5-[7-cyano-1-(oxan-2-yl)indazol-3-yl]-3-methylpyrazin-2-yl]oxy)propyl]carbamate (150 mg, 75.31%) as a white solid. MS m/z 493.3 [M+1]$^+$.

Step-2: To a mixture of tert-butyl N-[2-([5-[7-cyano-1-(oxan-2-yl)indazol-3-yl]-3-methylpyrazin-2-yl]oxy)propyl]carbamate (150 mg, 0.305 mmol) in DCM (5 mL) was added TFA (1.5 mL) at 0° C. The resulting mixture was stirred at room temperature for 1 h. The resulting mixture was concentrated under vacuum. The residue was basified to pH 8 with saturated $NaHCO_3$(aq.). The resulting mixture was extracted with EtOAc. The combined organic layers were washed with brine, dried over anhydrous $Na_2SO_4$. After filtration, the filtrate was concentrated under reduced pressure. The residue was purified by Prep-HPLC [Column: XBridge Prep OBD C18 Column, 30×150 mm 5 um; Mobile Phase A: water (10 mmol/L $NH_4HCO_3$), Mobile Phase B: ACN; Flow rate: 60 mL/min; Gradient: 23 B to 37 B in 8 min; 254/220 nm] to afford 3-[5-[(1-aminopropan-2-yl)oxy]-6-methylpyrazin-2-yl]-1H-indazole-7-carbonitrile (21.4 mg, 22.79%) as a white solid.

Example 322

3-[5-[(4,4-difluoropyrrolidin-3-yl)oxy]-6-methylpyrazin-2-yl]-1H-indole-7-carbonitrile Step-1: To a mixture of tert-butyl 3,3-difluoro-4-[(5-iodo-3-methylpyrazin-2-yl)oxy]pyrrolidine-1-carboxylate (50 mg, 0.113 mmol, 1 equiv) and 1-(tert-butoxycarbonyl)-7-cyanoindol-3-ylboronic acid (65 mg, 0.227 mmol) in dioxane (2 mL) and $H_2O$ (0.4 mL) were added $K_2CO_3$ (47 mg, 0.340 mmol) and Pd(dppf)$Cl_2$ (17 mg, 0.023 mmol). The resulting mixture was stirred at 80° C. for 16 h under nitrogen atmosphere. The mixture was concentrated under vacuum. The residue was purified by flash column chromatography with 0-40% ethyl acetate in PE to afford tert-butyl 3-(5-[[1-(tert-butoxycarbonyl)-4,4-difluoropyrrolidin-3-yl]oxy]-6-methylpyrazin-2-yl)-7-cyanoindole-1-carboxylate (90 mg, 38.12%) as a yellow solid. MS m/z 456.1 [M+1]$^+$.

Step-2: To a mixture of tert-butyl 4-[[5-(7-cyano-1H-indol-3-yl)-3-methylpyrazin-2-yl]oxy]-3,3-difluoropyrrolidine-1-carboxylate (90 mg, 0.198 mmol) in DCM (5 mL) were added TFA (0.5 mL). The resulting mixture was stirred at room temperature for 1 h. The mixture was basified to pH 8 with saturated $NaHCO_3$ (aq.). The resulting mixture was extracted with EtOAc (3×20 mL). The combined organic layers were washed with brine (1×5 mL), dried over anhydrous $Na_2SO_4$. The residue was purified by $C_{18}$ reverse phase column with 0-100% ACN in $H_2O$ ($NH_4HCO_3$) to afford 3-[5-[(4,4-difluoropyrrolidin-3-yl)oxy]-6-methylpyrazin-2-yl]-1H-indole-7-carbonitrile (28.1 mg, 15.12%) as a white solid.

Example 323

3-[5-[(1-acetyl-4,4-difluoropyrrolidin-3-yl)oxy]-6-methylpyrazin-2-yl]-1H-indole-7-carbonitrile To a mixture of 1-[3,3-difluoro-4-[(5-iodo-3-methylpyrazin-2-yl)oxy]pyrrolidin-1-yl]ethanone (75 mg, 0.196 mmol) and 1-(tert-butoxycarbonyl)-7-cyanoindol-3-ylboronic acid (113 mg, 0.392 mmol, 2 equiv) in dioxane (3 mL) and $H_2O$ (0.6 mL) were added $K_2CO_3$ (82 mg, 0.587 mmol) and Pd(dppf)$Cl_2$ (29 mg, 0.039 mmol). The resulting mixture was stirred at 80° C. for 16 h under nitrogen atmosphere. The mixture was concentrated under vacuum. The residue was purified by Prep-HPLC [Column: YMC-Actus Triart C18 ExRS, 30 mm×150 mm, 5 um; Mobile Phase A: Water (10 mmoL/L $NH_4HCO_3$), Mobile Phase B: ACN; Flow rate: 60 mL/min; Gradient: 40 B to 64 B in 8 min; 254/220 nm] to afford 3-[5-[(1-acetyl-4,4-difluoropyrrolidin-3-yl)oxy]-6-methylpyrazin-2-yl]-1H-indole-7-carbonitrile (28.8 mg, 37.02%) as a white solid.

Example 324

3-[5-[(1-aminopropan-2-yl)oxy]-6-methylpyrazin-2-yl]-1H-indazole-7-carbonitrile Step-1: To a mixture of 6-bromo-2-methyl-3-[2-methyl-2-(oxan-2-yloxy)propoxy]pyridine (250 mg, 0.72 mmol) and tert-butyl 7-cyano-3-(4,4,5,5-tetramethyl-1,3,2-dioxaborolan-2-yl)indole-1-carboxylate (267 mg, 0.72 mmol) in dioxane (3 mL) and H$_2$O (0.3 mL) were added K$_2$CO$_3$ (200 mg, 1.45 mmol) and Pd(dppf)Cl$_2$ (53.14 mg, 0.073 mmol). The resulting mixture was stirred at 100° C. for 16 h under nitrogen atmosphere. The mixture was concentrated under vacuum. The residue was purified by flash column chromatography with 0-50% ethyl acetate in PE to afford 3-[6-methyl-5-[2-methyl-2-(oxan-2-yloxy)propoxy]pyridin-2-yl]-1H-indole-7-carbonitrile (220 mg, 74.71%) as a white solid. MS m/z 406.2 [M+1]$^+$.

Step-2: To a mixture of 3-[6-methyl-5-[2-methyl-2-(oxan-2-yloxy)propoxy]pyridin-2-yl]-1H-indole-7-carbonitrile (120 mg, 0.29 mmol) in DCM (3 mL) were added TFA (0.3 mL). The resulting mixture was stirred at room temperature for 1 h. The mixture was basified to pH 8 with saturated NaHCO$_3$ (aq.). The resulting mixture was extracted with EtOAc. The combined organic layers were washed with brine, dried over anhydrous Na$_2$SO$_4$. The residue was purified by Prep-HPLC [Column: XBridge Prep OBD C18 Column, 30×150 mm 5 um; Mobile Phase A: water (10 mmol/L NH$_4$HCO$_3$), Mobile Phase B: ACN; Flow rate: 60 mL/min; Gradient: 33 B to 52 B in 8 min; 254/220 nm] to afford 3-[5-(2-hydroxy-2-methylpropoxy)-6-methylpyridin-2-yl]-1H-indole-7-carbonitrile (21.9 mg, 23.03%) as a white solid.

Example 325

3-[6-methyl-5-[(3-methyloxetan-3-yl)methoxy]pyrazin-2-yl]-1H-indole-7-carbonitrile To a mixture of 5-iodo-3-methyl-2-[(3-methyloxetan-3-yl)methoxy]pyrazine (120 mg, 0.375 mmol, 1.00 equiv) and 1-(tert-butoxycarbonyl)-7-cyanoindol-3-ylboronic acid (215 mg, 0.750 mmol, 2.00 equiv) in dioxane (2 mL) and H$_2$O (0.4 mL) were added K$_2$CO$_3$ (156 mg, 1.125 mmol, 3 equiv) and Pd(dppf)Cl$_2$ (55 mg, 0.075 mmol, 0.2 equiv). The resulting mixture was stirred at 80° C. for 16 h under nitrogen atmosphere. The mixture was concentrated under vacuum. The residue was purified by Prep-HPLC [Column: Xselect CSH OBD Column 30*150 mm 5 um, n; Mobile Phase A: Water (10 mmoL/L NH$_4$HCO$_3$), Mobile Phase B: ACN; Flow rate: 60 mL/min; Gradient: 49 B to 58 B in 8 min; 254/220 nm] to afford 3-[6-methyl-5-[(3-methyloxetan-3-yl)methoxy]pyrazin-2-yl]-1H-indole-7-carbonitrile (31.6 mg, 25.09%) as a white solid.

Example 328, Example 329, Example 330 and Example 331

3-(6-methyl-5-((3S,5S)-5-methylpyrrolidin-3-yloxy)pyrazin-2-yl)-1H-indole-7-carbonitrile, 3-(6-methyl-5-((3S,5R)-5-methylpyrrolidin-3-yloxy)pyrazin-2-yl)-1H-indole-7-carbonitrile, 3-(6-methyl-5-((3R,5S)-5-methylpyrrolidin-3-yloxy) pyrazin-2-yl)-1H-indole-7-carbonitrile and 3-(6-methyl-5-((3R,5R)-5-methylpyrrolidin-3-yloxy)pyrazin-2-yl)-1H-indole-7-carbonitrile To a mixture of tert-butyl 4-(5-(7-cyano-1H-indol-3-yl)-3-methylpyrazin-2-yloxy)-2-methylpyrrolidine-1-carboxylate (720 mg, 1.7 mmol) in DCM (6 mL) was added TFA (2 mL). The mixture was stirred at room temperature for 2 h. The mixture was diluted with ethyl acetate, washed with brine, dried over anhydrous sodium sulfate, filtered, and concentrated under vacuum. The crude product (1 g) was purified by Prep-SFC [Column: DZ-CHIRALPAK IH-3, 0.46*5, 3 um; Mobile Phase A: Mobile Phase B: MeOH (0.5% 2 mMNH3-MeOH); Flow rate: 4 mL/min; Gradient: 10% B;] to afford 3-(6-methyl-5-((3S,5S)-5-methylpyrrolidin-3-yloxy)pyrazin-2-yl)-1H-indole-7-carbonitrile (16.3 mg, 2.94%) as a white solid, 3-(6-methyl-5-((3S,5R)-5-methylpyrrolidin-3-yloxy)pyrazin-2-yl)-1H-indole-7-carbonitrile (4.0 mg, 0.72%) as a white solid, 3-(6-methyl-5-((3R,5S)-5-methylpyrrolidin-3-yloxy)pyrazin-2-yl)-1H-indole-7-carbonitrile (27.5 mg, 4.97%) as a white solid and -(6-methyl-54(3R,5R)-5-methylpyrrolidin-3-yloxy)pyrazin-2-yl)-1H-indole-7-carbonitrile (10.5 mg, 1.89%) as a white solid.

Example 336

1-[[5-(6-fluoro-1-benzothiophen-3-yl)-3-methylpyrazin-2-yl]oxy]-2-methylpropan-2-ol Step 1: To a mixture of 5-iodo-3-methyl-2-[2-methyl-2-(oxan-2-yloxy)propoxy]pyrazine (212 mg, 0.540 mmol) and 2-(6-fluoro-1-benzothiophen-3-yl)-4,4,5,5-tetramethyl-1,3,2-dioxaborolane (150 mg, 0.540 mmol) in dioxane (4 mL) and H$_2$O (0.4 mL) were added K$_2$CO$_3$ (149 mg, 1.081 mmol) and Pd(dppf)Cl$_2$ (40 mg, 0.054 mmol). The resulting mixture was stirred at 100° C. overnight under nitrogen atmosphere. The resulting mixture was concentrated under reduced pressure. The residue was purified by flash column chromatography with 0-50% ethyl acetate in PE to afford 5-(6-fluoro-1-benzothiophen-3-yl)-3-methyl-2-[2-methyl-2-(oxan-2-yloxy)propoxy]pyrazine (130 mg, 57.75%) as a yellow solid. MS m/z 417.2 [M+1]$^+$ Step 2: To a mixture of 5-(6-fluoro-1-benzothiophen-3-yl)-3-methyl-2-[2-methyl-2-(oxan-2-yloxy)propoxy]pyrazine (110 mg, 0.264 mmol) in DCM (3 mL) was added TFA (0.5 mL) at 0° C. The resulting mixture was stirred at room temperature for 1 h. The resulting mixture was concentrated under reduced pressure. The residue was basified to pH 8 with saturated NaHCO$_3$ (aq.). The resulting mixture was extracted with EtOAc. The combined organic layers were washed with brine, dried over anhydrous Na$_2$SO$_4$. After filtration, the filtrate was concentrated under reduced pressure. The residue was purified by reverse phase flash with 0-50% ACN in H$_2$O to afford 1-[[5-(6-fluoro-1-benzothiophen-3-yl)-3-methylpyrazin-2-yl]oxy]-2-methylpropan-2-ol (29.6 mg, 33.72%) as a white solid.

Example 337

1-[[5-(7-chloro-1-benzofuran-3-yl)-3-methylpyrazin-2-yl]oxy]-2-methylpropan-2-ol Step 1: To a mixture of 3-bromo-7-chloro-1-benzofuran (40 mg, 0.173 mmol) and 3-methyl-2-[2-methyl-2-(oxan-2-yloxy)propoxy]-5-(4,4,5,5-tetramethyl-1,3,2-dioxaborolan-2-yl)pyrazine (136 mg, 0.346 mmol) in dioxane (3 mL) and H$_2$O (0.6 mL) were added K$_2$CO$_3$ (72 mg, 0.518 mmol) and Pd(dppf)Cl$_2$ (26 mg, 0.035 mmol). The resulting mixture was stirred at 80° C. for 16 h under nitrogen atmosphere. The mixture was concentrated under vacuum. The residue was purified by flash column chromatography with 0-50% ethyl acetate in PE to afford 5-(7-chloro-1-benzofuran-3-yl)-

3-methyl-2-[2-methyl-2-(oxan-2-yloxy)propoxy]pyrazine (30 mg, 41.64%) as a white solid. MS m/z 417.1 [M+1]+

Step 2: To a mixture of 5-(7-chloro-1-benzofuran-3-yl)-3-methyl-2-[2-methyl-2-(oxan-2-yloxy) propoxy]pyrazine (30 mg, 0.072 mmol) in DCM (1.5 mL) were added TFA (0.5 mL). The resulting mixture was stirred at room temperature for 1 h. The mixture was basified to pH 8 with saturated NaHCO$_3$ (aq.). The resulting mixture was extracted with EtOAc. The combined organic layers were washed with brine, dried over anhydrous Na$_2$SO$_4$. After filtration, the filtrate was concentrated under reduced pressure. The residue was purified by reverse phase flash with 0~40% ACN in H$_2$O to afford 1-[[5-(7-chloro-1-benzofuran-3-yl)-3-methylpyrazin-2-yl]oxy]-2-methylpropan-2-ol (14.6 mg, 60.97%) as a white solid.

Example 338

1-[[5-(1-benzofuran-3-yl)-3-methylpyrazin-2-yl]oxy]-2-methylpropan-2-ol

Step 1: To a mixture of 5-iodo-3-methyl-2-[2-methyl-2-(oxan-2-yloxy)propoxy]pyrazine (250 mg, 0.637 mmol) and 1-benzofuran-3-ylboronic acid (103 mg, 0.637 mmol) in dioxane (4 mL) and H$_2$O (0.4 mL) were added K$_2$CO$_3$ (176 mg, 1.274 mmol) and Pd(dppf)Cl$_2$ (47 mg, 0.064 mmol). The resulting mixture was stirred at 100° C. overnight under nitrogen atmosphere. The residue was purified by flash column chromatography with 0-40% ethyl acetate in PE to afford 5-(1-benzofuran-3-yl)-3-methyl-2-[2-methyl-2-(oxan-2-yloxy)propoxy]pyrazine (151 mg, 61.94%) as a white solid. MS m/z 383.2 [M+1]+

Step 2: To a mixture of 5-(1-benzofuran-3-yl)-3-methyl-2-[2-methyl-2-(oxan-2-yloxy)propoxy]pyrazine (120 mg, 0.314 mmol) in DCM (5 mL) was added TFA (0.5 mL) at 0° C. The resulting mixture was stirred at room temperature for 1 h. The residue was basified to pH 8 with saturated NaHCO$_3$ (aq.). The resulting mixture was extracted with EtOAc. The combined organic layers were washed with brine, dried over anhydrous Na$_2$SO$_4$. After filtration, the filtrate was concentrated under reduced pressure. The residue was purified by Prep-HPLC [Column: XBridge Shield RP18 OBD Column, 19*250 mm, 10 um; Mobile Phase A: water (10 mmol/L NH$_4$HCO$_3$), Mobile Phase B: ACN; Flow rate: 60 mL/min; Gradient: 48 B to 65 B in 8 min, 220/254 nm] to afford 1-[[5-(1-benzofuran-3-yl)-3-methylpyrazin-2-yl]oxy]-2-methylpropan-2-ol (29.1 mg, 31.09%) as a white solid.

Example 339 and Example 346

3-[5-[(3-amino-1,1,1-trifluoropropan-2-yl)oxy]-6-methylpyrazin-2-yl]-1H-indole-7-carbonitrile and 3-[6-methyl-5-[(3,3,3-trifluoro-2-hydroxypropyl)amino]pyrazin-2-yl]-1H-indole-7-carbonitrile Step 1: To a mixture of 2-chloro-5-iodo-3-methylpyrazine (400 mg, 1.572 mmol) and tert-butyl 7-cyano-3-(4,4,5,5-tetramethyl-1,3,2-dioxaborolan-2-yl)indole-1-carboxylate (868.29 mg, 2.358 mmol) in dioxane (8 mL) and H$_2$O (0.8 mL) were added K$_2$CO$_3$ (434.51 mg, 3.144 mmol) and Pd(dppf)Cl$_2$ (115.02 mg, 0.157 mmol) in portions at room temperature. The resulting mixture was stirred at 60° C. under nitrogen atmosphere for 1 h. The resulting mixture was concentrated under reduced pressure. The residue was purified by flash column chromatography with 0-22% ethyl acetate in PE to afford tert-butyl 3-(5-chloro-6-methylpyrazin-2-yl)-7-cyanoindole-1-carboxylate (260 mg, 35.88%) as a white solid. MS m/z 369.1 [M+1]+.

Step 2: To a mixture of tert-butyl 3-(5-chloro-6-methylpyrazin-2-yl)-7-cyanoindole-1-carboxylate (200 mg, 0.542 mmol) and tert-butyl N-(3,3,3-trifluoro-2-hydroxypropyl) carbamate (621.44 mg, 2.711 mmol) in dioxane (10 mL) were added Cs$_2$CO$_3$ (530.05 mg, 1.627 mmol) and Pd-PEPPSI-IHeptCl 3-chloropyridine (105.61 mg, 0.108 mmol) in portions at room temperature. The resulting mixture was stirred at 90° C. under nitrogen atmosphere overnight. The residue was purified by reverse phase flash chromatography with 0-100% ACN in H$_2$O to afford tert-butyl N-(2-[[5-(7-cyano-1H-indol-3-yl)-3-methylpyrazin-2-yl]oxy]-3,3,3-trifluoropropyl)carbamate (80 mg, 28.77%) as a yellow solid. MS m/z 462.2 [M+1]+ and 3-[6-methyl-5-[(3,3,3-trifluoro-2-hydroxypropyl)amino]pyrazin-2-yl]-1H-indole-7-carbonitrile (10.2 mg, 4.95%, 346) as a yellow solid. MS m/z 362.1 [M+1]+

Step 3: To a mixture of tert-butyl N-(2-[[5-(7-cyano-1H-indol-3-yl)-3-methylpyrazin-2-yl]oxy]-3,3,3-trifluoropropyl)carbamate (70 mg, 0.152 mmol) in DCM (4 mL) were added TFA (1 mL) at room temperature. The resulting mixture was stirred at room temperature for 1 h. The resulting mixture was concentrated under vacuum. The residue was purified by reverse phase flash chromatography with 0-80% ACN in H$_2$O to afford 3-[5-[(3-amino-1,1,1-trifluoropropan-2-yl)oxy]-6-methylpyrazin-2-yl]-1H-indole-7-carbonitrile (7.0 mg, 12.75%) as an off-white solid.

Example 345

3-[5-(2-amino-2-methylpropoxy)-6-methylpyridin-2-yl]-1H-indole-7-carbonitrile

To a mixture of 1-[(6-bromo-2-methylpyridin-3-yl)oxy]-2-methylpropan-2-amine (80 mg, 0.309 mmol) and tert-butyl 7-cyano-3-(4,4,5,5-tetramethyl-1,3,2-dioxaborolan-2-yl)indole-1-carboxylate (89 mg, 0.309 mmol) in dioxane (3 mL) and H$_2$O (0.3 mL) were added K$_2$CO$_3$ (127.99 mg, 0.926 mmol) and Pd(dppf)Cl$_2$ (45.18 mg, 0.062 mmol). The resulting mixture was stirred at 100° C. for 16 h under nitrogen atmosphere. The mixture was concentrated under vacuum. The residue was purified by Prep-HPLC [Column: XBridge Prep OBD C18 Column, 30×150 mm 5 um; Mobile Phase A: Water (10 mmol/L NH$_4$HCO$_3$), Mobile Phase B: ACN; Flow rate: 60 mL/min; Gradient: 33 B to 52 B in 8 min; 254/220 nm] to afford 3-[5-(2-amino-2-methylpropoxy)-6-methylpyridin-2-yl]-1H-indole-7-carbonitrile (20 mg, 20.22%) as a white solid.

Example 342

3-[6-cyclopropyl-5-(2-hydroxy-2-methylpropoxy)pyrazin-2-yl]-1H-indole-7-carbonitrile To a mixture of 1-[(5-chloro-3-cyclopropylpyrazin-2-yl)oxy]-2-methylpropan-2-ol (250 mg, 1.03 mmol) and tert-butyl 7-cyano-3-(4,4,5,5-tetramethyl-1,3,2-dioxaborolan-2-yl)indole-1-carboxylate (568 mg, 1.545 mmol) in dioxane (10 mL) and H$_2$O (1 mL) were added K$_2$CO$_3$ (427 mg, 3.09 mmol) and Pd(dppf)Cl$_2$ (75 mg, 0.103 mmol). The resulting mixture was stirred at 100° C. overnight under nitrogen atmosphere. The resulting mixture was concentrated under vacuum. The residue was purified by Prep-HPLC [Column: XBridge Prep OBD C18 Column, 30×150 mm 5 um; Mobile Phase A: water (10 mmol/L NH$_4$HCO$_3$), Mobile Phase B: ACN; Flow rate: 60 mL/min; Gradient: 33 B to 52 B in 8

Example 343

1-[(5-[7-chloro-1H-pyrrolo[2,3-c]pyridin-3-yl]-3-methylpyrazin-2-yl)oxy]-2-methylpropan-2-ol Step-1: To a mixture of 5-iodo-3-methyl-2-[2-methyl-2-(oxan-2-yloxy)propoxy]pyrazine (200 mg, 0.510 mmol) and 7-chloro-1H-pyrrolo[2,3-c]pyridin-3-ylboronic acid (201 mg, 1.020 mmol) in dioxane (5 mL) and H$_2$O (0.5 mL) were added K$_2$CO$_3$ (212 mg, 1.530 mmol) and Pd(dppf)Cl$_2$ (75 mg, 0.102 mmol). The resulting mixture was stirred at 80° C. for 16 h under nitrogen atmosphere. The mixture was concentrated under vacuum. The residue was purified by flash column chromatography with 0-50% ethyl acetate in PE to afford 5-[7-chloro-1H-pyrrolo[2,3-c]pyridin-3-yl]-3-methyl-2-[2-methyl-2-(oxan-2-yloxy)propoxy]pyrazine (140 mg, 65.86%) as a yellow oil. MS m/z 417.2 [M+1]$^+$ Step-2: To a mixture of 5-[7-chloro-1H-pyrrolo[2,3-c]pyridin-3-yl]-3-methyl-2-[2-methyl-2-(oxan-2-yloxy)propoxy]pyrazine (120 mg, 0.288 mmol) in DCM (3 mL) was added TFA (0.3 mL). The resulting mixture was stirred at room temperature for 1 h. The mixture was basified to pH 8 with saturated NaHCO$_3$ (aq.). The resulting mixture was extracted with EtOAc. The combined organic layers were washed with brine, dried over anhydrous Na$_2$SO$_4$. After filtration, the filtrate was concentrated under reduced pressure. The residue was purified by reverse phase flash with 0-60% ACN in H$_2$O to afford 1-[(5-[7-chloro-1H-pyrrolo[2,3-c]pyridin-3-yl]-3-methylpyrazin-2-yl)oxy]-2-methylpropan-2-ol (41.8 mg, 43.59%) as a white solid.

Example 339 and Example 346

3-[5-[(3-amino-1,1,1-trifluoropropan-2-yl)oxy]-6-methylpyrazin-2-yl]-1H-indole-7-carbonitrile and 3-[6-methyl-5-[(3,3,3-trifluoro-2-hydroxypropyl)amino]pyrazin-2-yl]-1H-indole-7-carbonitrile Step 1: To a mixture of 2-chloro-5-iodo-3-methylpyrazine (400 mg, 1.572 mmol) and tert-butyl 7-cyano-3-(4,4,5,5-tetramethyl-1,3,2-dioxaborolan-2-yl)indole-1-carboxylate (868.29 mg, 2.358 mmol) in dioxane (8 mL) and H$_2$O (0.8 mL) were added K$_2$CO$_3$ (434.51 mg, 3.144 mmol) and Pd(dppf)Cl$_2$ (115.02 mg, 0.157 mmol) in portions at room temperature. The resulting mixture was stirred at 60° C. under nitrogen atmosphere for 1 h. The resulting mixture was concentrated under reduced pressure. The residue was purified by flash column chromatography with 0-22% ethyl acetate in PE to afford tert-butyl 3-(5-chloro-6-methylpyrazin-2-yl)-7-cyanoindole-1-carboxylate (260 mg, 35.88%) as a white solid. MS m/z 369.1 [M+1]$^+$.

Step 2: To a mixture of tert-butyl 3-(5-chloro-6-methylpyrazin-2-yl)-7-cyanoindole-1-carboxylate (200 mg, 0.542 mmol) and tert-butyl N-(3,3,3-trifluoro-2-hydroxypropyl) carbamate (621.44 mg, 2.711 mmol) in dioxane (10 mL) were added Cs$_2$CO$_3$ (530.05 mg, 1.627 mmol) and Pd-PEPPSI-IHeptCl 3-chloropyridine (105.61 mg, 0.108 mmol) in portions at room temperature. The resulting mixture was stirred at 90° C. under nitrogen atmosphere overnight. The residue was purified by reverse phase flash chromatography with 0-100% ACN in H$_2$O to afford tert-butyl N-(2-[[5-(7-cyano-1H-indol-3-yl)-3-methylpyrazin-2-yl]oxy]-3,3,3-trifluoropropyl)carbamate (80 mg, 28.77%) as a yellow solid. MS m/z 462.2 [M+1]$^+$ and 3-[6-methyl-5-[(3,3,3-trifluoro-2-hydroxypropyl)amino]pyrazin-2-yl]-1H-indole-7-carbonitrile (10.2 mg, 4.95%) as a yellow solid. MS m/z 362.1 [M+1]$^+$ Step 3: To a mixture of tert-butyl N-(2-[[5-(7-cyano-1H-indol-3-yl)-3-methylpyrazin-2-yl]oxy]-3,3,3-trifluoropropyl)carbamate (70 mg, 0.152 mmol) in DCM (4 mL) were added TFA (1 mL) at room temperature. The resulting mixture was stirred at room temperature for 1 h. The resulting mixture was concentrated under vacuum. The residue was purified by reverse phase flash chromatography with 0-80% ACN in H$_2$O to afford 3-[5-[(3-amino-1,1,1-trifluoropropan-2-yl)oxy]-6-methylpyrazin-2-yl]-1H-indole-7-carbonitrile (7.0 mg, 12.75%) as an off-white solid.

Example 327

3-[5-[ethyl(2-hydroxy-2-methylpropyl)amino]-6-methylpyrazin-2-yl]-1H-indole-7-carbonitrile To a mixture of 1-[(5-bromo-3-methylpyrazin-2-yl)(ethyl)amino]-2-methylpropan-2-ol (160 mg, 0.555 mmol) and tert-butyl 7-cyano-3-(4,4,5,5-tetramethyl-1,3,2-dioxaborolan-2-yl)indole-1-carboxylate (204 mg, 0.555 mmol) in dioxane (5 mL) and H$_2$O (0.5 mL) were added Pd(dppf)Cl$_2$ (40 mg, 0.056 mmol) and K$_2$CO$_3$ (153 mg, 1.110 mmol). The resulting mixture was stirred at 100° C. overnight under nitrogen atmosphere. The mixture was concentrated under vacuum. The residue was purified by Prep-HPLC [Column: XBridge Shield RP18 OBD Column, 19*250 mm, 10 um; Mobile Phase water (10 mmol/L NH$_4$HCO$_3$), Mobile Phase B: ACN; Flow rate: 60 mL/min; Gradient: 43 B to 61 B in 8 min, 220/254 nm] to afford 3-[5-[ethyl(2-hydroxy-2-methylpropyl)amino]-6-methylpyrazin-2-yl]-1H-indole-7-carbonitrile (36.6 mg, 18.87%) as a white solid.

Example 332

1-[[5-(7-fluoro-1H-indol-3-yl)-3-methylpyrazin-2-yl]oxy]-2-methylpropan-2-ol Step-1: To a mixture of 5-iodo-3-methyl-2-[2-methyl-2-(oxan-2-yloxy)propoxy]pyrazine (150 mg, 0.382 mmol) and tert-butyl 7-fluoro-3-(4,4,5,5-tetramethyl-1,3,2-dioxaborolan-2-yl)indole-1-carboxylate (207.21 mg, 0.574 mmol) in dioxane (10 mL) and H$_2$O (1 mL) were added K$_2$CO$_3$ (105.71 mg, 0.765 mmol) and Pd(dppf)Cl$_2$ (27.98 mg, 0.038 mmol) in portions at room temperature. The resulting mixture was stirred at 100° C. under nitrogen atmosphere overnight. The resulting mixture was concentrated under reduced pressure. The residue was purified by reverse phase flash chromatography with 0-100% ACN in H$_2$O to afford 7-fluoro-3-[6-methyl-5-[2-methyl-2-(oxan-2-yloxy)propoxy]pyrazin-2-yl]-1H-indole (64 mg, 37.71%) as a brown yellow solid. MS m/z 400.3 [M+1]$^+$.

Step-2: To a mixture of 7-fluoro-3-[6-methyl-5-[2-methyl-2-(oxan-2-yloxy)propoxy]pyrazin-2-yl]-1H-indole (64 mg, 0.16 mmol) in DCM (3 mL) was added TFA (0.8 mL) in portions at room temperature. The resulting mixture was stirred at room temperature for 1 h. The mixture was basified to pH 8 with saturated NaHCO$_3$ (aq.). The resulting mixture was concentrated under reduced pressure. The residue was purified by reverse phase flash chromatography with 0-90% ACN in H$_2$O to afford 1-[[5-(7-fluoro-1H-indol-3-yl)-3-methylpyrazin-2-yl]oxy]-2-methylpropan-2-ol (27.2 mg, 53.73%) as a white solid.

Example 333

3-[5-[(1-hydroxycyclopropyl)methoxy]-6-methylpyrazin-2-yl]-1H-indole-7-carbonitrile Step-1: To a mixture of 5-iodo-3-methyl-2-[[1-(oxan-2-yloxy)cyclopropyl]methoxy]pyrazine (210 mg, 0.538 mmol) and tert-butyl 7-cyano-3-(4,4,5,5-tetramethyl-1,3,2-dioxaborolan-2-yl)indole-1-carboxylate (198 mg, 0.538 mmol) in dioxane (4 mL) and H$_2$O (0.4 mL) were added Pd(dppf)Cl$_2$ (39 mg, 0.054 mmol) and K$_2$CO$_3$ (149 mg, 1.076 mmol). The resulting mixture was stirred at 100° C. overnight under nitrogen atmosphere. The resulting mixture was concentrated under vacuum. The residue was purified by flash column chromatography with 0-40% ethyl acetate in PE to afford 3-(6-methyl-5-[[1-(oxan-2-yloxy)cyclopropyl]methoxy]pyrazin-2-yl)-1H-indole-7-carbonitrile (200 mg, 91.88%) as a yellow solid. MS m/z 405.2 [M+1]$^+$ Step-2: To a mixture of 3-(6-methyl-5-[[1-(oxan-2-yloxy)cyclopropyl]methoxy]pyrazin-2-yl)-1H-indole-7-carbonitrile (200 mg, 0.494 mmol) in DCM (5 mL) was added TFA (0.7 mL). The resulting mixture was stirred at room temperature for 1 h. The residue was basified to pH 8 with saturated NaHCO$_3$ (aq.) The resulting mixture was extracted with EtOAc. The combined organic layers were washed with brine, dried over anhydrous Na$_2$SO$_4$. After filtration, the filtrate was concentrated under reduced pressure. The residue was purified by Prep-HPLC [Column: XBridge Prep OBD C18 Column, 30×150 mm 5 um; Mobile Phase A: water (10 mmol/L NH$_4$HCO$_3$), Mobile Phase B: ACN; Flow rate: 60 mL/min; Gradient: 25 B to 55 B in 8 min, 220 nm] to afford 3-[5-[(1-hydroxycyclopropyl)methoxy]-6-methylpyrazin-2-yl]-1H-indole-7-carbonitrile (30.9 mg, 19.51%) as an off-white solid.

Example 334

3-(5-[[(2R,3R)-3-hydroxybutan-2-yl]oxy]-6-methylpyrazin-2-yl)-1H-indole-7-carbonitrile To a mixture of (2R,3R)-3-[(5-iodo-3-methylpyrazin-2-yl)oxy]butan-2-ol (200 mg, 0.649 mmol) and tert-butyl 7-cyano-3-(4,4,5,5-tetramethyl-1,3,2-dioxaborolan-2-yl)indole-1-carboxylate (239 mg, 0.649 mmol) in dioxane (3 mL) and H$_2$O (0.3 mL) were added Pd(dppf)Cl$_2$ (47 mg, 0.065 mmol) and K$_2$CO$_3$ (179 mg, 1.298 mmol). The resulting mixture was stirred at 100° C. overnight under nitrogen atmosphere. The resulting mixture was concentrated under vacuum. The residue was purified by Prep-HPLC [Column: XBridge Prep OBD C18 Column, 30×150 mm 5 um; Mobile Phase A: water (10 mmol/L NH$_4$HCO$_3$), Mobile Phase B: ACN; Flow rate: 60 mL/min; Gradient: 35 B to 65 B in 8 min 220 nm] to afford 3-(5-[[(2R,3R)-3-hydroxybutan-2-yl]oxy]-6-methylpyrazin-2-yl)-1H-indole-7-carbonitrile (42.9 mg, 20.50%) as a white solid.

Example 335

3-(5-hydroxy-6-methylpyrazin-2-yl)-1H-indole-7-carbonitrile

To a mixture of 5-bromo-3-methylpyrazin-2-ol (300 mg, 1.587 mmol) and tert-butyl 7-cyano-3-(4,4,5,5-tetramethyl-1,3,2-dioxaborolan-2-yl)indole-1-carboxylate (584 mg, 1.587 mmol) in dioxane (4 mL) and H$_2$O (0.4 mL) were added K$_2$CO$_3$ (439 mg, 3.174 mmol) and Pd(dppf)Cl$_2$ (116 mg, 0.159 mmol). The resulting mixture was stirred at 100° C. overnight under nitrogen atmosphere. The mixture was concentrated under vacuum. The residue was purified by Prep-HPLC [Column: XBridge Prep OBD C18 Column, 30×150 mm 5 um; Mobile Phase A: water (10 mmol/L NH$_4$HCO$_3$), Mobile Phase B: ACN; Flow rate: 60 mL/min; Gradient: 10 B to 40 B in 8 min, 254/220 nm] to afford 3-(5-hydroxy-6-methylpyrazin-2-yl)-1H-indole-7-carbonitrile (11.6 mg, 2.92%) as a yellow solid.

Example 340

3-[5-(2-hydroxyethoxy)-6-methylpyrazin-2-yl]-1H-indole-7-carbonitrile

To a mixture of tert-butyl 3-(5-chloro-6-methylpyrazin-2-yl)-7-cyanoindole-1-carboxylate (120 mg, 0.325 mmol) and ethylene glycol (20.2 mg, 0.325 mmol) in dioxane (10 mL) were added Cs$_2$CO$_3$ (318 mg, 0.976 mmol) and Pd-PEPPSI-IHeptCl 3-chloropyridine (31.7 mg, 0.033 mmol) at room temperature. The resulting mixture was stirred at 90° C. under nitrogen atmosphere overnight. The resulting mixture was concentrated under vacuum. The residue was purified by reverse phase flash chromatography with 0-70% ACN in H$_2$O to afford 3-[5-(2-hydroxyethoxy)-6-methylpyrazin-2-yl]-1H-indole-7-carbonitrile (16.1 mg, 10.34%) as a white solid.

Example 341

3-[5-(2-hydroxypropoxy)-6-methylpyrazin-2-yl]-1H-indole-7-carbonitrile

To a mixture of 1-[(5-iodo-3-methylpyrazin-2-yl)oxy]propan-2-ol (60 mg, 0.204 mmol, 1.00 equiv) and 1-(tert-butoxycarbonyl)-7-cyanoindol-3-ylboronic acid (59 mg, 0.204 mmol) in dioxane (3 mL) and H$_2$O (0.6 mL) were added K$_2$CO$_3$ (85 mg, 0.612 mmol) and Pd(dppf)Cl$_2$ (30 mg, 0.041 mmol). The resulting mixture was stirred at 80° C. for 16 h under nitrogen atmosphere. The mixture was concentrated under vacuum. The residue was purified by C18 reverse phase column chromatography with 0-90% ACN in H$_2$O (NH$_4$HCO$_3$) to afford 3-[5-(2-hydroxypropoxy)-6-methylpyrazin-2-yl]-1H-indole-7-carbonitrile (14.0 mg, 21.65%) as a yellow solid.

Example 347

3-[5-(2-hydroxy-2-methylpropoxy)-6-methylpyrazin-2-yl]-1H-indazole-7-carbonitrile Step-1: To a mixture of 1-[(5-iodo-3-methylpyrazin-2-yl)oxy]-2-methylpropan-2-ol (130 mg, 0.422 mmol) and 7-cyano-1-(oxan-2-yl)indazol-3-ylboronic acid (228 mg, 0.844 mmol) in dioxane (5 mL) and H$_2$O (0.5 mL) was added K$_2$CO$_3$ (116 mg, 0.844 mmol) and Pd(dppf)Cl$_2$ (31 mg, 0.042 mmol). The resulting mixture was stirred at 100° C. for 3 h under nitrogen atmosphere. The resulting mixture was concentrated under vacuum. The residue was purified by flash column chromatography with 0-30% ethyl acetate in PE to afford 3-[6-methyl-5-[2-methyl-2-(oxan-2-yloxy)propoxy]pyrazin-2-yl]-1-(oxan-2-yl)indazole-7-carbonitrile (130 mg, 62.68%) as a white solid. MS m/z 492.2 [M+1]$^+$.

Step-2: To a mixture of 3-[6-methyl-5-[2-methyl-2-(oxan-2-yloxy)propoxy]pyrazin-2-yl]-1-(oxan-2-yl)indazole-7-carbonitrile (120 mg, 0.244 mmol) in DCM (3 mL) was added TFA (1 mL). The resulting mixture was stirred at room temperature for 2 h. The resulting mixture was concentrated under vacuum. The residue was basified to pH 8 with saturated NaHCO$_3$ (aq.). The resulting mixture was extracted with EtOAc. The combined organic layers were washed with brine, dried over anhydrous Na$_2$SO$_4$. After filtration, the filtrate was concentrated under vacuum. The residue was purified by Prep-HPLC [Column: XBridge Shield RP18 OBD Column, 19*250 mm, 10 um; Mobile Phase A: water (10 mmol/L NH$_4$HCO$_3$), Mobile Phase B: ACN; Flow rate: 60 mL/min; Gradient: 31 B to 44 B in 11 min; 220/254 nm] to afford 3-[5-(2-hydroxy-2-methyl-propoxy)-6-methylpyrazin-2-yl]-1H-indazole-7-carbonitrile (22.9 mg, 29.01%) as a white solid.

Example B: Biological Assay

LNCaP cells expressing ARR2PB-FireflyLuc and CMV-ReniliaLuc were treated with indicated concentrations of test compounds, enzalutamide (negative control), or DHT (positive control)+/−0.5 nM DHT for 48h at 37° C. Fluorescent signals were read with the ImageXpress Micro Confocal System. Remaining activity (antagonist mode) was calculated as % Remaining Activity=100×[(Reads$_{Sample}$−LC$_{ave}$)/(HC$_{ave}$)] where HC is cells treated with 0.5 nM DHT only and LC is cells treated with 10 uM enzalutamide 0.5 nM DHT. Activation (agonist mode) was calculated as % Activation=100×[(ReadSample−LC$_{ave}$)/(HC$_{ave}$−LC$_{ave}$)] where HC is cells treated with 1 uM DHT and LC is cells treated with DMSO. Dose response curves and IC$_{50}$ values were calculated using non-linear regression analysis in XLfit.

IC$_{50}$ values for the compounds provided herein are shown in Table 1 below. The designation "A" indicates an IC$_{50}$ value of >10 µM, "B" indicates an IC$_{50}$ value between 1 µM and 10 µM; "C" indicates an IC$_{50}$ value between 100 nM and 1 µM; and "D" indicates an IC$_{50}$ value of less than 100 nM.

TABLE 1

| No. | Structure | IC$_{50}$ (µM) | $^1$H NMR | LCMS |
|---|---|---|---|---|
| 1 | 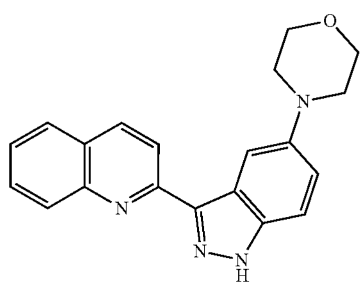 | B | $^1$H NMR (300 MHz, DMSO-d$_6$) δ 13.32 (bs, 1H), 8.40 (d, J = 8.7 Hz, 1H), 8.32-8.42 (m, 2H), 8.17 (d, J = 8.4 Hz, 1H), 7.98 (d, J = 8.1 Hz, 1H), 7.78-7.83 (m, 1H), 7.52-7.62 (m, 2H), 7.29-7.33 (m, 1H), 3.85 (m, 4H), 3.19-3.51 (m, 4H). | MS (ESI) calcd for C$_{20}$H$_{18}$N$_4$O [M + 1]$^+$, 331.1; found, 331.1. |
| 2 | 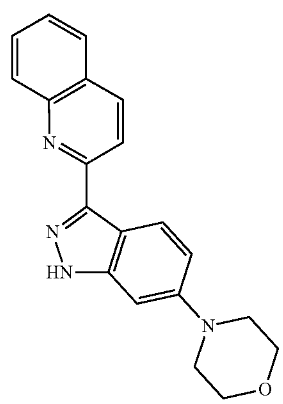 [SMILES: c1ccc2nc(-c3n[nH]c4cc(N5CCOCC5)ccc34)ccc2c1] | A | $^1$H NMR (300 MHz, DMSO-d$_6$) δ 13.12 (bs, 1H), 8.64 (d, J = 9.0 Hz, 1H), 8.38 (d, J = 8.7 Hz, 1H), 8.29 (d, J = 8.7 Hz, 1H), 8.16-8.08 (m, 1H), 7.95-7.96 (m, 1H), 7.75-7.78 (m, 1H), 7.57-7.60 (m, 1H), 7.15-7.12 (m, 1H), 6.85 (s, 1H), 3.77-3.80 (m, 4H), 3.18-3.21 (m, 4H). | MS (ESI) calcd for C$_{20}$H$_{18}$N$_4$O [M + 1]$^+$, 331.1; found, 331.1 |
| 3 | 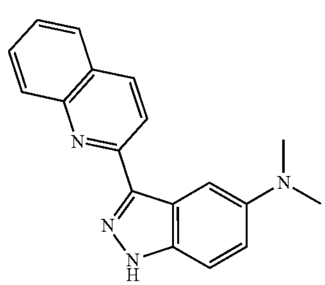 [SMILES: CN(C)c1ccc2[nH]nc(-c3ccc4ccccc4n3)c2c1] | A | $^1$H NMR (300 MHz, DMSO-d$_6$) δ 13.20 (bs, 1H), 8.41-8.24 (m, 2H), 8.18-8.04 (m, 2H), 7.99-7.91 (m, 1H), 7.81-7.75 (m, 1H), 7.60-7.55 (m, 1H), 7.47 (d, J = 9.0 Hz, 1H), 7.17 (dd, J = 9.0, 2.4 Hz, 1H), 2.99 (s, 6H). | MS (ESI) calcd for C$_{18}$H$_{16}$N$_4$ [M + 1]$^+$, 289.1; found, 289.1. |

TABLE 1-continued

| No. | Structure | IC$_{50}$ (μM) | $^1$H NMR | LCMS |
|---|---|---|---|---|
| 4 | 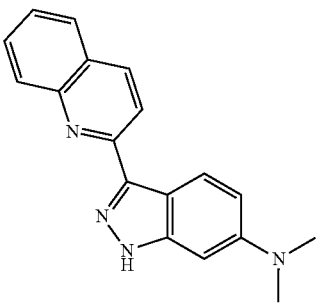 [SMILES: CN(C)c1ccc2c(-c3ccc4ccccc4n3)n[nH]c2c1] | A | $^1$H NMR (300 MHz, DMSO-d$_6$) δ 12.93 (bs, 1H), 8.60 (d, J = 9.0 Hz, 1H), 8.37 (d, J = 8.7 Hz, 1H), 8.28 (d, J = 8.7 Hz, 1H), 8.15-8.06 (m, 1H), 7.95 (dd, J = 8.1, 1.5 Hz, 1H), 7.76-7.77 (m, 1H), 7.54-7.59 (m, 1H), 6.92-6.96 (m, 1H), 6.59 (d, J = 2.1 Hz, 1H), 2.99 (s, 6H). | MS (ESI) calcd for C$_{18}$H$_{16}$N$_4$ [M + 1]$^+$, 289.1; found, 289.0. |
| 5 | 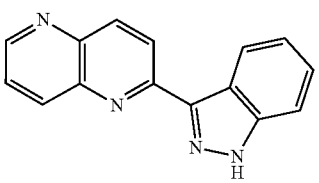 | D | $^1$H NMR (300 MHz, DMSO-d$_6$) δ 13.63 (bs, 1H), 9.02-8.94 (m, 1H), 8.88 (d, J = 8.1 Hz, 1H), 8.56-8.63 (m, 2H), 8.47-8.50 (m, 1H), 7.83 (dd, J = 8.4, 4.2 Hz, 1H), 7.66-7.69 (m, 1H), 7.46-7.51 (d, 1H), 7.34 (t, J = 7.5 Hz, 1H). | MS (ESI) calcd for C$_{15}$H$_{10}$N$_4$ [M + 1]$^+$, 247.0; found, 247.0. |
| 15 | 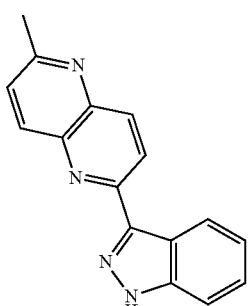 | | $^1$H NMR (300 MHz, DMSO-d$_6$) δ 8.86-8.81 (m, 1H), 8.53 (d, J = 8.7 Hz, 1H), 8.43 (d, J = 8.7 Hz, 1H), 8.35 (dd, J = 8.7, 0.9 Hz, 1H), 7.73-7.58 (m, 2H), 7.48-7.42 (m, 1H), 7.33-7.27 (m, 1H), 2.71 (s, 3H). | MS (ESI) calcd for C$_{16}$H$_{12}$N$_4$ [M + 1]$^+$, 261.1; found, 261.2. |
| 16 | 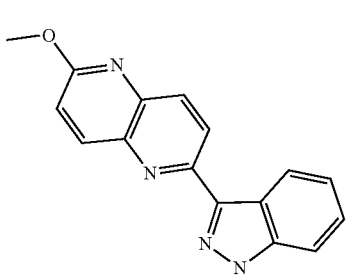 | A | $^1$H NMR (300 MHz, DMSO-d$_6$) δ 13.47 (bs, 1H), 8.81 (d, J = 8.1 Hz, 1H), 8.49-8.39 (m, 2H), 8.24 (d, J = 8.7 Hz, 1H), 7.62 (d, J = 8.4 Hz, 1H), 7.49-7.38 (m, 1H), 7.33-7.23 (m, 2H), 4.03 (s, 3H). | MS (ESI) calcd for (C$_{16}$H$_{12}$N$_4$O) [M + 1]$^+$, 277.1; found, 277.0. |
| 17 | 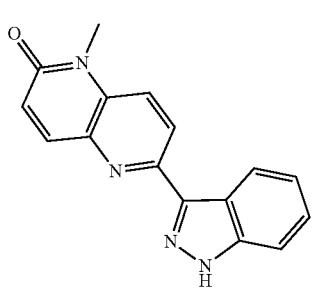 | B | $^1$H NMR (300 MHz, DMSO-d$_6$) δ 8.71 (d, J = 8.1 Hz, 1H), 8.38 (d, J = 9.0 Hz, 1H), 8.13-8.08 (m, 2H), 7.60 (d, J = 8.4 Hz, 1H), 7.48-7.36 (m, 1H), 7.28-7.22 (m, 1H), 6.91 (d, J = 9.6 Hz, 1H), 3.66 (s, 3H). | MS (ESI) calcd for (C$_{16}$H$_{12}$N$_4$O) [M + 1]$^+$, 277.1; found, 277.0. |

TABLE 1-continued

| No. | Structure | IC$_{50}$ (μM) | $^1$H NMR | LCMS |
|---|---|---|---|---|
| 6 | 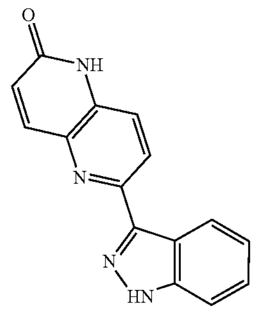 [SMILES: O=c1ccc2nc(-c3n[nH]c4ccccc34)ccc2[nH]1] | B | $^1$H NMR (300 MHz, DMSO-d$_6$) δ 13.36 (bs, 1H), 11.94 (bs, 1H), 8.69 (d, J = 8.1 Hz, 1H), 8.31 (d, J = 8.7 Hz, 1H), 8.10 (d, J = 9.9 Hz, 1H), 7.77 (d, J = 8.7 Hz, 1H), 7.58 (d, J = 8.4 Hz, 1H), 7.44-7.39 (m, 1H), 7.27-7.22 (m, 1H), 6.78 (d, J = 9.6 Hz, 1H). | MS (ESI) calcd for C$_{15}$H$_{10}$N$_4$O [M + 1]$^+$, 263.1; found, 263.2. |
| 7 | 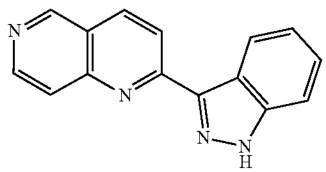 | C | $^1$H NMR (300 MHz, DMSO-d$_6$) δ 13.62 (s, 1H), 9.54 (s, 1H), 8.90 (d, J = 8.1 Hz, 1H), 8.63-8.56 (m, 2H), 8.51 (d, J = 8.7 Hz, 1H), 8.00-7.93 (m, 1H), 7.68 (d, J = 8.4 Hz, 1H), 7.66-7.47 (m, 1H), 7.39-7.34 (m, 1H). | MS (ESI) calcd for C$_{15}$H$_{10}$N$_4$ [M + 1]$^+$, 247.1; found, 247.1. |
| 18 | 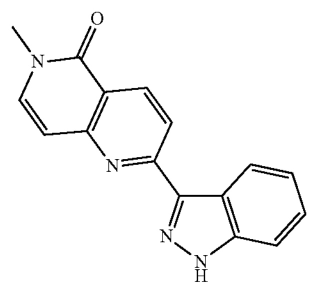 [SMILES: Cn1ccc2nc(-c3n[nH]c4ccccc34)ccc2c1=O] | B | $^1$H NMR (300 MHz, DMSO-d$_6$) δ 13.64 (bs, 1H), 8.76 (d, J = 8.1 Hz, 1H), 8.59 (d, J = 8.4 Hz, 1H), 8.29 (d, J = 8.4 Hz, 1H), 7.79 (d, J = 7.5 Hz, 1H), 7.64 (d, J = 8.1 Hz, 1H), 7.48-7.43 (m, 1H), 7.33-7.28 (m, 1H), 6.86 (d, J = 7.8 Hz, 1H), 3.55 (s, 3H). | MS (ESI) calcd for C$_{16}$H$_{12}$N$_4$O [M + 1]$^+$, 277.1; found, 277.2. |
| 19 | 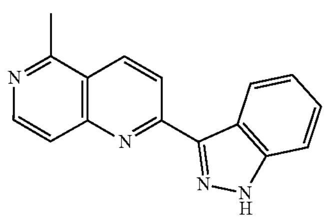 | D | $^1$H NMR (300 MHz, DMSO-d$_6$) δ 13.68 (bs, 1H), 8.86 (d, J = 8.1 Hz, 1H), 8.70 (d, J = 8.7 Hz, 1H), 8.60 (d, J = 6.6 Hz, 1H), 8.47 (d, J = 8.7 Hz, 1H), 7.88 (d, J = 6.0 Hz, 1H), 7.67 (d, J = 8.4 Hz, 1H), 7.51-7.48 (m, 1H), 7.46-7.32 (m, 1H), 2.93 (s, 3H). | MS (ESI) calcd for C$_{16}$H$_{12}$N$_4$ [M + 1]$^+$, 261.1; found, 261.1. |
| 12 | 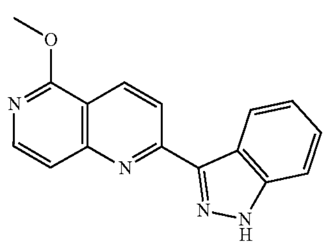 | D | $^1$H NMR (300 MHz, DMSO-d$_6$) δ 13.71 (bs, 1H), 8.83 (d, J = 8.4 Hz, 1H), 8.59 (d, J = 8.7 Hz, 1H), 8.43 (d, J = 8.7 Hz, 1H), 8.29-8.28 (m, 1H), 7.68-7.61 (m, 2H), 7.55-7.45 (m, 1H), 7.36-7.32 (m, 1H), 4.11 (s, 3H). | MS (ESI) calcd for C$_{16}$H$_{12}$N$_4$O [M + 1]$^+$, 277.1; found, 277.2. |
| 20 | 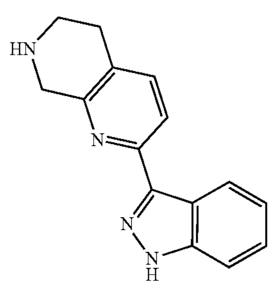 | A | $^1$H NMR (300 MHz, DMSO-d$_6$) δ 13.25 (bs, 1H), 8.58-8.55 (m, 1H), 7.91 (d, J = 8.1 Hz, 1H), 7.62-7.55 (m, 2H), 7.41-7.39 (m, 1H), 7.23-7.18 (m, 1H), 4.00 (s, 2H), 3.02-2.98 (m, 2H), 2.78-2.74 (m, 2H). | MS (ESI) calcd for C$_{15}$H$_{14}$N$_4$ [M + 1]$^+$, 251.1; found, 251.1. |

TABLE 1-continued

| No. | Structure | IC$_{50}$ (µM) | $^1$H NMR | LCMS |
|---|---|---|---|---|
| 21 | 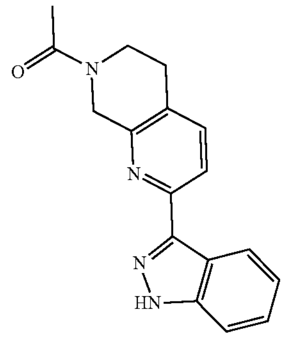 [SMILES: CC(=O)N1CCc2ccc(-c3n[nH]c4ccccc34)nc2C1] | A | $^1$H NMR (300 MHz, DMSO-d$_6$) δ 13.32 (bs, 1H), 8.61 (t, J = 7.2 Hz, 1H), 7.99 (d, J = 8.1 Hz, 1H), 7.69 (d, J = 8.1 Hz, 1H), 7.58 (d, J = 8.1 Hz, 1H), 7.46-7.35 (m, 1H), 7.26-7.21 (m, 1H), 4.83-4.78 (m, 2H), 3.76 (t, J = 5.7 Hz, 2H), 2.93-2.82 (m, 2H), 2.18 and 2.14 (s, 3H). | MS (ESI) calcd for C$_{17}$H$_{16}$N$_4$O [M + 1]$^+$, 293.1; found, 293.1. |
| 8 | 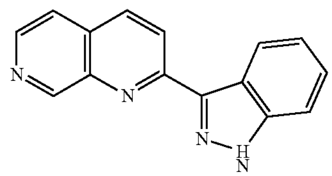 [SMILES: c1ccc2c(-c3ccc4ccncc4n3)n[nH]c2c1] | D | $^1$H NMR (300 MHz, DMSO-d$_6$) δ 13.63 (bs, 1H), 9.00-8.98 (m, 1H), 8.88 (d, J = 8.1 Hz, 1H), 8.63-8.50 (m, 2H), 8.47-8.41 (m, 1H), 7.86-7.81 (m, 1H), 7.67 (d, J = 8.4 Hz, 1H), 7.58-7.46 (m, 1H), 7.37-7.26 (m, 1H). | MS (ESI) calcd for C$_{15}$H$_{10}$N$_4$ [M + 1]$^+$, 247.1; found, 247.1. |
| 22 | 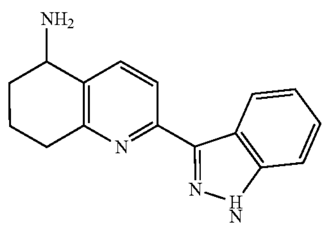 [SMILES: NC1CCCc2nc(-c3n[nH]c4ccccc34)ccc21] | A | $^1$H NMR (300 MHz, DMSO-d$_6$) δ 13.24 (bs, 1H), 8.60 (d, J = 8.1 Hz, 1H), 7.94 (s, 2H), 7.56 (d, J = 8.4 Hz, 1H), 7.44-7.35 (m, 1H), 7.20 (t, J = 7.5 Hz, 1H), 3.90-3.86 (m, 1H), 2.95-2.93 (m, 2H). 2.13-1.92 (m, 2H), 1.89-1.70 (m, 1H), 1.67-1.53 (m, 1H). | MS (ESI) calcd for C$_{16}$H$_{16}$N$_4$ [M + 1]$^+$, 265.1; found, 265.1. |
| 23 | 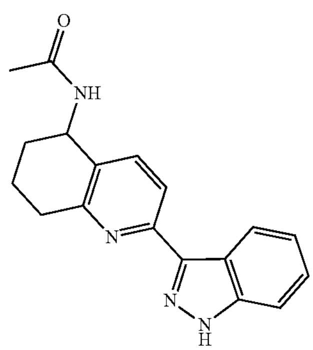 [SMILES: CC(=O)NC1CCCc2nc(-c3n[nH]c4ccccc34)ccc21] | A | $^1$H NMR (300 MHz, DMSO-d$_6$) δ 13.28 (bs, 1H), 8.59 (d, J = 8.1 Hz, 1H), 8.29 (d, J = 8.1 Hz, 1H), 8.96 (d, J = 8.7 Hz, 1H), 7.63-7.55 (m, 2H), 7.39 (t, J = 7.8 Hz, 1H), 7.21 (t, J = 7.8 Hz, 1H), 5.08-5.02 (m, 1H), 3.10-2.90 (m, 2H), 2.07-1.70 (m, 7H) | MS (ESI) calcd for C$_{18}$H$_{18}$N$_4$O [M + 1]$^+$, 307.1; found, 307.2. |
| 9 | 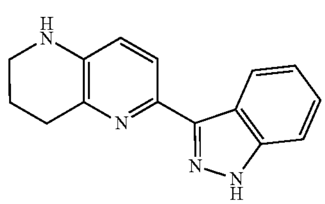 [SMILES: c1ccc2c(-c3ccc4c(n3)CCCN4)n[nH]c2c1] | C | $^1$H NMR (300 MHz, DMSO-d$_6$) δ 12.88 (bs, 1H), 8.55 (d, J = 8.1 Hz, 1H), 7.68 (d, J = 8.4 Hz, 1H), 7.49 (d, J = 8.4 Hz, 1H), 7.32 (t, J = 7.5 Hz, 1H), 7.11 (t, J = 7.5 Hz, 1H), 6.87 (d, J = 8.4 Hz, 1H), 6.00 (s, 1H), 3.16-3.14 (m, 2H), 2.91 (t, J = 6.3 Hz, 2H), 1.98-1.89 (m, 2H). | MS (ESI) calcd for C$_{15}$H$_{14}$N$_4$ [M + 1]$^+$, 251.1; found, 251.1. |
| 10 | 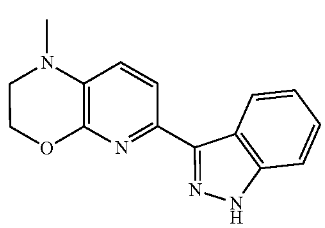 [SMILES: CN1CCOc2nc(-c3n[nH]c4ccccc34)ccc21] | A | $^1$H NMR (300 MHz, DMSO-d$_6$) δ 8.45 (d, J = 8.1 Hz, 1H), 7.62 (d, J = 8.1 Hz, 1H), 7.51 (d, J = 8.4 Hz, 1H), 7.37-7.32 (m, 1H), 7.17-7.10 (m, 2H), 4.41 (t, J = 4.5 Hz, 2H), 3.29 (t, J = 4.5 Hz, 2H), 2.87 (s, 3H). | MS (ESI) calcd for C$_{15}$H$_{14}$N$_4$O [M + 1]$^+$, 267.1; found, 267.1. |

TABLE 1-continued

| No. | Structure | IC$_{50}$ (μM) | $^1$H NMR | LCMS |
|---|---|---|---|---|
| 11 | 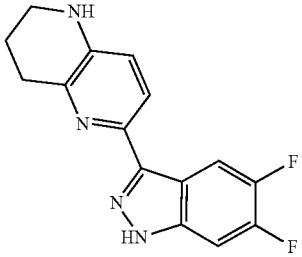 [SMILES: Fc1cc2[nH]nc(-c3ccc4c(n3)CCCN4)c2cc1F] | C | $^1$H NMR (300 MHz, DMSO-d$_6$) δ 13.11 (bs, 1H), 8.44-8.38 (m, 1H), 7.66 (d, J = 8.4 Hz, 1H), 7.59-7.53 (m, 1H), 6.87 (d, J = 8.4 Hz, 1H), 6.09 (s, 1H), 3.25-3.23 (m, 2H), 2.95-2.90 (m, 2H), 1.96-1.92 (m, 2H). | MS (ESI) calcd for C$_{15}$H$_{12}$F$_2$N$_4$ [M + 1]$^+$, 287.1; found, 287.1. |
| 24 | 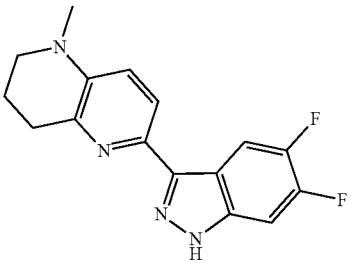 [SMILES: CN1CCCc2nc(-c3n[nH]c4cc(F)c(F)cc34)ccc21] | B | $^1$H NMR (300 MHz, Methanol-d$_4$) δ 8.34-8.28 (m, 1H), 7.75 (d, J = 8.7 Hz, 1H), 7.71-7.35 (m, 1H), 7.05 (d, J = 8.7 Hz, 1H), 3.36-3.29 (m, 2H), 3.06-3.02 (m, 2H), 2.97 (s, 3H), 2.18-2.05 (m, 2H). | MS (ESI) calcd for C$_{16}$H$_{14}$F$_2$N$_4$ [M + 1]$^+$, 301.1; found, 301.1 |
| 25 | 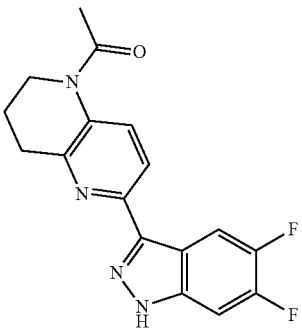 [SMILES: CC(=O)N1CCCc2nc(-c3n[nH]c4cc(F)c(F)cc34)ccc21] | C | $^1$H NMR (300 MHz, Methanol-d$_4$) δ 8.50-8.44 (m, 1H), 8.21-8.15 (m, 1H), 7.76 (d, J = 8.4 Hz, 1H), 6.90 (d, J = 8.4 Hz, 1H), 3.38-3.31 (m, 2H), 3.00 (s, 2H), 2.75 (s, 3H), 2.11-2.04 (m, 2H). | MS (ESI) calcd for C$_{17}$H$_{14}$F$_2$N$_4$O [M + 1]$^+$, 329.1; found, 329.1. |
| 13 | 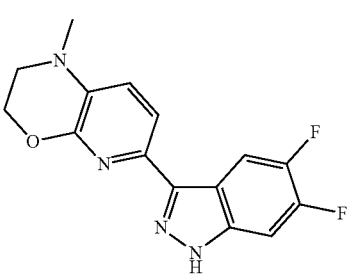 [SMILES: CN1CCOc2nc(-c3n[nH]c4cc(F)c(F)cc34)ccc21] | B | $^1$H NMR (300 MHz, DMSO-d$_6$) δ 13.22 (bs, 1H), 8.34 (dd, J = 10.5, 8.1 Hz, 1H), 7.64-7.56 (m, 2H), 7.14 (d, J = 8.1 Hz, 1H), 4.44 (t, J = 4.5 Hz, 2H), 3.34-3.31 (m, 2H), 2.90 (s, 3H). | MS (ESI) calcd for C$_{15}$H$_{12}$F$_2$N$_4$O [M + 1]$^+$, 303.1; found, 303.1. |
| 14 | 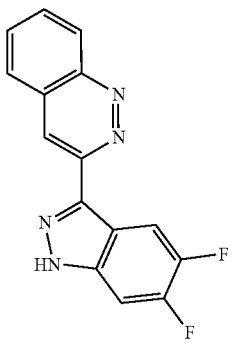 [SMILES: Fc1cc2[nH]nc(-c3cc4ccccc4nn3)c2cc1F] | A | $^1$H NMR (300 MHz, DMSO-d$_6$) δ 13.87 (bs, 1H), 8.89 (d, J = 1.2 Hz, 1H), 8.58-8.50 (m, 2H), 8.23 (d, J = 8.1 Hz, 1H), 7.98-7.81 (m, 2H), 7.81-7.75 (m, 1H). | MS (ESI) calcd for C$_{15}$H$_8$F$_2$N$_4$ [M + 1]$^+$, 283.1; found, 283.0. |

TABLE 1-continued

| No. | Structure | IC$_{50}$ (μM) | $^1$H NMR | LCMS |
|---|---|---|---|---|
| 26 | 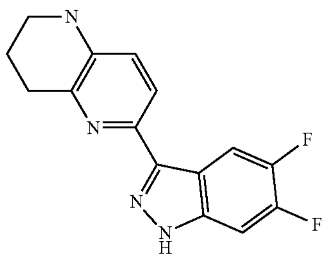 [SMILES: Fc1cc2[nH]nc(-c3ccc4c(n3)CCCN4)c2cc1F] | D | $^1$H NMR (300 MHz, DMSO-d$_6$) δ 13.81 (bs, 1H), 8.99-8.97 (m, 1H), 8.77-8.67 (m, 1H), 8.65 (d, J = 7.8 Hz, 1H), 8.57 (d, J = 9.0 Hz, 1H), 8.49 (d, J = 9.0 Hz, 1H), 7.85-7.73 (m, 2H). | MS (ESI) calcd for C$_{15}$H$_8$F$_2$N$_4$ [M + 1]$^+$ 283.1, found, 283.0. |
| 27 | 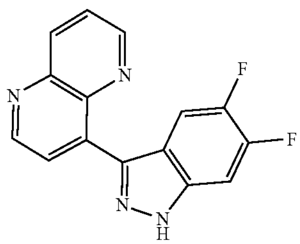 [SMILES: Fc1cc2[nH]nc(-c3ccnc4cccnc34)c2cc1F] | B | $^1$H NMR (300 MHz, DMSO-d$_6$) δ 13.80 (bs, 1H), 9.10 (d, J = 4.2 Hz, 1H), 9.04 (t, J = 2.7 Hz, 1H), 8.54 (dd, J = 8.4, 1.8 Hz, 1H), 8.05 (d, J = 1.5 Hz, 1H), 7.90-7.85 (m, 1H), 7.78-7.61 (m, 2H). | MS (ESI) calcd for C$_{15}$H$_8$F$_2$N$_4$ [M + 1]$^+$ 283.1, found, 283.1. |
| 28 | 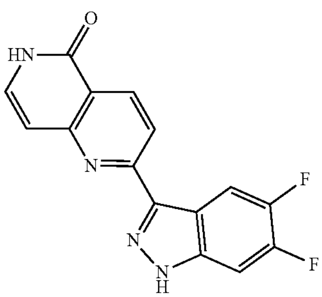 [SMILES: O=c1[nH]ccc2nc(-c3n[nH]c4cc(F)c(F)cc34)ccc12] | C | $^1$H NMR (400 MHz, DMSO-d$_6$) δ 11.47-11.37 (bs, 1H), 8.57-8.46 (m, 2H), 8.26 (d, J = 8.4 Hz, 1H), 7.68-7.63 (m, 1H), 7.44 (d, J = 7.2 Hz, 1H), 6.79 (d, J = 7.2 Hz, 1H). | MS (ESI) calcd for C$_{15}$H$_8$F$_2$N$_4$O [M + 1]$^+$, 299.1; found, 299.1. |
| 29 | 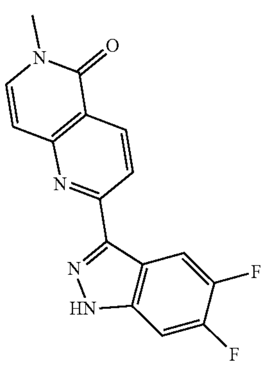 [SMILES: Cn1ccc2nc(-c3n[nH]c4cc(F)c(F)cc34)ccc2c1=O] | A | $^1$H NMR (300 MHz, DMSO-d$_6$) δ 13.86 (bs, 1H), 8.65-8.57 (m, 2H), 8.24 (d, J = 8.4 Hz, 1H), 7.82-7.71 (m, 2H), 6.93 (d, J = 7.5 Hz, 1H), 3.55 (s, 3H). | MS (ESI) calcd for C$_{16}$H$_{10}$F$_2$N$_4$O [M + 1]$^+$, 313.1; found, 313.1. |
| 30 | 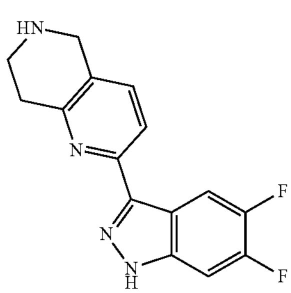 [SMILES: Fc1cc2[nH]nc(-c3ccc4c(n3)CCNC4)c2cc1F] | A | $^1$H NMR (300 MHz, DMSO-d$_6$) δ 8.42 (dd, J = 10.5, 8.1 Hz, 1H), 7.89 (d, J = 8.1 Hz, 1H), 7.69-7.62 (m, 1H), 7.57 (d, J = 8.1 Hz, 1H), 3.87 (s, 2H), 3.09-2.98 (t, J = 6.0 Hz, 2H), 2.93 (d, J = 6.0 Hz, 2H). | MS (ESI) calcd for C$_{15}$H$_{12}$F$_2$N$_4$ [M + 1]$^+$, 287.1; found, 287.1. |

TABLE 1-continued

| No. | Structure | IC$_{50}$ (μM) | $^1$H NMR | LCMS |
|---|---|---|---|---|
| 31 | 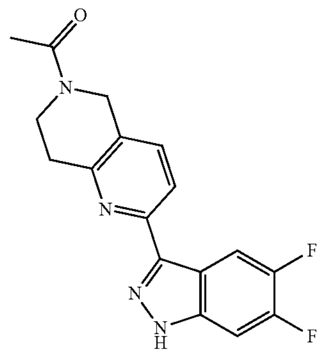 [SMILES: CC(=O)N1CCc2nc(-c3n[nH]c4cc(F)c(F)cc34)ccc2C1] | A | $^1$H NMR (300 MHz, DMSO-d$_6$) δ 8.48-8.42 (m, 1H), 8.00 (t, J = 8.1 Hz, 1H), 7.73-7.64 (m, 2H), 4.74-4.68 (m, 2H), 3.84 (t, J = 6.0 Hz, 2H), 3.13 (t, J = 6.0 Hz, 1H), 3.02 (d, J = 6.0 Hz, 1H), 2.17 and 2.14 (s, 3H). | MS (ESI) calcd for C$_{17}$H$_{14}$F$_2$N$_4$O [M + 1]$^+$, 329.1; found, 329.2. |
| 32 | 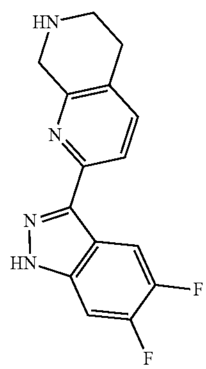 [SMILES: Fc1cc2[nH]nc(-c3ccc4c(n3)CNCC4)c2cc1F] | A | $^1$H NMR (300 MHz, DMSO-d$_6$) δ 8.44-3.78 (m, 1H), 7.89 (d, J = 8.1 Hz, 1H), 7.66-7.56 (m, 2H), 4.00 (s, 2H), 3.01-2.97 (m, 2H), 2.77 (t, J = 5.7 Hz, 2H). | MS (ESI) calcd for C$_{15}$H$_{12}$F$_2$N$_4$ [M + 1]$^+$, 287.1; found, 287.2. |
| 33 | 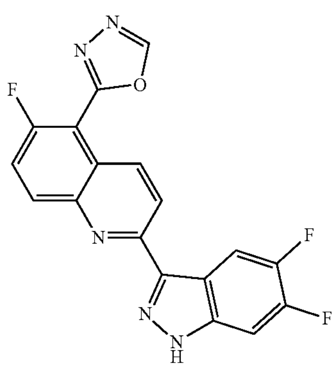 [SMILES: Fc1cc2[nH]nc(-c3ccc4c(-c5nnco5)c(F)ccc4n3)c2cc1F] | C | $^1$H NMR (300 MHz, DMSO-d$_6$) δ 9.63 (s, 1H), 8.94 (d, J = 9.0 Hz, 1H), 8.73 (dd, J = 10.5, 8.1 Hz, 1H), 8.61 (dd, J = 9.3, 5.1 Hz, 1H), 8.47 (d, J = 9.0 Hz, 1H), 7.95 (t, J = 9.6 Hz, 1H), 7.73 (dd, J = 10.5, 6.6 Hz, 1H). | MS (ESI) calcd for C$_{18}$H$_8$F$_3$N$_5$O [M + 1]$^+$, 368.1; found, 368.1. |
| 34 | 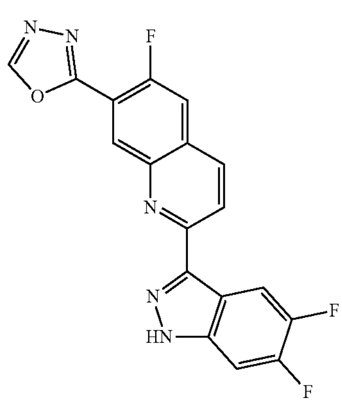 [SMILES: Fc1cc2[nH]nc(-c3ccc4cc(F)c(-c5nnco5)cc4n3)c2cc1F] | A | $^1$H NMR (300 MHz, DMSO-d$_6$) δ 13.83 (bs, 1H), 9.57 (s, 1H), 8.98 (d, J = 6.9 Hz, 1H), 8.84 (dd, J = 10.5, 8.1 Hz, 1H), 8.53 (d, J = 8.7 Hz, 1H), 8.47 (d, J = 8.7 Hz, 1H), 8.13 (d, J = 11.1 Hz, 1H), 7.76 (dd, J = 10.5, 6.9 Hz, 1H). | MS (ESI) calcd for C$_{18}$H$_8$F$_3$N$_5$O [M + 1]$^+$, 368.1; found, 368.1. |

TABLE 1-continued

| No. | Structure | IC$_{50}$ (μM) | $^1$H NMR | LCMS |
|---|---|---|---|---|
| 35 | 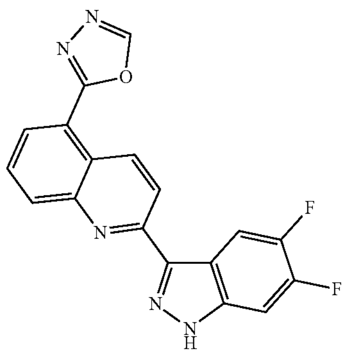 [SMILES: Fc1cc2[nH]nc(-c3ccc4c(-c5nnco5)cccc4n3)c2cc1F] | D | $^1$H NMR (400 MHz, DMSO-d$_6$) δ 9.56 (d, J = 8.8 Hz, 1H), 9.52 (s, 1H), 8.78-8.75 (m, 1H), 8.54-8.52 (m, 2H), 8.31-8.28 (m, 1H), 8.02-8.00 (m, 1H), 7.80-7.70 (m, 1H). | MS (ESI) calcd for C$_{18}$H$_9$F$_2$N$_5$O [M + 1]$^+$, 350.1; found, 350.2. |
| 36 | 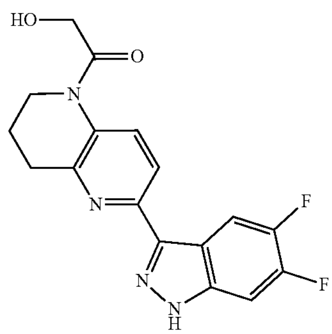 [SMILES: O=C(CO)N1CCCc2nc(-c3n[nH]c4cc(F)c(F)cc34)ccc21] | B | $^1$H NMR (300 MHz, DMSO-d$_6$) δ 13.52 (bs, 1H), 8.48-8.42 (m, 1H), 8.30 (d, J = 9.0 Hz, 1H), 7.95 (d, J = 8.7 Hz, 1H), 7.69-7.64 (m, 1 H), 4.92 (t, J = 5.7 Hz, 1H), 4.31 (d, J = 6.0 Hz, 2H), 3.74-3.70 (m, 2H), 3.08-3.03 (m, 2H), 2.07-1.99 (m, 2H). | MS (ESI) calcd for C$_{17}$H$_{14}$F$_2$N$_4$O$_2$ [M + 1]$^+$, 345.2; found, 345.2 |
| 37 | 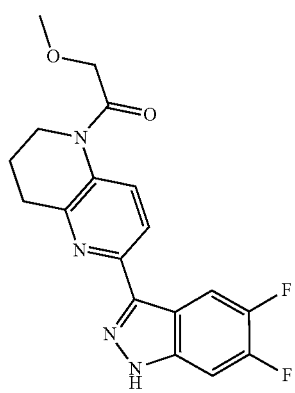 [SMILES: COCC(=O)N1CCCc2nc(-c3n[nH]c4cc(F)c(F)cc34)ccc21] | A | $^1$H NMR (300 MHz, Methanol-d$_4$) δ 8.45-8.38 (m, 1H), 8.23-8.19 (m, 1H), 7.96 (d, J = 8.7 Hz, 1H), 7.44-7.39 (m, 1H), 4.36 (s, 2H), 3.85-3.79 (m, 2H), 3.41 (s, 3H), 3.14-3.06 (m, 2H), 2.19-2.03 (m, 2H). | MS (ESI) calcd for C$_{18}$H$_{16}$F$_2$N$_4$O$_2$ [M + 1]$^+$, 359.1; found, 359.0. |
| 38 | 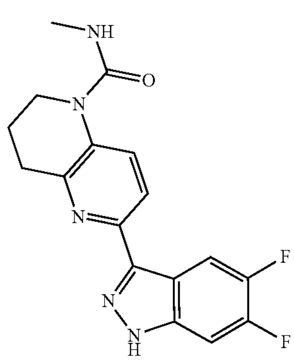 [SMILES: CNC(=O)N1CCCc2nc(-c3n[nH]c4cc(F)c(F)cc34)ccc21] | B | $^1$H NMR (300 MHz, Methanol-d$_4$) δ 8.42-8.38 (m, 1H), 7.99-7.76 (m, 2H), 7.50-7.37 (m, 1H), 3.71 (t, J = 6.0 Hz, 2H), 3.05 (t, J = 6.0 Hz, 2H), 2.81 (s, 3H), 2.13-2.05 (m, 2H). | MS (ESI) calcd for C$_{17}$H$_{15}$F$_2$N$_5$O [M + 1]$^+$, 344.1; found, 344.2. |

TABLE 1-continued

| No. | Structure | IC$_{50}$ (μM) | $^1$H NMR | LCMS |
|---|---|---|---|---|
| 39 | 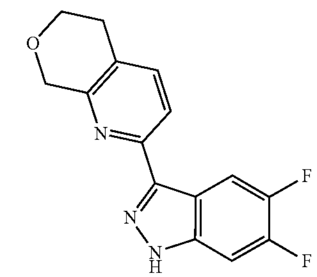 [SMILES: Fc1cc2[nH]nc(-c3ccc4c(n3)COCC4)c2cc1F] | B | $^1$H NMR (300 MHz, DMSO-d$_6$) δ 13.53 (bs, 1H), 8.42-8.36 (m, 1H), 7.96 (d, J = 8.1 Hz, 1H), 7.69-7.63 (m, 2H), 4.82 (s, 2H), 3.95 (t, J = 5.7 Hz, 2H), 2.80 (t, J = 6.0 Hz, 2H). | MS (ESI) calcd for C$_{15}$H$_{11}$F$_2$N$_3$O [M + 1]$^+$, 288.1; found, 288.0. |
| 40 | 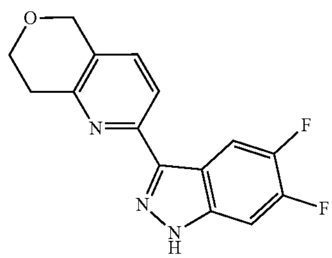 [SMILES: Fc1cc2[nH]nc(-c3ccc4c(n3)CCOC4)c2cc1F] | B | $^1$H NMR (300 MHz, DMSO-d$_6$) δ 13.52 (bs, 1H), 8.49-8.42 (m, 1H), 7.95 (d, J = 8.4 Hz, 1H), 7.70-7.64 (m, 1H), 7.58 (d, J = 7.8 Hz, 1H), 4.75 (s, 2H), 4.06-4.02 (m, 2H), 3.06-3.02 (m, 2H). | MS (ESI) calcd for C$_{15}$H$_{11}$F$_2$N$_3$O [M + 1]$^+$, 288.1; found, 288.1. |
| 41 | 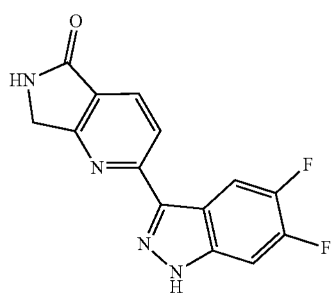 [SMILES: O=C1NCc2nc(-c3n[nH]c4cc(F)c(F)cc34)ccc21] | B | $^1$H NMR (300 MHz, Methanol-d$_4$) δ 8.53-8.50 (m, 1H), 8.35 (d, J = 8.1 Hz, 1H), 8.20 (d, J = 8.1 Hz, 1H), 7.50-7.44 (m, 1H), 4.64 (s, 2H). | MS (ESI) calcd for C$_{14}$H$_8$F$_2$N$_4$O [M + 1]$^+$, 287.1; found, 287.0. |
| 42 | 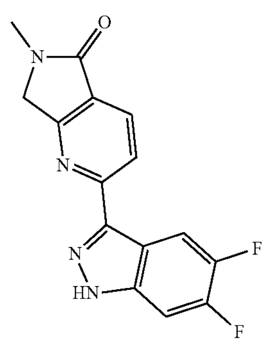 [SMILES: CN1Cc2nc(-c3n[nH]c4cc(F)c(F)cc34)ccc2C1=O] | B | $^1$H NMR (300 MHz, DMSO-d$_6$) δ 13.79 (bs, 1H), 8.48-8.45 (m, 1H), 8.24 (d, J = 8.1 Hz, 1H), 8.13 (d, J = 8.1 Hz, 1H), 7.77-7.71 (m, 1H), 4.64 (s, 2H), , 3.12 (s, 3H). | MS (ESI) calcd for C$_{15}$H$_{10}$F$_2$N$_4$O [M + 1]$^+$, 301.1; found, 301.2. |
| 43 | 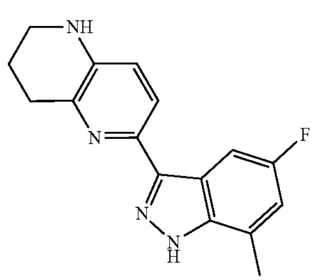 [SMILES: Cc1cc(F)cc2c(-c3ccc4c(n3)CCCN4)n[nH]c12] | C | $^1$H NMR (300 MHz, DMSO-d$_6$) δ 13.10 (bs, 1H), 8.08-7.99 (m, 1H), 7.68 (d, J = 8.4 Hz, 1H), 7.09-7.05 (m, 1H), 6.87 (d, J = 8.4 Hz, 1H), 6.03 (s, 1H), 3.30-3.23 (m, 2H), 2.94-2.89 (m, 2H), 2.53 (s, 3H), 1.98-1.93 (m, 2H). | MS (ESI) calcd for C$_{16}$H$_{15}$FN$_4$ [M + 1]$^+$, 283.1; found, 283.3. |

TABLE 1-continued

| No. | Structure | IC$_{50}$ (μM) | $^1$H NMR | LCMS |
|---|---|---|---|---|
| 44 | 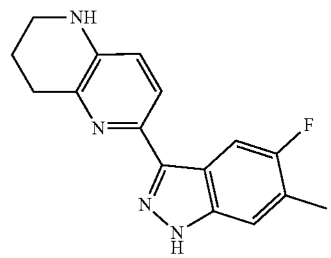 [SMILES: Cc1cc2[nH]nc(-c3ccc4c(n3)CCCN4)c2cc1F] | C | $^1$H NMR (300 MHz, DMSO-d$_6$) δ 12.88 (bs, 1H), 8.15 (d, J = 10.8 Hz, 1H), 7.65 (d, J = 8.4 Hz, 1H), 7.38 (d, J = 6.3 Hz, 1H), 6.86 (d, J = 8.4 Hz, 1H), 6.03 (s, 1H), 3.25-3.22 (m, 2H), 2.92 (t, J = 6.3 Hz, 2H), 2.36 (s, 3H), 1.99-1.89 (m, 2H). | MS (ESI) calcd for C$_{16}$H$_{15}$FN$_4$ [M + 1]$^+$, 283.1; found, 283.3. |
| 45 | 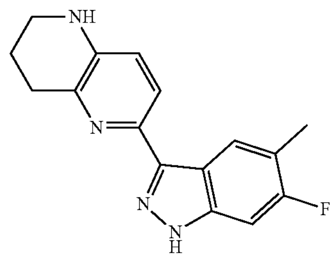 [SMILES: Cc1cc2c(-c3ccc4c(n3)CCCN4)n[nH]c2cc1F] | C | $^1$H NMR (400 MHz, DMSO-d$_6$) δ 12.83 (bs, 1H), 8.41 (d, J = 8.0 Hz, 1H), 7.65 (d, J = 8.4 Hz, 1H), 7.22 (d, J = 10.8 Hz, 1H), 6.86 (d, J = 8.4 Hz, 1H), 6.03 (s, 1H), 3.31-3.24 (m, 2H), 2.94-2.91 (m, 2H), 2.33 (s, 3H), 1.96-1.93 (m, 2H). | MS (ESI) calcd for C$_{16}$H$_{15}$FN$_4$ [M + 1]$^+$, 283.1; found, 283.1. |
| 46 | 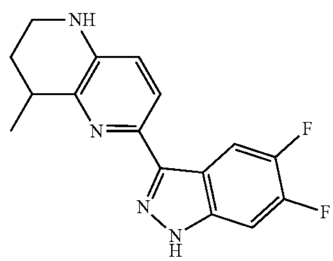 [SMILES: CC1CCNc2ccc(-c3n[nH]c4cc(F)c(F)cc34)nc21] | D | $^1$H NMR (300 MHz, DMSO-d$_6$) δ 13.12 (bs, 1H), 8.45-8.42 (m, 1H), 7.66 (d, J = 8.4 Hz, 1H), 7.58-7.54 (m, 1H), 6.86 (d, J = 8.4 Hz, 1H), 6.12 (s, 1H), 3.28-3.19 (m, 2H), 3.07-2.95 (m, 1H), 2.09-1.95 (m, 1H), 1.71-1.64 (m, 1H), 1.41 (d, J = 6.9 Hz, 3H). | MS (ESI) calcd for C$_{16}$H$_{14}$F$_2$N$_4$ [M + 1]$^+$, 301.1; found, 301.2. |
| 47 | 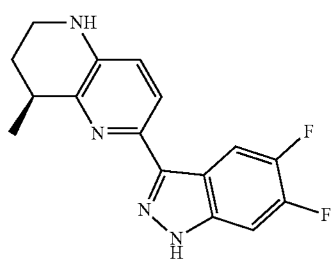 [SMILES: C[C@H]1CCNc2ccc(-c3n[nH]c4cc(F)c(F)cc34)nc21] | C | $^1$H NMR (400 MHz, Methanol-d$_4$) δ 8.40 (t, J = 9.6 Hz, 1H), 7.68 (d, J = 8.4 Hz, 1H), 7.38-7.33 (m, 1H), 6.94 (d, J = 8.4 Hz, 1H), 3.34-3.30 (m, 2H), 3.16-3.08 (m, 1H), 2.13-2.08 (m, 1H), 1.84-1.76 (m, 1H), 1.52 (d, J = 7.2 Hz, 3H). | MS (ESI) calcd for C$_{16}$H$_{14}$F$_2$N$_4$ [M + 1]$^+$, 301.1; found, 301.2. |
| 48 | 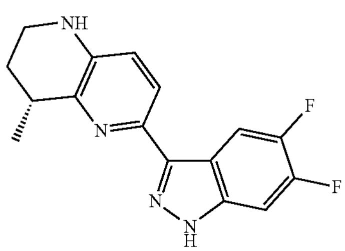 [SMILES: C[C@@H]1CCNc2ccc(-c3n[nH]c4cc(F)c(F)cc34)nc21] | D | $^1$H NMR (400 MHz, Methanol-d$_4$) δ 8.40 (t, J = 9.6 Hz, 1H), 7.68 (d, J = 8.4 Hz, 1H), 7.38-7.33 (m, 1H), 6.94 (d, J = 8.4 Hz, 1H), 3.34-3.30 (m, 2H), 3.16-3.08 (m, 1H), 2.13-2.08 (m, 1H), 1.84-1.76 (m, 1H), 1.52 (d, J = 7.2 Hz, 3H). | MS (ESI) calcd for C$_{16}$H$_{14}$F$_2$N$_4$ [M + 1]$^+$, 301.1; found, 301.2. |

TABLE 1-continued

| No. | Structure | IC$_{50}$ (μM) | $^1$H NMR | LCMS |
|---|---|---|---|---|
| 49 | 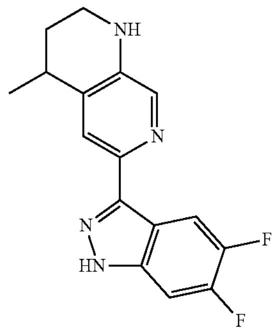 [SMILES: CC1CCNc2cnc(-c3n[nH]c4cc(F)c(F)cc34)cc21] | B | $^1$H NMR (300 MHz, Methanol-d$_4$) δ 8.22-8.16 (m, 1H), 7.92 (s, 1H), 7.73 (s, 1H), 7.40-7.34 (m, 1H), 3.44-3.32 (m, 2H), 3.08-2.94 (m, 1H), 2.09-1.93 (m, 1H), 1.76-1.66 (m, 1H), 1.39 (d, J = 7.2 Hz, 3H). | MS (ESI) calcd for C$_{16}$H$_{14}$F$_2$N$_4$ [M + 1]$^+$, 301.1; found, 301.1. |
| 50 | 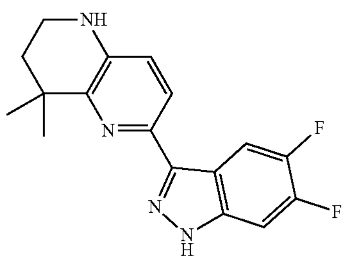 [SMILES: CC1(C)CCNc2ccc(-c3n[nH]c4cc(F)c(F)cc34)nc21] | C | $^1$H NMR (300 MHz, DMSO-d$_6$) δ 13.12 (bs, 1H), 8.43 (dd, J = 10.8, 8.1 Hz, 1H), 7.66 (d, J = 8.4 Hz, 1H), 7.58 (dd, J = 10.8, 8.1 Hz, 1H), 6.88 (d, J = 8.4 Hz, 1H), 6.17 (bs, 1H), 3.26 (t, J = 5.7 Hz, 2H), 1.79 (t, J = 5.7 Hz, 2H), 1.38 (s, 6H). | MS (ESI) calcd for C$_{17}$H$_{16}$F$_2$N$_4$ [M + 1]$^+$, 315.1; found, 315.0. |
| 51 | 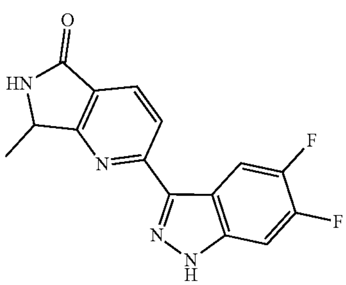 [SMILES: CC1NC(=O)c2ccc(-c3n[nH]c4cc(F)c(F)cc34)nc21] | C | $^1$H NMR (400 MHz, DMSO-d$_6$) δ 13.90 (bs, 1H), 8.90 (s, 1H), 8.50-8.45 (m, 1H), 8.26 (d, J = 8.4 Hz, 1H), 8.14 (d, J = 8.0 Hz, 1H), 7.77-7.26 (m, 1H), 4.80-4.75 (m, 1H), 1.53 (d, J = 6.8 Hz, 3H). | MS (ESI) calcd for C$_{15}$H$_{10}$F$_2$N$_4$O [M + 1]$^+$, 301.0; found, 301.0. |
| 52 | 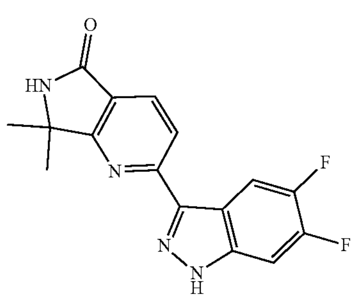 [SMILES: CC1(C)NC(=O)c2ccc(-c3n[nH]c4cc(F)c(F)cc34)nc21] | C | $^1$H NMR (300 MHz, DMSO-d$_6$) δ 13.79 (bs, 1H), 8.90 (s, 1H), 8.49-8.43 (m, 1H), 8.24 (d, J = 8.1 Hz, 1H), 8.11 (d, J = 8.1 Hz, 1H), 7.78-7.74 (m, 1H), 1.57 (s, 6H). | MS (ESI) calcd for C$_{16}$H$_{12}$F$_2$N$_4$O [M + 1]$^+$, 315.0; found, 315.0. |
| 53 | 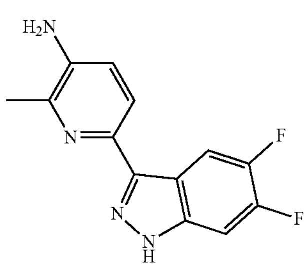 [SMILES: Cc1nc(-c2n[nH]c3cc(F)c(F)cc23)ccc1N] | B | $^1$H NMR (300 MHz, DMSO-d$_6$) δ 13.13 (bs, 1H), 8.48-8.42 (m, 1H), 7.71 (d, J = 8.1 Hz, 1H), 7.57-7.54 (m, 1H), 7.01 (d, J = 8.4 Hz, 1H), 5.28 (s, 2H), 2.41 (s, 3H). | MS (ESI) calcd for C$_{13}$H$_{10}$F$_2$N$_4$ [M + 1]$^+$, 261.1; found, 261.2. |

TABLE 1-continued

| No. | Structure | IC$_{50}$ (μM) | $^1$H NMR | LCMS |
|---|---|---|---|---|
| 54 | 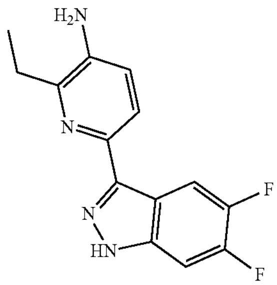 [SMILES: CCc1nc(-c2n[nH]c3cc(F)c(F)cc23)ccc1N] | C | $^1$H NMR (400 MHz, DMSO-d$_6$) δ 13.14 (bs, 1H), 8.51-8.46 (m, 1H), 7.72 (d, J = 8.0 Hz, 1H), 7.59-7.56 (m, 1H), 7.02 (d, J = 8.4 Hz, 1H), 5.30 (s, 2H), 2.76-2.67 (q, J = 7.2 Hz, 2H), 1.36 (t, J = 7.2 Hz, 3H). | MS (ESI) calcd for C$_{14}$H$_{12}$F$_2$N$_4$ [M + 1]$^+$, 275.2; found, 275.2. |
| 55 | 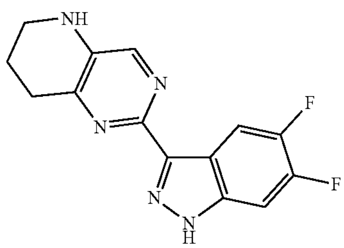 [SMILES: Fc1cc2[nH]nc(-c3ncc4c(n3)CCCN4)c2cc1F] | A | $^1$H NMR (300 MHz, DMSO-d$_6$) δ 13.35 (bs, 1H), 8.37-8.30 (m, 1H), 8.04 (s, 1H), 7.63-7.57 (m, 1H), 6.34 (s, 1H), 3.31-3.26 (m, 2H), 2.91-2.86 (m, 2H), 1.98-1.92 (m, 2H). | MS (ESI) calcd for C$_{14}$H$_{11}$F$_2$N$_5$ [M + 1]$^+$, 288.1; found, 288.1. |
| 56 | 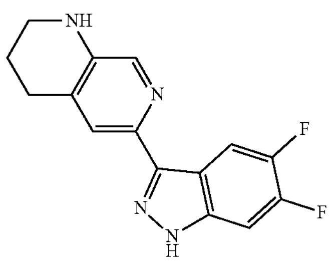 [SMILES: Fc1cc2[nH]nc(-c3cc4c(cn3)NCCC4)c2cc1F] | B | $^1$H NMR (300 MHz, DMSO-d$_6$) δ 13.13 (bs, 1H), 8.37-8.31 (m, 1H), 7.88 (s, 1H), 7.63 (s, 1H), 7.59-7.53 (m, 1H), 6.19 (s, 1H), 3.28-3.21 (m, 2H), 2.74 (t, J = 6.0 Hz, 2H), 1.84-1.80 (m, 2H). | MS (ESI) calcd for C$_{15}$H$_{12}$F$_2$N$_4$ [M + 1]$^+$, 287.1; found, 287.1. |
| 57 | 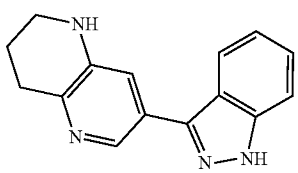 [SMILES: c1ccc2c(-c3cnc4c(c3)NCCC4)n[nH]c2c1] | A | $^1$H NMR (400 MHz, DMSO-d$_6$) δ 13.22 (bs, 1H), 8.25 (d, J = 1.6 Hz, 1H), 7.99 (d, J = 8.4 Hz, 1H), 7.58 (d, J = 8.4 Hz, 1H), 7.42-7.38 (m, 2H), 7.22-7.18 (m, 1H), 6.02 (s, 1H), 3.25-3.21 (m, 2H), 2.83 (t, J = 6.4 Hz, 2H), 1.96-1.92 (m, 2H). | MS (ESI) calcd for C$_{15}$H$_{14}$N$_4$ [M + 1]$^+$, 251.1; found, 251.1. |
| 58 | 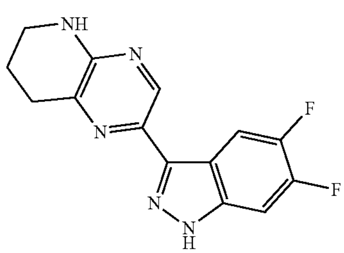 [SMILES: Fc1cc2[nH]nc(-c3cnc4c(n3)CCCN4)c2cc1F] | A | $^1$H NMR (300 MHz, DMSO-d$_6$) δ 13.49 (bs, 1H), 8.55-8.48 (m, 1H), 8.33 (s, 1H), 7.67-7.61 (m, 1H), 7.24 (s, 1H), 3.35-3.30 (m, 2H), 2.83 (t, J = 6.0 Hz, 2H), 1.95-1.91 (m, 2H). | MS (ESI) calcd for C$_{14}$H$_{11}$F$_2$N$_5$ [M + 1]$^+$, 288.1; found, 288.2. |
| 59 | 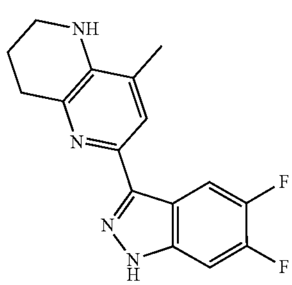 [SMILES: Cc1cc(-c2n[nH]c3cc(F)c(F)cc23)nc2c1NCCC2] | C | $^1$H NMR (300 MHz, DMSO-d$_6$) δ 8.44-8.37 (m, 1H), 7.62-7.49 (m, 2H), 3.32-3.28 (m, 2H), 2.96-2.89 (m, 2H), 2.09 (s, 3H), 1.96-1.93 (m, 2H). | MS (ESI) calcd for C$_{16}$H$_{14}$F$_2$N$_4$ [M + 1]$^+$, 301.1; found, 301.2. |

TABLE 1-continued

| No. | Structure | IC$_{50}$ (μM) | $^1$H NMR | LCMS |
|---|---|---|---|---|
| 60 | 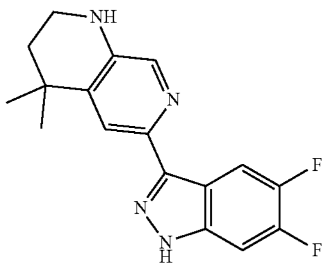 [SMILES: CC1(C)CCNc2cnc(-c3n[nH]c4cc(F)c(F)cc34)cc21] | A | $^1$H NMR (300 MHz, DMSO-d$_6$) δ 13.12 (bs, 1H), 8.36-8.30 (m, 1H), 7.91 (s, 1H), 7.82 (s, 1H), 7.56 (dd, J = 10.5, 6.9 Hz, 1H), 6.31-3.27 (m, 1H), 1.67-1.63 (m, 2H), 1.28 (s, 6H). | MS (ESI) calcd for C$_{17}$H$_{16}$F$_2$N$_4$ [M + 1]$^+$, 315.1; found, 315.1. |
| 118 | 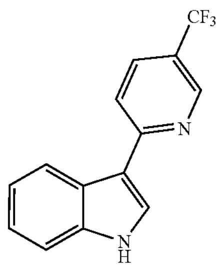 [SMILES: FC(F)(F)c1ccc(-c2c[nH]c3ccccc23)nc1] | C | $^1$H NMR (300 MHz, DMSO-d$_6$) δ 11.76 (bs, 1H), 8.92 (d, J = 0.9 Hz, 1H), 8.50-8.47 (m, 1H), 8.32 (s, 1H), 8.11-8.06 (m, 2H), 7.49-7.46 (m, 1H), 7.24-7.13 (m, 2H). | MS (ESI) calcd for C$_{14}$H$_9$F$_3$N$_2$ [M + 1]$^+$, 263.1; found, 263.1. |
| 119 | 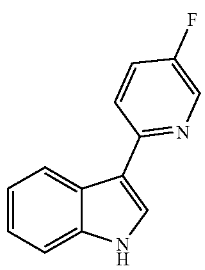 [SMILES: Fc1ccc(-c2c[nH]c3ccccc23)nc1] | C | $^1$H NMR (400 MHz, DMSO-d$_6$) δ 11.52 (bs, 1H), 8.57 (d, J = 2.8 Hz, 1H), 8.40 (d, J = 7.6 Hz, 1H), 8.08 (d, J = 2.4 Hz, 1H), 7.93-7.89 (m, 1H), 7.73-7.67 (m, 1H), 7.46-7.43 (m, 1H), 7.19-7.09 (m, 2H). | MS (ESI) calcd for C$_{13}$H$_9$FN$_2$ [M + 1]$^+$, 213.0; found, 213.0. |
| 120 | 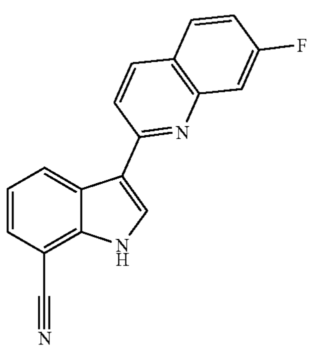 [SMILES: N#Cc1cccc2c(-c3ccc4ccc(F)cc4n3)c[nH]c12] | D | $^1$H NMR (400 MHz, DMSO-d$_6$) δ 12.58 (bs, 1H), 9.26 (d, J = 8.0 Hz, 1H), 8.57 (d, J = 2.4 Hz, 1H), 8.35 (d, J = 8.8 Hz, 1H), 8.13 (d, J = 8.8 Hz, 1H), 8.01-7.98 (m, 1H), 7.84-7.79 (m, 1H), 7.77-7.72 (m, 1H), 7.50-7.34 (m, 2H). | MS (ESI) calcd for C$_{18}$H$_{10}$FN$_3$ [M + 1]$^+$, 288.1; found, 288.1. |
| 61 | 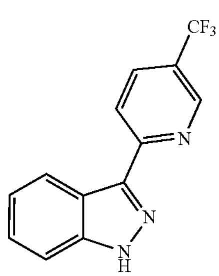 [SMILES: FC(F)(F)c1ccc(-c2n[nH]c3ccccc23)nc1] | B | $^1$H NMR (400 MHz, DMSO-d$_6$) δ 13.66 (bs, 1H), 9.10 (s, 1H), 8.58 (d, J = 8.4 Hz, 1H), 8.38 (d, J = 8.4 Hz, 1H), 8.30-8.26 (m, 1H), 7.65 (d, J = 8.4 Hz, 1H), 7.45 (t, J = 7.2 Hz, 1H), 7.29 (t, J = 7.2 Hz, 1H). | MS (ESI) calcd for C$_{13}$H$_8$F$_3$N$_3$ [M + 1]$^+$, 264.1; found, 264.0. |

TABLE 1-continued

| No. | Structure | IC$_{50}$ (μM) | $^1$H NMR | LCMS |
|---|---|---|---|---|
| 62 | 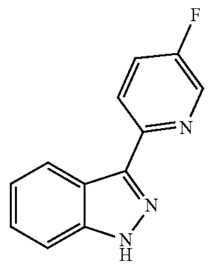 [SMILES: Fc1ccc(-c2n[nH]c3ccccc23)nc1] | B | $^1$H NMR (400 MHz, DMSO-d$_6$) δ 13.38 (bs, 1H), 8.72 (s, 1H), 8.51 (d, J = 8.0 Hz, 1H), 8.25-8.22 (m, 1H), 7.86-7.81 (m, 1H), 7.60 (d, J = 8.4 Hz, 1H) 7.44-7.40 (m, 1H), 7.25-7.21 (m, 1H). | MS (ESI) calcd for C$_{12}$H$_8$FN$_3$ [M + 1]$^+$, 214.1; found, 214.0. |
| 63 | 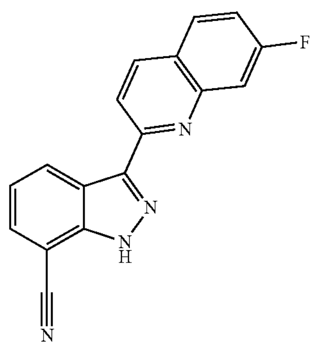 [SMILES: N#Cc1cccc2c(-c3ccc4ccc(F)cc4n3)n[nH]c12] | D | $^1$H NMR (400 MHz, DMSO-d$_6$) δ 14.50 (bs, 1H), 9.24 (d, J = 8.4 Hz, 1H), 8.53 (d, J = 8.8 Hz, 1H), 8.36 (d, J = 8.4 Hz, 1H), 8.15-8.11 (m, 1H), 8.05 (d, J = 7.2 Hz, 1H), 8.00-7.95 (m, 1H), 7.60-7.55 (m, 1H), 7.51-7.46 (m, 1H). | MS (ESI) calcd for C$_{17}$H$_9$FN$_4$ [M + 1]$^+$, 289.1; found, 289.1. |
| 121 | 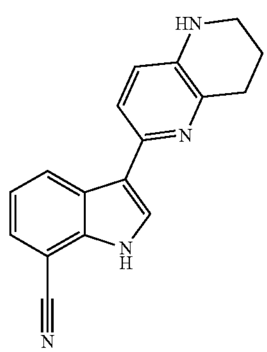 [SMILES: N#Cc1cccc2c(-c3ccc4c(n3)CCCN4)c[nH]c12] | D | $^1$H NMR (400 MHz, DMSO-d$_6$) δ 12.04 (bs, 1H), 8.81 (d, J = 8.0 Hz, 1H), 7.90 (d, J = 2.4 Hz, 1H), 7.62-7.60 (m, 1H), 7.43 (d, J = 8.4 Hz, 1H), 7.24-7.19 (m, 1H), 6.83 (d, J = 8.4 Hz, 1H), 5.77 (s, 1H), 3.25-3.18 (m, 2H), 2.88 (t, J = 6.4 Hz, 2H), 1.97-1.92 (m, 2H). | MS (ESI) calcd for C$_{17}$H$_{14}$N$_4$ [M + 1]$^+$, 275.1; found, 275.1. |
| 64 | 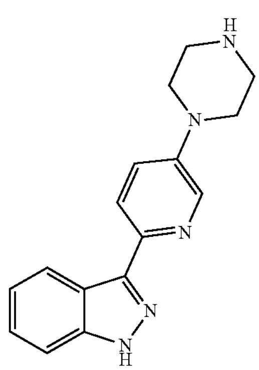 | A | $^1$H NMR (400 MHz, DMSO-d$_6$) δ 13.10 (bs, 1H), 8.53 (d, J = 8.0 Hz, 1H), 8.40 (d, J = 3.2 Hz, 1H), 7.99 (d, J = 8.8 Hz, 1H), 7.54 (d, J = 8.4 Hz, 1H), 7.46-7.42 (m, 1H), 7.39-7.35 (m, 1H), 7.19-7.15 (m, 1H), 3.20-3.17 (m, 4H), 2.89-2.86 (m, 4H). | MS (ESI) calcd for C$_{16}$H$_{17}$N$_5$ [M + 1]$^+$, 280.1; found, 280.2. |

TABLE 1-continued

| No. | Structure | IC$_{50}$ (μM) | $^1$H NMR | LCMS |
|---|---|---|---|---|
| 65 | 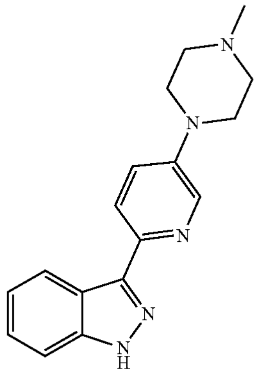 [SMILES: CN1CCN(c2ccc(-c3n[nH]c4ccccc34)nc2)CC1] | A | $^1$H NMR (400 MHz, Methanol-d$_4$) δ 8.45-8.43 (m, 2H), 8.04-8.03 (m, 1H), 7.58-7.53 (m, 2H), 7.45-7.41 (m, 1H), 7.222 (t, J = 7.6 Hz, 1H), 3.59-3.52 (m, 4H), 3.34-3.19 (m, 4H), 2.78 (s, 3H). | MS (ESI) calcd for C$_{17}$H$_{19}$N$_5$ [M + 1]$^+$, 294.1; found, 294.1. |
| 66 | 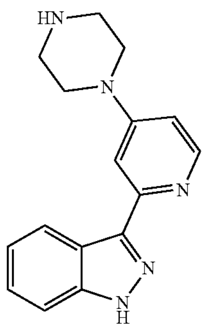 [SMILES: c1ccc2c(-c3cc(N4CCNCC4)ccn3)n[nH]c2c1] | A | $^1$H NMR (400 MHz, DMSO-d$_6$) δ 13.23 (bs, 1H), 8.55 (d, J = 8.4 Hz, 1H), 8.31 (d, J = 6.0 Hz, 1H), 7.57-7.54 (m, 2H), 7.40-7.35 (m, 1H), 7.19-7.15 (m, 1H), 6.85-6.82 (m, 1H), 3.33 (m, 1H), 3.31-3.27 (m, 4H), 2.85-2.81 (m, 4H). | MS (ESI) calcd for C$_{16}$H$_{17}$N$_5$ [M + 1]$^+$, 280.0; found, 280.2. |
| 67 | 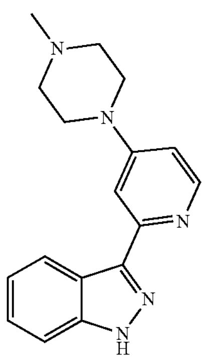 [SMILES: CN1CCN(c2ccnc(-c3n[nH]c4ccccc34)c2)CC1] | A | $^1$H NMR (400 MHz, DMSO-d$_6$) δ 13.24 (bs, 1H), 8.56 (d, J = 8.4 Hz, 1H), 8.33 (d, J = 6.4 Hz, 1H), 7.60-7.55 (m, 2H), 7.40-7.36 (m, 1H), 7.20-7.16 (m, 1H), 6.87-6.85 (m, 1H), 3.40-3.34 (m, 4H), 2.53-2.46 (m, 4H), 2.24 (s, 3H). | MS (ESI) calcd for C$_{17}$H$_{19}$N$_5$ [M + 1]$^+$, 294.2; found, 294.3. |
| 68 | 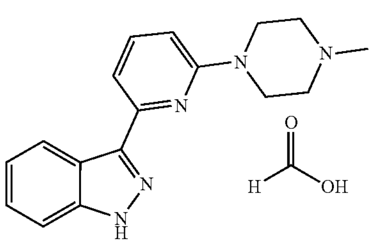 | A | $^1$H NMR (400 MHz, DMSO-d$_6$) δ 13.27 (bs, 1H), 8.47 (d, J = 8.4 Hz, 1H), 8.14 (s, 1H), 7.69-7.64 (m, 1H), 7.57 (d, J = 8.4 Hz, 1H), 7.51 (d, J = 8.0 Hz, 1H), 7.41-7.37 (m, 1H), 7.24-7.20 (m, 1H), 6.85 (d, J = 8.4 Hz, 1H), 3.70 (m, 4H), 2.76 (m, 4H), 2.44 (s, 3H). | MS (ESI) calcd for [C$_{17}$H$_{19}$N$_5$]$^+$ [M + 1]$^+$, 294.1; found, 294.1. |
| 69 | 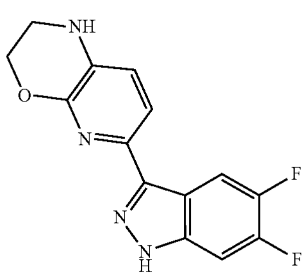 [SMILES: Fc1cc2[nH]nc(-c3ccc4c(n3)OCCN4)c2cc1F] | A | $^1$H NMR (400 MHz, DMSO-d6) δ 13.19 (bs, 1H), 8.35 (m, 1H), 7.85-7.29 (m, 2H), 7.01 (d, J = 8.4 Hz, 1H), 6.29 (s, 1H), 4.66-4.33 (m, 2H), 3.32-3.30 (m, 2H)). | MS (ESI) calcd for C$_{14}$H$_{10}$F$_2$N$_4$O [M + 1]$^+$, 289.1; found, 289.1. |

TABLE 1-continued

| No. | Structure | IC$_{50}$ (μM) | $^1$H NMR | LCMS |
|---|---|---|---|---|
| 70 | 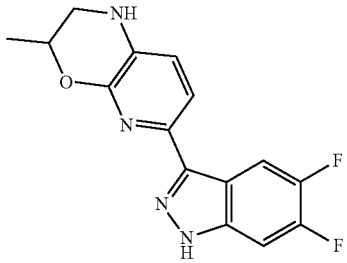 [SMILES: CC1CNc2ccc(-c3n[nH]c4cc(F)c(F)cc34)nc2O1] | A | $^1$H NMR (400 MHz, DMSO-d$_6$) δ 13.19 (bs, 1H), 8.38-8.33 (m, 1H), 7.60-7.54 (m, 2H), 7.01 (d, J = 8.0 Hz, 1H), 6.29 (s, 1H), 4.37-4.33 (m, 1H), 3.40-3.37 (m, 1H), 3.03-2.98 (m, 1H), 1.39 (d, J = 6.4 Hz, 3H). | MS (ESI) calcd for C$_{15}$H$_{12}$F$_2$N$_4$O [M + 1]$^+$, 303.1; found, 303.0. |
| 71 | 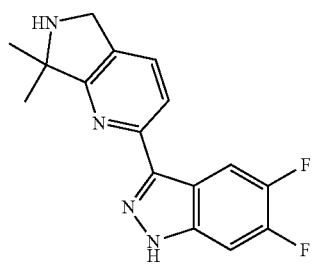 [SMILES: CC1(C)NCc2ccc(-c3n[nH]c4cc(F)c(F)cc34)nc21] | A | $^1$H NMR (400 MHz, Methanol-d$_4$) δ 8.50-8.45 (m, 1H), 8.01 (d, J = 8.0 Hz, 1H), 7.75 (d, J = 8.0 Hz, 1H), 7.46-7.42 (m, 1H), 4.21 (s, 2H), 1.57 (s, 6H). | MS (ESI) calcd for C$_{16}$H$_{14}$F$_2$N$_4$ [M + 1]$^+$, 301.1; found, 301.0. |
| 72 | 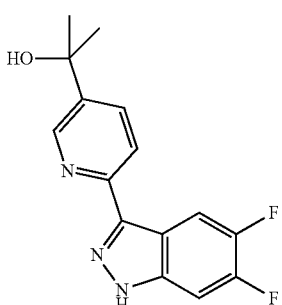 | A | $^1$H NMR (400 MHz, DMSO-d$_6$) δ 13.58 (bs, 1H), 8.83 (s, 1H), 8.45-8.41 (m, 1H), 8.12 (d, J = 8.4 Hz, 1H), 8.02-7.99 (m, 1H), 7.71-7.67 (m, 1H), 1.52 (s, 6H). | MS (ESI) calcd for C$_{15}$H$_{13}$F$_2$N$_3$O [M + 1]$^+$, 290.1; found, 290.1. |
| 73 | 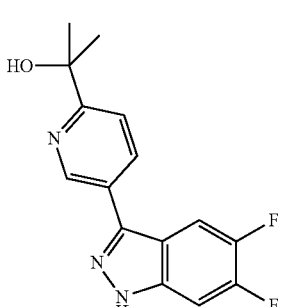 | A | $^1$H NMR (400 MHz, DMSO-d$_6$) δ 13.56 (bs, 1H), 9.08 (d, J = 2.0 Hz, 1H), 8.34-8.32 (m, 1H), 8.20-8.26 (m, 1H), 7.79 (m, J = 8.0 Hz, 1H), 7.71-7.67 (m, 1H), 5.31 (s, 1H), 1.50 (s, 6H). | MS (ESI) calcd for C$_{15}$H$_{13}$F$_2$N$_3$O [M + 1]$^+$, 290.1; found, 290.1. |
| 74 | 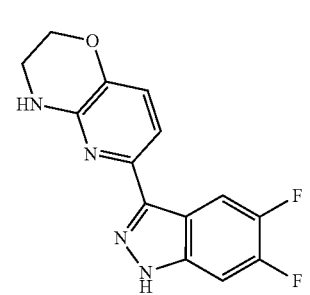 | B | $^1$H NMR (400 MHz, DMSO-d$_6$) δ 13.24 (bs, 1H), 8.63-8.58 (m, 1H), 7.61-7.57 (m, 1H), 7.28 (d, J = 8.0 Hz, 1H), 7.05-7.03 ($^m$, 2H), 4.18 (t, J = 4.4 Hz, 2H), 3.49-3.48 (m, 2H). | MS (ESI) calcd for C$_{14}$H$_{10}$F$_2$N$_4$O [M + 1]$^+$, 289.1; found, 289.1. |

TABLE 1-continued

| No. | Structure | IC$_{50}$ (μM) | $^1$H NMR | LCMS |
|---|---|---|---|---|
| 75 | 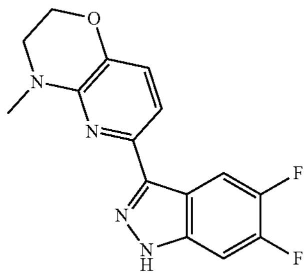 [SMILES: CN1CCOc2ccc(-c3n[nH]c4cc(F)c(F)cc34)nc21] | B | $^1$H NMR (400 MHz, DMSO-d$_6$) δ 13.29 (bs, 1H), 8.42-8.33 (m, 1H), 7.67-7.58 (m, 1H), 7.34 (d, J = 8.0 Hz, 1H), 7.05 (d, J = 8.0 Hz, 1H), 4.32-4.25 (m, 2H), 3.56-3.49 (m, 2H), 3.21 (s, 3H). | MS (ESI) calcd for C$_{15}$H$_{12}$F$_2$N$_4$O [M + 1]$^+$, 303.1; found, 303.1. |
| 76 | 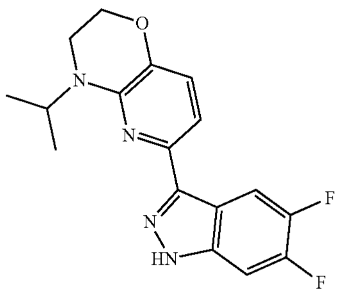 [SMILES: CC(C)N1CCOc2ccc(-c3n[nH]c4cc(F)c(F)cc34)nc21] | B | $^1$H NMR (400 MHz, DMSO-d$_6$) δ 13.29 (bs, 1H), 8.30-8.21 (m, 1H), 7.67-7.58 (m, 1H), 7.29 (d, J = 8.0 Hz, 1H), 7.06 (d, J = 8.0 Hz, 1H), 5.13-5.02 (m, 1H), 4.26-4.19 (m, 2H), 3.48-3.42 (m, 2H), 1.26 (d, J = 6.8 Hz, 6H). | MS (ESI) calcd for C$_{17}$H$_{16}$F$_2$N$_4$O [M + 1]$^+$, 331.1; found, 331.1. |
| 77 | 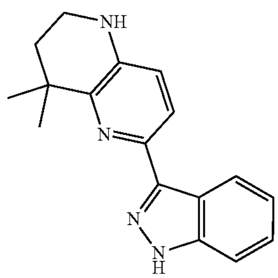 [SMILES: CC1(C)CCNc2ccc(-c3n[nH]c4ccccc34)nc21] | C | $^1$H NMR (400 MHz, DMSO-d6) δ 12.89 (bs, 1H), 8.61 (d, J = 8.0 Hz, 1H), 7.68 (d, J = 8.4 Hz, 1H), 7.51 (d, J = 8.4 Hz, 1H), 7.35 (m, 1H), 7.26-7.14 (m, 1H), 6.89 (d, J = 8.4 Hz, 1H), 6.09 (s, 1H), 3.25-3.24 (m, 2H), 1.80 (t, J = 5.6 Hz, 2H), 1.40 (s, 6H). | MS (ESI) calcd for C$_{17}$H$_{18}$N$_4$ [M + 1]$^+$, 279.1; found, 279.2. |
| 78 | 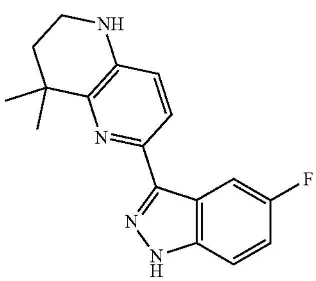 [SMILES: CC1(C)CCNc2ccc(-c3n[nH]c4ccc(F)cc34)nc21] | C | $^1$H NMR (400 MHz, DMSO-d6) δ 13.03 (bs, 1H), 8.27-8.24 (m, 1H), 7.67 (d, J = 8.4 Hz, 1H), 7.61-7.55 (m, 1H), 7.29-7.23 (m, 1H), 6.90 (d, J = 8.4 Hz, 1H), 6.12 (s, 1H), 3.32-3.26 (m, 2H), 1.93-1.79 (m, 2H), 1.39 (s, 6H). | MS (ESI) calcd for C$_{17}$H$_{17}$FN$_4$ [M + 1]$^+$, 297.1; found, 297.1. |
| 79 | 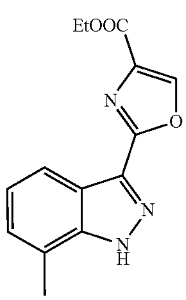 [SMILES: CCOC(=O)c1coc(-c2n[nH]c3c(C)cccc23)n1] | A | $^1$H NMR (400 MHz, DMSO-d$_6$) δ 13.95 (bs, 1H), 8.98 (s, 1H), 8.05-8.03 (m, 1H), 7.26-7.22 (m, 2H), 4.35 (q, J = 7.2 Hz, 2H), 2.58 (m, 3H), 1.34 (t, J = 7.2 Hz, 3H). | MS (ESI) calcd for C$_{14}$H$_{13}$N$_3$O$_3$ [M + 1]$^+$, 272.1; found, 272.1. |

TABLE 1-continued

| No. | Structure | IC$_{50}$ (μM) | $^1$H NMR | LCMS |
|---|---|---|---|---|
| 80 | 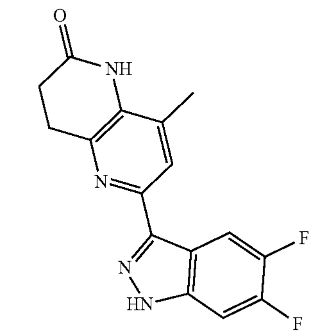 [SMILES: Cc1cc(-c2n[nH]c3cc(F)c(F)cc23)nc2c1NC(=O)CC2] | B | $^1$H NMR (400 MHz, DMSO-d$_6$) δ 13.44 (bs, 1H), 9.81 (s, 1H), 8.48-8.46 (m, 1H), 7.82 (s, 1H), 7.67-7.61 (m, 1H), 3.18 (t, J = 7.6 Hz, 2H), 2.70-2.61 (t, J = 7.6 Hz, 2H), 2.32 (s, 3H). | MS (ESI) calcd for C$_{16}$H$_{12}$F$_2$N$_4$O [M + 1]$^+$, 315.1; found, 315.1. |
| 122 | 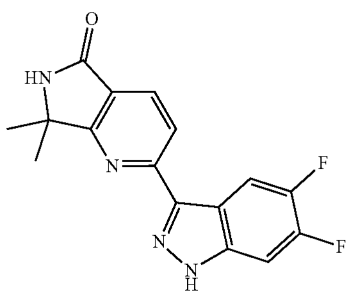 [SMILES: CC1(C)NC(=O)c2ccc(-c3n[nH]c4cc(F)c(F)cc34)nc21] | C | $^1$H NMR (400 MHz, DMSO-d$_6$) δ 11.88 (bs, 1H), 8.71 (s, 1H), 8.51-8.46 (m 1H), 8.39 (d, J = 2.8 Hz, 1H), 7.94 (s, 2H), 7.52-7.48 (m, 1H), 1.55 (s, 6H). | MS (ESI) calcd for C$_{17}$H$_{13}$F$_2$N$_3$O [M + 1]$^+$, 314.1; found, 314.0. |
| 81 | 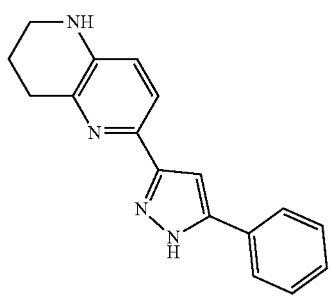 [SMILES: c1ccc(-c2cc(-c3ccc4c(n3)CCCN4)n[nH]2)cc1] | A | $^1$H NMR (400 MHz, DMSO-d$_6$) δ 13.00 (bs, 1H), 7.84-7.80 (m, 2H), 7.45-7.40 (m, 3H), 7.31 (d, J = 7.6 Hz, 1H), 6.99 (s, 1H), 6.84 (d, J = 8.4 Hz, 1H), 6.09 (s, 1H), 3.22-3.16 (m, 2H), 2.85 (t, J = 6.4 Hz, 2H), 1.95-1.89 (m, 2H). | MS (ESI) calcd for C$_{17}$H$_{16}$N$_4$ [M + 1]$^+$, 277.1; found, 277.1. |
| 82 | 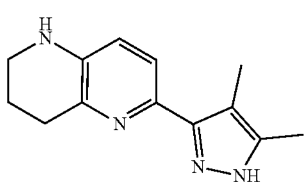 [SMILES: Cc1[nH]nc(-c2ccc3c(n2)CCCN3)c1C] | A | $^1$H NMR (400 MHz, DMSO-d$_6$) δ 12.23 (bs, 1H), 7.37-7.20 (br, 1H), 6.80 (d, J = 7.6 Hz, 1H), 5.99-5.80 (bs, 1H), 3.22-3.19 (m, 2H), 2.82-2.53 (m, 2H), 2.16 (s, 3H), 2.11 (s, 3H), 1.93-1.87 (m, 2H). | MS (ESI) calcd for C$_{13}$H$_{16}$N$_4$ [M + 1]$^+$, 229.1; found, 229.1. |
| 83 | 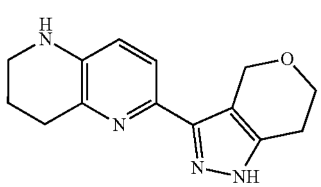 [SMILES: c1cc2c(nc1-c1n[nH]c3c1COCC3)CCCN2] | A | $^1$H NMR (400 MHz, DMSO-d$_6$) δ 12.73 (bs, 1H), 7.33 (d, J = 8.4 Hz, 1H), 6.88 (d, J = 8.0 Hz, 1H), 6.16-6.09 (br, 1H), 4.81 (s, 2H), 3.84-3.37 (m, 2H), 3.36-3.17 (m, 2H), 2.84-2.80 (m, 2H), 2.70-2.68 (m, 2H), 1.92-1.88 (m, 2H). | MS (ESI) calcd for C$_{14}$H$_{16}$N$_4$O [M + 1]$^+$, 257.1; found, 257.1. |

TABLE 1-continued

| No. | Structure | IC$_{50}$ (μM) | $^1$H NMR | LCMS |
|---|---|---|---|---|
| 84 | 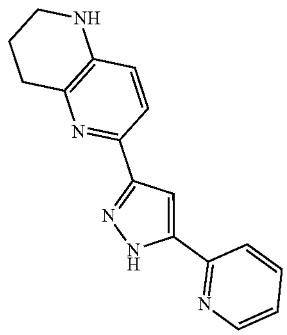 [SMILES: c1ccc(-c2cc(-c3ccc4c(n3)CCCN4)n[nH]2)nc1] | A | $^1$H NMR (400 MHz, DMSO-d$_6$) δ 8.59 (s, 1H), 7.96 (d, J = 8.0 Hz, 1H), 7.88-7.80 (m, 1H), 7.51-7.41 (m, 1H), 7.35-7.26 (m, 1H), 7.17-7.07 (m, 1H), 6.85 (d, J = 8.2 Hz, 1H), 6.09 (br, 1H), 3.26-3.19 (m, 2H), 2.91-2.80 (m, 2H), 1.99-1.85 (m, 2H). | MS (ESI) calcd for C$_{16}$H$_{15}$N$_5$ [M + 1]$^+$, 278.1; found, 278.1. |
| 85 | 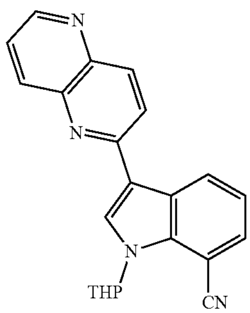 | A | $^1$H NMR (400 MHz, DMSO-d$_6$) δ 9.30 (d, J = 7.2 Hz, 1H), 9.04 (s, 1H), 8.65-8.55 (m, 3H), 8.15 (d, J = 6.8 Hz, 1H), 7.89-7.86 (m, 1H), 7.61-7.57 (m, 1H), 6.23 (d, J = 8.4 Hz, 1H), 3.98-3.96 (m, 1H), 3.88-3.84 (m 1H), 2.64-2.59 (m, 1H), 2.30-2.27 (m, 1H), 2.18-2.15 (m, 1H), 1.81-1.80 (m, 1H), 1.69-1.64 (m, 2H). | MS (ESI) calcd for C$_{21}$H$_{17}$N$_5$O [M + 1]$^+$, 356.1; found, 356.1. |
| 86 | 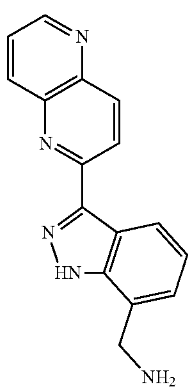 [SMILES: NCc1cccc2c(-c3ccc4ncccc4n3)n[nH]c12] | C | $^1$H NMR (400 MHz, DMSO-d$_6$) δ 8.97-8.95 (m, 1H), 8.74 (d, J = 8.0 Hz, 1H), 8.62-8.56 (m, 2H), 8.48 (d, J = 9.2 Hz, 1H), 7.85-7.81 (m, 1H), 7.45 (d, J = 6.4 Hz, 1H), 7.33-7.29 (m, 1H), 4.11 (s, 2 H). | MS (ESI) calcd for C$_{16}$H$_{13}$N$_5$ [M + 1]$^+$, 276.1; found, 276.1. |
| 87 | 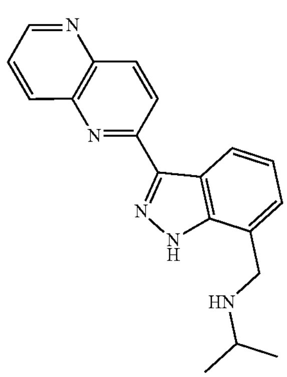 [SMILES: CC(C)NCc1cccc2c(-c3ccc4ncccc4n3)n[nH]c12] | B | $^1$H NMR (400 MHz, DMSO-d$_6$) δ 8.99-8.98-8.97 (m, 1H), 8.74 (d, J = 8.4 Hz, 1H), 8.64-8.56 (m, 2H), 8.49 (m, J = 8.0 Hz, 1H), 7.85-7.81 (m, 1H), 7.44 (d, J = 6.8 Hz, 1H), 7.31-7.27 (m, 1H), 4.12 (s, 2H), 2.81-2.76 (m, 1H), 1.06 (d, J = 6.0 Hz, 6H). | MS (ESI) calcd for C$_{19}$H$_{19}$N$_5$ [M + 1]$^+$, 318.1; found, 318.1. |

TABLE 1-continued

| No. | Structure | IC$_{50}$ (μM) | $^1$H NMR | LCMS |
|---|---|---|---|---|
| 123 | 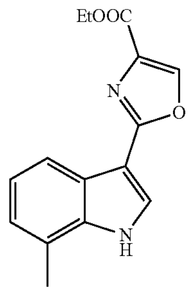 [SMILES: CCOC(=O)c1coc(-c2c[nH]c3c(C)cccc23)n1] | A | $^1$H NMR (400 MHz, Methanol-d$_4$) δ 8.53 (s, 1H), 8.05-8.03 (m, 2H), 7.14 (t, J = 7.6 Hz, 1H), 7.06 (d, J = 7.6 Hz, 1H), 4.43 (q, J = 7.2 Hz, 2H), 2.55 (s, 3H), 1.19 (t, J = 7.2 Hz, 3H). | MS (ESI) calcd for C$_{15}$H$_{14}$N$_2$O$_3$ [M + 1]$^+$, 271.1; found, 271.0. |
| 88 | 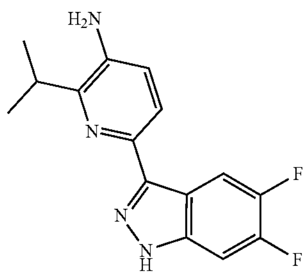 [SMILES: CC(C)c1nc(-c2n[nH]c3cc(F)c(F)cc23)ccc1N] | B | $^1$H NMR (400 MHz, Methanol-d4) δ 8.56-8.52 (m, 1H), 7.75 (d, J = 8.4 Hz, 1H), 7.43-7.33 (m, 1H), 7.12 (d, J = 8.4 Hz, 1H), 3.31-3.13 (m, 1H), 1.42 (d, J = 6.8 Hz, 6H). | MS (ESI) calcd for C$_{15}$H$_{14}$F$_2$N$_4$ [M + 1]$^+$, 289.1; found, 289.1. |
| 89 | 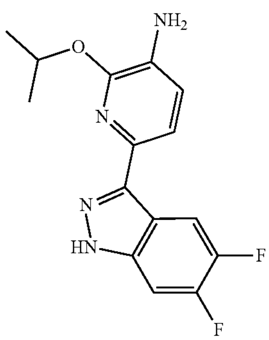 [SMILES: CC(C)Oc1nc(-c2n[nH]c3cc(F)c(F)cc23)ccc1N] | B | $^1$H NMR (400 MHz, DMSO-d6) δ 13.16 (bs, 1H), 8.40-8.22 (m, 1H), 7.64-7.54 (m, 1H), 7.52 (d, J = 8.0 Hz, 1H), 6.99 (d, J = 8.0 Hz, 1H), 5.44-5.34 (m, 1H), 5.07 (s, 2H), 1.45 (d, J = 6.4 Hz, 6H). | MS (ESI) calcd for C$_{15}$H$_{14}$F$_2$N$_4$O [M + 1]$^+$, 305.1; found, 305.1. |
| 90 | 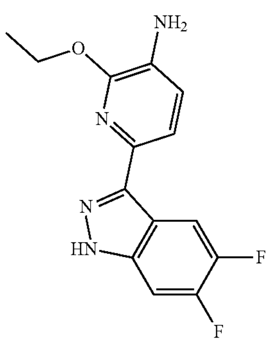 [SMILES: CCOc1nc(-c2n[nH]c3cc(F)c(F)cc23)ccc1N] | B | $^1$H NMR (400 MHz, DMSO-d6) δ 13.16 (bs, 1H), 8.36-8.31 (m, 1H), 7.61-7.56 (m, 1H), 7.53 (d, J = 8.0 Hz, 1H), 7.00 (d, J = 7.6 Hz, 1H), 5.12 (s, 2H), 4.57-4.47 (q, J = 7.2 Hz, 2H), 1.47 (t, J = 7.2 Hz, 3H). | MS (ESI) calcd for C$_{14}$H$_{12}$F$_2$N$_4$O [M + 1]$^+$, 291.2; found, 291.2. |
| 91 | 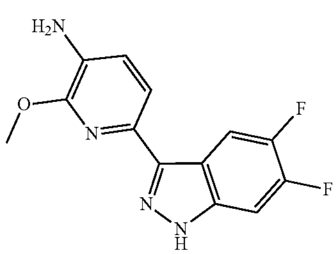 [SMILES: COc1nc(-c2n[nH]c3cc(F)c(F)cc23)ccc1N] | C | $^1$H NMR (400 MHz, DMSO-d6) δ 13.17 (bs, 1H), 8.42-8.39 (m, 1H), 7.72-7.42 (m, 2H), 6.99 (d, J = 7.6 Hz, 1H), 5.18 (s, 2H), 4.07 (s, 3H). | MS (ESI) calcd for C$_{13}$H$_{10}$F$_2$N$_4$O [M + 1]$^+$, 277.1; found, 277.1. |

TABLE 1-continued

| No. | Structure | IC$_{50}$ (μM) | $^1$H NMR | LCMS |
|---|---|---|---|---|
| 92 | 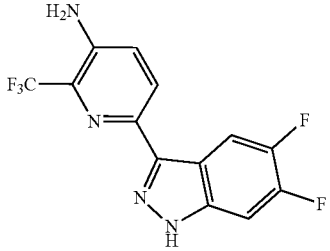 [SMILES: Nc1ccc(-c2n[nH]c3cc(F)c(F)cc23)nc1C(F)(F)F] | C | $^1$H NMR (400 MHz, DMSO-d6) δ 13.38 (bs, 1H), 8.35-8.250 (m, 1H), 8.08 (d, J = 8.8 Hz, 1H), 7.7-7.6 (m, 1H), 7.40 (d, J = 8.8 Hz, 1H), 6.05 (s, 2H). | MS (ESI) calcd for C$_{13}$H$_7$F$_5$N$_4$ [M + 1]$^+$, 315.1; found, 315.1. |
| 93 | 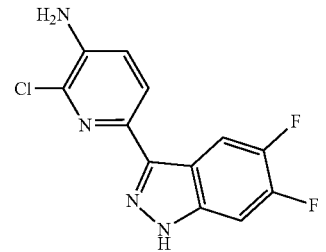 [SMILES: Nc1ccc(-c2n[nH]c3cc(F)c(F)cc23)nc1Cl] | C | $^1$H NMR (400 MHz, DMSO-d6) δ 13.34 (bs, 1H), 8.28-8.23 (m, 1H), 7.87 (d, J = 8.4 Hz, 1H), 7.65-8.61 (m, 1H), 7.26 (d, J = 8.4 Hz, 1H), 5.80 (s, 2H). | MS (ESI) calcd for C$_{12}$H$_7$ClF$_2$N$_4$ [M + 1]$^+$, 281.1; found, 281.1. |
| 124 | 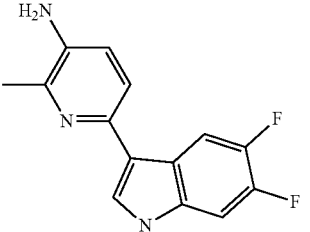 | B | $^1$H NMR (400 MHz, DMSO-d$_6$) δ 11.31 (bs, 1H), 8.40-8.36 (m, 1H), 7.85 (d, J = 2.4 Hz, 1H), 7.43-7.32 (m, 2H), 6.96 (d, J = 8.0 Hz, 1H), 4.92 (s, 2H), 2.37 (s, 3H). | MS (ESI) calcd for C$_{14}$H$_{11}$F$_2$N$_3$ [M + 1]$^+$, 260.1; found, 260.1. |
| 125 | 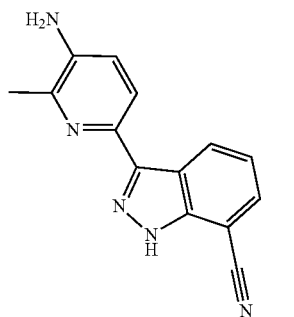 [SMILES: Cc1nc(-c2n[nH]c3c(C#N)cccc23)ccc1N] | C | $^1$H NMR (400 MHz, DMSO-d$_6$) δ 12.05 (bs, 1H), 8.84 (d, J = 8.0 Hz, 1H), 7.91 (d, J = 2.4 Hz, 1H), 7.62 (dd, J = 7.2, 1.2 Hz, 1H), 7.46 (d, J = 8.4 Hz, 1H), 7.23 (t, J = 7.8 Hz, 1H), 6.97 (d, J = 8.4 Hz, 1H), 4.99 (s, 2H), 2.37 (s, 3H). | MS (ESI) calcd for C$_{15}$H$_{12}$N$_4$ [M + 1]$^+$, 249.1; found, 249.1. |
| 94 | 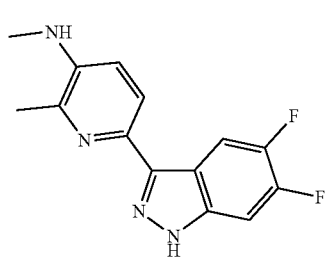 [SMILES: CNc1ccc(-c2n[nH]c3cc(F)c(F)cc23)nc1C] | B | $^1$H NMR (400 MHz, DMSO-d6) δ 13.13 (bs, 1H), 8.47-8.45 (m, 1H), 7.83 (d, J = 8.4 Hz, 1H), 7.59-8.55 (m, 1H), 6.92 (d, J = 8.4 Hz, 1H), 5.55 (s, 1H), 2.79 (d, J = 4.8 Hz, 3H), 2.44 (s, 3H). | MS (ESI) calcd for C$_{17}$H$_{12}$F$_2$N$_4$ [M + 1]$^+$, 275.1; found, 275.1. |

TABLE 1-continued

| No. | Structure | IC$_{50}$ (µM) | $^1$H NMR | LCMS |
|---|---|---|---|---|
| 95 | 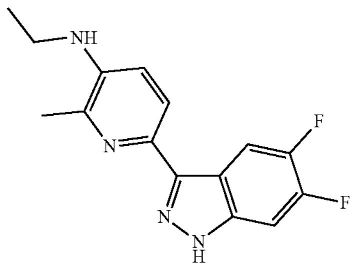 [SMILES: CCNc1ccc(-c2n[nH]c3cc(F)c(F)cc23)nc1C] | B | $^1$H NMR (400 MHz, DMSO-d6) δ 13.13 (bs, 1H), 8.48-8.44 (m, 1H), 7.81 (d, J = 8.4 Hz, 1H), 7.59-7.55 (m, 1H), 6.98 (d, J = 8.4 Hz, 1H), 5.31 (s, 1H), 3.28-3.06 (m, 2H), 2.46 (s, 3H), 1.23 (t, J = 7.2 Hz, 3H). | MS (ESI) calcd for C$_{15}$H$_{14}$F$_2$N$_4$ [M + 1]$^+$, 289.1; found, 289.1. |
| 96 | 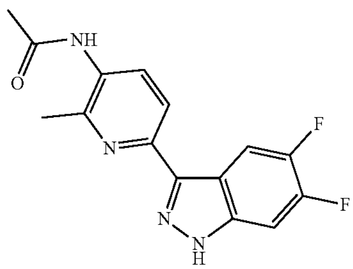 [SMILES: CC(=O)Nc1ccc(-c2n[nH]c3cc(F)c(F)cc23)nc1C] | A | $^1$H NMR (400 MHz, DMSO-d6) δ 13.51 (bs, 1H), 9.55 (s, 1H), 8.49-8.45 (m, 1H), 8.10-7.88 (m, 2H), 7.69-7.65 (m, 1H), 2.51 (s, 3H), 2.13 (s, 3H). | MS (ESI) calcd for C$_{15}$H$_{12}$F$_2$N$_4$O [M + 1]$^+$, 303.1; found, 303.0. |
| 97 | 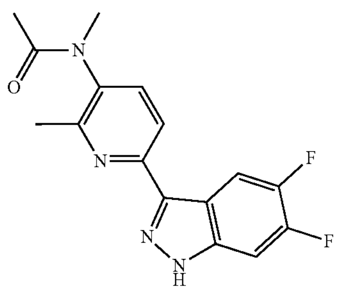 [SMILES: CC(=O)N(C)c1ccc(-c2n[nH]c3cc(F)c(F)cc23)nc1C] | A | $^1$H NMR (400 MHz, DMSO-d6) δ 11.11 (bs, 1H), 8.53-8.43 (m, 1H), 8.09-7.99 (m, 1H), 7.83 (d, J = 8.4 Hz, 1H), 7.77-7.59 (m, 1H), 3.12 (s, 3H), 2.55 (s, 3H), 1.74 (s, 3H). | MS (ESI) calcd for C$_{16}$H$_{14}$F$_2$N$_4$O [M + 1]$^+$, 317.1; found, 317.1. |
| 98 | 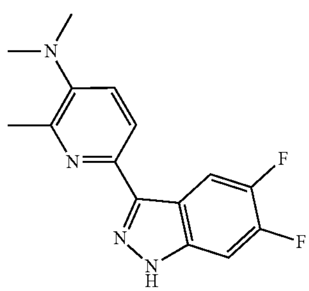 [SMILES: Cc1nc(-c2n[nH]c3cc(F)c(F)cc23)ccc1N(C)C] | B | $^1$H NMR (400 MHz, DMSO-d6) δ 8.48-8.44 (m, 1H), 7.92 (d, J = 8.4 Hz, 1H), 7.71-7.62 (m, 1H), 7.50 (d, J = 8.4 Hz, 1H), 2.73 (s, 6H), 2.61 (s, 3H). | MS (ESI) calcd for C$_{15}$H$_{14}$F$_2$N$_4$ [M + 1]$^+$, 289.1; found, 289.1. |
| 99 | 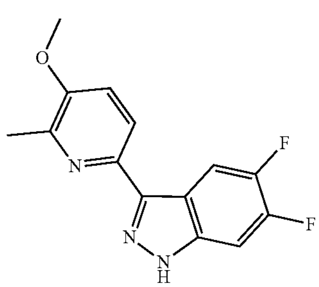 [SMILES: COc1ccc(-c2n[nH]c3cc(F)c(F)cc23)nc1C] | C | $^1$H NMR (400 MHz, Methanol-d$_4$) δ 8.44-8.34 (m, 1H), 7.95 (d, J = 8.4 Hz, 1H), 7.45-7.37 (m, 2H), 3.94 (s, 3H), 2.57 (s, 3H). | MS (ESI) calcd for C$_{14}$H$_{11}$F$_2$N$_3$O [M + 1]$^+$, 276.1; found, 276.1. |

TABLE 1-continued

| No. | Structure | IC$_{50}$ (μM) | $^1$H NMR | LCMS |
|---|---|---|---|---|
| 100 | 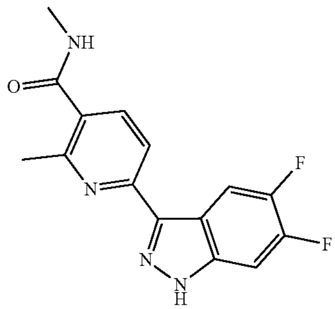 [SMILES: CNC(=O)c1ccc(-c2n[nH]c3cc(F)c(F)cc23)nc1C] | A | $^1$H NMR (400 MHz, DMSO-d6) δ 13.65 (bs, 1H), 8.51-8.46 (m, 1H), 8.40 (d, J = 4.8 Hz, 1H), 8.01 (d, J = 8.0 Hz, 1H), 7.84 (d, J = 8.0 Hz, 1H), 7.72-7.68 (m, 1H), 2.81 (d, J = 4.8 Hz, 3H), 2.68 (s, 3H). | MS (ESI) calcd for C$_{15}$H$_{12}$F$_2$N$_4$O [M + 1]$^+$, 303.1; found, 303.1. |
| 101 | 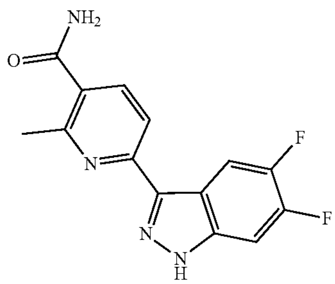 [SMILES: Cc1nc(-c2n[nH]c3cc(F)c(F)cc23)ccc1C(N)=O] | A | $^1$H NMR (300 MHz, DMSO-d$_6$) δ 8.52-8.46 (m, 1H), 8.01-7.99 (m, 2H), 7.95 (s, 1H), 7.87 (d, J = 8.1 Hz, 1H), 7.73-7.68 (m, 1H), 7.58 (s, 1H), 2.72 (s, 3H). | MS (ESI) calcd for C$_{14}$H$_{10}$F$_2$N$_4$O [M + 1]$^+$, 289.1; found, 289.1. |
| 102 | 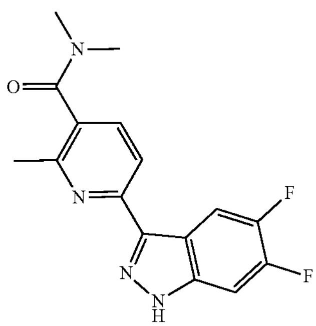 [SMILES: Cc1nc(-c2n[nH]c3cc(F)c(F)cc23)ccc1C(=O)N(C)C] | A | $^1$H NMR (400 MHz, DMSO-d$_6$) δ 13.64 (bs, 1H), 8.52-8.47 (m, 1H), 8.02 (d, J = 8.0 Hz, 1H), 7.73-7.69 (m, 2H), 3.06 (s, 3H), 2.85 (s, 3H), 2.54 (s, 3H). | MS (ESI) calcd for C$_{16}$H$_{14}$F$_2$N$_4$O [M + 1]$^+$, 317.1; found, 317.1. |
| 103 | 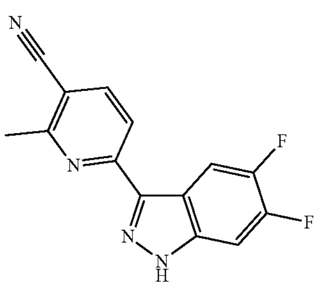 [SMILES: Cc1nc(-c2n[nH]c3cc(F)c(F)cc23)ccc1C#N] | D | $^1$H NMR (400 MHz, DMSO-d$_6$) δ 13.90 (bs, 1H), 8.49-8.47 (m, 1H), 8.29 (d, J = 8.0 Hz, 1H), 8.12 (d, J = 8.0 Hz, 1H), 7.77-7.73 (m, 1H), 2.83 (s, 3H). | MS (ESI) calcd for C$_{14}$H$_8$F$_2$N$_4$ [M + 1]$^+$, 271.1; found, 271.1. |
| 104 | 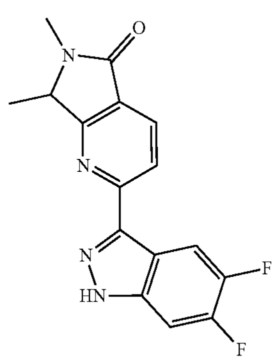 [SMILES: CC1c2nc(-c3n[nH]c4cc(F)c(F)cc34)ccc2C(=O)N1C] | C | $^1$H NMR (400 MHz, DMSO-d$_6$) δ 13.80 (s, 1H), 8.47 (dd, J = 10.4, 8.0 Hz, 1H), 8.26 (d, J = 8.0 Hz, 1H), 8.14 (d, J = 8.0 Hz, 1H), 7.74 (dd, J = 10.4, 6.8 Hz, 1H), 4.72 (q, J = 6.8 Hz, 1H), 3.09 (s, 3H), 1.59 (d, J = 6.8 Hz, 3H). | MS (ESI) calcd for C$_{16}$H$_{12}$F$_2$N$_4$O [M + 1]$^+$, 315.1; found, 315.1. |

TABLE 1-continued

| No. | Structure | IC$_{50}$ (μM) | $^1$H NMR | LCMS |
|---|---|---|---|---|
| 105 | 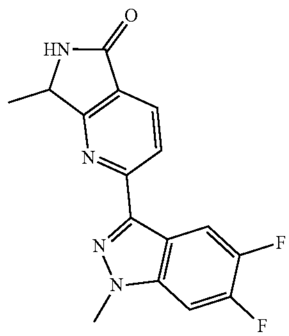 [SMILES: CC1NC(=O)c2ccc(-c3nn(C)c4cc(F)c(F)cc34)nc21] | A | $^1$H NMR (400 MHz, DMSO-d$_6$) δ 8.88 (s, 1H), 8.50-8.45 (m, 1H), 8.20 (d, J = 8.0 Hz, 1H), 8.13 (m, J = 8.0 Hz, 1H), 8.02-7.98 (m, 1H), 4.78 (q, J = 6.8 Hz, 1H), 4.18 (s, 3H), 1.53 (d, J = 6.8 Hz, 3H). | MS (ESI) calcd for C$_{16}$H$_{12}$F$_2$N$_4$O [M + 1]$^+$, 315.1; found, 315.1. |
| 106 | 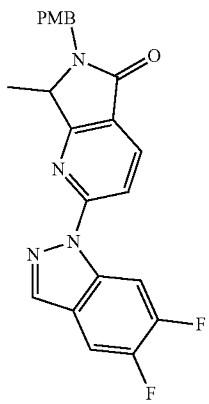 | A | $^1$H NMR (400 MHz, DMSO-d$_6$) δ 8.81-8.71 (m, 1H), 8.56 (s, 1H), 8.30 (d, J = 8.4 Hz, 1H), 8.12 (d, J = 8.4 Hz, 1H), 8.07-7.98 (m, 1H), 7.30 (d, J = 8.4 Hz, 2H), 6.93 (d, J = 8.8 Hz, 2H), 5.07-4.99 (m, 1H), 4.65-4.56 (m, 1H), 4.46-4.38 (m, 1H), 3.74 (s, 3H), 1.54 (d, J = 6.8 Hz, 3H). | MS (ESI) calcd for C$_{23}$H$_{18}$F$_2$N$_4$O$_2$ [M + 1]$^+$, 421.1; found, 421.2. |
| 107 | 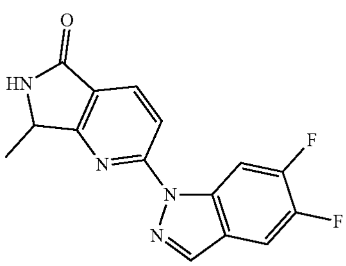 [SMILES: CC1NC(=O)c2ccc(-n3ncc4cc(F)c(F)cc43)nc21] | A | $^1$H NMR (400 MHz, DMSO-d$_6$) δ 8.88 (s, 1H), 8.81-8.72 (m, 1H), 8.57 (s, 1H), 8.25 (d, J = 8.2 Hz, 1H), 8.14-8.08 (m, 1H), 8.07-8.00 (m, 1H), 4.80 (q, J = 6.8 Hz, 1H), 1.53 (d, J = 6.8 Hz, 3H). | MS (ESI) calcd for C$_{15}$H$_{10}$F$_2$N$_4$O [M + 1]$^+$, 301.1; found, 301.0. |
| 108 | 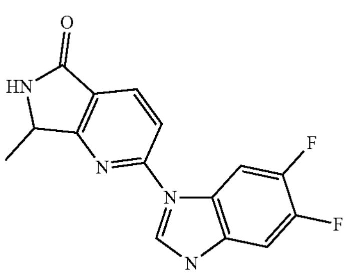 | A | $^1$H NMR (400 MHz, DMSO-d$_6$) δ 9.21 (s, 1H), 8.95 (s, 1H), 8.47-8.42 (m, 1H), 8.31 (d, J = 8.4 Hz, 1H), 8.09 (d, J = 8.4 Hz, 1H), 7.94-7.89 (m, 1H), 4.81 (q, J = 6.8 Hz, 1H), 1.51 (d, J = 6.8 Hz, 3H). | MS (ESI) calcd for C$_{15}$H$_{10}$F$_2$N$_4$O [M + 1]$^+$, 301.1; found, 301.0. |
| 109 | 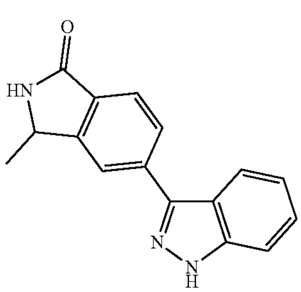 [SMILES: CC1NC(=O)c2ccc(-c3n[nH]c4ccccc34)cc21] | C | $^1$H NMR (400 MHz, DMSO-d$_6$) δ 13.40 (s, 1H), 8.66 (s, 1H), 8.17-8.10 (m, 3H), 7.77 (d, J = 7.6 Hz, 1H), 7.63 (d, J = 8.4 Hz, 1H), 7.46-7.42 (m, 1H), 7.28-7.24 (m, 1H), 4.74 (q, J = 6.8 Hz, 1H), 1.47 (d, J = 6.8 Hz, 3H). | MS (ESI) calcd for C$_{16}$H$_{13}$N$_3$O [M + 1]$^+$, 264.1; found, 264.1. |

TABLE 1-continued

| No. | Structure | IC$_{50}$ (μM) | $^1$H NMR | LCMS |
|---|---|---|---|---|
| 110 | 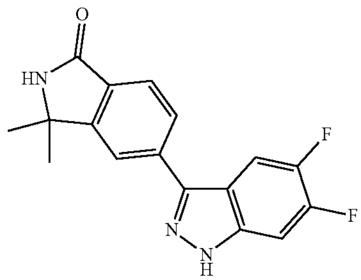 [SMILES: CC1(C)NC(=O)c2ccc(-c3n[nH]c4cc(F)c(F)cc34)cc21] | A | $^1$H NMR (400 MHz, DMSO-d$_6$) δ 13.61 (bs, 1H), 8.69 (s, 1H), 8.24-8.16 (m, 2H), 8.07 (d, J = 7.6 Hz, 1H), 7.73-7.68 (m, 2H), 1.55 (s, 6H). | MS (ESI) calcd for C$_{17}$H$_{13}$F$_2$N$_3$O [M + 1]$^+$, 314.1; found, 314.1 |
| 143 | 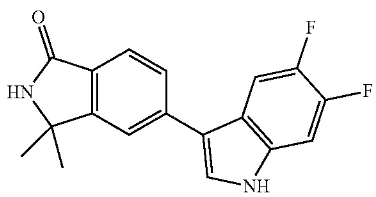 [SMILES: CC1(C)NC(=O)c2ccc(-c3c[nH]c4cc(F)c(F)cc34)cc21] | B | $^1$H NMR (400 MHz, DMSO-d$_6$) δ 11.69 (bs, 1H), 8.55 (s, 1H), 7.93-7.84 (m, 3H), 7.75 (d, J = 7.6 Hz, 1H), 7.63 (d, J = 8.0 Hz, 1H), 7.51-7.46 (m, 1H), 1.52 (s, 6H). | MS (ESI) calcd for C$_{18}$H$_{14}$F$_2$N$_2$O [M + 1]$^+$, 313.1; found, 313.1 |
| 126 | 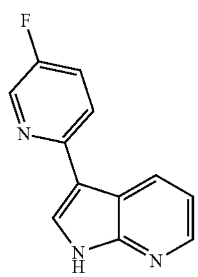 [SMILES: Fc1ccc(-c2c[nH]c3ncccc23)nc1] | C | $^1$H NMR (400 MHz, Methanol-d$_4$) δ 8.77-8.70 (m, 1H), 8.50 (d, J = 2.8 Hz, 1H), 8.30-8.24 (m, 1H), 7.99 (s, 1H), 7.89-7.81 (m, 1H), 7.66-7.56 (m, 1H), 7.28-7.19 (m, 1H). | MS (ESI) calcd for C$_{12}$H$_8$FN$_3$ [M + 1]$^+$, 214.1; found, 214.1. |
| 127 | 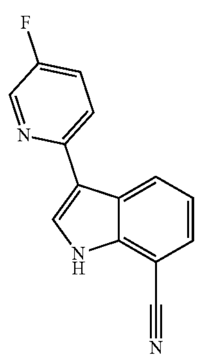 [SMILES: N#Cc1cccc2c(-c3ccc(F)cn3)c[nH]c12] | D | $^1$H NMR (400 MHz, DMSO-d$_6$) δ 12.36 (bs, 1H), 8.81-8.79 (m, 1H), 8.61 (d, J = 3.2 Hz, 1H), 8.27 (s, 1H), 8.03-8.00 (m, 1H), 7.80-7.68 (m, 2H), 7.29 (t, J = 8.0 Hz, 1H). | MS (ESI) calcd for C$_{14}$H$_8$FN$_3$ [M + 1]$^+$, 238.1; found, 238.1. |
| 111 | 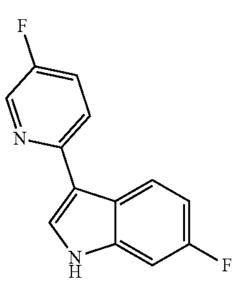 [SMILES: Fc1ccc(-c2c[nH]c3cc(F)ccc23)nc1] | C | $^1$H NMR (400 MHz, DMSO-d$_6$) δ 13.44 (bs, 1H), 8.71 (d, J = 2.8 Hz, 1H), 8.5-8.50 (m, 1H), 8.24-8.20 (m, 1H), 7.88-7.83 (m, 1H), 7.40-7.39 (m, 1H), 7.15-7.10 (m, 1H). | MS (ESI) calcd for C$_{12}$H$_7$F$_2$N$_3$ [M + 1]$^+$, 232.1; found, 232.0. |

TABLE 1-continued

| No. | Structure | IC$_{50}$ (μM) | $^1$H NMR | LCMS |
|---|---|---|---|---|
| 112 | 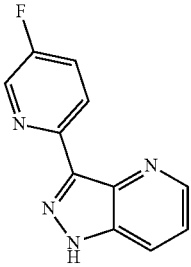 [SMILES: Fc1ccc(-c2n[nH]c3cccnc23)nc1] | A | $^1$H NMR (400 MHz, DMSO-d$_6$) δ 13.59 (bs, 1H), 8.73-8.72 (m, 2H), 8.67-8.66 (m, 1H), 8.11 (d, J = 8.4 Hz, 1H), 7.96-7.87 (m, 1H), 7.50-7.42 (m, 1H). | MS (ESI) calcd for C$_{11}$H$_7$FN$_4$ [M + 1]$^+$, 215.1; found, 215.1. |
| 128 | 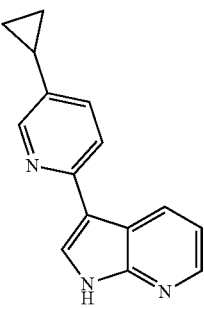 [SMILES: c1cnc2[nH]cc(-c3ccc(C4CC4)cn3)c2c1] | C | $^1$H NMR (400 MHz, DMSO-d$_6$) δ 11.95 (bs, 1H), 8.74 (dd, J = 8.0, 1.6 Hz, 1H), 8.43 (d, J = 2.4 Hz, 1H), 8.27 (dd, J = 4.8, 1.6 Hz, 1H), 8.17 (d, J = 2.4 Hz, 1H), 7.77 (d, J = 8.0 Hz, 1H), 7.41 (dd, J = 8.4, 2.4 Hz, 1H), 7.16 (dd, J = 8.0, 4.8 Hz, 1H), 2.02-1.91 (m, 1H), 1.05-0.96 (m, 2H), 0.80-0.72 (m, 2H). | MS (ESI) calcd for C$_{15}$H$_{13}$N$_3$ [M + 1]$^+$, 236.1; found, 236.1. |
| 129 | 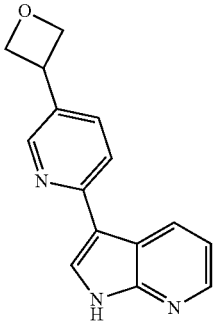 [SMILES: c1cnc2[nH]cc(-c3ccc(C4COC4)cn3)c2c1] | B | $^1$H NMR (400 MHz, DMSO-d$_6$) δ 12.02 (bs, 1H), 8.81-8.74 (m, 1H), 8.58 (d, J = 2.0 Hz, 1H), 8.31-8.24 (m, 2H), 7.94-7.89 (m, 2H), 7.22-7.14 (m, 1H), 5.02-4.94 (m, 2H), 4.72-4.65 (m, 2H), 4.34-4.27 (m, 1H). | MS (ESI) calcd for C$_{15}$H$_{13}$N$_3$O [M + 1]$^+$, 252.1; found, 252.1. |
| 130 | 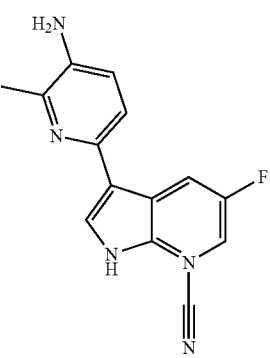 | C | $^1$H NMR (400 MHz, DMSO-d$_6$) δ 12.18 (bs, 1H), 8.66-8.59 (m, 1H), 8.03 (d, J = 2.8 Hz, 1H), 7.67-7.59 (m, 1H), 7.48 (d, J = 8.4 Hz, 1H), 6.97 (d, J = 8.4 Hz, 1H), 5.01 (s, 2H), 2.38 (s, 3H). | MS (ESI) calcd for C$_{15}$H$_{11}$FN$_4$ [M + 1]$^+$, 267.1; found, 267.1. |

US 11,667,624 B2

321 322

TABLE 1-continued

| No. | Structure | IC$_{50}$ (μM) | $^1$H NMR | LCMS |
|---|---|---|---|---|
| 131 | 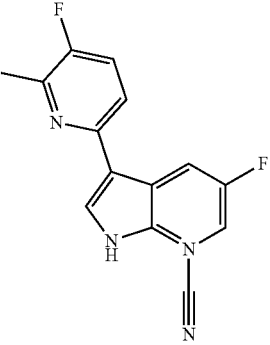 | D | $^1$H NMR (400 MHz, DMSO-d$_6$) δ 12.50 (bs, 1H), 8.67-8.59 (m, 1H), 8.35 (d, J = 2.8 Hz, 1H), 7.87-7.80 (m, 1H), 7.75-7.60 (m, 2H), 2.55 (s, 3H). | MS (ESI) calcd for C$_{15}$H$_9$F$_2$N$_3$ [M + 1]$^+$, 270.1; found, 270.1. |
| 113 | 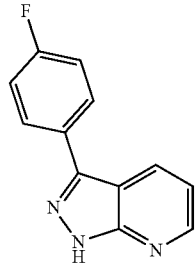 [SMILES: Fc1ccc(-c2n[nH]c3ncccc23)cc1] | B | $^1$H NMR (400 MHz, DMSO-d$_6$) δ 13.83 (bs, 1H), 8.61-8.53 (m, 2H), 8.13-8.03 (m, 2H), 7.42-7.32 (m, 2H), 7.30-7.27 (m, 1H). | MS (ESI) calcd for C$_{12}$H$_8$FN$_3$ [M + 1]$^+$, 214.1; found, 214.1. |
| 132 | 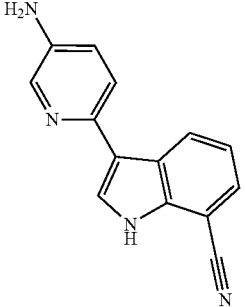 [SMILES: N#Cc1cccc2c(-c3ccc(N)cn3)c[nH]c12] | B | $^1$H NMR (400 MHz, DMSO-d$_6$) δ 12.07 (bs, 1H), 8.74 (d, J = 8.4 Hz, 1H), 8.02 (d, J = 2.8 Hz, 1H), 7.93 (d, J = 2.4 Hz, 1H), 7.63-7.56 (m, 2H), 7.21 (d, J = 7.6 Hz, 1H), 7.00-6.97 (m, 1H), 5.24 (s, 2H). | MS (ESI) calcd for C$_{14}$H$_{10}$N$_4$ [M + 1]$^+$, 235.1; found, 235.2. |
| 133 | 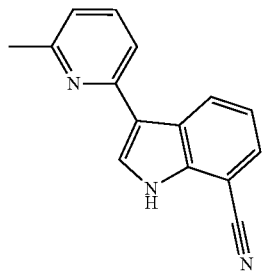 [SMILES: Cc1cccc(-c2c[nH]c3c(C#N)cccc23)n1] | C | $^1$H NMR (400 MHz, DMSO-d$_6$) δ 12.35 (bs, 1H), 8.93 (d, J = 8.0 Hz, 1H), 8.24 (d, J = 2.8 Hz, 1H), 7.73-7.65 (m, 3H), 7.32-7.27 (m, 1H), 7.04 (d, J = 7.2 Hz, 1H), 2.55 (s, 3H). | MS (ESI) calcd for C$_{15}$H$_{11}$N$_3$ [M + 1]$^+$, 234.1; found, 234.1. |
| 134 | 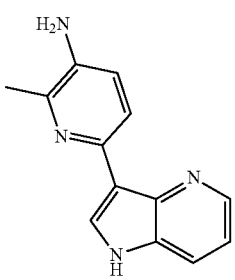 [SMILES: Cc1nc(-c2c[nH]c3cccnc23)ccc1N] | A | $^1$H NMR (400 MHz, DMSO-d$_6$) δ 11.38 (bs, 1H), 8.44-8.35 (m, 2H), 8.05 (t, J = 1.6 Hz, 1H), 7.78 (dd, J = 8.0, 1.6 Hz, 1H), 7.13 (dd, J = 8.0, 4.4 Hz, 1H), 6.99 (d, J = 8.4 Hz, 1H), 4.88 (s, 2H), 2.33 (s, 3H). | MS (ESI) calcd for C$_{13}$H$_{12}$N$_4$ [M + 1]$^+$, 225.1; found, 225.1. |

TABLE 1-continued

| No. | Structure | IC$_{50}$ (μM) | $^1$H NMR | LCMS |
|---|---|---|---|---|
| 135 | 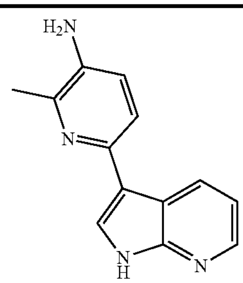 | B | $^1$H NMR (400 MHz, DMSO-d$_6$) δ 11.66 (bs, 1H), 8.76-8.74 (m, 1H), 8.22-8.21 (m, 1H), 7.88 (s, 1H), 7.43 (d, J = 8.0 Hz, 1H), 7.13-7.09 (m, 1H), 6.97 (d, J = 8.4 Hz, 1H), 4.92 (s, 2H), 2.37 (s, 3H). | MS (ESI) calcd for C$_{13}$H$_{12}$N$_4$ [M + 1]$^+$, 225.1; found, 225.1. |
| 136 | 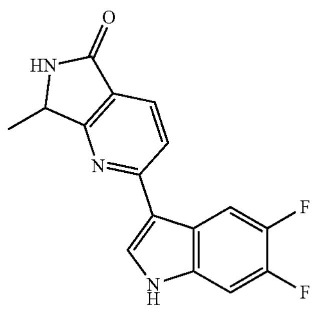 [SMILES: CC1NC(=O)c2ccc(-c3c[nH]c4cc(F)c(F)cc34)nc21] | C | $^1$H NMR (400 MHz, DMSO-d$_6$) δ 11.89 (bs, 1H), 8.71 (s, 1H), 8.52-8.47 (m, 1H), 8.39 (d, J = 2.8 Hz, 1H), 7.98-7.93 (m, 2H), 7.52-7.47 (m, 1H), 4.72-4.67 (q, J = 6.8 Hz, 1H), 1.50 (d, J = 6.8 Hz, 3H). | MS (ESI) calcd for C$_{16}$H$_{11}$F$_2$N$_3$O [M + 1]$^+$, 300.1; found, 300.1. |
| 137 | 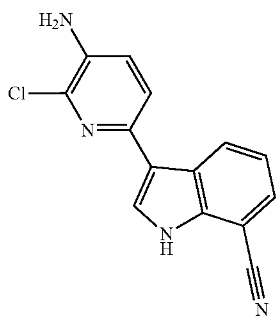 [SMILES: N#Cc1cccc2c(-c3ccc(N)c(Cl)n3)c[nH]c12] | C | $^1$H NMR (400 MHz, DMSO-d$_6$) δ 12.20 (bs, 1H), 8.71 (d, J = 8.0 Hz, 1H), 8.03 (d, J = 2.4 Hz, 1H), 7.68-7.64 (m, 2H), 7.29-7.25 (m, 1H), 7.19 (d, J = 8.0 Hz, 1H), 5.48 (s, 2H). | MS (ESI) calcd for C$_{14}$H$_9$ClN$_4$ [M + 1]$^+$, 269.1; found, 269.1. |
| 138 | 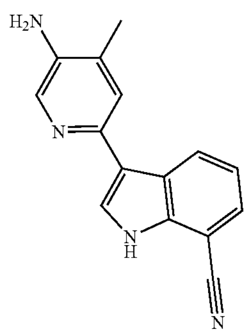 [SMILES: Cc1cc(-c2c[nH]c3c(C#N)cccc23)ncc1N] | B | $^1$H NMR (400 MHz, DMSO-d$_6$) δ 12.05 (bs, 1H), 8.75 (d, J = 8.0 Hz, 1H), 7.98 (s, 1H), 7.92 (d, J = 2.8 Hz, 1H), 7.63-7.60 (m, 1H), 7.50 (s, 1H), 7.21-7.19 (m, 1H), 5.01 (s, 2H), 2.14 (s, 3H). | MS (ESI) calcd for C$_{15}$H$_{12}$N$_4$ [M + 1]$^+$, 249.1; found, 249.2. |
| 139 | 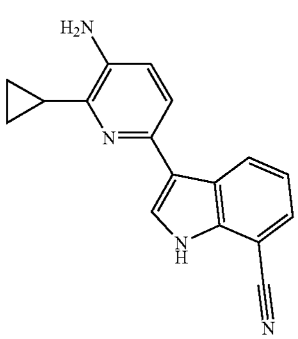 [SMILES: N#Cc1cccc2c(-c3ccc(N)c(C4CC4)n3)c[nH]c12] | D | $^1$H NMR (400 MHz, DMSO-d$_6$) δ 12.04 (bs, 1H), 8.71 (d, J = 8.0 Hz, 1H), 7.91 (d, J = 2.4 Hz, 1H), 7.62-7.60 (m, 1H), 7.40 (d, J = 8.4 Hz, 1H), 7.23 (t, J = 8.0 Hz, 1H), 6.96 (d, J = 8.4 Hz, 1H), 5.14 (s, 2H), 2.21-2.08 (m, 1H), 1.07-0.97 (m, 2H), 0.96-0.91 (m, 2H). | MS (ESI) calcd for C$_{17}$H$_{14}$N$_4$ [M + 1]$^+$, 275.1; found, 275.2. |

TABLE 1-continued

| No. | Structure | IC$_{50}$ (μM) | $^1$H NMR | LCMS |
|---|---|---|---|---|
| 140 | 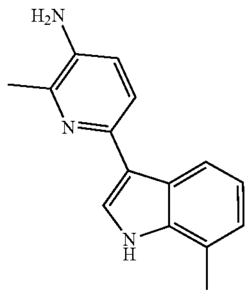 [SMILES: Cc1nc(-c2c[nH]c3c(C)cccc23)ccc1N] | B | $^1$H NMR (400 MHz, DMSO-d$_6$) δ 11.12 (bs, 1H), 8.20 (d, J = 7.6 Hz, 1H), 7.75-7.69 (m, 1H), 7.41 (d, J = 8.0 Hz, 1H), 6.98-6.89 (m, 3H), 4.88 (bs, 2H), 2.47 (s, 3H), 2.35 (s, 3H). | MS (ESI) calcd for C$_{15}$H$_{15}$N$_3$ [M + 1]$^+$, 238.1; found, 238.1 |
| 141 | 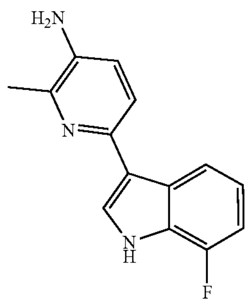 [SMILES: Cc1nc(-c2c[nH]c3c(F)cccc23)ccc1N] | B | $^1$H NMR (400 MHz, DMSO-d$_6$) δ 11.64 (bs, 1H), 8.24 (d, J = 8.0 Hz, 1H), 7.81 (d, J = 2.4 Hz, 1H), 7.42 (d, J = 8.0 Hz, 1H), 7.05-6.91 (m, 3H), 4.93 (s, 2H), 2.37 (s, 3H). | MS (ESI) calcd for C$_{14}$H$_{12}$FN$_3$ [M + 1]$^+$, 242.1; found, 242.1. |
| 142 | 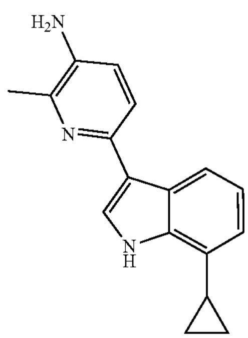 [SMILES: Cc1nc(-c2c[nH]c3c(C4CC4)cccc23)ccc1N] | B | $^1$H NMR (400 MHz, DMSO-d$_6$) δ 11.22 (bs, 1H), 8.19 (d, J = 8.0 Hz, 1H), 7.75 (d, J = 2.8 Hz, 1H), 7.40 (d, J = 8.4 Hz, 1H), 6.97-6.92 (m, 2H), 6.66 (d, J = 7.2 Hz, 1H), 4.89 (s, 2H), 2.35 (s, 3H), 2.30-2.19 (m, 1H), 1.02-0.92 (m, 2H), 0.75-0.70 (m, 2H). | MS (ESI) calcd for C$_{17}$H$_{17}$N$_3$ [M + 1]$^+$, 264.1; found, 264.1. |
| 144 | 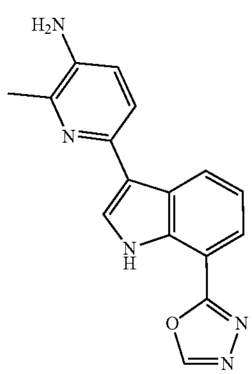 [SMILES: Cc1nc(-c2c[nH]c3c(-c4nnco4)cccc23)ccc1N] | A | $^1$H NMR (400 MHz, DMSO-d$_6$) δ 11.32 (bs, 1H), 9.42 (s, 1H), 8.85 (d, J = 8.0 Hz, 1H), 7.85-7.78 (m, 2H), 7.46 (d, J = 8.0 Hz, 1H), 7.36-7.27 (m, 1H), 7.02-6.95 (m, 1H), 4.98 (s, 2H), 2.38 (s, 3H). | MS (ESI) calcd for C$_{16}$H$_{13}$N$_5$O [M + 1]$^+$, 292.1; found, 292.1. |

TABLE 1-continued

| No. | Structure | IC$_{50}$ (μM) | $^1$H NMR | LCMS |
|---|---|---|---|---|
| 145 | 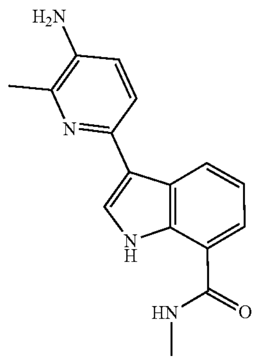 [SMILES: CNC(=O)c1cccc2c(-c3ccc(N)c(C)n3)c[nH]c12] | A | $^1$H NMR (400 MHz, DMSO-d$_6$) δ 11.19 (bs, 1H), 8.60 (d, J = 7.6 Hz, 1H), 8.51 (d, J = 4.8 Hz, 1H), 7.73 (d, J = 2.4 Hz, 1H), 7.64-7.61 (m, 1H), 7.40 (d, J = 8.0 Hz, 1H), 7.11 (t, J = 7.6 Hz, 1H), 6.96 (d, J = 8.4 Hz, 1H), 4.92 (s, 2H), 2.86 (d, J = 4.8 Hz, 3H), 2.36 (s, 3H). | MS (ESI) calcd for C$_{16}$H$_{16}$N$_4$O [M + 1]$^+$, 281.1; found, 281.2. |
| 146 | 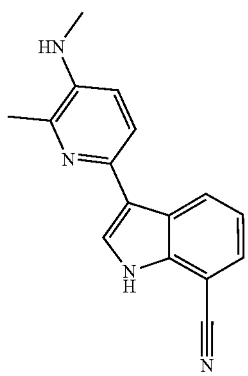 [SMILES: CNc1ccc(-c2c[nH]c3c(C#N)cccc23)nc1C] | D | $^1$H NMR (400 MHz, DMSO-d$_6$) δ 12.05 (bs, 1H), 8.83 (d, J = 8.0 Hz, 1H), 7.93 (d, J = 2.4 Hz, 1H), 7.65-7.54 (m, 2H), 7.27-7.19 (m, 1H), 6.86 (d, J = 8.4 Hz, 1H), 5.28-5.27 (m, 1H), 2.76 (d, J = 4.8 Hz, 3H), 2.40 (s, 3H). | MS (ESI) calcd for C$_{16}$H$_{14}$N$_4$ [M + 1]$^+$, 263.1; found, 263.1. |
| 147 | 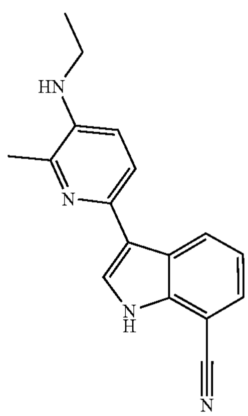 [SMILES: CCNc1ccc(-c2c[nH]c3c(C#N)cccc23)nc1C] | C | $^1$H NMR (300 MHz, DMSO-d$_6$) δ 12.05 (bs, 1H), 8.83 (d, J = 8.1 Hz, 1H), 7.93 (d, J = 2.7 Hz, 1H), 7.66-7.51 (m, 2H), 7.28-7.17 (m, 1H), 6.91 (d, J = 8.4 Hz, 1H), 5.03 (t, J = 5.4 Hz, 1H), 3.22-3.07 (m, 2H), 2.41 (s, 3H), 1.21 (t, J = 6.9 Hz, 3H). | MS (ESI) calcd for C$_{17}$H$_{16}$N$_4$ [M + 1]$^+$, 277.1; found, 277.1. |
| 148 | 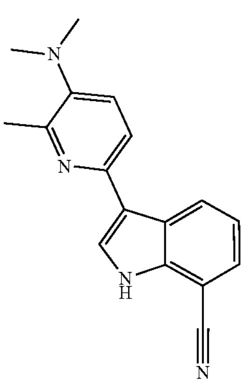 [SMILES: Cc1nc(-c2c[nH]c3c(C#N)cccc23)ccc1N(C)C] | D | $^1$H NMR (300 MHz, DMSO-d$_6$) δ 12.24 (s, 1H), 8.87 (d, J = 8.1 Hz, 1H), 8.11 (d, J = 2.4 Hz, 1H), 7.73-7.62 (m, 2H), 7.42 (d, J = 8.4 Hz, 1H), 7.32-7.21 (m, 1H), 2.68 (s, 6H), 2.55 (s, 3H). | MS (ESI) calcd for C$_{17}$H$_{16}$N$_4$ [M + 1]$^+$, 277.1; found, 277.1. |

TABLE 1-continued

| No. | Structure | IC$_{50}$ (μM) | $^1$H NMR | LCMS |
|---|---|---|---|---|
| 149 | 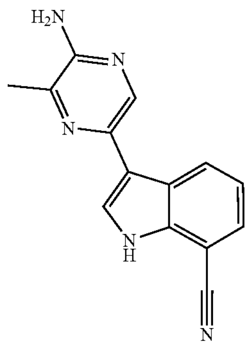 [SMILES: Cc1nc(-c2c[nH]c3c(C#N)cccc23)cnc1N] | C | $^1$H NMR (400 MHz, DMSO-d$_6$) δ 12.16 (bs, 1H), 8.69 (d, J = 8.0 Hz, 1H), 8.36 (s, 1H), 8.01 (d, J = 2.4 Hz, 1H), 7.68-7.61 (m, 1H), 7.28-7.20 (m, 1H), 6.07 (s, 2H), 2.40 (s, 3H). | MS (ESI) calcd for C$_{14}$H$_{11}$N$_5$ [M + 1]$^+$, 250.1; found, 250.1. |
| 150 | 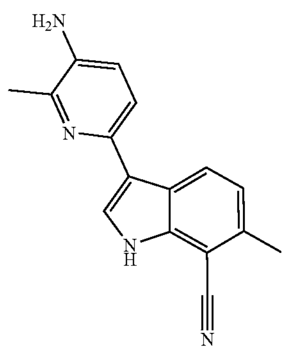 | B | $^1$H NMR (400 MHz, DMSO-d$_6$) δ 12.24-11.60 (bs, 1H), 8.67 (d, J = 8.0 Hz, 1H), 7.80 (s, 1H), 7.44 (d, J = 8.0 Hz, 1H), 7.12 (d, J = 8.0 Hz, 1H), 6.96 (d, J = 8.0 Hz, 1H), 4.95 (s, 2H), 2.59 (s, 3H), 2.37 (s, 3H). | MS (ESI) calcd for C$_{16}$H$_{14}$N$_4$ [M + 1]$^+$, 263.1; found, 263.2. |
| 151 | 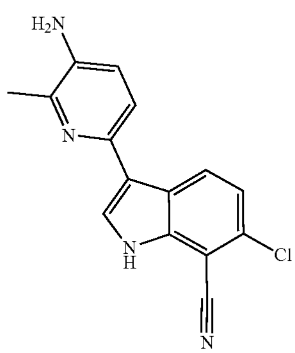 [SMILES: Cc1nc(-c2c[nH]c3c(C#N)c(Cl)ccc23)ccc1N] | C | $^1$H NMR (400 MHz, DMSO-d$_6$) δ 12.21 (bs, 1H), 8.84 (d, J = 8.8 Hz, 1H), 7.96 (s, 1H), 7.47 (d, J = 8.4 Hz, 1H), 7.35 (d, J = 8.8 Hz, 1H), 6.97 (d, J = 8.4 Hz, 1H), 5.02 (s, 2H), 2.37 (s, 3H). | MS (ESI) calcd for C$_{15}$H$_{11}$ClN$_4$ [M + 1]$^+$, 283.1; found, 283.1. |
| 152 | 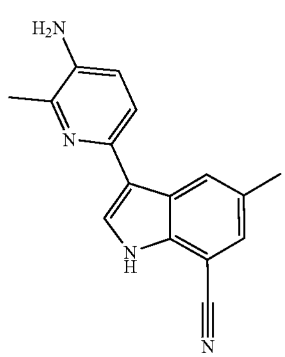 | B | $^1$H NMR (400 MHz, DMSO-d$_6$) δ 11.90 (bs, 1H), 8.61 (s, 1H), 7.85 (d, J = 2.4 Hz, 1H), 7.44-7.43 (m, 2H), 6.97 (d, J = 8.4 Hz, 1H), 4.96 (s, 2H), 2.45 (s, 3H), 2.38 (s, 3H). | MS (ESI) calcd for C$_{16}$H$_{14}$N$_4$ [M + 1]$^+$, 263.1; found, 263.1. |

TABLE 1-continued

| No. | Structure | IC$_{50}$ (μM) | $^1$H NMR | LCMS |
|---|---|---|---|---|
| 153 | 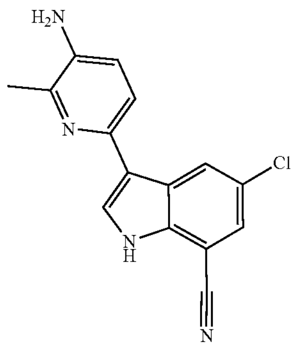 [SMILES: Cc1nc(-c2c[nH]c3c(C#N)cc(Cl)cc23)ccc1N] | B | $^1$H NMR (400 MHz, DMSO-d$_6$) δ 12.28 (bs, 1H), 8.89 (d, J = 2.0 Hz, 1H), 8.03 (d, J = 2.4 Hz, 1H), 7.75 (d, J = 2.0 Hz, 1H), 7.48 (d, J = 8.0 Hz, 1H), 6.98 (d, J = 8.4 Hz, 1H), 5.03 (s, 2H), 2.37 (s, 3H). | MS (ESI) calcd for C$_{15}$H$_{11}$ClN$_4$ [M + 1]$^+$, 283.1; found, 283.0. |
| 154 | 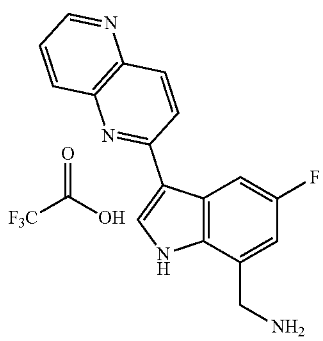 | C | $^1$H NMR (400 MHz, DMSO-d$_6$) δ 12.14 (bs, 1H), 8.89-8.87 (m, 1H), 8.68-8.65 (m, 2H), 8.49 (d, J = 8.0 Hz, 1H), 8.34-8.32 (m, 5H), 7.74-7.74 (m, 1H), 7.28-7.25 (m, 1H), 4.42 (s, 2H). | MS (ESI) calcd for C$_{17}$H$_{13}$FN$_4$ [M + 1]$^+$, 293.1; found, 293.1. |
| 155 | 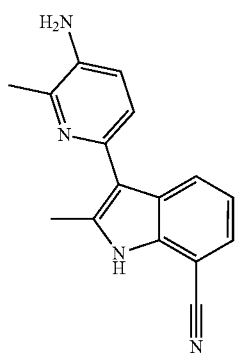 [SMILES: Cc1nc(-c2c(C)[nH]c3c(C#N)cccc23)ccc1N] | A | $^1$H NMR (400 MHz, DMSO-d$_6$) δ 11.85 (bs, 1H), 8.23 (d, J = 8.0 Hz, 1H), 7.51 (d, J = 7.6 Hz, 1H), 7.16-7.11 (m, 2H), 7.01 (d, J = 8.0 Hz, 1H), 5.01 (s, 2H), 2.57 (s, 3H), 2.34 (s, 3H). | MS (ESI) calcd for C$_{16}$H$_{14}$N$_4$ [M + 1]$^+$, 263.1; found, 263.1. |
| 156 | 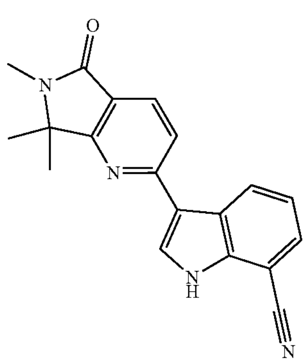 [SMILES: CN1C(=O)c2ccc(-c3c[nH]c4c(C#N)cccc34)nc2C1(C)C] | C | $^1$H NMR (400 MHz, DMSO-d$_6$) δ 12.56 (bs, 1H), 8.99 (d, J = 8.4 Hz, 1H), 8.47 (s, 1H), 8.04-7.99 (m, 2H), 7.73 (d, J = 7.2 Hz, 1H), 7.37 (t, J = 8.0 Hz, 1H), 3.00 (s, 3H), 1.54 (s, 6H). | MS (ESI) calcd for C$_{19}$H$_{16}$N$_4$O [M + 1]$^+$, 317.1; found, 317.1. |

TABLE 1-continued

| No. | Structure | IC$_{50}$ (μM) | $^1$H NMR | LCMS |
|---|---|---|---|---|
| 157 | 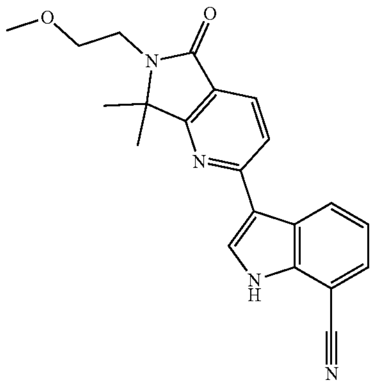 [SMILES: COCCN1C(=O)c2ccc(-c3c[nH]c4c(C#N)cccc34)nc2C1(C)C] | A | $^1$H NMR (400 MHz, DMSO-d$_6$) δ 12.61 (bs, 1H), 9.00 (dd, J = 8.0, 1.2 Hz, 1H), 8.49 (s, 1H), 8.04-7.98 (m, 2H), 7.74-7.72 (m, 1H), 7.39-7.34 (m, 1H), 3.65-3.55 (m, 4H), 3.30 (s, 3H), 1.57 (s, 6H). | MS (ESI) calcd for C$_{21}$H$_{20}$N$_4$O$_2$ [M + 1]$^+$, 361.2; found, 361.2. |
| 158 | 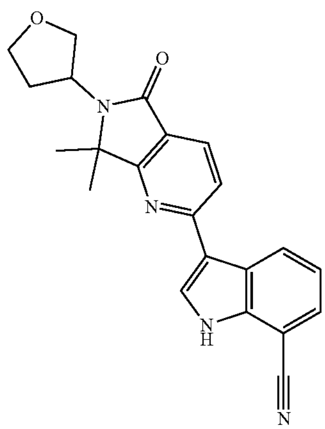 [SMILES: CC1(C)c2nc(-c3c[nH]c4c(C#N)cccc34)ccc2C(=O)N1C1CCOC1] | A | $^1$H NMR (400 MHz, DMSO-d$_6$) δ 12.60 (bs, 1H), 8.99 (d, J = 8.0 Hz, 1H), 8.48 (s, 1H), 8.03 (d, J = 8.0 Hz, 1H), 7.96 (d, J = 8.0 Hz, 1H), 7.73 (d, J = 7.6 Hz, 1H), 7.41-7.32 (m, 1H), 4.30-4.21 (m, 1H), 4.12-4.02 (m, 1H), 3.94-3.82 (m, 3H), 2.50-2.39 (m, 1H), 2.16-2.04 (m, 1H), 1.59 (s, 3H), 1.54 (s, 3H). | MS (ESI) calcd for C$_{22}$H$_{20}$N$_4$O$_2$ [M + 1]$^+$, 373.2; found, 373.2. |
| 159 | 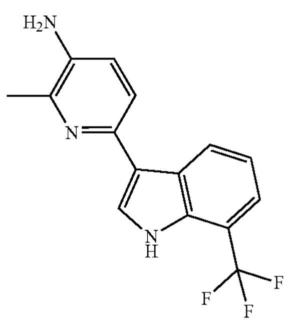 [SMILES: Cc1nc(-c2c[nH]c3c(C(F)(F)F)cccc23)ccc1N] | C | $^1$H NMR (400 MHz, DMSO-d$_6$) δ 11.51 (bs, 1H), 8.79 (d, J = 8.0 Hz, 1H), 7.85 (d, J = 2.8 Hz, 1H), 7.46 (d, J = 8.0 Hz, 2H), 7.24-7.20 (m, 1H), 6.98 (d, J = 8.4 Hz, 1H), 4.97 (s, 2H), 2.38 (s, 3H). | MS (ESI) calcd for C$_{15}$H$_{12}$F$_3$N$_3$ [M + 1]$^+$, 292.0; found, 292.0. |
| 160 | 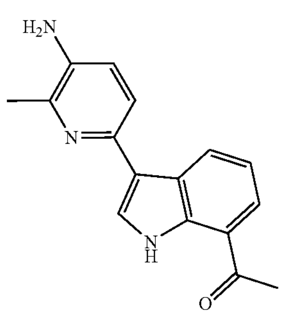 [SMILES: CC(=O)c1cccc2c(-c3ccc(N)c(C)n3)c[nH]c12] | A | $^1$H NMR (400 MHz, DMSO-d$_6$) δ 11.43 (bs, 1H), 8.80 (d, J = 7.6 Hz, 1H), 7.90 (d, J = 7.6 Hz, 1H), 7.76 (s, 1H), 7.48-7.40 (m, 1H), 7.27-7.19 (m, 1H), 6.97 (d, J = 8.0 Hz, 1H), 4.96 (s, 2H), 2.69 (s, 3H), 2.37 (s, 3H). | MS (ESI) calcd for C$_{16}$H$_{15}$N$_3$O [M + 1]$^+$, 266.1; found, 266.1. |

TABLE 1-continued

| No. | Structure | IC$_{50}$ (μM) | $^1$H NMR | LCMS |
|---|---|---|---|---|
| 161 | 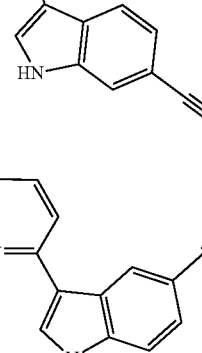 | B | $^1$H NMR (400 MHz, DMSO-d$_6$) δ 12.04 (bs, 1H), 8.71 (d, J = 8.4 Hz, 1H), 8.38 (d, J = 2.8 Hz, 1H), 7.99-7.89 (m, 1H), 7.72-7.62 (m, 2H), 7.51-7.41 (m, 1H), 7.10-7.01 (m, 1H), 2.55 (s, 3H). | MS (ESI) calcd for C$_{15}$H$_{11}$N$_3$ [M + 1]$^+$, 233.1; found, 234.1. |
| 162 | 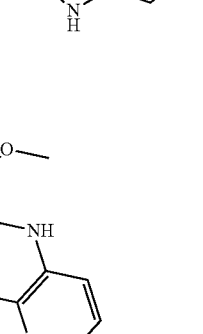 | B | $^1$H NMR (400 MHz, DMSO-d$_6$) δ 12.03 (bs, 1H), 8.99 (s, 1H), 8.30 (d, J = 2.8 Hz, 1H), 7.70-7.59 (m, 3H), 7.51 (d, J = 8.4 Hz, 1H), 7.05 (d, J = 7.2 Hz, 1H), 2.57 (s, 3H). | MS (ESI) calcd for C$_{15}$H$_{11}$N$_3$ [M + 1]$^+$, 234.1; found, 234.1. |
| 163 | 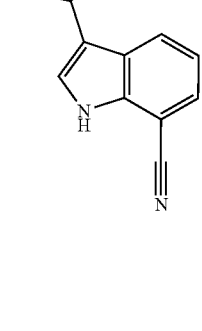 | C | $^1$H NMR (400 MHz, DMSO-d$_6$) δ 8.73-8.66 (m, 1H), 7.86 (s, 1H), 7.64-7.56 (m, 1H), 7.49 (d, J = 8.4 Hz, 1H), 7.28-7.19 (m, 1H), 6.99 (d, J = 8.4 Hz, 1H), 3.56-3.49 (m, 2H), 3.31-3.24 (m, 5H), 2.37 (s, 3H). | MS (ESI) calcd for C$_{18}$H$_{18}$N$_4$O [M + 1]$^+$, 307.1; found, 307.2. |
| 164 | 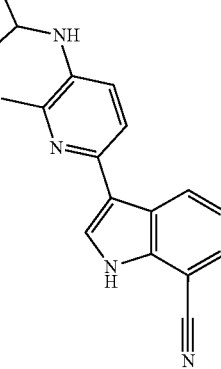 | C | $^1$H NMR (400 MHz, DMSO-d$_6$) δ 12.07 (bs, 1H), 8.83 (d, J = 8.0 Hz, 1H), 7.95 (d, J = 2.4 Hz, 1H), 7.66-7.59 (m, 1H), 7.56 (d, J = 8.4 Hz, 1H), 7.27-7.19 (m, 1H), 6.95 (d, J = 8.4 Hz, 1H), 5.02 (d, J = 6.0 Hz, 1H), 4.07-4.06 (m, 1H), 4.00-3.92 (m, 1H), 3.92-3.82 (m, 1H), 3.80-3.70 (m, 1H), 3.66-3.59 (m, 1H), 2.44 (s, 3H), 2.33-2.17 (m, 1H), 1.93-1.85 (m, 1H). | MS (ESI) calcd for C$_{19}$H$_{18}$N$_4$O [M + 1]$^+$, 319.1; found, 319.2. |

TABLE 1-continued

| No. | Structure | IC$_{50}$ (μM) | $^1$H NMR | LCMS |
|---|---|---|---|---|
| 165 | 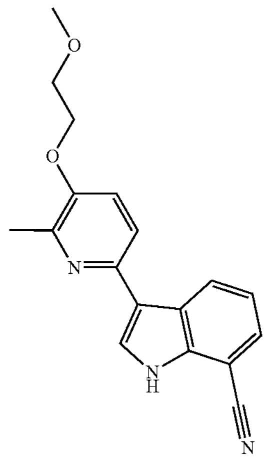 [SMILES: COCCOc1ccc(-c2c[nH]c3c(C#N)cccc23)nc1C] | C | $^1$H NMR (400 MHz, Methanol-d$_4$) δ 8.54 (dd, J = 8.4, 1.2 Hz, 1H), 7.84 (s, 1H), 7.62-7.55 (m, 2H), 7.41 (d, J = 8.4 Hz, 1H), 7.27 (dd, J = 8.0, 7.2 Hz, 1H), 4.26-4.19 (m, 2H), 3.87-3.80 (m, 2H), 3.49 (s, 3H), 2.55 (s, 3H). | MS (ESI) calcd for C$_{18}$H$_{17}$N$_3$O$_2$ [M + 1]$^+$, 308.1; found, 308.1. |
| 166 | 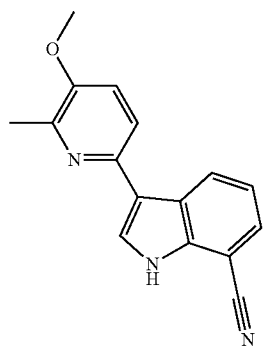 [SMILES: COc1ccc(-c2c[nH]c3c(C#N)cccc23)nc1C] | D | $^1$H NMR (400 MHz, Methanol-d$_4$) δ 8.54 (dd, J = 8.2, 1.2 Hz, 1H), 7.83 (s, 1H), 7.63-7.55 (m, 2H), 7.40 (d, J = 8.4 Hz, 1H), 7.27 (dd, J = 8.0, 7.6 Hz, 1H), 3.92 (s, 3H), 2.52 (s, 3H). | MS (ESI) calcd for C$_{16}$H$_{13}$N$_3$O [M + 1]$^+$, 264.1; found, 264.1. |
| 167 | 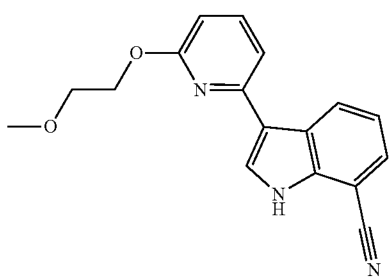 [SMILES: COCCOc1cccc(-c2c[nH]c3c(C#N)cccc23)n1] | B | $^1$H NMR (400 MHz, Methanol-d$_4$) δ 8.79 (d, J = 8.4 Hz, 1H), 8.04-7.99 (m, 1H), 7.72-7.64 (m, 1H), 7.59 (d, J = 7.6 Hz, 1H), 7.41 (d, J = 7.2 Hz, 1H), 7.33-7.25 (m, 1H), 6.64 (d, J = 8.4 Hz, 1H), 4.62 (t, J = 4.8 Hz, 2H), 3.85 (t, J = 4.8 Hz, 2H), 3.47 (s, 3H). | MS (ESI) calcd for C$_{17}$H$_{15}$N$_3$O$_2$ [M + 1]$^+$, 294.1; found, 294.1. |
| 168 | 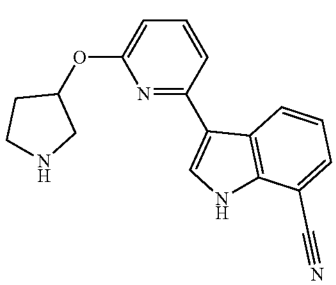 [SMILES: N#Cc1cccc2c(-c3cccc(OC4CCNC4)n3)c[nH]c12] | A | $^1$H NMR (400 MHz, DMSO-d$_6$) δ 8.85-8.74 (m, 1H), 8.26 (s, 1H), 7.76-7.65 (m, 2H), 7.58-7.49 (m, 1H), 7.36-7.27 (m, 1H), 6.67-6.55 (m, 1H), 5.60-5.58 (m, 1H), 3.24-3.16 (m, 1H), 3.08-2.90 (m, 3H), 2.23-2.12 (m, 1H), 1.97-1.86 (m, 1H). | MS (ESI) calcd for C$_{18}$H$_{16}$N$_4$O [M + 1]$^+$, 305.1; found, 305.1. |

TABLE 1-continued

| No. | Structure | IC$_{50}$ (μM) | $^1$H NMR | LCMS |
|---|---|---|---|---|
| 189 | 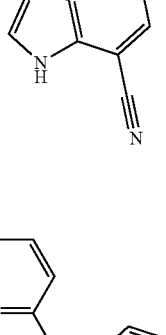 | B | $^1$H NMR (400 MHz, DMSO-d$_6$) δ 12.38 (bs, 1H), 8.79 (d, J = 7.2 Hz, 1H), 8.23 (s, 1H), 7.73-7.65 (m, 2H), 7.50 (d, J = 7.6 Hz, 1H), 7.36-7.28 (m, 1H), 6.59 (d, J = 8.0 Hz, 1H), 5.57-5.56 (m, 1H), 2.93-2.84 (m, 1H), 2.75-2.64 (m, 2H), 2.46-2.33 (m, 2H), 2.28 (s, 3H), 1.93-1.90 (m, 1H). | MS (ESI) calcd for C$_{19}$H$_{18}$N$_4$O [M + 1]$^+$, 319.1; found, 319.2. |
| 170 | 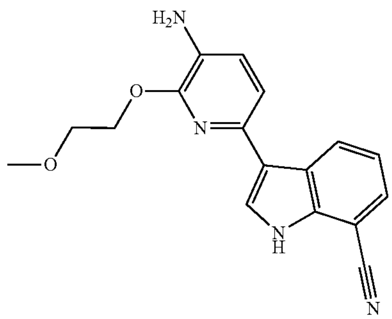 [SMILES: COCCOc1nc(-c2c[nH]c3c(C#N)cccc23)ccc1N] | C | $^1$H NMR (400 MHz, DMSO-d$_6$) δ 12.10 (bs, 1H), 8.75-8.68 (m, 1H), 7.93 (s, 1H), 7.66-7.60 (m, 1H), 7.31-7.20 (m, 2H), 6.96 (d, J = 8.0 Hz, 1H), 4.83 (s, 2H), 4.59-4.52 (t, J = 4.8 Hz, 2H), 3.82-3.75 (t, J = 4.8 Hz, 2H), 3.35 (s, 3H). | MS (ESI) calcd for C$_{17}$H$_{16}$N$_4$O$_2$ [M + 1]$^+$, 309.1; found, 309.1. |
| 171 | 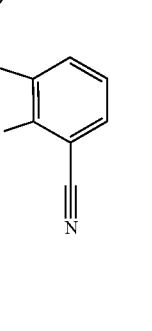 | D | $^1$H NMR (400 MHz, DMSO-d$_6$) δ 12.31 (bs, 1H), 7.80 (d, J = 2.4 Hz, 1H), 7.72-7.70 (m, 2H), 7.68 (t, J = 73.6 Hz, 1H), 7.44 (d, J = 2.0 Hz, 1H), 7.29-7.25 (m, 1H), 5.34 (s, 2H). | MS (ESI) calcd for C$_{15}$H$_{10}$F$_2$N$_4$O [M + 1]$^+$, 301.1; found, 301.1. |
| 172 | 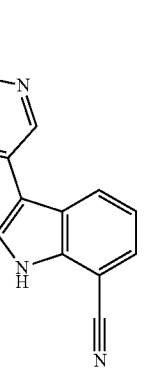 | D | $^1$H NMR (400 MHz, DMSO-d$_6$) δ 12.28 (bs, 1H), 8.56 (d, J = 8.4 Hz, 1H), 8.37 (s, 1H), 8.09 (d, J = 2.4 Hz, 1H), 7.87 (t, J = 72.4 Hz, 1H), 7.70-7.55 (m, 1H), 7.28-7.24 (m, 1H), 6.51 (s, 2H). | MS (ESI) calcd for C$_{14}$H$_9$F$_2$N$_5$O [M + 1]$^+$, 302.0; found, 302.1. |

TABLE 1-continued

| No. | Structure | IC$_{50}$ (μM) | $^1$H NMR | LCMS |
|---|---|---|---|---|
| 173 | 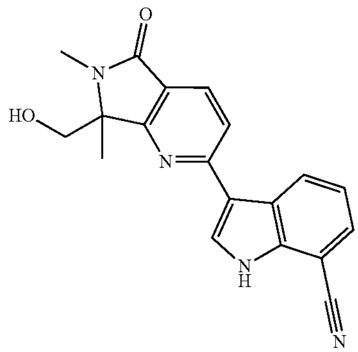 [SMILES: CN1C(=O)c2ccc(-c3c[nH]c4c(C#N)cccc34)nc2C1(C)CO] | B | $^1$H NMR (400 MHz, DMSO-d$_6$) δ 12.57 (bs, 1H), 8.99 (d, J = 8.0 Hz, 1H), 8.46 (d, J = 2.8 Hz, 1H), 8.04-7.93 (m, 2H), 7.77-7.70 (m, 1H), 7.40-7.33 (m, 1H), 4.88 (br, 1H), 3.96-3.82 (m, 2H), 2.97 (s, 3H), 1.45 (s, 3H). | MS (ESI) calcd for C$_{19}$H$_{16}$N$_4$O$_2$ [M + 1]$^+$, 333.1; found, 333.2. |
| 174 | 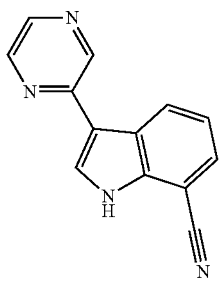 [SMILES: N#Cc1cccc2c(-c3cnccn3)c[nH]c12] | B | $^1$H NMR (400 MHz, DMSO-d$_6$) δ 12.61 (bs, 1H), 9.26 (d, J = 1.6 Hz, 1H), 8.85-8.78 (m, 1H), 8.67-8.62 (m, 1H), 8.50 (d, J = 2.4 Hz, 1H), 8.42 (d, J = 2.4 Hz, 1H), 7.77-7.70 (m, 1H), 7.37-7.29 (m, 1H). | MS (ESI) calcd for C$_{13}$H$_8$N$_4$ [M + 1]$^+$, 221.1; found, 221.1. |
| 175 | 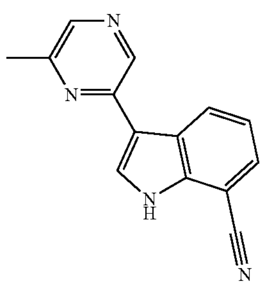 [SMILES: Cc1cncc(-c2c[nH]c3c(C#N)cccc23)n1] | C | $^1$H NMR (400 MHz, DMSO-d$_6$) δ 12.57 (bs, 1H), 9.04 (s, 1H), 8.86 (d, J = 8.0 Hz, 1H), 8.46 (d, J = 2.8 Hz, 1H), 8.31 (s, 1H), 7.76-7.69 (m, 1H), 7.38-7.29 (m, 1H), 2.58 (s, 3H). | MS (ESI) calcd for C$_{14}$H$_{10}$N$_4$ [M + 1]$^+$, 235.1; found, 235.1. |
| 176 | 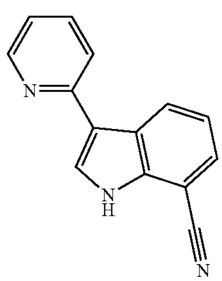 [SMILES: N#Cc1cccc2c(-c3ccccn3)c[nH]c12] | C | $^1$H NMR (400 MHz, DMSO-d$_6$) δ 12.39 (bs, 1H), 8.91-8.84 (m, 1H), 8.66-8.59 (m, 1H), 8.28 (d, J = 2.8 Hz, 1H), 7.97-7.90 (m, 1H), 7.83-7.75 (m, 1H), 7.72-7.66 (m, 1H), 7.34-7.25 (m, 1H), 7.24-7.16 (m, 1H). | MS (ESI) calcd for C$_{14}$H$_9$N$_3$ [M + 1]$^+$, 220.1; found, 220.1. |
| 177 | 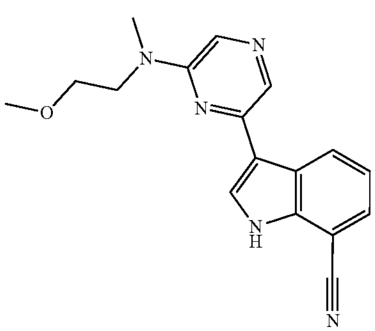 [SMILES: COCCN(C)c1cncc(-c2c[nH]c3c(C#N)cccc23)n1] | C | $^1$H NMR (400 MHz, DMSO-d$_6$) δ 12.46 (bs, 1H), 8.75 (d, J = 8.0 Hz, 1H), 8.39 (s, 1H), 8.31 (d, J = 2.4 Hz, 1H), 7.93 (s, 1H), 7.69 (d, J = 7.6 Hz, 1H), 7.33-7.24 (m, 1H), 3.86-3.78 (m, 2H), 3.64-3.57 (m, 2H), 3.24 (s, 3H), 3.17 (s, 3H). | MS (ESI) calcd for C$_{17}$H$_{17}$N$_5$O [M + 1]$^+$, 308.1; found, 308.1. |

TABLE 1-continued

| No. | Structure | IC$_{50}$ (μM) | $^1$H NMR | LCMS |
|---|---|---|---|---|
| 178 | 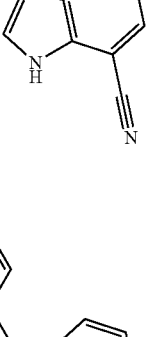 | C | $^1$H NMR (400 MHz, DMSO-d$_6$) δ 12.27 (bs, 1H), 8.90 (d, J = 8.0 Hz, 1H), 8.15 (d, J = 2.4 Hz, 1H), 7.65 (d, J = 7.6 Hz, 1H), 7.53-7.48 (m, 1H), 7.27-7.22 (m, 1H), 7.18 (d, J = 7.2 Hz, 1H), 6.17 (d, J = 8.0 Hz, 1H), 4.03 (t, J = 7.2 Hz, 4H), 2.39-2.34 (m, 2H). | MS (ESI) calcd for C$_{17}$H$_{14}$N$_4$ [M + 1]$^+$, 275.1; found, 275.1. |
| 179 | 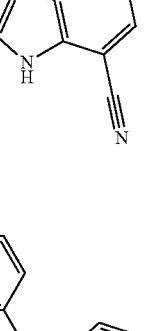 | C | $^1$H NMR (400 MHz, DMSO-d$_6$) δ 12.33 (bs, 1H), 8.37 (d, J = 1.2 Hz, 1H), 8.31 (d, J = 8.0 Hz, 1H), 8.03-7.86 (m, 2H), 7.86-7.76 (m, 1H), 7.70 (d, J = 7.2 Hz, 1H), 7.31-7.26 (m, 1H), 2.81 (s, 3H). | MS (ESI) calcd for C$_{17}$H$_{11}$N$_3$S [M + 1]$^+$, 290.1; found, 290.0. |
| 180 | 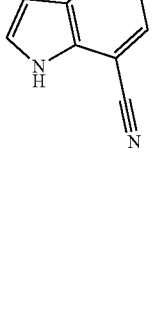 | B | $^1$H NMR (400 MHz, DMSO-d$_6$) δ 12.18 (bs, 1H), 8.22 (d, J = 8.0 Hz, 1H), 7.98 (d, J = 1.6 Hz, 1H), 7.77 (d, J = 2.4 Hz, 1H), 7.67 (d, J = 7.6 Hz, 1H), 7.58-7.48 (m, 1H), 7.46 (s, 2H), 7.40 (d, J = 8.4 Hz, 1H), 7.27-7.22 (m, 1H), | MS (ESI) calcd for C$_{16}$H$_{10}$N$_4$S [M + 1]$^+$, 291.1; found, 291.0. |
| 181 | 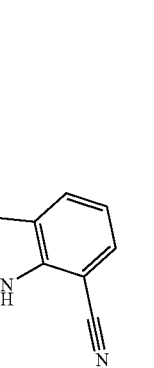 | C | $^1$H NMR (400 MHz, DMSO-d$_6$) δ 12.55-11.85 (bs, 1H), 8.78 (d, J = 8.0 Hz, 1H), 8.46-8.43 (m, 1H), 8.02 (s, 1H), 7.65 (d, J = 7.2 Hz, 1H), 7.26-7.21 (m, 1H), 6.36-6.18 (m, 1H), 4.50-4.30 (m, 1H), 3.73-3.40 (m, 1H), 3.30-3.18 (m, 1H), 3.16-2.94 (m, 1H), 2.93-2.67 (m, 1H), 2.44 (s, 3H), 2.25-1.88 (m, 1H), 1.84-1.70 (m, 1H). | MS (ESI) calcd for C$_{18}$H$_{18}$N$_6$ [M + 1]+, 319.2; found, 319.2. |

TABLE 1-continued

| No. | Structure | IC$_{50}$ (μM) | $^1$H NMR | LCMS |
|---|---|---|---|---|
| 182 | 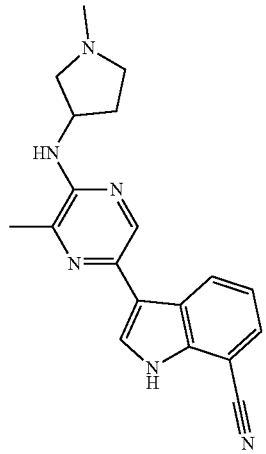 [SMILES: Cc1nc(-c2c[nH]c3c(C#N)cccc23)cnc1NC1CCN(C)C1] | C | $^1$H NMR (400 MHz, DMSO-d$_6$) δ 12.17 (bs, 1H), 8.68 (d, J = 7.6 Hz, 1H), 8.42 (s, 1H), 7.99 (d, J = 2.4 Hz, 1H), 7.65 (d, J = 7.2 Hz, 1H), 7.26-7.21 (m, 1H), 6.22 (d, J = 6.4 Hz, 1H), 4.60-4.28 (m, 1H), 2.83-2.79 (m, 1H), 2.67-2.60 (m, 1H), 2.49-2.39 (m, 5H), 2.28 (s, 3H), 2.27-2.17 (m, 1H), 1.88-1.72 (m, 1H). | MS (ESI) calcd for C$_{19}$H$_{20}$N$_6$ [M + 1]$^+$, 333.2; found, 333.1. |
| 183 | 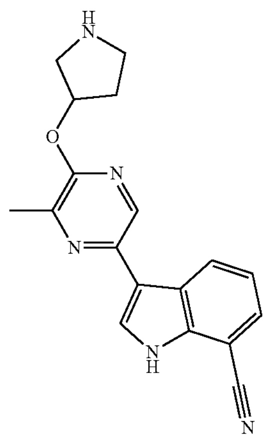 [SMILES: Cc1nc(-c2c[nH]c3c(C#N)cccc23)cnc1OC1CCNC1] | C | $^1$H NMR (400 MHz, DMSO-d6) δ 12.85-11.66 (bs, 1H), 8.72 (d, J = 8.0 Hz, 1H), 8.57 (s, 1H), 8.17 (s, 1H), 7.68 (d, J = 7.6 Hz, 1H), 7.30-7.25 (m, 1H), 5.51-5.33 (m, 1H), 3.73-3.37 (m, 1H), 3.16-3.06 (m, 1H), 2.97-2.64 (m, 2H), 2.47 (s, 3H), 2.1-2.0 (m, 1H), 1.85-1.82 (m, 1H). | MS (ESI) calcd for C$_{18}$H$_{17}$N$_5$O [M + 1]$^+$, 320.4; found, 320.1 |
| 184 | 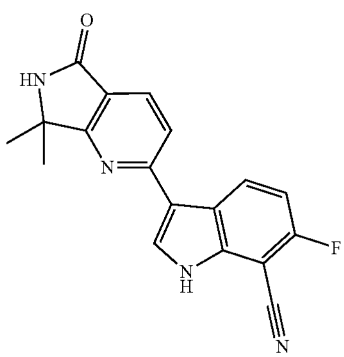 [SMILES: CC1(C)NC(=O)c2ccc(-c3c[nH]c4c(C#N)c(F)ccc34)nc21] | C | $^1$H NMR (400 MHz, DMSO-d$_6$) δ 12.73 (bs, 1H), 9.00-8.97 (m, 1H), 8.77 (s, 1H), 8.49 (d, J = 2.4 Hz, 1H), 8.03-7.97 (m, 2H), 7.35-7.30 (m, 1H), 1.54 (s, 6H). | MS (ESI) calcd for C$_{18}$H$_{13}$FN$_4$O [M + 1]$^+$, 321.1; found, 321.0. |
| 185 | 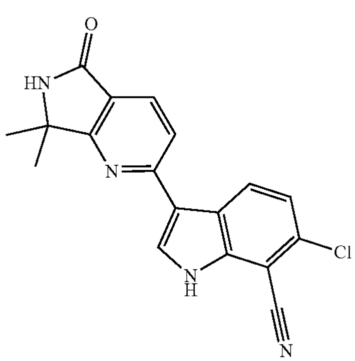 [SMILES: CC1(C)NC(=O)c2ccc(-c3c[nH]c4c(C#N)c(Cl)ccc34)nc21] | B | $^1$H NMR (400 MHz, Methanol-d$_4$) δ 8.94 (d, J = 8.8 Hz, 1H), 8.26 (s, 1H), 8.07 (d, J = 8.4 Hz, 1H), 7.94 (d, J = 8.4 Hz, 1H), 7.42 (d, J = 8.8 Hz, 1H), 1.66 (s, 6H). | MS (ESI) calcd for C$_{18}$H$_{13}$ClN$_4$O [M + 1]$^+$, 337.1; found, 337.1. |

TABLE 1-continued

| No. | Structure | IC$_{50}$ (μM) | $^1$H NMR | LCMS |
|---|---|---|---|---|
| 186 | 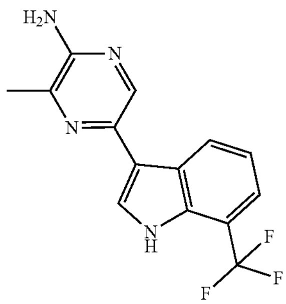 [SMILES: Cc1nc(-c2c[nH]c3c(C(F)(F)F)cccc23)cnc1N] | C | $^1$H NMR (400 MHz, DMSO-d6) δ 11.63 (s, 1H), 8.64 (d, J = 8.0 Hz, 1H), 8.36 (s, 1H), 7.95 (d, J = 2.4 Hz, 1H), 7.49 (d, J = 7.6 Hz, 1H), 7.24 (t, J = 7.6 Hz, 1H), 6.06 (s, 2H), 2.40 (s, 3H). | MS (ESI) calcd for C$_{14}$H$_{11}$F$_3$N$_4$ [M + 1]$^+$, 293.1. found, 293.1. |
| 187 | 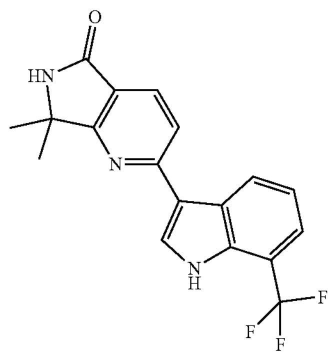 [SMILES: CC1(C)NC(=O)c2ccc(-c3c[nH]c4c(C(F)(F)F)cccc34)nc21] | D | $^1$H NMR (400 MHz, DMSO-d$_6$) δ 12.05 (bs, 1H), 8.95 (d, J = 8.0 Hz, 1H), 8.74 (s, 1H), 8.40 (d, J = 2.4 Hz, 1H), 8.04 (d, J = 8.0 Hz, 1H), 7.96 (d, J = 8.0 Hz, 1H), 7.57 (d, J = 7.2 Hz, 1H), 7.36 (t, J = 7.2 Hz, 1H), 1.55 (s, 6H). | MS (ESI) calcd for C$_{18}$H$_{14}$FN$_3$O [M + 1]$^+$, 346.1. found, 346.1. |
| 188 | 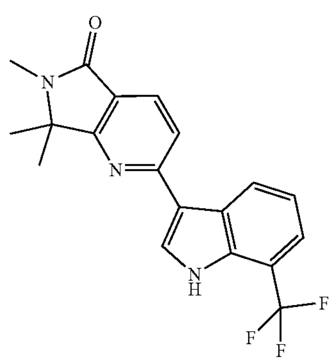 [SMILES: CN1C(=O)c2ccc(-c3c[nH]c4c(C(F)(F)F)cccc34)nc2C1(C)C] | C | $^1$H NMR (400 MHz, DMSO-d$_6$) δ 12.06 (bs, 1H), 8.97 (d, J = 8.0 Hz, 1H), 8.41 (d, J = 2.8 Hz, 1H), 8.06 (d, J = 8.0 Hz, 1H), 8.00 (d, J = 8.0 Hz, 1H), 7.57 (d, J = 7.6 Hz, 1H), 7.38 (t, J = 7.6 Hz, 1H), 3.00 (s, 3H), 1.55 (s, 6H). | MS (ESI) calcd for C$_{19}$H$_{16}$F$_3$N$_3$O [M + 1]$^+$, 360.1; found, 360.1. |
| 189 | 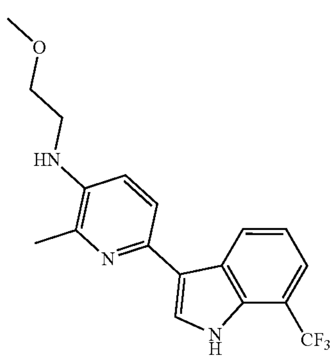 [SMILES: COCCNc1ccc(-c2c[nH]c3c(C(F)(F)F)cccc23)nc1C] | C | $^1$H NMR (400 MHz, Methanol-d$_4$) δ 8.42-8.32 (m, 1H), 7.70 (s, 1H), 7.53-7.43 (m, 2H), 7.29-7.19 (m, 1H), 7.15 (d, J = 8.4 Hz, 1H), 3.68 (t, J = 5.6 Hz, 2H), 3.43-3.36 (m, 5H), 2.48 (s, 3H). | MS (ESI) calcd for C$_{18}$H$_{18}$F$_3$N$_3$O [M + 1]$^+$, 350.2; found, 350.2. |

TABLE 1-continued

| No. | Structure | IC$_{50}$ (μM) | $^1$H NMR | LCMS |
|---|---|---|---|---|
| 190 | 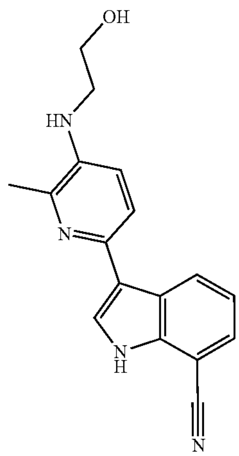 [SMILES: Cc1nc(-c2c[nH]c3c(C#N)cccc23)ccc1NCCO] | C | $^1$H NMR (400 MHz, DMSO-d$_6$) δ 12.06 (bs, 1H), 8.87-8.80 (m, 1H), 7.94 (d, J = 2.0 Hz, 1H), 7.65-7.62 (m, 1H), 7.56 (d, J = 8.4 Hz, 1H), 7.27-7.19 (m, 1H), 6.95 (d, J = 8.4 Hz, 1H), 5.01-4.94 (m, 1H), 4.82-4.74 (m, 1H), 3.66-3.57 (m, 2H), 3.24-3.15 (m, 2H), 2.42 (s, 3H). | MS (ESI) calcd for C$_{17}$H$_{16}$N$_4$O [M + 1]$^+$, 293.1; found, 293.1. |
| 191 | 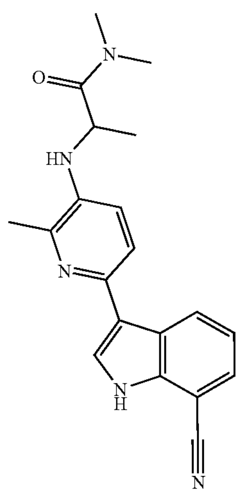 [SMILES: Cc1nc(-c2c[nH]c3c(C#N)cccc23)ccc1NC(C)C(=O)N(C)C] | B | $^1$H NMR (400 MHz, DMSO-d$_6$) δ 12.10 (bs, 1H), 8.84 (d, J = 8.0 Hz, 1H), 7.96 (d, J = 2.4 Hz, 1H), 7.63 (d, J = 7.2 Hz, 1H), 7.55 (d, J = 8.4 Hz, 1H), 7.26-7.21 (m, 1H), 6.94 (d, J = 8.4 Hz, 1H), 4.95 (d, J = 8.4 Hz, 1H), 4.63-4.55 (m, 1H), 3.10 (s, 3H), 2.87 (s, 3H), 2.45 (s, 3H), 1.32 (d, J = 6.8 Hz, 3H). | MS (ESI) calcd for C$_{20}$H$_{21}$N$_5$O [M + 1]$^+$, 348.0; found, 348.0. |
| 192 | 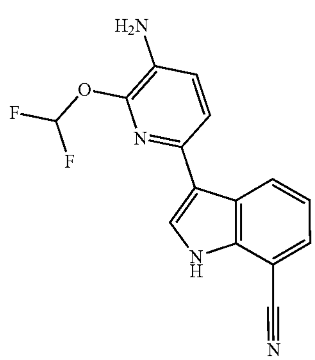 [SMILES: N#Cc1cccc2c(-c3ccc(N)c(OC(F)F)n3)c[nH]c12] | C | $^1$H NMR (400 MHz, DMSO-d$_6$) δ 12.18 (bs, 1H), 8.65 (d, J = 8.0 Hz, 1H), 8.03-8.00 (m, 1H), 7.83 (s, 1H), 7.65 (d, J = 6.8 Hz, 1H), 7.52 (d, J = 8.0 Hz, 1H), 7.28-7.23 (m, 1H), 7.15 (d, J = 8.0 Hz, 1H), 5.19 (s, 2H). | MS (ESI) calcd for C$_{15}$H$_{10}$F$_2$N$_4$O [M + 1]+, 301.1; found, 301.1. |

TABLE 1-continued

| No. | Structure | IC$_{50}$ (μM) | $^1$H NMR | LCMS |
|---|---|---|---|---|
| 193 | 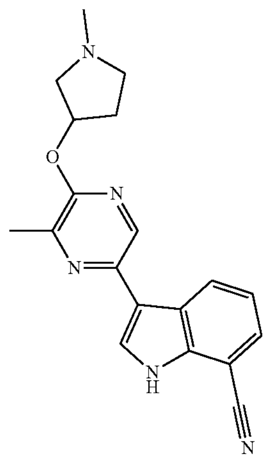 [SMILES: Cc1nc(-c2c[nH]c3c(C#N)cccc23)cnc1OC1CCN(C)C1] | B | $^1$H NMR (400 MHz, Methanol-d$_4$) δ 8.64-8.61 (m, 1H), 8.46-8.39 (m, 1H), 7.99-7.95 (m, 1H), 7.63-7.58 (m, 1H), 7.32-7.27 (m, 1H), 5.77-5.73 (m, 1H), 3.91-3.49 (m, 4H), 3.06 (s, 3H), 2.75-2.30 (m, 5H). | MS (ESI) calcd for C$_{19}$H$_{19}$N$_5$O [M + 1]$^+$, 334.1; found, 334.1. |
| 194 | 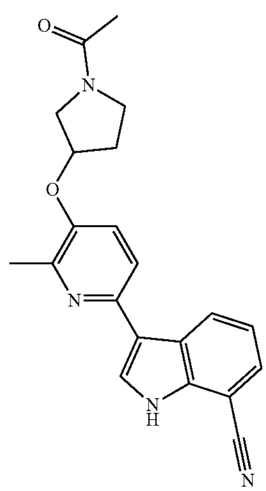 [SMILES: CC(=O)N1CCC(Oc2ccc(-c3c[nH]c4c(C#N)cccc34)nc2C)C1] | C | $^1$H NMR (400 MHz, Methanol-d$_4$) δ 11.88 (bs, 1H), 8.61-8.58 (m, 1H), 8.42 (d, J = 2.0 Hz, 1H), 7.95 (s, 1H), 7.60 (d, J = 7.2 Hz, 1H), 7.30-7.26 (m, 1H), 5.71-5.64 (m, 1H), 4.00-3.61 (m, 4H), 2.53 (s, 3H), 2.40-2.36 (m, 1H), 2.32-2.39 (m, 1H), 2.14 and 2.19 (s, 3H). | MS (ESI) calcd for C$_{20}$H$_{19}$N$_5$O$_2$ [M + 1]$^+$, 362.1; found, 362.1. |
| 195 | 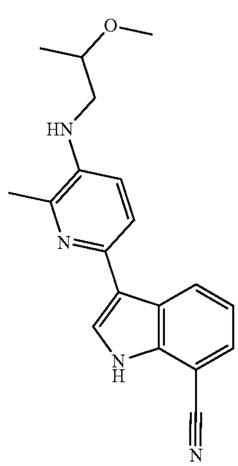 [SMILES: COC(C)CNc1ccc(-c2c[nH]c3c(C#N)cccc23)nc1C] | C | $^1$H NMR (400 MHz, Chloroform-d) δ 8.87-8.51 (m, 2H), 7.70 (d, J = 2.4 Hz, 1H), 7.57 (d, J = 7.4 Hz, 1H), 7.43 (d, J = 8.4 Hz, 1H), 7.34-7.21 (m, 1H), 6.95 (d, J = 8.4 Hz, 1H), 4.02 (bs, 1H), 3.74-3.64 (m, 1H), 3.44 (s, 3H), 3.36-3.29 (m, 1H), 3.17-3.07 (m, 1H), 2.54 (s, 3H), 1.30 (d, J = 6.0 Hz, 3H). | MS (ESI) calcd for C$_{19}$H$_{20}$N$_4$O [M + 1]$^+$, 321.1; found, 321.2 |

TABLE 1-continued

| No. | Structure | IC$_{50}$ (μM) | $^1$H NMR | LCMS |
|---|---|---|---|---|
| 196 | 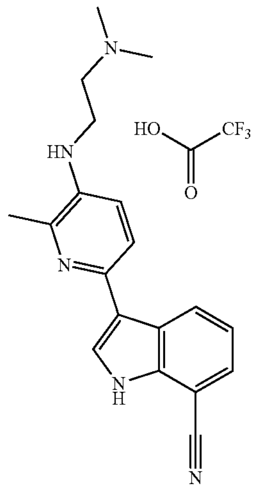 | B | $^1$H NMR (400 MHz, Methanol-d$_4$) δ 8.18-8.16 (m, 1H), 8.03 (s, 1H), 7.94 (d, J = 8.8 Hz, 1H), 7.83 (d, J = 8.8 Hz, 1H), 7.73-7.69 (m, 1H), 7.41-7.37 (m, 1H), 3.81 (t, J = 6.0 Hz, 2H), 3.51 (t, J = 6.0 Hz, 2H), 3.02 (s, 6H), 2.70 (s, 3H). | MS (ESI) calcd for C$_{21}$H$_{22}$F$_3$N$_5$O$_2$ [M + 1]$^+$, 320.2; found, 320.2. |
| 197 | 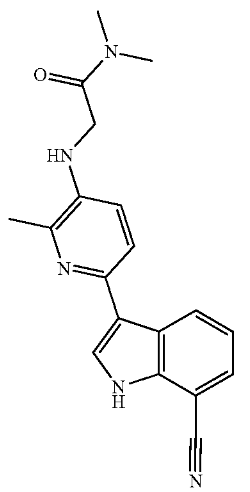 [SMILES: Cc1nc(-c2c[nH]c3c(C#N)cccc23)ccc1NCC(=O)N(C)C] | A | $^1$H NMR (400 MHz, DMSO-d$_6$) δ 12.08 (bs, 1H), 8.85 (d, J = 8.0 Hz, 1H), 7.97 (d, J = 2.8 Hz, 1H), 7.64-7.55 (m, 2H), 7.28-7.19 (m, 1H), 6.94 (d, J = 8.4 Hz, 1H), 5.14-5.11 (m, 1H), 3.99 (d, J = 4.8 Hz, 2H), 3.05 (s, 3H), 2.90 (s, 3H), 2.45 (s, 3H) | MS (ESI) calcd for C$_{19}$H$_{19}$N$_5$O [M + 1]$^+$, 334.2; found, 334.2. |
| 198 | 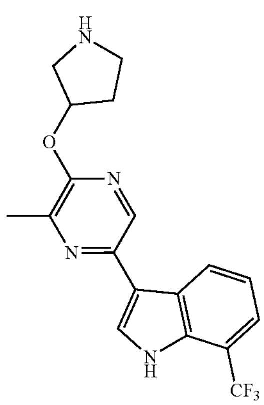 [SMILES: Cc1nc(-c2c[nH]c3c(C(F)(F)F)cccc23)cnc1OC1CCNC1] | C | $^1$H NMR (400 MHz, Methanol-d$_4$) δ 8.55 (d, J = 8.0 Hz, 1H), 8.46 (s, 1H), 7.94 (s, 1H), 7.52 (d, J = 7.6 Hz, 1H), 7.29 (t, J = 7.6 Hz, 1H), 5.82-5.72 (m, 1H), 3.66-3.61 (m, 2H), 3.58-3.51 (m, 2H), 2.59 (s, 3H), 2.5-2.4 (m, 2H) | MS (ESI) calcd for C$_{18}$H$_{17}$F$_3$N$_4$O [M + 1]$^+$, 363.1; found, 363.2 |

TABLE 1-continued

| No. | Structure | IC$_{50}$ (μM) | $^1$H NMR | LCMS |
|---|---|---|---|---|
| 199 | 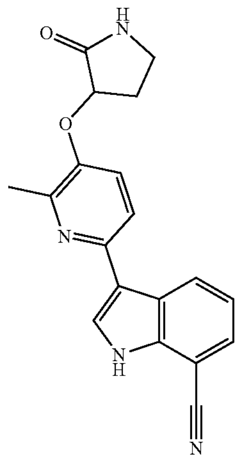 [SMILES: Cc1nc(-c2c[nH]c3c(C#N)cccc23)ccc1OC1CCNC1=O] | B | $^1$H NMR (400 MHz, Methanol-d$_4$) δ 8.33-8.31 (m, 1H), 8.25 (d, J = 8.8 Hz, 1H), 8.09 (s, 1H), 7.98 (d, J = 8.8 Hz, 1H), 7.73-7.71 (m, 1H), 7.41-7.37 (m, 1H), 5.30 (t, J = 7.6 Hz, 1H), 3.60-3.43 (m, 2H), 2.86-2.74 (m, 1H), 2.72 (s, 3H), 2.43-2.29 (m, 1H). | MS (ESI) calcd for C$_{19}$H$_{16}$N$_4$O$_2$ [M + 1]$^+$, 333.1; found, 333.1. |
| 116 | 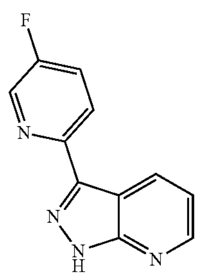 [SMILES: Fc1ccc(-c2n[nH]c3ncccc23)nc1] | B | $^1$H NMR (400 MHz, DMSO-d$_6$) δ 13.96 (bs, 1H), 8.84-8.81 (m, 1H), 8.73 (d, J = 2.8 Hz, 1H), 8.60-8.58 (m, 1H), 8.26-8.23 (m, 1H), 7.90-7.85 (m, 1H), 7.34-7.30 (m, 1H). | MS (ESI) calcd for C$_{11}$H$_7$FN$_4$ [M + 1]$^+$, 215.1; found, 215.1 |
| 200 | 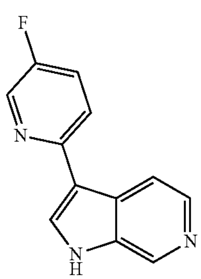 [SMILES: Fc1ccc(-c2c[nH]c3cnccc23)nc1] | A | $^1$H NMR (400 MHz, DMSO-d$_6$) δ 12.00 (bs, 1H), 8.81 (d, J = 1.2 Hz, 1H), 8.60 (d, J = 3.2 Hz, 1H), 8.32 (t, J = 1.2 Hz, 1H), 8.28 (dd, J = 5.6, 1.2 Hz, 1H), 8.21 (d, J = 5.6 Hz, 1H), 7.96 (dd, J = 8.8, 4.4 Hz, 1H), 7.75 (td, J = 8.8, 3.2 Hz, 1H) | MS (ESI) calcd for C$_{12}$H$_8$FN$_3$ [M + 1]$^+$, 214.1; found, 214.0. |
| 114 | 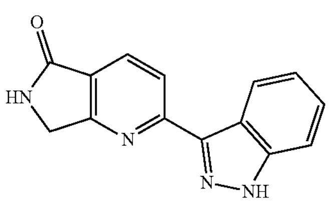 [SMILES: O=C1NCc2nc(-c3n[nH]c4ccccc34)ccc21] | B | $^1$H NMR (300 MHz, DMSO-d$_6$) δ 13.58 (bs, 1H), 8.76 (s, 1H), 8.63 (d, J = 8.1 Hz, 1H), 8.30 (d, J = 8.1 Hz, 1H), 8.14 (d, J = 8.1 Hz, 1H), 7.63 (d, J = 8.4 Hz, 1H), 7.47-7.42 (m, 1H), 7.30-7.25 (m, 1H), 4.57 (s, 2H). | MS (ESI) calcd for C$_{14}$H$_{10}$N$_4$O [M + 1]$^+$, 251.1; found, 251.2. |
| 115 | 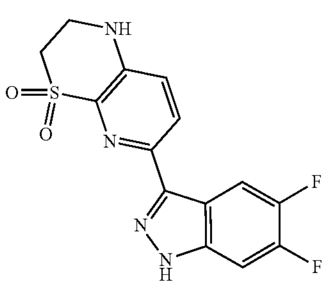 [SMILES: O=S1(=O)CCNc2ccc(-c3n[nH]c4cc(F)c(F)cc34)nc21] | A | $^1$H NMR (400 MHz, DMSO-d$_6$) δ 13.45 (bs, 1H), 8.39 (dd, J = 10.6, 8.0 Hz, 1H), 8.07 (d, J = 8.8 Hz, 1H), 7.67 (dd, J = 10.6, 6.8 Hz, 1H), 7.43-7.33 (m, 2H), 3.79-3.77 (m, 2H), 3.63-3.56 (m, 2H). | MS (ESI) calcd for C$_{14}$H$_{10}$F$_2$N$_4$O$_2$S [M + 1]$^+$, 337.0; found, 373.0. |

TABLE 1-continued

| No. | Structure | IC$_{50}$ (μM) | $^1$H NMR | LCMS |
|---|---|---|---|---|
| 117 | 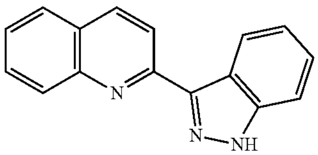 [SMILES: c1ccc2nc(-c3n[nH]c4ccccc34)ccc2c1] | C | $^1$H NMR (400 MHz, DMSO-d$_6$) δ 13.53 (bs, 1H), 8.90 (d, J = 8.0 Hz, 1H), 8.44 (d, J = 8.4 Hz, 1H), 8.37 (d, J = 8.8 Hz, 1H), 8.18 (d, J = 8.4 Hz, 1H), 8.00 (d, J = 7.2 Hz, 1H), 7.84-7.79 (m, 1H), 7.66-7.50 (m, 2H), 7.50-7.45 (m, 1H), 7.35-7.31 (m, 1H). | MS (ESI) calcd for C$_{16}$H$_{11}$N$_3$ [M + 1]$^+$, 246.1; found, 246.0 |
| 201 | 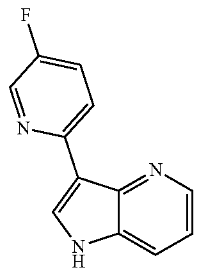 [SMILES: Fc1ccc(-c2c[nH]c3cccnc23)nc1] | B | $^1$H NMR (400 MHz, DMSO-d$_6$) δ 11.74 (bs, 1H), 8.92-8.86 (m, 1H), 8.54-8.48 (m, 2H), 8.29 (s, 1H), 7.89-786 (m, 1H), 7.80-7.75 (m, 1H), 7.24-7.20 (m, 1H). | MS (ESI) calcd for C$_{12}$H$_8$FN$_3$ [M + 1]$^+$, 214.1; found, 214.0. |
| 202 | 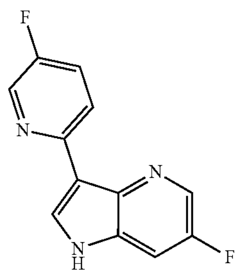 [SMILES: Fc1ccc(-c2c[nH]c3cc(F)cnc23)nc1] | C | $^1$H NMR (400 MHz, DMSO-d$_6$) δ 11.82 (bs, 1H), 8.80 (dd, J = 8.8, 4.8 Hz, 1H), 8.61-8.48 (m, 2H), 8.30 (d, J = 2.4 Hz, 1H), 7.81-7.75 (m, 2H). | MS (ESI) calcd for C$_{12}$H$_7$F$_2$N$_3$ [M + 1]$^+$, 232.0; found, 232.0. |
| 203 | 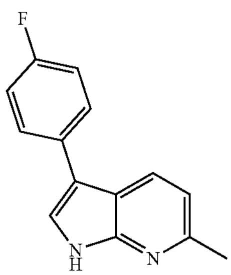 [SMILES: Cc1ccc2c(-c3ccc(F)cc3)c[nH]c2n1] | B | $^1$H NMR (400 MHz, DMSO-d$_6$) δ 11.70 (bs, 1H), 8.14 (d, J = 8.4 Hz, 1H), 7.75-7.71 (m, 3H), 7.25 (t, J = 8.8 Hz, 2H), 7.03 (d, J = 8.0 Hz, 1H), 2.54 (s, 3H). | MS (ESI) calcd for C$_{14}$H$_{11}$FN$_2$ [M + 1]$^+$, 227.1; found, 227.1. |
| 204 | 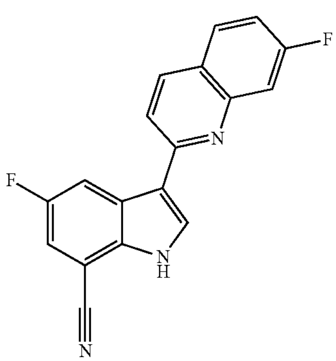 [SMILES: N#Cc1cc(F)cc2c(-c3ccc4ccc(F)cc4n3)c[nH]c12] | C | $^1$H NMR (400 MHz, DMSO-d$_6$) δ 12.71 (bs, 1H), 9.01 (d, J = 8.2 Hz, 1H), 8.66 (d, J = 2.8 Hz, 1H), 8.36 (d, J = 8.8 Hz, 1H), 8.13 (d, J = 8.8 Hz, 1H), 8.05-7.97 (m, 1H), 7.89 (d, J = 8.0 Hz, 1H), 7.77 (d, J = 8.0 Hz, 1H), 7.50-7.41 (m, 1H). | MS (ESI) calcd for C$_{18}$H$_9$F$_2$N$_3$ [M + 1]$^+$, 306.1; found, 306.1. |

TABLE 1-continued

| No. | Structure | IC$_{50}$ (μM) | $^1$H NMR | LCMS |
|---|---|---|---|---|
| 205 | 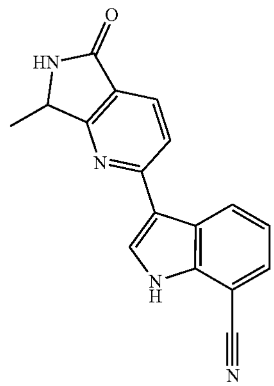 [SMILES: CC1NC(=O)c2ccc(-c3c[nH]c4c(C#N)cccc34)nc21] | C | $^1$H NMR (400 MHz, DMSO-d$_6$) δ 12.58 (bs, 1H), 8.99-8.96 (m, 1H), 8.73 (s, 1H), 8.47 (s, 1H), 8.05-7.98 (m, 2H), 7.74-7.71 (m, 1H), 7.38-7.33 (m, 1H), 4.72-4.68 (m, 1H), 1.51 (d, J = 6.8 Hz, 3H). | MS (ESI) calcd for C$_{17}$H$_{12}$N$_4$O [M + 1]$^+$, 289.1; found, 289.1. |
| 206 | 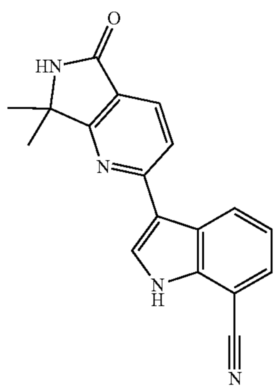 [SMILES: CC1(C)NC(=O)c2ccc(-c3c[nH]c4c(C#N)cccc34)nc21] | C | $^1$H NMR (400 MHz, DMSO-d$_6$) δ 12.56 (bs, 1H), 8.99-8.96 (m, 1H), 8.73 (s, 1H), 8.46 (s, 1H), 8.02 (d, J = 8.0 Hz, 1H), 7.97 (d, J = 8.4 Hz, 1H), 7.74-7.71 (m, 1H), 7.39-7.34 (m, 1H), 1.55 (s, 6H). | MS (ESI) calcd for C$_{18}$H$_{14}$N$_4$O [M + 1]$^+$, 303.1; found, 303.1. |
| 207 | 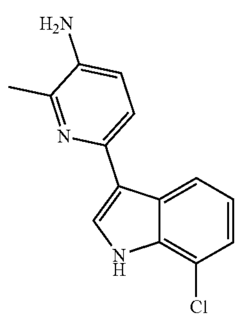 [SMILES: Cc1nc(-c2c[nH]c3c(Cl)cccc23)ccc1N] | C | $^1$H NMR (400 MHz, DMSO-d$_6$) δ 11.50 (bs, 1H), 8.43 (d, J = 8.0 Hz, 1H), 7.83 (d, J = 2.0 Hz, 1H), 7.44 (d, J = 8.4 Hz, 1H), 7.19 (dd, J = 7.6, 1.2 Hz, 1H), 7.06 (t, J = 7.6 Hz, 1H), 6.97 (d, J = 8.4 Hz, 1H), 4.94 (s, 2H), 2.37 (s, 3H). | MS (ESI) calcd for C$_{14}$H$_{12}$ClN$_3$ [M + 1]$^+$, 258.0; found, 258.0. |
| 208 | 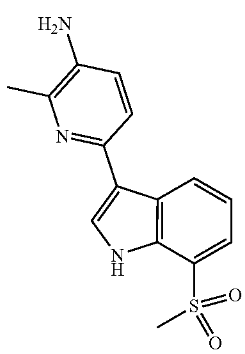 [SMILES: Cc1nc(-c2c[nH]c3c(S(C)(=O)=O)cccc23)ccc1N] | A | $^1$H NMR (400 MHz, DMSO-d$_6$) δ 11.36 (bs, 1H), 8.86 (d, J = 8.0 Hz, 1H), 7.86 (d, J = 2.4 Hz, 1H), 7.64 (d, J = 7.6 Hz, 1H), 7.47 (d, J = 8.4 Hz, 1H), 7.29 (t, J = 7.6 Hz, 1H), 6.98 (d, J = 8.4 Hz, 1H), 5.00 (s, 2H), 3.30 (s, 3H), 2.38 (s, 3H). | MS (ESI) calc'd for C$_{15}$H$_{15}$N$_3$O$_2$S [M + 1]$^+$, 302.1; found, 302.0. |

TABLE 1-continued

| No. | Structure | IC$_{50}$ (µM) | $^1$H NMR | LCMS |
|---|---|---|---|---|
| 209 | 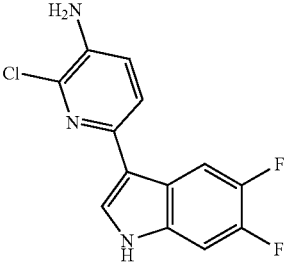 [SMILES: Nc1ccc(-c2c[nH]c3cc(F)c(F)cc23)nc1Cl] | C | $^1$H NMR (300 MHz, DMSO-d$_6$) δ 11.47 (bs, 1H), 8.26-8.19 (m, 1H), 7.95 (s, 1H), 7.59 (d, J = 8.0 Hz, 1H), 7.43-7.37 (m, 1H), 7.18 (d, J = 8.4 Hz, 1H), 5.40 (s, 2H). | MS (ESI) calcd for C$_{13}$H$_8$ClF$_2$N$_3$ [M + 1]$^+$, 280.1; found, 280.0. |
| 210 | 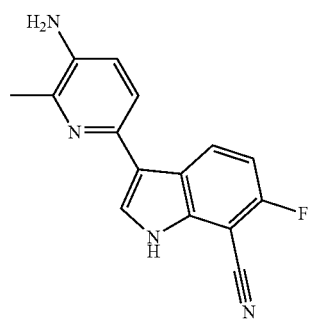 [SMILES: Cc1nc(-c2c[nH]c3c(C#N)c(F)ccc23)ccc1N] | D | $^1$H NMR (400 MHz, DMSO-d$_6$) δ 12.19 (bs, 1H), 8.89-8.85 (m, 1H), 7.92 (d, J = 2.4 Hz, 1H), 7.46 (d, J = 8.4 Hz, 1H), 7.20-7.15 (m, 1H), 6.97 (d, J = 8.4 Hz, 1H), 5.02 (s, 2H), 2.37 (s, 3H). | MS (ESI) calcd for C$_{15}$H$_{11}$FN$_4$ [M + 1]$^+$, 267.1; found, 267.1. |
| 211 | 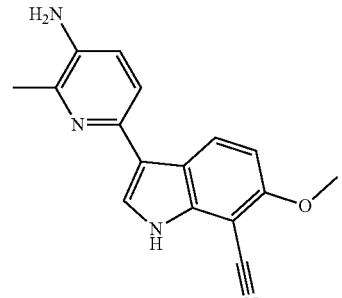 | A | $^1$H NMR (400 MHz, DMSO-d$_6$) δ 11.36 (bs, 1H), 7.76 (d, J = 8.8 Hz, 1H), 7.64 (d, J = 8.0 Hz, 1H), 6.95-6.91 (m, 2H), 6.86 (d, J = 1.6 Hz, 1H), 5.30 (s, 2H), 3.93 (s, 3H), 2.36 (s, 3H). | MS (ESI) calcd for C$_{16}$H$_{14}$N$_4$O [M + 1]$^+$, 279.1; found, 279.2. |
| 212 | 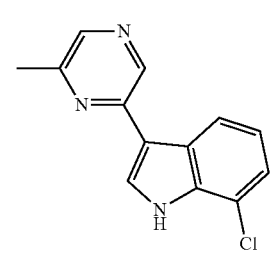 [SMILES: Cc1cncc(-c2c[nH]c3c(Cl)cccc23)n1] | D | $^1$H NMR (400 MHz, DMSO-d$_6$) δ 12.05 (bs, 1H), 9.01 (s, 1H), 8.47 (d, J = 8.0 Hz, 1H), 8.36 (d, J = 2.8 Hz, 1H), 8.27 (s, 1H), 7.29 (d, J = 7.6 Hz, 1H), 7.17 (t, J = 7.6 Hz, 1H), 2.56 (s, 3H). | MS (ESI) calc'd for C$_{13}$H$_{10}$ClN$_3$ [M + 1]$^+$, 244.0; found, 244.0. |
| 213 | 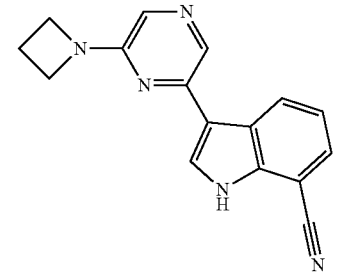 [SMILES: N#Cc1cccc2c(-c3cncc(N4CCC4)n3)c[nH]c12] | C | $^1$H NMR (400 MHz, DMSO-d$_6$) δ 12.47 (bs, 1H), 8.81 (dd, J = 8.4, 1.2 Hz, 1H), 8.45 (s, 1H), 8.32 (s, 1H), 7.69 (dd, J = 7.6, 1.2 Hz, 1H), 7.63 (s, 1H), 7.29 (t, J = 7.6 Hz, 1H), 4.14 (t, J = 7.6 Hz, 4H), 2.47-2.39 (m, 2H). | MS (ESI) calc'd for C$_{16}$H$_{13}$N$_5$ [M + 1]$^+$, 276.1; found, 276.1. |

TABLE 1-continued

| No. | Structure | IC$_{50}$ (μM) | $^1$H NMR | LCMS |
|---|---|---|---|---|
| 214 | 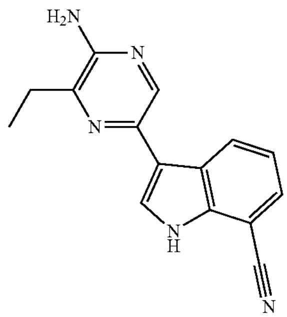 [SMILES: CCc1nc(-c2c[nH]c3c(C#N)cccc23)cnc1N] | C | $^1$H NMR (400 MHz, DMSO-d$_6$) δ 12.16 (bs, 1H), 8.74 (d, J = 8.0 Hz, 1H), 8.37 (s, 1H), 8.04 (d, J = 2.4 Hz, 1H), 7.65 (dd, J = 7.2, 1.2 Hz, 1H), 7.25 (t, J = 7.6 Hz, 1H), 6.08 (s, 2H), 2.72 (q, J = 7.2 Hz, 2H), 1.34 (t, J = 7.2 Hz, 3H). | MS (ESI) calcd for C$_{15}$H$_{13}$N$_5$ [M + 1]$^+$, 264.1; found, 264.1. |
| 215 | 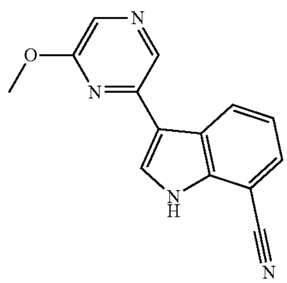 [SMILES: COc1cncc(-c2c[nH]c3c(C#N)cccc23)n1] | D | $^1$H NMR (400 MHz, Methanol-d$_4$) δ 8.84 (d, J = 8.4 Hz, 1H), 8.64 (s, 1H), 8.22 (s, 1H), 7.99 (s, 1H), 7.64 (d, J = 7.6 Hz, 1H), 7.34 (t, J = 7.6 Hz, 1H), 4.16 (s, 3H). | MS (ESI) calcd for C$_{14}$H$_{10}$N$_4$O [M + 1]$^+$, 251.1; found, 251.0. |
| 216 | 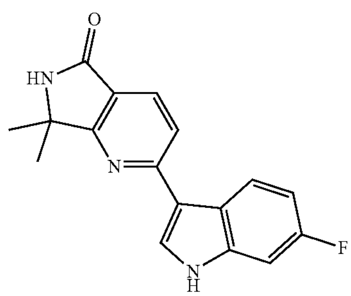 [SMILES: CC1(C)NC(=O)c2ccc(-c3c[nH]c4cc(F)ccc34)nc21] | C | $^1$H NMR (400 MHz, DMSO-d$_6$) δ 11.78 (bs, 1H), 8.69 (s, 1H), 8.60 (dd, J = 8.8, 5.6 Hz, 1H), 8.30 (d, J = 2.8 Hz, 1H), 7.92 (s, 2H), 7.26-7.23 (m, 1H), 7.06-7.04 (m, 1H), 1.54 (s, 6H). | MS (ESI) calcd for C$_{17}$H$_{14}$FN$_3$O [M + 1]$^+$, 296.1; found, 296.3. |
| 217 | 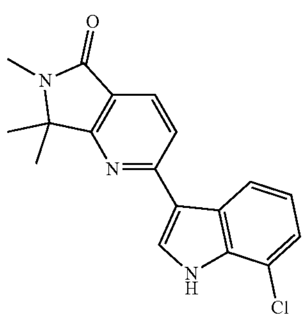 [SMILES: CN1C(=O)c2ccc(-c3c[nH]c4c(Cl)cccc34)nc2C1(C)C] | C | $^1$H NMR (400 MHz, DMSO-d$_6$) δ 12.09 (bs, 1H), 8.61 (d, J = 7.6 Hz, 1H), 8.39 (d, J = 3.2 Hz, 1H), 8.03-7.97 (m, 2H), 7.30 (d, J = 6.8 Hz, 1H), 7.21 (t, J = 8.0 Hz, 1H), 2.99 (s, 3H), 1.54 (s, 6H). | MS (ESI) calcd for C$_{18}$H$_{16}$ClN$_3$O [M + 1]$^+$, 326.1; found, 326.1. |
| 218 | 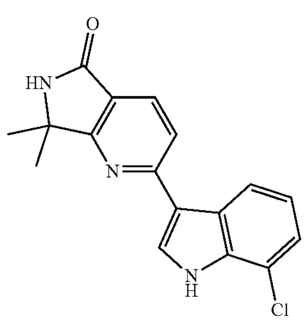 [SMILES: CC1(C)NC(=O)c2ccc(-c3c[nH]c4c(Cl)cccc34)nc21] | C | $^1$H NMR (400 MHz, Methanol-d$_4$) δ 8.54 (dd, J = 8.0, 1.2 Hz, 1H), 8.15 (s, 1H), 8.05 (d, J = 8.4 Hz, 1H), 7.91 (d, J = 8.4 Hz, 1H), 7.30-7.23 (m, 1H), 7.19 (t, J = 7.6 Hz, 1H), 1.66 (s, 6H). | MS (ESI) calcd for C$_{17}$H$_{14}$ClN$_3$O [M + 1]$^+$, 312.1; found, 312.1. |

TABLE 1-continued

| No. | Structure | IC$_{50}$ (μM) | $^1$H NMR | LCMS |
|---|---|---|---|---|
| 219 | 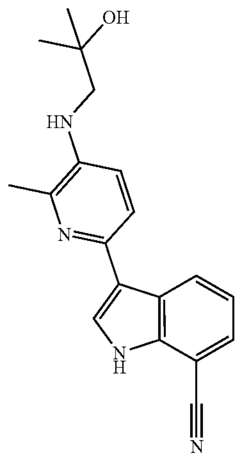 [SMILES: Cc1nc(-c2c[nH]c3c(C#N)cccc23)ccc1NCC(C)(C)O] | C | $^1$H NMR (400 MHz, DMSO-d$_6$) δ 12.06 (ds, 1H), 8.84 (d, J = 8.0 Hz, 1H), 7.94 (d, J = 2.4 Hz, 1H), 7.66-7.59 (m, 1H), 7.55 (d, J = 8.4 Hz, 1H), 7.27-7.19 (m, 1H), 7.01 (d, J = 8.4 Hz, 1H), 4.67-4.57 (m, 2H), 3.05 (d, J = 5.6 Hz, 2H), 2.45 (s, 3H), 1.20 (s, 6H). | MS (ESI) calcd for C$_{19}$H$_{20}$N$_4$O [M + 1]$^+$, 321.2; found, 321.2. |
| 220 | 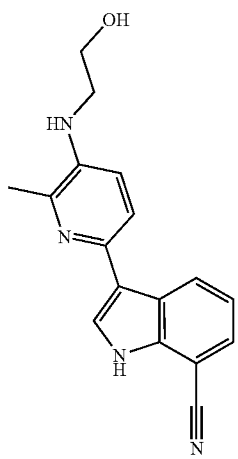 [SMILES: Cc1nc(-c2c[nH]c3c(C#N)cccc23)ccc1NCCO] | C | $^1$H NMR (400 MHz, Methanol-d$_4$) δ 8.47 (dd, J = 8.0, 1.2 Hz, 1H), 7.74 (s, 1H), 7.57 (dd, J = 7.6, 1.2 Hz, 1H), 7.49 (d, J = 8.4 Hz, 1H), 7.26-7.22 (m, 1H), 7.13 (d, J = 8.4 Hz, 1H), 3.39 (t, J = 6.4 Hz, 2H), 3.03 (t, J = 6.4 Hz, 2H), 2.50 (s, 3H). | MS (ESI) calcd for C$_{17}$H$_{17}$N$_5$ [M + 1]$^+$, 292.1; found, 292.1. |
| 221 | 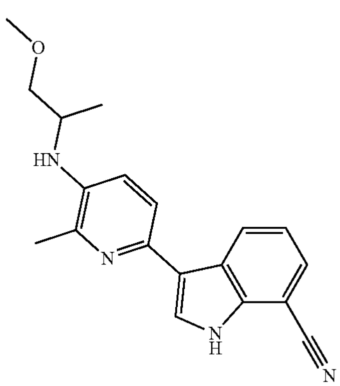 [SMILES: COCC(C)Nc1ccc(-c2c[nH]c3c(C#N)cccc23)nc1C] | C | $^1$H NMR (400 MHz, DMSO-d$_6$) δ 12.07 (bs, 1H), 8.83 (d, J = 8.0 Hz, 1H), 7.94 (d, J = 2.4 Hz, 1H), 7.63-7.61 (m, 1H), 7.55 (d, J = 8.8 Hz, 1H), 7.24-7.21 (m, 1H), 7.01 (d, J = 8.4 Hz, 1H), 4.58 (d, J = 8.0 Hz, 1H), 3.74-3.68 (m, 1H), 3.46-3.43 (m, 1H), 3.32-3.31 (m, 1H), 3.30 (s, 3H), 2.41 (s, 3H), 1.23 (d, J = 8.4 Hz, 3H). | MS (ESI) calcd for C$_{19}$H$_{20}$N$_4$O [M + 1]$^+$, 321.2; found, 321.1. |

TABLE 1-continued

| No. | Structure | IC$_{50}$ (μM) | $^1$H NMR | LCMS |
|---|---|---|---|---|
| 222 | 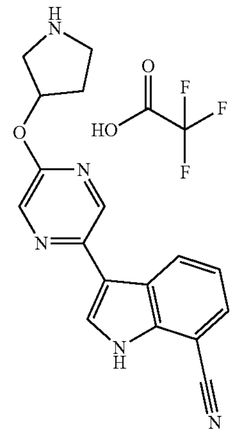 | B | $^1$H NMR (400 MHz, DMSO-d$_6$) δ 12.46 (bs, 1H), 9.11 (bs, 1H), 8.95 (br, 1H), 8.82 (d, J = 1.6 Hz, 1H), 8.69 (d, J = 8.0 Hz, 1H), 8.37 (d, J = 1.4 Hz, 1H), 8.30 (d, J = 2.8 Hz, 1H), 7.75-7.68 (m, 1H), 7.30 (t, J = 7.8 Hz, 1H), 5.67-5.60 (m, 1H), 3.54-3.49 (m, 2H), 3.39-3.35 (m, 2H), 2.32-2.21 (m, 2H). | MS (ESI) calcd for C$_{17}$H$_{15}$N$_5$O [M + 1]$^+$, 306.1; found, 306.1. |
| 223 | 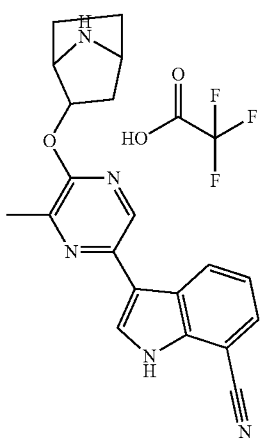 | B | $^1$H NMR (400 MHz, DMSO-d6) δ 12.40 (s, 1H), 9.09-8.70 (m, 3H), 8.60 (s, 1H), 8.24 (s, 1H), 7.70 (d, J = 7.6 Hz, 1H), 7.29 (dd, J = 8.0, 7.6 Hz, 1H), 5.17-5.16 (m, 1H), 4.3-4.28 (m, 2H), 2.56 (s, 3H), 2.39-2.34 (m, 1H), 2.01-1.61 (m, 5H). | MS (ESI) calcd for C$_{20}$H$_{19}$N$_5$O [M + 1]$^+$, 346.2; found, 346.1. |
| 224 | 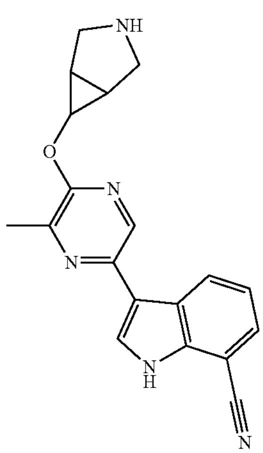 [SMILES: Cc1nc(-c2c[nH]c3c(C#N)cccc23)cnc1OC1C2CNCC21] | B | $^1$H NMR (400 MHz, DMSO-d$_6$) δ 12.38 (s, 1H), 8.73 (d, J = 8.0 Hz, 1H), 8.62 (s, 1H), 8.21 (s, 1H), 7.69 (d, J = 7.6 Hz, 1H), 7.28 (dd, J = 8.0, 7.6 Hz, 1H), 4.10 (s, 1H), 3.16-3.08 (m, 2H), 2.86-2.83 (m, 2H), 2.45 (s, 3H), 1.78 (s, 2H). | MS (ESI) calcd for C$_{19}$H$_{17}$N$_5$O [M + 1]$^+$, 332.1; found, 332.2. |

TABLE 1-continued

| No. | Structure | IC$_{50}$ (μM) | $^1$H NMR | LCMS |
|---|---|---|---|---|
| 225 | 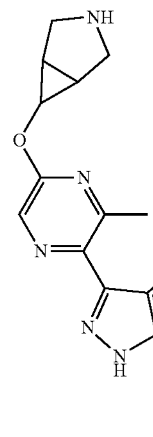 | A | $^1$H NMR (400 MHz, DMSO-d$_6$) δ 12.40 (s, 1H), 8.38-8.28 (m, 2H), 7.90 (s, 1H), 7.69 (d, J = 7.6 Hz, 1H), 7.24 (dd, J = 8.0, 7.6 Hz, 1H), 4.06 (s, 1H), 3.16 (d, J = 10.8 Hz, 2H), 2.85 (d, J = 10.8 Hz, 2H), 2.64 (s, 3H), 1.81-1.80 (m, 2H). | MS (ESI) calcd for C$_{19}$H$_{17}$N$_5$O [M + 1]$^+$, 332.1; found, 332.2. |
| 226 | 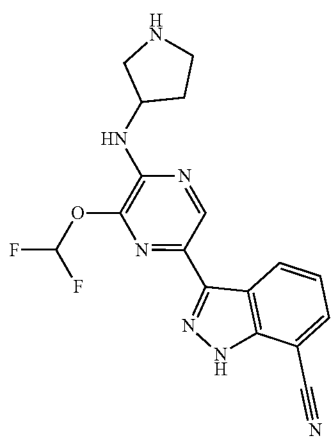 [SMILES: N#Cc1cccc2c(-c3cnc(NC4CCNC4)c(OC(F)F)n3)n[nH]c12] | C | $^1$H NMR (400 MHz, Chloroform-d) δ 9.03 (s, 1H), 8.45-8.35 (m, 1H), 8.27 (s, 1H), 7.75-7.58 (m, 3H), 7.54-7.38 (m, 2H), 5.09 (d, J = 6.8 Hz, 1H), 4.59-4.49 (m, 1H), 3.36-3.25 (m, 1H), 3.20 (m, 1H), 3.10-2.92 (m, 2H), 2.35-2.23 (m, 1H), 1.84-1.74 (m, 1H). | MS (ESI) calcd for C$_{18}$H$_{16}$F$_2$N$_6$O [M + 1]$^+$, 371.1; found, 371.1. |
| 227 | 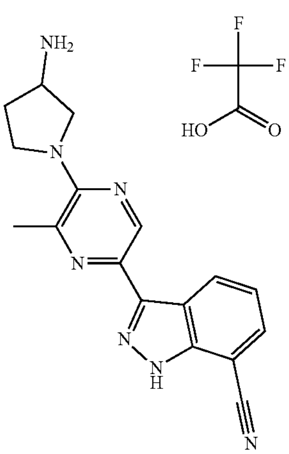 [SMILES: Cc1nc(-c2n[nH]c3c(C#N)cccc23)cnc1N1CCC(N)C1 ; O=C(O)C(F)(F)F] | A | $^1$H NMR (400 MHz, DMSO-d$_6$) δ 12.4 (s, 1H), 8.74 (d, J = 8.0 Hz, 1H), 8.55 (s, 1H), 8.25-7.89 (m, 4H), 7.68 (d, J = 7.6 Hz, 1H), 7.27 (dd, J = 8.0, 7.6 Hz, 1H), 3.99-3.55 (m, 5H), 2.66 (s, 3H), 2.34-2.25 (m, 1H), 2.07-1.97 (m, 1H). | MS (ESI) calcd for C$_{18}$H$_{18}$N$_6$ [M + 1]$^+$, 391.2; found, 391.0. |

TABLE 1-continued

| No. | Structure | IC$_{50}$ (μM) | $^1$H NMR | LCMS |
|---|---|---|---|---|
| 228 | 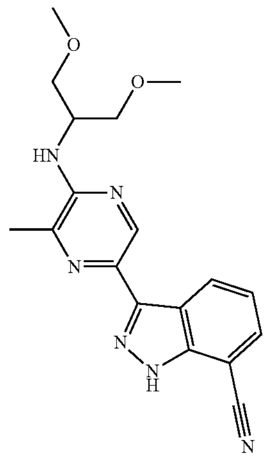 [SMILES: COCC(COC)Nc1ncc(-c2n[nH]c3c(C#N)cccc23)nc1C] | A | $^1$H NMR (400 MHz, Methanol-d$_4$) δ 8.51 (d, J = 8.0 Hz, 1H), 8.30 (s, 1H), 7.81 (s, 1H), 7.58 (d, J = 7.6 Hz, 1H), 7.25 (dd, J = 8.0, 7.6 Hz, 1H), 4.55-4.50 (m, 1H), 3.69-3.55 (m, 4H), 3.41 (s, 6H), 2.47 (s, 3H). | MS (ESI) calcd for C$_{19}$H$_{21}$N$_5$O$_2$ [M + 1]$^+$, 352.2; found, 352.3. |
| 229 | HCOOH | C | $^1$H NMR (400 MHz, DMSO-d$_6$) δ 12.30 (s, 1H), 8.32 (s, 1H), 8.20 (d, J = 8.4 Hz, 1H), 7.86 (s, 1H), 7.68 (d, J = 7.6 Hz, 1H), 7.58-7.47 (m, 2H), 7.28-7.24 (m, 2H), 5.08 (s, 1H), 3.30-3.11 (m, 4H), 2.11-2.02 (m, 2H). | MS (ESI) calcd for C$_{17}$H$_{15}$N$_5$O [M + 1]$^+$, 368.1; found, 368.1. |
| 230 | 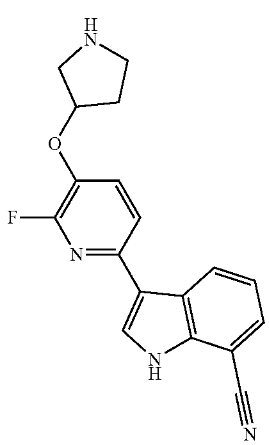 [SMILES: N#Cc1cccc2c(-c3ccc(OC4CCNC4)c(F)n3)c[nH]c12] | C | $^1$H NMR (400 MHz, Methanol-d$_4$) δ 8.59 (d, J = 8.0 Hz, 1H), 7.87 (s, 1H), 7.66-7.56 (m, 2H), 7.45 (d, J = 7.6 Hz, 1H), 7.27 (dd, J = 8.0, 7.6 Hz, 1H), 5.29 (s, 1H), 3.70-3.51 (m, 4H), 2.56 (s, 3H), 2.46-2.31 (m, 2H). | MS (ESI) calcd for C$_{19}$H$_{18}$N$_4$O [M + 1]$^+$, 319.2; found, 319.2. |

TABLE 1-continued

| No. | Structure | IC$_{50}$ (μM) | $^1$H NMR | LCMS |
|---|---|---|---|---|
| 231 | 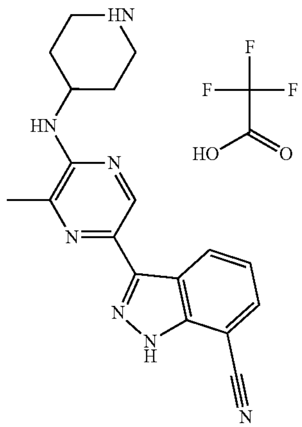 [SMILES: Cc1nc(-c2n[nH]c3c(C#N)cccc23)cnc1NC1CCNCC1 ; O=C(O)C(F)(F)F] | A | $^1$H NMR (400 MHz, Methanol-d$_4$) δ 8.49-8.47 (m, 1H), 8.33 (s, 1H), 7.84 (s, 1H), 7.63-7.56 (m, 1H), 7.31-7.22 (m, 1H), 4.30-4.18 (m, 1H), 3.57-3.47 (m, 2H), 3.26-3.14 (m, 2H), 2.52 (s, 3H), 2.38-2.29 (m, 2H), 1.97-1.82 (m, 2H). | MS (ESI) calcd for C$_{19}$H$_{20}$N$_6$ [M + 1]$^+$, 332.2; found, 332.2. |
| 232 | 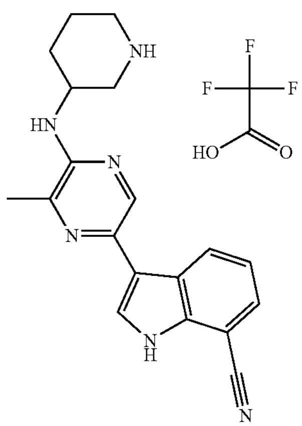 [SMILES: Cc1nc(-c2c[nH]c3c(C#N)cccc23)cnc1NC1CCCNC1 ; O=C(O)C(F)(F)F] | A | $^1$H NMR (400 MHz, Methanol-d$_4$) δ 8.51 (d, J = 8.0 Hz, 1H), 8.35 (s, 1H), 7.84 (s, 1H), 7.59 (d, J = 7.6 Hz, 1H), 7.27 (dd, J = 8.0, 7.6 Hz, 1H), 4.40-4.35 (m 1H), 3.68-3.63 (m 1H), 3.42-3.34 (m, 1H), 3.09-2.94 (m, 2H), 2.51 (s, 3H), 2.25-2.08 (m, 2H), 1.99-1.75 (m, 2H). | MS (ESI) calcd for C$_{19}$H$_{20}$N$_6$ [M + 1]$^+$, 333.2; found, 333.2. |
| 233 | 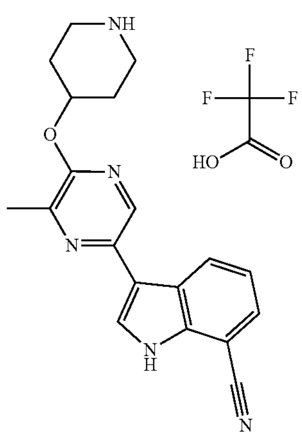 [SMILES: Cc1nc(-c2c[nH]c3c(C#N)cccc23)cnc1OC1CCNCC1 ; O=C(O)C(F)(F)F] | A | $^1$H NMR (400 MHz, Methanol-d$_4$) δ 8.63 (d, J = 8.0 Hz, 1H), 8.44 (s, 1H), 7.96 (s, 1H), 7.62 (d, J = 7.6 Hz, 1H), 7.30 (dd, J = 8.0, 7.6 Hz, 1H), 5.46-5.42 (m, 1H), 3.48-3.27 (m, 4H), 2.60 (s, 3H), 2.31-2.11 (m, 4H). | MS (ESI) calcd for C$_{19}$H$_{19}$N$_5$O [M + 1]$^+$, 334.2; found, 334.2. |

TABLE 1-continued

| No. | Structure | IC$_{50}$ (μM) | $^1$H NMR | LCMS |
|---|---|---|---|---|
| 234 | 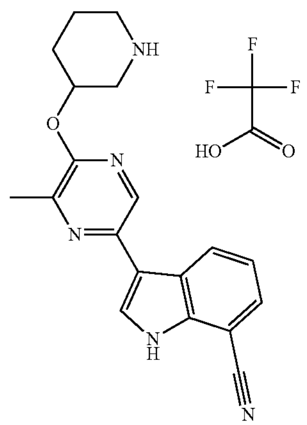 [SMILES: Cc1nc(-c2c[nH]c3c(C#N)cccc23)cnc1OC1CCCNC1 ; O=C(O)C(F)(F)F] | A | $^1$H NMR (400 MHz, Methanol-d$_4$) δ 8.63 (d, J = 8.0 Hz, 1H), 8.45 (s, 1H), 7.98 (s, 1H), 7.63 (d, J = 7.6 Hz, 1H), 7.29 (dd, J = 8.0, 7.6 Hz, 1H), 5.50-5.48 (m, 1H), 3.63-3.61 (m, 1H), 3.52-3.48 (m, 1H), 3.38-3.20 (m, 2H), 2.64 (s, 3H), 2.27-1.90 (m, 4H). | MS (ESI) calcd for C$_{19}$H$_{19}$N$_5$O [M + 1]$^+$, 334.2; found, 334.2. |
| 235 | 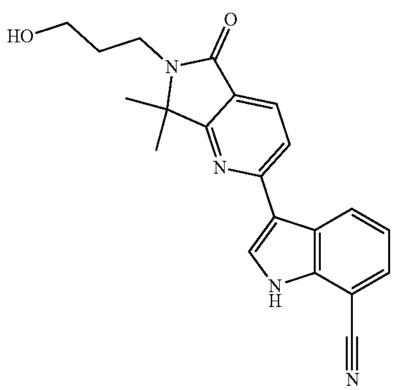 [SMILES: CC1(C)c2nc(-c3c[nH]c4c(C#N)cccc34)ccc2C(=O)N1CCCO] | A | $^1$H NMR (400 MHz, DMSO-d$_6$) δ 12.59 (s, 1H), 8.99 (d, J = 8.0 Hz, 1H), 8.48 (s, 1H), 8.03-7.98 (m, 2H), 7.73 (d, J = 7.6 Hz, 1H), 7.38 (dd, J = 8.0, 7.6 Hz, 1H), 4.57 (t, J = 5.2 Hz, 1H), 3.56-3.47 (m, 4H), 1.89-1.78 (m, 2H), 1.58 (s, 6H). | MS (ESI) calcd for C$_{21}$H$_{20}$N$_4$O$_2$ [M + 1]$^+$, 362.1; found, 361.1. |
| 236 | 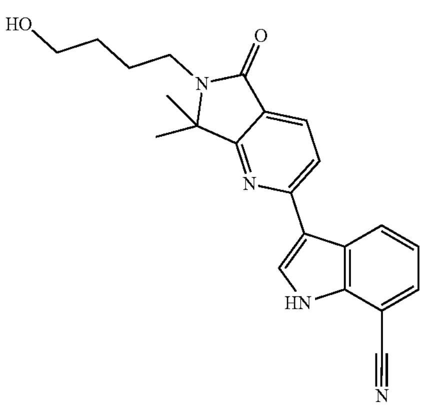 [SMILES: CC1(C)c2nc(-c3c[nH]c4c(C#N)cccc34)ccc2C(=O)N1CCCCO] | A | $^1$H NMR (400 MHz, DMSO-d$_6$) δ 12.57 (s, 1H), 9.01 (d, J = 8.0 Hz, 1H), 8.48 (s, 1H), 8.05-7.95 (m, 2H), 7.73 (d, J = 7.6 Hz, 1H), 7.38 (dd, J = 8.0, 7.6 Hz, 1H), 4.44 (t, J = 5.2 Hz, 1H), 3.51-3.41 (m, 4H), 1.74-1.64 (m, 2H), 1.58 (s, 6H), 1.56-1.45 (m, 2H). | MS (ESI) calcd for C$_{22}$H$_{22}$N$_4$O$_2$ [M + 1]$^+$, 375.2; found, 375.1. |

TABLE 1-continued

| No. | Structure | IC$_{50}$ (μM) | $^1$H NMR | LCMS |
|---|---|---|---|---|
| 237 | 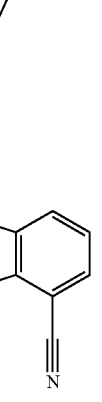 | C | $^1$H NMR (400 MHz, Methanol-d$_4$) δ 8.71 (d, J = 8.0 Hz, 1H), 7.96 (s, 1H), 7.75 (d, J = 7.6 Hz, 1H), 7.61-7.55 (m, 2H), 7.34-7.25 (m, 1H), 5.11-5.08 (m, 1H), 3.29-3.18 (m, 3H), 3.07-3.04 (m 1H), 2.26-2.12 (m, 2H). | MS (ESI) calcd for C$_{18}$H$_{15}$ClN$_4$O [M + 1]$^+$, 339.1; found, 319.1. |
| 238 | 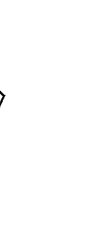 | B | $^1$H NMR (400 MHz, Chloroform-d) δ 8.51 (s, 1H), 8.24 (d, J = 7.6 Hz, 1H), 7.74 (d, J = 2.0 Hz, 1H), 7.48 (d, J = 8.4 Hz, 1H), 7.3-7.11 (m, 3H), 4.90-4.87 (m, 1H), 3.31-3.21 (m, 2H), 3.17-3.07 (m, 1H), 3.05-2.95 (m, 1H), 2.55 (s, 3H), 2.19-2.09 (m, 1H), 2.09-1.99 (m, 1H). | MS (ESI) calcd for C$_{18}$H$_{18}$ClN$_3$O [M + 1]$^+$, 328.1; found, 328.1. |
| 239 | 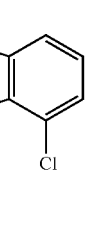 | B | $^1$H NMR (400 MHz, DMSO-d6) δ 12.38 (s, 1H), 8.73 (d, J = 8.0 Hz, 1H), 8.55 (s, 1H), 8.19 (s, 1H), 7.69 (d, J = 7.6 Hz, 1H), 7.28 (dd, J = 8.0, 7.6 Hz, 1H), 5.40-5.35 (m, 1H), 4.28-3.74 (m, 3H), 3.62-3.54 (m, 2H), 2.50 (s, 3H). | MS (ESI) calcd for C$_{17}$H$_{15}$N$_5$O [M + 1]$^+$, 306.1; found, 306.1. |

TABLE 1-continued

| No. | Structure | IC$_{50}$ (μM) | $^1$H NMR | LCMS |
|---|---|---|---|---|
| 240 | 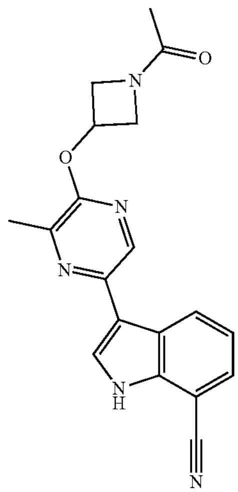 [SMILES: CC(=O)N1CC(Oc2ncc(-c3c[nH]c4c(C#N)cccc34)nc2C)C1] | C | $^1$H NMR (400 MHz, Chloroform-d) δ 9.02 (s, 1H), 8.57 (d, J = 8.0 Hz, 1H), 8.29 (s, 1H), 7.82 (s, 1H), 7.62 (d, J = 7.6 Hz, 1H), 7.34-7.28 (m, 1H), 5.48-5.38 (m, 1H), 4.65-4.56 (m, 1H), 4.53-4.44 (m, 1H), 4.27-4.19 (m, 1H), 4.18-4.15 (m, 1H), 2.64-2.61 (m, 3H), 1.96 (s, 3H). | MS (ESI) calcd for C$_{19}$H$_{17}$N$_5$O$_2$ [M + 1]$^+$, 348.1; found, 348.1. |
| 241 | 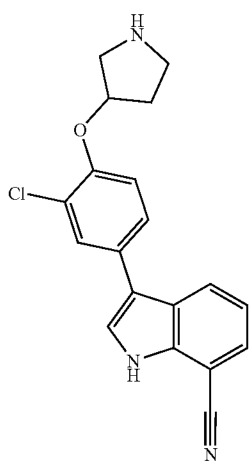 [SMILES: N#Cc1cccc2c(-c3ccc(OC4CCNC4)c(Cl)c3)c[nH]c12] | B | $^1$H NMR (400 MHz, Methanol-d$_4$) δ 8.12 (d, J = 8.0, 1H), 7.67 (s, 1H), 7.62-7.53 (m, 3H), 7.26-7.20 (m, 2H), 5.10-5.07 (m, 1H), 3.28-3.16 (m, 3H), 3.07-3.01 (m, 1H), 2.24-2.08 (m, 2H). | MS (ESI) calcd for C$_{19}$H$_{16}$ClN$_3$O [M + 1]$^+$, 338.1; found, 338.1. |
| 242 | 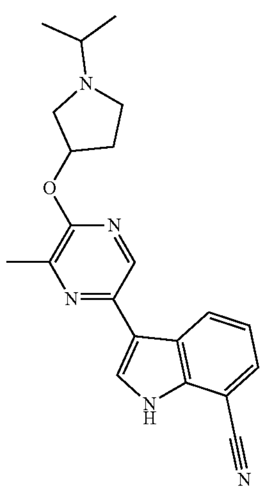 [SMILES: Cc1nc(-c2c[nH]c3c(C#N)cccc23)cnc1OC1CCN(C(C)C)C1] | | $^1$H NMR (400 MHz, DMSO-d$_6$) δ 12.35 (s, 1H), 8.73 (d, J = 8.0 Hz, 1H), 8.57 (s, 1H), 8.18 (s, 1H), 7.68 (d, J = 7.6 Hz, 1H), 7.28 (dd, J = 8.0, 7.6 Hz, 1H), 5.42-5.32 (m, 1H), 2.99-2.23 (m, 9H), 1.89-1.85 (m, 1H), 1.04 (d, J = 6.0 Hz, 6H). | MS (ESI) calcd for C$_{21}$H$_{23}$N$_5$O [M + 1]$^+$, 362.2; found, 362.4. |

TABLE 1-continued

| No. | Structure | IC$_{50}$ (μM) | $^1$H NMR | LCMS |
|---|---|---|---|---|
| 243 | 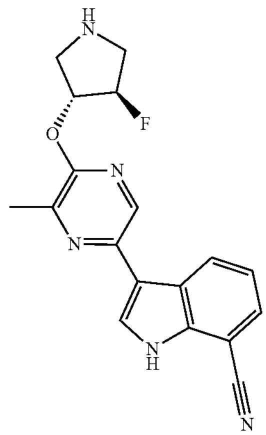 [SMILES: Cc1nc(-c2c[nH]c3c(C#N)cccc23)cnc1O[C@@H]1CNC[C@H]1F] | C | $^1$H NMR (400 MHz, Methanol-d$_4$) δ 8.64 (d, J = 8.0 Hz, 1H), 8.45 (s, 1H), 7.96 (s, 1H), 7.64 (d, J = 7.6 Hz, 1H), 7.29 (d, J = 8.0, 7.6 Hz, 1H), 5.60-5.33 (m, 2H), 3.53-3.04 (m, 4H), 2.55 (s, 3H). | MS (ESI) calcd for C$_{18}$H$_{16}$FN$_5$O [M + 1]$^+$, 338.1; found, 338.1. |
| 244 | 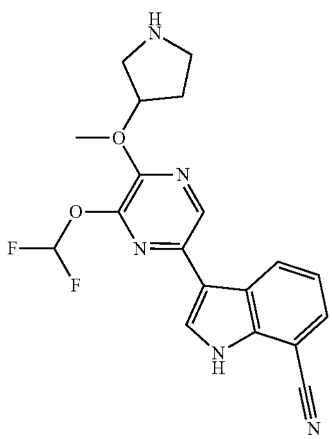 | A | $^1$H NMR (400 MHz, DMSO-d$_6$) δ 12.48 (s, 1H), 8.60 (d, J = 8.0 Hz, 2H), 8.29 (s, 1H), 8.16-7.68 (m, 2H), 7.31 (dd, J = 8.0, 7.6 Hz, 1H), 5.51-5.43 (m, 1H), 3.23-2.83 (m, 4H), 2.17-2.05 (m, 1H), 1.97-1.87 (m, 1H). | MS (ESI) calcd for C$_{18}$H$_{15}$F$_2$N$_5$O$_2$ [M + 1]$^+$, 372.1; found, 372.1. |
| 245 | 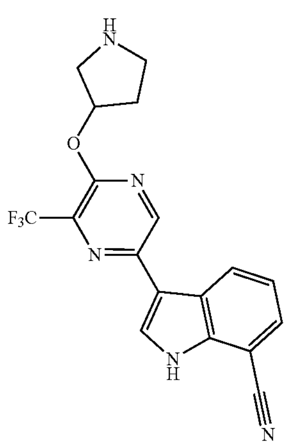 [SMILES: N#Cc1cccc2c(-c3cnc(OC4CCNC4)c(C(F)(F)F)n3)c[nH]c12] | B | $^1$H NMR (400 MHz, DMSO-d$_6$) δ 9.16 (s, 1H), 8.69 (d, J = 8.0 Hz, 1H), 8.45 (s, 1H), 7.74 (d, J = 7.6 Hz, 1H), 7.35 (dd, J = 8.0 Hz, 7.6 Hz, 1H), 5.57-5.55 (m, 1H), 3.27-3.16 (m, 1H), 2.93-2.81 (m, 3H), 2.18-2.00 (m, 1H), 1.98-1.82 (m, 1H). | MS (ESI) calcd for C$_{18}$H$_{14}$F$_3$N$_5$O [M + 1]$^+$, 374.1; found, 374.1. |

TABLE 1-continued

| No. | Structure | IC$_{50}$ (μM) | $^1$H NMR | LCMS |
|---|---|---|---|---|
| 246 | 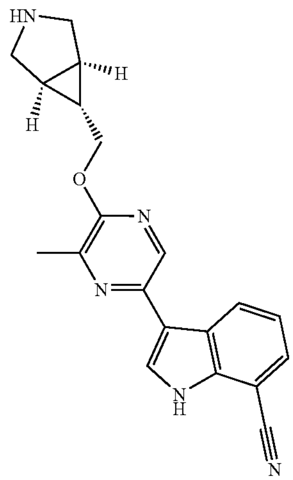 [SMILES: Cc1nc(-c2c[nH]c3c(C#N)cccc23)cnc1OC[C@H]1[C@@H]2CNC[C@@H]21] | C | $^1$H NMR (400 MHz, DMSO-d$_6$) δ 12.36 (s, 1H), 8.72 (dd, J = 8.2, 1.2 Hz, 1H), 8.58 (s, 1H), 8.19-7.17 (m, 1H), 7.69 (dd, J = 7.4, 1.2 Hz, 1H), 7.28 (dd, J = 8.7, 6.8 Hz, 1H), 4.50 (d, J = 7.8 Hz, 2H), 3.50-3.44 (m, 2H), 3.13 (d, J = 11.4 Hz, 2H), 2.50 (s, 3H), 1.94-1.85 (m, 2H), 1.57-1.41 (m, 1H). | MS (ESI) calcd for C$_{20}$H$_{19}$N$_5$O [M + 1]$^+$, 346.2; found, 346.1. |
| 247 | 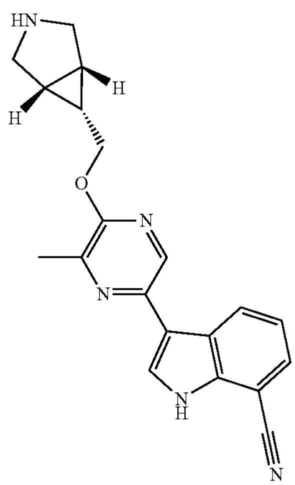 [SMILES: Cc1nc(-c2c[nH]c3c(C#N)cccc23)cnc1OC[C@@H]1[C@@H]2CNC[C@@H]21] | B | $^1$H NMR (400 MHz, DMSO-d$_6$) δ 12.36 (s, 1H), 8.72 (dd, J = 8.0, 1.2 Hz, 1H), 8.56 (s, 1H), 8.19 (s, 1H), 7.69 (dd, J = 7.6, 1.2 Hz, 1H), 7.28 (t, J = 7.8 Hz, 1H), 4.25 (d, J = 7.0 Hz, 2H), 3.01 (d, J = 11.2 Hz, 2H), 2.86 (d, J = 11.2 Hz, 2H), 2.50 (s, 3H), 1.60-1.58 (m, 2H), 1.36-1.21 (m, 1H). | MS (ESI) calcd for C$_{20}$H$_{19}$N$_5$O [M + 1]$^+$, 346.2; found, 346.1. |
| 248 | 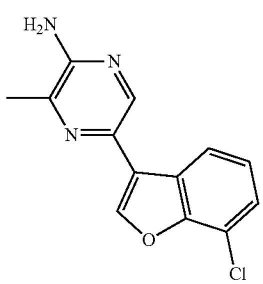 [SMILES: Cc1nc(-c2coc3c(Cl)cccc23)cnc1N] | B | $^1$H NMR (400 MHz, DMSO-d$_6$) δ 8.61 (s, 1H), 8.38 (s, 1H), 8.27 (d, J = 7.6 Hz, 1H), 7.49 (d, J = 7.6 Hz, 1H), 7.35 (t, J = 7.6 Hz, 1H), 6.40 (s, 2H), 2.40 (s, 3H). | MS (ESI) calcd for C$_{13}$H$_{10}$ClN$_3$O [M + 1]$^+$, 260.1; found, 260.0. |

TABLE 1-continued

| No. | Structure | IC$_{50}$ (μM) | $^1$H NMR | LCMS |
|---|---|---|---|---|
| 249 | 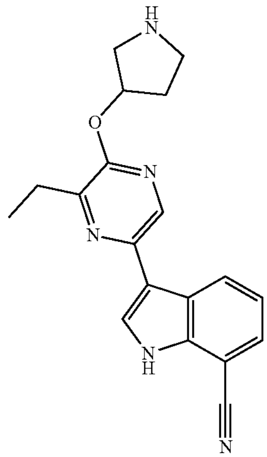 [SMILES: CCc1nc(-c2c[nH]c3c(C#N)cccc23)cnc1OC1CCNC1] | A | $^1$H NMR (400 MHz, DMSO-d$_6$) δ 12.38 (br, 1H), 8.75 (dd, J = 8.4, 1.2 Hz, 1H), 8.58 (s, 1H), 8.21 (s, 1H), 7.69 (dd, J = 7.6, 1.2 Hz, 1H), 7.29 (t, J = 8.0 Hz, 1H), 5.42-5.40 (m, 1H), 3.52-3.41 (m, 1H), 3.14-3.09 (m, 1H), 2.96-2.81 (m, 4H), 2.07-2.02 (m, 1H), 1.86-1.84 (m, 1H), 1.32 (t, J = 7.6 Hz, 3H). | MS (ESI) calcd for C$_{19}$H$_{19}$N$_5$O [M + 1]$^+$, 334.2; found, 334.2. |
| 250 | 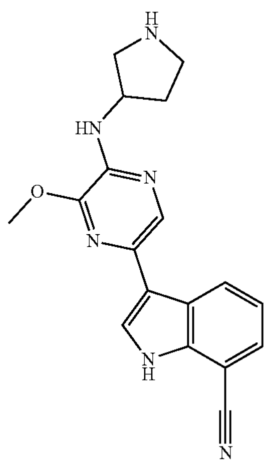 [SMILES: COc1nc(-c2c[nH]c3c(C#N)cccc23)cnc1NC1CCNC1] | C | $^1$H NMR (400 MHz, Methanol-d$_6$) δ 8.61-8.59 (m, 1H), 8.05 (s, 1H), 7.85 (s, 1H), 7.58 (d, J = 7.2 Hz, 1H), 7.26 (t, J = 7.6 Hz, 1H), 4.59-4.56 (m, 1H), 4.15 (s, 3H), 3.48-3.40 (m, 2H), 3.28-3.21 (m, 2H), 2.38-2.35 (m, 1H), 2.12-2.08 (m, 1H). | MS (ESI) calcd for C$_{18}$H$_{18}$N$_6$O [M + 1]$^+$, 335.2; found, 335.2. |
| 251 | 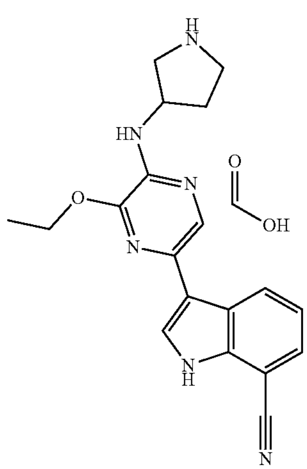 | B | $^1$H NMR (400 MHz, DMSO-d$_6$) δ 8.60-8.53 (m, 2H), 8.04 (s, 1H), 7.85 (s, 1H), 7.61-7.55 (m, 1H), 7.27-7.25 (m, 1H), 4.67-4.57 (m, 3H), 3.60-3.51 (m, 2H), 3.42-3.38 (m, 2H), 2.44-2.40 (m, 1H), 2.26-2.18 (m, 1H), 1.53 (t, J = 7.2 Hz, 3H). | MS (ESI) calcd for C$_{19}$H$_{20}$N$_6$O [M + 1]$^+$, 349.2; found, 349.2. |

TABLE 1-continued

| No. | Structure | IC$_{50}$ (μM) | $^1$H NMR | LCMS |
|---|---|---|---|---|
| 252 | 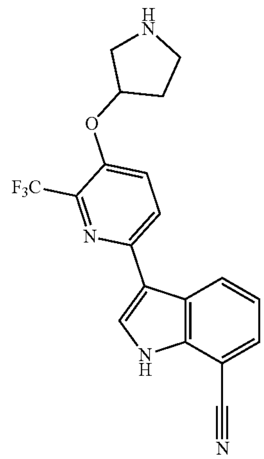 [SMILES: N#Cc1cccc2c(-c3ccc(OC4CCNC4)c(C(F)(F)F)n3)c[nH]c12] | B | $^1$H NMR (400 MHz, Methanol-d$_4$) δ 8.89 (dd, J = 8.0, 1.2 Hz, 1H), 8.03-8.02 (m, 2H), 7.71 (d, J = 8.8 Hz, 1H), 7.62-7.59 (m, 1H), 7.31-7.28 (m, 1H), 5.20-5.16 (m, 1H), 3.30-3.25 (m, 1H), 3.20-3.16 (m, 2H), 3.15-3.07 (m, 1H), 2.24-2.03 (m, 2H). | MS (ESI) calcd for C$_{19}$H$_{15}$F$_3$N$_4$O [M + 1]$^+$, 373.1; found, 373.1. |
| 253 | 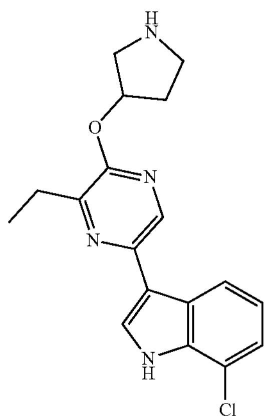 [SMILES: CCc1nc(-c2c[nH]c3c(Cl)cccc23)cnc1OC1CCNC1] | A | $^1$H NMR (400 MHz, DMSO-d$_6$) δ 11.82 (s, 1H), 8.55 (s, 1H), 8.36 (d, J = 8.0 Hz, 1H), 8.10 (s, 1H), 7.25 (d, J = 7.6 Hz, 1H), 7.13 (t, J = 7.6 Hz, 1H), 5.43-5.39 (m, 1H), 3.14-3.09 (m, 1H), 2.98-2.79 (m, 5H), 2.16-1.98 (m, 1H), 1.92-1.79 (m, 1H), 1.32 (t, J = 7.6 Hz, 3H). | MS (ESI) calcd for C$_{18}$H$_{19}$ClN$_4$O [M + 1]$^+$, 343.2; found, 343.2. |
| 254 | 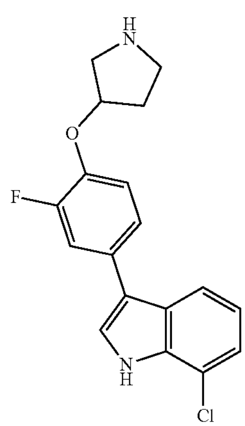 [SMILES: Fc1cc(-c2c[nH]c3c(Cl)cccc23)ccc1OC1CCNC1] | B | $^1$H NMR (400 MHz, Methanol-d$_4$) δ 7.77 (dd, J = 7.6, 1.2 Hz, 1H), 7.52 (s, 1H), 7.46-7.36 (m, 2H), 7.24-7.14 (m, 2H), 7.10 (t, J = 7.6 Hz, 1H), 5.06-5.04 (m, 1H), 3.30-3.14 (m, 3H), 3.05-3.00 (m, 1H), 2.17-2.12 (m, 2H), 1.32-1.29 (m, 1H). | MS (ESI) calcd for C$_{18}$H$_{16}$ClFN$_2$O [M + 1]$^+$, 331.1; found, 331.1. |

TABLE 1-continued

| No. | Structure | IC$_{50}$ (μM) | $^1$H NMR | LCMS |
|---|---|---|---|---|
| 255 | 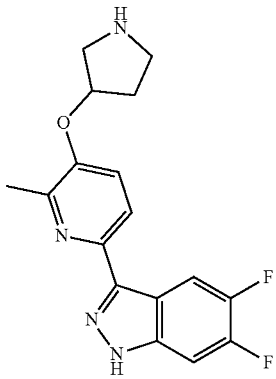 [SMILES: Cc1nc(-c2n[nH]c3cc(F)c(F)cc23)ccc1OC1CCNC1] | B | $^1$H NMR (400 MHz, Methanol-d$_4$) δ 8.39 (dd, J = 10.8, 8.0 Hz, 1H), 7.97-7.90 (m, 1H), 7.47-7.37 (m, 2H), 5.11-5.08 (m, 1H), 3.32-3.17 (m, 3H), 3.09-3.05 (m, 1H), 2.57 (s, 3H), 2.25-2.18 (m, 1H), 2.14-2.09 (m, 1H). | MS (ESI) calcd for C$_{17}$H$_{16}$F$_2$N$_4$O [M + 1]$^+$, 331.1; found, 331.1. |
| 256 | 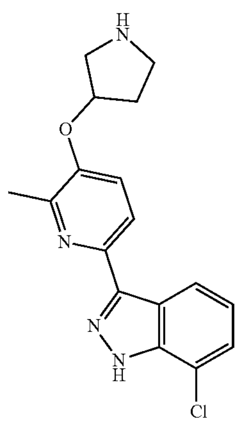 [SMILES: Cc1nc(-c2n[nH]c3c(Cl)cccc23)ccc1OC1CCNC1] | B | $^1$H NMR (400 MHz, Methanol-d$_4$) δ 8.48 (dd, J = 8.4, 0.8 Hz, 1H), 7.96 (d, J = 8.4 Hz, 1H), 7.47-7.33 (m, 2H), 7.20 (dd, J = 8.4, 7.6 Hz, 1H), 5.11-5.08 (m, 1H), 3.32-3.16 (m, 3H), 3.09-3.04 (m, 1H), 2.57 (s, 3H), 2.25-2.20 (m, 1H), 2.14-2.11 (m, 1H). | MS (ESI) calcd for C$_{17}$H$_{17}$ClN$_4$O [M + 1]$^+$, 329.1; found, 329.1. |
| 257 | 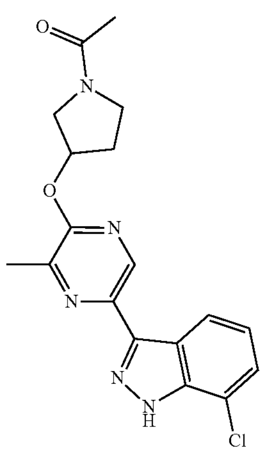 [SMILES: CC(=O)N1CCC(Oc2ncc(-c3n[nH]c4c(Cl)cccc34)nc2C)C1] | C | $^1$H NMR (400 MHz, DMSO-d$_6$) δ 11.85 (s, 1H), 8.60-8.55 (m, 1H), 8.34 (d, J = 8.0 Hz, 1H), 8.12 (t, J = 2.4 Hz, 1H), 7.26 (d, J = 7.6 Hz, 1H), 7.14-7.10 (m, 1H), 5.63-5.57 (m, 1H), 3.87-3.38 (m, 4H), 2.47 (s, 3H), 2.34-2.21 (m, 2H), 2.00 and 1.94 (s, 3H). | MS (ESI) calcd for C$_{19}$H$_{19}$ClN$_4$O$_2$ [M + 1]$^+$, 371.1; found, 371.1. |

TABLE 1-continued

| No. | Structure | IC$_{50}$ (μM) | $^1$H NMR | LCMS |
|---|---|---|---|---|
| 258 | 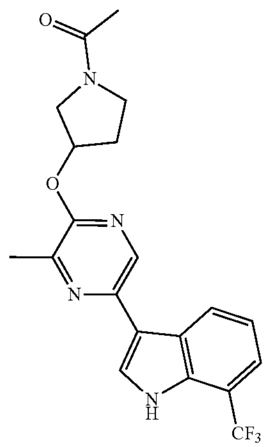 [SMILES: CC(=O)N1CCC(Oc2ncc(-c3c[nH]c4c(C(F)(F)F)cccc34)nc2C)C1] | C | $^1$H NMR (400 MHz, Methanol-d$_4$) δ 8.55-8.53 (m, 1H), 8.45-8.43 (m, 1H), 7.91 (s, 1H), 7.54-7.47 (m, 1H), 7.33-7.24 (m, 1H), 5.72-5.65 (m, 1H), 4.08-3.73 (m, 4H), 2.56 (s, 3H), 2.41-2.38 (m, 1H), 2.31-2.28 (m, 1H), 2.14 and 2.09 (s, 3H). | MS (ESI) calcd for C$_{20}$H$_{19}$F$_3$N$_4$O$_2$ [M + 1]$^+$, 405.1; found, 405.1. |
| 259 | 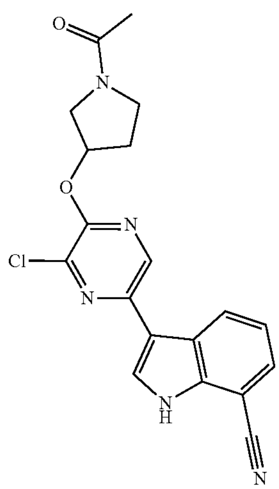 [SMILES: CC(=O)N1CCC(Oc2ncc(-c3c[nH]c4c(C#N)cccc34)nc2Cl)C1] | C | $^1$H NMR (400 MHz, DMSO-d$_6$) δ 12.53 (s, 1H), 8.82 (s, 1H), 8.64-8.61 (m, 1H), 8.35 (d, J = 2.8 Hz, 1H), 7.73 (d, J = 7.2 Hz, 1H), 7.38-7.29 (m, 1H), 5.65-5.57 (m, 1H), 3.88-3.35 (m, 4H), 2.33-2.14 (m, 2H), 2.00 and 1.94 (s, 3H). | MS (ESI) calcd for C$_{19}$H$_{16}$ClN$_5$O$_2$ [M + 1]$^+$, 382.1; found, 382.1. |
| 260 | 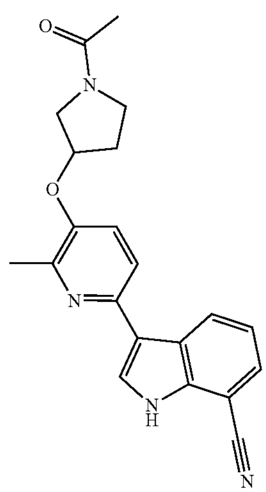 [SMILES: CC(=O)N1CCC(Oc2ccc(-c3c[nH]c4c(C#N)cccc34)nc2C)C1] | C | $^1$H NMR (400 MHz, DMSO-d$_6$) δ 12.24 (s, 1H), 8.87-8.84 (m, 1H), 8.13 (s, 1H), 7.73 (dd, J = 8.4, 3.2 Hz, 1H), 7.66 (d, J = 7.2 Hz, 1H), 7.46 (t, J = 8.4 Hz, 1H), 7.31-7.22 (m, 1H), 5.16-5.09 (m, 1H), 3.81-3.47 (m, 4H), 2.43 (s, 3H), 2.29-2.05 (m, 2H), 2.00 and 1.95 (s, 3H). | MS (ESI) calcd for C$_{21}$H$_{20}$N$_4$O$_2$ [M + 1]$^+$, 361.2; found, 361.2. |

TABLE 1-continued

| No. | Structure | IC$_{50}$ (μM) | $^1$H NMR | LCMS |
|---|---|---|---|---|
| 261 | 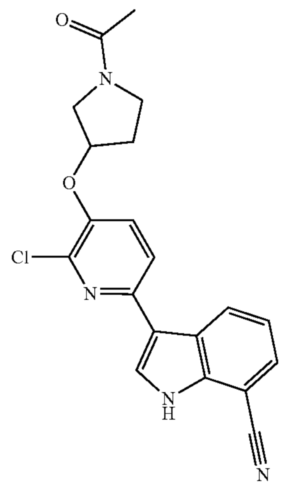 [SMILES: CC(=O)N1CCC(Oc2ccc(-c3c[nH]c4c(C#N)cccc34)nc2Cl)C1] | C | $^1$H NMR (400 MHz, DMSO-d$_6$) δ 12.40 (s, 1H), 8.76-8.73 (m, 1H), 8.27 (s, 1H), 7.96-7.93 (m, 1H), 7.77-7.53 (m, 2H), 7.35-7.30 (m, 1H), 5.30-5.19 (m, 1H), 3.88-3.52 (m, 4H), 2.27-2.03 (m, 2H), 2.01 and 1.95 (s, 3H). | MS (ESI) calcd for C$_{20}$H$_{17}$ClN$_4$O$_2$ [M + 1]$^+$, 381.1; found, 381.1. |
| 262 | 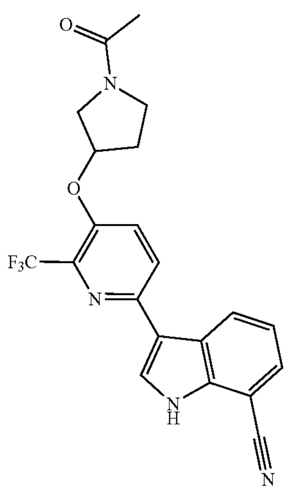 [SMILES: CC(=O)N1CCC(Oc2ccc(-c3c[nH]c4c(C#N)cccc34)nc2C(F)(F)F)C1] | C | $^1$H NMR (400 MHz, Methanol-d$_4$) δ 8.88-8.86 (m, 1H), 8.05-8.01 (m, 2H), 7.78-7.75 (m, 1H), 7.60 (m, 1H), 7.31-7.28 (m, 1H), 5.38-5.26 (m, 1H), 3.90-3.67 (m, 4H), 2.39-2.36 (m, 1H), 2.28-2.25 (m, 1H), 2.12 and 2.08 (s, 3H). | MS (ESI) calcd for C$_{21}$H$_{17}$F$_3$N$_4$O$_2$ [M + 1]$^+$, 415.1; found, 415.1. |
| 263 | 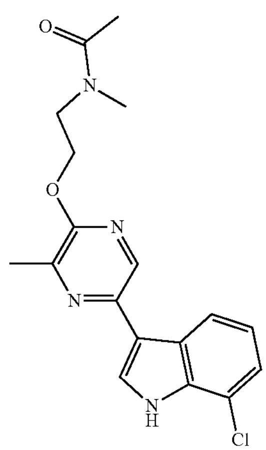 [SMILES: CC(=O)N(C)CCOc1ncc(-c2c[nH]c3c(Cl)cccc23)nc1C] | C | $^1$H NMR (400 MHz, DMSO-d$_6$) δ 11.85 (br, 1H), 8.56 (d, J = 8.8 Hz, 1H), 8.37-8.31 (m, 1H), 8.12 (dd, J = 7.6, 2.8 Hz, 1H), 7.26 (d, J = 7.6 Hz, 1H), 7.13 (t, J = 7.6 Hz, 1H), 4.48 (t, J = 5.2 Hz, 1H), 4.42 (t, J = 5.2 Hz, 1H), 3.76 (t, J = 5.2 Hz, 1H), 3.69 (t, J = 5.2 Hz, 1H), 3.08 and 2.88 (s, 3H), 2.48 (s, 3H), 2.08 and 1.99 (s, 3H). | MS (ESI) calcd for C$_{18}$H$_{19}$ClN$_4$O$_2$ [M + 1]+, 359.1; found, 359.1. |

TABLE 1-continued

| No. | Structure | IC$_{50}$ (μM) | $^1$H NMR | LCMS |
|---|---|---|---|---|
| 264 | 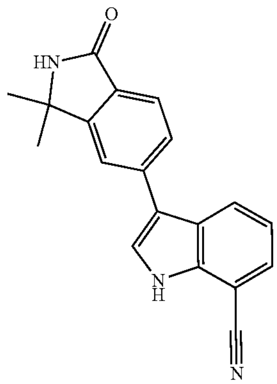 [SMILES: CC1(C)NC(=O)c2ccc(-c3c[nH]c4c(C#N)cccc34)cc21] | C | $^1$H NMR (400 MHz, DMSO-d$_6$) δ 12.42 (s, 1H), 8.59 (s, 1H), 8.28 (d, J = 8.0 Hz, 1H), 8.01 (d, J = 2.8 Hz, 1H), 7.94 (s, 1H), 7.85-7.75 (m, 1H), 7.77-7.67 (m, 1H), 7.66 (d, J = 7.6 Hz, 1H), 7.36-7.26 (m, 1H), 1.52 (s, 6H). | MS (ESI) calcd for C$_{19}$H$_{15}$N$_3$O [M + 1]+, 302.1; found, 302.1. |
| 265 | 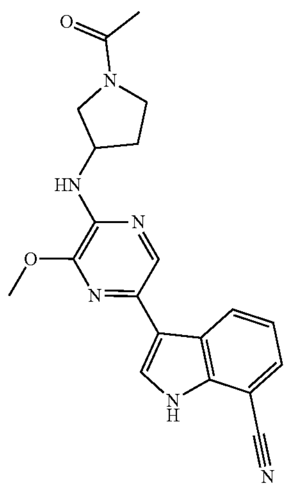 [SMILES: COc1nc(-c2c[nH]c3c(C#N)cccc23)cnc1NC1CCN(C(C)=O)C1] | D | $^1$H NMR (400 MHz, Methanol-d$_4$) δ 8.61-8.59 (m, 1H), 8.03 (d, J = 3.6 Hz, 1H), 7.84 (d, J = 1.6 Hz, 1H), 7.58-7.56 (m, 1H), 7.26-7.24 (m, 1H), 4.62-4.59 (m, 1H), 4.14 (s, 3H), 3.97-3.95 (m, 1H), 3.89-3.42 (m, 3H), 2.45-2.24 (m, 1H), 2.23-2.03 (m, 4H). | MS (ESI) calcd for C$_{20}$H$_{20}$N$_6$O$_2$ [M + 1]+, 377.2; found, 377.2. |
| 266 | 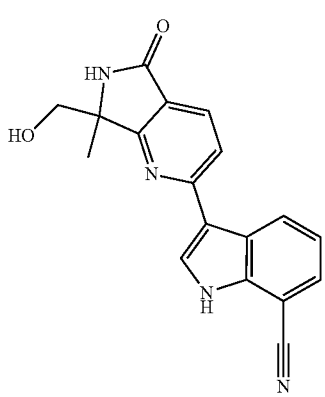 [SMILES: CC1(CO)NC(=O)c2ccc(-c3c[nH]c4c(C#N)cccc34)nc21] | A | $^1$H NMR (400 MHz, DMSO-d$_6$) δ 12.56 (s, 1H), 8.97 (d, J = 8.0 Hz, 1H), 8.51 (s, 1H), 8.45 (d, J = 2.4 Hz, 1H), 8.00 (d, J = 8.4 Hz, 1H), 7.94 (d, J = 8.4 Hz, 1H), 7.73 (d, J = 7.6 Hz, 1H), 7.36 (t, J = 7.6 Hz, 1H), 4.94 (t, J = 5.6 Hz, 1H), 3.82-3.69 (m, 2H), 1.48 (s, 3H). | MS (ESI) calcd for C$_{18}$H$_{14}$N$_4$O$_2$ [M + 1]$^+$, 319.1; found, 319.1. |

TABLE 1-continued

| No. | Structure | IC$_{50}$ (μM) | $^1$H NMR | LCMS |
|---|---|---|---|---|
| 267 | 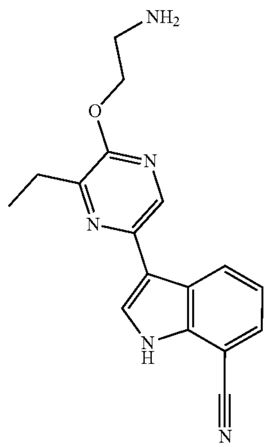 [SMILES: CCc1nc(-c2c[nH]c3c(C#N)cccc23)cnc1OCCN] | A | $^1$H NMR (400 MHz, Methanol-d$_4$) δ 8.51 (d, J = 8.0 Hz, 1H), 7.83 (s, 2H), 7.59 (d, J = 7.6 Hz, 1H), 7.26 (t, J = 7.6 Hz, 1H), 4.17 (t, J = 6.4 Hz, 2H), 3.12 (t, J = 6.4 Hz, 2H), 2.94 (q, J = 7.2 Hz, 2H), 1.38 (t, J = 7.6 Hz, 3H). | MS (ESI) calcd for C$_{17}$H$_{17}$N$_5$O [M + 1]$^+$, 308.1; found, 308.2. |
| 268 | 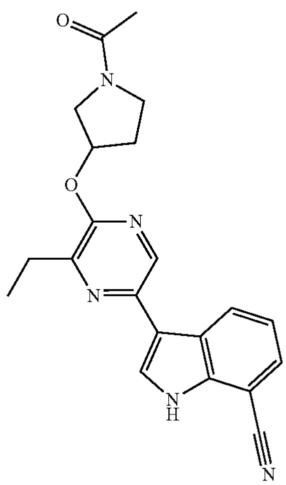 [SMILES: CCc1nc(-c2c[nH]c3c(C#N)cccc23)cnc1OC1CCN(C(C)=O)C1] | C | $^1$H NMR (400 MHz, DMSO-d$_6$) δ 12.38 (s, 1H), 8.77 (d, J = 8.4 Hz, 1H), 8.62 (s, 1H), 8.24 (t, J = 2.4 Hz, 1H), 7.70 (d, J = 7.2 Hz, 1H), 7.35-7.26 (m, 1H), 5.62-5.54 (m, 1H), 3.86-3.59 (m, 4H), 2.87-2.81 (m, 2H), 2.27-2.11 (m, 2H), 2.00 and 1.95 (s, 3H), 1.34-1.30 (m, 3H). | MS (ESI) calcd for C$_{21}$H$_{21}$N$_5$O$_2$ [M + 1]$^+$, 376.2; found, 376.1. |
| 269 | 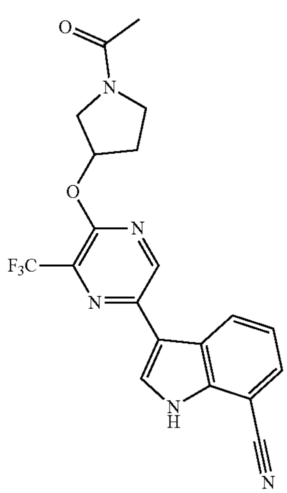 | C | $^1$H NMR (400 MHz, DMSO-d$_6$) δ 12.58 (s, 1H), 9.17 (s, 1H), 8.70-8.68 (m, 1H), 8.47 (d, J = 3.6 Hz, 1H), 7.73 (d, J = 7.2 Hz, 1H), 7.39-7.30 (m, 1H), 5.79-5.64 (m, 1H), 3.92-3.42 (m, 4H), 2.33-2.12 (m, 2H), 1.99 and 1.94 (s, 3H). | MS (ESI) calcd for C$_{20}$H$_{16}$F$_3$N$_5$O$_2$ [M + 1]$^+$, 416.1; found, 416.1. |

TABLE 1-continued

| No. | Structure | IC$_{50}$ (μM) | $^1$H NMR | LCMS |
|---|---|---|---|---|
| 270 | 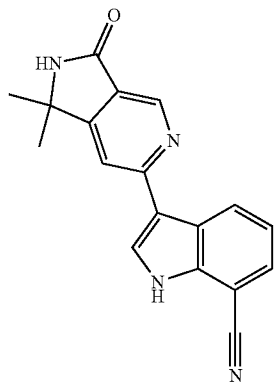 [SMILES: CC1(C)NC(=O)c2cnc(-c3c[nH]c4c(C#N)cccc34)cc21] | A | $^1$H NMR (400 MHz, DMSO-d$_6$) δ 12.57 (s, 1H), 8.94 (d, J = 8.0 Hz, 1H), 8.85 (s, 1H), 8.72 (s, 1H), 8.46 (d, J = 2.4 Hz, 1H), 8.28 (s, 1H), 7.72 (d, J = 7.6 Hz, 1H), 7.33 (t, J = 7.6 Hz, 1H), 1.52 (s, 6H). | MS (ESI) calcd for C$_{18}$H$_{14}$N$_4$O [M + 1]$^+$, 303.1; found, 303.1. |
| 271 | 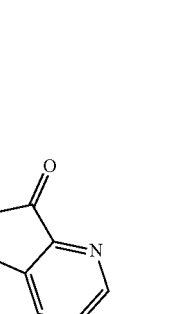 | A | $^1$H NMR (400 MHz, DMSO-d$_6$) δ 12.57 (s, 1H), 9.06 (d, J = 2.0 Hz, 1H), 9.01 (s, 1H), 8.44 (d, J = 2.0 Hz, 1H), 8.34 (d, J = 8.0 Hz, 1H), 8.17 (d, J = 2.4 Hz, 1H), 7.75 (d, J = 7.2 Hz, 1H), 7.34 (t, J = 7.6 Hz, 1H), 1.55 (s, 6H). | MS (ESI) calcd for C$_{18}$H$_{14}$N$_4$O [M + 1]$^+$, 303.1; found, 303.0. |
| 272 | 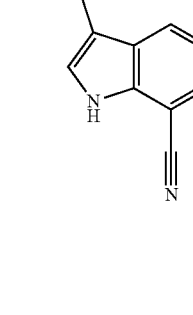 | C | $^1$H NMR (400 MHz, DMSO-d$_6$) δ 12.40 (s, 1H), 8.74 (d, J = 8.0 Hz, 1H), 8.65 (s, 1H), 8.26-8.24 (m, 1H), 7.71-7.69 (m, 1H), 7.30-7.28 (m, 1H), 5.64-5.60 (m, 1H), 5.57-5.47 (m, 1H), 4.06-3.66 (m, 4H), 2.48 (s, 3H), 2.03 and 2.01 (s, 3H). | MS (ESI) calcd for C$_{20}$H$_{18}$FN$_5$O$_2$ [M + 1]$^+$, 380.1; found, 380.2. |

TABLE 1-continued

| No. | Structure | IC$_{50}$ (μM) | $^1$H NMR | LCMS |
|---|---|---|---|---|
| 273 | 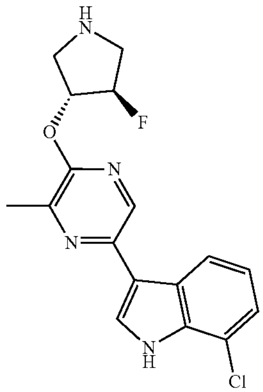 [SMILES: Cc1nc(-c2c[nH]c3c(Cl)cccc23)cnc1O[C@@H]1CNC[C@H]1F] | C | $^1$H NMR (400 MHz, DMSO-d$_6$) δ 11.85 (s, 1H), 8.59 (s, 1H), 8.34 (d, J = 8.0 Hz, 1H), 8.12 (d, J = 2.4 Hz, 1H), 7.26 (d, J = 7.6 Hz, 1H), 7.14-7.12 (m, 1H), 5.38-5.36 (m, 1H), 5.22-5.14 (m, 1H), 3.45-3.39 (m, 2H), 3.21-2.98 (m, 2H), 2.88-2.84 (m, 1H), 2.48 (s, 3H). | MS (ESI) calcd for C$_{17}$H$_{16}$ClFN$_4$O [M + 1]$^+$, 347.1; found, 347.1. |
| 274 | 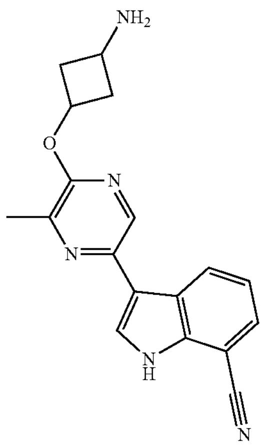 [SMILES: Cc1nc(-c2c[nH]c3c(C#N)cccc23)cnc1OC1CC(N)C1] | C | $^1$H NMR (400 MHz, Methanol-d$_4$) δ 8.59 (d, J = 8.0 Hz, 1H), 8.38 (s, 1H), 7.93 (s, 1H), 7.60 (d, J = 7.2 Hz, 1H), 7.28-7.26 (m, 1H), 5.44-4.93 (m, 1H), 3.81-3.23 (m, 1H), 2.94-2.92 (m, 1H), 2.63-2.48 (m, 4H), 2.42-2.40 (m, 1H), 2.03-2.01 (m, 1H). | MS (ESI) calcd for C$_{18}$H$_{17}$N$_5$O [M + 1]$^+$, 320.1; found, 320.2. |
| 275 | 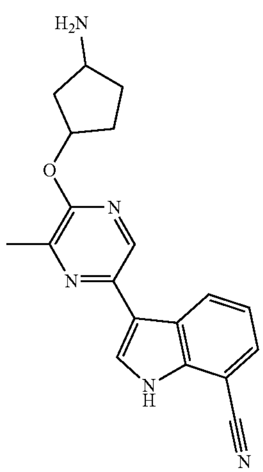 [SMILES: Cc1nc(-c2c[nH]c3c(C#N)cccc23)cnc1OC1CCC(N)C1] | A | $^1$H NMR (400 MHz, Methanol-d$_4$) δ 8.59 (dd, J = 8.2, 1.2 Hz, 1H), 8.39 (s, J = 0.8 Hz, 1H), 7.93 (s, 1H), 7.60 (dd, J = 7.4, 1.2 Hz, 1H), 7.28 (dd, J = 8.2, 7.4 Hz, 1H), 5.58-5.54 (m, 1H), 3.67-3.60 (m, 1H), 2.52 (s, 3H), 2.40-2.31 (m, 1H), 2.26-2.12 (m, 2H), 1.93-1.77 (m, 2H), 1.57-1.48 (m, 1H). | MS (ESI) calcd for C$_{19}$H$_{19}$N$_5$O [M + 1]$^+$, 334.2; found, 334.2. |

TABLE 1-continued

| No. | Structure | IC$_{50}$ (μM) | $^1$H NMR | LCMS |
|---|---|---|---|---|
| 276 | 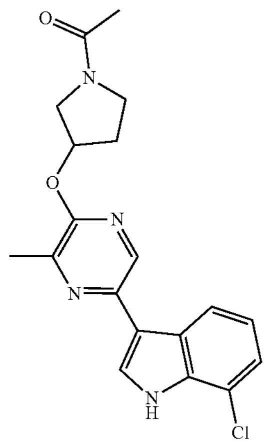 [SMILES: CC(=O)N1CCC(Oc2ncc(-c3c[nH]c4c(Cl)cccc34)nc2C)C1] | C | $^1$H NMR (400 MHz, Methanol-d$_4$) δ 8.77 (s, 1H), 8.47-8.44 (m, 1H), 7.46-7.44 (m, 1H), 7.23-7.19 (m, 1H), 5.76-5.70 (m, 1H), 3.85-3.72 (m, 4H), 2.59 (s, 3H), 2.47-2.36 (m, 1H), 2.34-2.29 (m, 1H), 2.14 and 2.09 (s, 3H). | MS (ESI) calcd for C$_{18}$H$_{18}$ClN$_5$O$_2$ [M + 1]$^+$, 372.1; found, 372.1. |
| 277 | 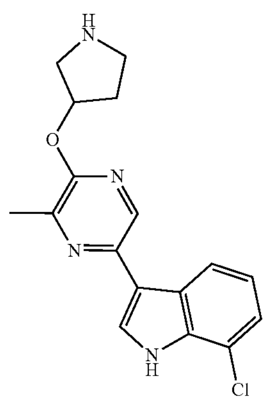 [SMILES: Cc1nc(-c2c[nH]c3c(Cl)cccc23)cnc1OC1CCNC1] | C | $^1$H NMR (400 MHz, Methanol-d$_4$) δ 8.75 (s, 1H), 8.46 (dd, J = 8.0, 0.8 Hz, 1H), 7.46 (dd, J = 7.6, 0.8 Hz, 1H), 7.22 (dd, J = 8.4, 7.6 Hz, 1H), 5.68-5.61 (m, 1H), 3.36-3.20 (m, 3H), 3.15-3.07 (m, 1H), 2.59 (s, 3H), 2.29-2.23 (m, 1H), 2.19-2.17 (m, 1H). | MS (ESI) calcd for C$_{16}$H$_{16}$ClN$_5$O [M + 1]$^+$, 330.1; found, 330.1. |
| 278 | 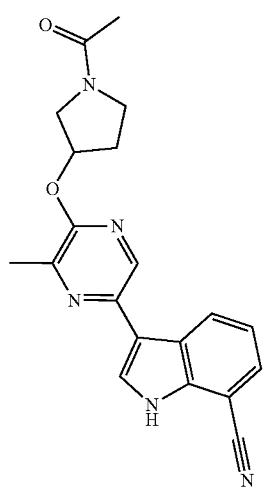 | B | $^1$H NMR (400 MHz, DMSO-d$_6$) δ 12.39 (s, 1H), 8.73-8.66 (m, 1H), 8.29 (s, 1H), 8.20 (d, J = 2.4 Hz, 1H), 7.70 (d, J = 7.6 Hz, 1H), 7.29 (t, J = 8.4 Hz, 1H), 5.62-5.53 (m, 1H), 4.07 (s, 3H), 3.87-3.56 (m, 4H), 2.33-2.15 (m, 2H), 1.99 and 1.95 (s, 3H). | MS (ESI) calcd for C$_{20}$H$_{19}$N$_5$O$_3$ [M + 1]$^+$, 378.1; found, 378.2. |

TABLE 1-continued

| No. | Structure | IC$_{50}$ (μM) | $^1$H NMR | LCMS |
|---|---|---|---|---|
| 279 | 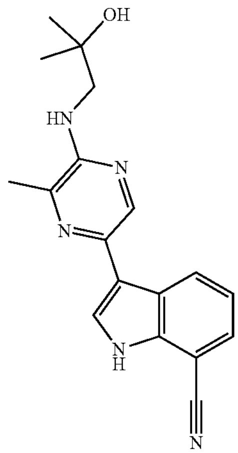 [SMILES: Cc1nc(-c2c[nH]c3c(C#N)cccc23)cnc1NCC(C)(C)O] | C | $^1$H NMR (400 MHz, DMSO-d$_6$) δ 12.17 (s, 1H), 8.68 (d, J = 8.0 Hz, 1H), 8.39 (s, 1H), 8.00 (d, J = 2.4 Hz, 1H), 7.65 (d, J = 7.2 Hz, 1H), 7.24 (t, J = 7.6 Hz, 1H), 5.99 (t, J = 5.6 Hz, 1H), 4.74 (s, 1H), 3.40 (d, J = 5.6 Hz, 2H), 2.46 (s, 3H), 1.14 (s, 6H). | MS (ESI) calcd for C$_{18}$H$_{19}$N$_5$O [M + 1]$^+$, 322.1; found, 322.2. |
| 280 | 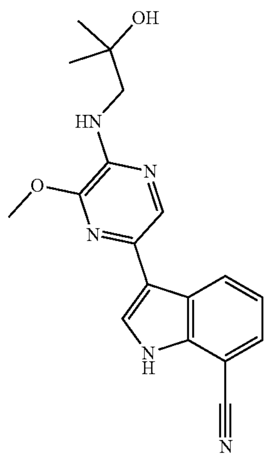 [SMILES: COc1nc(-c2c[nH]c3c(C#N)cccc23)cnc1NCC(C)(C)O] | C | $^1$H NMR (400 MHz, DMSO-d$_6$) δ 12.19 (s, 1H), 8.65 (d, J = 8.0 Hz, 1H), 8.11 (s, 1H), 7.99 (d, J = 2.4 Hz, 1H), 7.66 (dd, J = 7.6, 1.2 Hz, 1H), 7.29-7.21 (m, 1H), 6.05 (t, J = 5.6 Hz, 1H), 4.77 (s, 1H), 4.09 (s, 3H), 3.38-3.36 (m, 2H), 1.14 (s, 6H). | MS (ESI) calcd for C$_{18}$H$_{19}$N$_5$O$_2$ [M + 1]$^+$, 339.1; found, 339.1. |
| 281 | 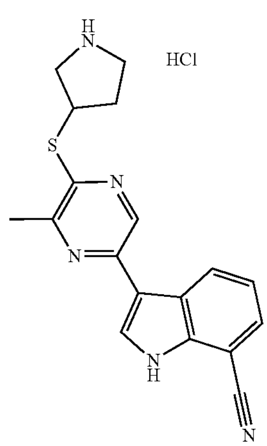 [SMILES: Cc1nc(-c2c[nH]c3c(C#N)cccc23)cnc1SC1CCNC1 ; Cl] | B | $^1$H NMR (400 MHz, DMSO-d$_6$) δ 12.56 (s, 1H), 9.63-9.52 (m, 2H), 8.98 (s, 1H), 8.81 (d, J = 8.4 Hz, 1H), 8.41 (d, J = 2.8 Hz, 1H), 7.72 (d, J = 7.6 Hz, 1H), 7.31 (t, J = 7.6 Hz, 1H), 4.41-4.36 (m, 1H), 3.83-3.75 (m, 1H), 3.41-3.30 (m, 2H), 3.20-3.15 (m, 1H), 2.52 (s, 3H), 2.50-2.43 (m, 1H), 2.08-2.00 (m, 1H). | MS (ESI) calcd for C$_{18}$H$_{17}$N$_5$S [M + 1]$^+$, 336.1; found, 336.1. |

TABLE 1-continued

| No. | Structure | IC$_{50}$ (μM) | $^1$H NMR | LCMS |
|---|---|---|---|---|
| 282 | 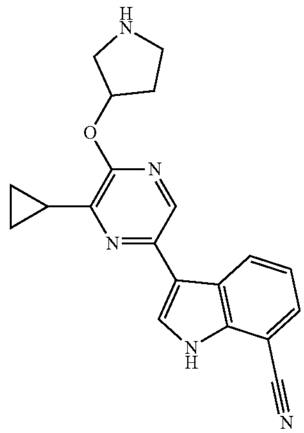 [SMILES: N#Cc1cccc2c(-c3cnc(OC4CCNC4)c(C4CC4)n3)c[nH]c12] | B | $^1$H NMR (400 MHz, DMSO-d$_6$) δ 12.42 (br, 1H), 8.58 (d, J = 8.4 Hz, 1H), 8.49 (s, 1H), 8.19 (s, 1H), 7.68 (d, J = 7.2 Hz, 1H), 7.29 (t, J = 7.6 Hz, 1H), 5.43-5.38 (m, 1H), 3.48-3.33 (m, 1H), 3.03-2.95 (m, 2H), 2.89-2.83 (m, 1H), 2.46-2.38 (m, 2H), 2.17-2.03 (m, 1H), 1.94-1.86 (m, 1H), 1.12-1.09 (m, 4H). | MS (ESI) calcd for C$_{20}$H$_{19}$N$_5$O [M + 1]$^+$, 346.1; found, 346.1. |
| 283 | 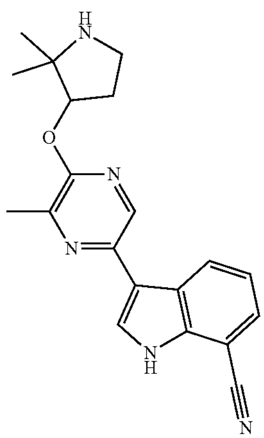 [SMILES: Cc1nc(-c2c[nH]c3c(C#N)cccc23)cnc1OC1CCNC1(C)C] | A | $^1$H NMR (400 MHz, Methanol-d$_4$) δ 8.61 (dd, J = 8.4, 1.2 Hz, 1H), 8.41 (d, J = 0.8 Hz, 1H), 7.95 (s, 1H), 7.60 (dd, J = 7.6, 1.2 Hz, 1H), 7.33-7.24 (m, 1H), 5.25-5.22 (m, 1H), 3.23-3.17 (m, 1H), 3.09-3.02 (m, 1H), 2.56 (s, 3H), 2.56-2.45 (m, 1H), 2.08-1.92 (m, 1H), 1.32 (s, 3H), 1.27 (s, 3H). | MS (ESI) calcd for C$_{20}$H$_{21}$N$_5$O [M + 1]$^+$, 348.2; found, 348.2. |
| 284 | 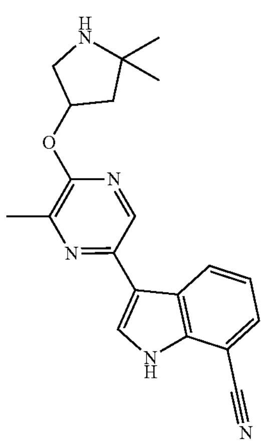 [SMILES: Cc1nc(-c2c[nH]c3c(C#N)cccc23)cnc1OC1CNC(C)(C)C1] | A | $^1$H NMR (400 MHz, Methanol-d$_4$) δ 8.60 (dd, J = 8.0, 1.2 Hz, 1H), 8.40 (d, J = 0.8 Hz, 1H), 7.94 (s, 1H), 7.60 (dd, J = 7.6, 1.2 Hz, 1H), 7.28 (dd, J = 8.0, 7.6 Hz, 1H), 5.60-5.55 (m, 1H), 3.50-3.33 (m, 1H), 3.19-3.15 (m, 1H), 2.55 (s, 3H), 2.19-2.14 (m, 1H), 1.98-1.94 (m, 1H), 1.39 (s, 3H), 1.29 (s, 3H). | MS (ESI) calcd for C$_{20}$H$_{21}$N$_5$O [M + 1]$^+$, 348.2; found, 348.2. |

TABLE 1-continued

| No. | Structure | IC$_{50}$ (μM) | $^1$H NMR | LCMS |
|---|---|---|---|---|
| 285 | 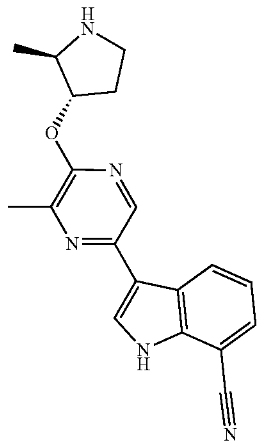 [SMILES: Cc1nc(-c2c[nH]c3c(C#N)cccc23)cnc1O[C@H]1CCN[C@@H]1C] | B | $^1$H NMR (400 MHz, DMSO-d$_6$) δ 12.35 (s, 1H), 8.73 (dd, J = 8.0, 1.2 Hz, 1H), 8.63-8.56 (m, 1H), 8.19 (s, 1H), 7.69 (dd, J = 7.6, 1.2 Hz, 1H), 7.28 (t, J = 7.6 Hz, 1H), 4.94 (dt, J = 6.8, 3.2 Hz, 1H), 3.18-3.13 (m, 1H), 3.02-2.88 (m, 2H), 2.48 (s, 3H), 2.24-2.06 (m, 1H), 1.80-1.74 (m, 1H), 1.15 (d, J = 6.4 Hz, 3H). | MS (ESI) calcd for C$_{19}$H$_{19}$N$_5$O [M + 1]$^+$, 334.2; found, 334.2. |
| 286 | 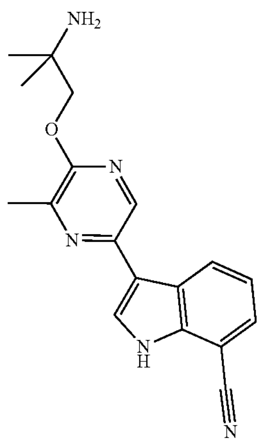 [SMILES: Cc1nc(-c2c[nH]c3c(C#N)cccc23)cnc1OCC(C)(C)N] | B | $^1$H NMR (400 MHz, DMSO-d$_6$) δ 12.36 (s, 1H), 8.73 (dd, J = 8.0, 1.2 Hz, 1H), 8.56 (s, 1H), 8.20 (s, 1H), 7.69 (dd, J = 7.6, 1.2 Hz, 1H), 7.29 (t, J = 7.6 Hz, 1H), 4.04 (s, 2H), 2.55 (s, 3H), 2.00 (s, 1H), 1.15 (s, 6H). | MS (ESI) calcd for C$_{18}$H$_{19}$N$_5$O [M + 1]$^+$, 322.2; found, 322.2. |
| 287 | 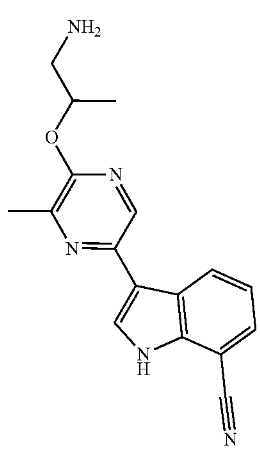 [SMILES: Cc1nc(-c2c[nH]c3c(C#N)cccc23)cnc1OC(C)CN] | C | $^1$H NMR (400 MHz, Methanol-d$_4$) δ 8.60 (dd, J = 8.0, 1.2 Hz, 1H), 8.41 (s, 1H), 7.94 (s, 1H), 7.60 (d, J = 7.2 Hz, 1H), 7.28 (t, J = 7.6 Hz, 1H), 5.31-5.24 (m, 1H), 3.03-2.90 (m, 2H), 2.57 (s, 3H), 1.40 (d, J = 6.2 Hz, 3H). | MS (ESI) calcd for C$_{17}$H$_{17}$N$_5$O [M + 1]+, 308.1; found, 308.1. |

TABLE 1-continued

| No. | Structure | IC$_{50}$ (μM) | $^1$H NMR | LCMS |
|---|---|---|---|---|
| 288 | 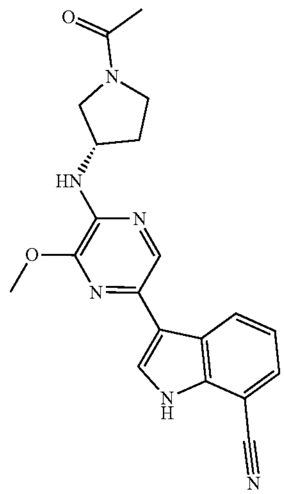 [SMILES: COc1nc(-c2c[nH]c3c(C#N)cccc23)cnc1N[C@H]1CCN(C(C)=O)C1] | D | $^1$H NMR (400 MHz, DMSO-d$_6$) δ 12.22-12.09 (m, 1H), 8.68-8.62 (m, 1H), 8.16 (d, J = 2.8 Hz, 1H), 8.02-7.99 (m, 1H), 7.66 (d, J = 7.2 Hz, 1H), 7.29-7.21 (m, 1H), 6.73-6.71 (m, 1H), 4.49-4.47 (m, 1H), 4.07 and 4.06 (s, 3H), 3.82-3.39 (m, 3H), 3.31 (s, 1H), 2.27-1.97 (m, 2H), 1.94 and 1.92 (s, 3H). | MS (ESI) calcd for C$_{20}$H$_{20}$N$_6$O$_2$ [M + 1]$^+$, 377.2; found, 377.3. |
| 289 | 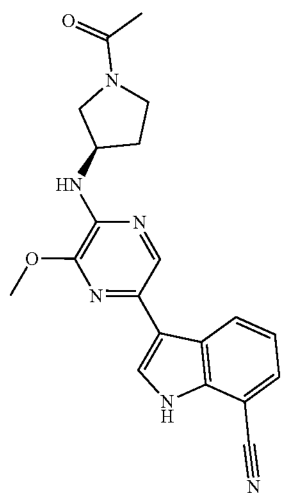 [SMILES: COc1nc(-c2c[nH]c3c(C#N)cccc23)cnc1N[C@@H]1CCN(C(C)=O)C1] | D | $^1$H NMR (400 MHz, DMSO-d$_6$) δ 12.21 (s, 1H), 8.66-8.64 (m, 1H), 8.16 (d, J = 2.8 Hz, 1H), 8.01 (d, J = 1.6 Hz, 1H), 7.66 (d, J = 7.2 Hz, 1H), 7.29-7.21 (m, 1H), 6.77 (d, J = 6.4 Hz, 1H), 4.49-4.47 (m, 1H), 4.07 and 4.06 (s, 3H), 3.55-3.35 (m, 3H), 3.30 (m, 1H), 2.17-2.04 (m, 2H), 1.94 and 1.92 (s, 3H). | MS (ESI) calcd for C$_{20}$H$_{20}$N$_6$O$_2$ [M + 1]$^+$, 377.2; found, 377.3. |
| 290 | 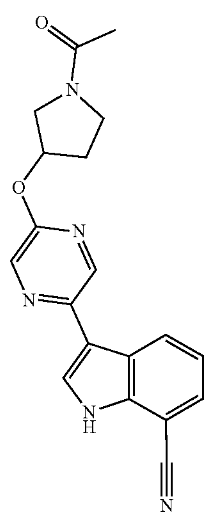 [SMILES: CC(=O)N1CCC(Oc2cnc(-c3c[nH]c4c(C#N)cccc34)cn2)C1] | B | $^1$H NMR (400 MHz, DMSO-d6) δ 12.44 (s, 1H), 8.81 (t, J = 1.2 Hz, 1H), 8.68-8.66 (m, 1H), 8.37 (dd, J = 5.6, 1.2 Hz, 1H), 8.27 (d, J = 2.8 Hz, 1H), 7.74-7.67 (m, 1H), 7.33-7.25 (m, 1H), 5.64-5.55 (m, 1H), 3.90-3.37 (m, 4H), 2.38-2.12 (m, 2H), 2.00-1.95 (m, 3H). | MS (ESI) calcd for C$_{19}$H$_{17}$N$_5$O$_2$ [M + 1]$^+$, 348.1; found, 348.1. |

TABLE 1-continued

| No. | Structure | IC$_{50}$ (μM) | $^1$H NMR | LCMS |
|---|---|---|---|---|
| 291 | 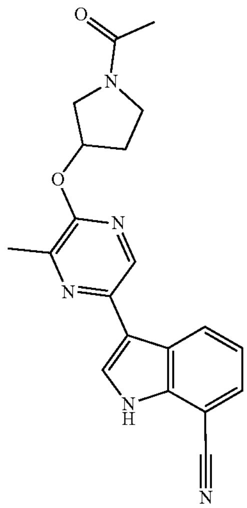 | C | $^1$H NMR (400 MHz, DMSO-d6) δ 12.00 (d, J = 2.8 Hz, 1H), 8.56 (s, 1H), 8.16 (d, J = 8.0 Hz, 1H), 8.10 (t, J = 2.4 Hz, 1H), 7.13-6.96 (m, 2H), 5.52 (dq, J = 4.8, 2.4 Hz, 1H), 3.88 (dd, J = 11.6, 4.8 Hz, 1H), 3.72-3.62 (m, 3H), 2.47 and 2.46 (s, 3H), 2.22 (m, 2H), 2.00 (s, 3H). | MS (ESI) calcd for C$_{19}$H$_{19}$FN$_4$O$_2$ [M + 1]$^+$, 355.1; found, 355.1. |
| 292 | 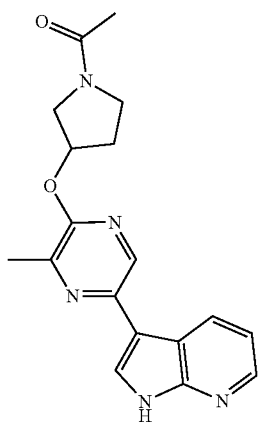 [SMILES: CC(=O)N1CCC(Oc2ncc(-c3c[nH]c4ncccc34)nc2C)C1] | A | $^1$H NMR (400 MHz, DMSO-d$_6$) δ 12.02 (s, 1H), 8.71-8.64 (m, 1H), 8.58 (s, 1H), 8.32-8.25 (m, 1H), 8.18 (t, J = 2.4 Hz, 1H), 7.22-7.14 (m, 1H), 5.70-5.44 (m, 1H), 3.94-3.44 (m, 4H), 2.47 and 2.46 (s, 3H), 2.34-2.09 (m, 2H), 2.02-1.94 (m, 3H). | MS (ESI) calcd for C$_{18}$H$_{19}$N$_5$O$_2$ [M + 1]$^+$, 338.2; found, 338.1. |
| 293 | 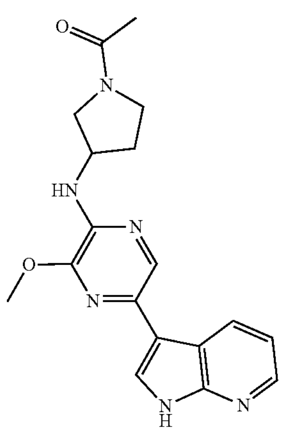 [SMILES: COc1nc(-c2c[nH]c3ncccc23)cnc1NC1CCN(C(C)=O)C1] | A | $^1$H NMR (400 MHz, DMSO-d6) δ 11.84 (s, 1H), 8.64-8.58 (m, 1H), 8.26 (dd, J = 4.8, 1.6 Hz, 1H), 8.14 (d, J = 2.8 Hz, 1H), 7.98 (t, J = 2.4 Hz, 1H), 7.14 (dd, J = 8.0, 4.4 Hz, 1H), 6.71-6.65 (m, 1H), 4.53-4.39 (m, 1H), 4.07 and 4.06 (s, 3H), 3.79-3.41 (m, 4H), 2.51-2.02 (m, 2H), 1.94 and 1.92 (s, 3H). | MS (ESI) calcd for C$_{18}$H$_{20}$N$_6$O$_2$ [M + 1]$^+$, 353.1; found, 353.1. |

TABLE 1-continued

| No. | Structure | IC$_{50}$ (μM) | $^1$H NMR | LCMS |
|---|---|---|---|---|
| 294 | 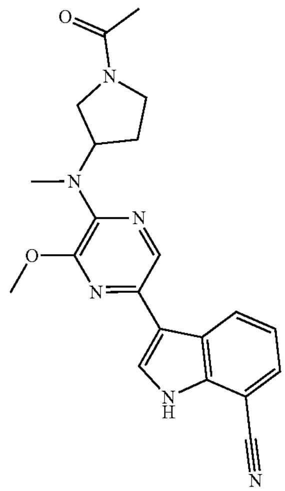 [SMILES: COc1nc(-c2c[nH]c3c(C#N)cccc23)cnc1N(C)C1CCN(C(C)=O)C1] | C | $^1$H NMR (400 MHz, DMSO-d$_6$) δ 12.33 (d, J = 2.8 Hz, 1H), 8.71 (d, J = 8.0 Hz, 1H), 8.34 (d, J = 1.2 Hz, 1H), 8.15 (d, J = 2.4 Hz, 1H), 7.68 (d, J = 7.6 Hz, 1H), 7.28 (t, J = 7.6 Hz, 1H), 4.74-4.61 (m, 1H), 4.08 (d, J = 3.6 Hz, 3H), 3.80-3.52 (m, 2H), 3.52-3.38 (m, 1H), 3.28-3.15 (m, 1H), 2.91 and 2.89 (s, 3H), 2.19-2.01 (m, 2H), 1.96 and 1.95 (s, 3H). | MS (ESI) calcd for C$_{21}$H$_{22}$N$_6$O$_2$ [M + 1]$^+$, 391.1; found, 391.1. |
| 295 | 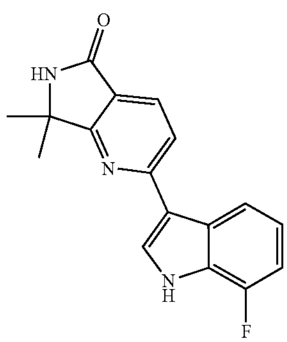 [SMILES: CC1(C)NC(=O)c2ccc(-c3c[nH]c4c(F)cccc34)nc21] | C | $^1$H NMR (400 MHz, DMSO-d$_6$) δ 12.21 (s, 1H), 8.71 (s, 1H), 8.42 (d, J = 8.0 Hz, 1H), 8.37 (d, J = 2.8 Hz, 1H), 8.01-7.91 (m, 2H), 7.17-7.15 (m, 1H), 7.09-7.00 (m, 1H), 1.51 (s, 6H). | MS (ESI) calcd for C$_{17}$H$_{14}$FN$_3$O [M + 1]$^+$, 296.1; found, 296.2. |
| 296 | 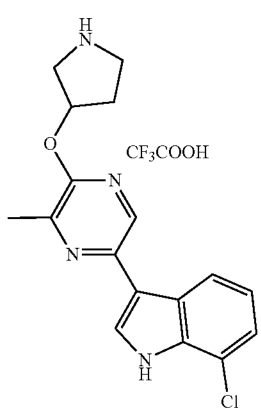 | D | $^1$H NMR (400 MHz, DMSO-d$_6$) δ 11.87 (s, 1H), 9.13 (br, 1H), 8.99 (br, 1H), 8.58 (s, 1H), 8.34 (d, J = 8.0 Hz, 1H), 8.14 (d, J = 2.4 Hz, 1H), 7.27 (dd, J = 7.6, 0.8 Hz, 1H), 7.16-7.11 (m, 1H), 5.65-5.61 (m, 1H), 3.48-3.39 (s, 4 H), 2.49 (s, 3H), 2.38-2.19 (m, 2H). | MS (ESI) calcd for C$_{17}$H$_{17}$ClN$_4$O [M + 1]$^+$, 329.1; found, 329.1. |

TABLE 1-continued

| No. | Structure | IC$_{50}$ (μM) | $^1$H NMR | LCMS |
|---|---|---|---|---|
| 297 | 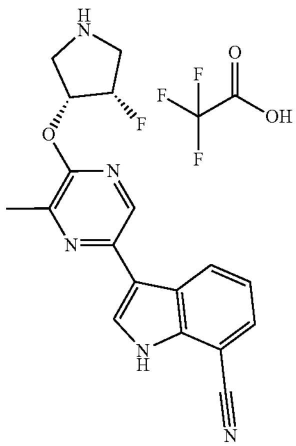 | C | $^1$H NMR (400 MHz, Methanol-d$_4$) δ 8.66 (dd, J = 8.2, 1.2 Hz, 1H), 8.48 (s, 1H), 8.02 (s, 1H), 7.62 (dd, J = 7.6, 1.2 Hz, 1H), 7.30 (dd, J = 8.4, 7.6 Hz, 1H), 5.77-5.56 (m, 2H), 4.01-3.98 (m, 1H), 3.89-3.56 (m, 3H), 2.62 (s, 3H). | MS (ESI) calcd for C$_{18}$H$_{16}$FN$_5$O [M + 1]$^+$, 338.1; found, 338.1. |
| 298 | 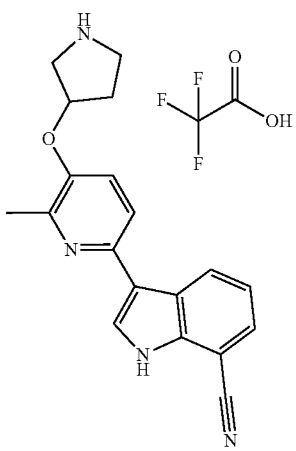 | B | $^1$H NMR (400 MHz, Methanol-d$_4$) δ 8.20 (d, J = 8.4 Hz, 1H), 8.03 (d, J = 3.2 Hz, 1H), 7.95 (d, J = 8.8 Hz, 1H), 7.79 (d, J = 8.8 Hz, 1H), 7.72 (d, J = 7.6 Hz, 1H), 7.39 (t, J = 7.6 Hz, 1H), 4.51-4.50 (m, 1H), 3.73-3.42 (m, 4H), 2.71 (s, 3H), 2.55-2.46 (m, 1H), 2.31-2.19 (m, 1H). | MS (ESI) calcd for C$_{19}$H$_{19}$N$_5$ [M + 1]$^+$, 318.2; found, 318.2. |
| 299 | 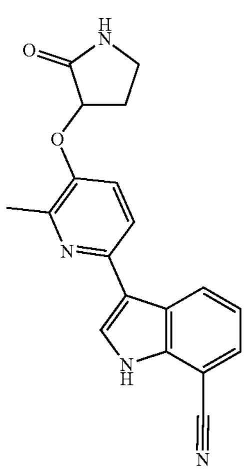 [SMILES: Cc1nc(-c2c[nH]c3c(C#N)cccc23)ccc1OC1CCNC1=O] | B | $^1$H NMR (400 MHz, Methanol-d$_4$) δ 8.33-8.31 (m, 1H), 8.25 (d, J = 8.8 Hz, 1H), 8.09 (s, 1H), 7.98 (d, J = 8.8 Hz, 1H), 7.73-7.71 (m, 1H), 7.41-7.37 (m, 1H), 5.30 (t, J = 7.6 Hz, 1H), 3.60-3.43 (m, 2H), 2.86-2.74 (m, 1H), 2.72 (s, 3H), 2.43-2.29 (m, 1H). | MS (ESI) calcd for C$_{19}$H$_{16}$N$_4$O$_2$ [M + 1]$^+$, 333.1; found, 333.1. |

TABLE 1-continued
| No. | Structure | IC$_{50}$ (μM) | $^1$H NMR | LCMS |
|---|---|---|---|---|
| 300 | 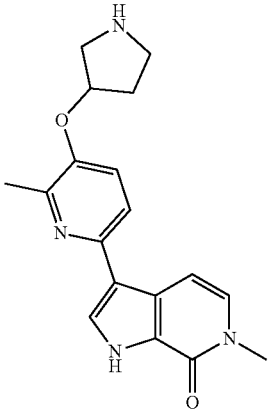 | A | $^1$H NMR (400 MHz, Methanol-d$_4$) δ 7.76 (d, J = 1.6 Hz, 1H), 7.54-7.46 (m, 1H), 7.37 (d, J = 8.4 Hz, 1H), 7.32-7.20 (m, 2H), 5.03-5.01 (m, 1H), 3.68 (s, 3H), 3.26-3.12 (m, 3H), 3.08-2.97 (m, 1H), 2.50 (s, 3H), 2.25-2.12 (m, 1H), 2.12-2.025 (m, 1H). | MS (ESI) calcd for C$_{18}$H$_{20}$N$_4$O$_2$ [M + 1]$^+$, 325.2; found, 325.2. |
| 301 | 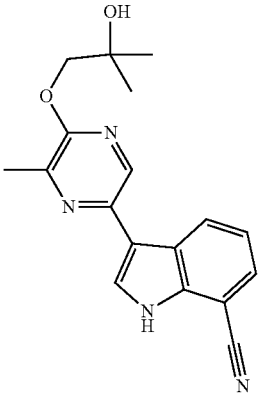 [SMILES: Cc1nc(-c2c[nH]c3c(C#N)cccc23)cnc1OCC(C)(C)O] | D | $^1$H NMR (400 MHz, DMSO-d$_6$) δ 12.35 (s, 1H), 8.73 (d, J = 8.0 Hz, 1H), 8.56 (s, 1H), 8.19 (d, J = 2.4 Hz, 1H), 7.69-7.67 (m, 1H), 7.28 (t, J = 8.0 Hz, 1H), 4.70 (br, 1H), 4.10 (s, 2H), 2.54 (s, 3H), 1.24 (s, 6H). | MS (ESI) calcd for C$_{18}$H$_{18}$N$_4$O$_2$ [M + 1]$^+$, 323.1; found, 323.0. |
| 303 | 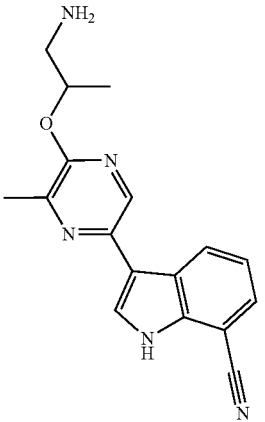 [SMILES: Cc1nc(-c2c[nH]c3c(C#N)cccc23)cnc1OC(C)CN] | C | | |

TABLE 1-continued
| No. | Structure | IC$_{50}$ (μM) | $^1$H NMR | LCMS |
|---|---|---|---|---|
| 304 | 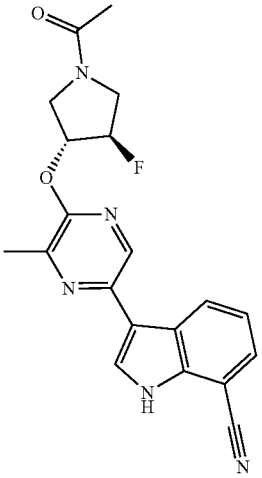 [SMILES: CC(=O)N1C[C@@H](F)[C@H](Oc2ncc(-c3c[nH]c4c(C#N)cccc34)nc2C)C1] | C | $^1$H NMR (400 MHz, DMSO-d$_6$) δ 12.42 (d, J = 2.8 Hz, 1H), 8.74 (d, J = 8.0 Hz, 1H), 8.65 (s, 1H), 8.25 (t, J = 2.4 Hz, 1H), 7.70 (d, J = 7.2 Hz, 1H), 7.30-7.28 (m, 1H), 5.62-5.30 (m, 2H), 4.06-3.60 (m, 4H), 2.48 (s, 3H), 2.03 (d, J = 7.6 Hz, 3H). | MS (ESI) calc'd for (C$_{20}$H$_{18}$FN$_5$O$_2$) [M + 1]$^+$, 380.1; found, 380.1. |
| 305 | 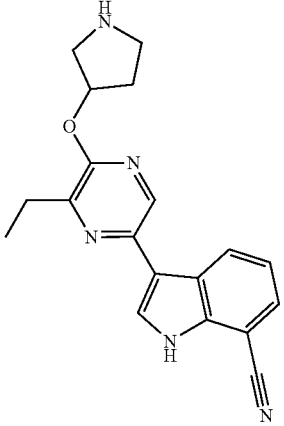 [SMILES: CCc1nc(-c2c[nH]c3c(C#N)cccc23)cnc1OC1CCNC1] | A | | |
| 306 | 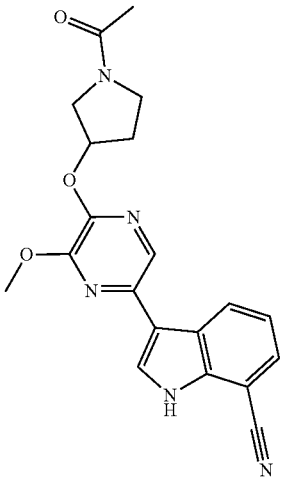 [SMILES: COc1nc(-c2c[nH]c3c(C#N)cccc23)cnc1OC1CCN(C(C)=O)C1] | B | | |

TABLE 1-continued

| No. | Structure | IC$_{50}$ (μM) | $^1$H NMR | LCMS |
|---|---|---|---|---|
| 307 | 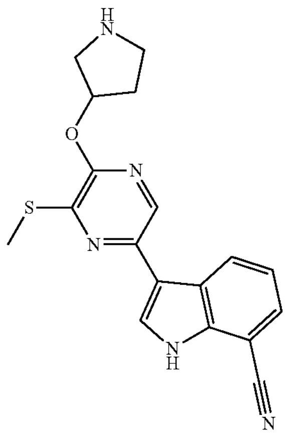 | A | $^1$H NMR (400 MHz, DMSO-d$_6$) δ 12.46 (s, 1H), 8.70 (d, J = 8.0 Hz, 1H), 8.46 (s, 1H), 8.27 (s, 1H), 7.72 (d, J = 7.2 Hz, 1H), 7.32-7.29 (m, 1H), 5.59 (s, 1H), 3.66-3.48 (m, 2H), 3.24 (s, 2H), 2.67 (s, 3H), 2.32-2.19 (m, 1H), 2.18-2.05 (m, 1H). | MS (ESI) calc'd for (C$_{18}$H$_{17}$N$_5$OS) [M + 1]$^+$, 352.1; found, 352.1. |
| 308 | 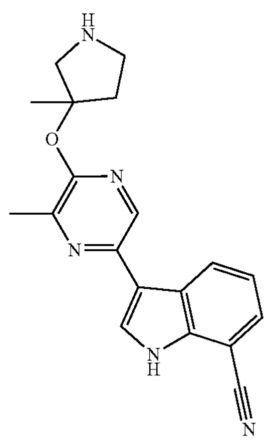 [SMILES: Cc1nc(-c2c[nH]c3c(C#N)cccc23)cnc1OC1(C)CCNC1] | B | $^1$H NMR (400 MHz, Methanol-d$_4$) δ 8.65-8.55 (m, 1H), 8.52 (s, 1H), 8.01 (s, 1H), 7.67-7.60 (m, 1H), 7.33-7.29 (m, 1H), 4.26-4.21 (m, 1H), 3.65-3.51 (m, 2H), 3.44-3.37 (m, 1H), 2.93-2.83 (m, 1H), 2.60 (s, 3H), 2.34-2.24 (m, 1H), 1.90 (s, 3H). | MS (ESI) calc'd for (C$_{19}$H$_{19}$N$_5$O) [M + 1]$^+$, 334.1; found, 334.1. |
| 309 | 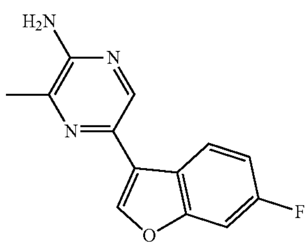 [SMILES: Cc1nc(-c2coc3cc(F)ccc23)cnc1N] | C | $^1$H NMR (400 MHz, DMSO-d$_6$) δ 8.52 (s, 1H), 8.37 (s, 1H), 8.32-8.25 (m, 1H), 7.63-7.54 (m, 1H), 7.27-7.18 (m, 1H), 6.36 (s, 2H), 2.40 (s, 3H) | MS (ESI) calc'd for (C$_{13}$H$_{10}$FN$_3$O) [M + 1]$^+$, 244.1, found 244.1. |
| 310 | 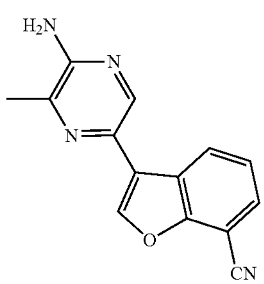 [SMILES: Cc1nc(-c2coc3c(C#N)cccc23)cnc1N] | A | $^1$H NMR (400 MHz, DMSO-d$_6$) δ 8.71 (s, 1H), 8.68-8.66 (m, 1H), 8.41 (s, 1H), 7.92-7.90 (m, 1H), 7.55-7.51 (m, 1H), 6.45 (s, 2H), 2.42 (s, 3H). | MS (ESI) calc'd for (C$_{14}$H$_{10}$N$_4$O) [M + 1]$^+$, 251.1; found, 251.1. |

TABLE 1-continued

| No. | Structure | IC$_{50}$ (μM) | $^1$H NMR | LCMS |
|---|---|---|---|---|
| 311 | 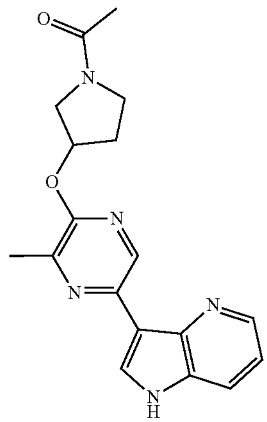 [SMILES: CC(=O)N1CCC(Oc2ncc(-c3c[nH]c4cccnc34)nc2C)C1] | A | $^1$H NMR (400 MHz, DMSO-d$_6$) δ 11.73-11.70 (m, 1H), 9.33 (d, J = 2.8 Hz, 1H), 8.51-8.45 (m, 1H), 8.21 (d, J = 2.4 Hz, 1H), 7.90-7.84 (m, 1H), 7.25-7.20 (m, 1H), 5.70-5.47 (m, 1H), 3.94-3.37 (m, 4H), 2.44 (d, J = 1.6 Hz, 3H), 2.35-2.07 (m, 2H), 2.03-1.90 (m, 3H). | MS (ESI) calculated for (C$_{18}$H$_{19}$N$_5$O$_2$) [M + 1]$^+$, 338.2; found, 338.1. |
| 312 | 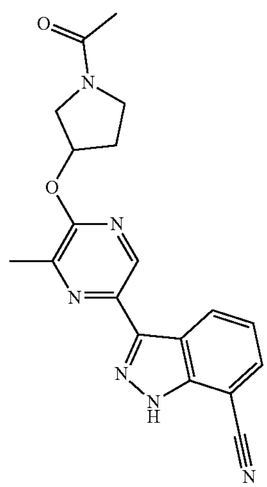 [SMILES: CC(=O)N1CCC(Oc2ncc(-c3n[nH]c4c(C#N)cccc34)nc2C)C1] | B | $^1$H NMR (400 MHz, DMSO-d$_6$) δ 14.27 (s, 1H), 9.09-8.43 (m, 2H), 8.01 (d, J = 7.2 Hz, 1H), 7.40-7.42 (m, J = 8.0 Hz, 1H), 5.78-5.26 (m, 1H), 3.98-3.35 (m, 4H), 2.54 (s, 3H), 2.35-2.03 (m, 2H), 2.01-1.90 (m, 3H). | MS (ESI) calc'd for (C$_{19}$H$_{18}$N$_6$O$_2$) [M + 1]$^+$, 363.1; found, 363.1. |
| 313 | 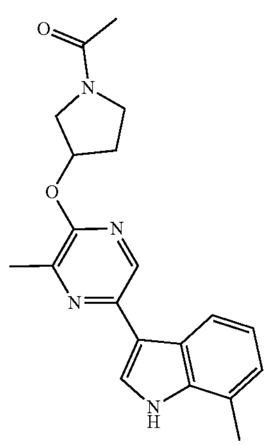 [SMILES: CC(=O)N1CCC(Oc2ncc(-c3c[nH]c4c(C)cccc34)nc2C)C1] | B | $^1$H NMR (400 MHz, DMSO-d$_6$) δ 11.45 (d, J = 2.8 Hz, 1H), 8.53 (s, 1H), 8.15 (d, J = 8.0 Hz, 1H), 8.07-7.97 (m, 1H), 7.04-6.95 (m, 2H), 5.64-5.54 (m, 1H), 3.71-3.52 (m, 4H), 2.54-2.44 (m, 3H), 2.27-2.17 (m, 3H), 2.00 (s, 2H), 1.95 (s, 3H). | MS (ESI) calc'd for (C$_{20}$H$_{22}$N$_4$O$_2$) [M + 1]$^+$, 351.2; found, 351.2. |

TABLE 1-continued

| No. | Structure | IC$_{50}$ (μM) | $^1$H NMR | LCMS |
|-----|-----------|----------------|-----------|------|
| 314 | 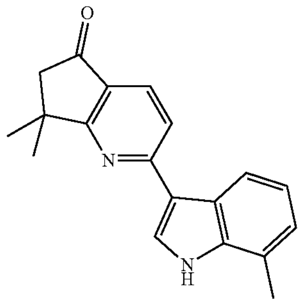 [SMILES: Cc1cccc2c(-c3ccc4c(n3)C(C)(C)CC4=O)c[nH]c12] | C | $^1$H NMR (400 MHz, Methanol-d$_4$) δ 8.37 (d, J = 8.0 Hz, 1H), 8.07 (s, 1H), 8.01 (d, J = 8.4 Hz, 1H), 7.88 (d, J = 8.0 Hz, 1H), 7.13-7.11 (m, 1H), 7.06-7.01 (m, 1H), 2.56 (s, 3H), 1.65-1.63 (m, 6H). | MS (ESI) calc'd for (C$_{18}$H$_{17}$N$_3$O) [M + 1]$^+$, 292.1; found, 292.2. |
| 315 | 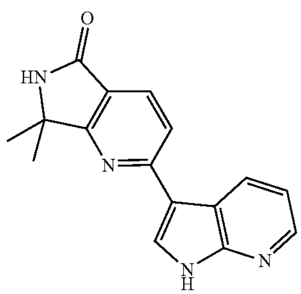 [SMILES: CC1(C)NC(=O)c2ccc(-c3c[nH]c4ncccc34)nc21] | C | $^1$H NMR (400 MHz, DMSO-d$_6$) δ 12.24 (s, 1H), 8.91-8.90 (m, 1H), 8.72 (s, 1H), 8.45 (d, J = 2.8 Hz, 1H), 8.33-8.30 (m, 1H), 8.00-7.87 (m, 2H), 7.26-7.24 (m, 1H), 1.56-1.54 (m, 6H). | MS (ESI) calc'd for (C$_{16}$H$_{14}$N$_4$O) [M + 1]$^+$, 279.1; found, 279.2. |
| 316 | 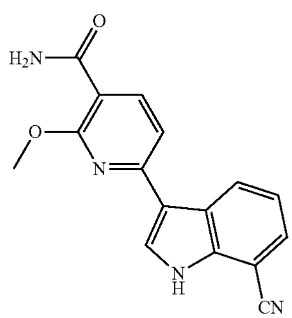 [SMILES: COc1nc(-c2c[nH]c3c(C#N)cccc23)ccc1C(N)=O] | A | $^1$H NMR (400 MHz, DMSO-d$_6$) δ 12.58 (s, 1H), 8.91-8.88 (m, 1H), 8.42 (s, 1H), 8.23-8.21 (m, 1H), 7.75-7.67 (m, 3H), 7.64 (s, 1H), 7.37-7.33 (m, 1H), 4.18 (s, 3H). | MS (ESI) calc'd for (C$_{16}$H$_{12}$N$_4$O$_2$) [M + 1]$^+$, 293.1, found 293.0. |
| 317 | 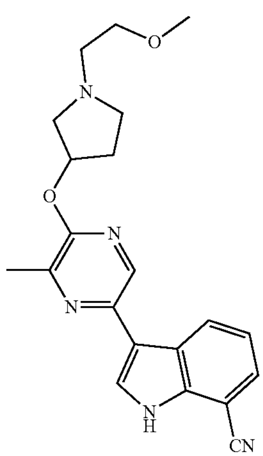 [SMILES: COCCN1CCC(Oc2ncc(-c3c[nH]c4c(C#N)cccc34)nc2C)C1] | B | $^1$H NMR (400 MHz, Methanol-d$_4$) δ 8.58 (d, J = 8.0 Hz, 1H), 8.38 (s, 1H), 7.92 (s, 1H), 7.59 (d, J = 7.2 Hz, 1H), 7.25-7.27 (m, 1H), 5.45-5.47 (m, 1H), 3.55-3.57 (m, 2H), 3.37 (s, 3H), 3.11-3.04 (m, 1H), 2.99-2.84 (m, 2H), 2.79-2.68 (m, 2H), 2.68-2.60 (m, 1H), 2.54 (s, 3H), 2.45-2.38 (m, 1H), 2.10-1.90 (m, 1H). | MS (ESI) calc'd for (C$_{21}$H$_{23}$N$_5$O$_2$) [M + 1]$^+$, 378.1; found, 378.1. |

TABLE 1-continued

| No. | Structure | IC$_{50}$ (μM) | $^1$H NMR | LCMS |
|---|---|---|---|---|
| 318 | 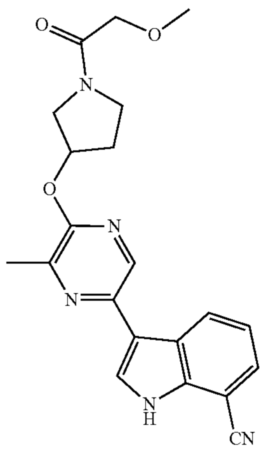 [SMILES: COCC(=O)N1CCC(Oc2ncc(-c3c[nH]c4c(C#N)cccc34)nc2C)C1] | C | $^1$H NMR (400 MHz, Methanol-d$_4$) δ 8.65-8.58 (m, 1H), 8.44 (s, 1H), 7.97 (s, 1H), 7.64-7.58 (m, 1H), 7.33-7.24 (m, 1H), 5.78-5.61 (m, 1H), 4.19 (s, 1H), 4.11 (s, 1H), 3.98-3.58 (m, 4H), 3.48-3.39 (m, 3H), 2.54 (s, 3H), 2.41-2.36 (m, 1H), 2.33-2.26 (m, 1H). | MS (ESI) calc'd for (C$_{21}$H$_{21}$N$_5$O$_3$) [M + 1]$^+$, 392.2; found, 392.2. |
| 321 | 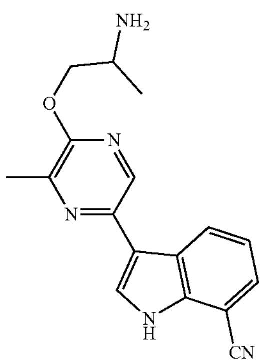 [SMILES: Cc1nc(-c2c[nH]c3c(C#N)cccc23)cnc1OCC(C)N] | B | $^1$H NMR (400 MHz, CD$_3$OD) δ 8.87-8.80 (m, 1H), 8.77-8.72 (m, 1H), 7.89-7.82 (m, 1H), 7.40-7.31 (m, 1H), 5.40-5.28 (m, 1H), 3.06-2.92 (m, 2H), 2.65-2.53 (m, 3H), 1.42 (d, J = 6.4 Hz, 3H). | MS (ESI) calculated for (C$_{16}$H$_{16}$N$_6$O) [M + 1]$^+$, 309.1; found, 309.2. |
| 322 | 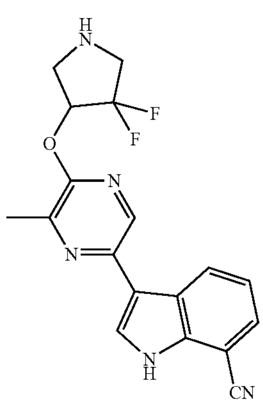 [SMILES: Cc1nc(-c2c[nH]c3c(C#N)cccc23)cnc1OC1CNCC1(F)F] | B | $^1$H NMR (400 MHz, Methanol-d$_4$) δ 8.66-8.60 (m, 1H), 8.43 (s, 1H), 7.97 (s, 1H), 7.60 (d, J = 7.2 Hz, 1H), 7.33-7.24 (m, 1H), 5.61-5.50 (m, 1H), 3.69-3.60 (m, 1H), 3.33-3.09 (m, 3H), 2.59 (s, 3H). | MS (ESI) calc'd for (C$_{18}$H$_{15}$F$_2$N$_5$O) [M + 1]$^+$, 356.1; found, 356.1. |

TABLE 1-continued

| No. | Structure | IC$_{50}$ (μM) | $^1$H NMR | LCMS |
|---|---|---|---|---|
| 323 | 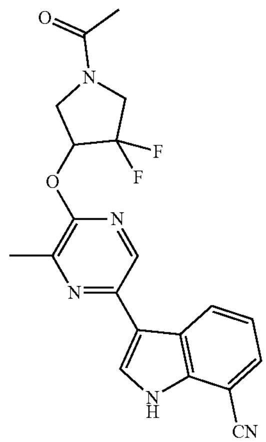 [SMILES: CC(=O)N1CC(Oc2ncc(-c3c[nH]c4c(C#N)cccc34)nc2C)C(F)(F)C1] | C | $^1$H NMR (300 MHz, Methanol-d$_4$) δ 8.70-8.61 (m, 1H), 8.47 (s, 1H), 8.01 (s, 1H), 7.61 (d, J = 7.5 Hz, 1H), 7.35-7.24 (m, 1H), 5.89-5.76 (m, 1H), 4.32-4.10 (m, 2H), 4.07-3.77 (m, 2H), 2.59 (s, 3H), 2.18-2.02 (m, 3H). | MS (ESI) calc'd for (C$_{20}$H$_{17}$F$_2$N$_5$O$_2$) [M + 1]$^+$, 398.1; found, 398.1. |
| 324 | 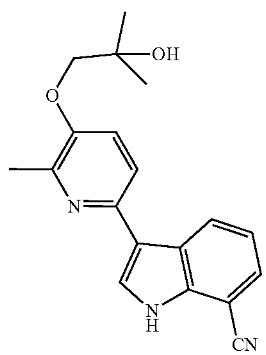 [SMILES: Cc1nc(-c2c[nH]c3c(C#N)cccc23)ccc1OCC(C)(C)O] | B | $^1$H NMR (400 MHz, Methanol-d$_4$) δ 8.57-8.51 (m, 1H), 7.83 (s, 1H), 7.61-7.54 (m, 2H), 7.41-7.34 (m, 1H), 7.30-7.22 (m, 1H), 3.88 (s, 2H), 2.58 (s, 3H), 1.40 (s, 6H). | MS (ESI) calc'd for (C$_{19}$H$_{19}$N$_3$O$_2$) [M + 1]$^+$, 322.1, found 322.2. |
| 325 | 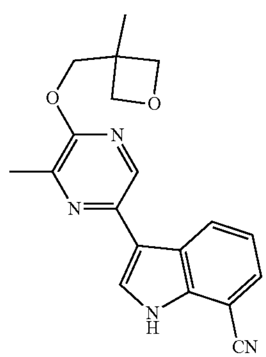 [SMILES: Cc1nc(-c2c[nH]c3c(C#N)cccc23)cnc1OCC1(C)COC1] | C | $^1$H NMR (300 MHz, Methanol-d$_4$) δ 8.63-8.54 (m, 1H), 8.38 (s, 1H), 7.92 (s, 1H), 7.62-7.53 (m, 1H), 7.31-7.20 (m, 1H), 4.71 (d, J = 6.0 Hz, 2H), 4.52-4.41 (m, 4H), 2.55 (s, 3H), 1.47 (s, 3H). | MS (ESI) calc'd for (C$_{19}$H$_{18}$N$_4$O$_2$) [M + 1]$^+$, 335.1; found, 335.0 |
| 326 | 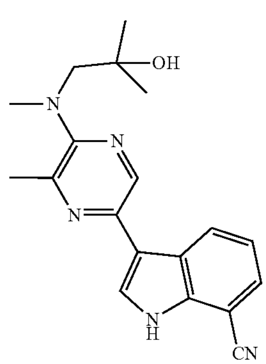 [SMILES: Cc1nc(-c2c[nH]c3c(C#N)cccc23)cnc1N(C)CC(C)(C)O] | B | $^1$H NMR (400 MHz, Methanol-d$_4$) δ 8.66-8.59 (m, 1H), 8.41 (s, 1H), 7.93 (s, 1H), 7.62-7.56 (m, 1H), 7.31-7.23 (m, 1H), 3.58 (s, 2H), 3.14 (s, 3H), 2.68 (s, 3H), 1.20 (s, 6H). | MS (ESI) calculated for (C$_{19}$H$_{21}$N$_5$O) [M + 1]$^+$, 336.2; found, 336.1. |

TABLE 1-continued

| No. | Structure | IC$_{50}$ (μM) | $^1$H NMR | LCMS |
|---|---|---|---|---|
| 327 | 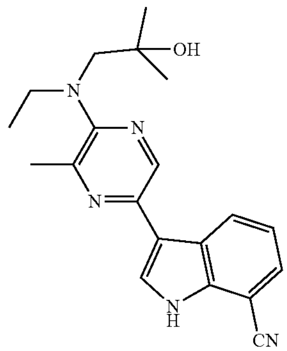 [SMILES: CCN(CC(C)(C)O)c1ncc(-c2c[nH]c3c(C#N)cccc23)nc1C] | B | $^1$H NMR (400 MHz, Methanol-d$_4$) δ 8.70-8.63 (m, 1H), 8.51 (s, 1H), 7.99 (s, 1H), 7.64-7.57 (m, 1H), 7.33-7.25 (m, 1H), 3.58 (s, 2H), 3.45-3.36 (m, 2H), 2.67 (s, 3H), 1.17-1.05 (m, 9H). | MS (ESI) calculated for (C$_{20}$H$_{23}$N$_5$O) [M + 1]$^+$, 350.2; found, 350.3. |
| 328 | 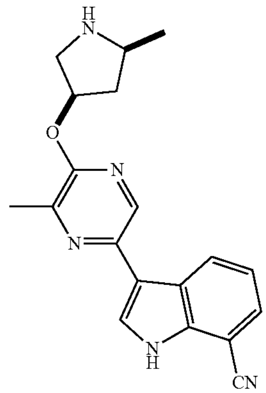 | A | $^1$H NMR (400 MHz, DMSO-d$_6$) δ 12.40 (s, 1H), 8.74 (d, J = 8.0 Hz, 1H), 8.60 (s, 1H), 8.24 (s, 1H), 7.70 (d, J = 7.2 Hz, 1H), 7.29 (t, J = 7.6 Hz, 1H), 5.55 (s, 1H), 3.53 (d, J = 6.0 Hz, 1H), 3.48-3.37 (m, 2H), 2.66-2.64 (m, 1H), 2.53 (s, 3H), 1.94-1.74 (m, 1H), 1.40 (d, J = 6.4 Hz, 3H). | MS (ESI) calc'd for (C$_{20}$H$_{18}$FN$_5$O$_2$) [M + 1]$^+$, 334.0; found, 334.1. |
| 329 | 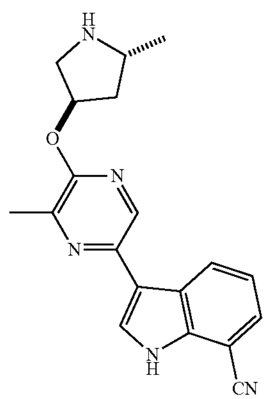 | A | $^1$H NMR (400 MHz, DMSO-d$_6$) δ 12.35 (s, 1H), 8.79-8.65 (m, 1H), 8.57 (s, 1H), 8.19 (s, 1H), 7.72-7.66 (m, 1H), 7.29-7.26 (m, 1H), 5.43 (d, J = 7.6 Hz, 1H), 3.50-3.30 (m, 2H), 2.87-2.85 (m, 1H) 2.48 (s, 3H), 2.06-2.04 (m, 1H), 1.64-1.51 (m, 1H), 1.13 (d, J = 6.4 Hz, 3H). | MS (ESI) calc'd for (C$_{20}$H$_{18}$FN$_5$O$_2$) [M + 1]$^+$, 334.0; found, 334.1. |
| 330 | 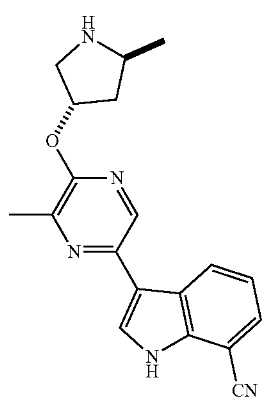 | A | $^1$H NMR (400 MHz, DMSO-d$_6$) δ 12.30 (s, 1H), 8.72 (d, J = 8.0 Hz, 1H), 8.57 (s, 1H), 8.19 (s, 1H), 7.69 (d, J = 7.2 Hz, 1H), 7.29-7.27 (m, 1H), 5.6-5.4 (m, 1H), 3.47-3.41 (m, 1H), 3.39-3.26 (m, 1H), 2.89-2.84 (m, 1H), 2.48 (s, 3H), 2.07-2.01 (m, 1H), 1.63-1.60 (m, 1H), 1.15 (d, J = 6.4 Hz, 3H). | MS (ESI) calc'd for (C$_{20}$H$_{18}$FN$_5$O$_2$) [M + 1]$^+$, 334.0; found, 334.1. |

TABLE 1-continued

| No. | Structure | IC$_{50}$ (μM) | $^1$H NMR | LCMS |
|---|---|---|---|---|
| 331 | 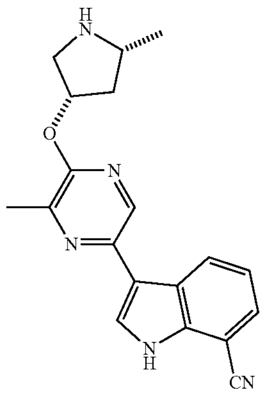 | A | $^1$H NMR (400 MHz, DMSO-d$_6$) δ 12.35 (s, 1H), 8.73 (d, J = 8.0 Hz, 1H), 8.57 (s, 1H), 8.19 (s, 1H), 7.69 (d, J = 7.2 Hz, 1H), 7.29-7.26 (m, 1H), 5.41-5.38 (m, 1H). 3.18-3.15 (m, 1H), 3.12-3.09 (m, 2H), 2.49-2.43 (m, 3H), 2.42-2.37 (m, 1H), 1.48-1.45 (m, 1H), 1.21 (d, J = 6.4 Hz, 3H), | MS (ESI) calc'd for (C$_{20}$H$_{18}$FN$_5$O$_2$) [M + 1]$^+$, 334.0; found, 334.1. |
| 332 | 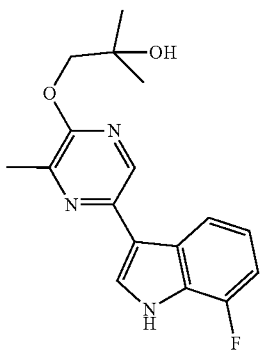 [SMILES: Cc1nc(-c2c[nH]c3c(F)cccc23)cnc1OCC(C)(C)O] | B | $^1$H NMR (300 MHz, Methanol-d$_4$) δ 8.35 (s, 1H), 7.95 (d, J = 8.1 Hz, 1H), 7.80 (s, 1H), 7.13-7.00 (m, 1H), 6.97-6.84 (m, 1H), 4.20 (s, 2H), 2.57 (s, 3H), 1.36 (s, 6H). | MS (ESI) calc'd for (C$_{17}$H$_{18}$FN$_3$O$_2$) [M + 1]$^+$, 316.1, found 316.2. |
| 333 | 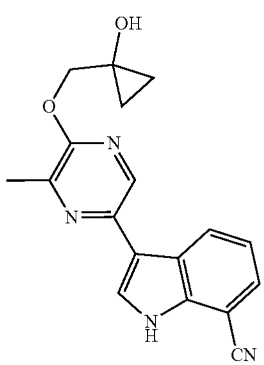 [SMILES: Cc1nc(-c2c[nH]c3c(C#N)cccc23)cnc1OCC1(O)CC1] | A | $^1$H NMR (400 MHz, Methanol-d$_4$) δ 8.57 (d, 1H), 8.35 (s, 1H), 7.91 (s, 1H), 7.59 (d, 1H), 7.31-7.22 (m, 1H), 4.45 (s, 2H), 2.60 (s, 3H), 0.91-0.83 (m, 2H), 0.83-0.76 (m, 2H). | MS (ESI) calculated for (C$_{18}$H$_{16}$N$_4$O$_2$) [M + 1]$^+$, 321.1; found, 321.1 |
| 334 | 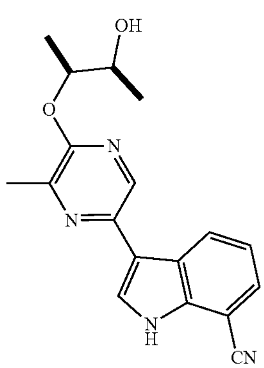 [SMILES: Cc1nc(-c2c[nH]c3c(C#N)cccc23)cnc1O[C@@H](C)[C@H](C)O] | B | $^1$H NMR (400 MHz, DMSO-d$_6$) δ 12.32 (s, 1H), 8.75-8.68 (m, 1H), 8.54 (s, 1H), 8.17 (s, 1H), 7.71-7.65 (m, 1H), 7.32-7.23 (m, 1H), 5.12-5.02 (m, 1H), 4.81 (d, J = 4.8 Hz, 1H), 3.89-3.79 (m, 1H), 2.49 (s, 1H), 1.25 (d, J = 6.4 Hz, 3H), 1.12 (d, J = 6.4 Hz, 3H). | MS (ESI) calculated for (C$_{18}$H$_{18}$N$_4$O$_2$) [M + 1]$^+$, 323.1; found, 323.2. |

TABLE 1-continued

| No. | Structure | IC$_{50}$ (μM) | $^1$H NMR | LCMS |
|---|---|---|---|---|
| 335 | 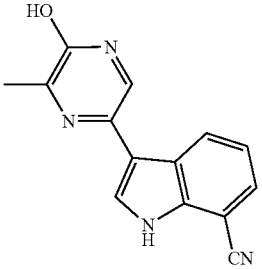 [SMILES: Cc1nc(-c2c[nH]c3c(C#N)cccc23)cnc1O] | B | $^1$H NMR (400 MHz, DMSO-d$_6$) δ 12.18 (s, 2H), 8.52-8.50 (m, 1H), 7.94 (s, 1H), 7.79 (s, 1H), 7.66-7.64 (m, 1H), 7.28-7.20 (m, 1H), 2.40 (s, 3H). | MS (ESI) calculated for (C$_{14}$H$_{10}$N$_4$O) [M + 1]$^+$, 251.1; found, 251.1 |
| 336 | 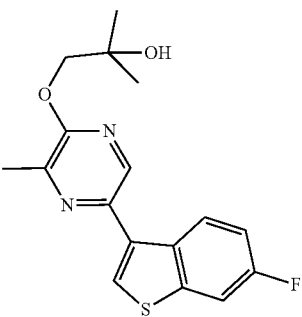 [SMILES: Cc1nc(-c2csc3cc(F)ccc23)cnc1OCC(C)(C)O] | C | $^1$H NMR (400 MHz, DMSO-d$_6$) δ 8.59-8.50 (m, 2H), 8.21 (s, 1H), 8.03-7.96 (m, 1H), 7.40-7.30 (m, 1H), 4.72 (s, 1H), 4.14 (s, 2H), 2.55 (s, 3H), 1.25 (s, 6H). | MS (ESI) calculated for (C$_{17}$H$_{17}$FN$_2$O$_2$S) [M + 1]+, 333.1; found, 333.1. |
| 337 | 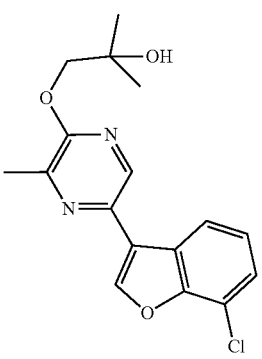 [SMILES: Cc1nc(-c2coc3c(Cl)cccc23)cnc1OCC(C)(C)O] | C | $^1$H NMR (400 MHz, Methanol-d$_4$) δ 8.46-8.38 (m, 2H), 8.19 (d, J = 7.6 Hz, 1H), 7.42 (d, J = 7.6 Hz, 1H), 7.37-7.29 (m, 1H), 4.25 (s, 2H), 2.61 (s, 3H), 1.38 (s, 6H). | MS (ESI) calc'd for (C$_{17}$H$_{17}$Cl$_2$N$_2$O$_3$) [M + 1]$^+$, 333.1; found, 333.0. |
| 338 | 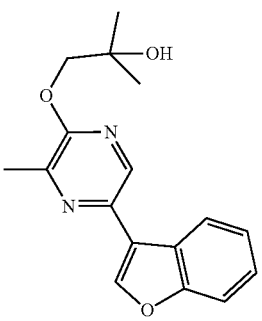 [SMILES: Cc1nc(-c2coc3ccccc23)cnc1OCC(C)(C)O] | A | $^1$H NMR (400 MHz, DMSO-d$_6$) δ 8.63 (s, 1H), 8.60-8.55 (m, 1H), 8.35-8.28 (m, 1H), 7.70-7.63 (m, 1H), 7.45-7.33 (m, 2H), 4.71 (s, 1H), 4.13 (s, 2H), 2.57-2.53 (m, 3H), 1.25 (s, 6H). | MS (ESI) calculated for (C$_{17}$H$_{18}$N$_2$O$_3$) [M + 1]$^+$, 299.1; found, 299.2. |

TABLE 1-continued

| No. | Structure | IC$_{50}$ (μM) | $^1$H NMR | LCMS |
|---|---|---|---|---|
| 339 | 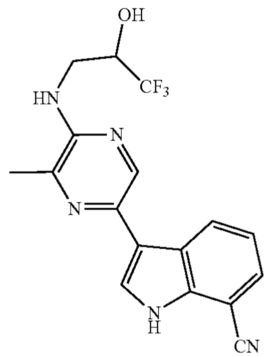 [SMILES: Cc1nc(-c2c[nH]c3c(C#N)cccc23)cnc1NCC(O)C(F)(F)F] | C | $^1$H NMR (300 MHz, CD$_3$COCD) δ 8.84-8.75 (m, 1H), 8.53 (s, 1H), 8.20 (s, 1H), 7.66 (d, J = 7.2 Hz, 1H), 7.39-7.28 (m, 1H), 6.25-6.10 (m, 1H), 3.81 (d, J = 6.0 Hz, 2H), 2.54 (s, 3H), 1.94 (s, 2H), 1.29 (d, J = 6.6 Hz, 1H). | MS (ESI) calc'd for (C$_{17}$H$_{14}$F$_3$N$_5$O) [M + 1]$^+$, 362.1, found 362.3 |
| 340 | 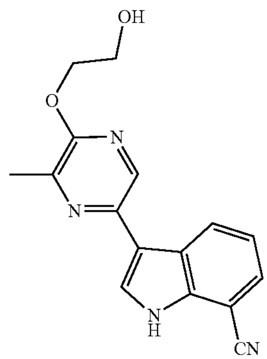 [SMILES: Cc1nc(-c2c[nH]c3c(C#N)cccc23)cnc1OCCO] | A | $^1$H NMR (300 MHz, Methanol-d$_4$) δ 8.63-8.54 (m, 1H), 8.38 (s, 1H), 7.92 (s, 1H), 7.65-7.58 (m, 1H), 7.32-7.21 (m, 1H), 4.52-4.42 (m, 2H), 3.99-3.90 (m, 2H), 2.58 (s, 3H). | MS (ESI) calc'd for (C$_{16}$H$_{14}$N$_4$O$_2$) [M + 1]$^+$, 295.3, found 295.3. |
| 341 | 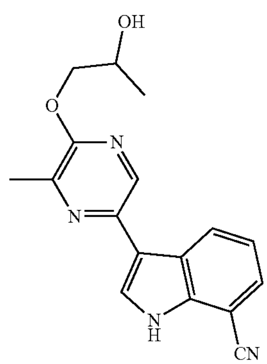 [SMILES: Cc1nc(-c2c[nH]c3c(C#N)cccc23)cnc1OCC(C)O] | B | $^1$H NMR (400 MHz, Methanol-d$_4$) δ 8.37 (d, J = 8.0 Hz, 1H), 7.83 (d, J = 9.6 Hz, 2H), 7.59 (d, J = 7.2 Hz, 1H), 7.31-7.22 (m, 1H), 5.14-5.05 (m, 1H), 3.99-3.90 (m, 1H), 3.90-3.82 (m, 1H), 2.54 (s, 3H), 1.50 (d, J = 7.2 Hz, 3H). | MS (ESI) calc'd for (C$_{17}$H$_{16}$N$_4$O$_2$) [M + 1]$^+$, 309.1, found 309.1. |
| 342 | 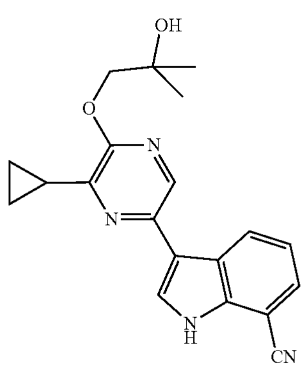 [SMILES: CC(C)(O)COc1ncc(-c2c[nH]c3c(C#N)cccc23)nc1C1CC1] | A | $^1$H NMR (400 MHz, Methanol-d$_4$) δ 8.39-8.32 (m, 1H), 7.78-7.72 (d, J = 3.2 Hz, 2H), 7.61-7.55 (m, 1H), 7.29-7.21 (m, 1H), 4.16-4.11 (s, 2H), 2.78-2.67 (m, 1H), 1.32-1.24 (s, 6H), 1.22-1.07 (m, 4H). | MS (ESI) calc'd for (C$_{20}$H$_{20}$N$_4$O$_2$) [M + 1]$^+$, 349.2, found 349.1. |

TABLE 1-continued

| No. | Structure | IC$_{50}$ (µM) | $^1$H NMR | LCMS |
|---|---|---|---|---|
| 343 | 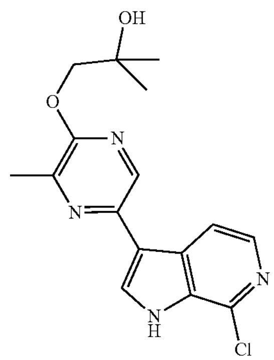 [SMILES: Cc1nc(-c2c[nH]c3c(Cl)nccc23)cnc1OCC(C)(C)O] | A | $^1$H NMR (400 MHz, Methanol-d$_4$) δ 8.62 (s, 1H), 7.92-7.86 (m, 1H), 7.58-7.52 (m, 1H), 7.13 (d, J = 1.6 Hz, 1H), 4.27 (d, J = 1.6 Hz, 2H), 2.61 (d, J = 1.6 Hz, 3H), 1.38 (d, J = 1.6 Hz, 6H). | MS (ESI) calc'd for (C$_{16}$H$_{17}$ClN$_4$O$_2$) [M + 1]$^+$, 333.1, found 333.1. |
| 344 | 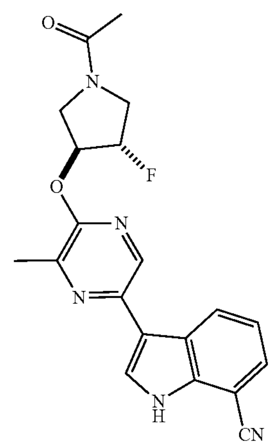 | | $^1$H NMR (400 MHz, DMSO-d$_6$) δ 12.42 (d, J = 2.8 Hz, 1H), 8.74 (d, J = 8.0 Hz, 1H), 8.65 (s, 1H), 8.25 (t, J = 2.4 Hz, 1H), 7.70 (d, J = 7.2 Hz, 1H), 7.30-7.28 (m, 1H), 5.62-5.30 (m, 2H), 4.06-3.60 (m, 4H), 2.48 (s, 3H), 2.03 (d, J = 7.6 Hz, 3H). | MS (ESI) calc'd for (C$_{20}$H$_{18}$FN$_5$O$_2$) [M + 1]$^+$, 380.1; found, 380.1. |
| 345 | 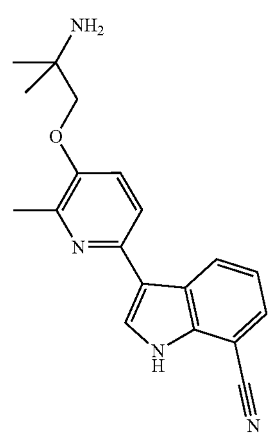 [SMILES: Cc1nc(-c2c[nH]c3c(C#N)cccc23)ccc1OCC(C)(C)N] | | $^1$H NMR (400 MHz, Methanol-d$_4$) δ 8.38 (d, J = 8.0 Hz, 1H), 8.06 (s, 1H), 7.94 (s, 2H), 7.67 (d, J = 7.6 Hz, 1H), 7.42-7.33 (m, 1H), 4.25 (s, 2H), 2.74 (s, 3H), 1.57 (s, 6H). | MS (ESI) calc'd for (C$_{19}$H$_{20}$N$_4$O) [M + 1]$^+$, 321.2, found 321.0. |

TABLE 1-continued

| No. | Structure | IC$_{50}$ (μM) | $^1$H NMR | LCMS |
|---|---|---|---|---|
| 346 | 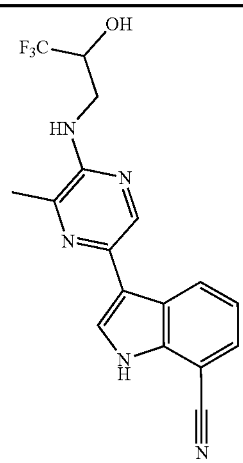 | | $^1$H NMR (300 MHz, CDCOCD$_3$) δ 11.23 (s, 1H), 8.80-8.71 (m, 1H), 8.43 (s, 1H), 8.04 (s, 1H), 7.66-7.57 (m, 1H), 7.34-7.22 (m, 1H), 6.22-6.20 (m, 1 H), 4.43-4.32 (m, 1H), 3.99-3.91 (m, 1H), 3.68-3.53 (m, 1H), 2.51 (s, 3H), 1.28 (s, 1H). | MS (ESI) calc'd for (C$_{17}$H$_{14}$F$_3$N$_5$O) [M + 1]$^+$, 362.1, found 362.1 |
| 347 | 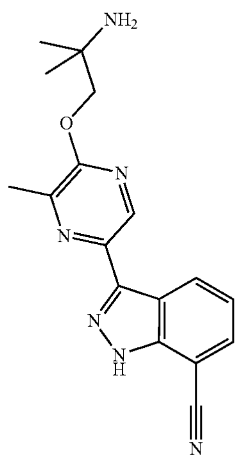 [SMILES: Cc1nc(-c2n[nH]c3c(C#N)cccc23)cnc1OCC(C)(C)N] | | $^1$H NMR (400 MHz, Methanol-d$_4$) δ 8.83-8.81 (m, 1H), 8.72 (s, 1H), 7.85-7.83 (m, 1H), 7.36-7.32 (m, 1H), 4.27 (s, 2H), 2.63 (s, 3H), 1.39 (s, 6H). | MS (ESI) calculated for (C$_{17}$H$_{17}$N$_5$O$_2$) [M + 1]$^+$, 324.1; found, 324.2. |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A compound of Formula V:

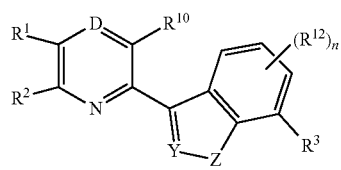

or a pharmaceutically acceptable salt thereof; wherein:
D is CH or N;
Y is CH or N;
Z is O or NH;

R$^1$ and R$^2$, together with the atoms to which they are attached, form a ring of formula:

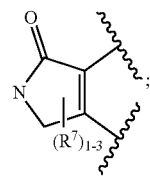

R$^3$ is selected from the group consisting of CN, NH$_2$, halo, C$_{2-3}$ alkenyl, C$_{2-3}$ alkynyl, and C$_{1-3}$ haloalkyl;
each R$^7$ is independently, at each occurrence, selected from the group consisting of C$_{1-3}$ alkyl, C$_{1-6}$ alkyl-OH, C$_{1-3}$ haloalkyl, =O, halo, OH, NH$_2$, NO$_2$, and COR$^9$;
each R$^9$ is independently, at each occurrence, selected from the group consisting of H, C$_{1-6}$ alkyl, C$_{3-10}$ cycloalkyl, C$_{6-10}$ aryl, C(O)C$_{1-3}$ alkyl, and 5-10 membered heteroaryl;
R$^{10}$ is selected from the group consisting of H, C$_{1-3}$ alkyl, C$_{1-6}$ alkyl-OH, C$_{1-3}$ haloalkyl, halo, OH, NH$_2$, NO$_2$, COR$^{11}$, and CO$_2$R$^{11}$;
R$^{11}$ is selected from the group consisting of H, C$_{1-3}$ alkyl, NH$_2$, NH(C$_{1-3}$ alkyl), and N(C$_{1-3}$ alkyl)$_2$;

each $R^{12}$ is independently, at each occurrence, selected from the group consisting of halo, OH, $NH_2$, $NO_2$, $COR^9$, $CO_2R^9$, $OSO_3H$ $C_{1-3}$ alkyl, $C_{1-3}$ alkoxy, $C_{1-3}$ haloalkyl, $NH(C_{1-3}$ alkyl), $N(C_{1-3}$ alkyl$)_2$, $C_{3-10}$ cycloalkyl, 3-10 membered heterocycloalkyl, $C_{6-10}$ aryl, and 5-10 membered heteroaryl; and n is 0, 1, or 2.

2. The compound of claim 1, wherein

D is CH or N;

Y is CH or N;

Z is O or NH;

$R^1$ and $R^2$, together with the atoms to which they are attached, form a ring of formula:

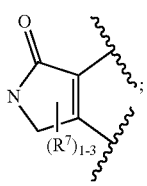

$R^3$ is selected from the group consisting of CN, Cl, and $CF_3$;

each $R^7$ is independently, at each occurrence, selected from the group consisting of $C_{1-3}$ alkyl, $C_{1-3}$ haloalkyl, =O, $C_{1-6}$ alkyl-OH, and halo;

$R^{10}$ is selected from the group consisting of H, $C_{1-3}$ alkyl, $C_{1-3}$ haloalkyl, halo, $COR^{11}$, and $CO_2R^{11}$;

each $R^{12}$ is independently, at each occurrence, selected from the group consisting of H, halo, OH, $NH_2$, $NO_2$, $CO_2R^9$, $C_{1-3}$ alkyl, and $C_{1-3}$ alkoxy; and n is 1.

3. The compound of claim 1, wherein the compound of Formula V is a compound of Formula Vb:

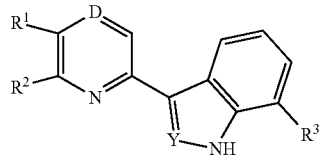

(Vb)

or a pharmaceutically acceptable salt thereof.

4. The compound of claim 1, wherein the compound of Formula V is a compound of Formula VII':

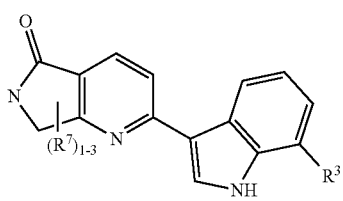

(VII')

or a pharmaceutically acceptable salt thereof;

wherein $R^3$ is selected from the group consisting of CN, halo, and $C_{1-3}$ haloalkyl; and each $R^7$ is independently, at each occurrence, selected from the group consisting of $C_{1-3}$ alkyl, $C_{1-3}$ haloalkyl, $C_{1-6}$ alkyl-OH, and halo;

wherein when the nitrogen atom in the lactam ring is not substituted by $R^7$, it is substituted with H.

5. The compound of claim 4, wherein each $R^7$ is independently $C_{1-3}$ alkyl.

6. The compound of claim 1, wherein the compound of Formula V is selected from the group consisting of

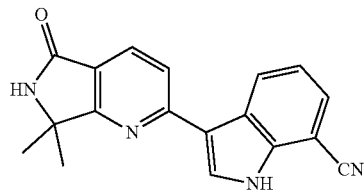 [SMILES: CC1(C)NC(=O)c2ccc(-c3c[nH]c4c(C#N)cccc34)nc21]

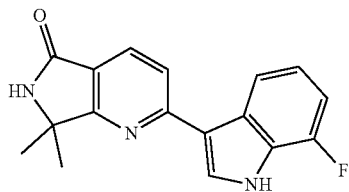 [SMILES: CC1(C)NC(=O)c2ccc(-c3c[nH]c4c(F)cccc34)nc21]

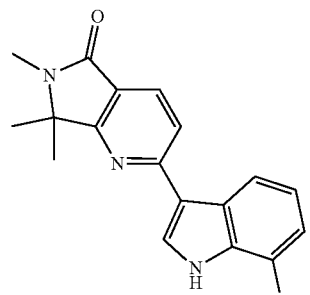

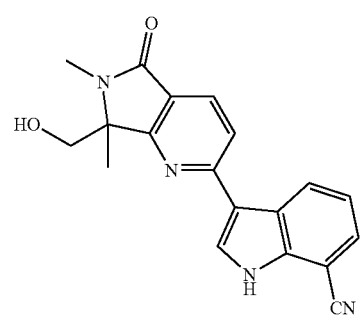 [SMILES: CN1C(=O)c2ccc(-c3c[nH]c4c(C#N)cccc34)nc2C1(C)CO]

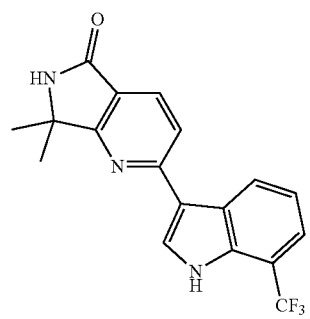 [SMILES: CC1(C)NC(=O)c2ccc(-c3c[nH]c4c(C(F)(F)F)cccc34)nc21]

-continued

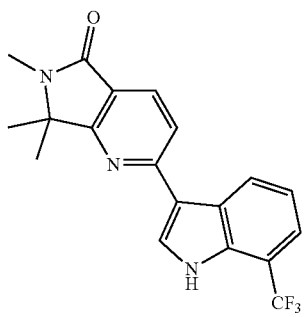 [SMILES: CN1C(=O)c2ccc(-c3c[nH]c4c(C(F)(F)F)cccc34)nc2C1(C)C]

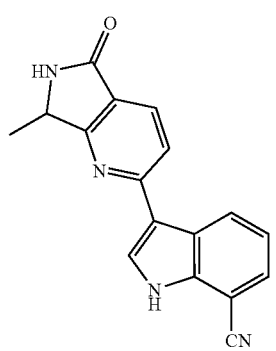 [SMILES: CC1NC(=O)c2ccc(-c3c[nH]c4c(C#N)cccc34)nc21]

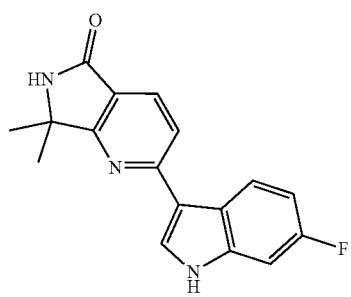 [SMILES: CC1(C)NC(=O)c2ccc(-c3c[nH]c4cc(F)ccc34)nc21]

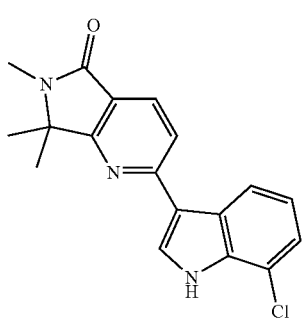 [SMILES: CN1C(=O)c2ccc(-c3c[nH]c4c(Cl)cccc34)nc2C1(C)C]

-continued

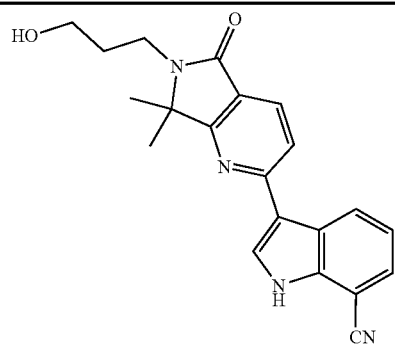

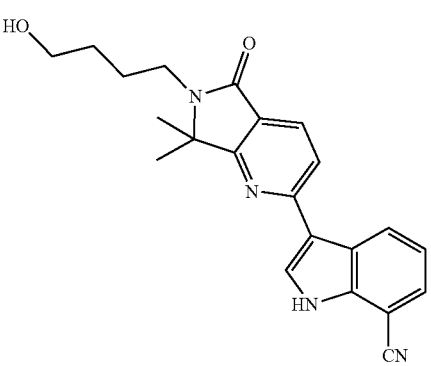 [SMILES: CC1(C)c2nc(-c3c[nH]c4c(C#N)cccc34)ccc2C(=O)N1CCCCO]

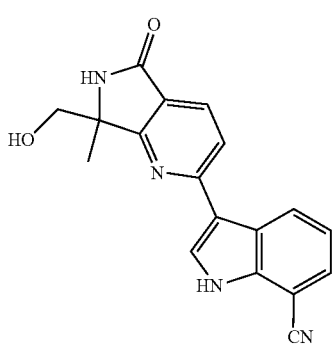 [SMILES: CC1(CO)NC(=O)c2ccc(-c3c[nH]c4c(C#N)cccc34)nc21]

or a pharmaceutically acceptable salt thereof.

7. A pharmaceutical composition comprising a compound of claim 1 and a pharmaceutically acceptable carrier.

8. A compound of Formula X:

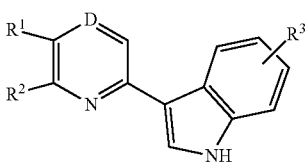

(X)

or a pharmaceutically acceptable salt thereof;
wherein
D is CH or N;
$R^1$ is selected from the group consisting of $C_{1-6}$ alkyl, $OC_{1-6}$ alkyl, and NH (3-7 membered heterocycloalkyl), all of which are optionally independently substituted with OH or $C(O)C_{1-6}$ alkyl;
$R^2$ is selected from the group consisting of H, $C_{1-6}$ alkyl, and $OC_{1-6}$ alkyl;

and

R³ is selected from the group consisting of CN, halo, and C₁₋₃ haloalkyl.

9. The compound of claim 8, wherein the compound of Formula X a compound of Formula VIII:

(VIII)

or a pharmaceutically acceptable salt thereof;

wherein

R¹ is selected from the group consisting of C$_{1-6}$ alkyl, OC$_{1-6}$ alkyl, and NH (3-7 membered heterocycloalkyl), all of which are optionally independently substituted with OH or C(O)C$_{1-6}$ alkyl;

R² is selected from the group consisting of H, C$_{1-6}$ alkyl, and OC$_{1-6}$ alkyl; and R³ is selected from the group consisting of CN, halo, and C$_{1-3}$ haloalkyl.

10. The compound of claim 8, wherein D is N.

11. The compound of claim 8, wherein D is CH.

12. The compound of claim 8, wherein R¹ is OC$_{1-6}$ alkyl or NH (3-7 membered heterocycloalkyl), wherein alkyl and heterocycloalkyl are optionally substituted with OH or C(O)C$_{1-6}$ alkyl.

13. The compound of claim 8, wherein R² is C$_{1-6}$ alkyl or OC$_{1-6}$ alkyl.

14. The compound of claim 8, wherein R³ is CN or halo.

15. The compound of claim 8, wherein the compound of Formula X is selected from the group consisting of

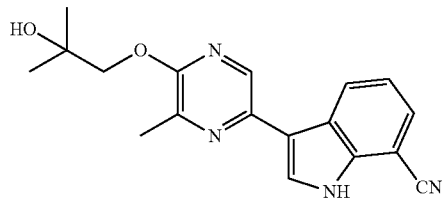 [SMILES: Cc1nc(-c2c[nH]c3c(C#N)cccc23)cnc1OCC(C)(C)O]

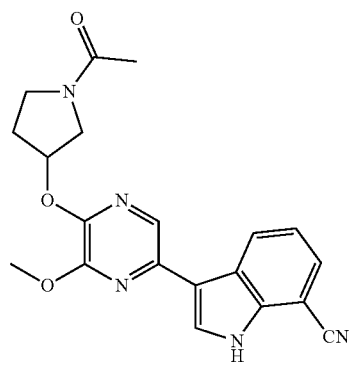 [SMILES: COc1nc(-c2c[nH]c3c(C#N)cccc23)cnc1OC1CCN(C(C)=O)C1]

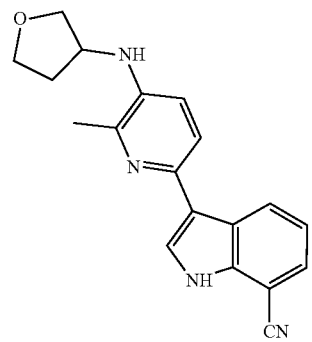 [SMILES: Cc1nc(-c2c[nH]c3c(C#N)cccc23)ccc1NC1CCOC1]

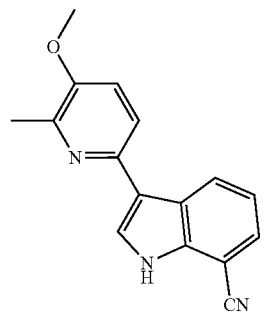 [SMILES: COc1ccc(-c2c[nH]c3c(C#N)cccc23)nc1C]

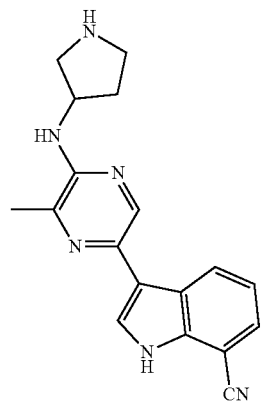 [SMILES: Cc1nc(-c2c[nH]c3c(C#N)cccc23)cnc1NC1CCNC1]

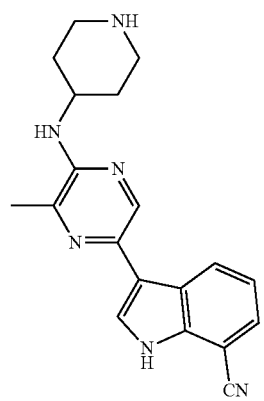 [SMILES: Cc1nc(-c2c[nH]c3c(C#N)cccc23)cnc1NC1CCNCC1]

451
-continued
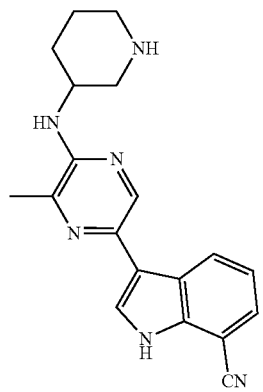 [SMILES: Cc1nc(-c2c[nH]c3c(C#N)cccc23)cnc1NC1CCCNC1]
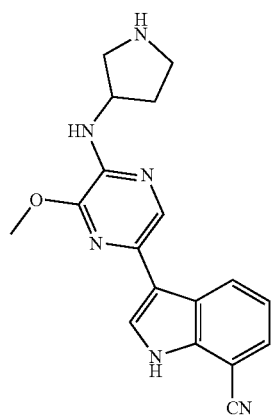 [SMILES: COc1nc(-c2c[nH]c3c(C#N)cccc23)cnc1NC1CCNC1]
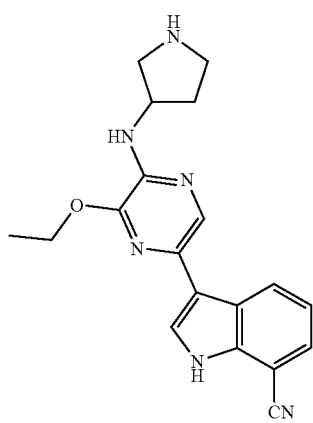 [SMILES: CCOc1nc(-c2c[nH]c3c(C#N)cccc23)cnc1NC1CCNC1]
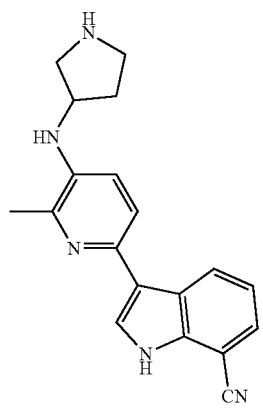 [SMILES: Cc1nc(-c2c[nH]c3c(C#N)cccc23)ccc1NC1CCNC1]
452
-continued
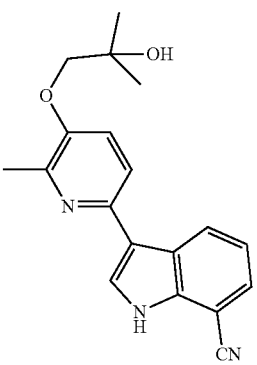 [SMILES: Cc1nc(-c2c[nH]c3c(C#N)cccc23)ccc1OCC(C)(C)O]
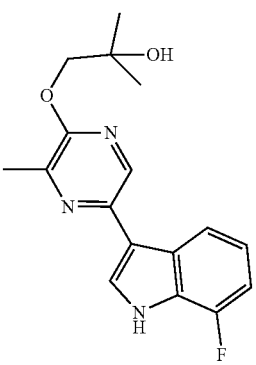 [SMILES: Cc1nc(-c2c[nH]c3c(F)cccc23)cnc1OCC(C)(C)O]
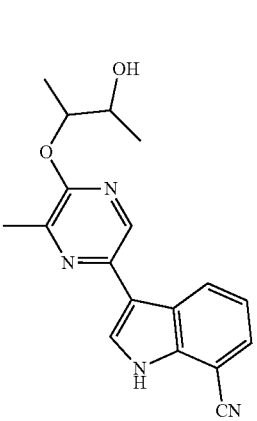 [SMILES: Cc1nc(-c2c[nH]c3c(C#N)cccc23)cnc1OC(C)C(C)O]
or a pharmaceutically acceptable salt thereof.
16. The compound of claim 8, wherein the compound of Formula X is
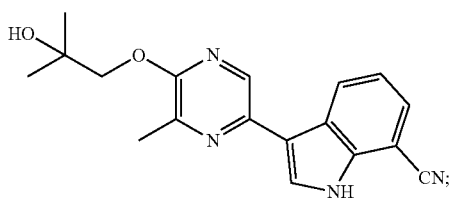 [SMILES: Cc1nc(-c2c[nH]c3c(C#N)cccc23)cnc1OCC(C)(C)O]
or a pharmaceutically acceptable salt thereof.

17. The compound of claim 8, wherein the compound of Formula X is
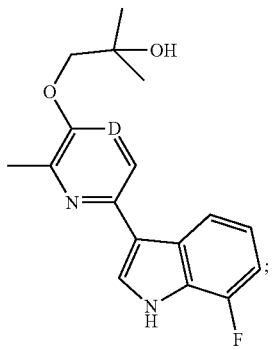
or a pharmaceutically acceptable salt thereof.
18. The compound of claim 8, wherein the compound of Formula X is
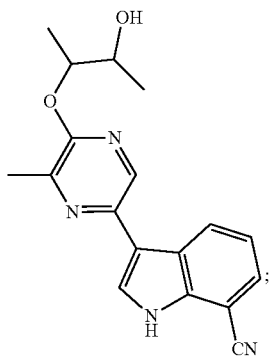 [SMILES: Cc1nc(-c2c[nH]c3c(C#N)cccc23)cnc1OC(C)C(C)O]
or a pharmaceutically acceptable salt thereof.
19. A pharmaceutical composition comprising a compound of claim 8 and a pharmaceutically acceptable carrier.
* * * * *

UNITED STATES PATENT AND TRADEMARK OFFICE
CERTIFICATE OF CORRECTION

PATENT NO. : 11,667,624 B2
APPLICATION NO. : 17/380736
DATED : June 6, 2023
INVENTOR(S) : Bakary-Barry Toure et al.

Page 1 of 1

It is certified that error appears in the above-identified patent and that said Letters Patent is hereby corrected as shown below:

In the Claims

Claim 15, Column 449, Lines 52-65 Should Read:

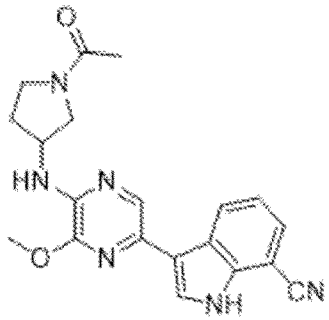

Claim 17, Column 453, Lines 5-15 Should Read:

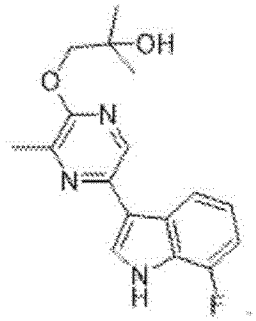

Signed and Sealed this
Fourth Day of July, 2023

Katherine Kelly Vidal
Director of the United States Patent and Trademark Office